(12) United States Patent
Hudyma et al.

(10) Patent No.: US 7,153,848 B2
(45) Date of Patent: Dec. 26, 2006

(54) INHIBITORS OF HCV REPLICATION

(75) Inventors: Thomas W. Hudyma, Durham, CT (US); Xiaofan Zheng, Cheshire, CT (US); Feng He, Arlington, MA (US); Min Ding, Glastonbury, CT (US); Carl P. Bergstrom, Madison, CT (US); Piyasena Hewawasam, Middletown, CT (US); Scott W. Martin, Middletown, CT (US); Robert G. Gentles, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/181,639

(22) Filed: Jul. 14, 2005

(65) Prior Publication Data

US 2006/0046983 A1 Mar. 2, 2006

Related U.S. Application Data

(60) Provisional application No. 60/660,555, filed on Mar. 11, 2005, provisional application No. 60/608,932, filed on Aug. 9, 2004.

(51) Int. Cl.
| | |
|---|---|
| A61K 31/55 | (2006.01) |
| A61K 31/5377 | (2006.01) |
| A61K 31/496 | (2006.01) |
| A61K 31/454 | (2006.01) |
| A61K 31/4439 | (2006.01) |
| A61K 31/425 | (2006.01) |
| A61K 31/427 | (2006.01) |
| A61K 31/4178 | (2006.01) |
| A61K 31/4184 | (2006.01) |
| A61K 31/4025 | (2006.01) |
| A61K 31/403 | (2006.01) |
| C07D 233/32 | (2006.01) |
| C07D 413/14 | (2006.01) |
| C07D 409/14 | (2006.01) |

(52) U.S. Cl. .................... 514/214.01; 514/233.2; 514/254.08; 514/323; 514/339; 514/364; 514/365; 514/394; 514/397; 514/410; 514/414; 514/422; 540/576; 544/142; 544/372; 546/200; 546/276.7; 548/131; 548/132; 548/181; 548/305.1; 548/312.1; 548/420; 548/455; 548/518

(58) Field of Classification Search .......... 514/214.01, 514/233.2, 254.08, 323, 339, 364, 365, 394, 514/397, 410, 414, 422; 540/576; 544/142, 544/372; 546/200, 276.7; 548/131, 132, 548/181, 305.1, 312.1, 420, 455, 518
See application file for complete search history.

(56) References Cited

U.S. PATENT DOCUMENTS

2005/0119318 A1 6/2005 Hudyma et al.

FOREIGN PATENT DOCUMENTS

| WO | WO 01/47883 A1 | 7/2001 |
|---|---|---|
| WO | WO 02/04425 A2 | 1/2002 |
| WO | WO 03/007945 A1 | 1/2003 |
| WO | WO 03/010140 A2 | 2/2003 |
| WO | WO 03/010141 A2 | 2/2003 |
| WO | WO 2004/064925 A1 | 8/2004 |
| WO | WO 2004/065367 A1 | 8/2004 |
| WO | WO 2004/087714 A1 | 10/2004 |
| WO | WO 2004/099241 A1 | 11/2004 |
| WO | WO 2005/012288 A1 | 2/2005 |
| WO | WO 2005/014543 A1 | 2/2005 |
| WO | WO 2005/034941 A1 | 4/2005 |
| WO | WO 2005/080388 A1 | 9/2005 |
| WO | WO 2005/080399 A1 | 9/2005 |

OTHER PUBLICATIONS

Rivara et al. "Three-Dimensional Quantitative Structure-Activity Relationship Studies on Selected MT1 and MT2 Melatonin Receptor Ligands: Requirements for Subtype Selectivity and Intrinsic Activity Modulation" J. Med. Chem. 2003, vol. 46, pp. 1429-1439.*
S. Harper, et al, "Potent Inhibitors of Subgenomic Hepatitis C Virus RNA Replication Through Optimization of Indole-N-Acetamide Allosteric Inhibitors of the Viral NS5B Polymerase," J. Med. Chem., 48(14), pp. 4547-4557, 2005.
S. Harper, et al, "Development and Preliminary Optimization of Indole-N-Acetamide Inhibitors of Hepatitis C Virus NS5B Polymerase," J. Med. Chem., 48(5), pp. 1314-1317, 2005.
Grinev, A.N., et al, "Synthesis and Biological Activity of Aminoacetyl and Aminoethyl Derivatives of Indole [1,2-c] Quinazoline," Khimiko-Farmatsevticheskii Zhurnal, Vses. Nauchno-Issled. Khim-Farm. Inst., 12(2), pp. 97-101, 1978-Coden: Khfzan; ISSN: 0023-1134 (English Abstract).

* cited by examiner

*Primary Examiner*—Joseph K. McKane
*Assistant Examiner*—Joseph R. Kosack
(74) *Attorney, Agent, or Firm*—James Epperson; Pamela A. Mingo

(57) ABSTRACT

Indole compounds of Formula I are described. The compounds have activity against hepatitis C virus (HCV) and are useful in treating those infected with HCV. Different forms and compositions comprising the compounds are also described as well as methods of preparing the compounds.

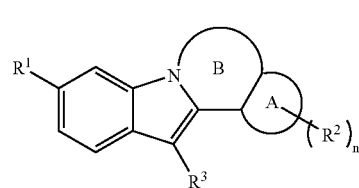

32 Claims, No Drawings

INHIBITORS OF HCV REPLICATION

CROSS-REFERENCE TO RELATED APPLICATIONS

This application claims the benefit of U.S. provisional application Ser. No. 60/608,932 filed Aug. 9, 2004 and U.S. provisional application Ser. No. 60/660,555 filed Mar. 11, 2005.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41–52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2–NS3 junction; the second one is a serine protease contained within the N-terminal region of NS3 (also referred to herein as NS3 protease) and mediates all the subsequent cleavages downstream of NS3, both in cis, at the NS3–NS4A cleavage site, and in trans, for the remaining NS4A–NS4B, NS4B–NS5A, NS5A–NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Presently, the most effective HCV therapy employs a combination of alpha-interferon and ribavirin, leading to sustained efficacy in 40% of patients (Poynard, T. et al. *Lancet* 1998, 352, 1426–1432). Recent clinical results demonstrate that pegylated alpha-interferon is superior to unmodified alpha-interferon as monotherapy (Zeuzem, S. et al. *N. Engl. J. Med.* 2000, 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

Among the compounds that have demonstrated efficacy in inhibiting HCV replication as selective HCV serine protease inhibitors are the peptide compounds disclosed in U.S. Pat. No. 6,323,180. NS5B polymerase inhibitors have also demonstrated activity. However, none of these compounds have, to date, progressed beyond clinical trials (De Clercq, E. *J. Clin. Virol.* 2001, 22, 73–89).

Compounds useful for treating HCV-infected patients are desired which selectively inhibit HCV viral replication. In particular, compounds which are effective to inhibit the function of the NS5B protein are desired. The HCV NS5B protein is described, for example, in "Structural Analysis of the Hepatitis C Virus RNA Polymerase in Complex with Ribonucleotides: S. Bressanelli, et al., *Journal of Virology*, April 2002, 3482–3492; and Defrancesco and Rice, *Clinics in Liver Disease* 2003, 7, 211–242.

DESCRIPTION OF INVENTION

The invention encompasses compounds of Formula I, including pharmaceutically acceptable salts and solvates thereof, compositions of these compounds, and use of the compounds in treating hepatitis C.

One aspect of the invention is a compound of formula (I)

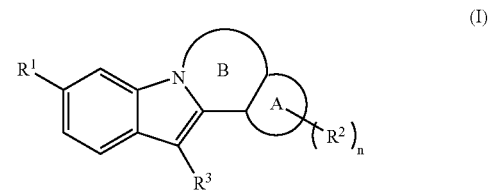

(I)

wherein n is 0, 1, 2, or 3;

A is a five- or six-membered aromatic ring optionally containing one or two heteroatoms independently selected from nitrogen, oxygen, and sulfur;

B is a five- to twelve-membered ring containing 0 or 1 double bonds and optionally containing one or two additional heteroatoms selected from nitrogen, oxygen, and sulfur; wherein said ring is optionally substituted with one, two, three, or four substituents independently selected from alkoxy, alkoxycarbonyl, alkyl, carboxy, cyano, cycloalkyl, halo, hydroxy, hydroxyalkyl, alkylaminoalkyl, dialkylaminoalkyl, $NR^4R^5$, $(NR^4R^5)$carbonyl, and oxo;

$R^1$ is selected from —C(O)$NR^4R^5$, —$CO_2R^4$, 5-tetrazolyl, cyano,

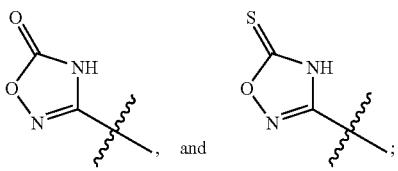, and each R² is independently selected from alkoxy, alkoxyalkyl, alkyl, alkylamino, amino, arylalkoxy, aryloxy, dialkylamino, halo, haloalkoxy, haloalkyl, hydroxy, and hydroxyalkyl;

R³ is a five- to seven-membered cycloalkyl ring;

R⁴ is selected from hydrogen, alkyl, hydroxyalkyl, aminoalkyl, (alkylamino)alkyl, (dialkylamino)alkyl, aryl, arylalkyl, and (NR⁶R⁷)alkyl;

R⁵ is selected from hydrogen, alkyl, hydroxyalkyl, aminoalkyl, (alkylamino)alkyl, (dialkylamino)alkyl, aryl, arylalkyl, (NR⁶R⁷)alkyl, alkylcarbonyl, arylcarbonyl, (NR⁶R⁷)carbonyl, —S(O)₂R⁸, —S(O)₂NR⁶R⁷,

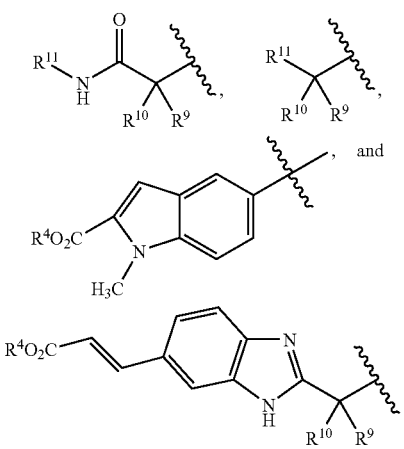

or NR⁴R⁵ taken together is pyrrolidinyl, piperidinyl, piperazinyl, homopiperidinyl, morpholinyl, or thiomorpholinyl and is substituted with 0–2 substituents selected from the group consisting of alkyl, hydroxy, amino, alkylamino, dialkylamino, pyrrolidinyl, piperidinyl, and pyridinyl;

R⁶ and R⁷ are independently selected from hydrogen and alkyl;

R⁸ is selected from alkyl, cycloalkyl, aryl, and heteroaryl;

R⁹ and R¹⁰ are independently selected from hydrogen and alkyl; or

R⁹ and R¹⁰, together with the carbon atom to which they are attached, form a four- to seven-membered saturated ring optionally containing 1 or 2 heteroatoms selected from nitrogen, oxygen, and sulfur, wherein said ring is optionally substituted with one or two substituents independently selected from alkoxycarbonyl, alkyl; and oxo; and R¹¹ is a five- or six-membered saturated, partially saturated, or aromatic ring containing 0, 1, 2, or 3 heteroatoms selected from nitrogen, oxygen, and sulfur, wherein said ring is optionally substituted with one or two substituents independently selected from alkoxycarbonylalkenyl, alkoxycarbonylalkyl, alkyl, aryl, carboxy, carboxyalkenyl, carboxyalkyl, and heteroaryl, wherein said aryl and heteroaryl are further optionally substituted with one or two substituents independently selected from alkoxycarbonyl, alkoxycarbonylalkenyl, alkoxycarbonylalkyl, carboxy carboxyalkenyl, carboxyalkyl, and hydroxy;

or a pharmaceutically acceptable salt or solvate thereof.

Another aspect of the invention is a compound of formula (I), or a pharmaceutically acceptable salt thereof, wherein A is selected from furyl, phenyl, and pyridinyl.

Another aspect of the invention is a compound of formula (I), or a pharmaceutically acceptable salt thereof, wherein B is a five- to nine-membered ring containing 0 or 1 double bonds and optionally containing one additional heteroatom selected from nitrogen and oxygen, wherein said ring is optionally substituted with one or two substituents independently selected from alkoxy, alkoxycarbonyl, carboxy, hydroxy, (NR⁴R⁵)carbonyl, and oxo.

Another aspect of the invention is a compound of formula (I), or a pharmaceutically acceptable salt thereof, wherein B is a seven-membered ring containing 0 or 1 double bonds and optionally containing one additional heteroatom selected from nitrogen and oxygen, wherein said ring is optionally substituted with one or two substituents independently selected from alkoxy, alkoxycarbonyl, carboxy, hydroxy, (NR⁴R⁵)carbonyl, and oxo.

Another aspect of the invention is a compound of formula (I), or a pharmaceutically acceptable salt thereof where R⁴ is selected from hydrogen, alkyl, hydroxyalkyl, aminoalkyl, (alkylamino)alkyl, (dialkylamino)alkyl, and (NR⁶R⁷)alkyl, R⁵ is selected from hydrogen, alkyl, hydroxyalkyl, aminoalkyl, (alkylamino)alkyl, (dialkylamino)alkyl, (NR⁶R⁷)alkyl, alkylcarbonyl, —S(O)₂R⁸, and —S(O)₂NR⁶R⁷, or NR⁴R⁵ taken together is pyrrolidinyl, piperidinyl, piperazinyl, homopiperidinyl, morpholinyl, or thiomorphblinyl and is substituted with 0–2 substituents selected from the group consisting of alkyl, hydroxy, amino, alkylamino, dialkylamino, pyrrolidinyl, piperidinyl, and pyridinyl.

Another aspect of the invention is a compound of formula (I), or a pharmaceutically acceptable salt thereof, wherein R¹ is selected from—C(O)NR⁴R⁵ and —CO₂R⁴.

Another aspect of the invention is a compound of formula (I), or a pharmaceutically acceptable salt thereof where R¹ is —C(O)NR⁴R⁵, R⁴ is hydrogen, and R⁵ is —S(O)₂R⁸ or —S(O)₂NR⁶R⁷.

Another aspect of the invention is a compound of formula (I), or a pharmaceutically acceptable salt thereof where wherein R¹ is —C(O)NR⁴R⁵, R⁴ is hydrogen, R⁵ is

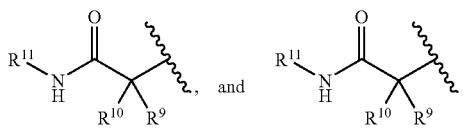

is selected from the group consisting of

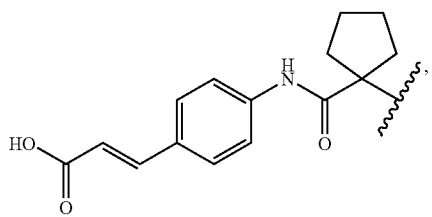

-continued

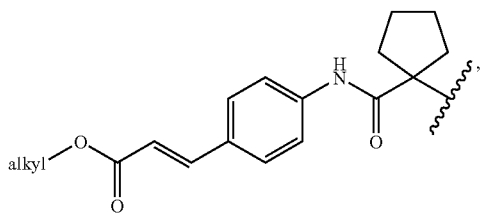

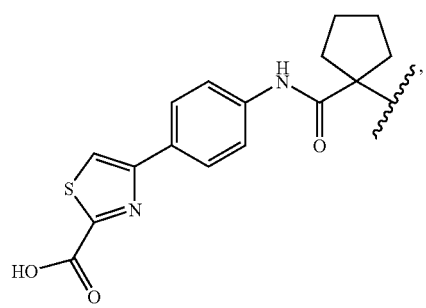

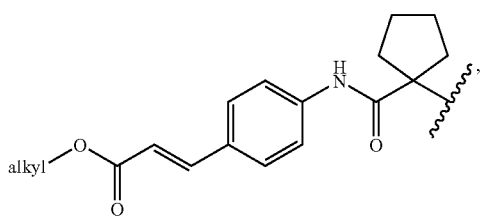

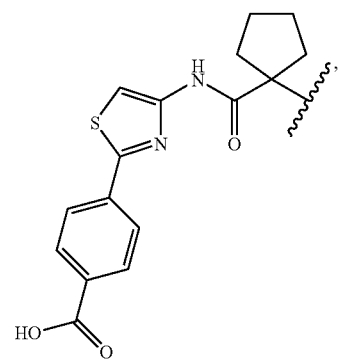

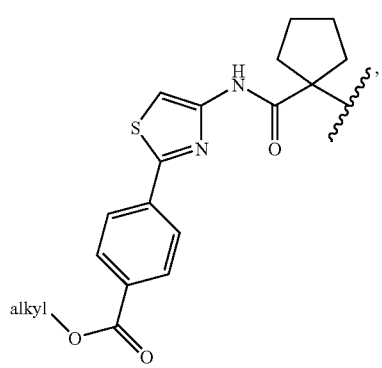

-continued

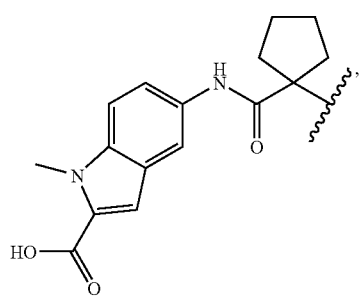

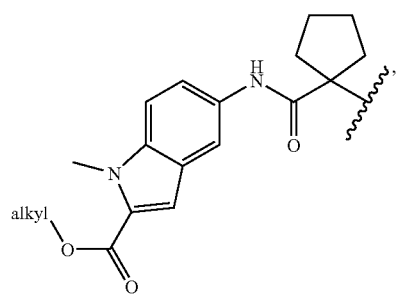

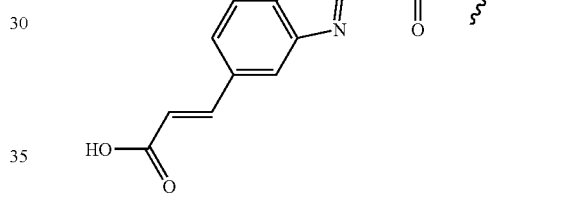

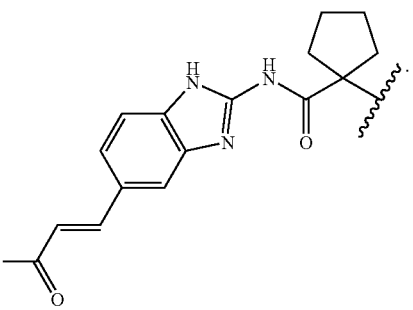

Another aspect of the invention is a compound of formula (I), or a pharmaceutically acceptable salt thereof where each $R^2$ is independently selected from halo, alkoxy, arylalkoxy, and hydroxy.

Another aspect of the invention is a compound of formula (I), or a pharmaceutically acceptable salt thereof where n is 0 or n is 1 and $R^2$ is halo or $C_{1-3}$alkoxy.

Another aspect of the invention is a compound of formula (I), or a pharmaceutically acceptable salt thereof, wherein each $R^2$ is independently selected from alkoxy, arylalkoxy, and hydroxy.

Another aspect of the invention is a compound of formula (I), or a pharmaceutically acceptable salt thereof, wherein $R^4$ is selected from hydrogen and alkyl; and
$R^5$ is selected from —S(O)$_2$R$^8$, —S(O)$_2$NR$^6$R$^7$,

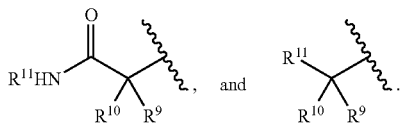

Another aspect of the invention is a compound of formula (II)

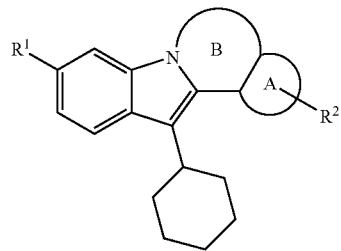

or a pharmaceutically acceptable salt thereof, wherein
n is 0 or 1;
A is selected from furyl, phenyl, and pyridinyl;
B is a five- to nine-membered ring containing 0 or 1 double bonds and optionally containing one additional heteroatom selected from nitrogen and oxygen; wherein said ring is optionally substituted with one or two substituents independently selected from alkoxy, alkoxycarbonyl, carboxy, hydroxy, (NR$^4$R$^5$)carbonyl, and oxo;
R$^1$ is selected from —C(O)NR$^4$R$^5$, and —CO$_2$R$^4$;
R$^2$ is selected from alkoxy, arylalkoxy, and hydroxy;
R$^4$ is selected from hydrogen, alkyl, hydroxyalkyl, aminoalkyl, (alkylamino)alkyl, (dialkylamino)alkyl, alkyl;
R$^5$ is selected from hydrogen, alkyl, hydroxyalkyl, aminoalkyl, (alkylamino)alkyl, (dialkylamino)alkyl, alkyl, —S(O)$_2$R$^8$, —S(O)$_2$NR$^6$R$^7$, or NR$^4$R$^5$ taken together is pyrrolidinyl, piperidinyl, piperazinyl, homopiperidinyl, morpholinyl, or thiomorpholinyl and is substituted with 0–2 substituents selected from the group consisting of alkyl, hydroxy, amino, alkylamino, dialkylamino, pyrrolidinyl, piperidinyl, and pyridinyl;
R$^6$ and R$^7$ are independently selected from hydrogen and alkyl;
R$^8$ is selected from aryl, cycloalkyl, and heteroaryl;
R$^9$ and R$^{10}$ are independently selected from hydrogen and alkyl; or
R$^9$ and R$^{10}$, together with the carbon atom to which they are attached, form a four- to seven-membered saturated ring optionally containing 1 or 2 heteroatoms selected from nitrogen, oxygen, and sulfur; and
R$^{11}$ is a five- or six-membered aromatic ring containing 0, 1, 2, or 3 heteroatoms selected from nitrogen, oxygen, and sulfur, wherein said ring is optionally substituted with one substituent independently selected from alkoxycarbonylalkenyl, alkoxycarbonylalkyl, aryl, carboxyalkenyl, and carboxyalkyl, wherein said aryl is further optionally substituted with one substituent independently selected from carboxy and carboxyalkenyl.

Another aspect of the invention is a compound selected from

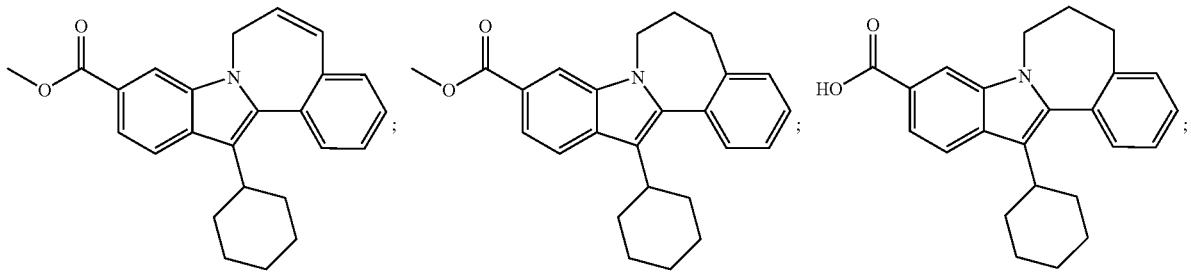

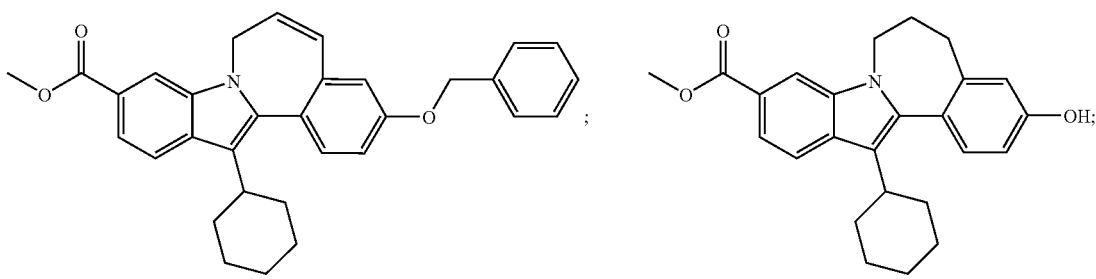

-continued
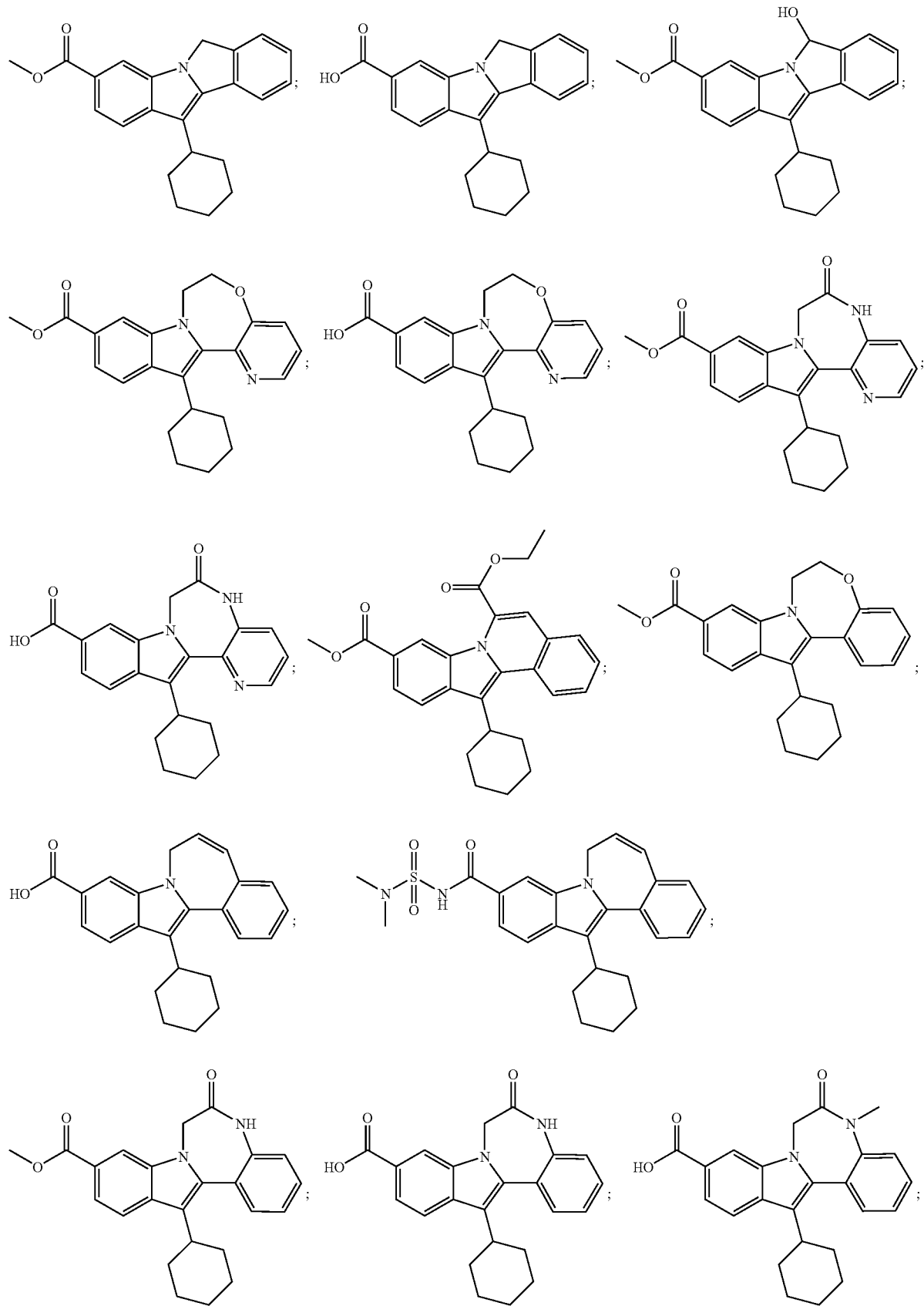

-continued
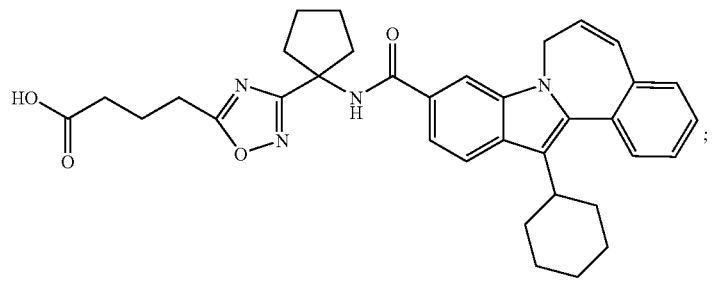
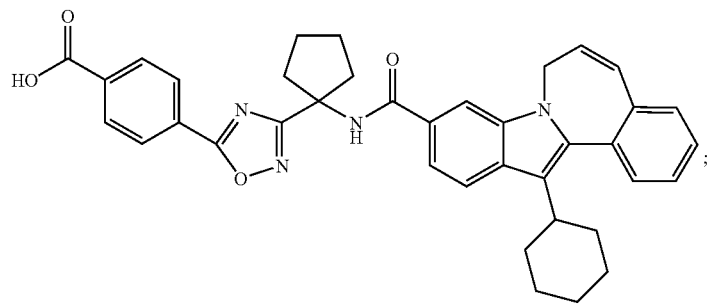
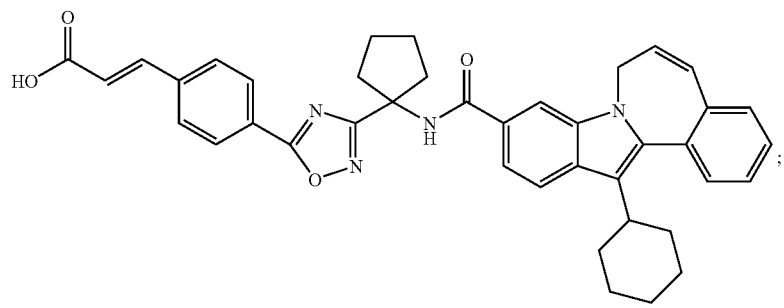
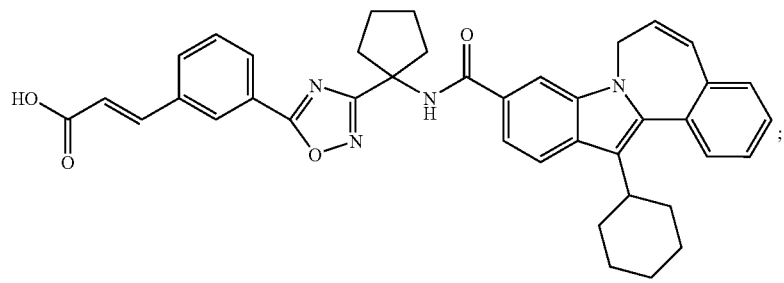
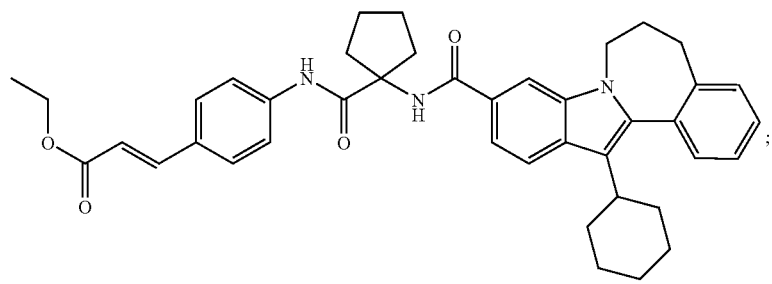

-continued
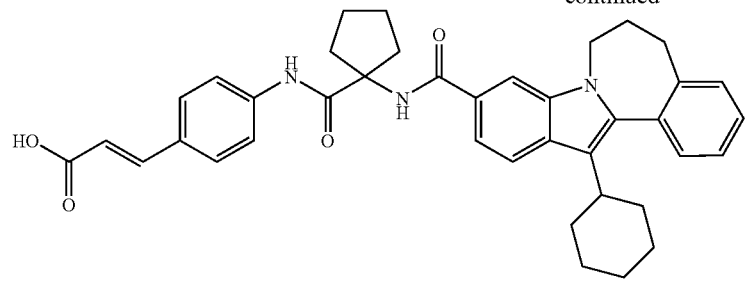
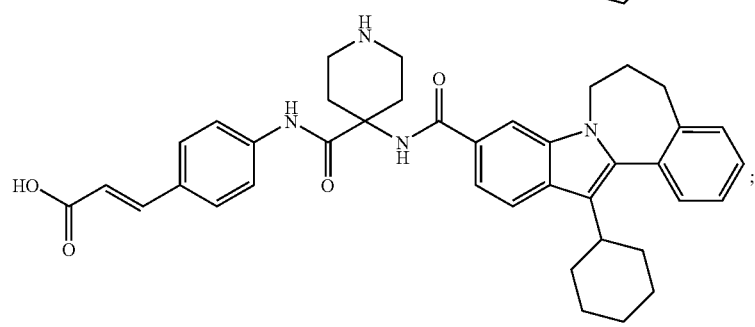
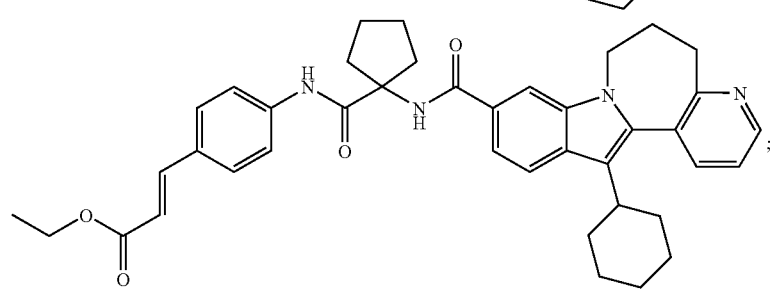
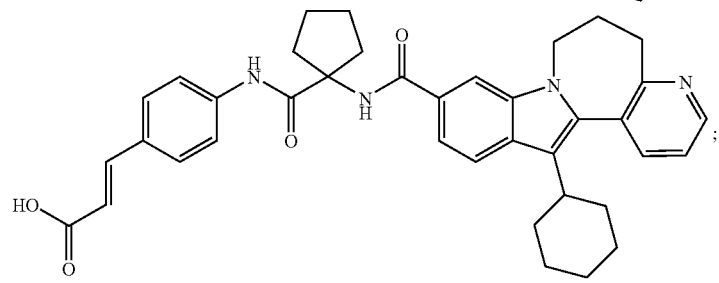
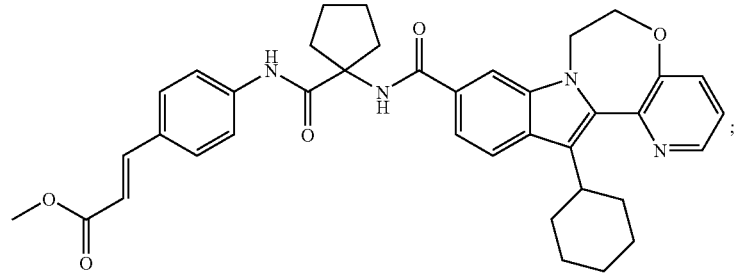
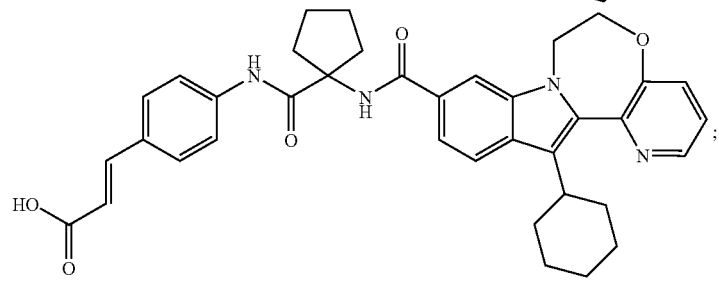

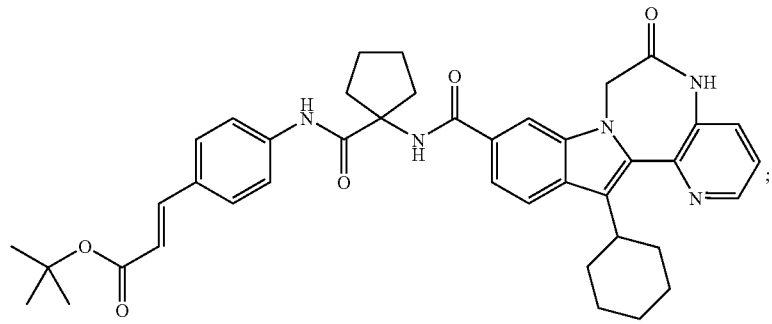
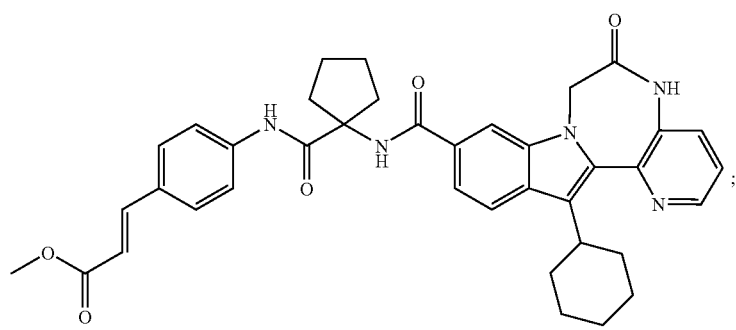
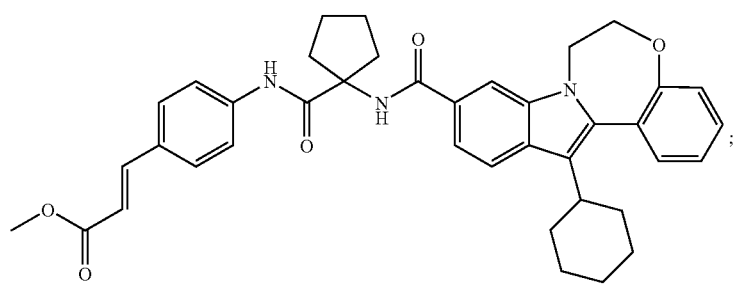
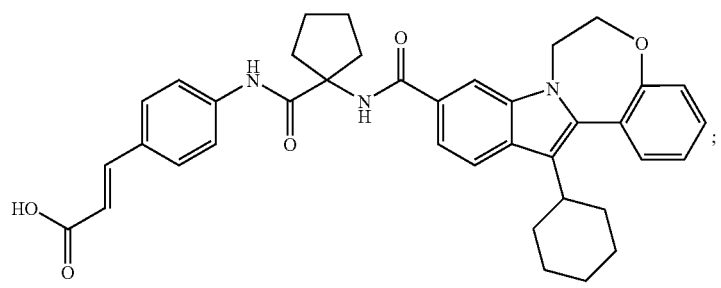
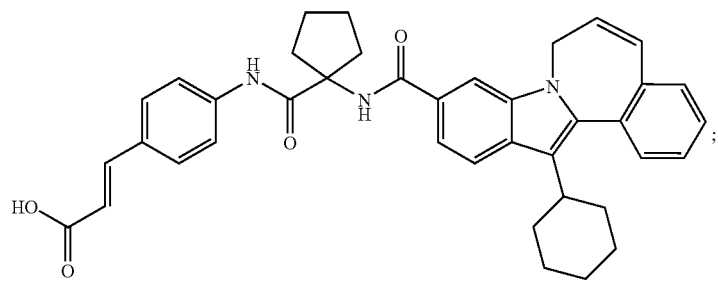

-continued
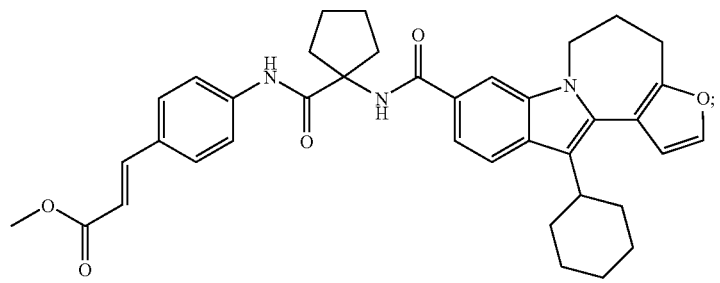
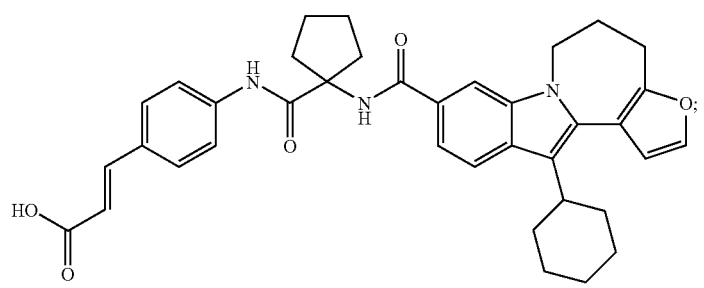
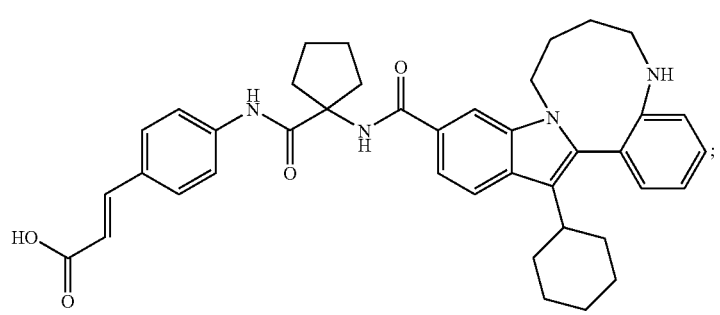
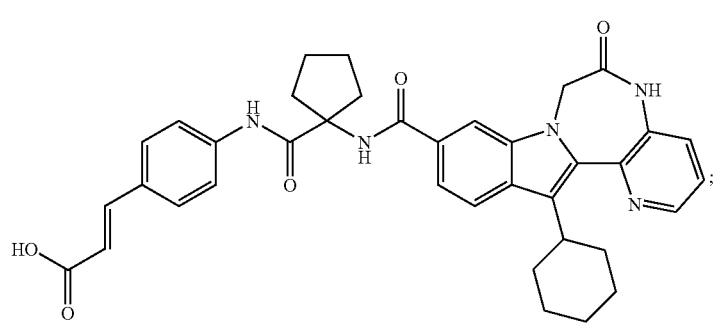
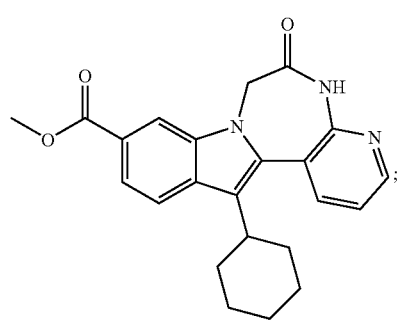
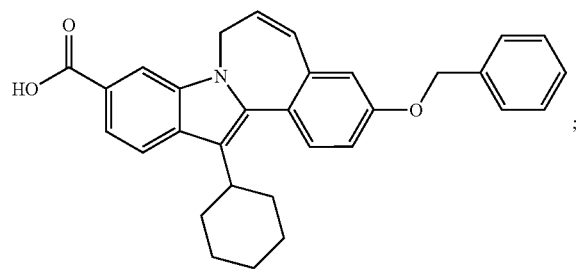

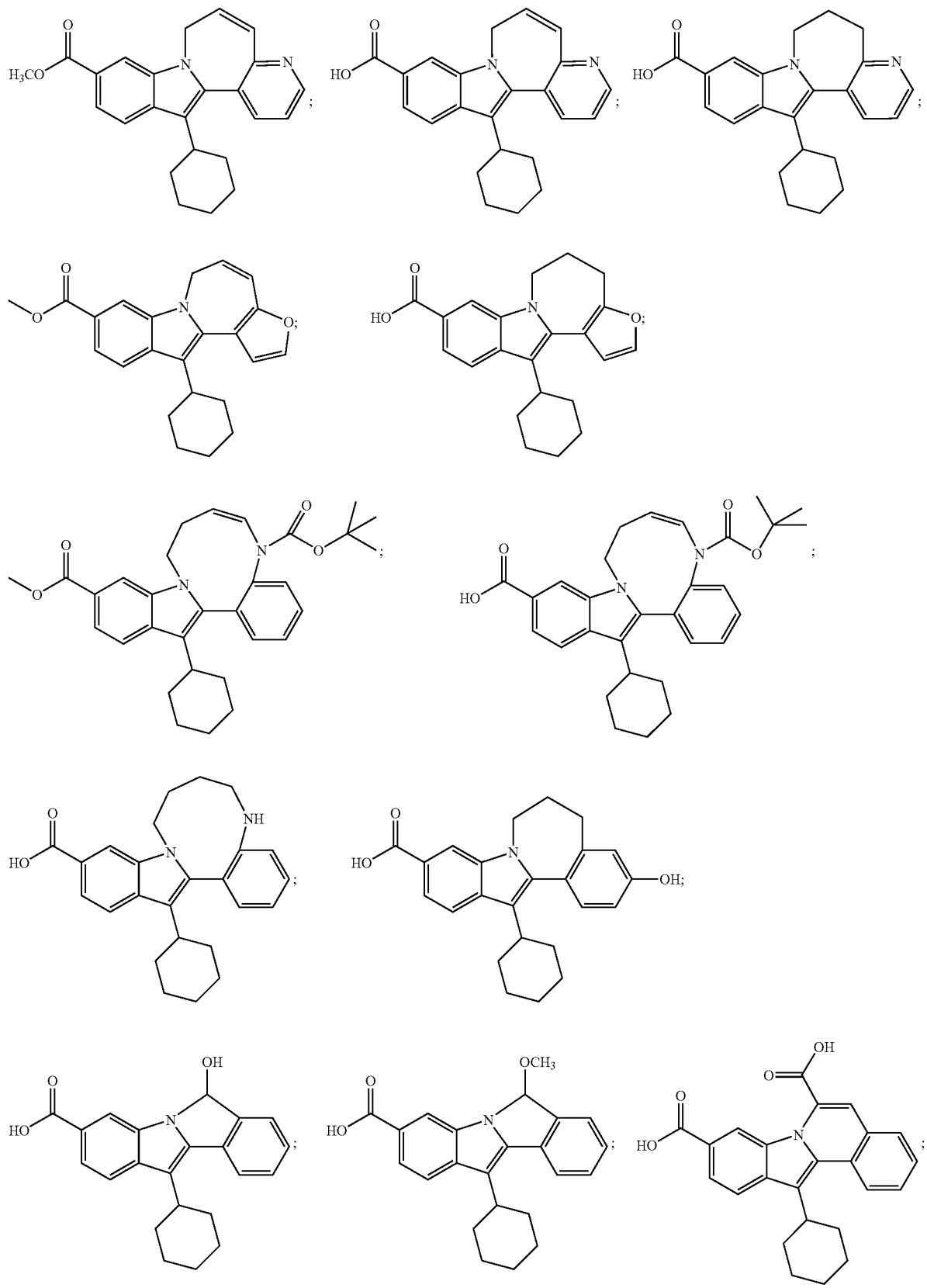

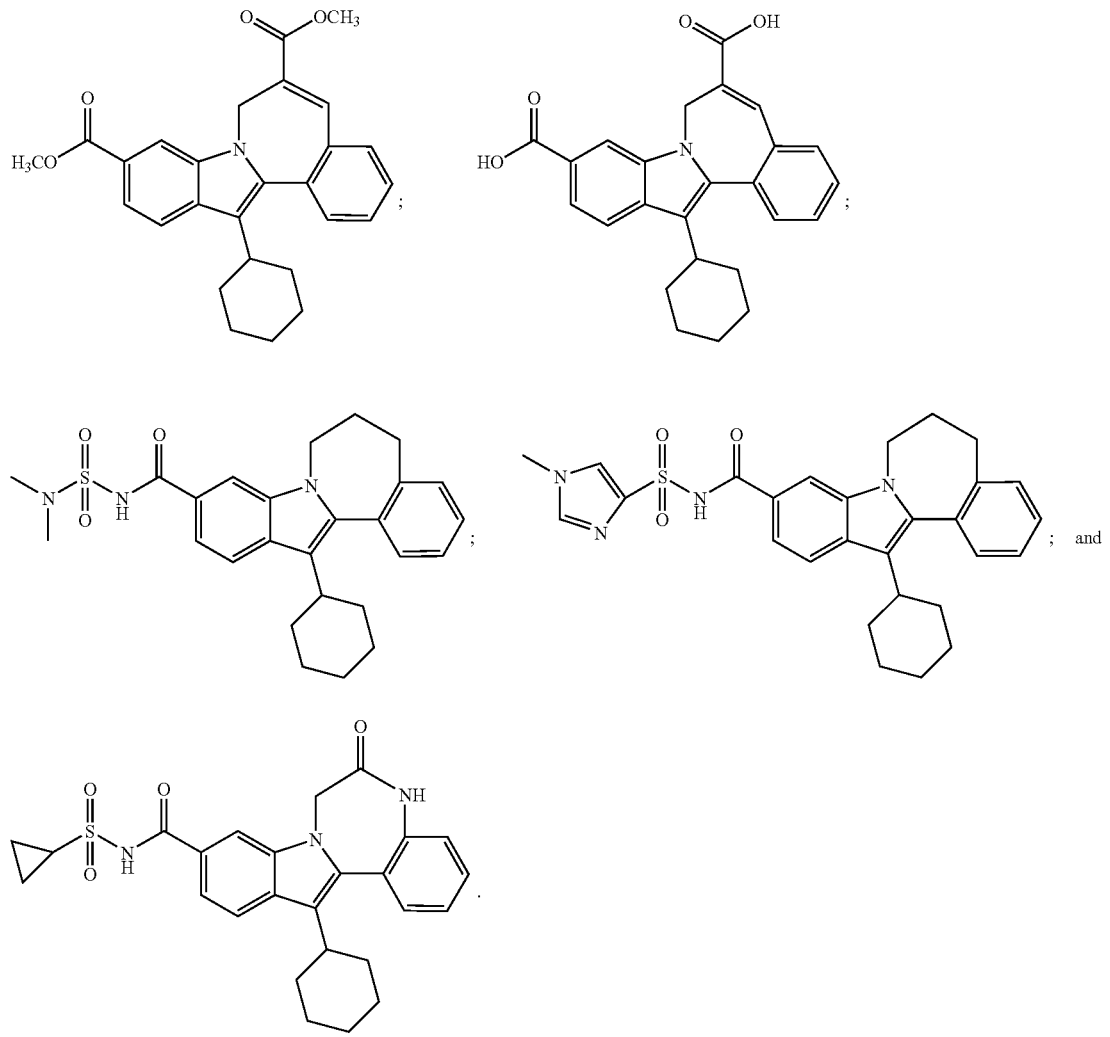
Another aspect of the invention is a compound selected from the group consisting of
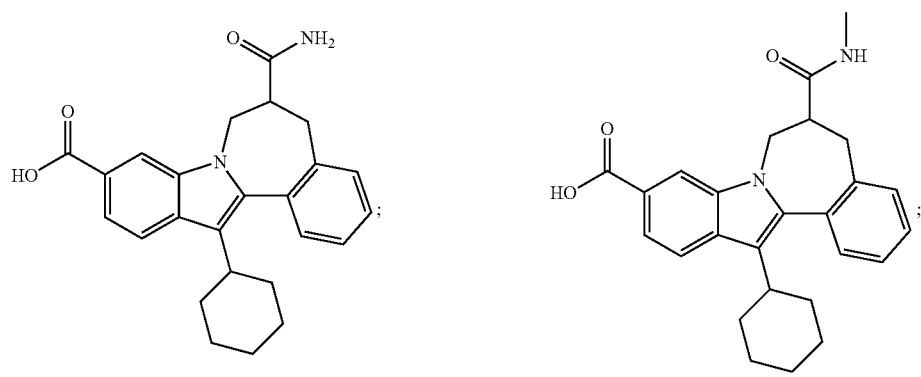

-continued
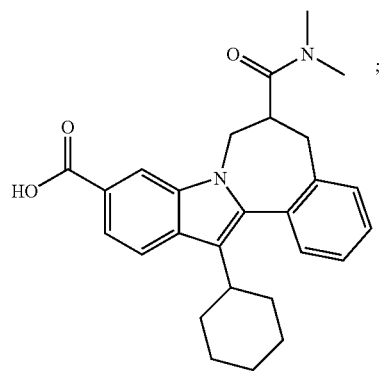 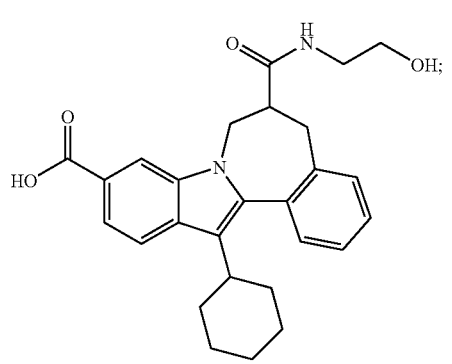
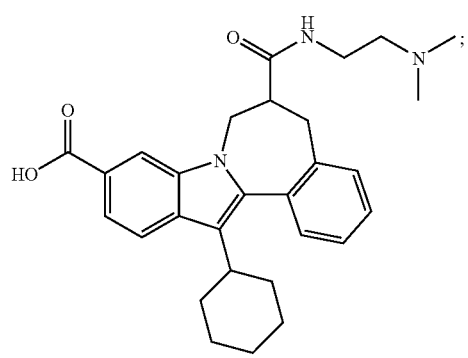 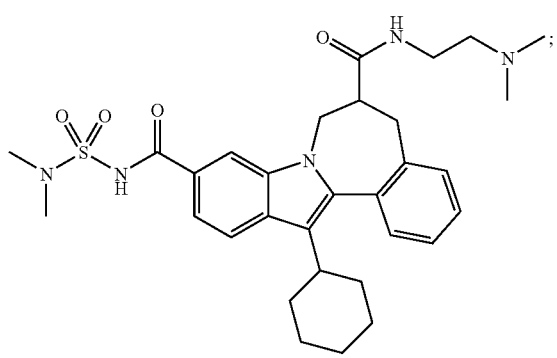
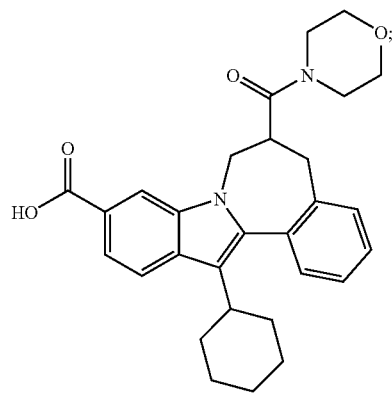 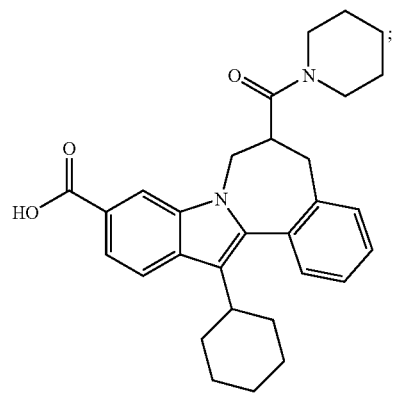
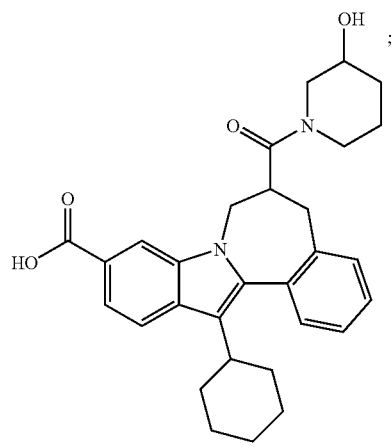 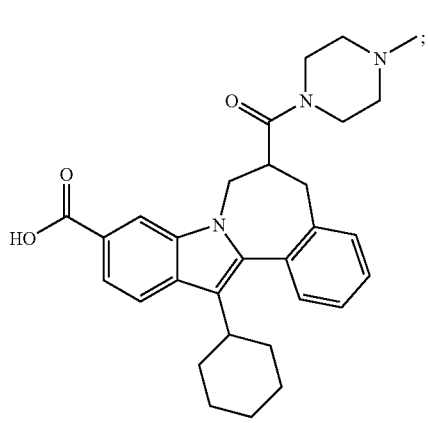

-continued
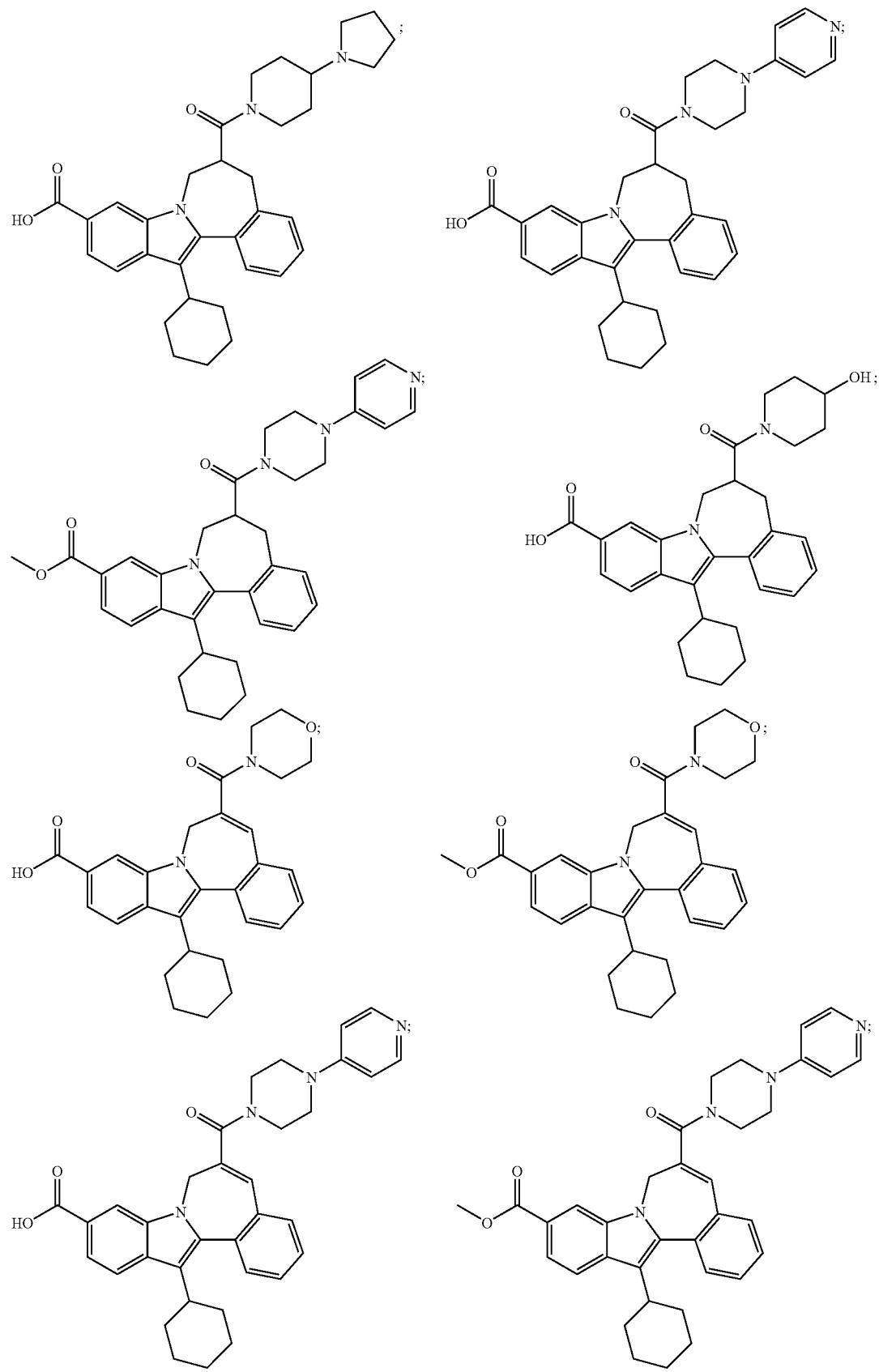

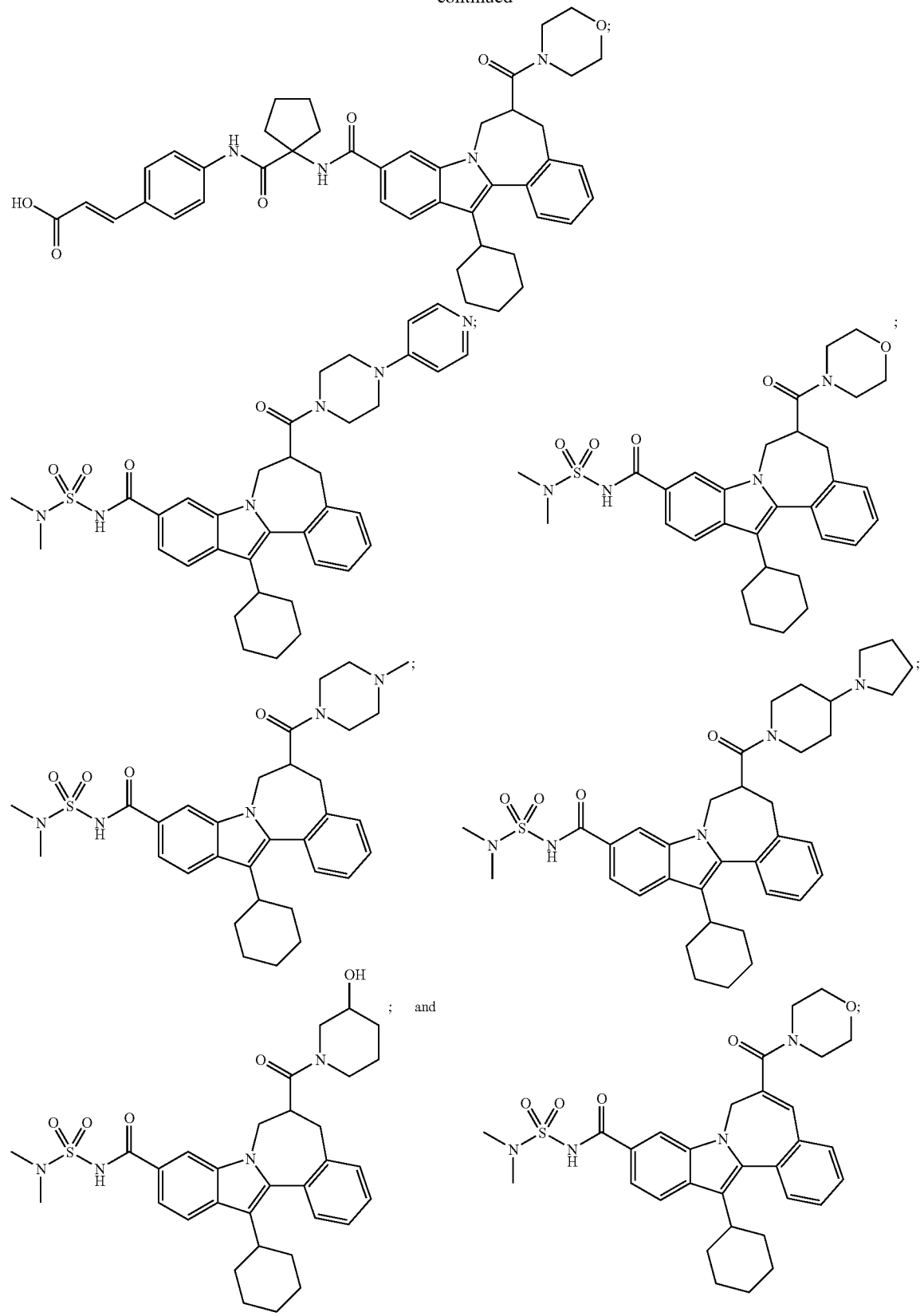
or a pharmaceutically acceptable salt or solvate thereof

As used in the present specification the following terms have the meanings indicated:

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms. Some examples of alkyl groups include, but are not limited to, methyl, ethyl, isopropyl, and tert-butyl.

The term "alkylamino," as used herein, refers to —NHR$^a$, wherein R$^a$ is an alkyl group.

The term "alkylcarbonyl," as used herein, refers to an alkyl group attached to the parent molecular moiety through a carbonyl group.

The term "amino," as used herein, refers to —NH$_2$.

The term "alkylaminoalkyl," as used herein, refers to an amino group substituted with an alkyl group and attached to the parent molecular moiety through a alkyl group.

The term "dialkylaminoalkyl," as used herein, refers to an amino group substituted with two alkyl groups and attached to the parent molecular moiety through a alkyl group.

The term "aminoalkyl," as used herein, refers to an amino group attached to the parent molecular moiety through a alkyl group.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present disclosure can be attached to the parent molecular moiety through any substitutable carbon atom in the group. Representative examples of aryl groups include, but are not limited to, anthracenyl, azulenyl, bicyclooctatrienyl, fluorenyl, indanyl, indenyl, naphthyl, phenyl, and tetrahydronaphthyl. The aryl groups of the present disclosure can be optionally substituted with one, two, three, four, or five substituents independently selected from the group consisting of alkoxy, alkyl, carboxy, cyano, halo, haloalkoxy, haloalkyl, hydroxy, nitro, and oxo.

The term "arylalkoxy," as used herein, refers to an aryl group attached to the parent molecular moiety through an alkoxy group.

The term "arylalkyl," as used herein, refers to an alkyl group substituted with one, two, or three aryl groups.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "carbonyl," as used herein, refers to —C(O)—.

The term "carboxy," as used herein, refers to —CO$_2$H.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, adamantyl, bicyclo[3,1,1]heptyl, cyclobutyl, cyclohexyl, cyclopentyl, and cyclopropyl.

The terms "halo," and "halogen," as used herein, refer to Br, Cl, F, or I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heteroaryl," as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkenyl group, as defined herein, a monocyclic cycloalkyl group, as defined herein, a monocyclic heterocyclyl group, as defined herein, or an additional monocyclic heteroaryl group; and tricyclic systems where a bicyclic system is fused to a phenyl group, a monocyclic cycloalkenyl group, as defined herein, a monocyclic cycloalkyl group, as defined herein, a heterocyclyl group, as defined herein, or an additional monocyclic heteroaryl group. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, cinnolinyl, dibenzofaranyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. The heteroaryl groups of the present disclosure can be optionally substituted with one, two, three, four, or five substituents independently selected from the group consisting of alkoxy, alkyl, carboxy, cyano, halo, haloalkoxy, haloalkyl, hydroxy, nitro, and oxo.

The term "hydroxy," as used herein, refers to —OH.

The term "hydroxyalkyl," as used herein, refers to an alkyl group substituted with one, two, or three hydroxy groups.

The term "(NR$^6$R$^7$)alkyl," refers to an alkyl group substituted with one, two, or three —NR$^6$R$^7$ groups.

The term "(NR$^4$R$^5$)carbonyl," as used herein, refers to an —NR$^4$R$^5$ group attached to the parent molecular moiety through a carbonyl group.

The term "(NR$^6$R$^7$)carbonyl," as used herein, refers to an —NR$^6$R$^7$ group attached to the parent molecular moiety through a carbonyl group.

The term "oxo," as used herein, refers to =O.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The invention encompasses various geometric isomers and mixtures thereof resulting from the arrangement of substituents around these carbon-carbon double bonds. It should be understood that the disclosure encompasses both isomeric forms, and mixtures thereof, which possess the ability to inhibit the NS5B polymerase of HCV.

The term "E" represents higher order substituents on opposite sides of the carbon-carbon double bond, and the term "Z" represents higher order substituents on the same side of the carbon-carbon double bond.

Some of the compounds of the invention possess asymmetric carbon atoms, for example the compound illustrated below. The invention includes all stereoisomeric forms, including enantiomers and diastereomers. Stereoisomeric mixtures of the compounds and related intermediates can be separated into individual isomers according to methods commonly known in the art.

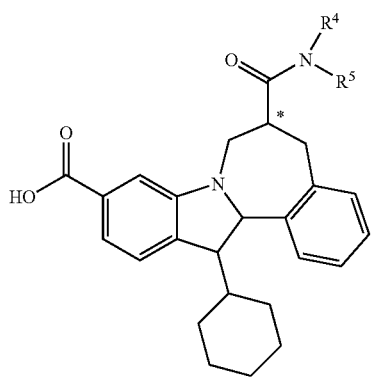

The term "compounds of the disclosure", and equivalent expressions, are meant to embrace compounds of Formula (I), stereoisomers, enantiomers, diastereomers, and pharmaceutically acceptable salts or solvates thereof. Similarly, references to intermediates are meant to embrace their salts and solvates where the context so permits.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. In other instances, the solvate will consist of adventitious solvent. The term "solvate" encompasses both solution-phase and isolable solvates. Exemplary solvates include hydrates, ethanolates, methanolates, and the like.

Some of the compounds of the present disclosure can exist as salts. The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Some pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Synthetic Methods

The compounds and processes of the present disclosure will be better understood in connection with the following synthetic schemes which illustrate some methods by which the compounds of the disclosure may be prepared. The following methods set forth below are provided for illustrative purposes and are not intended to limit the scope of the present disclosure. Variations of the reactions, for example choices of reactants, solvents, temperatures, and the like, are known to those skilled in the art. Variables in the structural formulas refered to in the synthetic methods section and the specific embodiments section are for illustrative purposes only and are distinct from and should not be confused with the variables in the claims and the description of the invention section. Starting materials can be obtained from commercial sources or prepared by literature methods. In addition, it may be necessary to introduce or remove protecting groups in order to carry certain substituents through the indicated reaction conditions. A compendium of protecting groups which may be useful, together with reaction conditions for their introduction and removal may be found in Greene, T. W.; Wuts, P. G. M. *Protective Groups in Organic Synthesis*, Third Edition; Wiley: N.Y., 1999.

It will be readily apparent to one of ordinary skill in the art that the compounds defined above can be synthesized by substitution of the appropriate reactants and agents in the syntheses shown below. It will also be readily apparent to one of ordinary skill in the art that the selective protection and deprotection steps, as well as the order of the steps themselves, can be carried out in varying order, depending on the nature of the variables to successfully complete the syntheses below.

Abbreviations used within the schemes and generally follow conventions used in the art. Some examples are as follows: THF for tetrahydrofuran; DMF for N,N-dimethylformamide; RCM for ring-closing methasis; Boc for tert-butoxycarbonyl; TFA for trifluoracetic acid; DMA for N,N-dimethylacetamide; PPh$_3$ for triphenylphosphine; OAc for acetate; Me for methyl; COD (or cod) for 1,5-cyclooctadiene; dtbpy for 4,4'-di-tert-butyl-2,2'-bipyridine; dba for dibenzylideneacetone; Xantphos for 4,5-bis(diphenylphosphino)-9,9-dimethylxanthine; aq for aqueous; EtOH for ethanol; MeOH for methanol; TBTU for 2-(1H-benzotriazole-1-yl)-1,1,3,3-tetramethyluronium tetrafluroborate; DMSO for dimethylsulfoxide; HATU for O-(7-azabenzotriazol-1-yl)-N,N,N',N'-tetramethyluronium hexafluorophosphate; EEDQ for 2-ethoxy-1-ethoxycarbonyl-1,2-dihydroquinoline; WSC for 1-[3-(dimethylamino)propyl]-3-ethylcarbodiimide hydrochloride; DMAP for 4-dimethylaminopyridine; n-Bu for n-butyl; BEMP for 2-tert-butylimino-2-diethylamino-1,3-dimethylperhydro-1,3,2-diazaphosphorine, polymer-bound; DIPEA for diisopropylethylamine; and TEA for triethylamine.

Method A describes a general method of preparing certain compounds of formula (I) (Schemes 1–3).

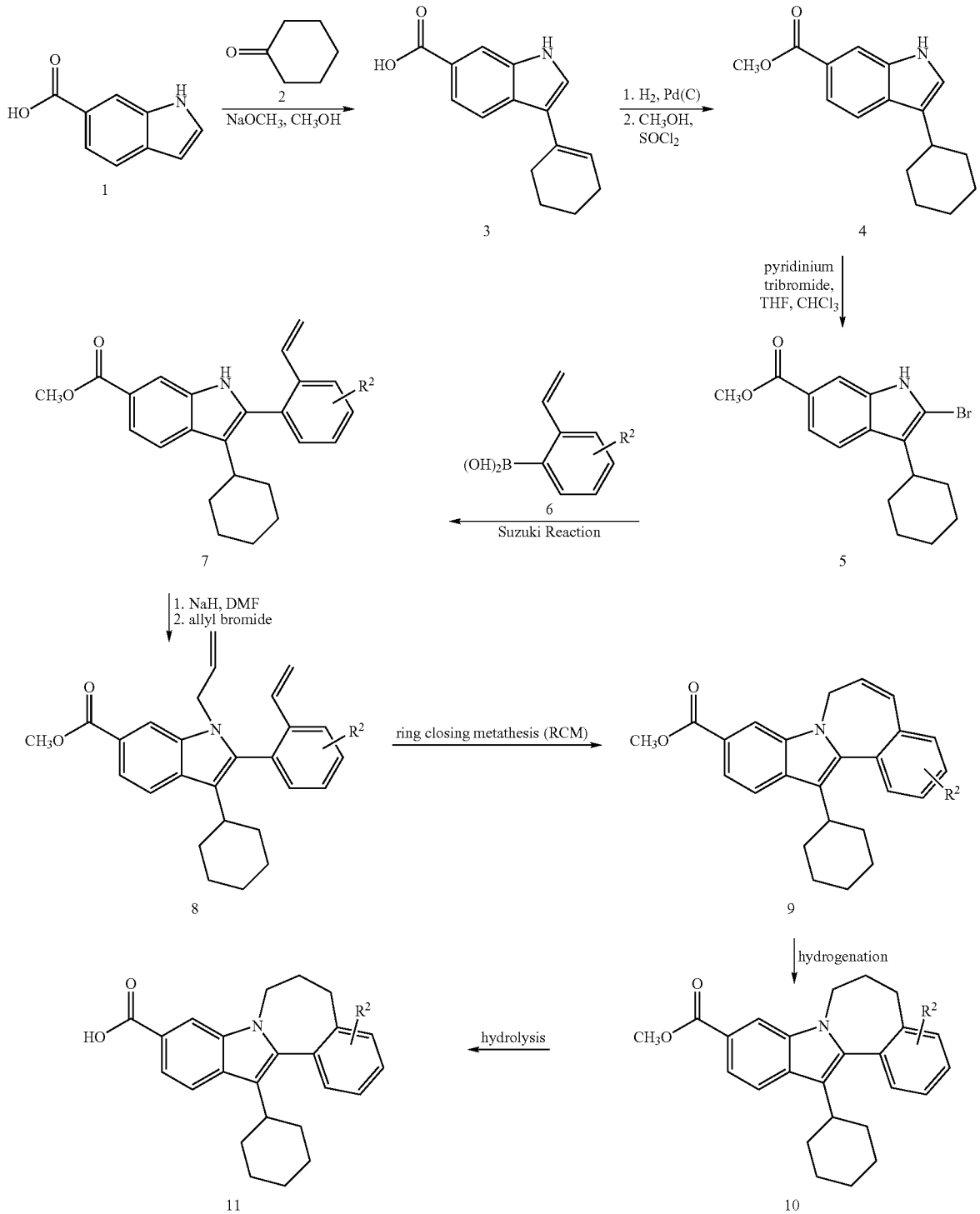

As illustrated in Schemes 1–3, many compounds of Formula I can be synthesized utilizing a ring closing metathesis (RCM) reaction as the primary carbon-carbon bond forming reaction. As shown in Scheme 1, indole 7 can be alkylated with allyl bromide to provide diene 8 which can undergo RCM in the presence of an appropriate RCM catalyst (such as Grubb's second generation catalyst) to provide benzazepine 9. The alkylation step the allyl bromide can be replaced by other terminal olefins. For example, Scheme 2 shows the alkylation of indole 7 ($R^2=H$) with methyl-, or tert-butyl-2-(bromomethyl)acrylate (12) (R=methyl, or tert-butyl) which can provide indoles 13. Alkylation of 7 ($R^2=H$) with bromomethylacrylic acid (12, R=H) can provide 13 (R=H) which can afford benzyl ester 13 (R=benzyl) after alkylation with benzyl bromide in the presence of cesium carbonate. RCM of the indole esters 13 can provide the fused compounds 14. In these examples the 7-membered ring is functionalized with an ester moiety.

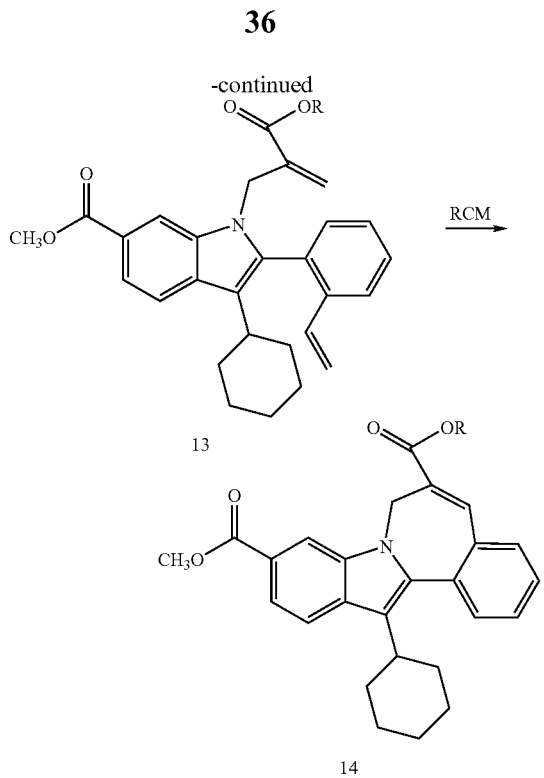

The ester moieties on the ring can be selectively converted to the carboxylic acid 14a using methodlogy known in the art. For example, as shown in Scheme 2a, partial hydrogenation of the benzyl ester 14 (R=benzyl), selective base-catalyzed hydrolysis of the dimethyl ester 14 (R=methyl), and cleavage of the tert-butyl ester 14 (R=tert-butyl) with trifluoroacetic acid can provide acid 14a. Further reduction of 14a with hydrogen and palladium can give saturated acid 14b.

Scheme 2

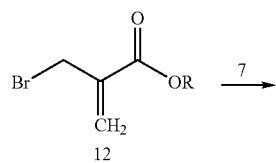

Scheme 2a

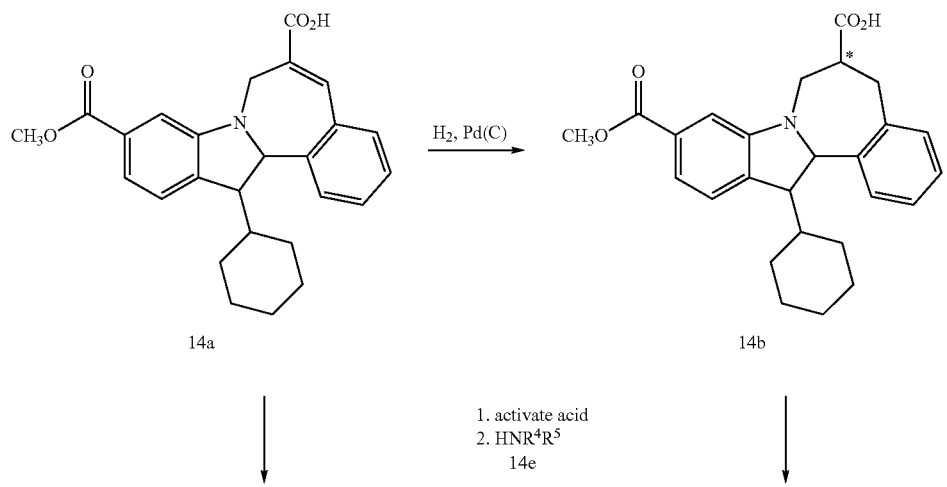

1. activate acid
2. $HNR^4R^5$
14e

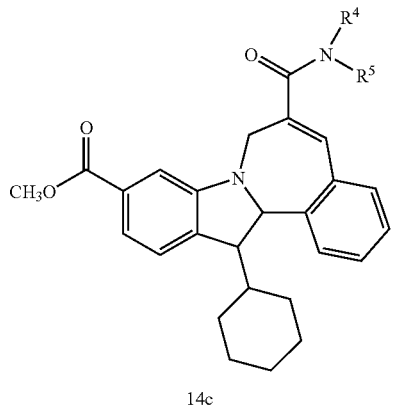

14c

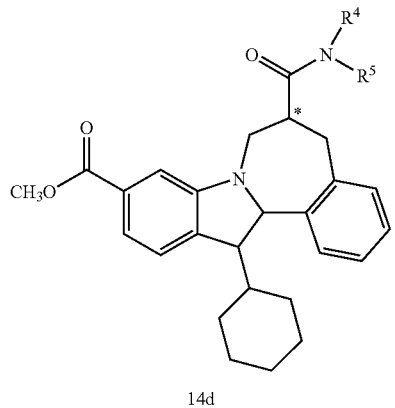

14d

In another aspect, carboxylic acids 14a and 14b can be transformed into their respective amides 14c and 14d. The acids can be activated for the coupling reaction by conversion to their acid chlorides with, for example, oxalyl chloride or thionyl chloride. Alternatively, TBTU (2-(1H-benzotriazole-1-yl)-1,1,3,3-tetramethyluronium tetrafluroborate) is used to effect the coupling of the acids with the amines (14e). DMF, DMSO, and THF can be used as solvents. Additonal examples of peptide coupling reagents are described after Scheme 9. Base-catalyzed hydrolysis of the methyl esters of 14c and 14d can afford acids 14f and 14g. These compounds can be further elaborated as shown in Scheme 9 to provide additional compounds of formula I.

-continued

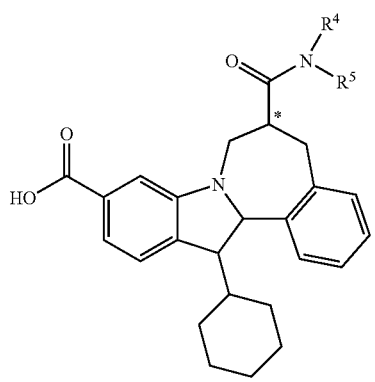

14g

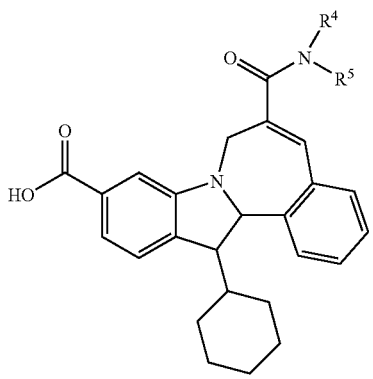

14f

As noted in Scheme 2a, compounds 14g can possess an asymmetric center (*). Racemic mixtures can be resolved into their enantiomers by HPLC chromatography using a chiral column. Additionally, diasteroisomeric salts of 14g can be formed with optically active organic amines. These salts are usually separated by fractional recrystallization. Both the racemates and enantiomers inhibit the HCV polymerase and are an integral part of this invention.

An additional example, shown in Scheme 3, illustrates the construction of a functionalized nine-membered core (18). Palladium-mediated cross-coupling of bromide 5 (prepared by the method shown in Scheme 1) with protected boronic acid 15 can provide indole 16. Simultaneous alkylation of the indole and protected amine can provide 17. RCM of 17 subsequently yields 18 from which the core structures 19 and 20 are obtained after removal of the Boc group and hydrogenolysis, respectively.

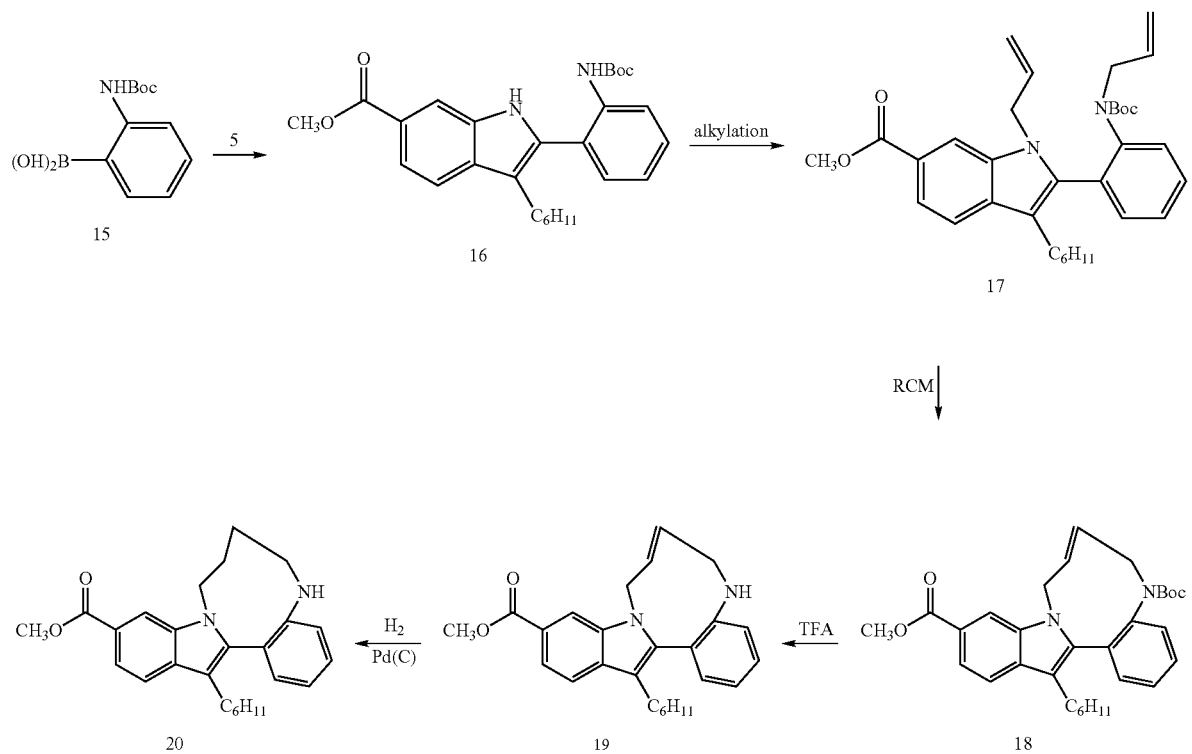

Numerous boronic acids and their pinacolatoborane equivalents are either available commercially or readily synthesized (see, for example, *J. Org. Chem.* 2000, 65, 164 and *Tetrahedron Lett.*, 1997, 38 (19), 3447–3450), allowing for the preparation of analogs using this procedure.

Method B provides an alternative to the RCM reaction method of preparing compounds of formula (I) (Schemes 4–5).

As shown in Scheme 4, the bridged indole cores can also be synthesized from indole 4 (prepared by the method shown in Scheme 1) by utilizing palladium-mediated chemistry (Heck reaction). The explicit synthesis of 10 ($R^2$=H, structure shown in Scheme 1) from intermediate 4 (prepared by the method described in Scheme 1) is illustrated.

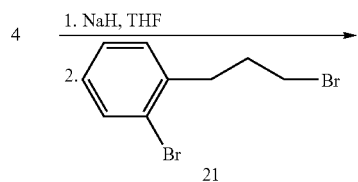

-continued

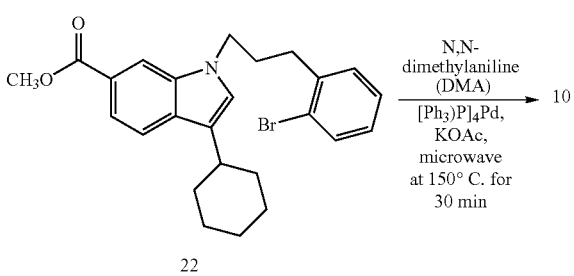

This methodology is also applicable for the synthesis of many of the heterocyclic cores of the present disclosure as illustrated in Scheme 5. Alkylation of indole 4 (prepared by the method shown in Scheme 1) with 2-benzyloxy-1-bromoethane can provide 24. The benzyl protecting group can be removed by hydrogenolysis, and the resulting alcohol 25 can be coupled with 2-bromo-3-pyridinol (26) under Mitsunobu conditions (known to those of ordinary skill in the art) to provide 27 which can be cyclized in the presence of catalytic palladium (0) to provide fused heterocycle 28 which can be hydrolyzed to provide acid 29.

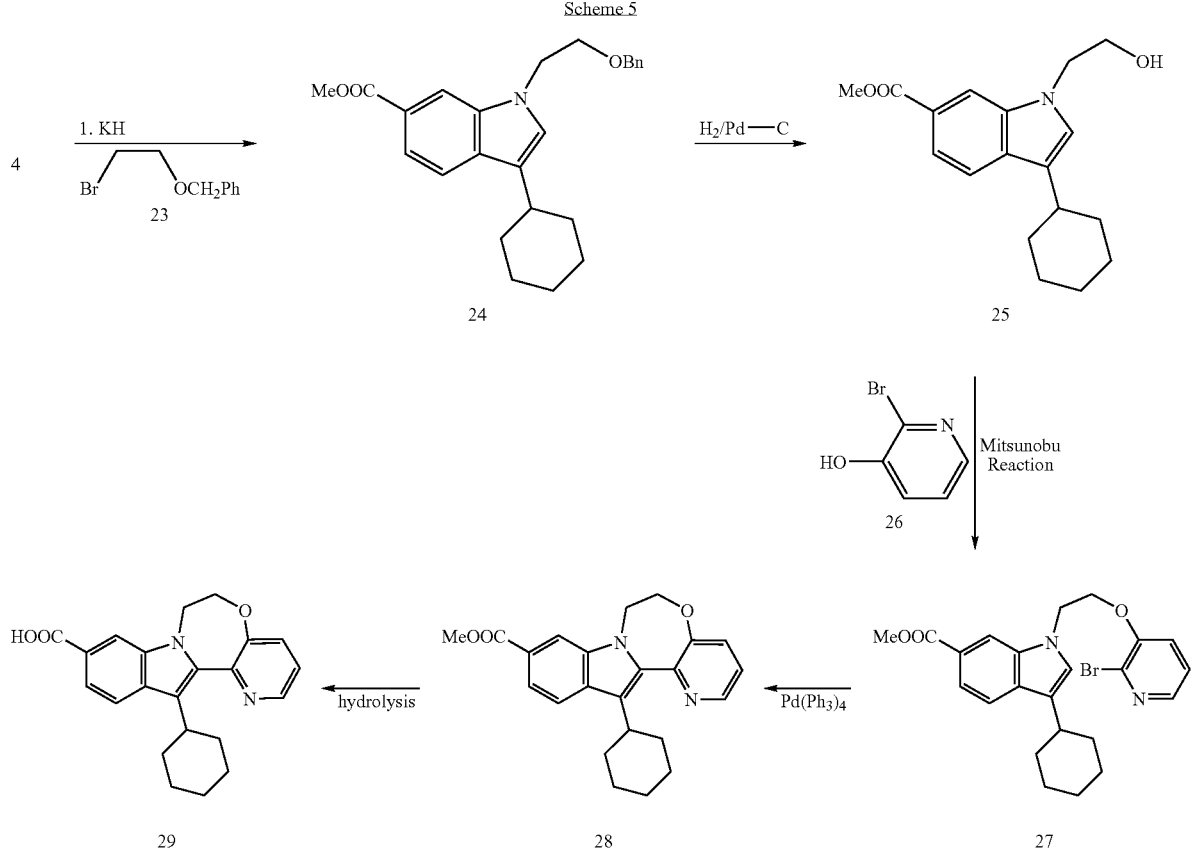
Method C describes the synthesis of intermediate 33 and its utility for the synthesis of various compounds of formula (I) compounds (Scheme 6).
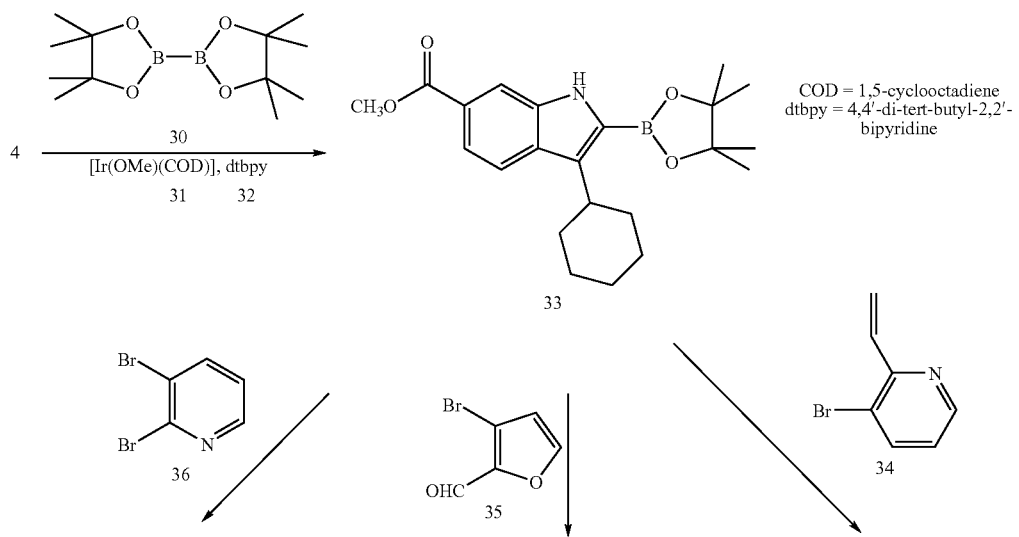

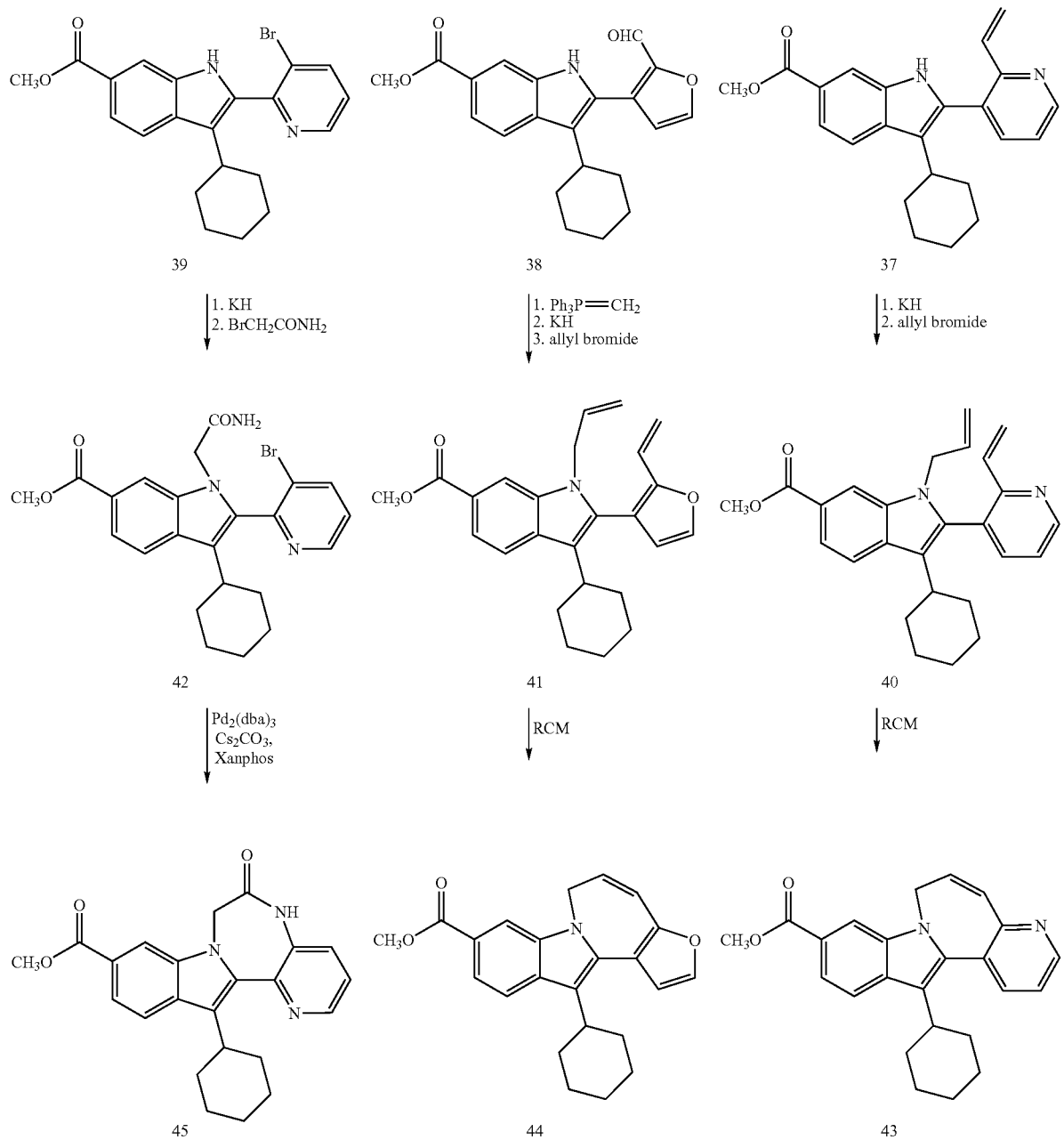

Indole 4 (prepared by the method shown in Scheme 1) can be borylated with bis(pinacolato)diboron (30) in the presence of an iridium catalyst (31) according to the methodology of Ishiyama (see, for example, *Angew. Chem. Int. Ed.* 2002, 41(16), 3056 and *Chem. Comm.* 2003, 2924). Boronate 33 can be coupled with bromoheteroarenes 34, 35, and 36. This cross-coupling is not limited to bromoarenes, but can carried out with aryl and heteroaryl triflates, iodides, and chlorides as well.

Using an adaptation of the methodology described in *Organic Letters*, 2000, 2(8), 1101–1104, intramolecular cyclization of the primary amide 42 provides lactam 45.

Dienes 41 and 40 can be subjected to RCM as described above to provide compounds 44 and 43, respectively.

The ester groups in 43, 44, and 45 can be hydrolyzed to their respective acids which can be transformed to the amides described in the present disclosure. The unconjugated double bond in compounds 44 and 43 can be hydrogenated to the corresponding saturated analogs using conditions known to those in the art.

Method D describes the synthesis of compounds of formula (I) using an intramolecular Aldol reaction to form the bridge (Scheme 7).

Scheme 7

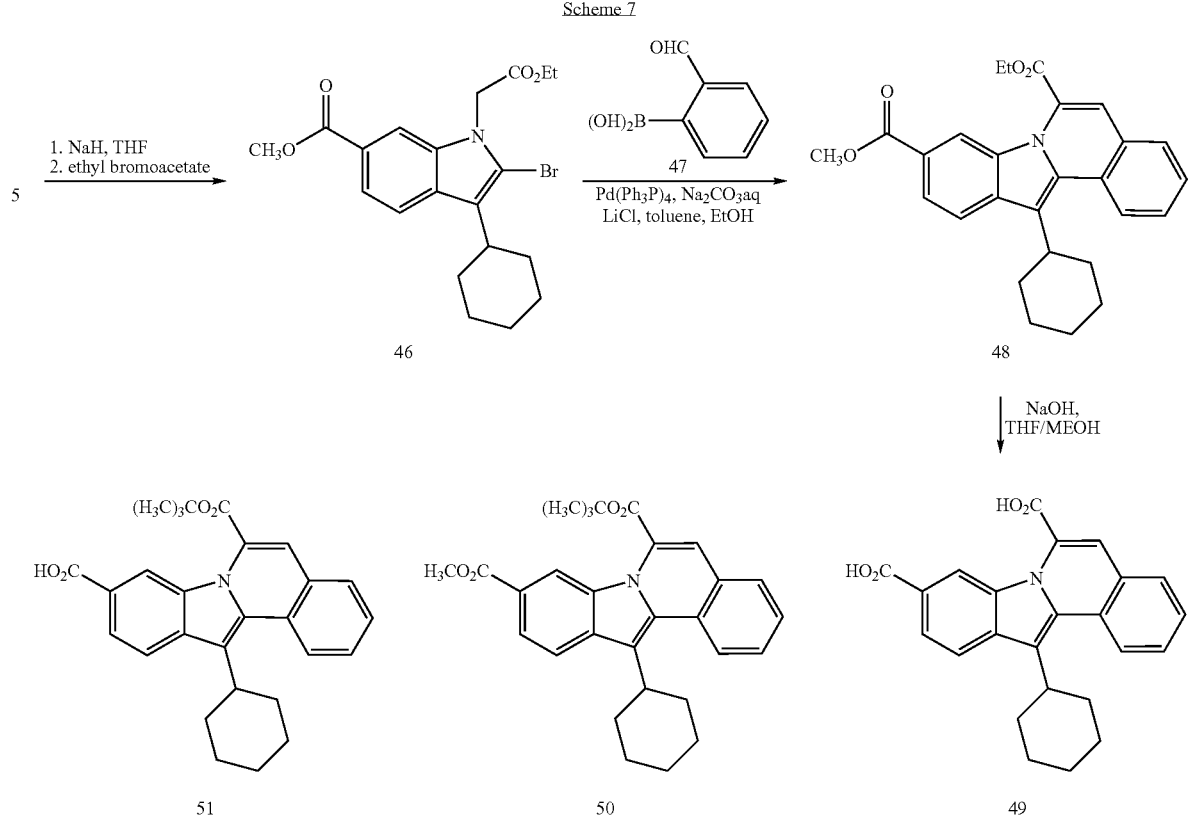

Intermediate 5 (prepared by the method described in Scheme 1) can be allylated with ethyl bromoacetate to give 46. Under prolonged refluxing the Suzuki product from the cross coupling of 46 and 47 can undergo cyclization via an Aldol reaction to provide diester 48. In an analogous manner, utilization of tert-butyl bromacetate in the reaction sequence can afford 50 in which the acid functionalities are differentially protected. Hydrolysis of diester 48 can provide diacid 49. Alternatively, selective hydrolysis of the methyl ester in 50 can provide 51 which can be elaborated to provide additional compounds of formula (I).

Method E shows an alternative for the construction of compounds of formula (I) containing an ether bridge (Scheme 8).

Scheme 8

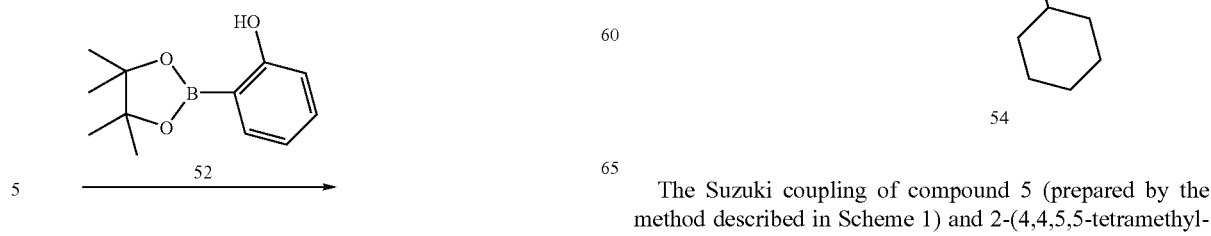

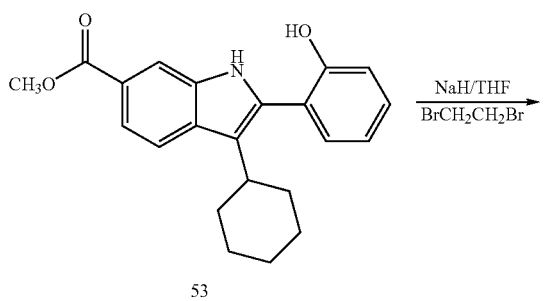

The Suzuki coupling of compound 5 (prepared by the method described in Scheme 1) and 2-(4,4,5,5-tetramethyl- 1,3,2-dioxaborolan-2-yl)phenol (52) can provide indole 53 which can be alkylated with 1,3-dibromoethane to provide the ether bridged indole 54.

Method F provides a method for preparing compounds of formula (I) where the carboxylic acid moieties of the core structures are transformed into substituted amides (Scheme 9).

HATU (O—(7-azabenzotriazol-1-yl)-N,N,N',N'-tetramethyluronium hexafluorophosphate), EEDQ (2-ethoxy-1-ethoxycarbonyl-1,2-dihydroquinoline), and the like. A mixed anhydride of acid 60 is an additional example of an activated carboxylic acid which is used advantageously. Examples of protecting groups for the carboxylic acid moieties include methyl, ethyl, allyl, benzyl, and tert-butyl esters. Represen-

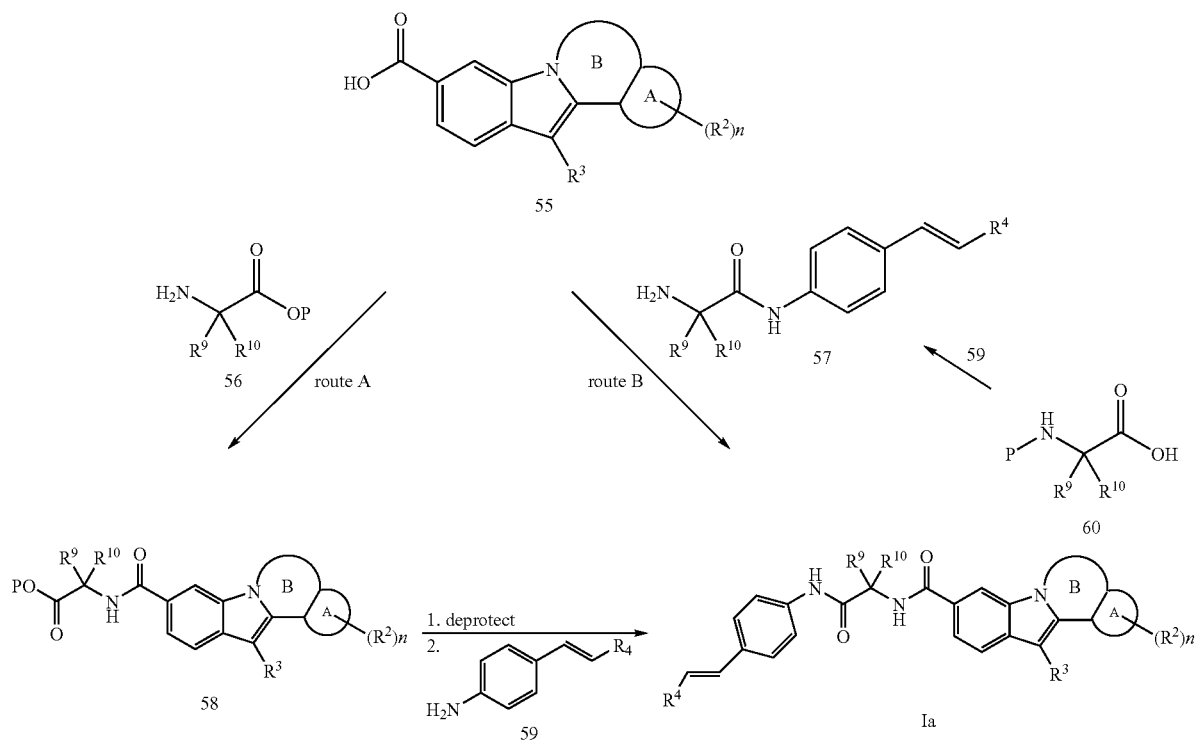

Scheme 9

Scheme 9 shows the general methodology used to synthesize compounds of formula (Ia) wherein $R^2$, $R^3$, $R^4$, $R^5$, $R^9$, and $R^{10}$ have been previously defined. Optionally a core carboxylic acid (55) is suitably activated and then coupled with either carboxy protected amino acid 56 or amide 57 to provide either protected intermediate 58 or compound Ia, respectively. In path A the carboxylic acid protecting group of 58 is removed and the resulting acid is coupled with amine 59 to provide Ia. The path chosen is most often at the discretion of the experimentalist and both paths have been utilized to provide the identical formula (Ia) compounds. The intermediate 57 is synthesized from the coupling of N-protected amino acid 60 and amine 59. The nitrogen protecting group is subsequently removed to provide 57.

The synthetic sequences in this scheme are examples of peptide bond formation and the sequential manipulation of protecting groups. The art is rich in these methodologies (see, for example, The Practice of Peptide Synthesis, M. Bodanszky and A. Bodanszky, Springer-Verlag, 1984, and Tetrahedron 2004, 60, 2447–2467. TBTU (2-(1H-benzotriazole-1-yl)-1,1,3,3-tetramethyluronium tetrafluroborate) is one coupling reagent used for the coupling of 55 with either 56 or 57. Examples of solvents include dimethyl sulfoxide (DMSO), N,N-dimethyl formamide (DMF), and tetrahydrofuran (THF). Additional coupling reagents for the synthesis of compounds of formula (I) and the intermediates include tative amino protecting groups include Boc (benzyloxycarbonyl) and Fmoc (9-fluorenylmethoxycarbonyl).

The general Scheme was developed using protected amino acids 56a and 56b. Replacement of either 56a or 56b with protected amino acids 56c–56e can provide formula (Ia) compounds which incorporate these amino acids.

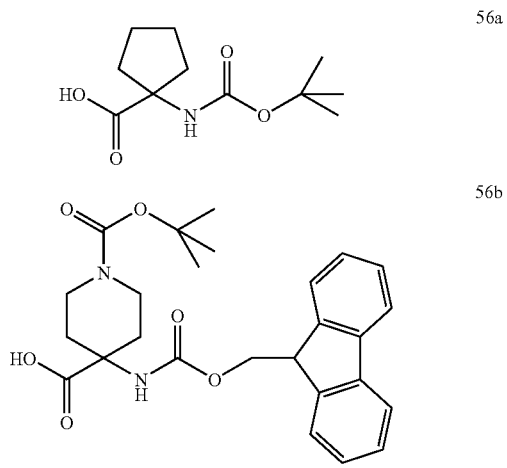

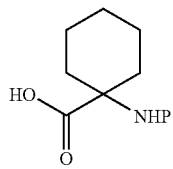
56c

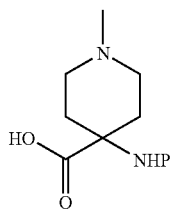
56d

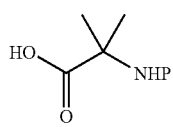
56e

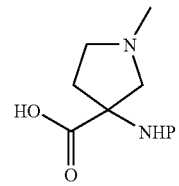
56d

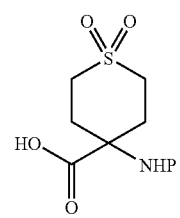
56e

Compounds of formula Ib–Io are also within the scope of the present disclosure. Replacement of the amino cinnamate 59 with heterocyclic variants, substituted amino heterocyles, or bicyclic cinnamic acid bioisosteres will provide these compounds. These disclosed structures are for illustrative purposes only and are not intented to limit the scope of the present disclosure.

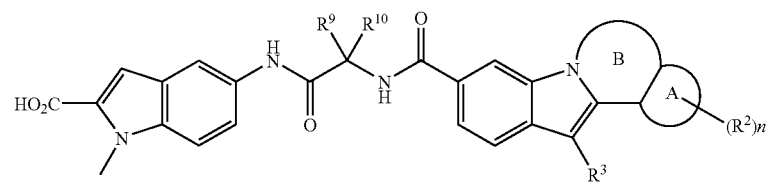
Ib

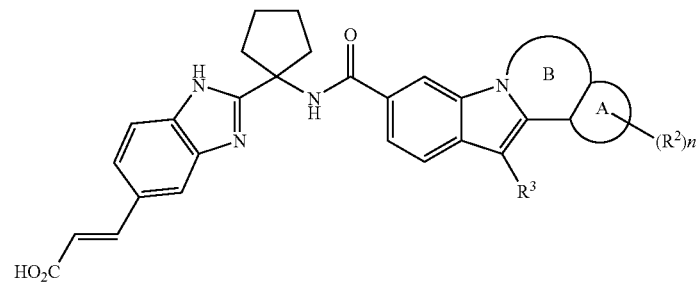
Ic

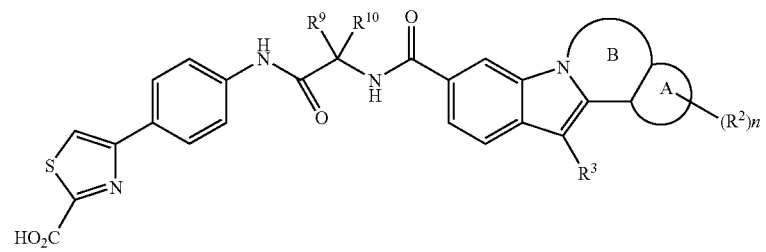
Id

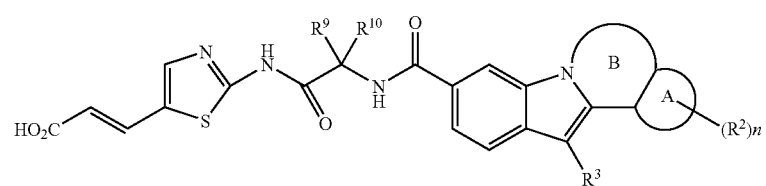
Ie

-continued
If
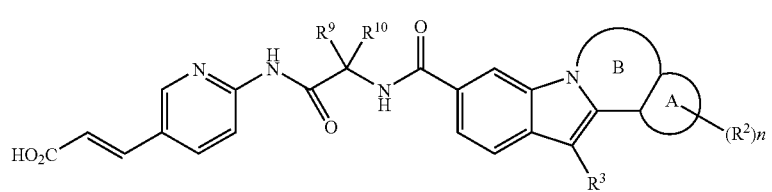
Ig
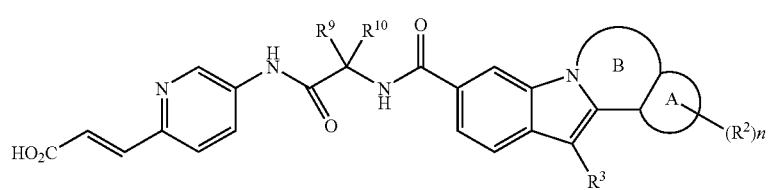
Ih
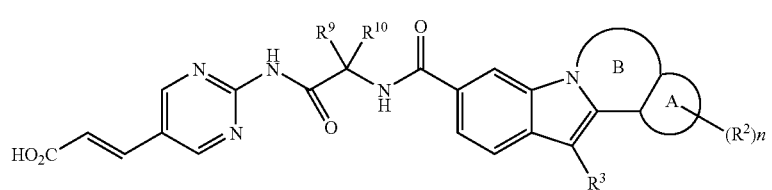
Ii
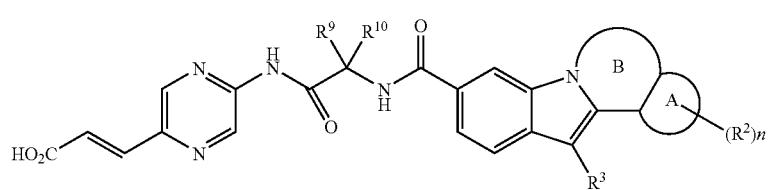
Ij
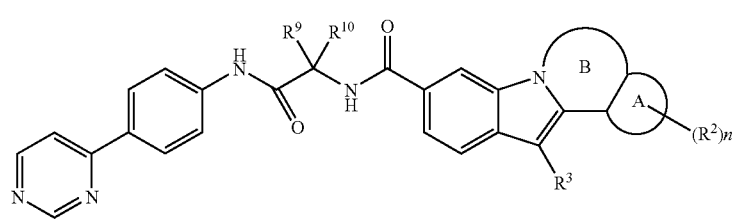
Ik
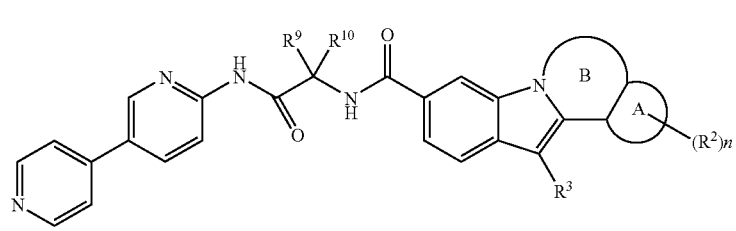
Il
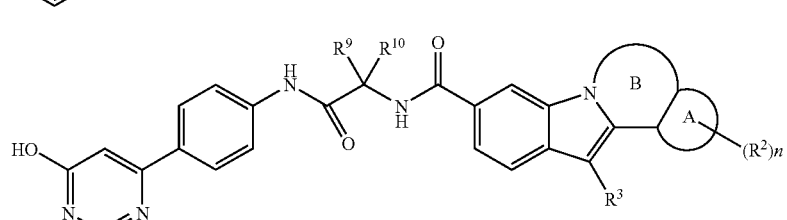
Im
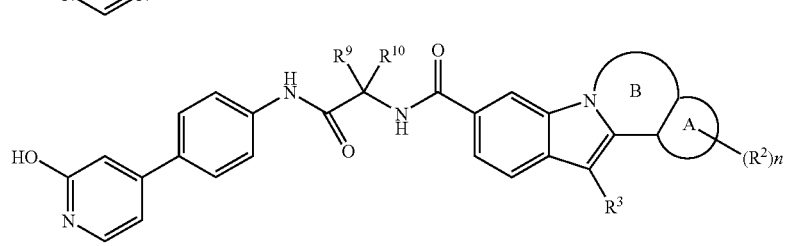

In

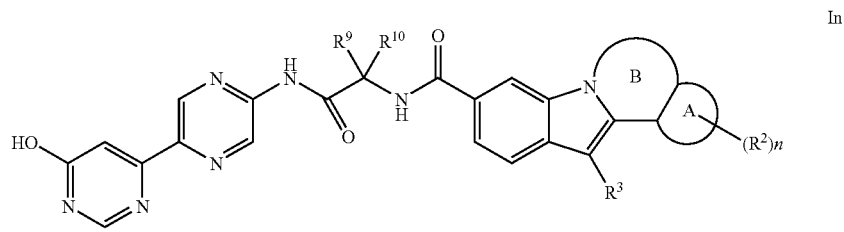

Io

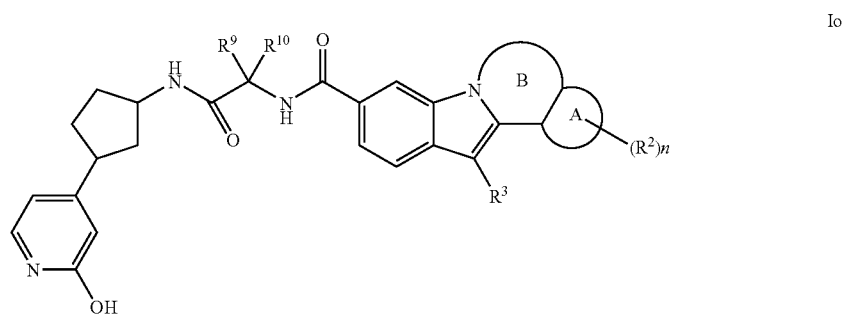

Method G is descriptive for the synthesis of a subset of the formula (I) compounds (I$_{2a}$) and is exemplified in Scheme 10.

Scheme 10

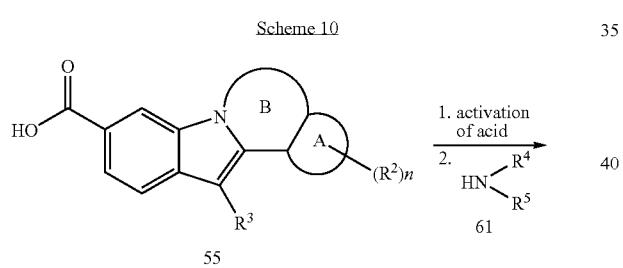

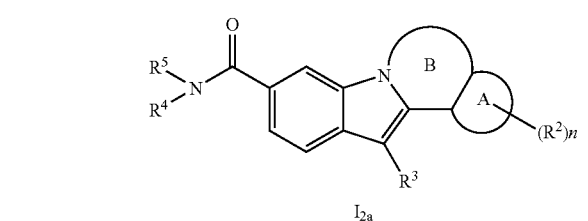

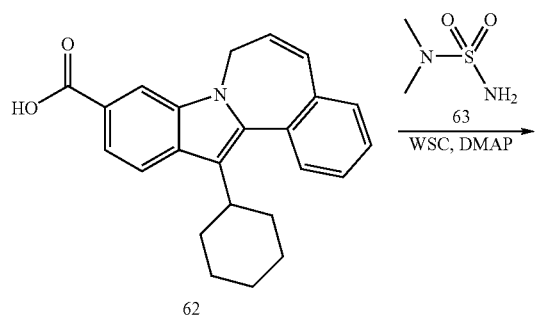

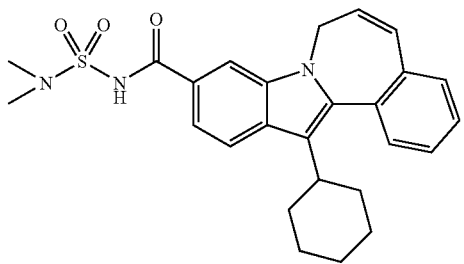

Scheme 10 shows a general route for the synthesis of compounds of formula (I) where R$^4$ and R$^5$ have been previously defined. The general method is explicitly illustrated for the synthesis of 64 in which carboxylic acid 62 is activated with the water soluble carbodiimide (WSC) 1-[3-(dimethylamino)propyl]-3-ethylcarbodiimide hydrochloride. A solution of the activated acid is coupled in DMF-dichloromethane with sulfonamide 63 in the presence of DMAP (4-dimethylaminopyridine) and diisopropylethylamine to provide acylsulfonamide 64. The coupling can be done in a microwave reactor at about 160° C. for about ten minutes. Alternative procedures for activation of the acids 55 include formation of the acid chloride or imidazole.

Acylsulfonamides such as 64 are acidic and form salts with alkali metal hydroxides. These salts have enhanced solubilities in aqueous media.

Scheme 11

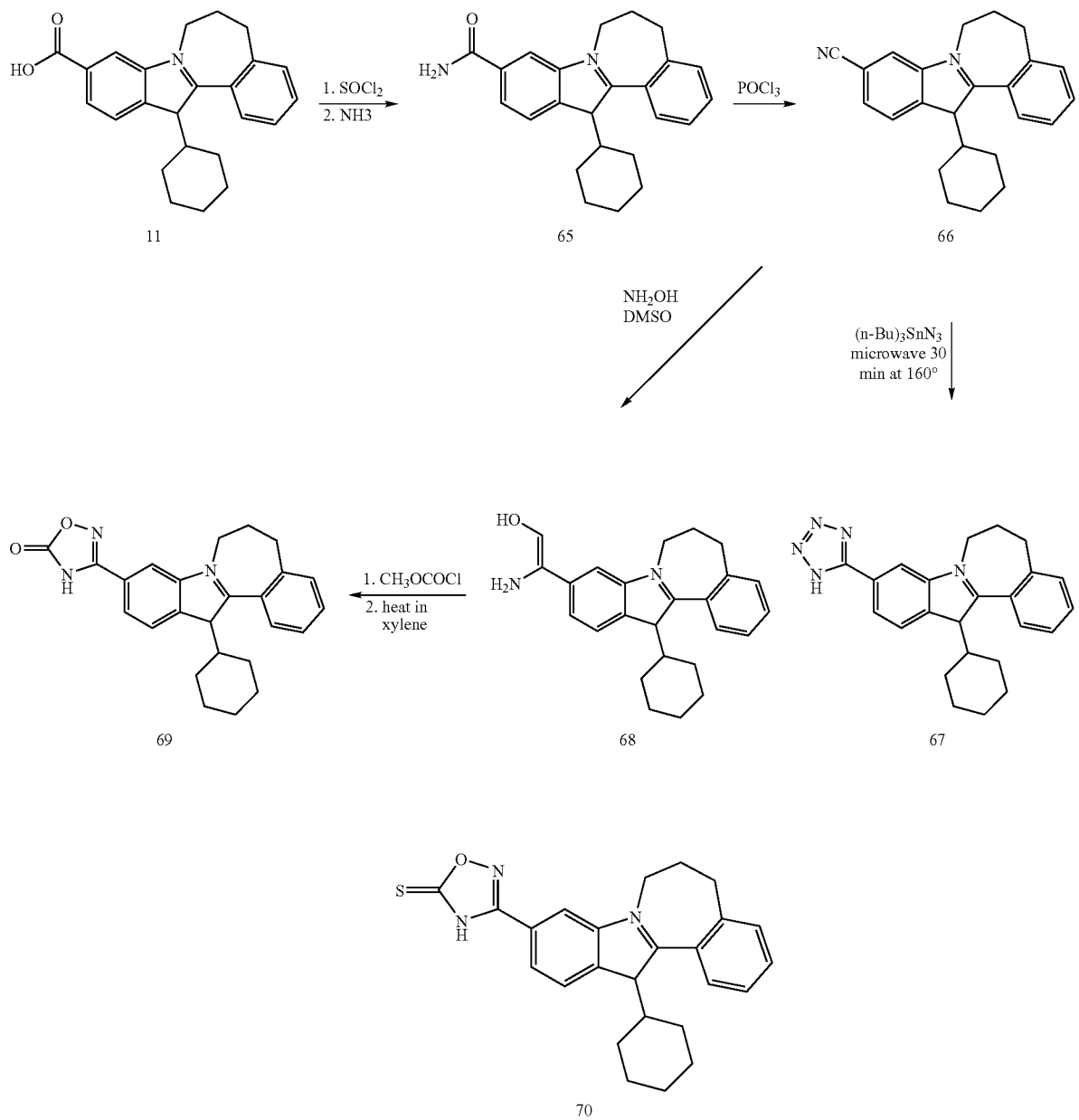

Scheme 11 is illustrative for the synthesis of compounds of formula (I) wherein $R^1$ is 5-tetrazolyl, 5-oxo-4,5-dihydro-1,2,4-oxadiazol-3-yl, or 5-thioxo-4,5-dihydro-1,2,4-oxadiazol-3-yl. For example, treatment of a mixture of carboxylic acid 11 (prepared by the method described in Scheme 1) in dichloromethane with thionyl chloride and a catalytic amount of DMF can provide the acid chloride which upon treatment with methanolic ammonia can provide amide 65. Dehydration of the amide with phosphorous oxychloride can provide nitrile 66 which can be converted to tetrazole 67 as indicated. The transformations of carboxylic acids into tetrazoles via a nitrile intermediate are well documented in the literature and numerous alternative reagents are known to those in the art (see, for example, Recent Developments in Tetrazole Chemistry, A Review, S. J. Wittenberger, *Organic Preparations and Procedures Int,* 1994, 26(5), 400–531).

Treatment of nitrile 66 with hydroxylamine in DMSO can provide amidoxime 68 which upon treatment with methyl chloroformate or thiocarbonyldiimidazloe can provide the acidic heterocycles 69 and 70, respectively.

Scheme 12

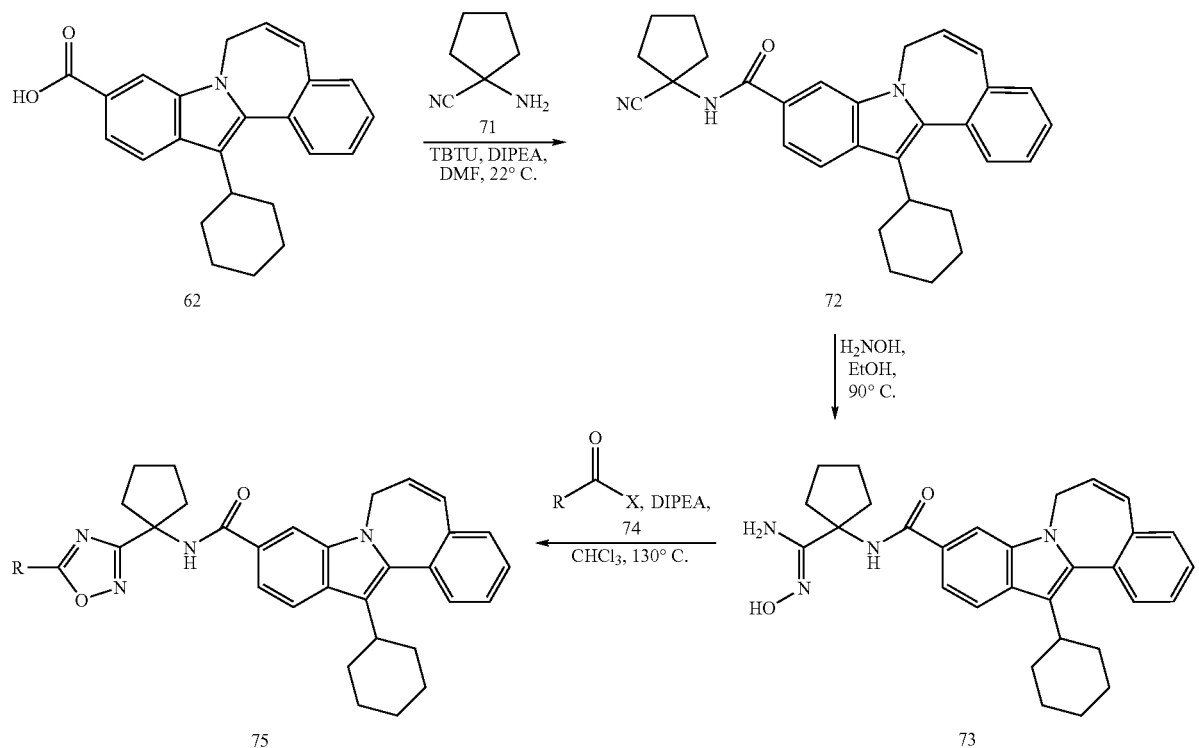

Scheme 12 shows a method of converting 62 (prepared by the method described in Scheme 10) to a substituted (1,2,4-oxadiazol-3-yl)cyclopentyl amide 75, wherein R is as previously defined. The acid (62) can be coupled with 1-cyanocyclohexylamine (71) to provide 72. Treatment of 72 with hydroxylamine can provide substituted aminohydroxylimino intermediate 73 which can be reacted with an acylating agent such as an acid chloride (74, X=Cl) to provide the oxadiazole 75.

Method H shows an alternative way to construct a bridged indole wherein the bridge is a lactam (Scheme 13).

Scheme 13

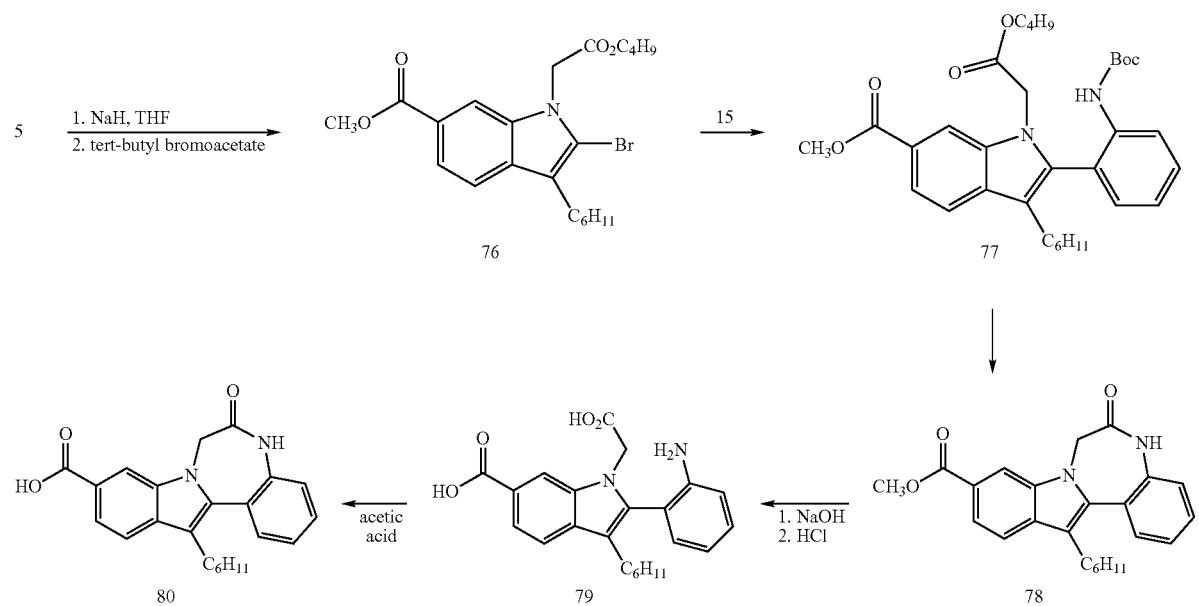

Bromoindole 5 (prepared by the method described in Scheme 1) can be treated with sodium hydride in THF to generate the indole anion which can be alkylated with tert-butyl bromoacetate to provide 76. Suzuki cross-coupling of 76 with the Boc-protected boronic acid 15 (shown in Scheme 3) can give 77. Upon removal of the Boc protecting group with TFA, cyclization occurs providing lactam 78. Base-catalyzed hydrolysis provides a mixture of the carboxylic acid core 80 as well as the dicarboxlic acid 79. The latter can be readily cyclized by heating in acetic acid. The hydrolysis of 78 to 80 can be done in a refluxing mixture of acetic acid and 37% hydrochloric acid (2:1) to allow for cyclization of any amount of 79 that is formed during the course of the reaction.

The majority of the final compounds were purified by reverse phase chromatography using a preparative C-18 column employing gradients of methanol-water containing 0.1% of trifluoroacetic acid (TFA), and using a Shimadzu High Perfomance Liquid Preparative Chromatographic System employing an XTERRA 30×100 mm S5 column at 40 mL/min flow rate with a 12 min gradient. The final compounds usually precipitated from the aqueous eluent mixture when the methanol co-solvent was removed. An Emrys Optimizer personal microwave reactor was used for the microwave assisted reactions. Molecular weights and purities were usually determined using a Shimadzu LCMS using a Phenomenex-Luna 3.0×50 mm S 10 reverse phase column employing a flow rate of 4 mL min using a 0.1% TFA in methanol/$H_2O$ gradient [0–100% in 2 min, with 3 min run time]. NMR spectra were usually obtained on either a Bruker 500 or 300 MHz instrument. The preparative silicic acid plates were 20×20 cm with a 1000 micron layer of silica gel GF.

Biological Methods

HCV RdRp assays utilized in the present invention were prepared, conducted, and validated as follows:

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15–24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM $MgCl_2$, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5–50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM $MgCl_2$, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-$dT_{12}$ primer was used at 180 nM final concentration. Template was obtained commercially (Amersham 27-4110). Biotinylated primer was prepared by Sigma Genosys. $^3$H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo $dT_{12}$ primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), $^3$H-UTP (0.6 μCi, 0.29 μM), and primer-bound beads, to initiate the reaction; concentrations given are final. Reactions were allowed to proceed for 4 hours at 30° C.

The $IC_{50}$ values for compounds were determined using seven different [I]. $IC_{50}$ values were calculated from the inhibition using the formula y=A+((B−A)/(1+((C/x)^D))) .FRET Assay Preparation. To perform the HCV FRET screening assay, 96-well cell culture plates were used. The FRET peptide (Anaspec, Inc.) (Taliani et al., *Anal. Biochem.* 240:60–67 (1996), hereby incorporated by reference in its entirety) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO2 incubator at 37 degrees C.

Assays. Subsequent to addition of the test compounds described above (FRET Assay Preparation), at various times the plate was removed and Alamar blue solution (Trek Diagnostics, #00–100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytotoxicity and percent activity were used to determine compounds of interest for further analysis.

Representative data for compounds of Formula I are reported in the Description of Specific Embodiments section.

Pharmaceutical Compositions and Methods of Treatment

Another aspect of the invention is a composition comprising a compound of formula (I), or a pharmaceutically acceptable salt thereof, and a pharmaceutically acceptable carrier. In another embodiment the composition further comprises a compound having anti-HCV activity. In another embodiment the compound having anti-HCV activity is an interferon. In another embodiment the interferon is selected from interferon alpha 2B, pegylated interferon alpha, consensus interferon, interferon alpha 2A, and lymphoblastoid interferon tau.

Another aspect of the invention is a composition comprising a compound of formula (I), or a pharmaceutically acceptable salt thereof, a pharmaceutically acceptable carrier, and a compound having anti-HCV activity, wherein the compound having anti-HCV activity is a cyclosporin. In another embodiment the cyclosporin is cyclosporin A.

Another aspect of the invention is a composition comprising a compound of formula (I), or a pharmaceutically acceptable salt thereof, a pharmaceutically acceptable carrier, and a compound having anti-HCV activity, wherein the compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition comprising a compound of formula (I), or a pharmaceutically acceptable salt thereof, a pharmaceutically acceptable carrier, an interferon and ribavirin.

Another aspect of the invention is a composition comprising a compound of formula (I), or a pharmaceutically acceptable salt thereof, a pharmaceutically acceptable carrier, and a compound having anti-HCV activity, wherein the compound having anti-HCV activity is a small molecule compound.

Another aspect of the invention is a composition comprising a compound of formula (I), or a pharmaceutically acceptable salt thereof, a pharmaceutically acceptable carrier, and a compound having anti-HCV activity, wherein the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a method of inhibiting the function of the HCV replicon comprising contacting the HCV replicon with a compound of formula (I) or a pharmaceutically acceptable salt thereof.

Another aspect of the invention is a method of inhibiting the function of the HCV NS5B protein comprising contacting the HCV NS5B protein with a compound of formula (I) or a pharmaceutically acceptable salt thereof.

Another aspect of the invention is a method of treating an HCV infection in a patient comprising administering to the patient a therapeutically effective amount of a compound of formula (I) or a pharmaceutically acceptable solvate or salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I). In another embodiment the other compound having anti-HCV activity is an interferon. In another embodiment the interferon is selected from interferon alpha 2B, pegylated interferon alpha, consensus interferon, interferon alpha 2A, and lymphoblastoid interferon tau.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I), wherein the other compound having anti-HCV activity is a cyclosporin. In another embodiment the cyclosporin is cyclosporin A.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I), wherein the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I), wherein the other compound having anti-HCV activity is a small molecule.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I), wherein the other compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a method of treating an HCV infection in a patient comprising administering to the patient a therapeutically effective amount of a compound of formula (I), or a pharmaceutically acceptable solvate or salt thereof, and administering another compound having anti-HCV activity prior to, after, or concurrently with the compound of formula (I), wherein the other compound having anti-HCV activity is effective to inhibit the function of target in the HCV life cycle other than the HCV NS5B protein.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof are as described above. The carrier(s), diluent(s), or excipient(s) must be acceptable in the sense of being compatible with the other ingredients of the formulation and not deleterious to the recipient thereof.

In accordance with another aspect of the disclosure there is also provided a process for the preparation of a pharmaceutical formulation including admixing a compound of formula (I), and/or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, for example between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, more likely between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrastemal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylrnethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are most often applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Certain illustrative HCV inhibitor compounds which can be administered with the compounds of the present disclosure include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000, WO 02/08198, published Jan. 31, 2002, WO 02/08187, published Jan. 31, 2002, WO 02/08244, published Jan. 31, 2002, WO 02/08251, published Jan. 31, 2002, WO 02/08256, published Jan. 31, 2002, WO 03/062228, published Jul. 31, 2003, WO 03/062265, published Jul. 31, 2003, WO 01/77113, published Oct. 18, 2001, WO 02/48172, published Jun. 20, 2002, WO 01/81325, published Nov. 1, 2001, and WO 01/58929, published Aug. 16, 2001.

The compounds of the present disclosure can also be administered with a cyclosporin such as cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |

TABLE 1-continued

| Brand Name | Type of Inhibitor or Target | Source Company |
| --- | --- | --- |
| VX-950/ LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

When these compounds or their pharmaceutically acceptable enantiomers, diastereomers, salts, or solvates are formulated together with a pharmaceutically acceptable carrier, the resulting composition may be administered in vivo to mammals, such as man, to inhibit HCV NS5B and/or treat and/or prevent HCV virus infection.

The compounds of the disclosure may also be used as laboratory reagents. Compounds may be instrumental in providing research tools for designing viral replication assays, validation of animal assay systems, and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the disclosure can be used for the manufacture of a medicament for treating HCV infection in a patient.

DESCRIPTION OF SPECIFIC EMBODIMENTS

The following intermediates are correlated where possible to the compounds depicted in the schemes shown above. Intermediates not specifically shown in the schemes are given the number of the closest shown structure followed by a letter (i.e., "Intermediate 3A").

The examples are numbered sequentially and are correlated to the structures shown in the above schemes.

Intermediate 3A 3-cyclohexenyl-1H-indole-6-carboxylic acid. Cyclohexanone (96 mL, 0.926 mol) was added to a stirred mixture of indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl. The resulting precipitate was collected by filtration, washed with cold water, and dried over phosphorous pentoxide (0.1 mm) to provide the desired product (80.9 g, 97.5% yield).

Intermediade 4A 3-cyclohexyl-1H-indole-6-carboxylic acid. Intermediate 3A (38 g) was added to a Parr bottle, followed by methanol (100 mL) and THF (100 mL). The bottle was flushed with argon and 10% palladium on carbon (1.2 g) was added. The mixture was shaken under 55 psi of $H_2$ for 18 hours. The catalyst was removed by filtration. Concentration of the filtrate provided the desired product as a pale purple solid (30.6 g, 79%). ESI-MS m/z 244 ($MH^+$).

Intermediate 4

Methyl 3-cyclohexyl-1H-indole-6-carboxylate. Thionyl chloride (1 mL) was added to a stirred mixture of Intermediate 4A (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid was washed with cold methanol followed by diethyl ether to provide the desired product as a pale purple solid (22.2 g, 69% yield). ESI-MS m/z 258 ($MH^+$); $^1$H NMR (300 MHz, $CDCl_3$) δ 1.35 (m, 4H), 1.63 (s, 1H), 1.78 (m, 3H), 2.06 (d, J=8.05 Hz, 2H, 3.90 (m, 1H), 7.08 (d, J=1.83 Hz, 1H), 7.62 (s, 1H), 7.65 (s, 1H), 7.74 (d, J=1.46 Hz, 1H), 7.77 (d, J=1.46 Hz, 1H), 8.08 (s, 1H).

Intermediate 5

Methyl 2-bromo-3-cyclohexyl-2-1H-indole-6-carboxylate. Dry pyridinium tribromide (12.0 g, 38 mmol) was added in one portion to a stirred and cooled (ice/water bath), solution of Intermediate 4 (7.71 g, 30 mmol) in a mixture of THF (80 mL) and chloroform (80 mL). The flask was removed from the cooling bath and stirring was continued for 2 hours at room temperature. The mixture was sequentially washed with 1M $NaHSO_3$ (2×50 mL), 1N HCl (50 mL), dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, $CDCl_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

Intermediate 6A ($R^2$=4-$PhCH_2O$—)

4-(benzyloxy)-2-vinylphenylboronic acid. Methyltriphenylphosphonium bromide (12.4 g, 0.0347 mol) and 18-crown-6 (90 mg, 0.41 mmol) were added to THF (100 mL). The mixture was cooled in a ice-water bath. Potassium tert-butoxide (34.7 mL of 1.0M in THF, 0.0347 mol) was added via cannula to the stirred solution. 5-(Benzyloxy)-2-bromobenzaldehyde (9.2 g, 0.0316 mol) was added in one portion which resulted in a slight exotherm. After 30 minutes the cooling bath was removed and stirring was continued at 22° C. for 5 hours. The mixture was concentrated and the residue was purified by flash column chromatography on $SiO_2$ (75 g) with hexanes/ethyl acetate (95:5) to provide 4-(benzyloxy)-1-bromo-2-vinylbenzene as a clear oil (7.9 g, 86% yield). $^1$H NMR (300 MHz, $CDCl_3$) δ 5.03 (s, 2H), 5.32 (d, J=10.98 Hz, 2H,) 5.63 (d, J=17.20 Hz, 2H), 6.74 (dd, J=8.78, 2.93 Hz, 2H), 6.98 (dd, J=17.57, 10.98 Hz, 2H), 7.13 (d, J=2.93 Hz, 2H), 7.33 (m, 6H).

Triisopropyl borate (683 mg, 3.63 mmol) was added to a stirred solution of 4-(benzyloxy)-1-bromo-2-vinylbenzene (1.0 g, 0.346 mmol) in THF (9 mL). The solution was cooled in a $CO_2$/acetone bath. A solution of n-butyllithium (1.45 mL of 2.5M in hexanes, 3.63 mmol) was added dropwise over 5 minutes. The cooling bath was left in place and was allowed to warm to room temperature. The mixture was treated with HCl (5 mL of 1N) and water (5 mL), stirred for 1 hour, and extracted with ethyl acetate (3×15 mL). The combined extracts were washed with brine, dried ($MgSO_4$), filtered, and concentrated to an oil which crystallized from diethyl ether/hexanes to provide colorless crystals of the desired product (530 mg, 57% yield). $^1$H NMR (300 MHz, $CDCl_3$) δ 5.14 (s, 2H), 5.34 (d, J=12.44 Hz, 1H), 5.68 (d, J=17.57 Hz, 1H), 6.97 (dd, J=8.42, 2.56 Hz, 1H), 7.36 (m, 6H), 7.83 (dd, J=17.57, 10.98 Hz, 1H), 8.16 (d, J=8.42 Hz, 1H).

Intermediate 7A ($R^2$=H)

Methyl 3-cyclohexyl-2-(2-vinylphenyl)-1H-indole-6-carboxylate. A stirred mixture of Intermediate 5 (1.01 g, 3.0 mmol), 2-vinylphenylboronic acid (666 mg, 4.5 mmol), lithium chloride (504 mg, 6.0 mol), and 1.0M sodium carbonate (7.5 mL, 7.5 mmol) in ethanol (11 mL) and toluene (11 mL) was degassed at 22° C. with a gentle stream of argon. Tetrakis(triphenylphosphine)palladium(0) was added (348 mg, 0.3 mmol), the mixture was stirred at reflux for 2 hours, and then stored at 22° C. for 18 hours. The mixture was concentrated and the residue was partitioned between ethyl acetate and water. The ethyl acetate layer was washed sequentially with water (3×) and brine, dried ($MgSO_4$), filtered, and concentrated. The crystalline residue was purified by flash column chromatography on silica gel (40 g) with dichloromethane to provide the desired product (815 mg, 75% yield). ESI-MS m/z 360 ($MH^+$), $^1$H NMR (500 MHz, $CDCl_3$) 1.18–1.36 (m, 3H), 1.69–2.01 (m, 7H), 2.60 (m, 1H), 3.92 (s, 3H), 5.19 (d, J=10.99 Hz, 1H), 5.72 (m, 1H), 6.57 (dd, J=17.70, 10.99 Hz, 1H), 7.34 (m, 2H), 7.44 (m, 1H), 7.71 (m, 1H), 7.79 (m, 2H), 8.08 (m, 2H).

Intermediate 7B ($R^2$=4-$PhCH_2O$—)

Methyl 2-(4-(benzyloxy)-2-vinylphenyl)-3-cyclohexyl-1H-indole-6-carboxylate ($R^2$=4-$PhCH_2O$). The desired product was prepared as as a colorless solid in 50% yield by substituting Example 6A for 2-vinylphenylboronic acid in Example 7A. $^1$H NMR (300 MHz, $CDCl_3$) δ 1.45 (m, 10H), 2.57 (m, 1H), 3.90 (s, 3H), 5.15 (m, 3H), 5.66 (d, J=17.57 Hz, 1H), 6.51 (dd, J=17.57, 10.98 Hz, 1H), 6.95 (dd, J=8.60, 2.38 Hz, 1H), 7.33 (m, 6H), 7.78 (m, 2H), 7.96 (s, 1H), 8.03 (s, 1H).

Intermediate 8A ($R^2$=H)

Methyl 3-cyclohexyl-2-(2-vinylphenyl)-1-(2-propenyl)-indole-6-carboxylate. Sodium hydride (85.6 mg of a 95% dispersion, 3.39 mmol) was added to a stirred and cooled (ice/water bath), solution of Intermediate 7A (813 mg, 2.26 mmol) in THF (8 mL). The ice bath was removed when the vigorous evolution of $H_2$ subsided. Stirring was continued for 6 minutes at ambient temperatures when the cooling bath was replaced. Allyl bromide (301 mg, 2.5 mmol) was added in one portion. After 5 minutes the ice bath was removed and stirring continued for 30 minutes when the reaction was judged to be complete by LC/MS. The mixture was left to stand for 18 hours at 22° C. when it was diluted with ethyl acetate/water. The organic layer was washed (water, brine), dried ($Na_2SO_4$), filtered, and concentrated to an oil. The oil was purified by flash column chromatography on silica gel (30 g) with hexanes/ethyl acetate (10:1) to provide the desired product as an oil. ESI-MS m/z 399 ($MH^+$); $^1$H NMR (300 MHz, $CDCl_3$) δ 1.21 (m, J=6.22 Hz, 3H), 1.72 (m, 7H), 2.44 (m, 1H), 3.93 (s, 3H), 4.29 (m, 1H), 4.53 (m, 1H), 4.80 (m, 1H), 5.00 (d, J=10.25 Hz, 1H), 5.12 (d, J=10.98 Hz, 1H), 5.70 (m, 2H), 6.38 (dd, J=17.57, 10.98 Hz, 1H), 7.22 (d, J=7.32 Hz, 1H), 7.33 (m, 1H), 7.46 (m, 1H), 7.71 (d, J=7.32 Hz, 1H), 7.80 (s, 2H), 8.05 (s, 1H).

Intermediate 8B ($R^2$=4-$PhCH_2O$—)

Methyl 2-(4-(benzyloxy)-2-vinylphenyl)-3-cyclohexyl-1-(2-propenyl)-1H-indole-6-carboxylate ($R^2$=4-$PhCH_2O$—). The desired product was prepared as a viscous oil by substituting Example 7B for Example 7A in Example 8A. $^1$H NMR (300 MHz, $CDCl_3$) δ 1.20 (m, J=6.22 Hz, 3H), 1.71 (m, J=5.86 Hz, 7H), 2.44 (m, 1H), 3.91 (s, 3H), 4.28 (dd, J=16.83, 5.12 Hz, 1H), 4.50 (m, 1H), 4.77 (d, J=16.83 Hz, 1H), 4.98 (d, J=10.25 Hz, 1H), 5.13 (m, 3H), 5.68 (m, 2H), 6.32 (dd, J=17.57 10.98 Hz, 1H), 6.95 (dd, J=8.42, 2.56 Hz, 1H), 7.12 (d, J=8.42 Hz, 1H), 7.37 (m, 6H), 7.75 (m, 2H), 8.02 (s, 1H).

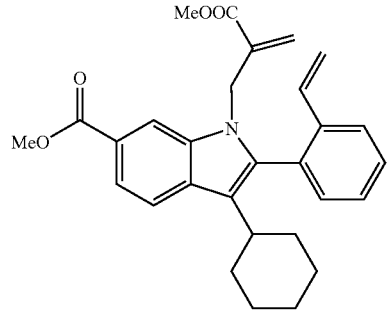

INTERMEDIATE 13

Methyl 3-cyclohexyl-1-(2-(methoxycarbonyl)allyl)-2-(2-vinylphenyl)-1H-indole-6-carboxylate (13, R=methyl). Methyl 3-cyclohexyl-2-(2-vinylphenyl)-1H-indole-6-carboxylate (7, $R^2$=H) 508 mg, 1.4 mmol) was dissolved in THF (5 mL) under $N_2$ and cooled to 0° C. Sodium hydride (143 mg, 60% suspension in mineral oil, 3.57 mmol) was added and the mixture was stirred at 0° C. for 5 min, when a solution of methyl 2-(bromomethyl)acrylate (276 mg, 1.54 mmol) in THF (1.5 mL) was added dropwise. Stirring was continued for 30 min at 22° C. The reaction was quenched with a saturated aqueous solution of ammonium chloride (20 mL) and extracted with EtOAc (2×30 mL) and $CH_2Cl_2$ (30 mL). The organic extracts were combined and dried over sodium sulfate, filtered and concentrated. The residue was chromatographed on silica gel using hexane/ethyl acetate (0–20%) to afford the title compound as a pale yellow solid (641 mg, 99%). ESI-MS m/z 458 ($MH^+$).

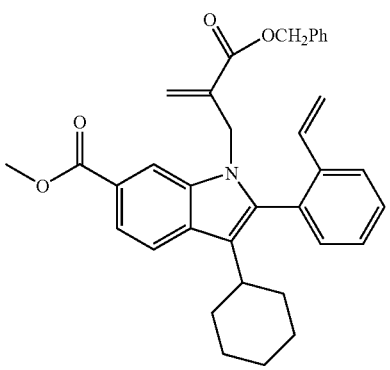

Methyl 3-cyclohexyl-1-(2-(benzyloxycarbonyl)allyl)-2-(2-vinylphenyl)-1H-indole-6-carboxylate (13, R=benzyl). Sodium hydride (155 mg of a 95% dispersion in mineral oil, 6.13 mmol) was added in portions during 5 min to a stirred and cooled solution (ice-water bath) of 7 (1.0 g, 2.79 mmol) in THF (7 mL). When the evolution of hydrogen subsided DMF (2 mL) was added followed by a solution of bromomethylacrylic acid (505 mg, 3.06 mmol) in THF (1.5 mL). Stirring was continued with cooling (10 min) and then at 22° C. for 30 min. The mixture was concentrated and the residue partitioned between ethyl acetate and water. The organic layer was washed (water, brine), dried (sodium sulfate) and concentrated. The residue was chromatographed on silicic acid (15 g) using the flash technique and eluting with methylene chloride:ethyl acetate:acetic acid (10:1:0.005). The product containing fraction was concentrated on a rotary evaporator to leave 2-((3-cyclohexyl-6-(methoxycarbonyl)-2-(2-vinylphenyl)-1H-indol-1-yl)methyl)acrylic acid (568 mg, 40%) as a yellow gum. A sample (142 mg) was further purified on a Shimadzu preparatory liquid chromatograph. The fraction containing the product was concentrated to leave 13 (R=H) as a granular solid. ESI-MS m/z 433 (MH$^+$), 1H NMR (500 MHz, CHLOROFORM-D) δ ppm 1.07–1.37 (m, 3 H) 1.58–1.88 (m, 7 H) 2.41–2.53 (m, 1 H) 3.93 (s, 3 H) 4.50 (d, J=18.31 Hz, 1 H) 4.84 (d, J=18.31 Hz, 1 H) 4.89 (s, 1 H) 5.13 (d, J=10.99 Hz, 1 H) 5.29 (s, 1 H) 5.68 (d, J=17.70 Hz, 1 H) 6.19 (s, 1 H) 6.36 (dd, J=17.55, 11.14 Hz, 1 H) 7.15 (d, J=7.63 Hz, 1 H) 7.31 (t, J=7.48 Hz, 1 H) 7.45 (t, J=7.63 Hz, 1 H) 7.70 (d, J=7.93 Hz, 1 H) 7.76–7.87 (m, 2 H) 7.96 (s, 1 H).

Benzyl bromide (1.87 mL, 0.0158 mol) was added to a stirred ice cold mixture of cesium carbonate (7.3 g, 0.0225 mol) and acid 13(R=H, 6.5 g, 0.015 mol) in DMF (30 mL). The cooling bath was removed and stirring was continued for 18 hr at ambient temperature. The mixture was partitioned between ethyl acetate and cold water. The organic layer was washed with water (2×) followed by brine. The solution was dried over magnesium sulfate and concentrated to leave the titled compound as a hazy oil (8.5 g, 105%) which was used in the RCM reaction. ESI-MS m/z 533 (MH$^+$). A small sample (78 mg) was purified on a Shimadzu preparatory liquid chromatograph. The product containing fraction was extracted with ethyl acetate. The extract was washed with water (2×), brine and dried over sodium sulfate. Removal of the solvent left 13 (R=benzyl) as a hazy oil, 1 H NMR (300 MHz, CHLOROFORM-D) δ ppm 1.12–1.22 (m, J=8.42 Hz, 3 H) 1.60–1.90 (m, 7 H) 2.34–2.56 (m, J=9.33, 5.31 Hz, 1 H) 3.90 (s, 3 H) 4.51 (d, J=18.30 Hz, 1 H) 4.70–4.95 (m, 1 H) 5.07 (s, 1 H) 5.11 (s, 2 H) 5.64 (d, J=17.57 Hz, 1 H) 6.08 (s, 1 H) 6.33 (dd, J=17.57, 10.98 Hz, 1 H) 7.20–7.47 (m, 9 H) 7.66 (d, J=7.68 Hz, 1 H) 7.72–7.85 (m, 2 H) 7.94 (s, 1 H).

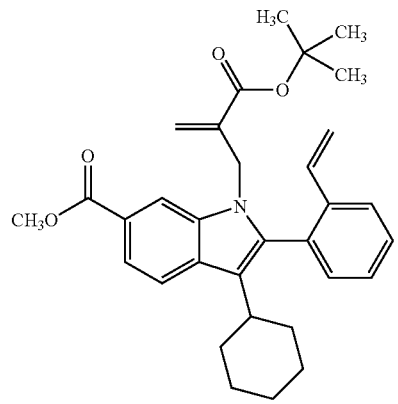

Methyl 3-cyclohexyl-1-(2-(tert-butoxycarbonyl)allyl)-2-(2-vinylphenyl)-1H-indole-6-carboxylate (13, R=tert-butyl). Alkylation of 7 (R$^2$=H) with tert-butyl 2-(bromomethyl)acrylate provided the titled compound. ESI-MS m/z 500 (MH$^+$).

INTERMEDIATE 14

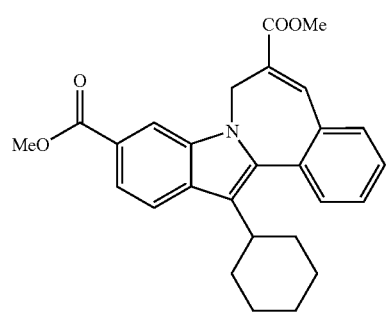

Methyl 13-cyclohexyl-6-(carbomethoxy)-5H-indolo[2,1a][2]benzazepine-10-carboxylate (14, R=methyl). A mixture of methyl 3-cyclohexyl-1-(2-(methoxycarbonyl)allyl)-2-(2-vinylphenyl)-1H-indole-6-carboxylate (13, R=methyl), (3.1 g, 6.77 mmol) and Grubbs' 2nd generation catalyst (1.7 g, 1.35 mmol) in methylene chloride (350 mL) were heated at 45° C. for 96 hr. Solvent was removed in vacuo and the residue was chromatographed on silica gel using hexane/ethyl acetate (0–15%) to afford pure title compound as a bright yellow solid (1.36 g). The mixed fractions were combined and concentrated in vacuo and the residue was recrystallized using methanol to afford the title compound (175 mg). Total title compound obtained: 1.805 g, 53%. ESI-MS m/z 430 (MH+).

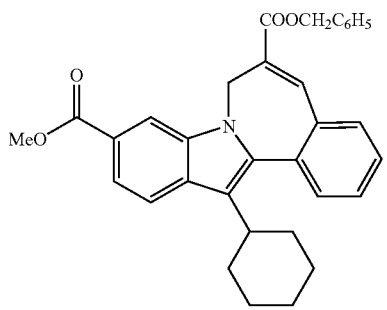

Methyl 13-cyclohexyl-6-(benzyloxycarbonyl)-5H-indolo[2,1-a][2]benzazepine-10-carboxylate (14, R=benzyl). In a similar manner ring closing metathesis of methyl 3-cyclohexyl-1-(2-(benzyloxycarbonyl)allyl)-2-(2-vinylphenyl)-1H-indole-6-carboxylate (13, R=benzyl) with Grubbs' 2nd generation catalyst in boiling methylene chloride or ethylene dichloride provided the title compound. ESI-MS m/z 506 (MH+).

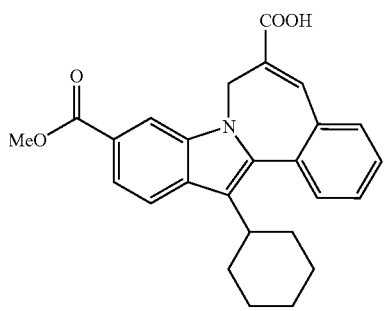

Methyl 13-cyclohexyl-6-(carboxy)-5H-indolo[2,1-a][2]benzazepine-10-carboxylate (14a). Method A: Ester 14 (R=H, 308 mg, 0.72 mmol) was dissolved in N,N-dimethylformamide (5 mL) and treated with LiOH (173 mg, 7.2 mmol). The mixture was heated at 50° C. for 4 hr. The solvent was removed in vacuo. The residue was dissolved in H₂O (5 mL) and treated with HCl (10% in water) to acidic pH. A precipitate formed which was collected by filtration and air dried to afford the title compound as abright yellow solid (290 mg, 97%). ESI-MS m/z [M+1]=415.

Method B: Ten percent palladium on carbon (200 mg) was added to a solution of methyl 13-cyclohexyl-6-(benzyloxycarbonyl)-5H-indolo[2,1-a][2]benzazepine-10-carboxylate (14, R=benzyl, 2.9 g) in 95% ethanol (200 mL) and ethyl acetate (50 mL). The mixture was stirred at 22° C. and under hydrogen (balloon pressure) for 3 h. A portion of the mixture (50 mL) was removed and was filtered to remove the catalyst. Concentration of the filtrate on a rotary evaporator left the titled compound (710 mg) which was identical to the product from Method A.

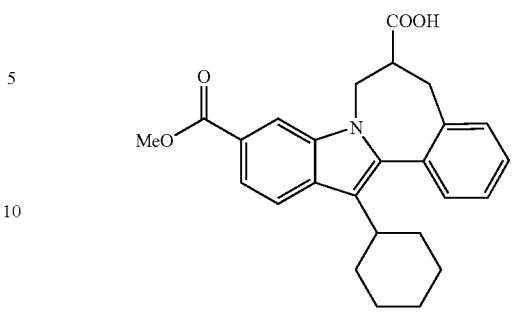

Methyl 13-cyclohexyl-6,7-dihydro-6-(carboxy)-5H-indolo[2,1-a][2]benzazepine-10-carboxylate (14b). Method A: The intermediate ester (14, R=H, 53 mg, 0.13 mmol) in a 1:1 mixture of THF/MeOH (2 mL) was treated with a catalytic amount of Pd (10% on C) under hydrogen (balloon pressure). The mixture was stirred at 22° C. for 18 hr. The catalyst was removed by filtration through a fine pad of celite and the solution was concentrated in vacuo to afford the title compound as a pale tan solid (50 mg, 92%). ESI-MS m/z 418 (MH+).

Method B: Additional palladium on carbon (1 g) was added to the reduction mixture from the preceding experiment (200 mL). Stirring was continued at 22° C. for 72 h. The mixture was filtered and the filtrate was concentrated to dryness on a rotary evaporator. A solution of the residue in methanol was purified on a Shimadzu preparatory liquid chromatograph to afford the titled compound (630 mg) which was identical to the product from Method A.

Intermediate 16

Methyl 2-(2-(tert-butoxyycarbonylamino)phenyl)-3-cyclohexyl)-1H-indole-6-carboxylate. The desired product was prepared as a pale brown solid by substituting 2-(tert-butoxylcarbonylamino)phenylboronic acid for 2-vinylphenylboronic acid in Example 7A. ESI-MS m/z 449 (MH+).

Intermediate 17

Methyl 2-(2-(tert-butoxycarbonylamino)-3-cyclohexyl-1-(2-propenyl)-1H-indole-6-carboxylate. The desired product was prepared by substituting Intermediate 16 for Intermediate 7A in Intermediate 8A. ¹H NMR (500 MHz, CDCl₃) δ 1.11–1.56 (m, 13H), 1.63–1.94 (m, 5H), 2.09 (m, 1H), 2.42 (s, 1H), 3.94 (m, 3H), 4.09 (1H) 4.59 (m, J=26.25 Hz, 2H), 4.78 (m, 1H), 4.87–5.10 (m, 4H), 5.52–5.87 (m, 2H), 7.27 (m, 1H), 7.33 (m, 1H), 7.46 (d, J=6.10 Hz, 2H), 7.80 (d, J=8.55 Hz, 1H), 7.86 (d, J=8.55 Hz, 1H), 8.09 (s, 1H).

Intermediate 22

Methyl 1-(3-(2-bromophenyl)propyl)-3-cyclohexyl-1H-indole-6-carboxylate. Sodium hydride (129 mg of a 95% dispersion, 5.1 mmol) was added to a stirred and cooled (ice/water bath), solution of Intermediate 4 (515 mg, 2.0 mmol) in THF (6 mL). The ice bath was removed when the vigorous evolution of H₂ subsided. Stirring was continued for 6 minutes at ambient temperature when the cooling bath was replaced. 1-Bromo-2-(3-bromopropyl)benzene (908 mg, 4.2 mmol) was added. The ice bath was removed and stirring was continued at 22° C. for 3 hours. The mixture was cooled to room temperature and was diluted with saturated ammonium chloride followed by extraction with ethyl acetate. The organic layer was washed (water, brine), dried ($Na_2SO_4$), filtered, and concentrated to a brown oil. The oil was purified by flash column chromatography on silica gel (30 g) with hexanes/ethyl acetate (6:4) to provide the desired product as an oil contaminated with Intermediate 4. An additional purification was done on a silicic acid thick layer plate. The plate was eluted with hexanes/ethyl acetate (100: 5). The product band was extracted with dichloromethane. Removal of the solvent provided the desired product as a viscous oil. ESI-MS m/z 455 ($MH^+$); $^1H$ NMR (300 MHz, $CDCl_3$) δ 1.34 (m, 5H), 1.77 (m, 3H), 2.12 (m, 4H), 2.74 (m, 3H), 3.96 (m, 3H), 4.17 (t, J=7.14 Hz, 2H), 7.04 (m, 2H), 7.16 (m, 2H), 7.49 (d, J=8.05 Hz, 1H), 7.62 (d, J=8.42 Hz, 1H), 7.73 (m, 1H), 8.03 (s, 1H).

Intermediate 22A

Methyl 1-(2-bromobenzyl)-3-cyclohexyl-1H-indole-6-carboxylate. The desired product was prepared as a viscous oil in 90% yield by substituting 2-bromobenzyl bromide for 1-bromo-2-(3-bromopropyl)benzene in Example 22. ESI-MS m/z 427 ($MH^+$), $^1H$ NMR (300 MHz, $CDCl_3$) δ 1.37 (m, 5H), 1.77 (m, 3H), 2.09 (m, 2H), 2.83 (m, 1H), 3.87 (s, 3H), 5.35 (s, 2H), 6.44 (dd, J=5.67, 3.84 Hz, 1H), 6.99 (s, 1H), 7.09 (m, 2H), 7.57 (m, 1H), 7.67 (d, J=8.42 Hz, 1H), 7.77 (m, 2H), 7.96 (s, 1H).

Intermediate 24

Methyl 1-(2-(benzyloxy)ethyl)-3-cyclohexyl-1H-indole-6-carboxylate. Intermediate 4 (1.029 g, 4.0 mmol) was added to a suspension of NaH (192 mg of 60% dispersion in mineral oil, 4.8 mmol) in DMF (5 mL). The reaction mixture was stirred at room temperature for 15 minutes, treated with benzyl 2-bromoethyl ether (0.7 mL, 4.4 mmol), stirred at room temperature for 2 hours, quenched with water, and extracted with ethyl acetate (2×50 mL). The organic layers were combined and washed (1N HCl), dried ($MgSO_4$), filtered, and concentrated. The residue was purified by flash column chromatography (silica gel, 3:1 hexanes/ethyl acetate) to provide the desired product as a colorless thick oil (1.19 g, 76% yield). MS m/z 392($MH^+$); $^1H$ NMR (500 MHz, $CDCl_3$) δ 1.31 (m, 1H), 1.45 (m, 4H), 1.80 (d, J=13.12 Hz, 1H), 1.87 (m, 2H), 2.10 (m, 2H), 2.84 (m, 1H), 3.79 (t, J=5.34 Hz, 2H), 3.94 (s, 3H), 4.33 (t, J=5.49 Hz, 2H), 4.45 (s, 2H), 7.12 (s, 1H), 7.20 (m, 2H), 7.27 (m, 3H), 7.66 (d, J=8.55 Hz, 1H), 7.78 (d, J=8.55 Hz, 1H), 8.08 (s, 1H).

Intermediate 25

Methyl 3-cyclohexyl-1-(2-hydroxyethyl)-1H-indole-6-carboxylate. A solution of Intermediate 24 (1.19 g, 3.04 mmol) in ethyl acetate (50 mL) was treated with 10% Pd on carbon (0.12 g). About five drops of 1N HCl solution was added and the mixture stirred at room temperature under a hydrogen atmosphere (balloon pressure) for three days. The mixture was filtered through diatomaceous earth (Celite®). The filter cake was washed with ethyl acetate. The filtrate was concentrated to provide the desired product as a light yellow solid (0.9 g, 98% yield). MS m/z 302($MH^+$); $^1H$ NMR (300 MHz, $CDCl_3$) δ 1.22 (m, 1H), 1.41 (m, 4H), 1.78 (m, 3H), 2.06 (m, 2H), 2.79 (m, 1H), 3.90 (s, 3H), 3.95 (m, 2H), 4.26 (t, J=5.31 Hz, 2H), 7.05 (s, 1H), 7.62 (d, J=8.42 Hz, 1H), 7.74 (dd, J=8.42, 1.46 Hz, 1H), 8.05 (s, 1H).

Intermediate 27

Methyl 1-(2-(2-bromopyridin-3-yloxy)ethyl)-3-cyclohexyl-1H-indole-6-carboxylate. A solution of 2-bromo-3-pyridinol (26, 173 mg, 0.995 mmol) in THF (10 mL) was treated with triphenylphosphine (261 mg, 0.995 mmol) and di-tert-butyl azodicarboxylate (229 mg, 0.995 mmol). The reaction mixture was stirred at room temperature for 0.5 hours, treated with a solution of Intermediate 25 (200 mg, 0.66 mmol) in THF (2.5 mL), stirred 18 hours at room temperature, and concentrated to provide a brown oil which solidified upon standing. Trituration of the solid with methanol provided the desired product as a gray solid (175 mg, 58% yield). MS m/z 457($MH^+$); $^1H$ NMR (300 MHz, $CDCl_3$) δ 1.22 (m, 1H), 1.41 (m, 4H), 1.81 (m, 3H), 2.02 (m, 2H), 2.78 (m, 1H), 3.91 (s, 3H), 4.27 (t, J=4.94 Hz, 2H), 4.59 (t, J=4.94 Hz, 2H), 6.92 (dd, J=8.05, 1.46 Hz, 1H), 7.09 (dd, J=8.23, 4.57 Hz, 1H), 7.28 (s, 1H), 7.61 (d, J=8.42 Hz, 2H), 7.74 (dd, J=8.42, 1.46 Hz, 2H), 7.93 (dd, J=4.76, 1.46 Hz, 1H), 8.08 (s, 1H).

Intermediate 33

Methyl 3-cyclohexyl-2-(4,4,5,5-tetramethyl-1,3,2,-dioxaborolan-2-yl)-1H-indole-6-carboxylate. In a flame-dried flask equipped with magnetic stirrer was added [Ir(OMe)(cod)]$_2$ (150 mg, 0.225 mmol), 4,4'-di-tert-butyl-2,2'-bipyridine (dtbpy, 120 mg, 0.45 mmol), and bis(pinacolato)diboron ($B_2Pin_2$, 7.62 g, 30 mmol). The flask was flushed with $N_2$ and sealed with a septum. Anhydrous THF (45 mL) was added with a syringe and the solution was stirred at room temperature for 10 minutes, during which time the solution turned dark purple. Under a flow of $N_2$, Intermediate 4 (7.71 g, 30 mmol) was added in one portion. The flask was then quickly sealed with a septum and flushed with $N_2$. The reaction mixture was stirred at 30° C. for 3 hours, during which time the solution turned red-brown. The disappearance of the red color indicated the completion of the reaction. The solvents were removed under reduced pressure and the residue was treated with hexane (10 mL). The crystalline product was collected by filtration, washed with ethyl acetate/hexane (1:3), and air dried to provide the desired product (4.7 g, 41% yield) as colorless crystals. $^1H$ NMR (500 MHz, $CDCl_3$) δ 1.36 (s, 6H), 1.05 (s, 9H), 1.35–1.50 (m, 4H), 1.70–1.90 (m, 4H), 1.90–2.05 (m, 2H), 3.30 (m, 1H), 3.93 (s, 3H), 7.70 (d, 1H, J=8.5 Hz), 7.84 (d, 1H, J=8.5 Hz), 8.07 (s, 1H), 8.55(s, br, 1H, NH).

The mother liquor was concentrated under reduced pressure to substantially remove the pinacolborane by-product. Hexane was added and the crystalline solid was collected, washed with ethyl acetate/hexane (1:3) to give 3.3 g solid as a mixture of the desired product and Intermediate 4 which can be recycled.

Intermediate 34

3-bromo-2-vinylpyridine. A solution of 2,3-dibromopyridine (2.0 g, 8.44 mmol) in DMF (10 mL) was treated with tributyl(vinyl)tin (2.94 g, 9.29 mmol), LiCl (1.07 g, 25.32 mmol), and $PdCl_2(PPh_3)_2$ (0.296 g, 0.422 mmol). The reaction mixture was heated at 100° C. for 18 hours. The mixture was extracted with hexanes (3×50 mL). The combined hexane layers were extracted with 1N HCl. The aqueous layer was neutralized with 1N NaOH, extracted with hexanes, and the extracts were dried ($MgSO_4$), filtered, and concentrated to provide the desired product as a yellowish oil (0.83 g, 53% yield). MS m/z 184($MH^+$); $^1H$ NMR (300

MHz, CD$_3$OD) δ 5.53 (dd, J=10.80, 2.01 Hz, 1H), 6.33 (dd, J=16.83, 1.83 Hz, 1H), 7.08–7.26 (m, 2H), 7.96 (dd, J=8.05, 1.46 Hz, 1H), 8.44 (dd, J=4.76, 1.46 Hz, 1H); $^{13}$C NMR (300 MHz, CD$_3$OD) δ 121.9, 122.4, 125.7, 134.9, 142.8, 149.5, 154.5.

Intermediate 37

Methyl 3-cyclohexyl-2-(2-vinylpyridin-3-yl)-1H-indole-6-carboxylate. A mixture of Intermediate 33 (580 mg, 1.51 mmol), Intermediate 34 (362 mg, 1.97 mmol) and LiCl (128 mg, 3.02 mmol) in ethanol (6 mL) and toluene (6 mL) was treated with Na$_2$CO$_3$ (1.89 mL of 2M, 3.78 mmol). The mixture was degassed with N$_2$, treated with Pd(PPh$_3$)$_4$ (87 mg, 0.0755 mmol), heated at 80° C. for 3 hours, filtered, and concentrated. The residue was purified by preparative HPLC to provide the desired product as a pale yellow solid (145 mg, 27% yield). MS m/z 361 (MH$^+$); $^1$H NMR (300 MHz, CDCl$_3$) δ 1.10–1.29 (m, 3H), 1.63–1.89 (m, 7H), 2.53 (m, 1H), 3.91 (s, 3H), 5.39 (dd, J=10.61, 1.83 Hz, 1H), 6.40 (dd, J=17.02, 2.01 Hz, 1H), 6.63 (dd, J=16.83, 10.61 Hz, 1H), 7.28 (dd, J=7.68, 4.76 Hz, 1H), 7.64 (dd, J=7.68, 1.83 Hz, 1H), 7.75–7.84 (m, 2H), 8.07 (d, J=1.10 Hz, 1H), 8.22 (s, 1H), 8.68 (dd, J=4.76, 1.83 Hz, 1H).

Intermediate 38

Methyl 3-cyclohexyl-2-(2-formylfuran-3-yl)-1H-indole-6-carboxylate. The desired product was prepared by substituting 3-bromo-2-furaldehyde for Intermediate 34 in Intermediate 37. $^1$H NMR (500 MHz, CDCl$_3$) δ 1.40–2.15 (m, 10H), 3.14 (m, 1H), 3.94 (s, 3H), 7.08 (d, 1H, J=1 Hz), 7.72 (dd, 1H, J=1.5, 8.5 Hz), 7.79 (d, 1H, J=2.0 Hz), 7.88 (dd, 1H, J=1.5, 8.5 Hz), 8.19 (d, 1H, J=1.0 Hz), 9.87 (s, 1H).

Intermediate 39

Methyl 2-(3-bromopyridin-2-yl)-3-cyclohexyl-1H-indole-6-carboxylate. The desired product was prepared (60% yield) as a pale yellow solid by substituting 2,3-dibromopyridine for Intermediate 34 in Intermediate 37. MS m/z 413 (MH$^+$), $^1$H NMR (300 MHz, CDCl$_3$) δ 1.16–1.35 (m, 3H), 165–1.95 (m, 7H), 2.72 (m, 1H), 3.90 (s, 3H), 7.22 (m, 1H), 7.75 (dd, J=8.42, 1.10 Hz, 1H), 7.84 (m, 1H), 8.01 (dd, J=8.42, 1.46 Hz, 1H), 8.08 (s, 1H), 8.32 (s, 1H), 8.64 (dd, J=4.39, 1.46 Hz, 1H).

Intermediate 40

Methyl 1-allyl-3-cyclohexyl-2-(2-vinylpyridin-3-yl)-1H-indole-6-carboxylate. The desired product was prepared in 62% yield as a yellow solid by substituting Intermediate 37 for Intermediate 7A in Intermediate 8A. MS m/z 401 (MH$^+$); $^1$H NMR (500 MHz, CDCl$_3$) δ 1.09–1.36 (m, 3H), 1.51–1.82 (m, 7H), 2.43 (m 1H), 3.94 (s, 3H), 4.30 (dd, J=17.09, 5.19 Hz, 1H), 4.57 (dd, J=17.24, 4.12 Hz, 1H), 4.73 (d, J=17.40 Hz, 1H), 5.01 (d, J=10.38 Hz, 1H), 5.37 (dd, J=10.38, 1.22 Hz, 1H), 5.70 (m, 1H), 6.38–6.53 (m, 2H), 7.28 (dd, J=7.32, 4.88 Hz, 1H), 7.56 (d, J=7.32 Hz, 1H), 7.82 (m, 2H), 8.07 (s, 1H), 8.72 (d, J=4.27 Hz, 1H).

Intermediate 41

Methyl 3-cyclohexyl-2-(2-vinylfuran-3-yl)-1H-indole-6-carboxylate. A solution of methyl triphenylphosphonium bromide (428 mg, 1.2 mmol) in anhydrous THF (4 mL) at room temperature was treated with n-BuLi (1.6 M, 0.70 mL, 1.12 mmol). The phosphonium salt gradually dissolved and the solution turned yellow. After 10 minutes, the yellow solution was transferred to a solution of Intermediate 38 (176 mg, 0.5 mmol) in anhydrous THF (1 mL). The mixture was heated in an oil bath at 65° C. for 1 hour. After cooling to room temperature, the solution was treated with dichloromethane (10 mL) and the resulting mixture was washed with 1N HCl and water, dried (Na$_2$SO$_4$), and concentrated. The residue was purified by flash column chromatogaphy on silica gel (hexane/ethyl acetate, 5:1) to provide the desired product (95 mg, 54%) as a powder. $^1$H NMR (300MH, CDCl$_3$) δ 1.20–2.0 (m, 10H), 2.73 (m, 1H), 5.24 (dd, 1H, J=1.2, 11.4 Hz), 5.75 (dd, 1H, J=1.2, 17.4 Hz), 6.48 (d, 1H, J=2.1 Hz), 6.51 (dd, 1H, J=11.4, 17.4 Hz), 7.43 (d, 1H, J=2.1 Hz), 7.73 (d, 1H, J=8.4 Hz), 7.78 (d, 1H, J=8.4 Hz), 8.01 (s, br, 1H, NH), 8.05 (s, 1H).

Intermediate 41A

Methyl 1-allyl-3-cyclohexyl-2-(2-vinylfuran-3-yl)-1H-indole-6-carboxylate. The desired product was prepared by substituting Intermediate 41 for Intermediate 7A and potassium hydride for sodium hydride in Intermediate 8A. $^1$H NMR (300 MHz, CDCl$_3$) δ 1.20–1.90 (m, 10H), 2.59 (m, 1H), 4.55 (m, 1H), 4.84 (dd, 1H, J=1.2, 17.5 Hz), 5.05 (dd, 1H, J=1.2, 10.5), 5.15 (dd, 1H, J=1.2, 11.1), 5.68 (dd, 1H, J=1.2, 17.5), 5.74–5.88 (m, 1H), 6.25 (d, 1H, J=11.4 Hz), 6.31 (d, 1H, J=11.4 Hz), 6.39 (d, 1H, J=1.8 Hz), 7.46 (d, 1H, J=1.8 Hz), 7.77 (m, 2H), 8.02 (s, 1H).

Intermediate 42

Methyl 1-(2-amino-2-oxoethyl)-2-(3-bromopyridin-2-yl)-3-cyclohexyl-1H-indole-6-carboxylate. The desired product was prepared in 63% yield as a viscous clear oil by substituting Intermediate 39 and 2-bromoacetamide for Intermediate 7A and allyl bromide, respectively, in Intermediate 8A. MS m/z 470 (MH$^+$); $^1$H NMR (300 MHz, CD$_3$OD) δ 1.18–1.40 (m, 3H), 1.65–1.94 (m, 6H), 2.05 (m, 1H), 2.53 (m, J=11.16, 3.84 Hz, 1H), 3.94 (s, 3H), 4.55 (d, J=17.20 Hz, 1H), 4.70 (d, J=17.57 Hz, 1H), 7.50 (dd, J=8.23, 4.57 Hz, 1H), 7.81 (dd, J=8.42, 1.10 Hz, 1H), 7.90 (d, J=8.42 Hz, 1H), 8.13 (s, 1H), 8.28 (d, J=8.05 Hz, 1H), 8.72 (d, J=4.76 Hz, 1H).

Intermediate 46

Methyl 2-bromo-3-cyclohexyl-1-(2-ethoxy-2-oxoethyl)-1H-indole-6-carboxylate. The desired product was prepared by substituting Intermediate 5 and ethyl bromoacetate for Intermediate 7A and allyl bromide, respectively, in Intermediate 8A. ESI-MS m/z 422 (MH$^+$).

Intermediate 53

Methyl 3-cyclohexyl-2-(2-hydroxyphenyl)-1H-indole-6-carboxylate. A mixture of Intermediate 5 (600 mg, 1.79 mmol), Intermediate 52 (0.45 mL, 2.15 mmol), and LiCl (300 mg, 3.8 mmol) in 1N NaHCO$_3$ (6 mL), ethanol (12 mL), and toluene (12 mL) was degassed with a stream of argon. Pd(PPh$_3$)$_4$ (90 mg, 0.078 mmol) was added and the mixture was stirred at reflux for 18 hours. The mixture was diluted with ethyl acetate, washed with waster (3×) and brine, dried (Na$_2$SO$_4$), filtered, and concentrated. The concentrate was purified by flash column chromatography on silica gel with hexane/ethyl acetate (4/1) to provide the desired product as a colorless solid (450 mg, 72% yield).

ESI-MS m/z 349 (MH⁺); ¹H NMR (500 MHz, CDCl₃) δ 1.32 (m, 3H), 1.59 (m, 1H), 1.81 (s, 4H), 1.93 (m, 2H), 2.70 (t, J=12.05 Hz, 1H), 3.93 (s, 3H), 5.49 (s, 1H), 7.04 (m, 2H), 7.31 (d, J=6.71 Hz, 1H), 7.36 (t, J=7.48 Hz, 1H), 7.79 (d, J=7.93 Hz, 1H), 7.85 (m, 1H), 8.10 (s, 1H), 8.27 (s, 1H).

Intermediate 57A (E)-ethyl (3-(4-(1-aminocyclopentanecarboxamido)phenyl)acrylate. EEDQ (593 mg, 2.4 mmol) was added to a solution of (E)-ethyl 3-(4-aminophenyl)acrylate (417 mg, 2.18 mmol) and 1-(tert-butoxycarbonylamino)cyclopentanecarboxylic acid (500 mg, 2.18 mmol) in THF (6 mL). The solution was stirred at reflux for 3–4 hours. The mixture was concentrated and the residue partitioned between dichloromethane and water. The organic layer was washed sequentially with dilute HCl, water, and brine. The solution was dried over Na₂SO₄ and filtered. Dilution of the filtrate with hexanes resulted in the crystallization of (E)-ethyl 3-(4-(1-(tert-butoxycarbonylamino)cyclopentanecarboxamido)phenyl)acrylate as a pale yellow solid (360 mg, 37% yield). ESI-MS m/z 403 (MH⁺).

(E)-ethyl 3-(4-(1-(tert-butoxycarbonylamino)cyclopentanecarboxamido)-phenyl) acrylate (350 mg) was dissolved in dichloromethane (2 mL) at 22° C. TFA (2 mL) was added and stirring was continued for 2 hours. The solution was concentrated and the residue partitioned between ethyl acetate and dilute Na₂CO₃. The ethyl acetate layer was washed (water), dried (Na₂SO₄), filtered, and concentrated to provide the desired product as a crystalline solid: ¹H NMR (300 MHz, DMSO-d₆) δ 1.25 (t, J=6.95 Hz, 3H), 1.54 (m, 2H), 1.73 (m, 4H), 2.03 (m, 2H), 4.17 (q, J=6.95 Hz, 2H), 6.52 (d, J=16.10 Hz, 1H), 7.59 (d, J=15.74 Hz, 7.71 (m, 4H).

INTERMEDIATE 57B

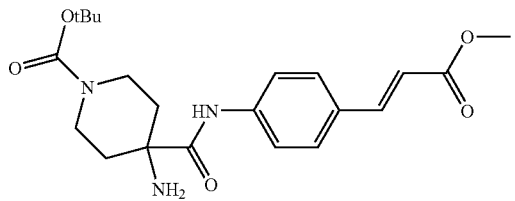

(E)-tert-butyl 4-amino-4-((4-(3-ethoxy-3-oxoprop-1-enyl)phenyl)carbamoyl)piperidine-1-carboxylate.

A solution of 4-((((9H-fluoren-9-yl)methoxy)carbonyl)amino)-1-(tert-butoxycarbonyl)piperidine-4-carboxylic acid (1.0 g, 2.14 mmol), (E)-ethyl 3-(4-aminophenyl)acrylate (409 mg, 2.12 mmol), and EEDQ (582 mg, 2.35 mmol) in THF (12 mL) was stirred at reflux for 1 hour. The reaction mixture was partitioned between ethyl acetate and water. The organic layer was washed sequentially with dilute HCl, water, and brine, dried over Na₂SO₄, filtered, and concentrated. The residue was purified by flash column chromatography on silica gel (40 g) with dichloromethane/ethyl acetate (100:15) to provide impure Fmoc-protected product as a cloudy oil (900 mg). A second purification by flash column chromatography on silica gel (40 g) with hexanes/ethyl acetate (100:20 to 1:1) provided the Fm-c-protected product as a colorless solid: ESI-MS m/z 640 (MH⁺); ¹H NMR (300 MHz, CDCl₃) δ 1.30 (t, J=7.14 Hz, 3H), 1.43 (s, 9H), 2.00 (m, 2H), 2.12 (m, 2H), 3.04 (m, 2H), 3.75 (m, J=13.91 Hz, 2H), 3.75 (d, J=13.91 Hz, 2H), 4.22 (q, J=6.95 Hz, 2H), 4.54 (d, J=5.86 Hz, 2H), 4.85 (s, 1H), 6.33 (d, J=16.10 Hz, 1H), 7.23 (m, 2H), 7.35 (t, J=7.50 Hz, 2H), 7.45 (s, 4H), 7.52 (d, J=7.68 Hz, 2H), 7.60 (d, J=16.10 Hz, 1H), 7.73 (d, J=7.68 Hz, 2H), 9.06 (s, 1H).

The preceding compound (350 mg) was dissolved in DMF (2 mL) at 22° C. An ethanolic solution of dimethylamine (0.5 mL of 33%) was added to water (0.5 mL). The resulting solution was added to the DMF solution. After about 1 hour the resulting precipitate was collected by filtration and washed with methanol followed by diethyl ether to provide the desired product (125 mg, 55% yield). ESI-MS m/z360(MH⁻); ¹H NMR (300 MHz, DMSO-d₆) δ 1.24 (t, J=7.14 Hz, 3H), 1.39 (m, 11H), 3.14 (s, 2H), 3.71 (s, 2H), 4.17 (q, J=6.95 Hz, 2H), 6.52 (d, J=15.74 Hz, 1H), 7.58 (d, J=16.10 Hz, 2H), 7.67 (d, J=8.78 Hz, 2H), 7.74 (m, 2H).

Intermediate 76

Methyl 2-bromo-1-(2-tert-butoxy-2-oxoethyl)-3-cyclohexyl-1H-indole-6-carboxylate. The desired product was prepared in 89% yield as a brown crystalline solid by substituting Intermediate 5 and tert-butyl bromoacetate for Intermediate 7A and allyl bromide, respectively, in Intermediate 8A. ESI-MS m/z 452 (MH⁺); ¹H NMR (500 MHz, DMSO-d₆) δ 1.44 (m, 12H), 1.73 (m, 3H), 1.85 (m, 2H), 1.94 (m, 2H), 2.87 (m, 1H), 3.88 (s, 3H), 5.12 (s, 2H), 7.68 (d, J=8.24 Hz, 1H), 7.84 (m, 1H), 8.16 (s, 1H).

Intermediate 77

Methyl 1-(2-tert-butoxy-2-oxoethyl)-2-(2-(tert-butoxycarbonylamino)phenyl)-3-cyclohexyl-1H-indole-6-carboxylate. Substitution of Intermediate 15 for 2-vinylphenylboronic acid in Example 7A provided a mixture of the desired product (60%) and methyl 1-(2-tert-butoxy-2-oxoethyl)-2-(2-aminophenyl)-3-cyclohexyl-1H-indole-6-carboxylate (40%) which was used directly in the next step. A sample of pure 72 was isolated from a similar experiment run on a smaller scale. ESI-MS m/z 563 (MH⁺); ¹H NMR (500 MHz, CDCl₃) δ 1.26 (m, 2H), 1.32 (s, 9H), 1.43 (m, 9H), 1.45–1.82 (m, 6H), 1.88 (m, 2H), 2.46 (m, 1H), 3.94 (s, 3H), 4.50 (d, J=5.80 Hz, 2H), 6.64 (s, 1H), 7.10 (m, 1H), 7.14 (m, 1H), 7.45 (m, 1H), 7.84 (m, 2H), 7.99 (s, 1H), 8.22 (d, J=8.24 Hz, 1H).

Intermediate 72

N-(1-cyanocyclopentyl)-13-cyclohexyl-7H-indolo[2,1-a][2]benzazepine-10-carboxamide. A solution of Example 15 (600 mg, 1.68 mmol) in DMF (8.4 mL) and DIPEA (1.75 mL, 10.1 mmol) was treated with TBTU (674 mg, 2.10 mmol). The resulting solution was stirred at 22° C. for 15 minutes, treated with 1-aminocyclopentanecarbonitrile (370 mg, 3.36 mmol), stirred at 22° C. for 18 hours, and treated with 1M HCl (25 mL). The aqueous layer was extracted with CHCl₃ (2×50 mL). The organic phase was dried over Na₂SO₄, filtered, and concentrated under reduced pressure. Purification by flash column chromatography on silica gel with 1:4 ethyl acetate/hexanes provided the desired product (612 mg, 81%) as a yellow oil. MS m/z 450 (MH⁺); ¹H NMR (300 MHz, CDCl₃) δ 1.12–1.65 (m, 6H), 1.80 (m, 2H), 1.87–1.99 (m, 4H), 2.05 (m, 2H), 2.24 (m, 2H), 2.58 (m, 2H), 2.86 (m, 1H), 4.18 (broad m, 1H), 4.89 (broad m, 1H), 6.35 (dd, J=11.4, 3.0 Hz 1H), 6.42 (s, 1 NH), 6.80 (d, J=11.4 Hz, 1H), 7.30 (dd, J=2.0, 4.0 Hz, 1H), 7.36 (m, 1H), 7.42 (m, 2H), 7.53 (m, 1H), 7.87 (dd, J=8.0, 2.0 Hz, 1H), 8.08 (d, J=2.0 Hz, 1H).

Intermediate 73

N-[1-[(Z)-amino(hydroxyimino)methyl]cyclopentyl]-13-cyclohexyl-7H-indolo[2,1-a][2]benzazepine-10-carboxamide. A solution of Intermediate 72 (290 mg, 0.645 mmol) in ethanol (6.4 mL) was treated with 50% aqueous $NH_2OH$ (0.085 mL, 1.29 mmol). The resulting solution was stirred at 90° C. for 3 hours. 1M HCl (15 mL) was added and the aqueous layer was extracted with $CHCl_3$ (2×30 mL). The organic phase was dried over $Na_2SO_4$, filtered, and concentrated under reduced pressure to provide the desired product (299 mg, 96%) as a yellow oil. MS m/z 483 (MH$^+$); $^1$H NMR (300 MHz, CD$_3$OD) δ 1.13–1.61 (m, 6H), 1.72–2.29 (m, 10H), 2.40 (m, 2H), 2.88 (m, 1H), 4.22 (broad m, 1H), 5.10 (broad m, 1H), 6.48 (dd, J=11.4, 3.0 Hz 1H), 6.90 (d, J=11.4 Hz, 1H), 7.39–7.52 (m, 3H), 7.56 (m, 2H), 7.88 (dd, J=8.0, 2.0 Hz, 1H), 8.17 (d, J=2.0 Hz, 1H).

EXAMPLE 1

(Compound 9, $R^2$=H)(EC$_{50}$=C*)

Methyl 13-cyclohexyl-7H-indolo[2,1-a][2]benzazepine-10-carboxylate. Grubbs 2$^{nd}$ Generation catalyst (85 mg, 0.1 mmol) was added to a solution of Example 8A (800 mg, 2.0 mmol) in 100 mL of dichloromethane under Ar. The mixture was stirred at reflux for 3 hours. After removal of the solvent, the residue was purified by flash column chromatography on silica gel with dichloromethane/hexanes (1:2) to give 520 mg (70%) of the desired product as a colorless solid. ESI-MS m/z 371 (MH$^+$); $^1$H NMR (500 MHz, CDCl$_3$) δ 0.97–2.11 (m, 10H), 2.86 (m, 1H), 3.95 (m, 3H), 4.21 (s, 1H), 4.91 (s, 1H), 6.29 (m, 1H), 6.82 (d, J=10.38 Hz, 1H), 7.37 (m, 1H), 7.43 (m, 2H), 7.54 (m, 1H), 7.72 (dd, J=8.55, 1.22 Hz, 1H), 7.88 (d, J=8.55 Hz, 1H), 8.15 (s, 1H).

EXAMPLE 2

(Compound 10, $R^2$=H)(IC$_{50}$=A*, EC$_{50}$=C*)

Methyl 13-cyclohexyl-6,7-dihydro-5H-indolo[2,1-a][2]benzazepine-10-carboxylate. Method A: Palladium on carbon (60 mg of 10%) was added to a solution of Example 1 (60 mg, 0.16 mmol) in 60 mL of ethanol and 10 mL of ethyl acetate. The reaction vessel was flushed with $H_2$. The resulting mixture was stirred at room temperature under an atmosphere of hydrogen (balloon pressure) for 4 hours. The mixture was filtered and concentrated to provide the desired product (60 mg, 100% yield) as a colorless solid. ESI-MS m/z 373 (MH$^+$); $^1$H NMR (500 MHz, CDCl$_3$) δ 1.22 (m, 1H), 1.39 (m, 2H), 1.65 (m, J=12.51 Hz, 1H), 1.76 (d, J=8.85 Hz, 2H), 1.91 (d, J=11.90 Hz, 1H), 1.91 (d, J=11.90 Hz, 1H), 2.06 (m, 3H), 2.38 (m, 1H), 2.56 (m, 1H), 2.68 (dd, J=13.43, 6.71 Hz, 1H), 2.91 (m, 1H), 3.70 (m, 1H), 3.97 (m, 3H), 4.43 (dd, J=14.34, 6.71 Hz, 1H), 7.35 (m, 4H), 7.73 (dd, J=8.54, 1.53 Hz, 1H), 7.87 (d, J=8.54 Hz, 1H), 8.08 (s, 1H).

Method B: Tetrakis(triphenylphosphine)palladium(0)(11 mg, 0.01 mmol) was added to a mixture, under argon, of Intermediate 22 (21.9 mg, 0.048 mmol) and potassium acetate (4.7 mg, 0.048 mmol) in N,N-dimethylacetamide (0.6 mL) in a microwave vial. The mixture was microwaved for 30 minutes at 150° C. The reaction mixture was diluted with DMF and filtered. The filtrate was injected on a Shimadzu preparatory liquid chromatograph. The methanol eluent was removed from the appropriate fraction. The aqueous mixture was extracted with ethyl acetate. The extract was washed (water, brine), dried ($Na_2SO_4$), filtered, and concentrated to provide the desired product.

EXAMPLE 3

(Compound 11, $R^2$=H) (IC$_{50}$=B*, EC$_{50}$=E*)

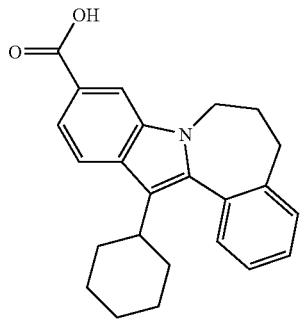

13-cyclohexyl-6,7-dihydro-5H-indolo[2,1-a][2]benzazepine-10-carboxylic acid. Example 2 (60 mg, 0.16 mmol) was dissolved in a mixture of 1 mL each of THF, methanol, and 1N NaOH. The mixture was microwaved at 100° C. for 10 minutes. After removal of the organic solvents, the mixture was acidified with dilute HCl and the precipitated solid was extracted into ethyl acetate. Removal of the solvent and crystallization of the residue from methanol provided the desired product as a pale yellow solid. $^1$H NMR (300 MHz, DMSO-d$_6$) δ 1.07–2.10 (m, 10H), 2.34 (m, 2H), 2.60–2.90 (m, 2H), 3.19–3.65 (m, 2H), 4.58 (d, J=8.78 Hz, 1H), 7.41 (m, 4H), 7.60 (m, 1H), 7.86 (d, J=8.42 Hz, 1H), 8.12 (s, 1H), 12.57 (s, 1H).

EXAMPLE 4

(Compound 9, $R^2$=3-PhCH$_2$O—)(EC$_{50}$=C*)

Methyl 13-cyclohexyl-3-benzyloxy-7H-indolo[2,1-a][2]benzazepine-10-carboxylate. The desired product was prepared as colorless crystals by substituting Example 8B for Example 8A in Example 1 and recrystallizing from methanol (80% yield). $^1$H NMR (500 MHz, CDCl$_3$) δ 1.59 (m, 10H), 2.84 (m, 1H), 3.90 (m, 3H), 4.21 (s, 1H), 4.90 (s, 1H), 5.15 (s, 2H), 6.29 (m, 1H), 6.76 (d, J=10.38 Hz, 1H), 6.96 (d, J=2.75 Hz, 1H), 7.06 (m, 1H), 7.42 (m, 6H), 7.72 (m, 1H), 7.86 (d, J=8.55 Hz, 1H), 8.14 (s, 1H).

EXAMPLE 5

(Compound 10, $R^2$=3-OH) (EC$_{50}$=C*)

Methyl 13-cyclohexyl-3-hydroxy-6,7-dihydro-5H-indolo[2,1-a][2]benzazepine-10-carboxylate. Example 4 (87 mg) was added to a mixture of THF (10 mL) and methanol (10 mL) in a Parr bottle under argon. Palladium on carbon (30 mg of 10%) was added and the mixture shaken with $H_2$ at 50 psi for 3 hours. Removal of the catalyst left a residue which when macerated with hexanes provided the desired product as a colorless solid. $^1$H NMR (500 MHz, CDCl$_3$) δ 1.40–2.02 (m, 10H), 2.35 (m, 1H), 2.56 (m, 2H), 2.87 (m, 1H), 3.69 (m, 1H), 3.97 (m, 3H), 4.42 (m, 1H), 5.03 (m, 1H), 6.84 (m, 2H), 7.26 (m, 1H), 7.73 (m, 1H), 7.85 (d, J=8.55 Hz, 1H), 8.07 (s, 1H).

EXAMPLE 6

(IC$_{50}$=A*, EC$_{50}$=C*)

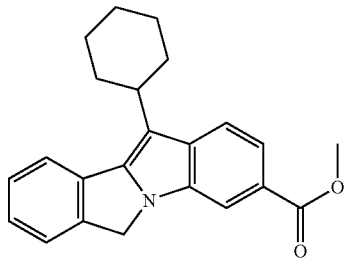

Methyl 11-cyclohexyl-6H-isoindolo[2,1-a]indole-3-carboxylate. Palladium acetate (40 mg, 0.18 mmol) was added to a mixture, under argon, of Intermediate 22A (130 mg, 0.31 mmol) and potassium acetate (61 mg, 0.62 mmol) in N,N-dimethylacetamide (3 mL) in a microwave vial. The mixture was microwaved for 20 minutes at 160° C. The reaction mixture was diluted with ethyl acetate, washed (3× with water, 1× with brine), dried (MgSO$_4$), filtered, and concentrated to provide a black residue. A solution of the residue in dichloromethane was applied to a silicic acid thick layer plate. The plate was eluted with hexanes/ethyl acetate (95:5), dried, and eluted again with hexanes/ethyl acetate (90:10). The band containing the product was extracted with dichloromethane. The solvent was removed and the residue crystallized from methanol to provide the desired product. ESI-MS m/z 346 (MH$^+$), $^1$H NMR (300 MHz, CDCl$_3$) δ 1.45 (m, 3H), 1.92 (m, 7H), 3.18 (m, 1H), 3.92 (s, 3H), 5.07 (s, 2H), 7.30 (t, J=7.50 Hz, 1H), 7.43 (m, 2H), 7.84 (d, J=7.32 Hz, 1H), 8.03 (s, 1H).

EXAMPLE 7

(IC$_{50}$=B*, EC$_{50}$=C*)

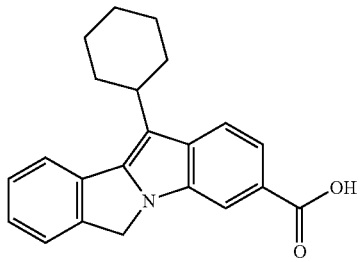

11-cyclohexyl-6H-isoindolo[2,1-a]indole-3-carboxylic acid. A mixture of Example 6 in ethanol (8 mL) and 1N NaOH (2.0 mL) was stirred at reflux for 1 hour and cooled to room temperature. The solution was acidified with 1N HCl (2.1 mL) and partially concentrated. The precipitated solid was collected by filtration, washed with water, dissolved in methanol, and filtered. The filtrate was concentrated by boiling to about 0.4 mL, and diluted with diethyl ether. The resulting precipitate was collected by filtration to provide the desired product as a colorless solid. ESI-MS, both positive and negative ion consistent for MW 331, $^1$H NMR (500 MHz, CD$_3$OD) δ 1.42 (m, 3H), 1.86 (m, 7H), 3.14 (m, J=12.05, 12.05 Hz, 1H), 5.01 (s, 2H), 7.21 (t, J=7.48 Hz, 1H), 7.32 (t, J=7.48 Hz, 1H), 7.44 (d, J=7.63 Hz, 1H), 7.58 (s, 2H), 7.73 (d, J=7.63 Hz, 1H), 7.89 (s, 1H), 7.89 (s, 1H).

EXAMPLE 8

(IC$_{50}$=A*, EC$_{50}$=D*)

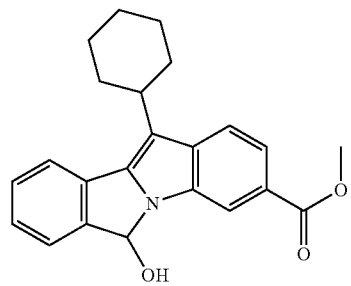

Methyl 11-cyclohexyl-6-hydroxy-6H-isoindolo[2,1-a]indole-3-carboxylate. The desired product was prepared as a tan crystalline solid by substituting 2-formylphenylboronic acid for 2-vinylphenylboronic acid in Intermediate 7A (83% yield). The compound exists as the hemi-animal as shown by the spectral data. ESI-MS m/z 360 (MH$^-$), $^1$H NMR (300 MHz, DMSO-d$_6$) δ 1.49 (m, 3H), 1.83 (m, J=13.17 Hz, 7H), 3.21 (m, 1H), 3.88 (m, 3H), 6.64 (m, 1H), 7.28 (d, J=8.78 Hz 1H), 7.40 (t, J=7.14 Hz, 1H), 7.52 (t, J=7.14 Hz, 1H), 7.62 (m, 2H), 7.83 (m, 2H), 8.21 (s, 1H).

EXAMPLE 9

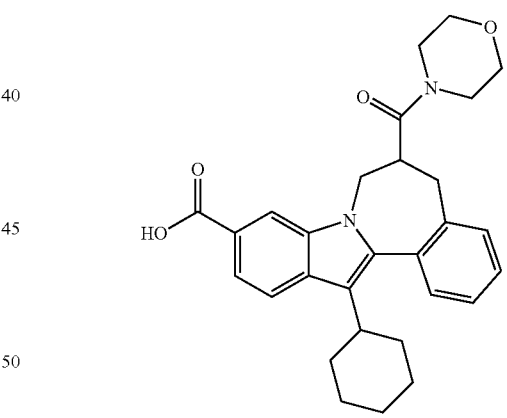

(±)-13-Cyclohexyl-6,7-dihydro-6-(morpholinylcarbonyl)-5H-indolo[2,1-a][2]benzazepine-10-carboxylic acid. TBTU (69 mg, 0.22 mmol) was added to a stirred solution of racemic 14b (60 mg, 0.0.144 mmol), morpholine (19 μL, 0.22 mmol), and N,N-diisopropylethylamine (300 μL, 1.7 mmol) in DMF (3 mL). The mixture was shaken at 22° C. for 18 hr. The resulting solution was injected on a Shimadzu preparative liquid chromatograph. The product containing fraction was concentrated on a Speed Vac® to leave methyl 13-cyclohexyl-6,7-dihydro-6-(morpholinylcarbonyl)-5H-indolo[2,1-a][2]benzazepine-10-carboxylate as a colorless solid (60 mg, 86%). ESI-MS m/z 487 (MH$^+$).

Sodium hydroxide (200 μL, 0.2 mmol) was added to a solution of the preceding methyl ester (60 mg, 0.127 mmol)

in methanol (1.2 mL) and tetrahydrofuran (1.2 mL) in a microwave vial. The vial was sealed and the contents heated at 90° C. for 10 min in a microwave apparatus, at which time the vial was cooled and additional NaOH was added (200 μL, 0.2 mmol). The solution was heated for another 5 min at 90° C. when LC/MS showed complete hydrolysis of the ester. The solution was acidified with dilute hydrochloric acid to precipitate the crude acid. The solid was collected and purified on the Shimadzu preparative liquid chromatograph. The product containing fraction was concentrated on a Speed Vac® to leave the titled compound as a colorless solid (50 mg, 83%). ESI-MS m/z 473 (MH+), $^1$H NMR (500 MHz, CD$_3$OD) δ 1.24–1.35 (m, 1 H), 1.40–1.55 (m, 2 H), 1.60–1.68 (m, 1 H), 1.77–2.22 (m, 6 H), 2.76 (m, 1 H), 2.88–3.04 (m, 1 H), 3.44–3.51 (m, 1 H), 3.58–3.93 (m, 9 H), 4.47–4.59 (m, 1 H), 4.89 (m, 1 H), 7.31–7.43 (m, 1 H), 7.47 (m, 3 H), 7.72 (m, 1 H), 7.88 (m, 1 H), 8.16 (m, 1 H).

Optical resolution of (±)-13-Cyclohexyl-6,7-dihydro-6-(morpholinylcarbonyl)-5H-indolo[2,1-a][2]benzazepine-10-carboxylic acid. A solution of the racemic acid (1.7 mg) in ethanol (1 mL) was injected on a Chiralpak® AD column (20×250 mm, 5 μm). The column was eluted with a mixture of 70% heptane and 30% ethanol at a flow rate of 10 mL/min for 60 min to give a complete separation of the enantiomers. A total of three injections were made. The fractions containing the enantiomers were combined and concentrated to provide the isomers as colorless solids. Enantiomer 1 (2.5 mg), retention time 14.5 min, ESI-MS m/z 487 (MH+); enantiomer 2 (2.5 mg), retention time 42.8 min, ESI-MS m/z 487 (MH+).

EXAMPLE 10

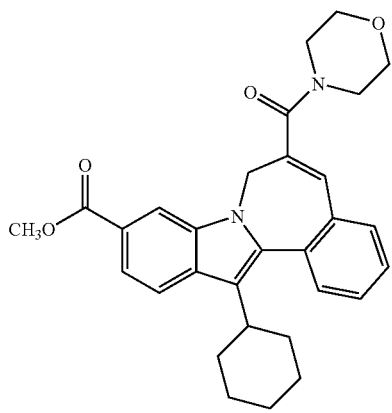

Methyl 13-cyclohexyl-6-(morpholinylcarbonyl)-5H-indolo[2,1-a][2]benzazepine-10-carboxylate. TBTU (145 mg, 0.45 mmol) was added to a stirred solution of 14a (R=H, 125 mg, 0.30 mmol), morpholine (26 μL, 0.30 mmol), and N,N-diisopropylethylamine 200 μL, 1.15 mmol) in DMF (2 mL). The mixture was stirred at 22° C. for 20 min. The resulting solution was injected on a Shimadzu preparative liquid chromatograph. The product containing fraction was concentrated on a Speed Vac® to leave methyl 13-Cyclohexyl-6-(morpholinylcarbonyl)-5H-indolo[2,1-a][2]benzazepine-10-carboxylic acid as a yellow solid (64 mg, 44%). ESI-MS m/z 487 (MH+), $^1$H NMR (500 MHz, CDCl$_3$) δ 1.21 (m, 1 H), 1.34–1.55 (m, 3 H), 1.77 (m, 2 H), 1.91 (m, 1 H), 2.06 (m, 3 H), 2.83 (m, 1 H), 2.97–3.85 (m, 8 H), 3.97 (s, 3 H), 4.45 (m, 1 H), 5.07 (m, 1 H), 6.89 (s, 1 H), 7.41 (d, 1 H), 7.49 (m, 2 H), 7.57 (m, 1 H), 7.75 (m, 1 H), 7.89 (d, J=8.55 Hz, 1 H), 8.15 (s, 1 H).

EXAMPLE 11

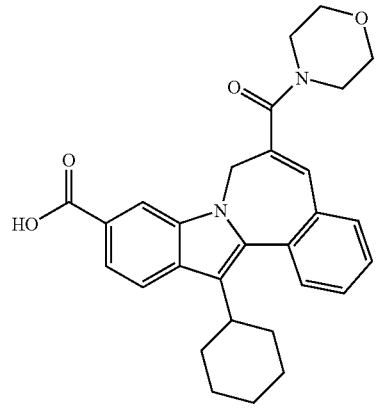

13-Cyclohexyl-6-(morpholinylcarbonyl)-5H-indolo[2,1-a][2]benzazepine-10-carboxylic acid. Sodium hydroxide (84 μL, 0.084 mmol) was added to a solution of the preceding methyl ester (25 mg, 0.052 mmol) in methanol (0.5 mL) and tetrahydrofuran (0.5 mL) in a microwave vial. The vial was sealed and the contents heated at 90° C. for 15 min in a microwave apparatus. The solution was acidified with dilute hydrochloric acid to precipitate the crude acid. The solid was collected and purified on the Shimadzu preparative liquid chromatograph. The product containing fraction was concentrated on a Speed Vac® to leave the titled compound as a colorless solid (17.3 mg, 71%). ESI-MS m/z 471 (MH+), $^1$H NMR (500 MHz, DMSO-D6) δ 1.14 (m, 1 H), 1.43 (m, 3 H), 1.70 (m, 2 H), 1.89 (m, 1 H), 2.05 (m, 3 H), 2.79 (t, J=15.87 Hz, 1 H), 3.49 (m, 8 H), 4.27 (m, 1 H), 5.17 (m, 1 H), 7.01 (s, 1 H), 7.52–7.65 (m, 5 H), 7.90 (d, J=8.55 Hz, 1 H), 8.21 (s, 1 H), 12.62 (s, 1 H).

EXAMPLE 12

Compound 28

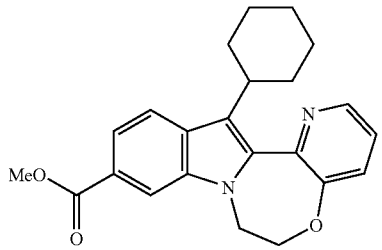

Methyl 13-cyclohexyl-6,7-dihydropyrido[2',3':6,7][1,4]oxazepino[4,5-a]indole-10-carboxylate Methyl 13-cyclohexyl-6,7-dihydropyrido[2',3':6,7][1,4]oxazepino[4,5-a]indole-10-carboxylate. A mixture of Intermediate 27 (174 mg, 0.38 mmol), potassium acetate (75 mg, 0.76 mmol), Pd(PPh$_3$)$_4$ (22 mg, 0.019 mmol), and dimethylacetamide (2 mL) in a sealed tube was heated at 160° C. for 5 hours. The mixture was filtered and the solid was washed with ethyl acetate. The filtrate was concentrated and the residue was purified on a Shimadzu preparatory liquid chromatograph to provide the desired product as a light yellow solid (60 mg, 42% yield). MS m/z 377(MH+); $^1$H NMR (300 MHz, CDCl$_3$) δ 1.30–1.65 (m, 5H), 1.69–2.07 (m, 5H), 3.40 (m, 1H), 3.91 (m, 3H), 4.35 (m, 2H), 4.54 (t, J=5.49 Hz, 2H), 7.28 (dd, J=8.23, 4.57 Hz, 1H), 7.49 (dd, J=8.42, 1.46 Hz, 1H), 7.73 (dd, J=8.42, 1.10 Hz, 1H), 7.92 (d, J=8.42 Hz, 1H), 8.05 (s, 1H), 8.54 (dd, J=4.76, 1.46 Hz, 1H).

EXAMPLE 13

(Compound 29)(EC$_{50}$=E*)

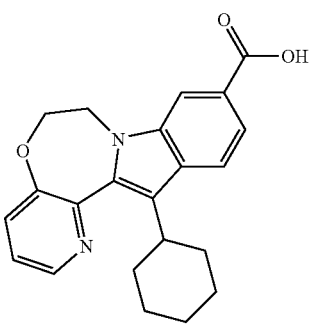

13-cyclohexyl-6,7-dihydropyrido[2',3':6,7][1,4]oxazepino[4,5-a]indole-10carboxylic acid. Sodium hydroxide (1.0 mL of 2N) was added to a solution of Example 9 (60 mg, 0.16 mmol) in THF/methanol (1.5 mL each). The mixture was microwaved at 100° C. for 15 minutes. The mixture was partially concentrated. The pH of the aqueous residue was adjusted to 4–5 with 1N HCl. The solid was collected by filtration and dried to provide the desired product (58 mg, 100% yield) as a pale yellow solid. MS m/z 363(MH+); $^1$H NMR (500 MHz, CD$_3$OD) δ 1.42 (m, 3H), 1.80 (m, 1H), 1.84–1.94 (m, 4H), 2.01–2.13 (m, 2H), 3.34 (m, 1H), 4.50 (t, J=5.49 Hz, 2H), 4.59 (t, J=5.49 Hz, 2H), 7.54 (dd, J=8.24, 4.88 Hz, 1H), 7.74–7.80 (m, 2H), 7.98 (d, J=8.24 Hz, 1H), 8.24 (s, 1H), 8.58 (dd, J=4.88, 1.53 Hz, 1H); $^{13}$C NMR (500 MHz, CD$_3$OD) δ 26.4, 27.3, 33.1, 36.3, 41.3, 74.7, 111.6, 120.0, 121.3, 122.7, 124.5, 124.9, 130.5, 132.0, 134.8, 135.9, 144.5, 145.4, 151.8, 170.0.

EXAMPLE 14

(Compound 45)(IC$_{50}$=A*, EC$_{50}$=C*)

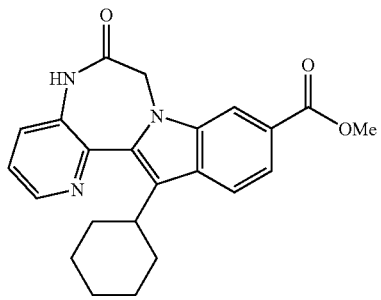

Methyl 13-cyclohexyl-6,7-dihydro-6-oxo-5H-pyrido[3',2':5,6][1,4]diazepino[1,7-a]indole-10-carboxylate. Intermediate 42 (500 mg, 1.06 mmol), Xanphos (92 mg, 0.16 mmol), Pd$_2$(dba)$_3$ (97 mg, 0.106 mmol), and Cs$_2$CO$_3$ (518 mg, 1.59 mmol) were added to a microwave reactor tube. The tube was flushed with nitrogen, sealed, and treated with 1,4 dioxane (10 mL). The mixture was heated at 100° C. for 5 hours in the microwave reactor. The mixture was cooled to room temperature, diluted with water, and extracted with ethyl acetate (2×75 mL). The organic layers were combined, dried (MgSO$_4$), filtered, and concentrated. The residue was purified by SiO$_2$ chromatography (Horizon™ HPFC system) using 2% ethyl acetate/hexanes to 60% ethyl acetate/hexanes to provide the desired product as a yellow solid(235 mg, 57% yield). MS m/z 390 (MH+); $^1$H NMR (500 MHz, CD$_3$OD) δ 1.30–1.51 (m, 3H), 1.11–1.98 (m, 5H), 2.01–2.17 (m, 2H), 3.44 (m, 1H), 4.00 (s, 3H), 4.61 (s, 2H), 7.52 (dd, J=8.24, 4.58 Hz, 1H), 7.68 (dd, J=8.24, 1.53 Hz, 1H), 7.80 (m, 1H), 8.01 (d, J=8.55 Hz, 1H), 8.32 (s, 1H), 8.64 (dd, J=4.73, 1.37 Hz, 1H).

EXAMPLE 15

(IC$_{50}$=B*, EC$_{50}$=D*)

13-cyclohexyl-6,7-dihydro-6-oxo-5H-pyrido[3',2':5,6][1,4]diazepino[1,7-a]indole-10-carboxylic acid. A solution of Example 11 (180 mg, 0.462 mmol) in pyridine (7 mL) was treated with LiI (186 mg, 1.39 mmol), heated at 180° C. in a microwave reactor for 2.5 hours, diluted with water, and adjusted to pH 4–5 with 1N HCl. The precipitate was collected by filtration to provide the desired product as a pale brown solid (170 mg, 98% yield). MS m/z 376 (MH+); $^1$H NMR (500 MHz, DMSO-d$_6$) δ 1.22–1.43 (m, 3H), 1.69–1.85 (m, 5H), 1.93–2.04 (m, 2H), 3.37 (m, 1H), 4.90 (s, 2H), 7.52 (dd, J=8.24, 4.58 Hz, 1H), 7.65 (dd, J=8.24, 1.53 Hz, 1H), 7.69 (dd, J=8.39, 1.37 Hz, 1H), 7.97 (d, J=8.55 Hz, 1H), 8.27 (s, 1H), 8.62 (dd, J=4.58, 1.53 Hz, 1H), 10.44 (s, 1H).

EXAMPLE 16

(IC$_{50}$=A*, EC$_{50}$=C*)

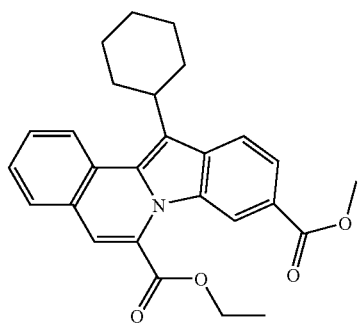

6-ethyl-9-methyl-12-cyclohexyl-indolo[2,1-a]isoquinoline-6,9-dicarboxylic acid. A mixture of Intermediate 46 (43 mg, 0.01 mmol), 2-formylphenylboronic acid (18 mg, 0.12 mmol), and [(Ph)$_3$P]$_4$Pd (12 mg, 0.01 mmol) in Na$_2$CO$_3$ (1.2 mL of 1N), ethanol (2 mL), and toluene (2 mL) was stirred at reflux for 18 hours. The mixture was partitioned between ethyl acetate and water. The ethyl acetate layer was washed (water), dried (Na$_2$SO$_4$), filtered, and concentrated. The crude product was purified by flash column chromatography on SiO$_2$ with hexanes-ethyl acetate (4:1) followed by a final purification on the Shimadzu preparatory HPLC using a gradient of 30% methanol/water containing 0.1% TFA to 100% methanol during 12 minutes at a flow rate of 40 mL per

EXAMPLE 17

Compound 54

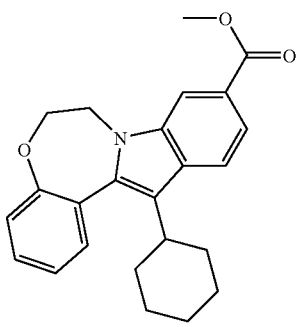

Methyl 13-cyclohexyl-6,7-dihydroindolo[1,2-d][1,4]benzoxazepine-10-carboxylate. BEMP (0.155 mL, 0.5 mmol), and 1,2-dibromoethane (21 μL, 0.24 mmol) were added to a solution of Intermediate 53 (70 mg, 0.2 mmol) in DMF (6 mL). The solution was microwaved for 20 minutes at 120° C. and cooled to room temperature. The mixture was diluted with ethyl acetate, washed with water (3×), brine (3×), dried over $Na_2SO_4$, filtered, and concentrated. The product was purified by flash column chromatography on silica gel with hexanes/ethyl acetate (10:1) to provide the desired product as a colorless solid (60 mg, 80% yield). ESI-MS m/z 375 (MH$^+$); $^1$H NMR (500 MHz, CDCl$_3$) δ 1.38 (m, 3H), 1.60 (m, 1H), 1.86 (m, 4H), 2.06 (m, 2H), 2.97 (m, 1H), 3.93 (s, 3H), 4.30(t, J=5.5 Hz, 2H), 4.51 (t, J=5.5 Hz, 2H), 7.24 (m, 1H), 7.30 (m, 1H), 7.42 (m, 2H), 7.76 (d, J=8.5 Hz, 1H), 7.89 (d, J=8.5 Hz, 1H), 8.07 (s, 1H).

EXAMPLE 18

(Compound 62)(IC$_{50}$=A*, EC$_{50}$=D*)

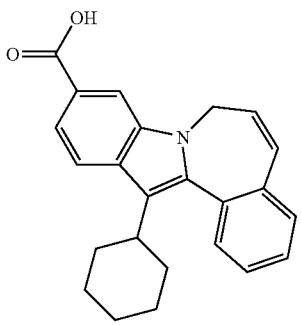

13-cyclohexyl-7H-indolo[2,1-a][2]benzazepine-10-carboxyiic acid. A mixture of Example 1 (371 mg, 1 mmol) in THF (4 mL), methanol (3 mL), and 1.7M LiOH (3 mL, 5.1 mmol) was stirred at reflux for 1.5 hours. The mixture was cooled to room temperature, diluted with water, and acidified with dilute HCl. The resulting precipitate was collected by filtration, washed with cold water, and dried to provide 324 mg of the desired product (91% yield). ESI-MS m/z 358 (MH$^+$); $^1$H NMR (300 MHz, DMSO-d$_6$) δ 1.37–2.05 (m, 10H), 2.78 (m, 1H), 4.06 (s, 1H), 5.17 (s, 1H), 6.39 (m, 1H), 6.89 (d, J=10.61 Hz, 1H), 7.50 (m, 4H), 7.60 (m, 1H), 7.88 (d, J=8.78 Hz, 1H), 8.24 (s, 1H), 12.59, (s, 1H).

EXAMPLE 19

(Compound 64) (IC$_{50}$=B*, EC$_{50}$=E*)

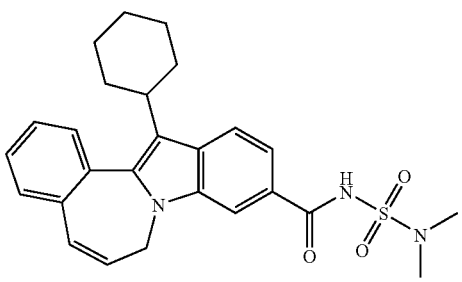

13-cyclohexyl-N-(dimethylaminosulfonyl)-7H-indolo[2,1-a][2]benzazepine-10-carboxamide. A mixture of Example 15 (50 mg, 0.14 mmol), N,N-dimethylsulfamide (21 mg, 0.17 mmol), 4-(dimethylamino)pyridine (17 mg, 0.14 mmol), and 1-[3-(dimethylamino)propyl]-3-ethylcarbodiimide hydrochloride (40 mg, 0.21 mmol) in dichloromethane (1 mL) and DMF (1 mL) was stirred for 18 hours at 22° C. The mixture was poured into ethyl acetate and dilute aqueous acetic acid. The ethyl acetate layer was washed (water, brine), dried (Na$_2$SO$_4$), filtered, and concentrated. The residue was crystallized from ethyl acetate to provide the desired product (17 mg, 26% yield) as pale yellow crystals. ESI-MS m/z 358 (MH$^+$); $^1$H NMR (300 MHz, CDCl$_3$) δ 1.20–2.30 (m, 10H), 2.81 (m, 1H), 3.05 (s, 3H), 3.47 (m, 2H), 4.11 (m, 1H,) 4.89 (s, 1H), 6.27 (m, 1H), 6.80 (d, J=10.61 Hz, 1H), 7.38 (m, 4H), 7.51 (m, 1H), 7.89 (d, J=8.42 Hz, 1H), 8.02 (s, 1H), 8.75 (s, 1H).

EXAMPLE 20

(Compound 78)(IC$_{50}$=A*, EC$_{50}$=D*)

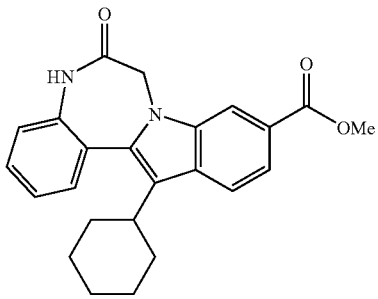

Methyl 13-cyclohexyl-6,7-dihydro-6-oxo-5H-indolo[]1,2-d][1,4]benzodiazepine-10-carboxylate. The mixture described in Intermediate 77 (7.1 g) was dissolved in TFA (30 mL) and dichloromethane (30 mL). The solution was stirred for 1 hour at 22° C. and concentrated. LC/MS showed that about 8% of the non-cyclized tert-butyl ester remained. The residual red gum was dissolved in neat TFA (30 mL). The solution was stirred for 1 hour at 55° C. and concentrated to dryness. Acetic acid (50 mL) was added and the flask was immersed in a hot oil bath (120° C.) for 3 minutes. The resulting crysallized product was collected by filtration, and washed with acetic acid and diethyl ether (2×) to provide 4.1 g of the desired product. ESI-MS m/z 389 (MH$^+$), $^1$H NMR (500 MHz, CDCl$_3$) δ 1.44 (m, 2H), 1.63 (m, 2H), 1.81 (m, 2H), 1.96 (m, 1H), 2.07 (m, 3H), 2.92 (m, 1H), 3.97 (m, 3H), 4.53 (m, 1H), 5.03 (m, 1H), 7.17 (d, J=7.93 Hz, 1H), 7.39 (m, 1H), 7.48 (m, 1H), 7.57 (d, J=7.93 Hz, 1H), 7.60 (s, 1H), 7.81 (d, J=8.55 Hz, 1H), 7.92 (d, J=8.54 Hz, 1H), 8.24 (s, 1H).

EXAMPLE 21

(Compound 80)(IC$_{50}$=B*, EC$_{50}$=E*)

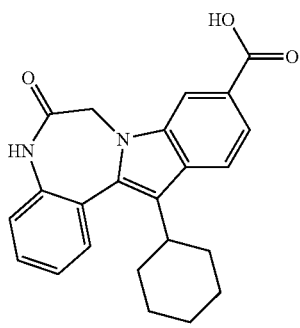

13-cyclohexyl-6,7-dihydro-6-oxo-5H-indolo[1,2-d][1,4]benzodiazepine-10-carboxylic acid. Example 17 (200 mg) was dissolved in a mixture of methanol (6 mL) and THF (6 mL). NaOH (3 mL of 1N) was added and the mixture was microwaved at 100° C. for 15 minutes. The mixture was cooled to room temperature, acidified with 1N HCl, and extracted with ethyl acetate. The ethyl acetate solution was washed with 1N HCl (3×) and concentrated. Acetic acid (5 mL) was added to the residue. The mixture was heated at 80° C. for 1 hour, during which time the desired product crystallized. The solid was collected by filtration and washed with methanol (2×) to provide the desired product as a colorless solid (150 mg, 78% yield). ESI-MS m/z 375 (MH$^+$); $^1$H NMR (500 MHz, DMSO-d$_6$) δ 1.19 (m, 2H), 1.43 (m, 2H), 1.53 (m, 1H), 1.78 (m, 2H), 2.04 (m, 3H), 2.88 (m, 1H), 4.55 (d, J=14.65 Hz, 1H), 5.07 (d, J=14.95 Hz, 1H), 7.31 (d, J=7.93 Hz, 1H), 7.41 (m, 1H), 7.54 (m, 1H), 7.70 (d, J=8.24 Hz, 1H), 7.96 (d, J=8.55 Hz, 1H), 8.26 (s, 1H), 10.37 (s, 1H), 12.34 (s, 1H).

EXAMPLE 22

(IC$_{50}$=B*, EC$_{50}$=E*)

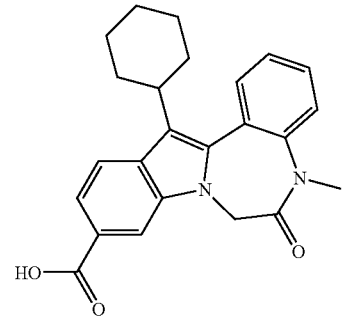

13-cyclohexyl-6,7-dihydro-6-oxo-5-methyl-5H-indolo[1,2-d][1,4]benzodiazepine-10-carboxylic acid. Iodomethane (1.7 μL, 0.027 mmol) was added to a stirred mixture of BEMP (8.2 μL, 0.027 mmol) and Example 17 (8.6 mg, 0.022 mmol) in DMF (1 mL) at room temperature. Stirring was continued for 20 minutes when LC/MS indicated that the alkylation was completed. The DMF solution was injected on a Shimadzu preparatory liquid chromatograph. The appropriate fraction from the chromatography was concentrated to provide the alkylated ester. ESI-MS m/z 403 (MH$^+$).

Hydrolysis of the ester following the procedure described in Example 18 provided the desired product as a colorless film. ESI-MS m/z 389 (MH$^+$); $^1$H NMR (500 MHz, CD$_3$OD) δ 1.27–1.39 (m, 1H), 1.44–1.59 (m, 2H), 1.61–1.72 (m, 1H), 1.79–1.92 (m, 2H), 1.95–2.04 (m, 1H), 2.05–2.24 (m, 3H), 2.97–3.08 (m, 1H), 3.36 (s, 3H), 4.52 (d, J=14.65 Hz, 1H), 5.06 (d, J=14.65 Hz, 1H), 7.47–7.53 (m, 1H), 7.60–7.68 (m, 3H), 7.79 (d, J=8.55 Hz, 1H), 7.95 (d, J=8.55 Hz, 1H), 8.30 (s, 1H).

EXAMPLE 23

(IC$_{50}$=A*, EC$_{50}$=E*)

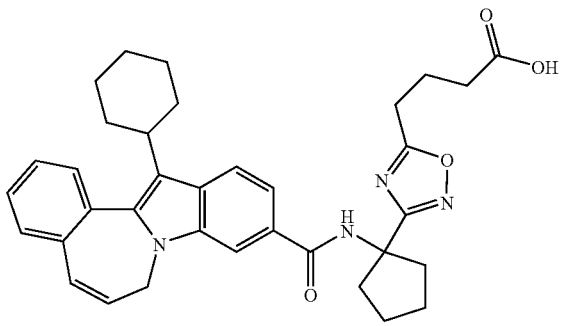

3-[1-[[(13-cyclohexyl-7H-indolo[2,1-a][2]benzazepin-10-yl)carbonyl]amino]cyclopentyl]-1,2,4-oxadiazole-5-butanoic acid. A solution of Intermediate 73 (20.0 mg, 0.041 mmol) in CHCl$_3$ (0.50 mL) and DIPEA (0.036 mL, 0.207 mmol) was treated with dihydro-3H-pyran-2,6-dione (10.0 mg, 0.082 mmol). The resulting mixture was stirred in a sealed tube in an Emrys microwave at 130° C. for 15 minutes. 1M HCl (10 mL) was added and the aqueous layer was extracted with CHCl₃ (2×20 mL). The organic phase was dried over Na₂SO₄, filtered, and concentrated under reduced pressure. Purification by flash column chromatography on silica gel with 1:3 ethyl acetate/hexanes provide the desired product (13 mg, 52%) as a yellow paste. MS m/z 579 (MH⁺); ¹H NMR (300 MHz, CDCl₃) δ 1.16–1.62 (m, 6H), 1.77 (m, 2H), 1.91–2.02 (m, 4H), 2.11 (m, 2H), 2.16 (t, J=2.0, 14.0, 14.0 Hz, 2H), 2.29 (m, 2H), 2.52 (m, 2H), 2.64 (m, 2H), 2.83 (m, 1H), 4.13 (broad m, 1H), 2.90 (t, J=2.0, 14.0, 14.0 Hz, 2H), 4.90 (broad m, 1H), 6.22 (dd, J=11.4, 3.0 Hz 1H), 6.79 (d, J=11.4 Hz, 1H), 7.30 (dd, J=2.0, 4.0 Hz, 1H), 7.39 (m, 1H), 7.45 (m, 2H), 7.58 (m, 1H), 7.84 (dd, J=8.0, 2.0 Hz, 1H), 8.02 (d, J=2.0 Hz, 1H).

EXAMPLE 24

(IC₅₀=A*, EC₅₀=E*)

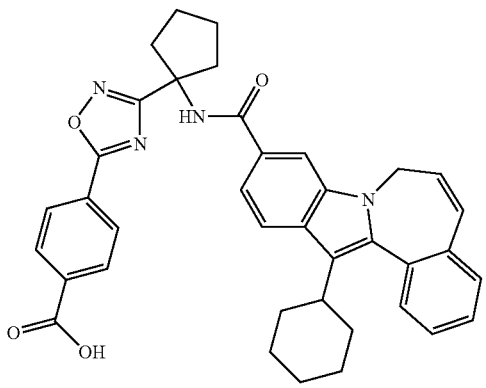

4-[3-[1-[[(13-cyclohexyl-7H-indolo[2,1-a][2]benzazepin-10-yl)carbonyl]amino]cyclopentyl]-1,2,4-oxadiazol-5-yl]-benzoic acid. A solution of Intermediate 73 (20.0 mg, 0.041 mmol) in CHCl₃ (0.50 mL) and DIPEA (0.036 mL, 0.207 mmol) was treated with methyl 4-(chlorocarbonyl) benzoate (16.0 mg, 0.082 mmol). The resulting mixture was stirred in a sealed tube in an Emrys microwave at 130° C. for 15 minutes. The resulting mixture was concentrated under reduced pressure, treated with 1M NaOH (1.0 mL) and methanol (2.0 mL), and stirred at 22° C. for 6 hours. 1M HCl (10 mL) was added and the aqueous layer was extracted with CHCl₃ (2×20 mL). The organic phase was dried over Na₂SO₄, filtered, and concentrated under reduced pressure. Flash column chromatography on silica gel with 1:3 ethyl acetate/hexanes provided the desired product (12 mg, 43%) as a yellow paste. MS m/z 613 (MH⁺); ¹H NMR (300 MHz, CDCl₃) δ 1.09–1.66 (m, 6H), 1.81 (m, 2H), 1.87–1.99 (m, 4H), 2.08 (m, 2H), 2.24 (m, 2H), 2.58 (m, 2H), 2.84 (m, 1H), 4.18 (broad m, 1H), 4.89 (broad m, 1H), 6.33 (dd, J=11.4, 3.0 Hz 1H), 6.80 (d, J=11.4 Hz, 1H), 7.30 (dd, J=2.0, 4.0 Hz, 1H), 7.36 (m, 1H), 7.42 (m, 2H), 7.53 (m, 1H), 7.89 (dd, J=8.0, 2.0 Hz, 1H), 8.03 (d, J=2.0 Hz, 1H), 8.12 (d, J=8.2 Hz, 2H), 8.29 (d, J=8.2 Hz, 2H).

EXAMPLE 25

(IC₅₀=A*, EC₅₀=E*)

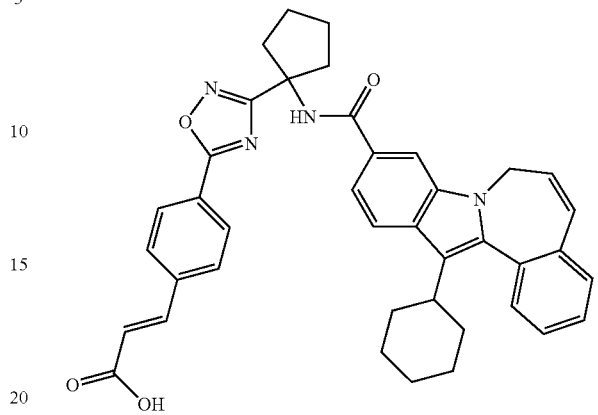

3-[4-[3-[1-[[(13-cyclohexyl-7H-indolo[2,1-a][2]benzazepin-10-yl)carbonyl]amino]cyclopentyl-]1,2,4-oxadiazol-5-ylphenyl]-(2E)-2-propenoic acid. A solution of Intermediate 73 (20.0 mg, 0.041 mmol) in CHCl₃ (0.50 mL) and DIPEA (0.036 mL, 0.207 mmol) was treated with (E)-methyl 3-(4-(chlorocarbonyl)phenyl)acrylate (19.0 mg, 0.082 mmol). The resulting mixture was stirred in a sealed tube in an Emrys microwave at 130° C. for 15 minutes. The resulting mixture was concentrated under reduced pressure, treated with 1M NaOH (1.0 mL) and methanol (2.0 mL), and stirred at 22° C. for 6 hours. 1M HCl (10 mL) was added and the aqueous layer was extracted with CHCl₃ (2×20 mL). The organic phase was dried over Na₂SO₄, filtered, and concentrated under reduced pressure. Flash column chromatography on silica gel with 1:3 ethyl acetate/hexanes provided the desired product (15 mg, 54%) as a yellow paste. MS m/z 639 (MH⁺), ¹H NMR (300 MHz, CDCl₃) δ 1.10–1.65 (m, 6H), 1.81 (m, 2H), 1.89–1.99 (m, 4H), 2.07 (m, 2H), 2.26 (m, 2H), 2.58 (m, 2H), 2.84 (m, 1H), 4.20 (broad m, 1H), 4.90 (broad m, 1H), 6.33 (dd, J=1 1.4, 3.0 Hz 1H), 6.63 (d, J=14 Hz, 2H), 6.79 (d, J=11.4 Hz, 1H), 7.28 (dd, J=2.0, 4.0 Hz, 1H), 7.35 (m, 1H), 7.42 (m, 1H), 7.55 (m, 1H), 7.69 (d, J=14 Hz, 2H), 7.79 (d, J=8.2 Hz, 2H), 7.88 (dd, J=8.0, 2.0 Hz, 1H), 8.03 (d, J=2.0 Hz, 1H), 8.17 (d, J=8.2 Hz, 2H).

EXAMPLE 26

(IC₅₀=A*, EC₅₀=E*)

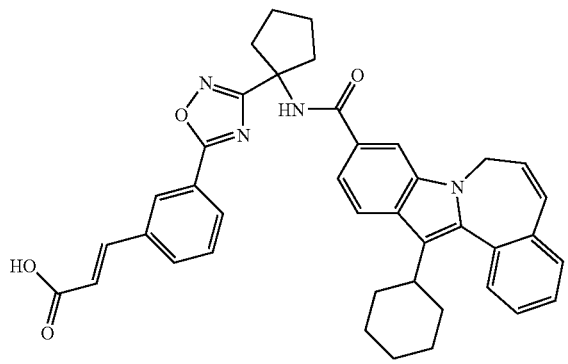

3-[3-[3-[1-[[(13-cyclohexyl-7H-indolo[2,1-a][2]benza-zepin-10-yl)carbonyl]amino]cyclopentyl]-1,2,4-oxadiazol-5-yl]phenyl]-(2E)-2-propenoic acid. A solution of Intermediate 73 (20.0 mg, 0.041 mmol) in CHCl₃ (0.50 mL) and DIPEA (0.036 mL, 0.207 mmol) was treated with (E)-methyl 3-(3-(chlorocarbonyl)phenyl)acrylate (19.0 mg, 0.082 mmol). The resulting mixture was stirred in a sealed tube in an Emrys microwave at 130° C. for 15 minutes. The resulting mixture was concentrated under reduced pressure, treated with 1 M NaOH (1.0 mL) and methanol (2.0 mL), and stirred at 22° C. for 6 hours. 1M HCl (10 mL) was added and the aqueous layer was extracted with CHCl₃ (2×20 mL). The organic phase was dried over Na₂SO₄, filtered, and concentrated under reduced pressure. Flash column chromatography on silica gel with 1:3 ethyl acetate/hexanes provided the desired product (18 mg, 67%) as a yellow paste. MS m/z 639 (MH⁺); ¹H NMR (300 MHz, CDCl₃) δ 1.12–1.59 (m, 6H), 1.71 (m, 2H), 1.86–1.95 (m, 4H), 2.03 (m, 2H), 2.40 (m, 2H), 2.52 (m, 2H), 2.82 (m, 1H), 4.13 (broad m, 1H), 4.87 (broad m, 1H), 6.22 (dd, J=11.4, 3.0 Hz, 1H), 6.48 (dd, J=14 Hz, 1H), 6.74 (d, J=11.4 Hz, 1H), 7.30 (dd, J=2.0, 4.0 Hz, 1H), 7.43–7.52 (m, 3H), 7.49 (m, 2H), 7.62 (dd, J=7.7, 7.6 Hz, 1H), 7.67 (dd, J=8.0, 2.0 Hz, 1H), 7.83 (d, J=7.7 Hz, 1H), 7.99 (d, J=2.0 Hz, 1H), 8.03 (d, J=7.6 Hz, 1H), 8.21 (s, 1H).

EXAMPLE 27

(IC₅₀=A*, EC₅₀=E*)

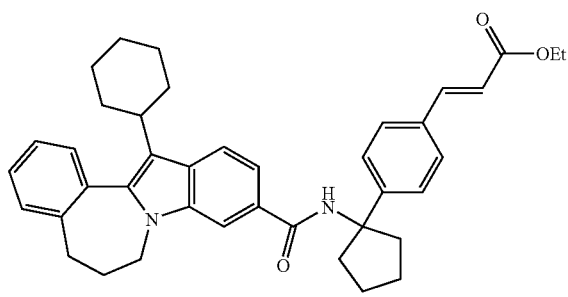

Ethyl 3-[4-[1-[[(13-cyclohexyl-6,7-dihydro-5H-indolo[2,1-a][2]benzazepin-10-yl)carbonylamino]cyclopentyl]phenyl]-(2E)-propenoate TBTU (44.7 mg, 0.14 mmol) was added to a stirred solution of Intermediate 57A, TEA (56 mg, 0.56 mmol), and Example 3 (50 mg, 0.14 mmol) in DMSO (1 mL) at 22° C. under argon. The mixture was stirred for 2.5 hours when LC/MS indicated that the coupling was completed. The mixture was diluted with ethyl acetate and washed sequentially with water (3×), dilute HCl, and brine. The solution was dried over Na₂SO₄, filtered, and concentrated. A solution of the residue in dichloromethane was applied to a silica gel thick layer plate. The plate was eluted with dichloromethane/ethyl acetate (150:10). Concentration of an extract of the appropriate band provided the desired product as a colorless solid (34.3 mg, 38% yield). MS m/z 644 (MH⁺); ¹H NMR (300 MHz, CDCl₃) δ 1.31 (t, J=7.14 Hz, 3H), 1.37–2.70 (m, , 22H), 2.91 (d, J=4.03 Hz, 1H), 3.71 (m, 1H), 4.24 (q, J=6.95 Hz, 2H), 4.43 (dd, J=14.27, 5.86 Hz, 1H), 6.34 (d, J=16.10 Hz, 1H), 6.48 (s, 1H), 7.35 (m, 5H), 7.46 (d, J=8.42 Hz, 2H), 7.61 (m, 3H), 7.88 (d, J=8.42 Hz, 1H), 7.95 (s, 1H), 10.39 (s, 1H).

EXAMPLE 28

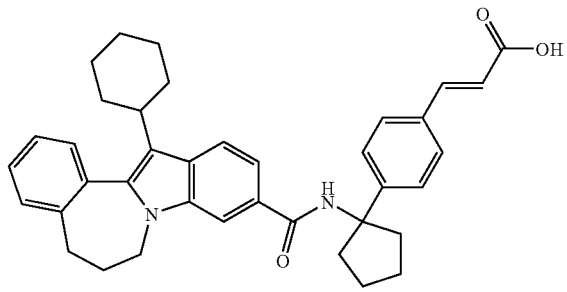

3-[4-[1-[[(13-cyclohexyl-6,7-dihydro-5H-indolo[2,1-a][2]benzazepin-10-yl)carbonyl]amino]cyclopentyl]phenyl]-(2E)-propenoic acid. A mixture of Example 27 (249 mg, 0.387 mmol) in THF (3 mL), methanol (3 mL), and LiOH (6 mL of 0.65N) was stirred at reflux for 1 hour. The mixture was diluted with cold H₂O (20 mL) and acidified with 37% HCl (1 mL) to form a precipitate. The solid was collected and washed with cold H₂O. The damp solid was crystallized from methanol to provide the desired product as a colorless solid (191 mg, 80% yield). ESI-MS m/z 616 (MH⁺); ¹H NMR (300 MHz, DMSO-d₆) δ 1.20–2.34 (m, 17H), 2.35 (s, 4H), 2.79(m, 2H), 3.56 (s, 1H), 4.59 (s, 1H), 6.38 (d, J=16.10 Hz, 1H), 7.40 (m, 3H), 7.50 (d, J=16.10 Hz, 1H), 7.58 (d, J=8.78 Hz, 2H), 7.65 (m, 2H), 7.82 (d, J=8.42 Hz, 1H), 8.22 (d, J=27.45 Hz, 2H), 9.64 (s, 1H), 12.19 (s, 1H).

EXAMPLE 29

(IC₅₀=B*, EC₅₀=F*)

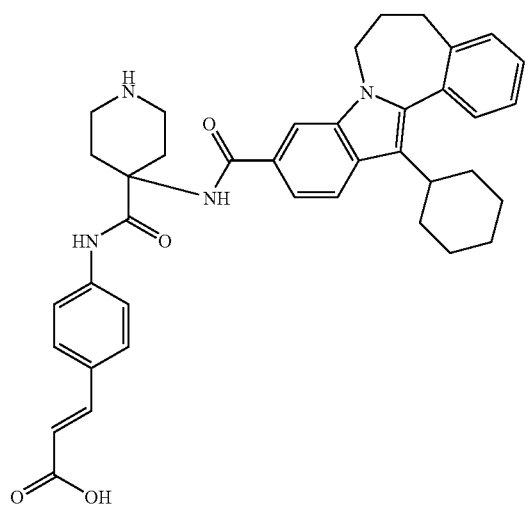

2-propenoic acid, 3-[4-[[[4-[[(13-cyclohexyl-6,7-dihydro-5H-indolo[2,1-a][2]benzazepin-10-yl)carbonyl]amino]-4-piperidinyl]carbonyl]amino]phenyl]-, (2E)-. TBTU (97 mg, 0.30 mmol) was added to a stirred solution of Intermediate 57B, (120 mg, 0.287 mmol), TEA (116 mg, 1.15 mmol), and Example 3 (103 mg, 0.0.287 mmol) in DMSO (1.2 mL) at 22° C. under argon. The solution was stirred for 1 hour and diluted with water. The precipitated solid was collected by filtration and dried to provide the fully-protected coupled product (219 mg). ESI-MS m/z 759 (MH+). The crude solid (205 mg) was added to a stirred solution of dichloromethane (1.5 mL) and TFA (1.5 mL) at room temperature. After 1 hour the solution was concentrated. THF (1.5 mL), methanol (1.5 mL), and LiOH (1.5 mL of 1.4N) were added to the residue. The mixture was stirred at reflux for 3 minutes and stored for 18 hours at ambient temperature. The mixture was acidified with dilute HCl. The resulting gel was collected, washed with cold water, and purified on a Shimadzu preparatory liquid chromatograph. Partial concentration of the eluate resulted in the precipitation of the desired product (17.1 mg) as a colorless solid (mono acid addition salt with TFA). ESI-MS m/z 631 (MH+); $^1$H NMR (300 MHz, DMSO-$d_6$) δ 1.99–1.16 (m, 14H), 2.37 (s, 6H), 3.56 (s, 1H), 4.59 (s, 1H), 6.37 (d, J=15.3 Hz, 1H), 7.52 (m, 11H), 7.83 (s, 1H), 8.20 (s, 1H,) 8.47 (s, 1H), 9.89 (s, 1H).

By substituting the appropriate starting materials and reagents into the procedures described above, the following compounds were prepared:

| Structure | Spectral Data | IC$_{56}$* | EC$_{50}$* |
|---|---|---|---|
| 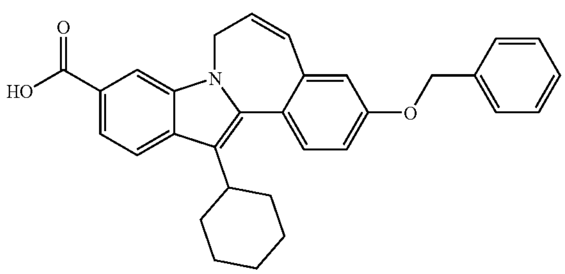 | $^1$H NMR (300 MHz, CDCl$_3$) δ 1.35–2.04 (m, 10H), 2.83 (s, 1H), 4.21 (s, 1H), 4.89 (s, 1H), 5.13 (s, 2H), 6.28 (m, 1H), 6.75 (d, J=10.25 Hz, 1H), 6.94 (d, J=2.56 Hz, 1H), 7.05 (dd, J=8.78, 2.56 Hz, 1H), 7.31–7.47 (m, 6H), 7.78 (d, J=8.78 Hz, 1 H, 7.87 (m, 1H), 8.20 (s, 1H) | A | E |
| 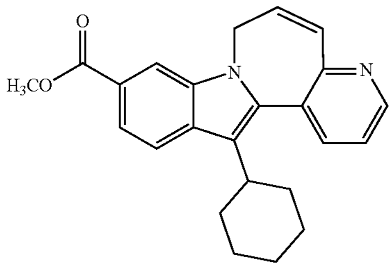 | $^1$H NMR (500 MHz, CD$_3$OD) δ 1.23–1.53(m, 5H), 1.75–1.98 (m, 3H), 2.07–2.22 (m, 2H), 2.80 (m, 1H), 3.97 (s, 3H), 4.95 (m, 2H), 6.69 (m, 1H), 6.97 (d, J=10.68 Hz, 1H), 7.55 (m, 1H), 7.73 (d, J=8.55 Hz, 1H), 7.94 (d, J=8.55 Hz, 1H), 8.03 (d, J=7.94 Hz, 1H), 8.28 (s, 1H), 8.67 (m, 1H) | | |
| 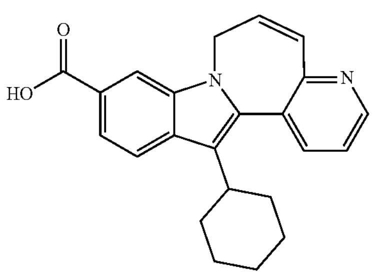 | MS m/z 359 (MH+) | A | D |
| 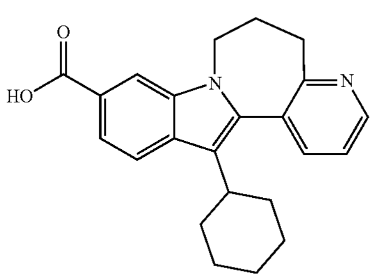 | $^1$H NMR (500 MHz, DMSO-$d_6$) δ 1.19 (m, 1H), 1.32–1.47 (m, 2H), 1.58 (m, 1H), 1.66–1.79 (m, 2H), 1.87 (m, 1H), 1.92–2.08 (m, 3H), 2.13 (m, 1H), 2.39 (m, 1H), 2.61 (m, 1H), 2.76 (m, 1H), 2.86 (m, 1H), 3.57 (m, 1H), 4.66 (m, 1H), 7.49 (dd, J=7.63, 4.88 Hz, 1H), 7.64 (dd, J=8.39, 1.37 Hz, 1H), 7.77 (dd, J=7.48, 1.68 Hz, 1H), 7.90 (d, J=8.54 Hz, 1H), 8.17 (s, 1H), 8.57 (dd, J=4.88, 1.53 Hz, 1H), 12.61 (s, 1H) | B | E |

-continued

| Structure | Spectral Data | IC$_{56}$* | EC$_{50}$* |
|---|---|---|---|
| 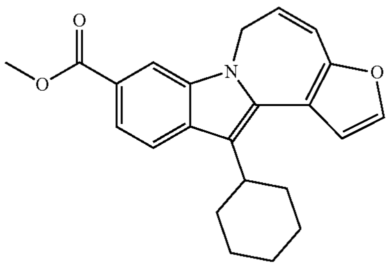 | $^1$H NMR (500 MHz, CDCl$_3$) δ 1.36–1.48 (m, 4 H), 1.70–1.95 (m, 6H), 2.00–2.10(m, 2 H), 3.05 (tt, 1H, J=3.5, 6.0 Hz), 3.95 (s, 3H), 4.62 (d, 2H, J=6.5 Hz), 6.14 (m, 1H), 6.81 (m, 2H), 7.53 (d, 1H, J=2.0 Hz), 7.72 (dd, 1H, J=1.0, 8.5 Hz), 7.84 (d, 1H, J=8.5), 8.15 (s, 1H) | | |
| 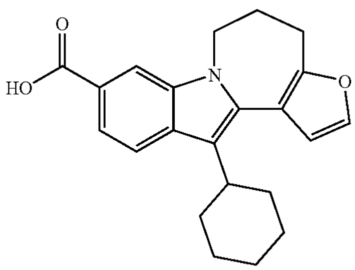 | $^1$H NMR (500 MHz, DMSO-d$_6$) δ 1.30–1.50 (m, 4H), 1.70–1.90 (m, 6H), 1.90–2.10(m, 4H), 3.03 (t, 1H, J=12.0 Hz), 3.08 (t, 2H, J=6.5 Hz), 4.28 (d, 2H, J=6.5 Hz), 6.64 (s, 1H), 7.58 (d, 2H, J=8.5 Hz), 7.76 (s, 1H), 7.79 (d, 2H, J=8.5 Hz), 8.08 (s, 1H) | A | D |
| 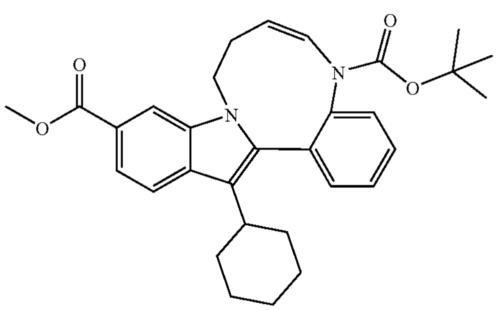 | $^1$H NMR (500 MHz, CDCl$_3$) δ 1.06 (m, 5H), 1.28 (s, 9H), 1.55 (m, 3H), 1.72 (m, 2H), 2.65 (m, 1H), 3.95 (s, 3H), 4.04 (m, 1H), 4.22 (s, 1H), 4.52 (m, 1H), 5.30 (m, 1H), 5.97 (m, 1H), 6.25 (m, 1H), 7.31 (d, J=9.16 Hz, 3H), 7.47 (m, 1H), 7.74 (m, 1H), 7.82 (d, J=8.24 Hz, 1H), 8.11 (s, 1H) | | |
| | $^1$H NMR (500 MHz, CD$_3$OD) δ 1.00–1.16 (m, 6H), 1.29–1.46 (m, 6H), 1.70–2.05 (m, 9H), 2.59–2.71 (m, 1H), 4.00–4.20 (m, 2H), 4.21–4.30 (m, 1H), 6.04–6.14 (m, 1H), 7.38 (d, J=6.10 Hz, 1H), 7.41–7.53 (m, 2H), 7.56–7.66 (m, 1H), 7.68–7.76 (m, 1H), 7.83 (d, J=8.24 Hz, 1H), 8.19 (s, 1H) | A | D |
| 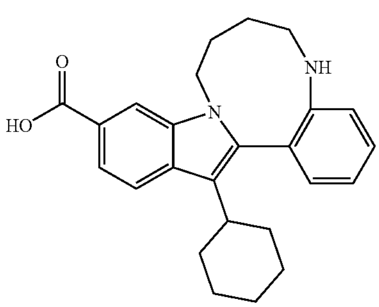 | $^1$H NMR (500 MHz, CD$_3$OD) δ 1.31 (m, 4H), 1.82 (m, 10H), 2.23 (m, 1H), 2.70 (m, 1H), 3.02 (m, 1H), 3.38 (m, 2H), 3.59 (m, 1H), 4.42 (m, 1H), 7.30 (m, 1H), 7.35 (d, J=8.24 Hz, 1H), 7.39 (d, J=7.63 Hz, 1H), 7.58 (t, J=7.17 Hz, 1H), 7.81 (m, 1H), 7.87 (m, 1H), 8.12 (s, 1H) | A | E |

-continued

| Structure | Spectral Data | IC$_{56}$* | EC$_{50}$* |
|---|---|---|---|
| 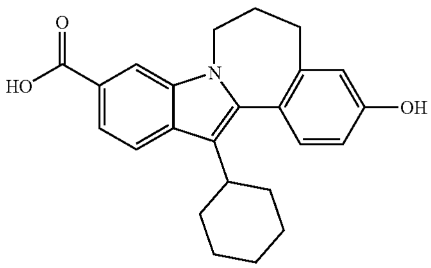 | $^1$H NMR (300 MHz, CD$_3$OD) δ 1.23–2.08 (m, 10H), 2.44 (m, J=12.08 Hz, 2H), 2.58 (m, J=5.86 Hz, 1H), 2.91 (m, 1H), 3.66 (s, 1H), 4.48 (d, J=14.64 Hz, 1H), 6.82 (s, 2H), 7.23 (d, J=8.42 Hz, 1H), 7.69 (d, J=8.05 Hz, 1H), 7.83 (d, 18.42 Hz, 2H), 8.10 (s, 1H) | B | E |
| 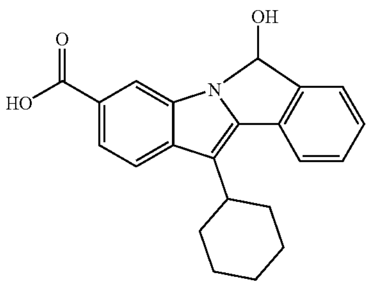 | $^1$H NMR (300 MHz, DMSO-d$_6$) δ 1.49 (m, 3H), 1.83 (m, 7H), 3.21 (m, 1H), 6.62 (s, 1H), 7.39 (t, J=7.32 Hz, 1H), 7.51 (t, J=7.50 Hz, 1H), 7.60 (m, 2H), 7.76 (d, J=8.78 Hz, 4H), 7.84 (d, J=7.32 Hz, 1H), 8.19 (s, 1H) | A | C |
| 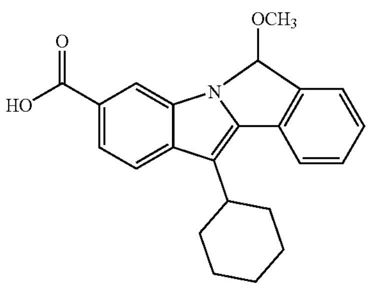 | $^1$H NMR (300 MHz, CDCl$_3$) δ 1.45 (m, J=7.32 Hz, 3H), 1.95 (m, 7H), 2.86 (s, 3H), 3.17 (m, 1H), 6.61 (s, 1H), 7.25 (s, 1H), 7.36 (t, J=7.50 Hz, 1H), 7.48 (t, J=7.14 Hz, 1H), 7.56 (d, J=7.32 Hz, 1H), 7.81 (m, 3H), 8.28 (s, 1H) | A | C |
| 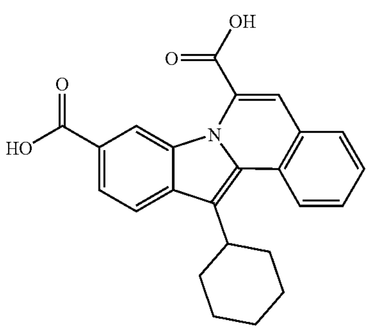 | MS m/z 388 (MH$^+$) | A | C |
| 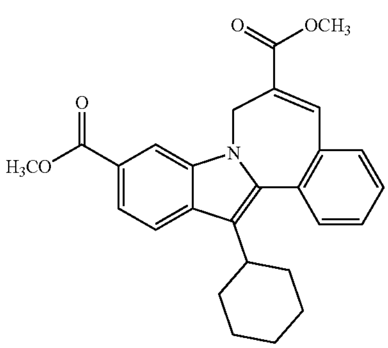 | $^1$H NMR (500 MHz, CDCl$_3$) δ 1.13–2.17 (m, 10H), 2.87 (m, 1H), 3.86 (s, 3H), 3.95 (s, 3H), 4.13 (m, 2H), 7.27 (m, 1H), 7.53 (m, 2H), 7.61 (d, J=7.32 Hz, 1H), 7.76 (d, J=8.24 Hz, 1H), 7.89 (m, 2H), 8.31 (s, 1H) | | |

-continued

| Structure | Spectral Data | IC$_{56}$* | EC$_{50}$* |
|---|---|---|---|
| 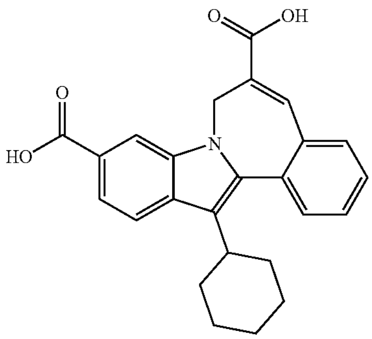 | $^1$H NMR (500 MHz, CD$_3$OD) δ 1.31 (m, 2H), 1.47 (m, 3H), 1.81 (m, 2H), 2.02 (m, 1H), 2.13 (m, 2H), 2.91 (m, 1H), 4.20 (m, 1H), 5.73 (m, 1H), 7.57 (m, 1H), 7.62 (t, J=7.63 Hz, 2H), 7.68 (d, J=7.63 Hz, 1H), 7.73 (d, J=8.55 Hz, 1H), 7.91 (d, J=8.55 Hz, 1H), 7.96 (s, 1H), 8.32 (s, 1H) | B | C |
| 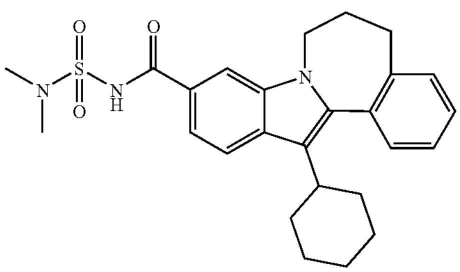 | MS m/z 466 (MH+) | B | E |
| 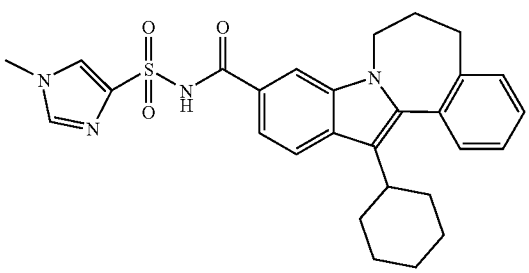 | MS m/z 503 (MH+) | A | D |
| 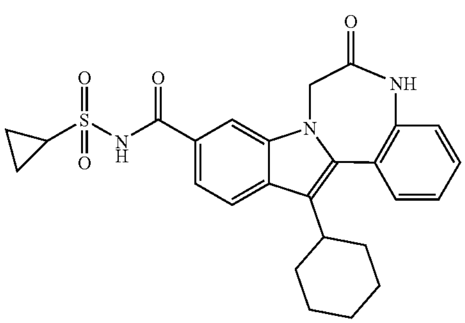 | $^1$H NMR (500 MHz, CD$_3$OD) δ 1.18 (dd, J=7.78, 2.29 Hz, 2H), 1.24–1.33(m, 1H), 1.36 dd, J=4.73, 2.29 Hz, 2H), 1.43–1.57 (m, 2H), 1.58–1.67 (m, 1H), 1.78–1.87 (m, 2H), 1.96–2.03 (m, 1H), 2.06–2.23 (m, 4H), 2.96–3.05 (m, 1H), 4.61 (d, J=13.73 Hz, 1H), 5.05 (d, J=13.43 Hz, 1H), 7.32 (d, J=8.24 Hz, 1H), 7.43 (t, J=7.63 Hz, 1H), 7.55 (t, J=7.93 Hz, 1H), 7.63 (d, J=7.93 Hz, 1H), 7.69 (d, J=8.55 Hz, 1H), 8.01 (d, J=8.54 Hz, 1H), 8.24 (s, 1H) | B | E |
| 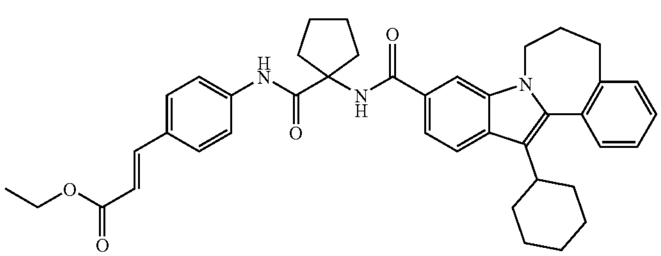 | $^1$H NMR (500 MHz, CD$_3$OD) δ 1.26–1.36 (m, 4H), 1.41–1.52 (m, 2H), 1.77–2.00 (m, 8H), 2.07–2.24 (m, 6H), 2.46–2.55 (m, 4H), 2.84 (m, 1H), 2.87 (s, br, 1H), 3.82 (s, br, 1H), 4.24 (q, J=7.02 Hz, 2H), 4.70 (s, br, 1H), 6.43 (d, J=16.17 Hz, 1H), 7.54 (d, J=8.85 Hz, 2H), 7.58–7.65 (m, 3H), 7.68 (dd, J=8.55, 1.53 Hz, 1H), 8.00 (d, J=8.54 Hz, 1H), 8.07 (dd, J=7.78, 5.95 Hz, 1H), 8.16 (s, 1H), 8.48 (dd, J=7.78, 1.37 Hz, 1H), 8.78 (dd, J=5.80, 1.22 Hz, 1H) | A | F |

-continued

| Structure | Spectral Data | IC$_{56}$* | EC$_{50}$* |
|---|---|---|---|
| 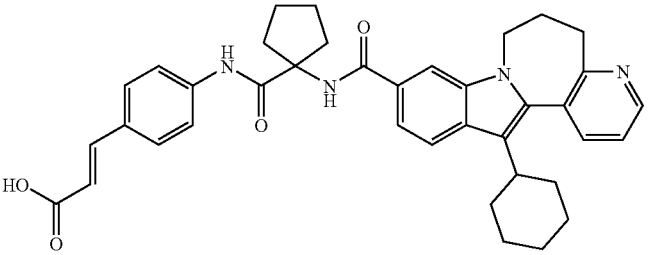 | $^1$H NMR (500 MHz, CD$_3$OD) δ 1.26 (m, 1H), 1.37–1.57 (m, 2H), 1.67 (m, 1H), 171–2.31 (m, 13H), 2.40–2.57 (m, 3H), 2.69 (m, 1H), 2.87 (m, 1H), 2.95 (m, 1H), 3.68 (m, 1H), 4.63 (m, 1H), 6.40 (d, J=16.17 Hz, 1H), 7.44–7.55 (m, 3H), 7.55–7.68 (m, 3H), 7.87 (dd, J=7.78, 1.68 Hz, 1H), 7.93 (d, J=8.55 Hz, 1H), 8.12 (s, 1H), 8.45 (s, 1H), 8.53 (dd, J=4.88, 1.53 Hz, 1H), 9.66 (s, 1H) | B | F |
| 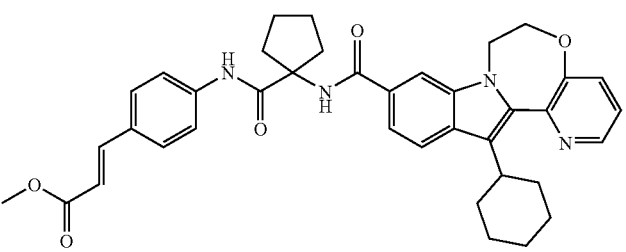 | $^1$H NMR (500 MHz, CD$_3$OD) δ 1.37–1.45 (m, 3H), 1.79 (m, 1H), 1.83–1.96 (m, 8H), 1.99–2.11 (m, 2H), 2.15–2.24 (m, 2H), 2.46–2.56 (m, 2H), 3.36 (m, 1H), 3.79 (s, 3H), 4.47 (t, J=5.19 Hz, 2H), 4.57 (t, J=5.19 Hz, 2H), 6.45 (d, J=15.87 Hz, 1H), 7.51–7.58 (m, 3H), 7.60–7.68 (m, 4H), 7.75 (dd, J=8.09, 1.37 Hz, 1H), 7.98 (d, J=8.54 Hz, 1H), 8.12 (s, 1H), 8.57 (dd, J=4.88, 1.53 Hz, 1H) | A | E |
| 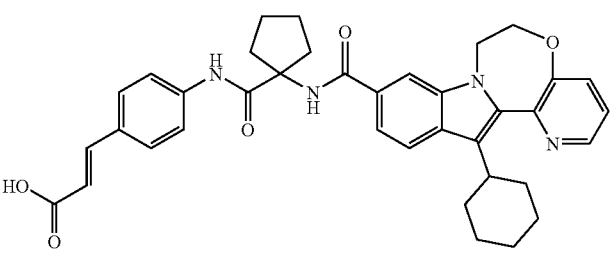 | $^1$H NMR (500 MHz, CD$_3$OD) δ 1.36–1.48 (m, 3H), 1.80 (m, 1H), 1.82–1.96 (m, 8H), 1.99–2.12 (m, 2H), 2.15–2.24 (m, 2H), 2.44–2.55 (m, 2H), 3.33 (m, 1H), 4.49 (t, J=5.34 Hz, 2H), 4.58 (t, J=5.19 Hz, 2H), 6.40 (d, J=15.87 Hz, 1H), 7.54 (d, J=8.55 Hz, 2H), 7.58 (dd, J=8.24, 4.88 Hz, 1H), 7.59–7.68 (m, 4H), 7.80 (dd, J=8.24, 1.22 Hz, 1H), 8.00 (d, J=8.55 Hz, 1H), 8.13 (s, 1H), 8.58 (dd, J=4.88, 1.53 Hz, 1H) | B | F |
| 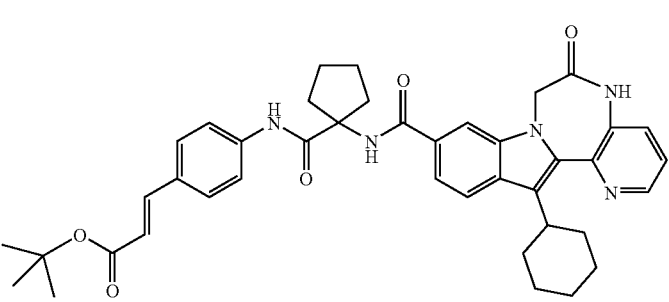 | $^1$H NMR (300 MHz, CD$_3$OD) δ 1.30–1.48 (m, 3H), 1.54 (s, 9H), 1.74–1.98 (m, 9H), 1.99–2.13 (m, 2H), 2.15–2.29 (m, 2H), 2.43–2.58 (m, 2H), 3.43 (m, 1H), 4.93 (s, 2H), 6.36 (d, J=16.10 Hz, 1H), 7.46–7.70 (m, 7H), 8.00 (d, J=8.78 Hz, 1H), 8.25 (s, 1H), 8.48 (s, 1H), 8.63 (dd, J=4.76, 1.46 Hz, 1H), 9.68 (s, 1H) | A | E |
| 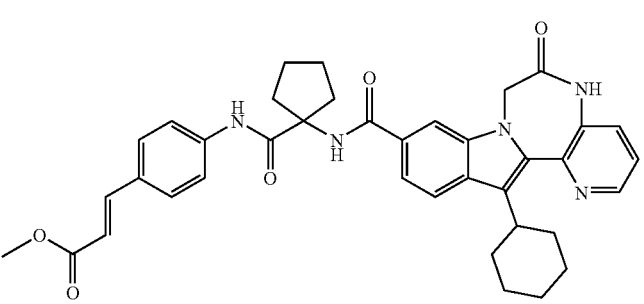 | $^1$H NMR (500 MHz, CD$_3$OD) δ 1.33–1.49 (m, 3H), 1.81 (m, 1H), 1.83–2.00 (m, 8H), 2.01–2.15 (m, 2H), 2.15–2.28 (m, 2H), 2.47–2.59 (m, 2H), 3.44 (m, 1H), 3.79 (s, 3H), 4.96 (s, 2H), 6.47 (d, J=15.87 Hz, 1H), 7.51 (dd, J=8.09, 4.73 Hz, 1H), 7.54–7.61 (m, 2H), 7.62–7.72 (m, 5H), 8.00 (d, J=8.55 Hz, 1H), 8.26 (s, 1H), 8.64 (dd, J=4.58, 1.22 Hz, 1H) | A | F |

-continued

| Structure | Spectral Data | IC$_{56}$* | EC$_{50}$* |
|---|---|---|---|
| 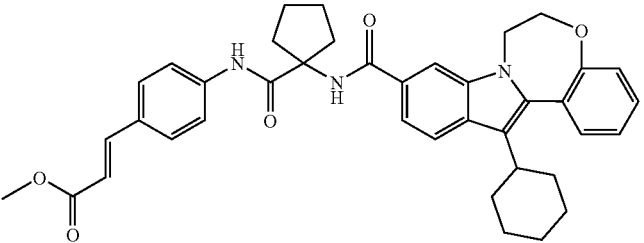 | $^1$H NMR (500 MHz, CDCl$_3$) δ 1.33–1.41 (m, 3H), 1.76–1.93 (m, 10H), 2.03 (m, 1H), 2.21–2.30 (m, 2H), 2.54–2.62 (m, 2H), 2.92–3.01 (m, 1H), 3.78 (s, 3H), 4.27–4.33 (m, 2H), 4.51 (t, J=5.65 Hz, 2H), 6.35 (d, J=16.17 Hz, 1H), 6.43 (br, 1H), 7.23 (d, J=7.32 Hz, 1H), 7.31 (m, 2H), 7.41 (m, 2H), 7.47 (d, J=8.55 Hz, 2H), 7.59–7.66 (m, 3H), 7.90 (d, J=8.55 Hz, 1H), 7.95 (s, 1H), 10.40 (br, 1H) | A | |
| 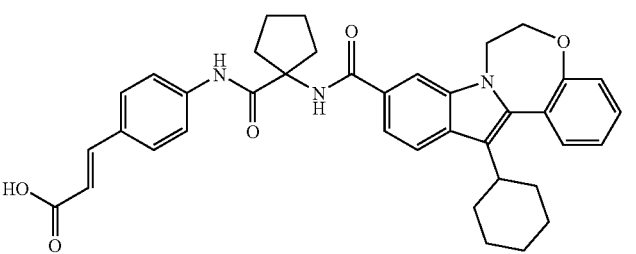 | $^1$H NMR (500 MHz, acetone-d$_6$) δ 1.34–1.49 (m, 3H), 1.75–1.91 (m, 10H), 2.09–2.18 (m, 1H), 2.20–2.29 (m, 2H), 2.48–2.56 (m, 2H), 3.02 (m, 1H), 4.43 (m, 2H), 4.54 (t, J=5.34 Hz, 2H), 6.43 (d, J=15.87 Hz, 1H), 7.26 (d, J=7.93 Hz, 1H), 7.36 (t, J=7.48 Hz, 1H), 7.48 (dd, J=7.63, 1.83 Hz, 1H), 7.53 (d, J=7.63 Hz, 1H), 7.58–7.69 (m, 4H), 7.73 (m, 2H), 7.85 (s, 1H), 7.94 (d, J=8.55 Hz, 1H), 8.17 (s, 1H), 9.82 (br, 1H), 10.65 (br, 1H) | B | F |
| 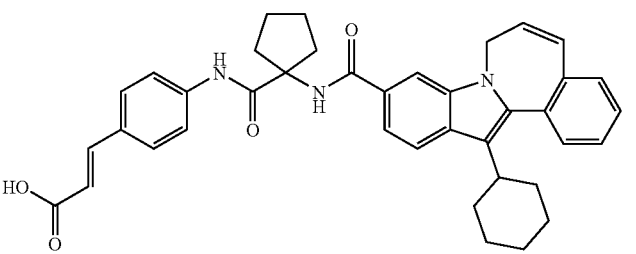 | MS m/z 614 (MH$^+$) | B | F |
| 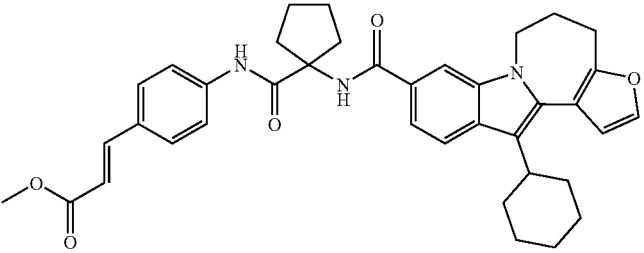 | $^1$H NMR (300 MHz, CDCl$_3$) δ 1.30–2.30 (m, 18H), 2.45–2.60 (m, 2H), 3.05 (t, 1H, J=12.0 Hz), 3.08 (t, 2H, J=7.2 Hz), 3.75 (s, 3H), 4.24 (m, 2H), 6.31 (d, 1H, J=16.2 Hz), 6.41 (s, 1H, NH), 6.57 (d, 1H, J=2.1 Hz), 7.24 (dd, 1H, J=1.2, 8.4 Hz), 7.42 (s, 1H), 7.43 (d, 2H, J=8.8 Hz), 7.59 (d, 1H, J=16.2 Hz), 7.61 (d, 2H, J=8.8 Hz), 7.79 (d, 1H, J=8.4 Hz), 7.89 (d, 1H, J=2.1 Hz) | | E |
| 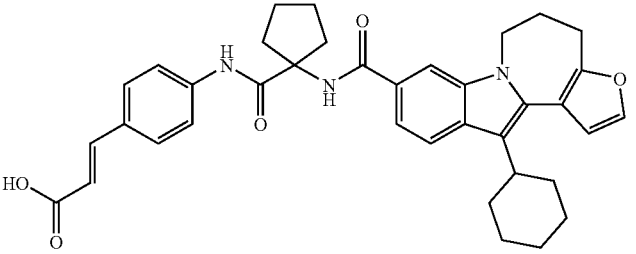 | $^1$H NMR (500 MHz, CD$_3$OD) δ 1.30–2.30 (m, 18H), 2.45–2.60 (m, 2H), 3.10 (t, 2H, J=7.0 Hz), 3.13 (tt, 1H, J=3.0, 12.0 Hz), 4.30 (m, 2H), 6.38 (d, 1H, J=16.0 Hz), 6.64 (d, 1H, J=2.0 Hz), 7.50–7.65 (m, 7H), 7.80 (d, 1H, J=8.5 Hz), 8.02 (s, 1H), 8.37 (s, 1H, NH), 9.65 (s, 1H, NH) | | F |
| 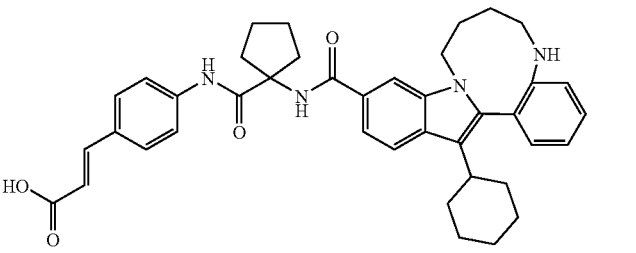 | $^1$H NMR (500 MHz, CD$_3$OD) δ 1.25–1.38 (m, 3H), 1.71–1.96 (m, 14H), 2.16–2.25 (m, 3H), 2.47–2.55 (m, 2H), 2.68 (m, 1H), 3.08 (t, J=13.12 Hz, 1H), 3.40 (m, 1H), 3.61 (m, 1H), 4.45 (dd, J=15.11 Hz, J=7.17 Hz, 1H), 6.42 (d, J=15.87 Hz, 1H), 7.42 (m, 3H), 7.57 (d, J=8.85 Hz, 2H), 7.61–7.67 (m, 4H), 7.72 (d, J=8.24 Hz, 1H), 7.89 (d, J=8.24 Hz, 1H), 8.03 (s, 1H), 9.67 (br, 1H) | A | F |

-continued

| Structure | Spectral Data | IC$_{56}$* | EC$_{50}$* |
|---|---|---|---|
| 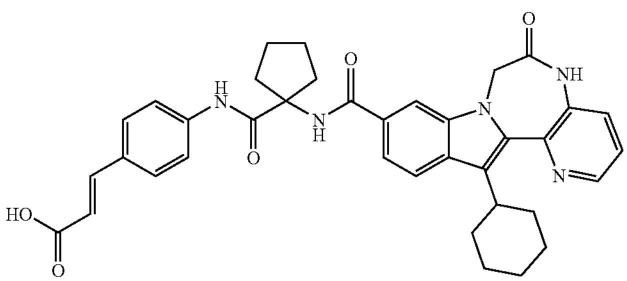 | $^1$H NMR (500 MHz, CD$_3$OD) δ 1.31–1.48 (m, 3H), 1.76–1.97 (m, 9H), 2.02–2.12 (m, 2H), 2.18–2.23 (m, 2H), 2.48–2.53 (m, 2H), 3.42 (m, 1H), 4.91 (s, 2H), 6.41 (d, J=15.87 Hz, 1H), 7.52 (dd, J=8.24, 4.58 Hz, 1H), 7.56 (d, J=8.85 Hz, 2H), 7.60–7.70 (m, 5H), 8.01 (d, J=8.54 Hz, 1H), 8.26 (s, 1H), 8.64 (dd, J=4.73, 1.37 Hz, 1H), 9.69 (s, 1H) | B | F |
| 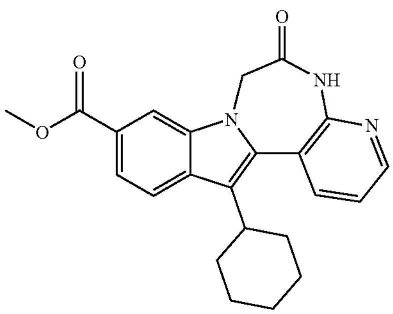 | $^1$H NMR (300 MHz, DMSO-d$_6$) δ 1.07–1.59(m, 3H), 1.62–2.11(m, 5H), 2.68–2.78 (m, 2H), 3.30 (m, 1H), 3.89 (s, 3H), 4.68 (m, 1H), 5.14 (m, 1H), 7.45 (dd, J=7.87, 4.57 Hz, 1H), 7.70 (dd, J=8.42, 1.46 Hz, 1H), 7.97 (m, 2H), 8.32 (s, 1H), 8.54 (dd, J=4.57, 1.65 Hz, 1H), 10.75 (s, 1H) | | |
| 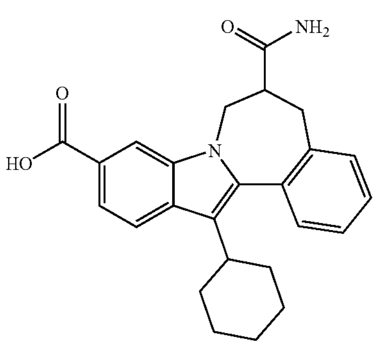 | MS m/z 403 (MH$^+$), Rt 2.52 min | B | E |
| 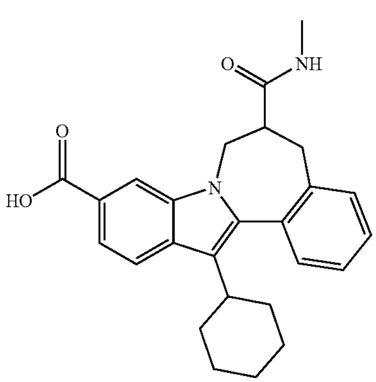 | MS m/z 417 (MH$^+$), Rt 2.43 min | B | E |

-continued

| Structure | Spectral Data | IC₅₆* | EC₅₀* |
|---|---|---|---|
| | MS m/z 431 (MH⁺), Rt 3.29 min | B | E |
| | MS m/z 447 (MH⁺), Rt 3.21 min | B | E |
| | MS m/z 474 (MH⁺), Rt 2.25 min | B | E |
| | MS m/z 580 (MH⁺), Rt 2.23 min | B | E |

-continued
| Structure | Spectral Data | IC$_{56}$* | EC$_{50}$* |
|---|---|---|---|
| 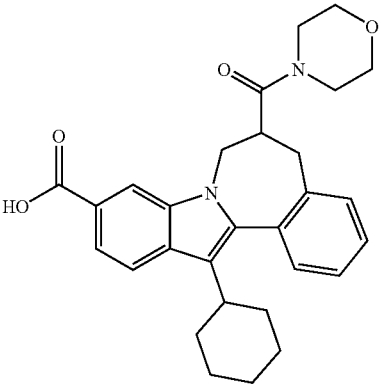 | MS m/z 473 (MH$^+$), Rt 2.37 min | B | E |
| 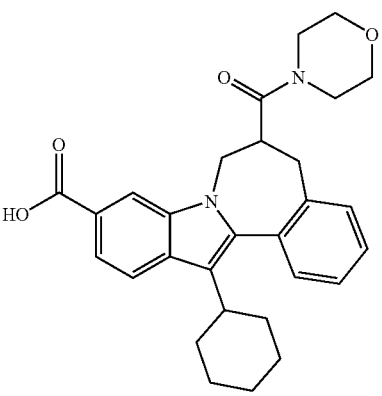<br>(Chiral) | $^1$H NMR (500 MHz, CD$_3$OD) δ 1.24–1.35 (m, 1 H), 1.40–1.55 (m, 2 H), 1.60–1.68 (m, 1 H), 1.76–1.87 (m, 2 H), 1.93–2.20 (m, 4 H), 2.76 (m, 1 H), 2.87–3.02 (m, 1 H), 3.44–3.51 (m, 1 H), 3.59–3.92 (m, 9 H), 4.47–4.59 (m, 1 H), 4.90 (m, 1 H), 7.31–7.42 (m, 1 H), 7.48 (m, 3 H), 7.72 (m, 1 H), 7.88 (m, 1 H), 8.16 (m, 1 H). MS m/z 473 (MH$^+$), Rt 2.37 min | A | D |
| 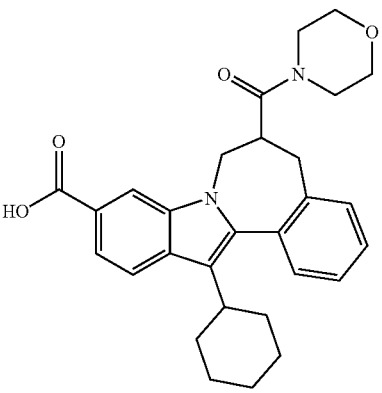<br>(Chiral) | MS m/z 473 (MH$^+$), Rt 2.37 min | B | E |

| Structure | Spectral Data | IC₅₆* | EC₅₀* |
|---|---|---|---|
| 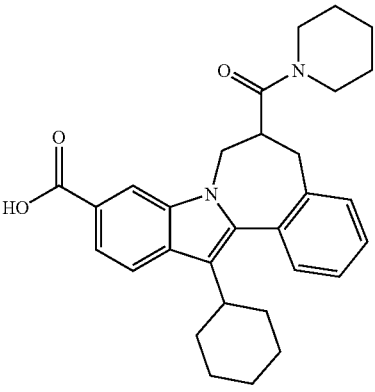 | MS m/z 471 (MH⁺), Rt 2.56 min | B | E |
| 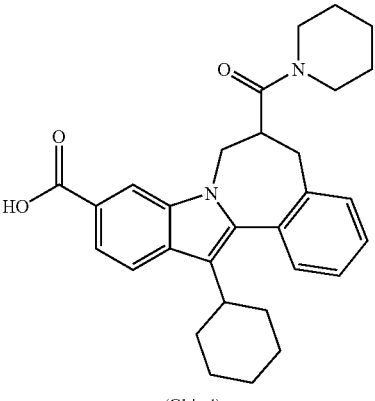 (Chiral) | MS m/z 471 (MH⁺), Rt 2.55 min | A | D |
| 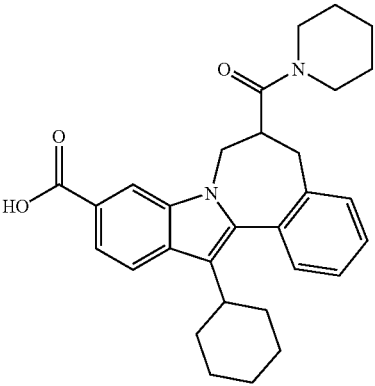 (Chiral) | MS m/z 471 (MH⁺), Rt 2.55 min | B | E |

| Structure | Spectral Data | IC$_{56}$* | EC$_{50}$* |
|---|---|---|---|
| 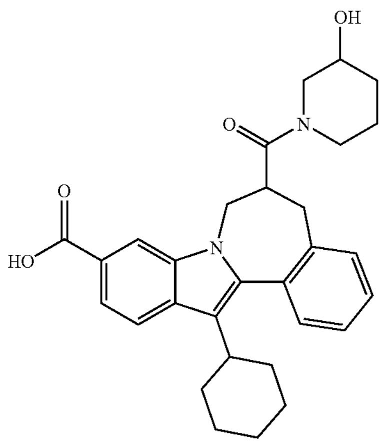 | MS m/z 487 (MH$^+$), Rt 2.44 min | B | E |
| | MS m/z 487 (MH$^+$), Rt 2.11 min | A | D |
| | MS m/z 487 (MH$^+$), Rt 2.11 min | B | E |

-continued

| Structure | Spectral Data | IC$_{56}$* | EC$_{50}$* |
|---|---|---|---|
| 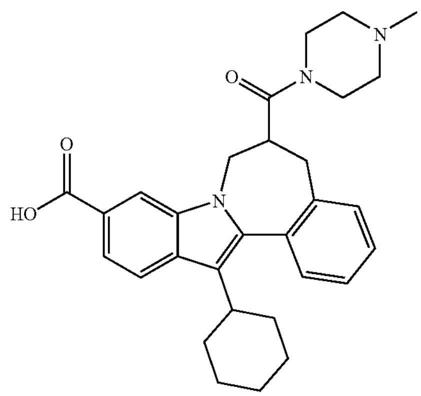 | MS m/z 486 (MH$^+$), Rt 2.23 min | B | E |
| 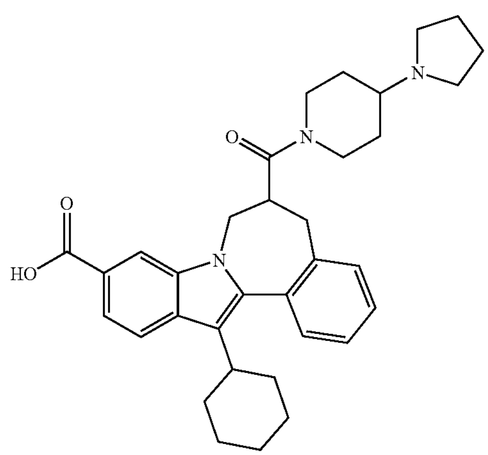 | MS m/z 540 (MH$^+$), Rt 2.25 min | B | E |
| 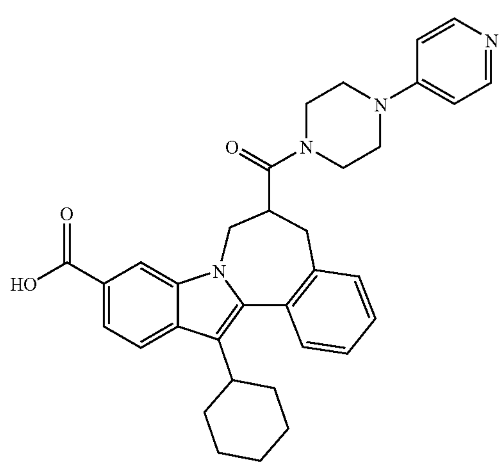 | MS m/z 549 (MH$^+$), Rt 2.26 min | B | E |

-continued

| Structure | Spectral Data | IC$_{56}$* | EC$_{50}$* |
|---|---|---|---|
| | MS m/z 563 (MH⁺), Rt 3.29 min | A | E |
| | MS m/z 487 (MH⁺), Rt 3.26 min | B | E |
| | MS m/z 471 (MH⁺), Rt 2.48 min | B | E |

-continued

| Structure | Spectral Data | IC$_{56}$* | EC$_{50}$* |
|---|---|---|---|
| | MS m/z 485 (MH⁺), Rt 2.62 min | A | D |
| | MS m/z 547 (MH⁺), Rt 3.13 min | B | E |
| | MS m/z 561 (MH⁺), Rt 1.92 min | A | D |

-continued

| Structure | Spectral Data | IC$_{56}$* | EC$_{50}$* |
|---|---|---|---|
| 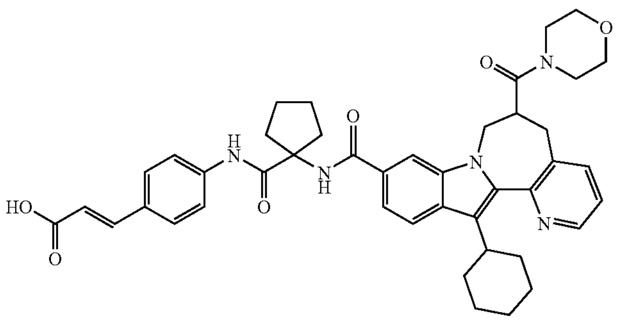 | MS m/z 729 (MH$^+$), Rt 2.49 min | B | F |
| 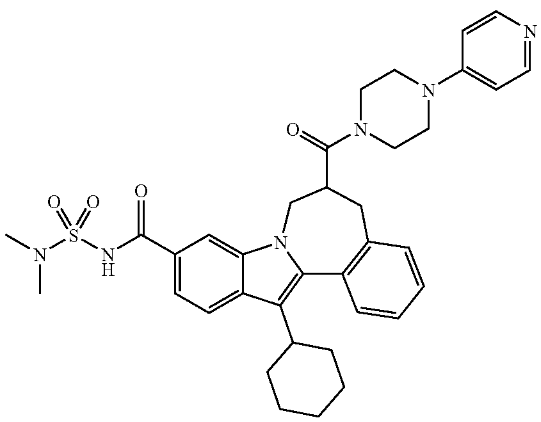 | MS m/z 655 (MH$^+$), Rt 2.23 min | B | F |
| 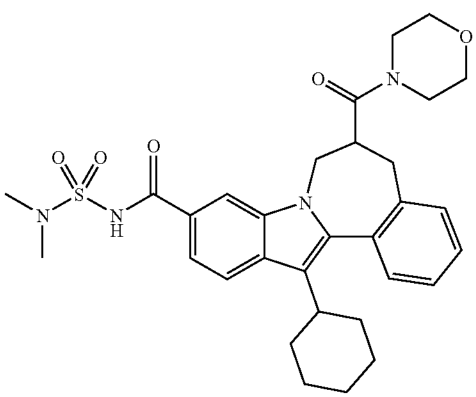 | MS m/z 579 (MH$^+$), Rt 2.42 min | B | F |
| 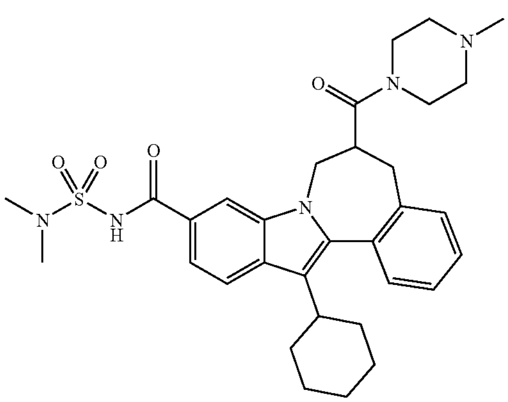 | MS m/z 592 (MH$^+$), Rt 2.22 min | B | E |

-continued

| Structure | Spectral Data | IC₅₀* | EC₅₀* |
|---|---|---|---|
| | MS m/z 646 (MH⁺), Rt 2.24 min | B | F |
| | MS m/z 593 (MH⁺), Rt 2.07 min | B | E |
| | MS m/z 577 (MH⁺), Rt 2.44 min | B | F |

*IC₅₀: A > 1 μM; B 0.1 μM–1 μM (standard method); EC₅₀: C > 10 μM; D 1 μM–10 μM; E 0.1 μM–1 μM; F <0.1 μM (luciferase method).

The following table contains additional compounds of Formula I and results from biological evaluation. The compounds were prepared using procedures or general methods described herein. Their characterization data is described in the text or in tables that follow.
| Structure | IC$_{50}$* | EC$_{50}$* |
|---|---|---|
| 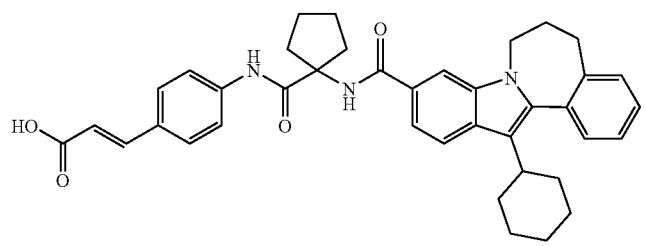 | B | E** |
| 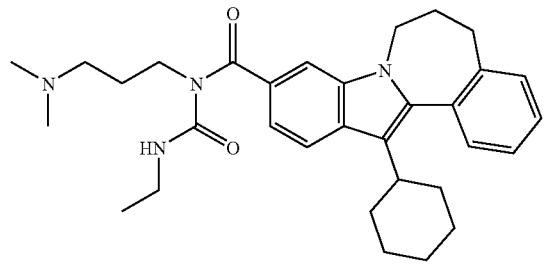 |  | D** |
| 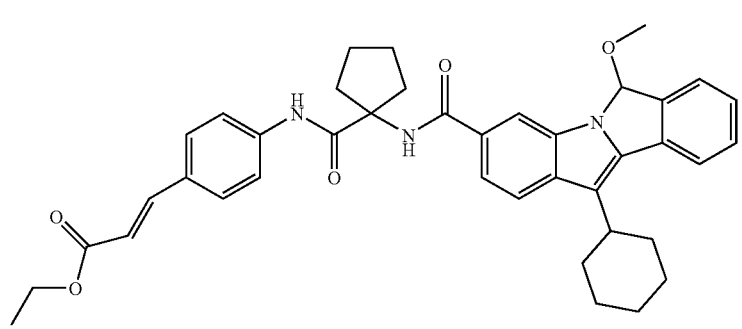 |  | D** |
| 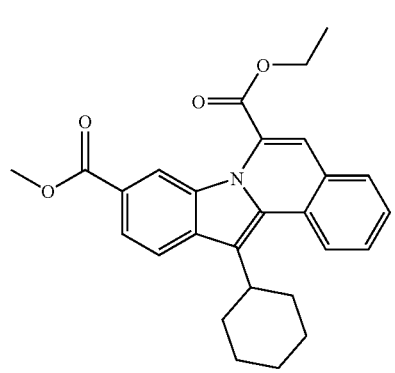 |  | C** |

-continued
| Structure | IC$_{50}$* | EC$_{50}$* |
|---|---|---|
| 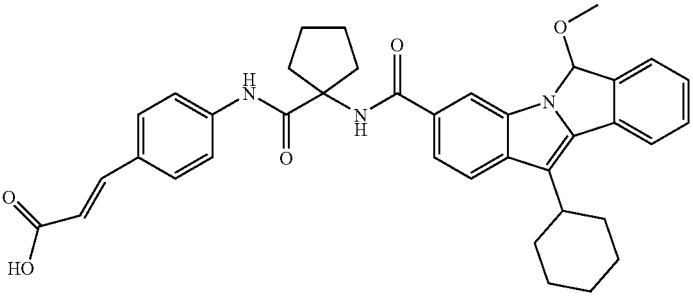 | B | E** |
| 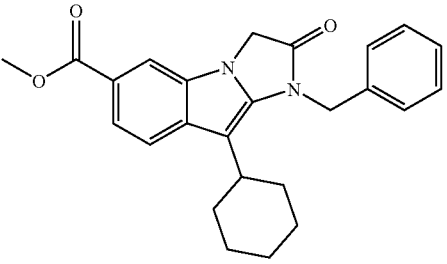 | | D** |
| 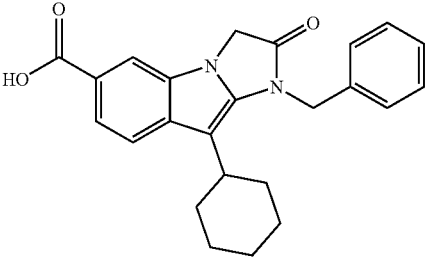 | | C** |
| 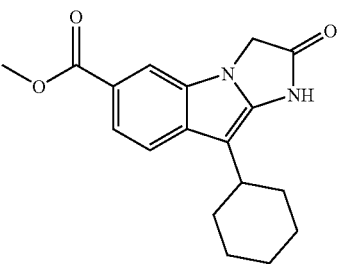 | | D** |
| 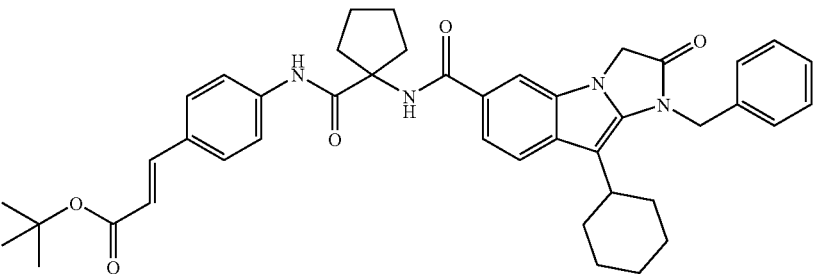 | | C** |

| Structure | IC$_{50}$* | EC$_{50}$* |
|---|---|---|
| 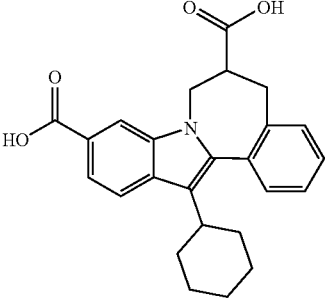 | C** | |
| 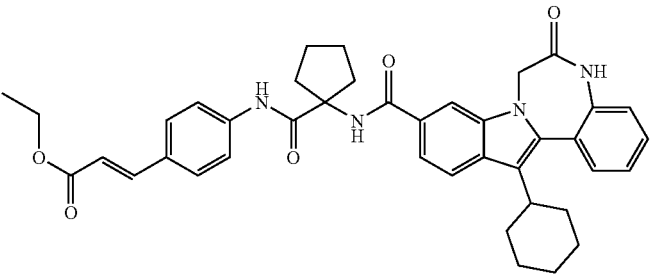 | E** | |
| 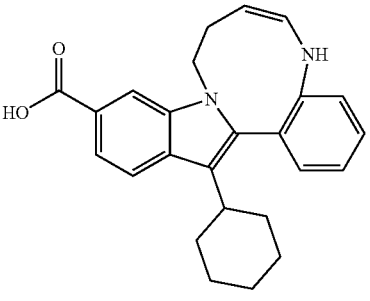 | D** | |
| 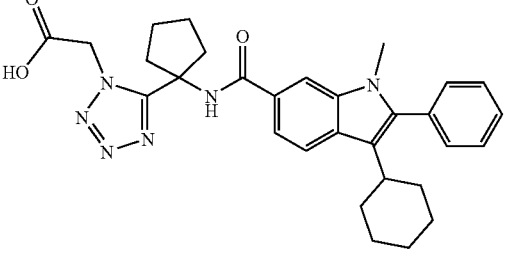 | C** | |
| 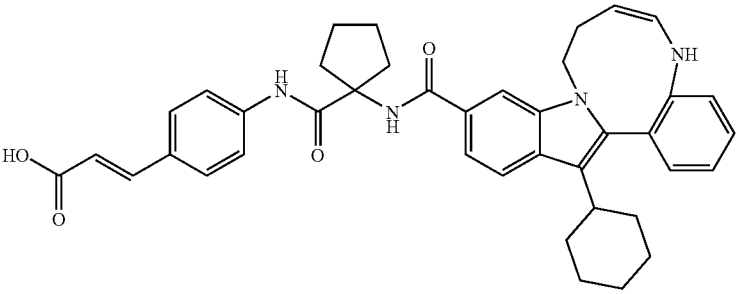 | B | E** |

-continued

| Structure | IC$_{50}$* | EC$_{50}$* |
|---|---|---|
| 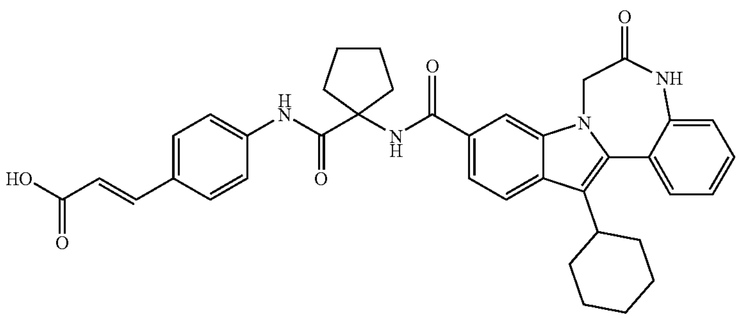 | B | E |
| | | C** |
| | | C** |
| | | C** |
| | | E** |

-continued
| Structure | IC$_{50}$* | EC$_{50}$* |
|---|---|---|
| 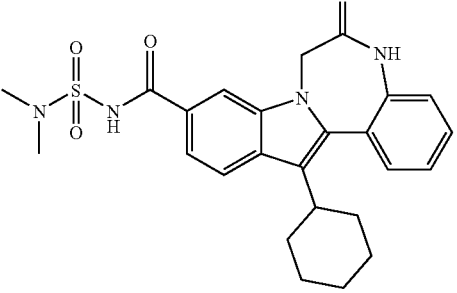 | B | E |
| 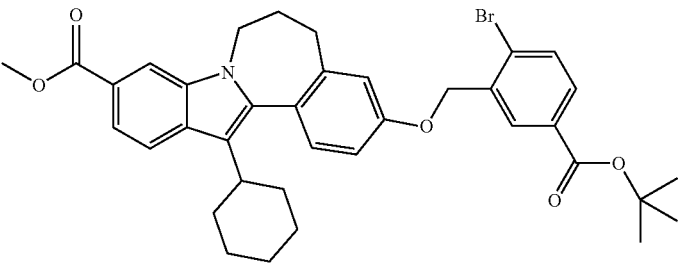 | | |
| 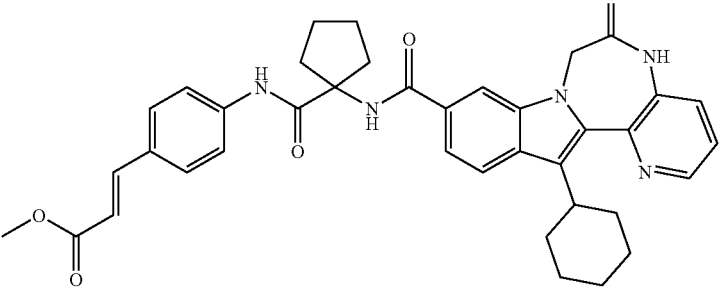 | B | F |
| 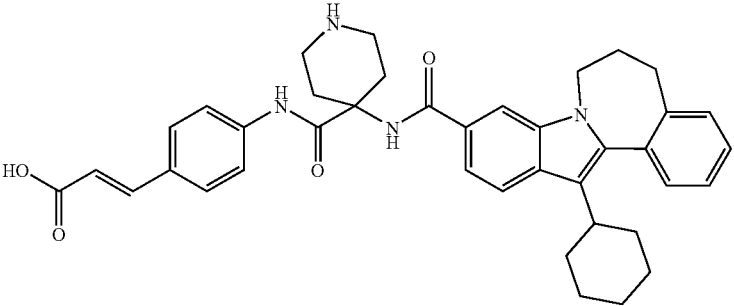 | B | E |
| 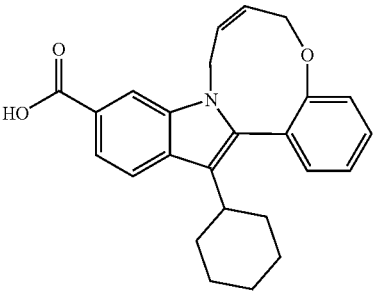 | | D |

-continued
| Structure | IC$_{50}$* | EC$_{50}$* |
| --- | --- | --- |
| 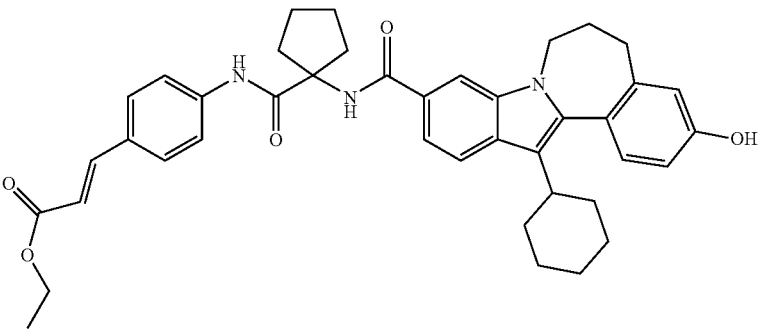 | A | E |
| 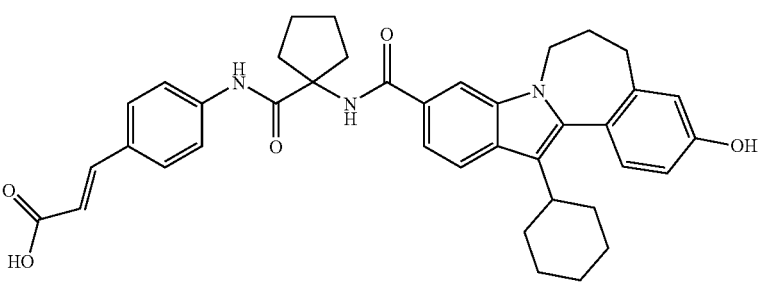 | B | E |
| 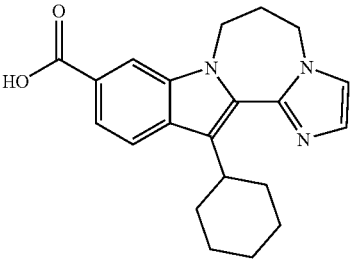 | C** | |
| 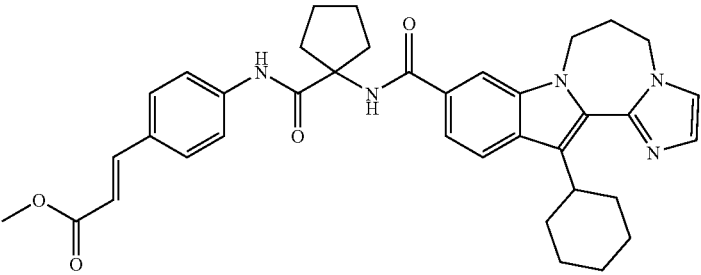 | D | |
| 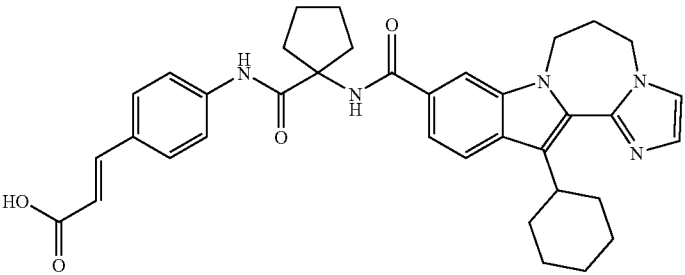 | B | D** |

-continued
| Structure | IC$_{50}$* | EC$_{50}$* |
|---|---|---|
| 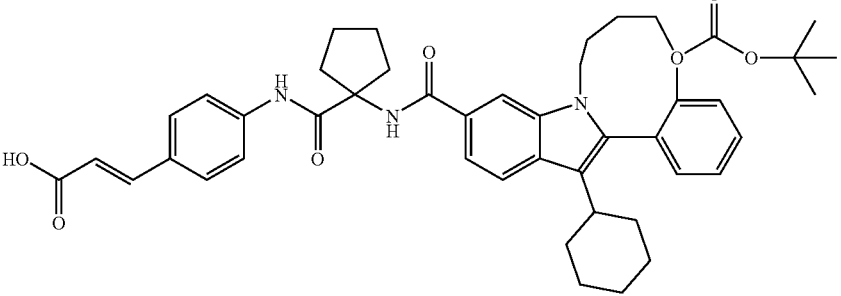 | | D |
| 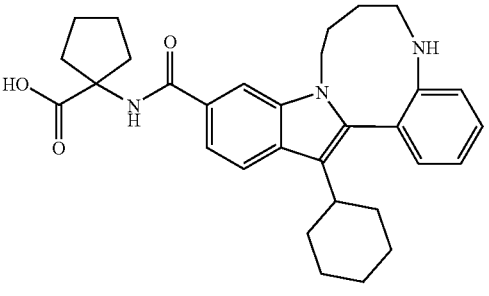 | | D |
| 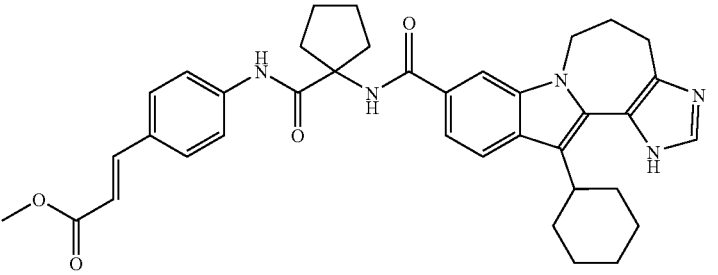 | | D |
| 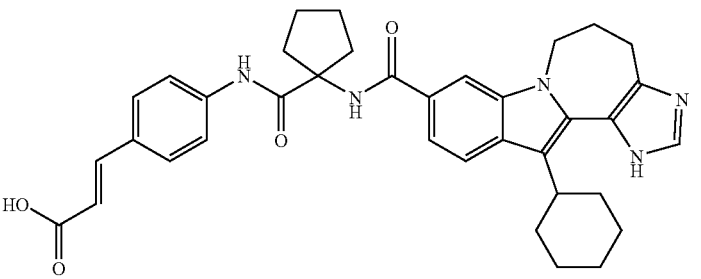 | | D |
| 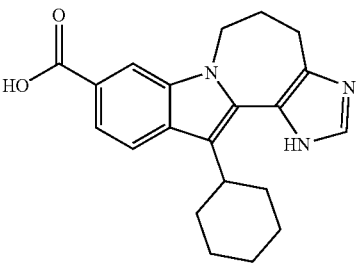 | | C |

| Structure | IC$_{50}$* | EC$_{50}$* |
|---|---|---|
| 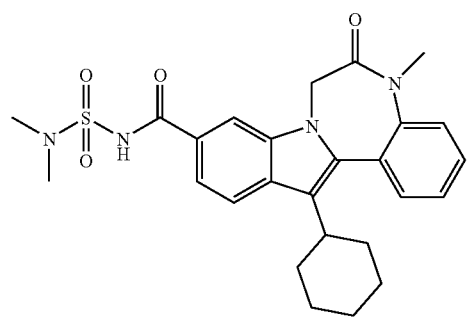 | | E |
| 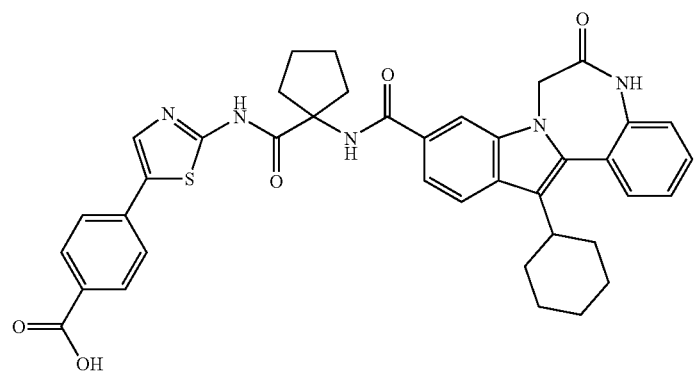 | B | E |
| 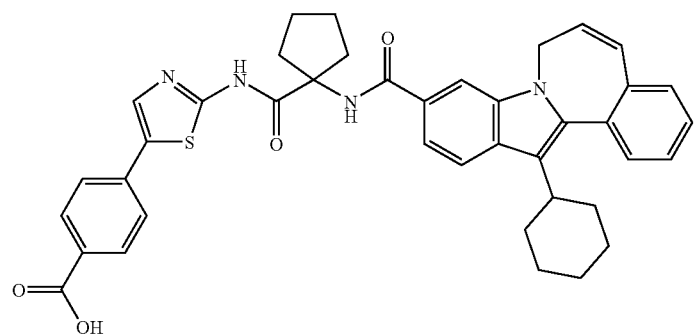 | | E |
| 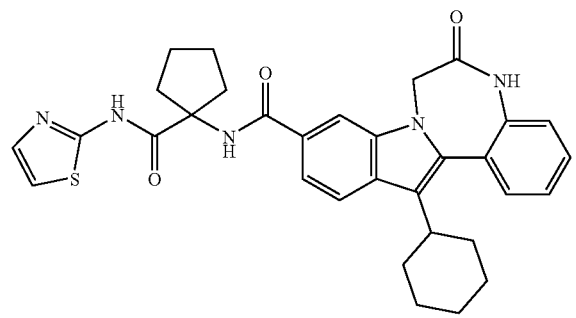 | B | E |

-continued
| Structure | IC$_{50}$* | EC$_{50}$* |
|---|---|---|
| 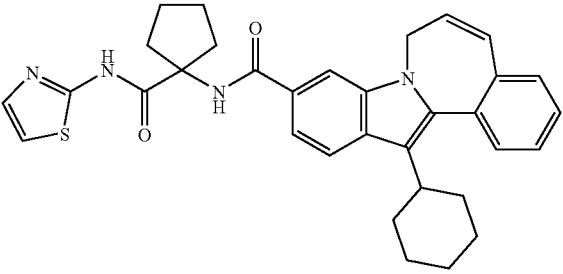 | | E |
| 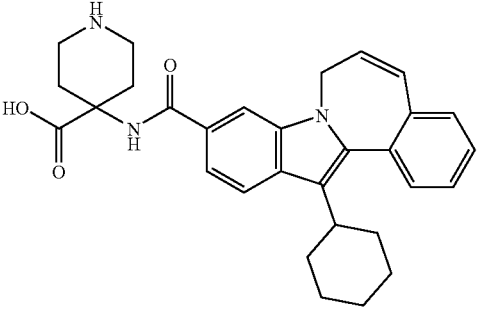 | | D |
| 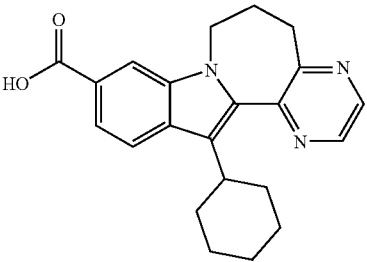 | | D |
| 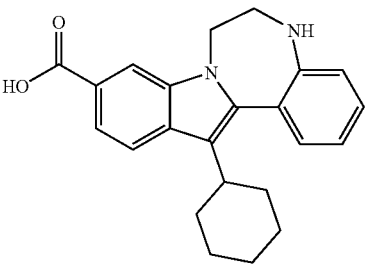 | | D |
| 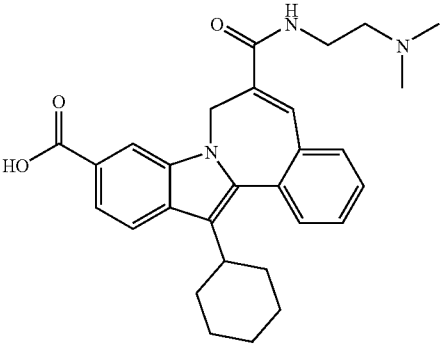 | B | E |

-continued

| Structure | IC$_{50}$* | EC$_{50}$* |
|---|---|---|
| | | D |
| | B | F |
| | | E |
| | B | E |

-continued
| Structure | IC$_{50}$* | EC$_{50}$* |
|---|---|---|
| 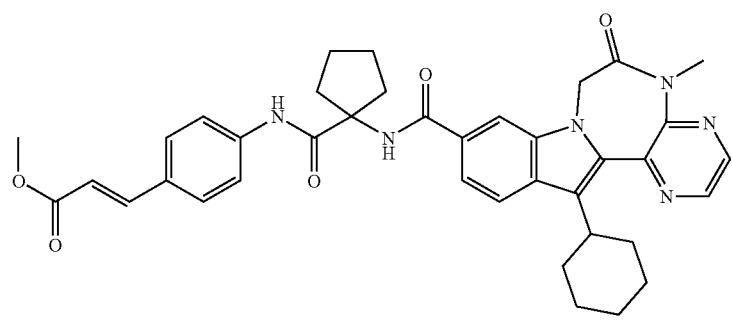 | | E |
| 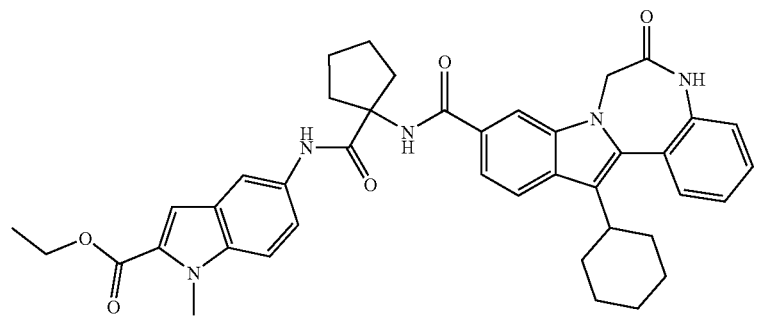 | B | E |
| 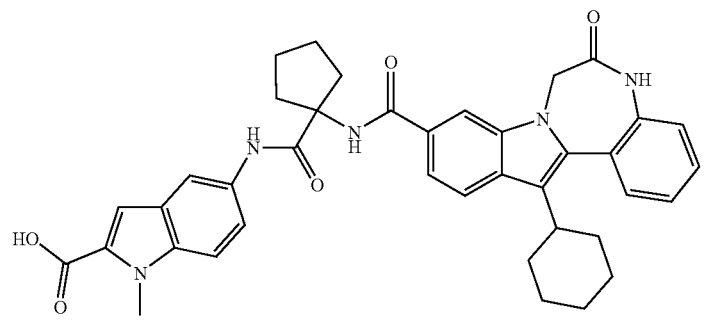 | B | E |
| 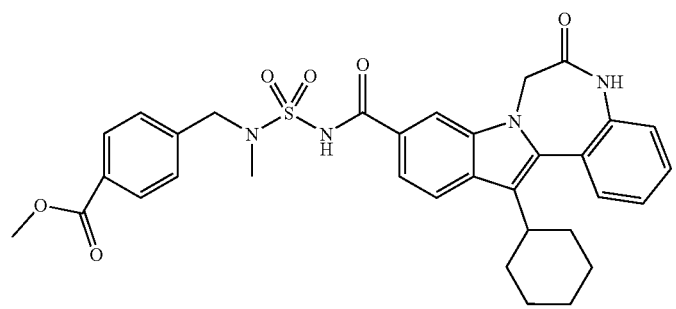 | | |

-continued
| Structure | IC$_{50}$* | EC$_{50}$* |
| --- | --- | --- |
| 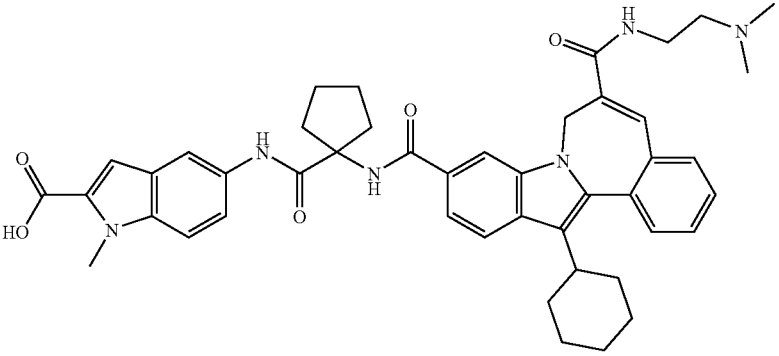 | B | E |
| 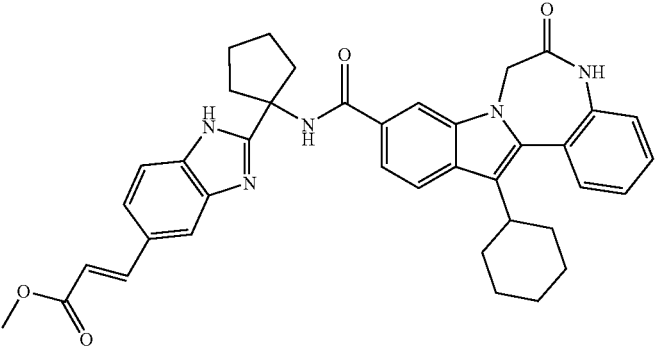 | B | F |
| 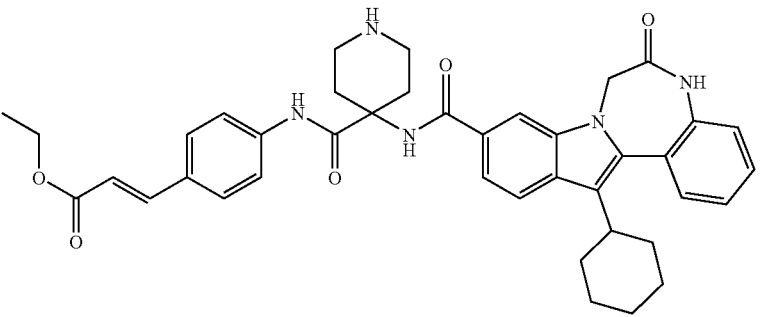 | B | E |
| 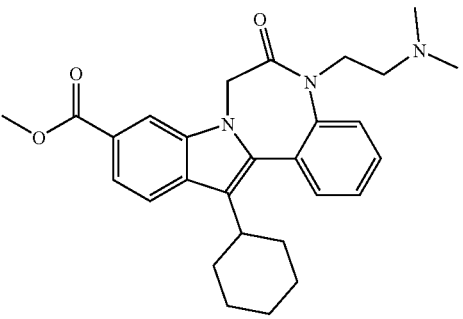 | A | D |

-continued
| Structure | IC$_{50}$* | EC$_{50}$* |
|---|---|---|
| 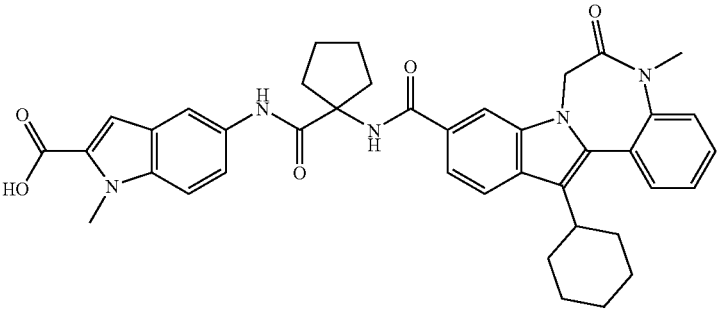 | B | E |
| 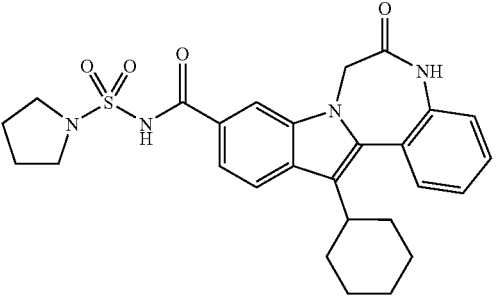 | B | E |
| 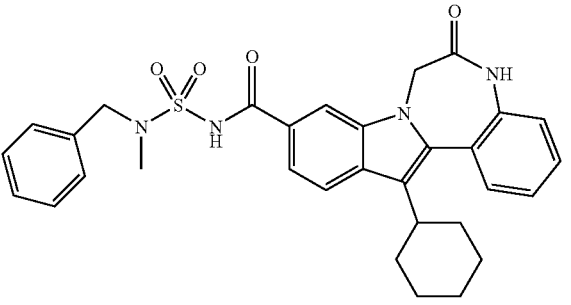 | B | E |
| 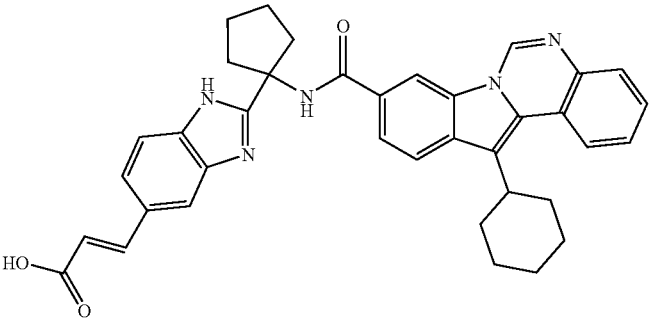 | B | E |
| 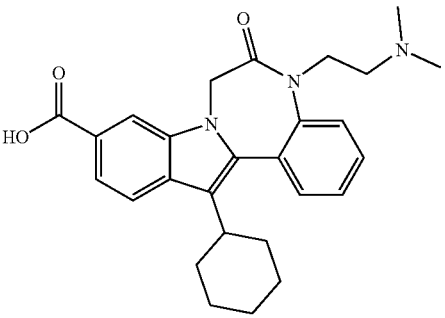 | B | E |

-continued

| Structure | IC$_{50}$* | EC$_{50}$* |
|---|---|---|
| | B | E |
| | B | E |
| | B | D |
| | B | D |
| 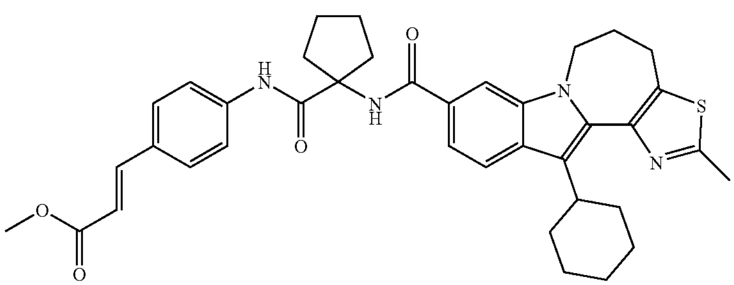 | A | C |

-continued
| Structure | IC$_{50}$* | EC$_{50}$* |
|---|---|---|
| 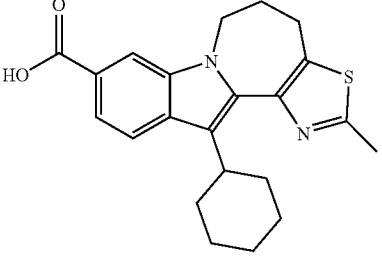 | A | C |
| 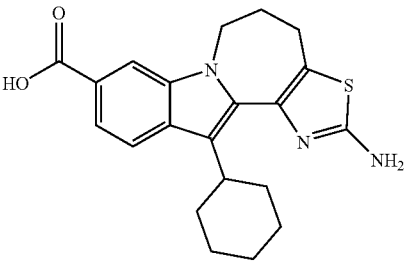 | A | C |
| 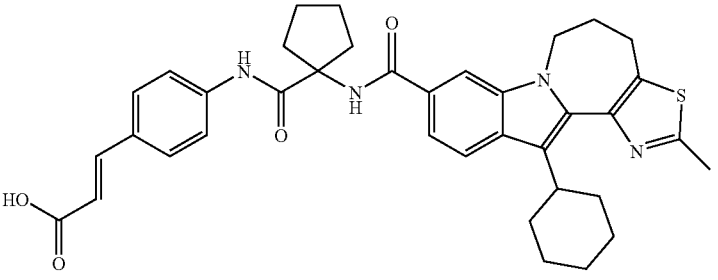 | B | D |
| 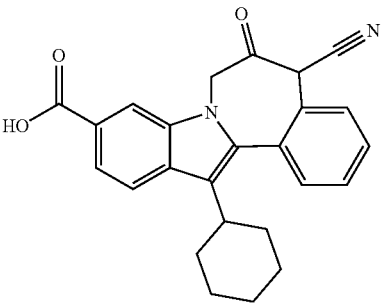 | B | C |
| 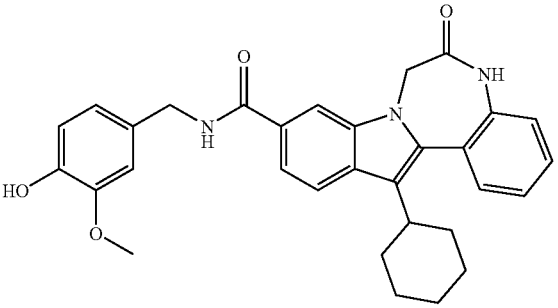 | B | F |

-continued

| Structure | IC$_{50}$* | EC$_{50}$* |
|---|---|---|
| | A | C |
| | A | C |
| | B | D |
| | B | E |
| | B | D |

-continued
| Structure | IC$_{50}$* | EC$_{50}$* |
|---|---|---|
| 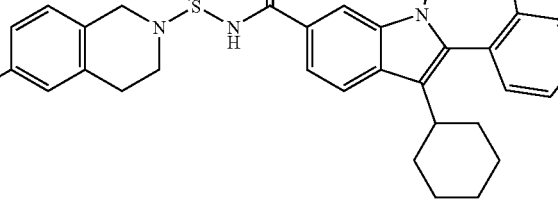 | B | D |
| 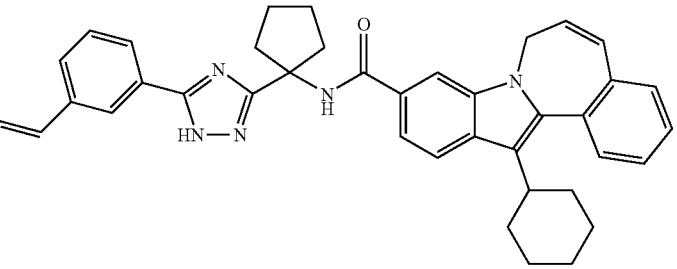 | B | E |
| 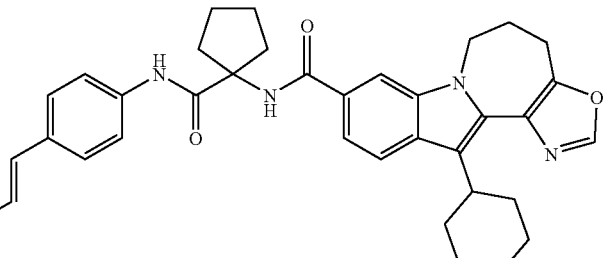 | A | D |
| 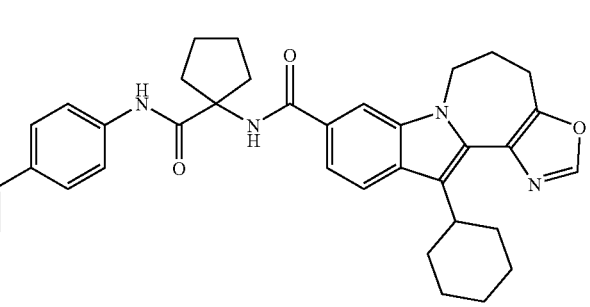 | B | E |
| 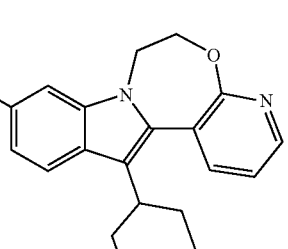 | | |

-continued
| Structure | IC$_{50}$* | EC$_{50}$* |
|---|---|---|
| 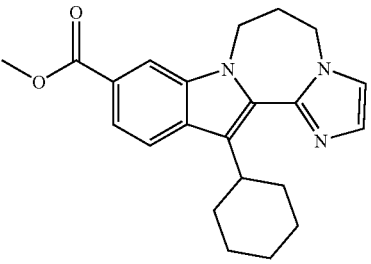 | | |
| 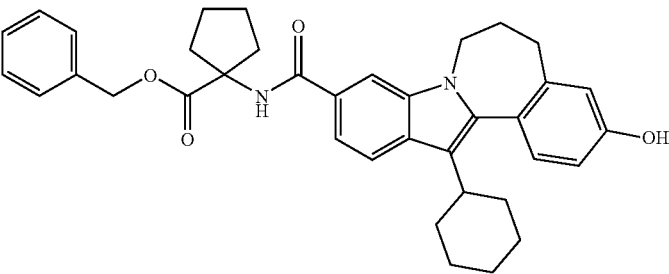 | A | D |
| 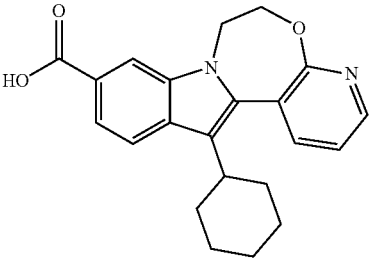 | B | D |
| 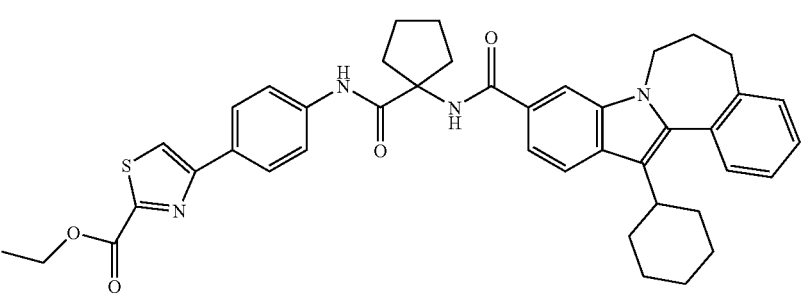 | A | E |
| 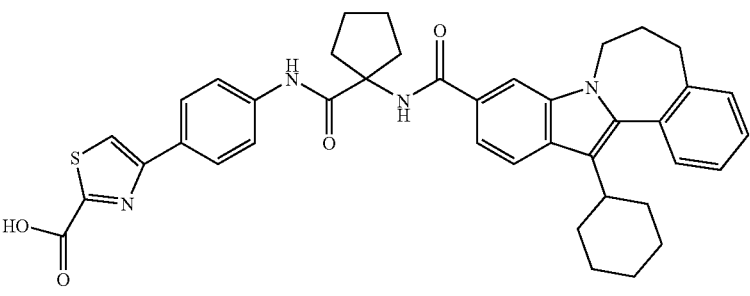 | B | E |

-continued

| Structure | IC$_{50}$* | EC$_{50}$* |
|---|---|---|
| | A | D |
| | A | D |
| | A | D |
| 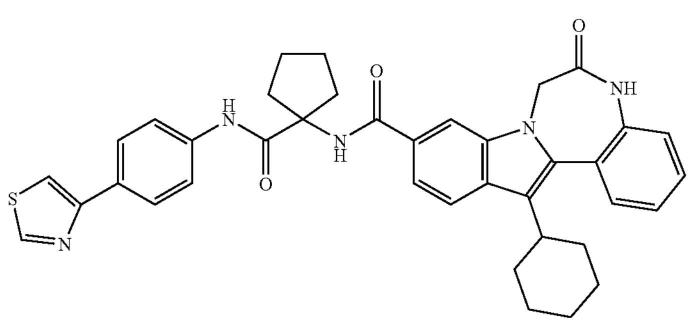 | B | E |

-continued

| Structure | IC$_{50}$* | EC$_{50}$* |
|---|---|---|
| | A | C |
| | B | E |
| | A | C |
| | B | E |
| | A | C |

-continued

| Structure | IC$_{50}$* | EC$_{50}$* |
|---|---|---|
| | A | C |
| | A | D |
| | B | E |
| | B | D |
| | B | D |

-continued

| Structure | IC₅₀* | EC₅₀* |
|---|---|---|
| | B | D |
| | B | E |
| | B | E |
| | B | E |

| Structure | IC$_{50}$* | EC$_{50}$* |
| --- | --- | --- |
| | B | E |
| | B | E |
| | B | E |

-continued
| Structure | IC$_{50}$* | EC$_{50}$* |
|---|---|---|
| 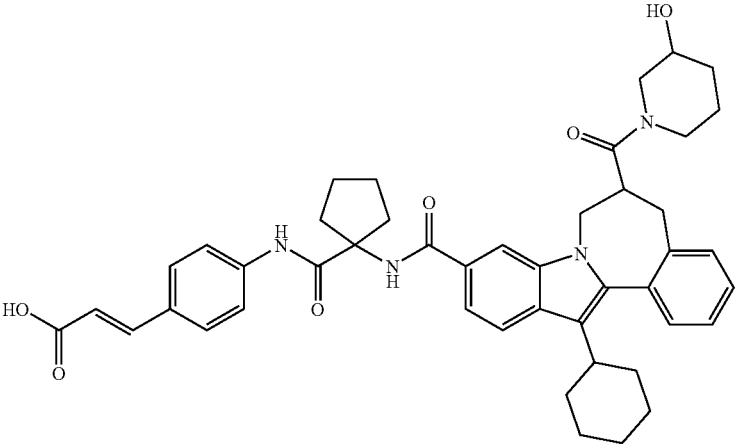 | B | E |
| 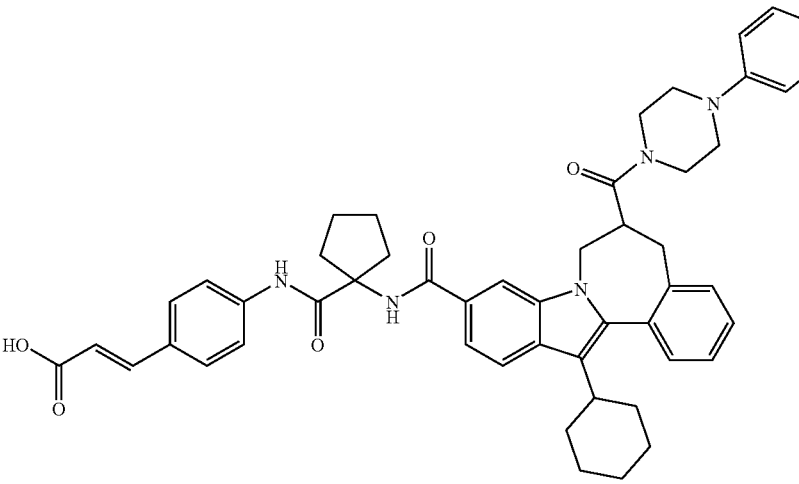 | B | E |
| 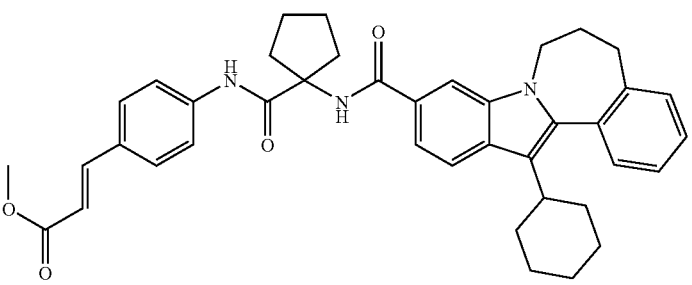 | | |
| 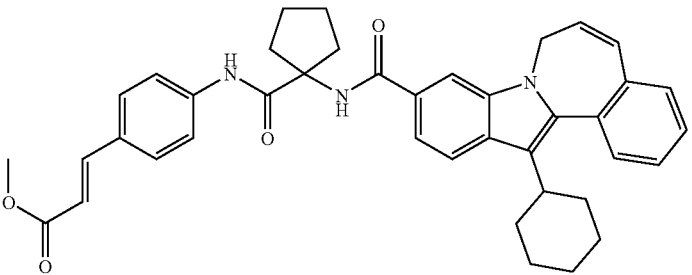 | | |

| Structure | IC$_{50}$* | EC$_{50}$* |
|---|---|---|
| 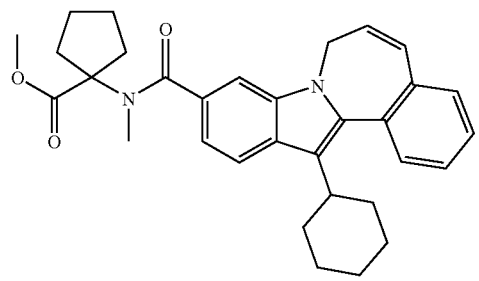 | | |
| | B | E |
| 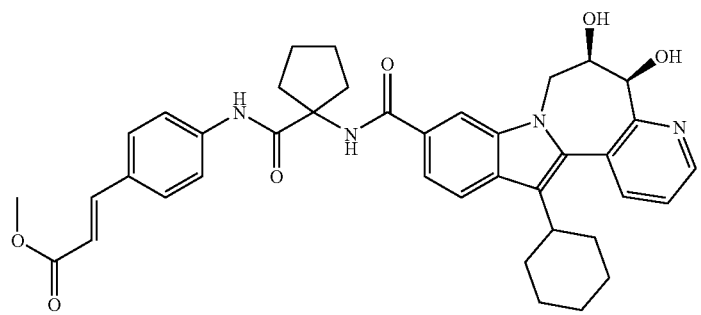 | | |
| | B | E |
| 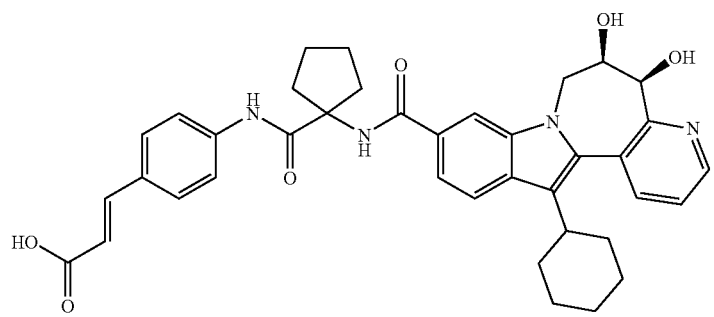 | | |
| 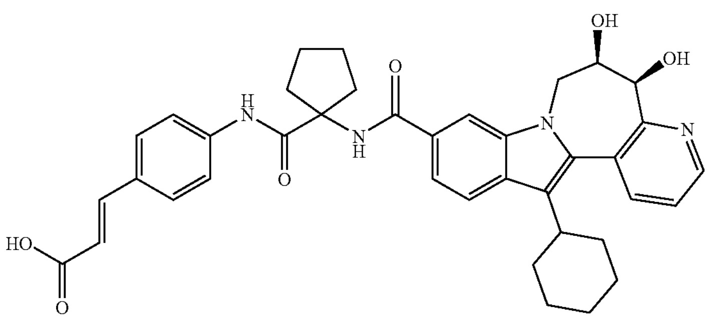 | A | D |
| 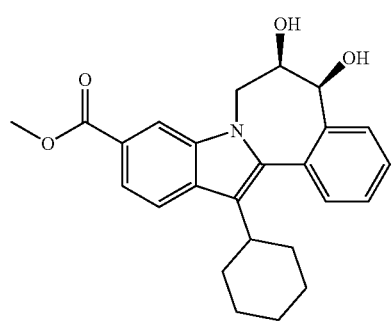 | | |

-continued
| Structure | IC$_{50}$* | EC$_{50}$* |
|---|---|---|
| 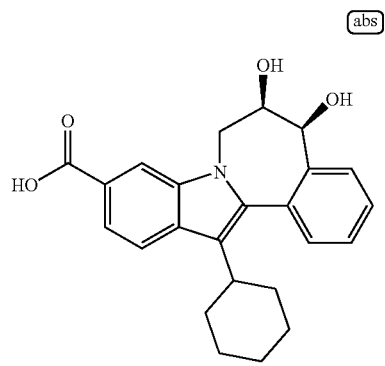 | B | D |
| 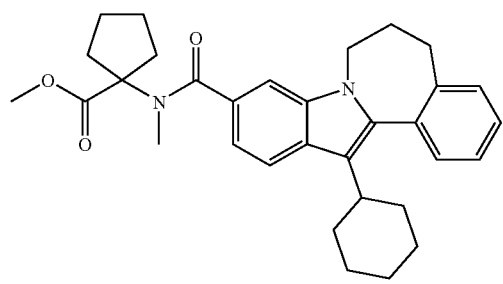 | B | C |
| 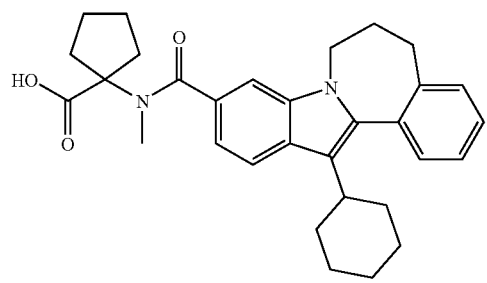 | A | E |
| 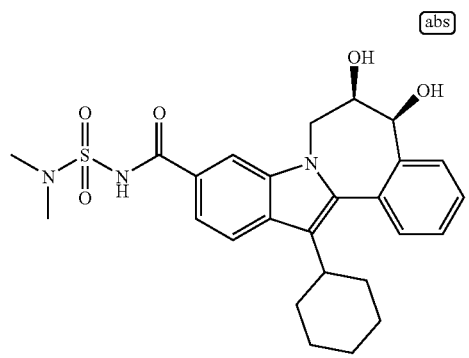 | | |

-continued

| Structure | IC₅₀* | EC₅₀* |
|---|---|---|
| | B | F |
| | B | D |
| | B | E |
| 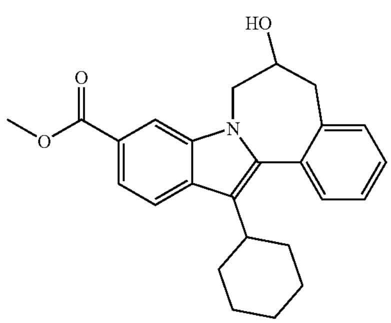 | A | E |
| | B | D |

-continued
| Structure | IC$_{50}$* | EC$_{50}$* |
|---|---|---|
| 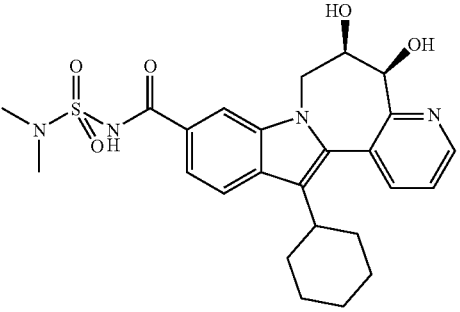 | B | C |
| 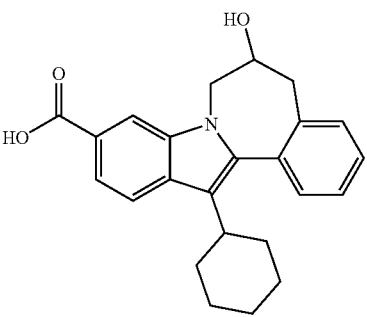 | B | D |
| 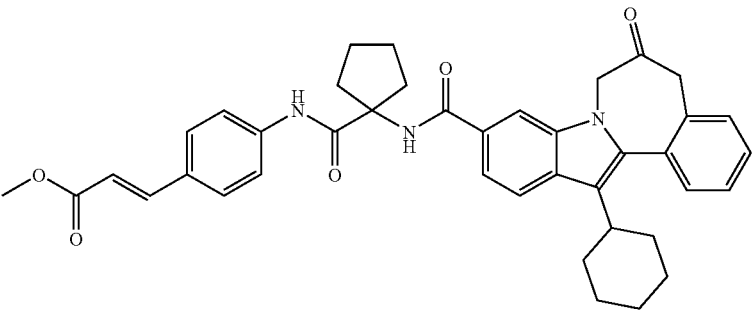 | A | E |
| 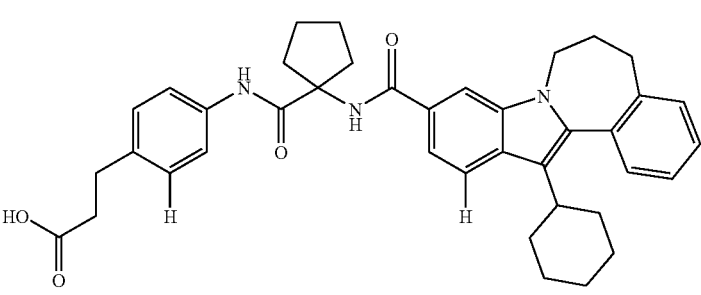 | | |
| 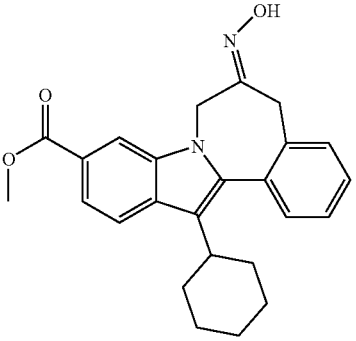 | A | E |

-continued
| Structure | IC$_{50}$* | EC$_{50}$* |
|---|---|---|
| 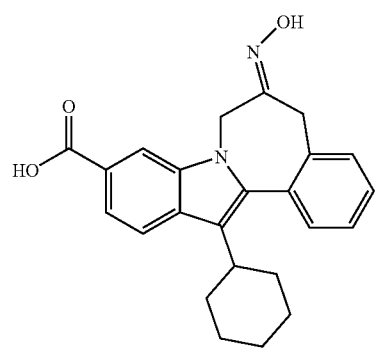 | B | D |
| 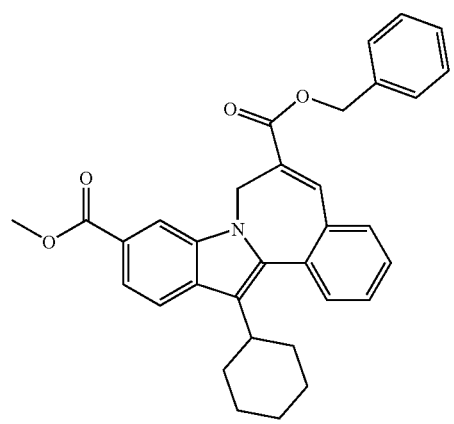 | A | D |
| 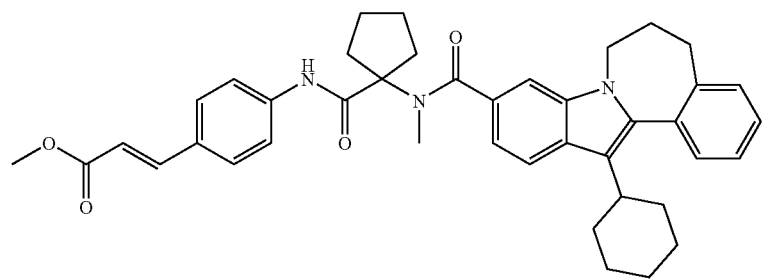 | A | D** |
| 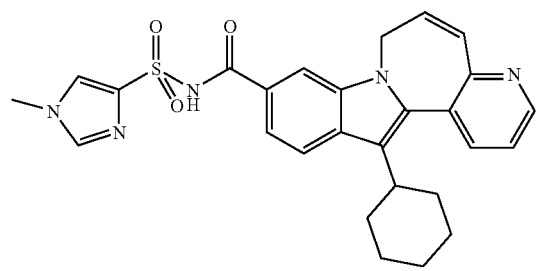 | B | C |

-continued

| Structure | IC$_{50}$* | EC$_{50}$* |
|---|---|---|
| | B | C |
| | B | C |
| | B | C |
| | B | D |
| 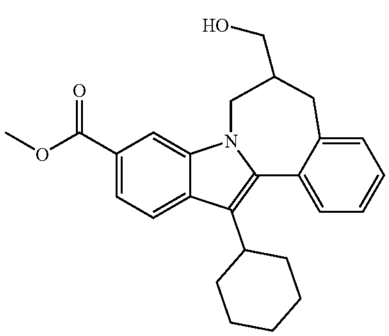 | A | E |

-continued
| Structure | IC$_{50}$* | EC$_{50}$* |
|---|---|---|
| 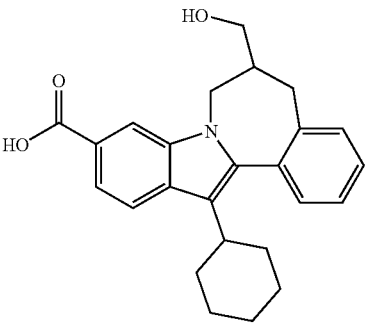 | B | D |
| 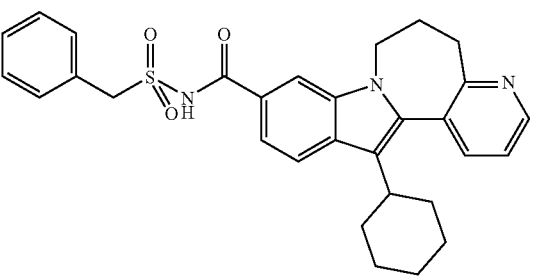 | B | D |
| 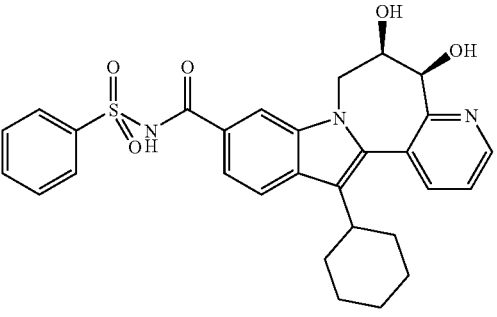 | B | D |
| 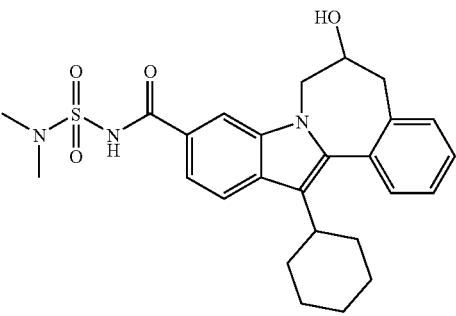 | B | E |
| 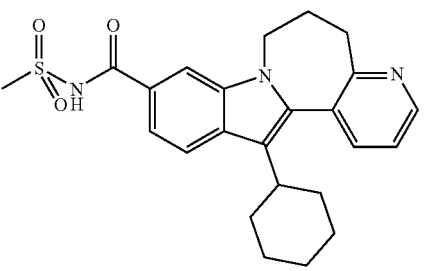 | B | D |

-continued
| Structure | IC$_{50}$* | EC$_{50}$* |
|---|---|---|
| | B | D |
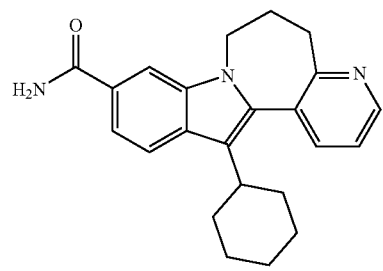 | | |
| | B | D |
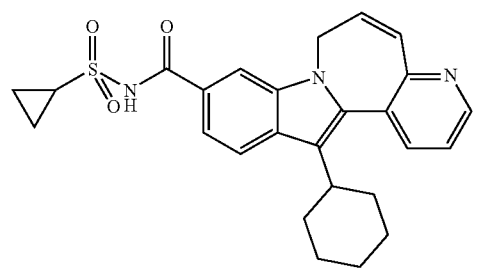 | | |
| | B | E |
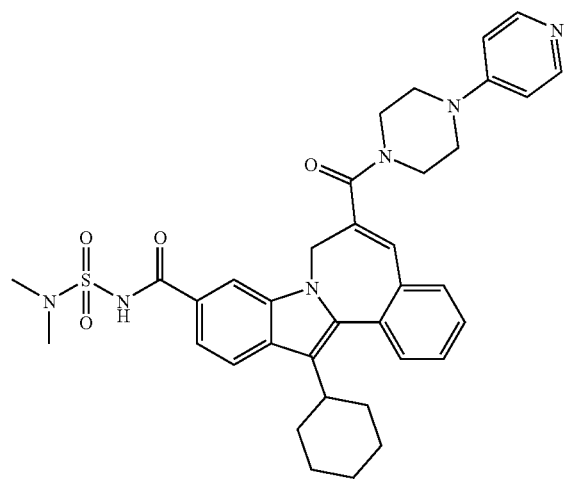 | | |
| | A | D |
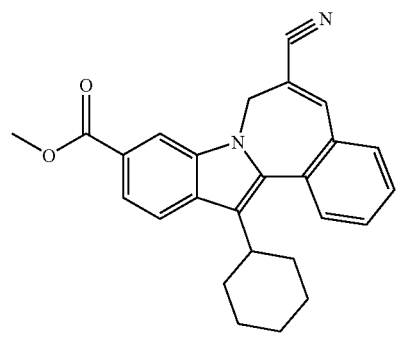 | | |

-continued
| Structure | IC$_{50}$* | EC$_{50}$* |
|---|---|---|
| 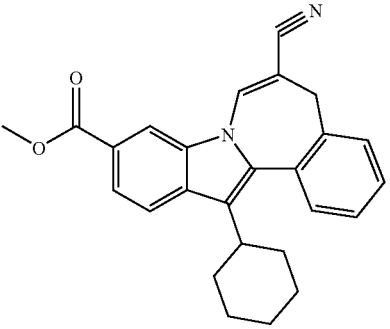 | A | E |
| 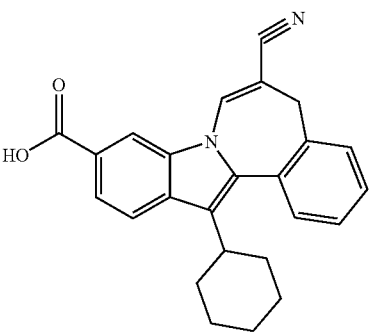 | B | D |
| 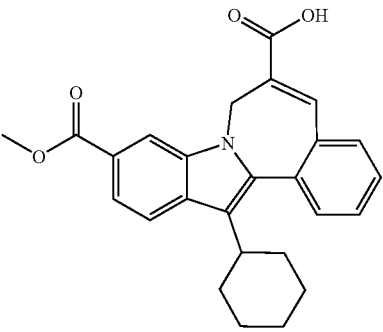 | B | E |
| 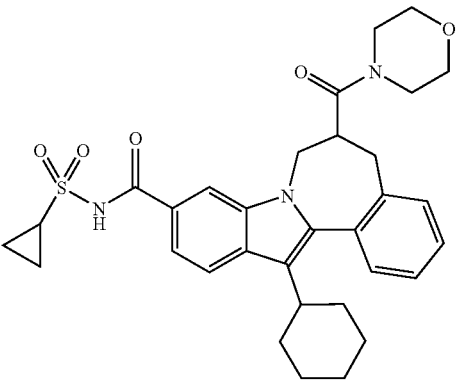 | B | E |

-continued
| Structure | IC$_{50}$* | EC$_{50}$* |
|---|---|---|
| 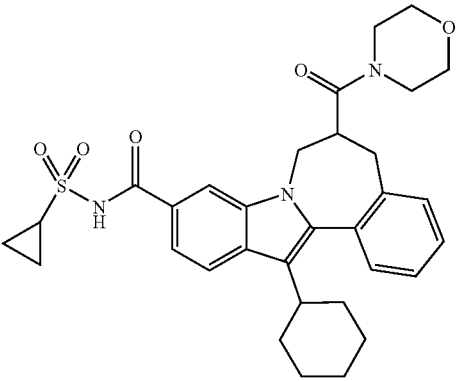 | B | E |
| 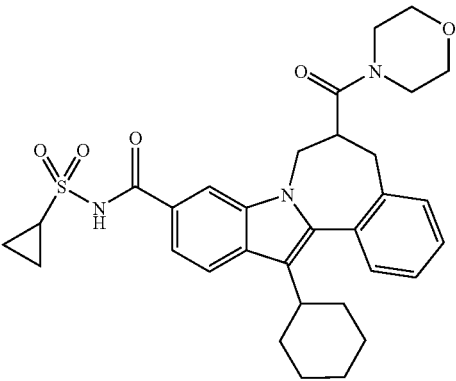 | B | E |
| 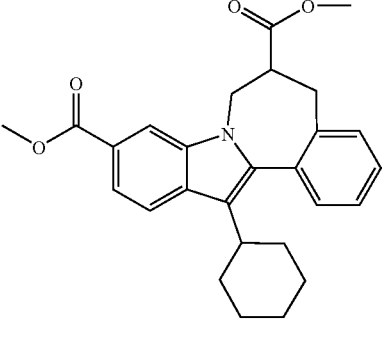 | B | |
| 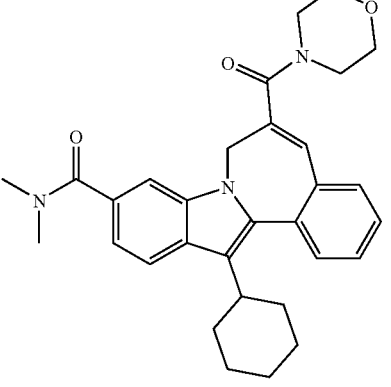 | B | D |

-continued

| Structure | IC$_{50}$* | EC$_{50}$* |
|---|---|---|
| 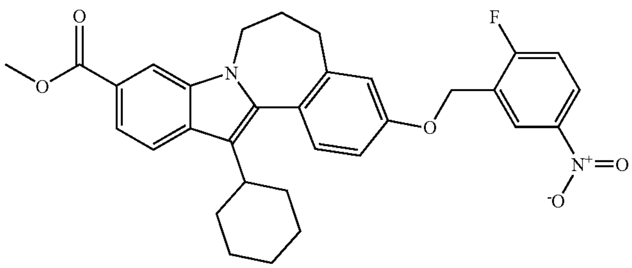 | A | D |
| | B | E |
| | B | E |
| | B | E |

-continued

| Structure | IC$_{50}$* | EC$_{50}$* |
|---|---|---|
| | A | D |
| | A | E |
| | B | D |
| | B | E |
| | B | D |

-continued

| Structure | IC$_{50}$* | EC$_{50}$* |
|---|---|---|
| | B | E |
| | B | D |
| | B | E |
| 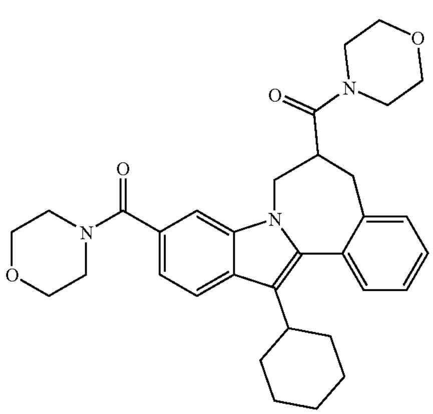 | A | E |

-continued
| Structure | IC50* | EC50* |
|---|---|---|
| 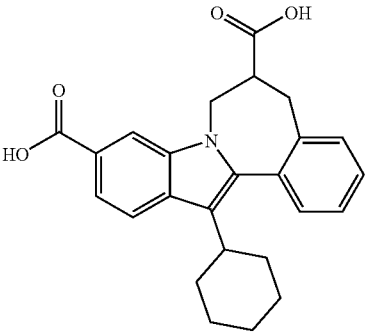 | B | C |
| 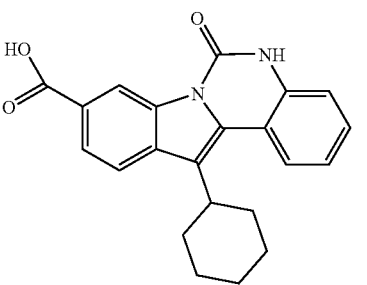 | A | E |
| 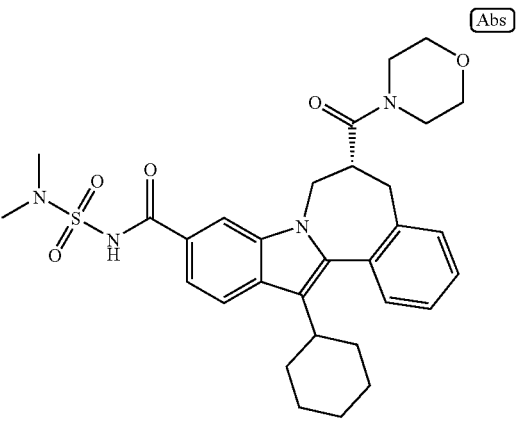 | B | E |
| 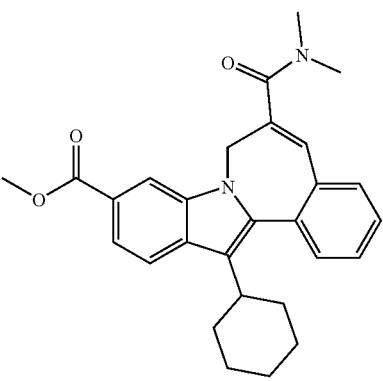 | A | D |

-continued

| Structure | IC$_{50}$* | EC$_{50}$* |
| --- | --- | --- |
| | B | E |
| | B | E |
| | A | D |
| | A | D |

-continued
| Structure | IC$_{50}$* | EC$_{50}$* |
|---|---|---|
| 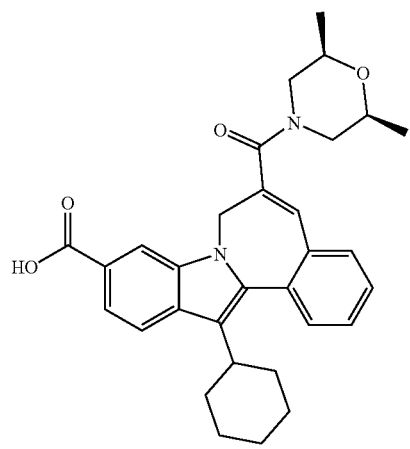 | B | E |
| 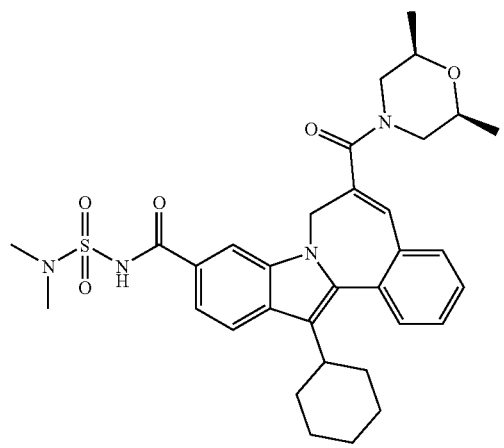 | B | E |
| 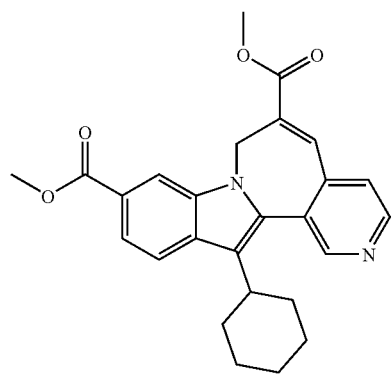 | A | D |

-continued

| Structure | IC$_{50}$* | EC$_{50}$* |
|---|---|---|
| | A | D |
| | A | D |
| | A | D |
| 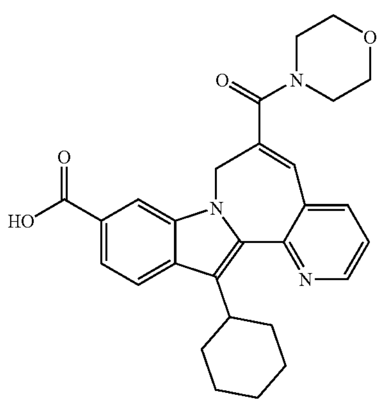 | B | E |

-continued

| Structure | IC$_{50}$* | EC$_{50}$* |
|---|---|---|
| | B | E |
| | B | E |
| 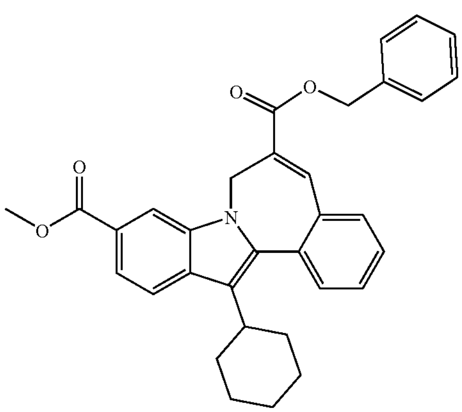 | A | D |
| | B | D |

-continued

| Structure | IC$_{50}$* | EC$_{50}$* |
|---|---|---|
| | B | E |
| 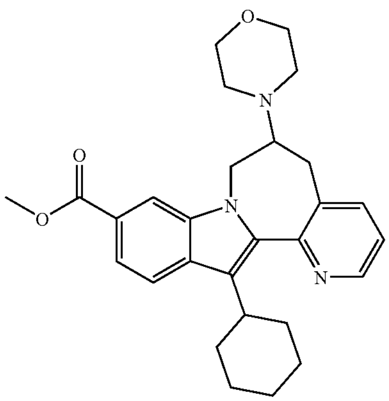 | A | E |
| | B | E |
| | | |

-continued

| Structure | IC$_{50}$* | EC$_{50}$* |
|---|---|---|
| | B | D |
| | B | E |
| | B | E |
| | B | E |

-continued
| Structure | IC$_{50}$* | EC$_{50}$* |
|---|---|---|
| 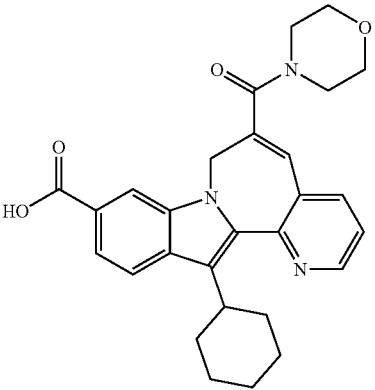 | B | D |
| 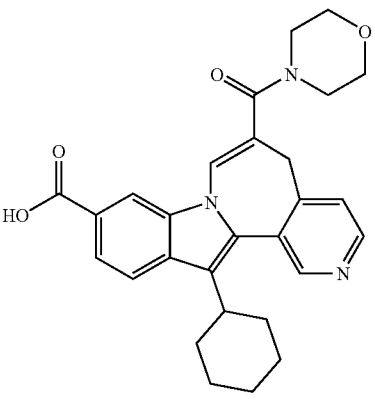 | A | C |
| 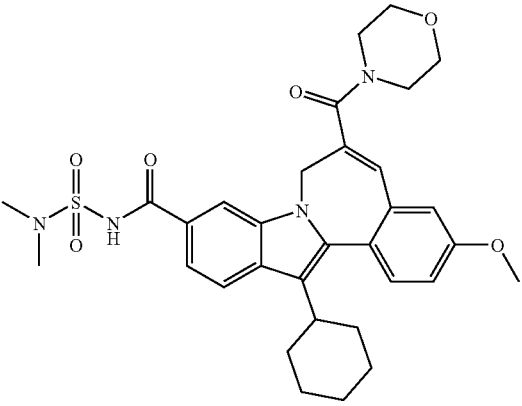 | B | E |
| 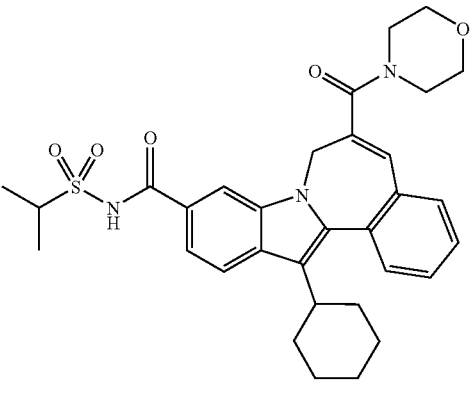 | B | E |

-continued

| Structure | IC$_{50}$* | EC$_{50}$* |
|---|---|---|
| | B | E |
| | B | E |
| | B | E |
| | B | E |

-continued

| Structure | IC$_{50}$* | EC$_{50}$* |
|---|---|---|
| | B | E |
| | B | E |
| | B | E |
| | B | E |

-continued
| Structure | IC$_{50}$* | EC$_{50}$* |
|---|---|---|
| 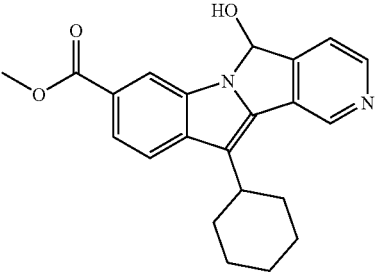 | | |
| 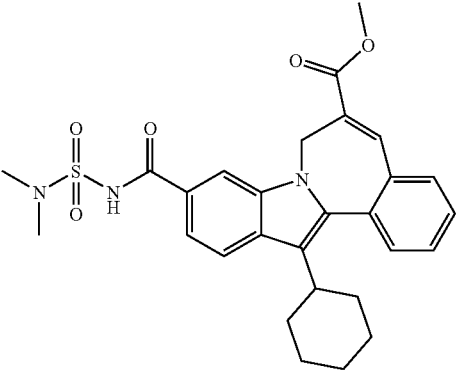 | B | E |
| 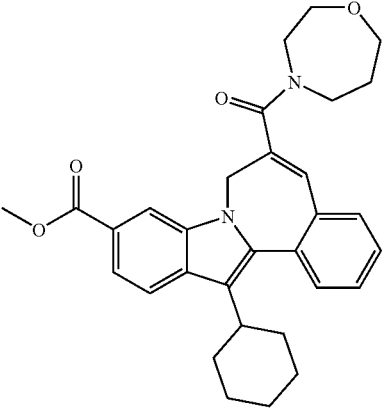 | A | D |
| 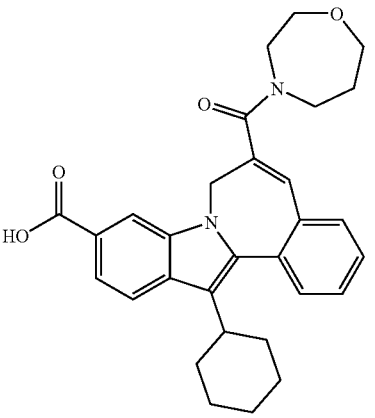 | B | E |

-continued
| Structure | IC$_{50}$* | EC$_{50}$* |
|---|---|---|
| 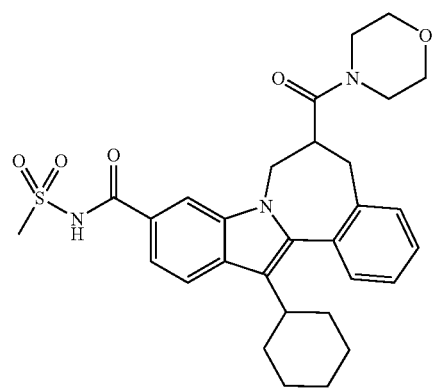 | B | E |
| 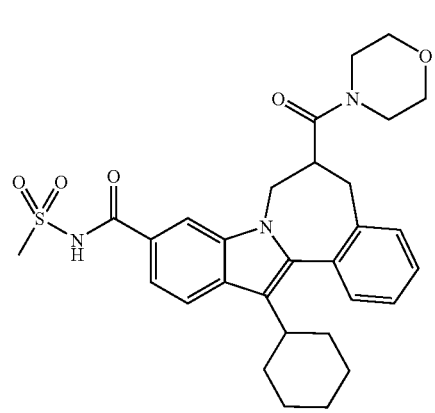 | B | E |
| 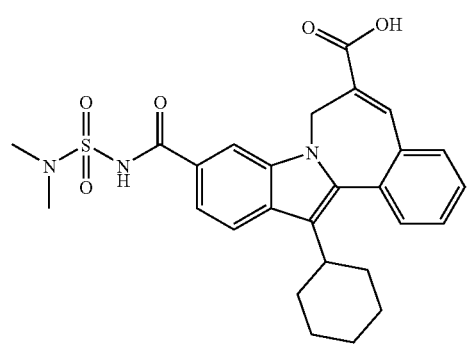 | B | C |
| 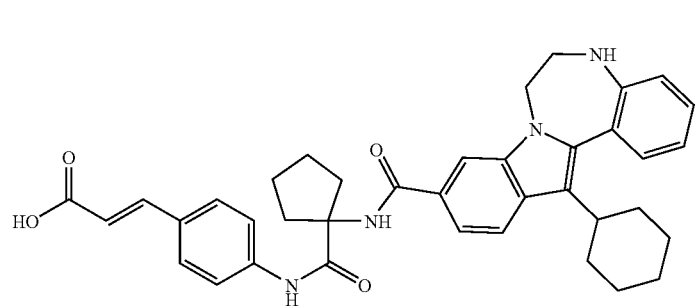 | B | E |

-continued

| Structure | IC$_{50}$* | EC$_{50}$* |
|---|---|---|
| 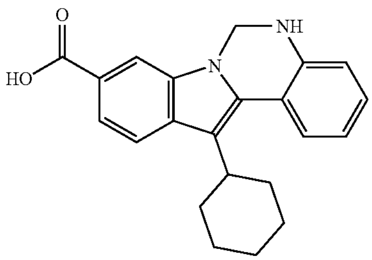 | B | E |
| | A | E |
| | A | E |
| | | |
| | | |

-continued

| Structure | IC$_{50}$* | EC$_{50}$* |
|---|---|---|
| 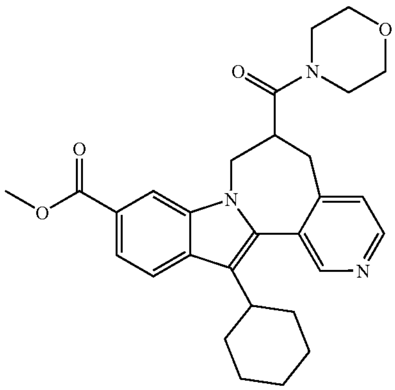 | A | E |
| | B | E |
| | B | E |
| | B | E |

-continued

| Structure | IC$_{50}$* | EC$_{50}$* |
|---|---|---|
| | B | E |
| | B | E |
| | B | E |
| | | |

-continued
| Structure | IC$_{50}$* | EC$_{50}$* |
|---|---|---|
| 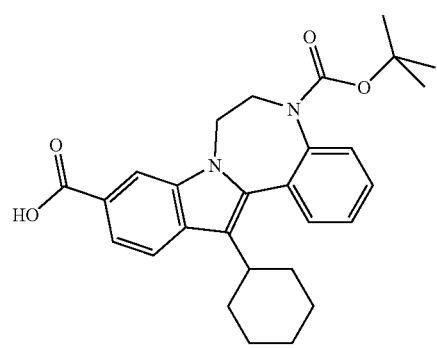 | B | D |
| 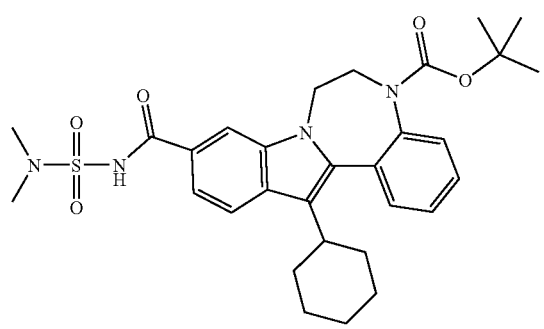 | B | E |
| 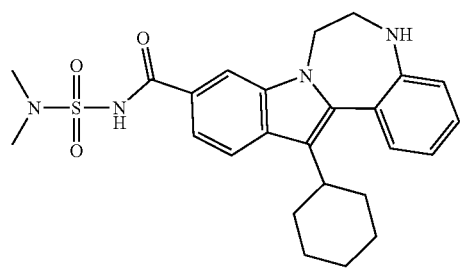 | B | E |
| 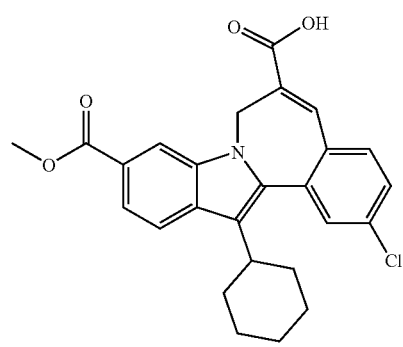 | A | D |

-continued

| Structure | IC$_{50}$* | EC$_{50}$* |
|---|---|---|
| | A | B |
| | B | D |
| | B | D |
| | A | E |

-continued

| Structure | IC$_{50}$* | EC$_{50}$* |
|---|---|---|
| | B | E |
| | A | D |
| | B | E |
| | A | D |

-continued
| Structure | IC$_{50}$* | EC$_{50}$* |
|---|---|---|
| 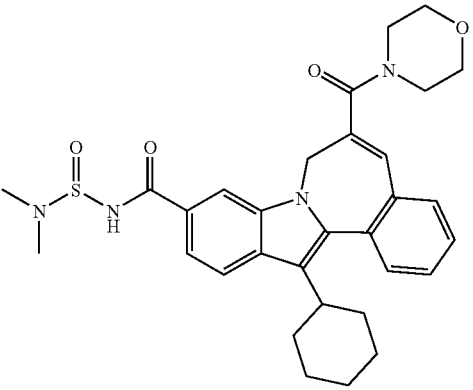 | B | D |
| 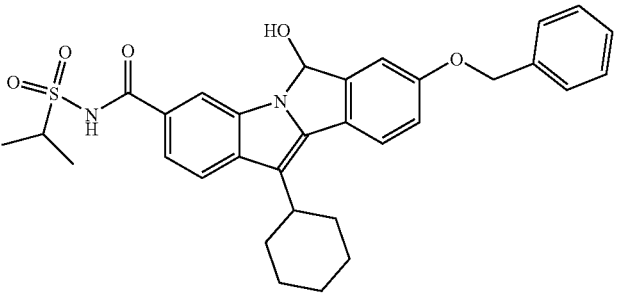 | B | E |
| 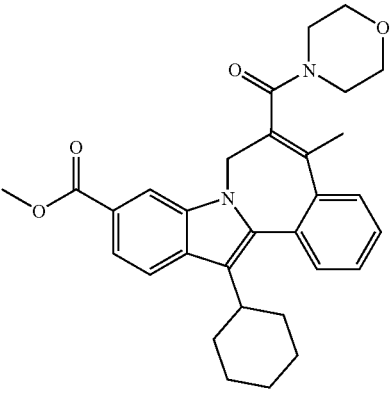 | A | D |
| 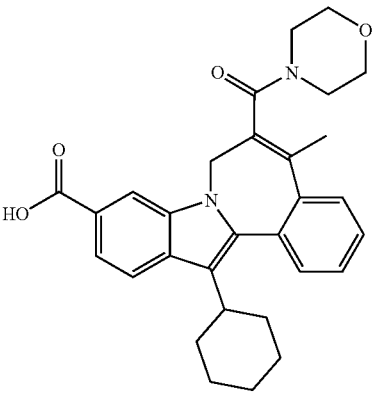 | B | E |

-continued

| Structure | IC$_{50}$* | EC$_{50}$* |
|---|---|---|
| | A | E |
| | B | E |
| | A | D |
| | B | E |

-continued

| Structure | IC$_{50}$* | EC$_{50}$* |
|---|---|---|
| | B | E |
| | B | D |
| | B | E |

-continued
| Structure | IC$_{50}$* | EC$_{50}$* |
|---|---|---|
| | B | E |
| 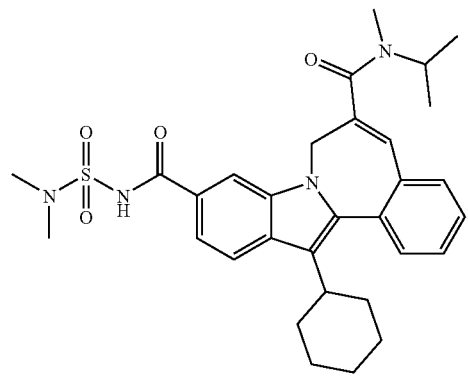 | B | E |
| 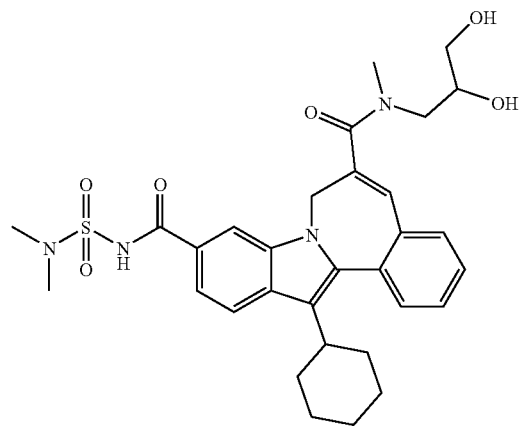 | B | E |
| 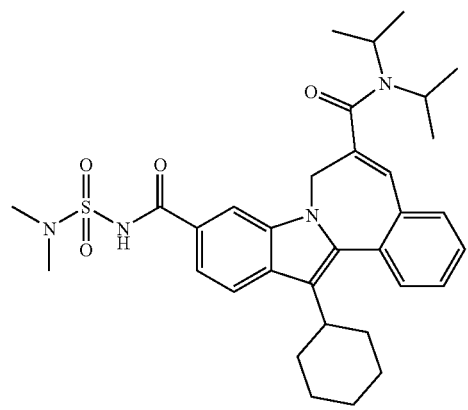 | | |

-continued

| Structure | IC₅₀* | EC₅₀* |
|---|---|---|
| | B | E |
| | B | E |
| | B | E |
| | B | E |

-continued

| Structure | IC$_{50}$* | EC$_{50}$* |
|---|---|---|
| | B | E |
| | B | E |
| | B | E |
| | B | E |
| | B | E |

-continued
| Structure | IC$_{50}$* | EC$_{50}$* |
|---|---|---|
| 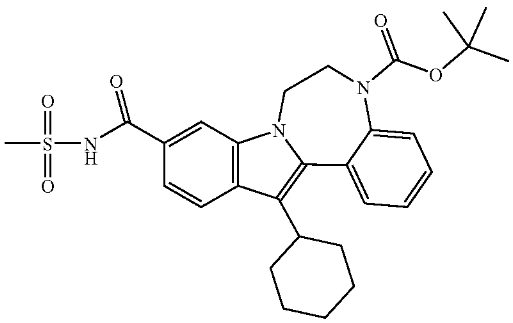 | B | E |
| 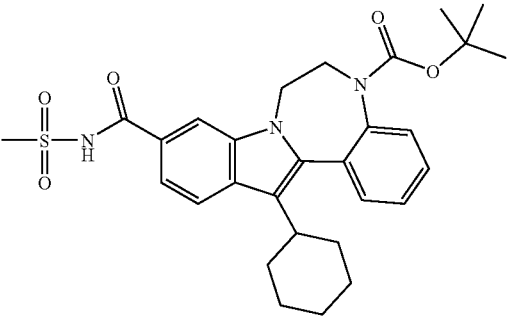 | | E |
| 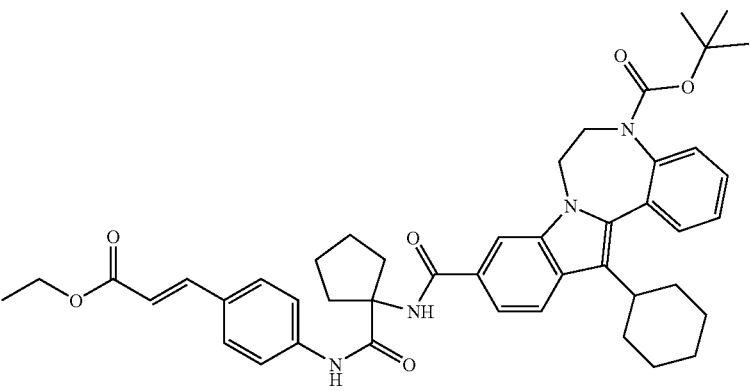 | | E |
| 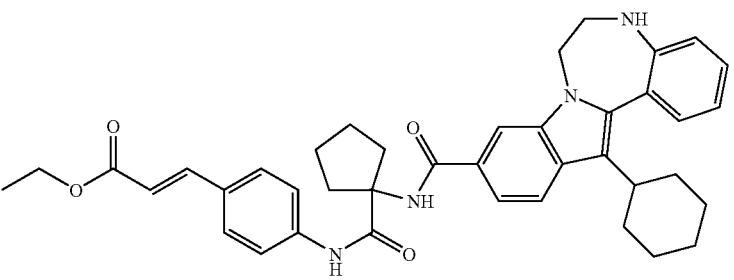 | | C |
| 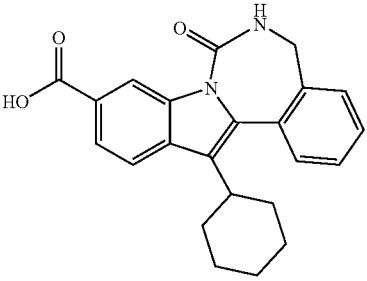 | | |

-continued
| Structure | IC$_{50}$* | EC$_{50}$* |
|---|---|---|
| 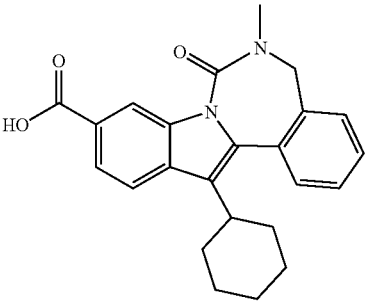 | | C |
| 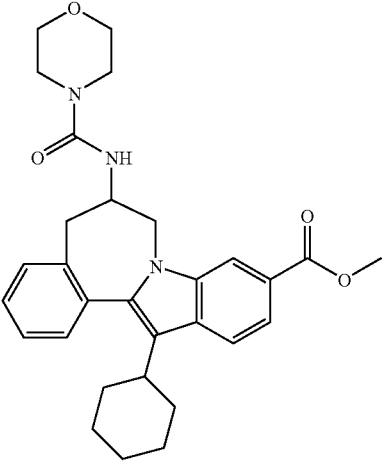 | | D** |
| 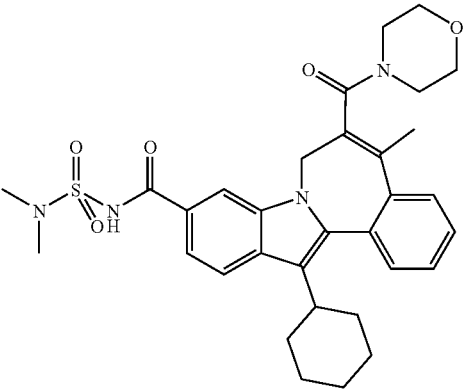 | | E |
| 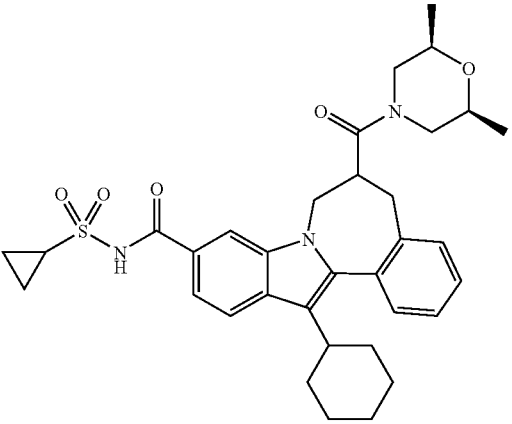 | | |

| Structure | IC₅₀* | EC₅₀* |
|---|---|---|
| 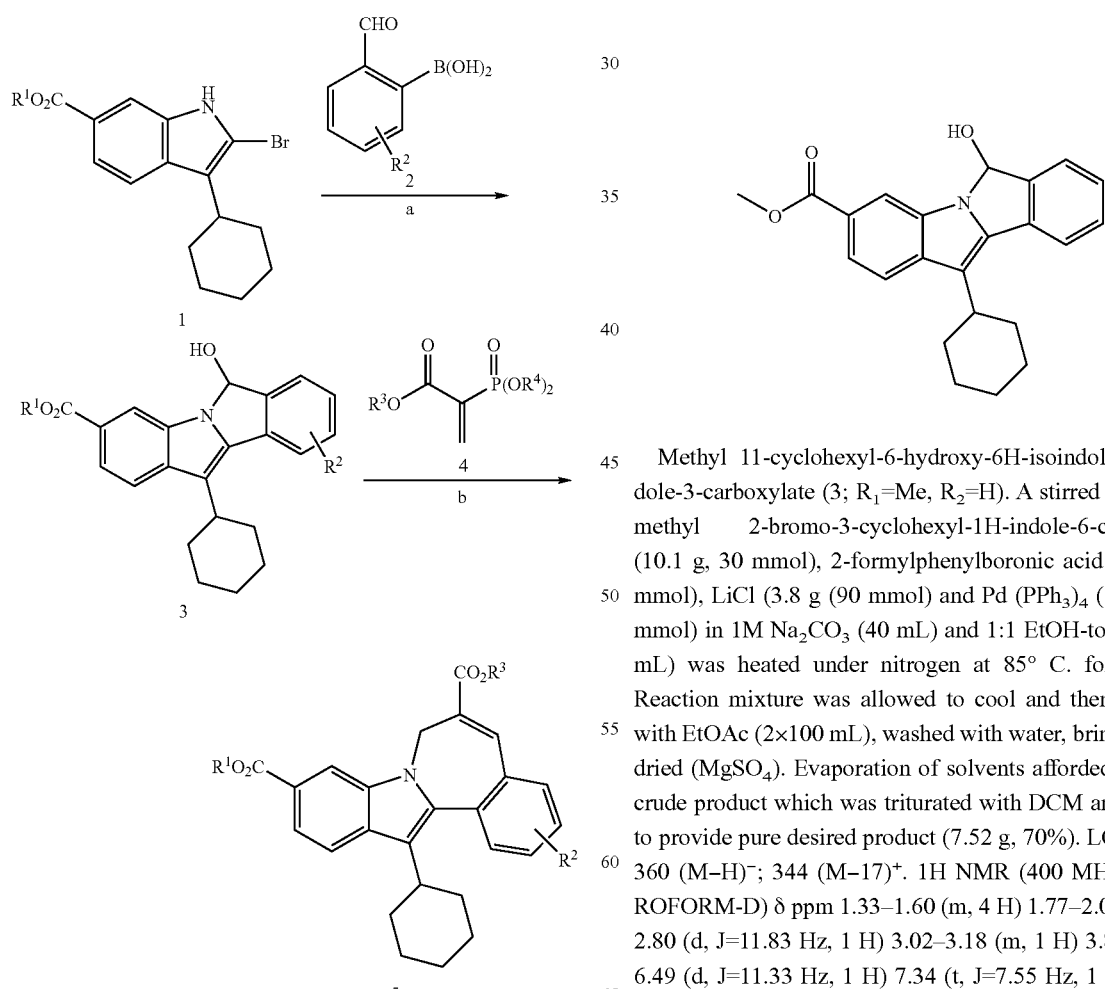 | | |

General procedure for the preparation of 13-cyclohexyl-7H-indolo[2,1-a][2]benzazepine-6,10-dicarboxylic acid, diesters (a) 1.2 equiv of 2, LiCl (3 equiv), Pd(PPh$_3$)4 (0.04 equiv), 1M Na$_2$CO$_3$, EtOH-toluene, 85–90° C. (b) 1.2–1.5 equiv of 4, Cs$_2$CO$_3$ (1.2 equiv), DMF, 50–60° C.

Methyl 11-cyclohexyl-6-hydroxy-6H-isoindolo[2,1-a]indole-3-carboxylate (3; R$_1$=Me, R$_2$=H). A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. Reaction mixture was allowed to cool and then extracted with EtOAc (2×100 mL), washed with water, brine and then dried (MgSO$_4$). Evaporation of solvents afforded 13.3 g of crude product which was triturated with DCM and hexanes to provide pure desired product (7.52 g, 70%). LC-MS: m/e 360 (M–H)⁻; 344 (M–17)⁺. 1H NMR (400 MHz, CHLOROFORM-D) δ ppm 1.33–1.60 (m, 4 H) 1.77–2.01 (m, 6 H) 2.80 (d, J=11.83 Hz, 1 H) 3.02–3.18 (m, 1 H) 3.89 (s, 3 H) 6.49 (d, J=11.33 Hz, 1 H) 7.34 (t, J=7.55 Hz, 1 H) 7.46 (t, J=7.55 Hz, 1 H) 7.62 (d, J=7.30 Hz, 1 H) 7.66–7.74 (m, 2 H) 7.77 (d, J=7.81 Hz, 1 H) 8.21 (s, 1 H).

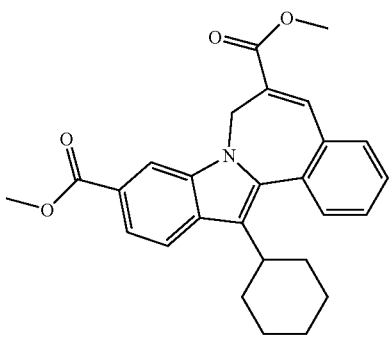

Methyl 13-cyclohexyl-6-(methoxycarbonyl)-7H-indolo[2,1-a][2]benzazepine-10-carboxylate (5; $R_1=R_3=Me$, $R_2=H$). A stirred suspension of methyl 11-cyclohexyl-6-hydroxy-6H-isoindolo[2,1-a]indole-3-carboxylate (3.61 g, 10 mmol), $Cs_2CO_3$ (3.91 g, 12 mmol) and trimethyl 2-phosphonoacetate (2.86 g, 14 mmol) in an. DMF (40 mL) was heated at 60° C. under nitrogen for 3 h. Resultant yellow suspension was cooled to rt and water was added with vigorous stirring. The yellow precipitate was filtered off, washed with water and then air dried overnight to afford the designated compound (4.124 g, 96%). LC/MS: m/e 430 ($MH^+$); 1H NMR (400 MHz, CHLOROFORM-D) δ ppm 1.30–1.46 (m, J=14.86 Hz, 2 H) 1.55 (s, 2 H) 1.77 (s, 2 H) 1.85–2.18 (m, 4 H) 2.76–2.89 (m, 1 H) 3.84 (s, 3 H) 3.95 (s, 3 H) 4.19 (s, 1 H) 5.68 (s, 1 H) 7.38–7.63 (m, 4 H) 7.74 (dd, J=8.44, 1.39 Hz, 1 H) 7.81–7.98 (m, 2 H) 8.29 (d, J=1.01 Hz, 1 H).

Part I. Preparation of Sulfamide and N-Boc-Sulfamide

Method

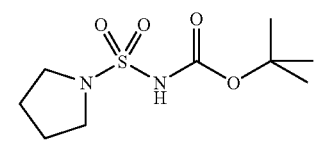

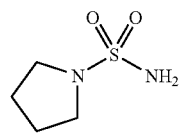

$^1$H NMR (400 MHz, MeOD) δ ppm 1.85–1.93 (m, 4 H) 3.17–3.28 (m, 4 H)

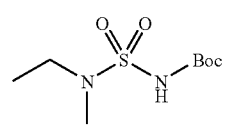

$^1$H NMR (400 MHz, CHLOROFORM-D) δ ppm 1.20 (t, J=7.18 Hz, 3 H) 1.47 (s, 9 H) 2.95 (s, 3 H) 3.35 (q, J=7.05 Hz, 2 H) 7.00 (s, 1 H)

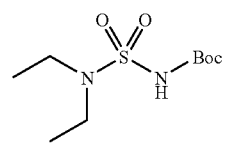

$^1$H NMR (400 MHz, CHLOROFORM-D) δ ppm 1.20 (t, J=7.18 Hz, 6 H) 1.47 (s, 9 H) 3.41 (q, J=7.30 Hz, 3 H) 7.04 (s, 1 H)

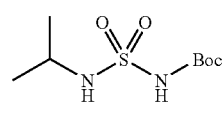

$^1$H NMR (400 MHz, CHLOROFORM-D) δ ppm 1.21 (d, J=6.55 Hz, 6 H) 1.48 (s, 9 H) 3.47–3.66 (m, 1 H)

Part II. Final Compounds

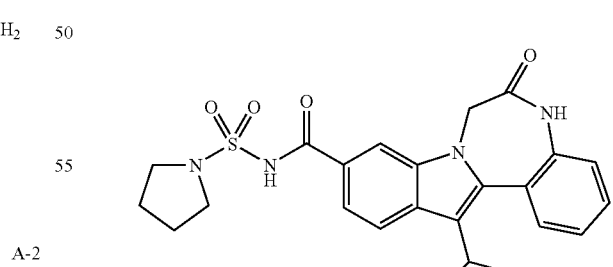

$^1$H NMR (400 MHz, CHLOROFORM-D) δ ppm 1.47 (s, 9 H) 1.85–1.98 (m, 4 H) 3.42–3.57 (m, 4 H) 7.00 (s, 1 H)

-continued

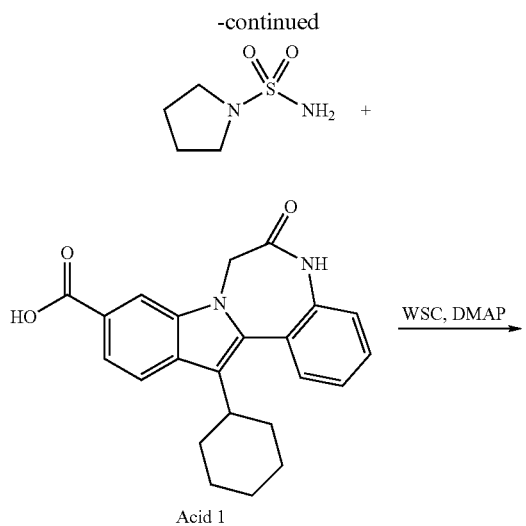

Acid 1

Tert-butyl pyrrolidin-1-ylsulfonylcarbamate (160 mg, 0.64 mmol) was dissolved in TFA/DCM (1/1, 1 mL) and stirred for 1 h. removed the solvents in vacuo and added acid 2 (40 mg, 0.1 mmol), DMAP (104 mg, 0.8 mmol), N1-((ethylimino)methylene)-N3,N3-dimethylpropane-1,3-diamine hydrochloride (102 mg, 0.53 mmol), DCM (2 mL). The mixture was stirred o/n and purified by prep HPLC to afford the product as a redish solid (18.4 mg, 34%). 1H NMR (400 MHz, CHLOROFORM-D) δ ppm 1.05–2.28 (m, 14 H) 2.83–3.05 (m, 1 H) 3.39–3.76 (m, 4 H) 4.61 (s, 1 H) 5.50 (d, J=15.61 Hz, 1 H) 7.04–7.60 (m, 4 H) 7.86 (dd, J=8.56, 1.26 Hz, 1 H) 7.92–8.02 (m, 1 H) 8.63 (s, 1 H) 9.55 (s, 1 H) 10.47 (s, 1 H) LC-MS (retention time: 3.08; MS m/z 507 (M+H).

-continued

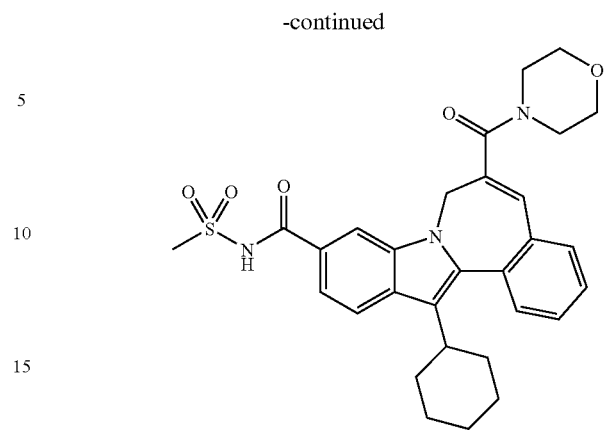

A mixture of cyclopropylsulfonamide (77 mg, 0.64 mmol) added acid 2 (60 mg, 0.13 mmol), DMAP (71 mg, 0.58 mmol), N1-((ethylimino)methylene)-N3,N3-dimethylpropane-1,3-diamine hydrochloride (49 mg, 0.26 mmol) in DMF (2 mL) was stirred o/n and purified by prep HPLC to afford the product as a solid (14.2 mg, 29%). 1H NMR (400 MHz, CHLOROFORM-D) ☐ ppm 1.03–1.70 (m, 10 H) 1.69–2.13 (m, 4 H) 2.52–2.68 (m, J=7.93, 7.93 Hz, 1 H) 2.93–3.93 (m, 9 H) 4.64 (d, 1 H) 4.91 (d, 1 H) 6.88 (d, J=19.64 Hz, 1 H) 7.37–7.65 (m, 5 H) 7.92 (d, J=8.56 Hz, 1 H) 8.07 (s, 1 H) (retention time: 2.98; MS m/z 574 (M+H).

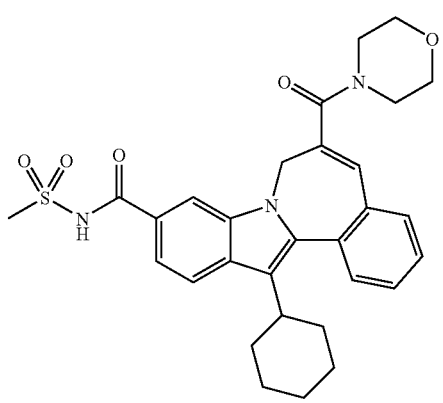

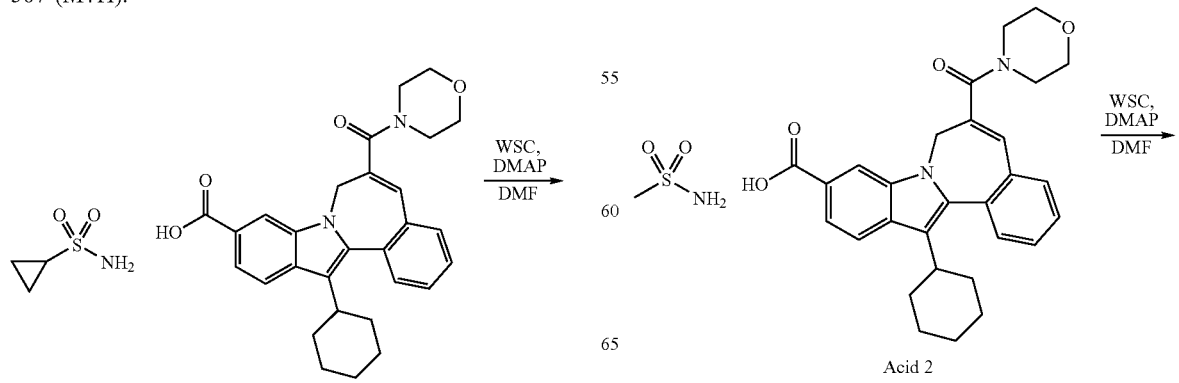

Acid 2

263

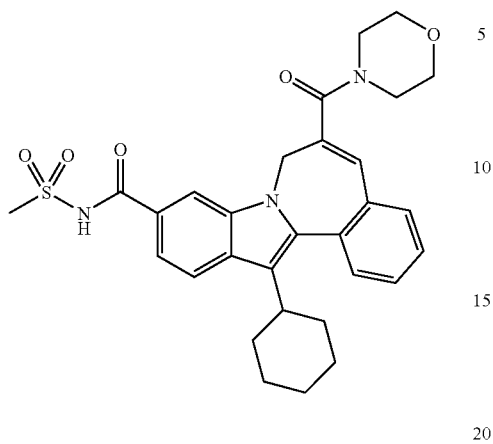

A mixture of methanesulfonamide (50 mg, 0.53 mmol), added acid 2 (50 mg, 0.11 mmol), DMAP (104 mg, 0.85 mmol), N1-((ethylimino)methylene)-N3,N3-dimethylpropane-1,3-diamine hydrochloride (51 mg, 0.27 mmol) in DMF (1.5 mL) was stirred o/n and purified by prep HPLC to afford the product as a solid (19.9 mg, 29%). 1H NMR (400 MHz, CHLOROFORM-D) δ ppm 1.13–1.63 (m, 4 H) 1.76 (d, J=7.30 Hz, 2 H) 1.84–2.16 (m, 4 H) 2.73–2.90 (m, 1 H) 3.27–3.80 (m, 8 H) 3.48 (s, 3 H) 4.37 (s, 1 H) 5.12 (s, 1 H) 6.91 (s, 1 H) 7.38–7.45 (m, 1 H) 7.46–7.60 (m, 4 H) 7.91 (d, J=8.56 Hz, 1 H) 8.11 (s, 1 H); LC-MS (retention time: 2.94; MS m/z 548 (M+H).

264

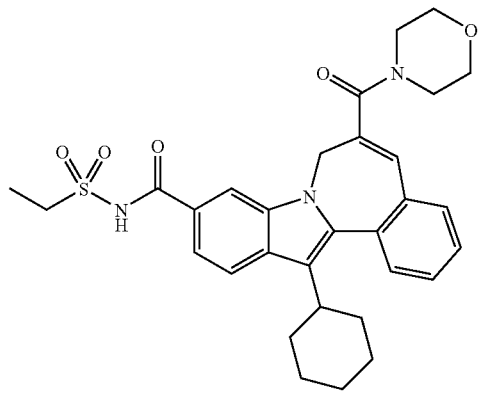

A mixture of ethanesulfonamide (46 mg, 0.4 mmol), added acid 1 (40 mg, 0.08 mmol), DMAP (45 mg, 0.37 mmol), N1-((ethylimino)methylene)-N3,N3-dimethylpropane-1,3-diamine hydrochloride (41 mg, 0.21 mmol) in DMF (1.5 mL) was stirred o/n and purified by prep HPLC to afford the product as a solid (19.1 mg, 40%). 1H NMR (400 MHz, CHLOROFORM-D) δ ppm 1.10–1.53 (m, 7 H) 1.64–1.82 (m, 2 H) 2.02 (s, 4 H) 2.84 (d, J=15.11 Hz, 1 H) 3.14–3.82 (m, 10 H) 4.35 (s, 1 H) 5.12 (s, 1 H) 6.90 (s, 1 H) 7.32–7.63 (m, 5 H) 7.78–7.94 (m, 1 H) 8.16 (s, 1 H)LC-MS (retention time: 3.00; MS m/z 562 (M+H).

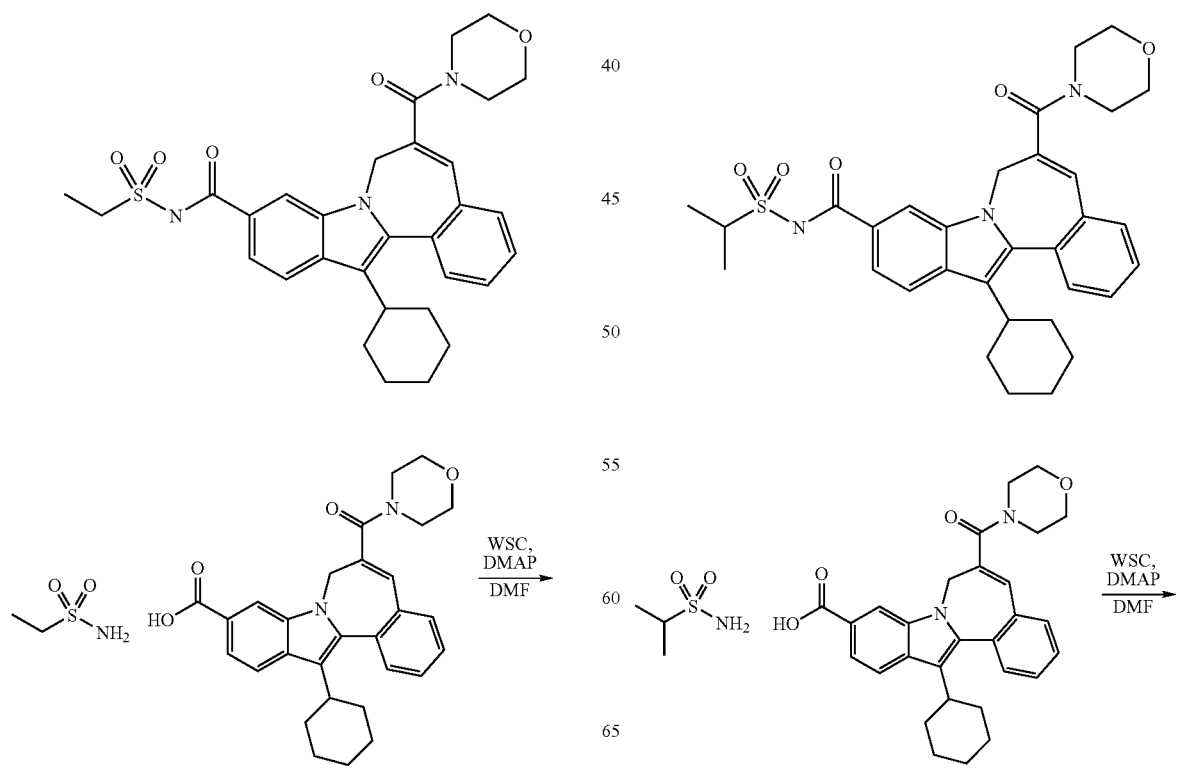

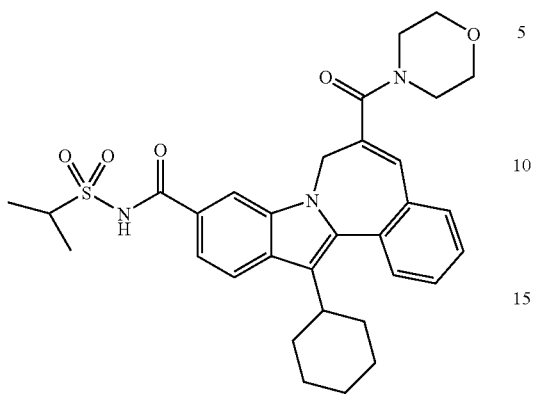

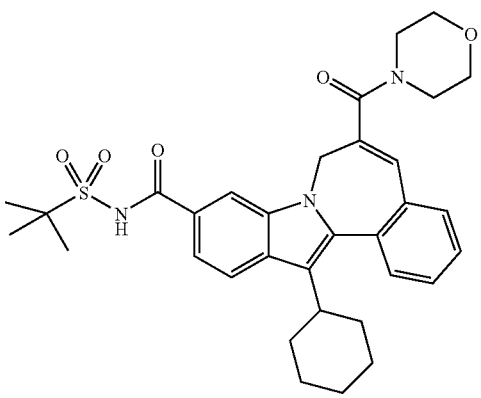

A mixture of propane-2-sulfonamide (52 mg, 0.4 mmol), added acid 1 (40 mg, 0.1 mmol), DMAP (52 mg, 0.43 mmol), N1-((ethylimino)methylene)-N3,N3-dimethylpropane-1,3-diamine hydrochloride (41 mg, 0.21 mmol) in DMF (1.5 mL) was stirred o/n and purified by prep HPLC to afford the product as a solid (19 mg, 39%). 1H NMR (400 MHz, CHLOROFORM-D) δ ppm 1.08–1.58 (m, 4 H) 1.48 (d, J=7.05 Hz, 6 H) 1.69–1.82 (m, 2 H) 1.85–2.22 (m, 4 H) 2.75–2.89 (m, 1 H) 3.30–3.71 (m, 8 H) 4.03–4.15 (m, 1 H) 4.35 (s, 1 H) 5.10 (s, 1 H) 6.90 (s, 1 H) 7.34–7.63 (m, 5 H) 7.82–7.90 (m, 1 H) 8.13 (s, 1 H); LC-MS (retention time: 2.98; MS m/z 576 (M+H).

A mixture of 2-methylpropane-2-sulfonamide (58 mg, 0.4 mmol), added acid 1 (40 mg, 0.08 mmol), DMAP (54 mg, 0.44 mmol), N1-((ethylimino)methylene)-N3,N3-dimethyl-propane-1,3-diamine hydrochloride (41 mg, 0.21 mmol) in DMF (1.5 mL) was stirred o/n and purified by prep HPLC to afford the product as a solid (3.5 mg, 7%).

1H NMR (400 MHz, CHLOROFORM-D) δ ppm 1.12–1.58 (m, 4 H) 1.58 (s, 9 H) 1.67–2.19 (m, J=120.61 Hz, 5 H) 2.82 (s, 1 H) 3.05–3.76 (m, 10 H) 4.37 (s, 1 H) 5.06 (s, 1 H) 6.85 (s, 1 H) 7.34–7.60 (m, 4 H) 7.83–7.97 (m, 1 H) 8.08 (s, 1 H) LC-MS (retention time: 3.02; MS m/z 590 (M+H).

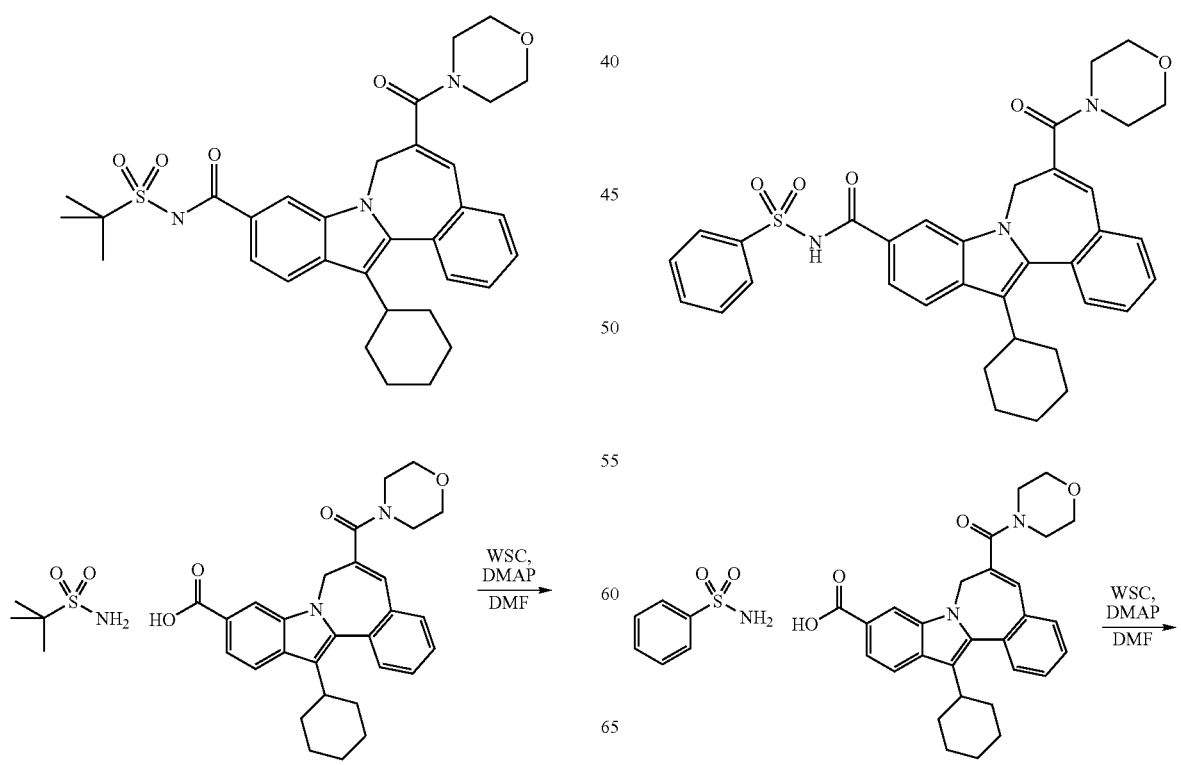

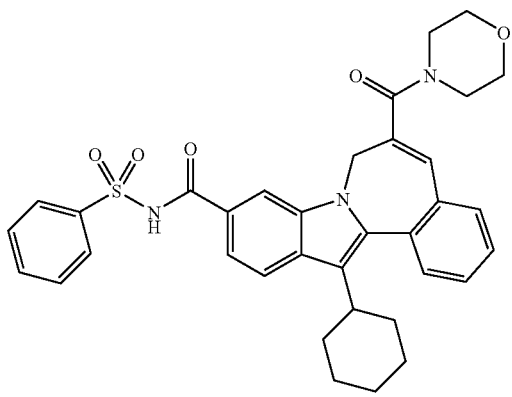
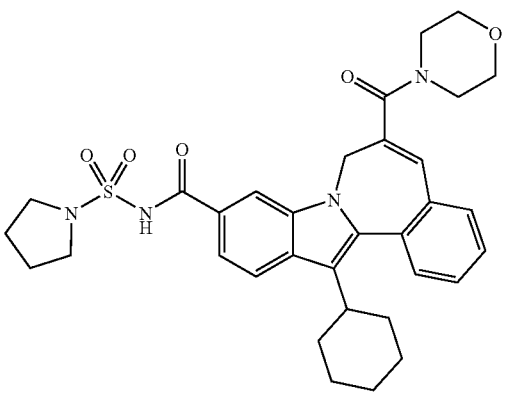

A mixture of benzenesulfonamide (67 mg, 0.4 mmol), added acid 1 (40 mg, 0.08 mmol), DMAP (52 mg, 0.43 mmol), N1-((ethylimino)methylene)-N3,N3-dimethylpropane-1,3-diamine hydrochloride (41 mg, 0.21 mmol) in DMF (1.5 mL) was stirred o/n and purified by prep HPLC to afford the product as a solid (22 mg, 40%). 1H NMR (500 MHz, CHLOROFORM-D) δ ppm 1.14–1.60 (m, 4 H) 1.75 (d, J=8.85 Hz, 2 H) 2.01 (s, 4 H) 2.70–2.95 (m, 1 H) 3.16–3.81 (m, 8 H) 4.32 (s, 1 H) 5.08 (s, 1 H) 6.89 (s, 1 H) 7.36–7.42 (m, 1 H) 7.43–7.57 (m, 6 H) 7.59–7.68 (m, 1 H) 7.85 (d, J=8.55 Hz, 1 H) 8.11 (s, 1 H) 8.18 (d, J=7.32 Hz, 2 H); LC-MS (retention time: 3.06; MS m/z 610 (M+H).

A mixture of pyrrolidine-1-sulfonamide (64 mg, 0.4 mmol), added acid 1 (40 mg, 0.08 mmol), DMAP (82 mg, 0.66 mmol), N1-((ethylimino)methylene)-N3,N3-dimethylpropane-1,3-diamine hydrochloride (57 mg, 0.30 mmol) in DMF (1.5 mL) was stirred o/n and purified by prep HPLC to afford the product as a solid (17 mg, 33%). 1H NMR (400 MHz, CHLOROFORM-D) δ ppm 1.14–1.56 (m, 4 H) 1.77 (d, J=6.80 Hz, 2 H) 1.85–2.20 (m, 8 H) 2.71–2.93 (m, 1 H) 3.26–3.83 (m, 12 H) 4.37 (s, 1 H) 5.13 (s, 1 H) 6.86–6.90 (m, 1 H) 7.34–7.62 (m, 5 H) 7.86–7.93 (m, 1 H) 8.13 (s, 1 H). LC-MS (retention time: 3.05; MS m/z 603 (M+H).

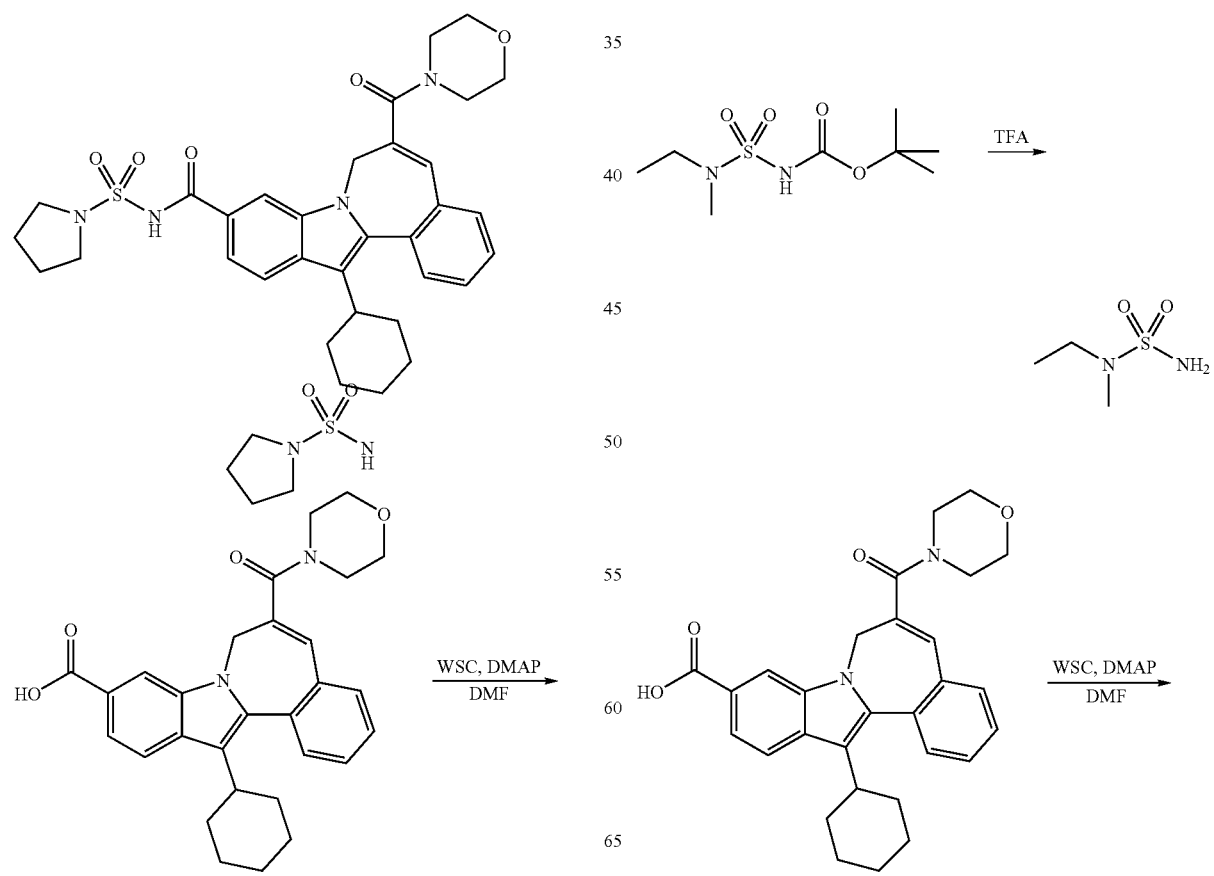

-continued

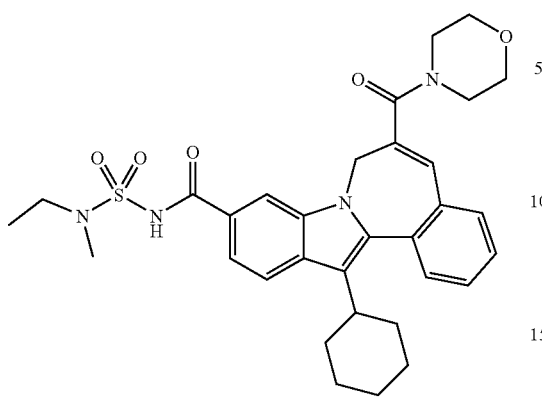

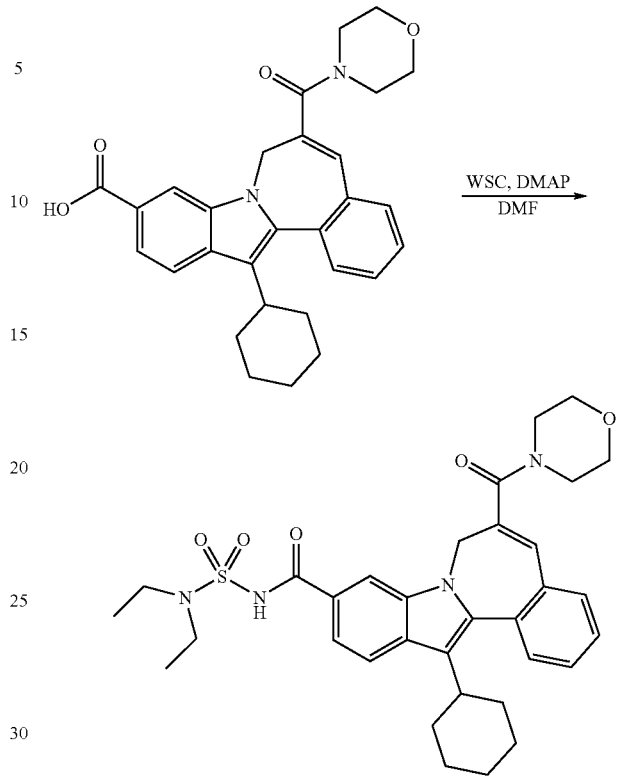

The Boc sulfamide compound (121 mg, 0.51 mmol) was dissolved in TFA/DCM (1/1, 1 mL) and stirred for 1.5 h. and removed the solvents in vacuo. To the residue was added acid (40 mg, 0.1 mmol), DMAP (125 mg, 1.02 mmol), N1-((ethylimino)methylene)-N3,N3-dimethylpropane-1,3-diamine hydrochloride (57 mg, 0.3 mmol), DMF (1.5 mL). the mixture was stirred o/n and purified by prep HPLC to afford the product as a solid (8.3 mg, 17%).1H NMR (400 MHz, CHLOROFORM-D) δ ppm 1.23 (t, J=7.18 Hz, 3 H) 1.31–1.61 (m, 4 H) 1.77 (d, J=8.06 Hz, 2 H) 1.85–2.18 (m, 4 H) 2.77–2.88 (m, 1 H) 3.06 (s, 3 H) 3.29–3.72 (m, 10 H) 4.36 (s, 1 H) 5.15 (s, 1 H) 6.87 (s, 1 H) 7.38–7.43 (m, 1 H) 7.45–7.54 (m, 3 H) 7.52–7.64 (m, 1 H) 7.90 (d, J=8.31 Hz, 1 H) 8.11 (d, J=1.01 Hz, 1 H) LC-MS (retention time: 3.09; MS m/z 591 (M+H).

The Boc sulfamide compound (128 mg, 0.51 mmol) was dissolved in TFA/DCM (1/1, 1 mL) and stirred for 1.5 h. and removed the solvents in vacuo. To the residue was added acid (40 mg, 0.1 mmol), DMAP (125 mg, 1.02 mmol), N1-((ethylimino)methylene)-N3,N3-dimethylpropane-1,3-diamine hydrochloride (57 mg, 0.53 mmol), DMF (1.5 mL). the mixture was stirred o/n and purified by prep HPLC to afford the product as a solid. (11 mg, 21%).1H NMR (400 MHz, CHLOROFORM-D) δ ppm 1.17–1.27 (m, 6 H) 1.32–1.62 (m, 4 H) 1.76 (d, J=7.81 Hz, 2 H) 1.87–2.13 (m, 4 H) 2.78–2.88 (m, 1 H) 3.04 (d, J=26.69 Hz, 4 H) 3.34–3.69 (m, 8 H) 4.36 (s, 1 H) 5.16 (s, 1 H) 6.87 (s, 1 H) 7.37–7.42 (m, 1 H) 7.43–7.53 (m, 3 H) 7.55–7.62 (m, 1 H) 7.90 (d, J=8.56 Hz, 1 H) 8.11 (s, 1 H) LC-MS (retention time: 3.17; MS m/z 605 (M+H).

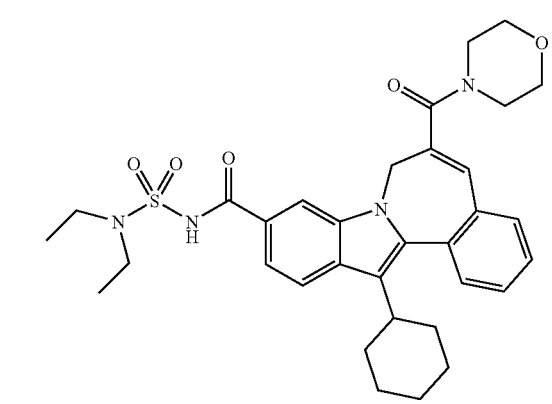

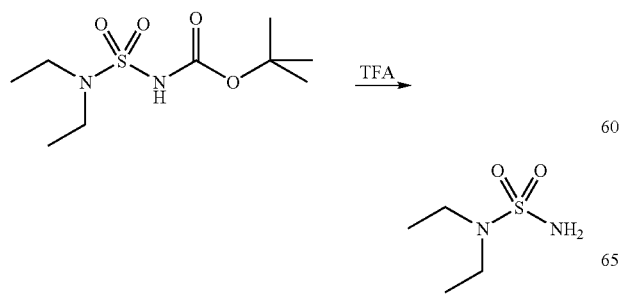

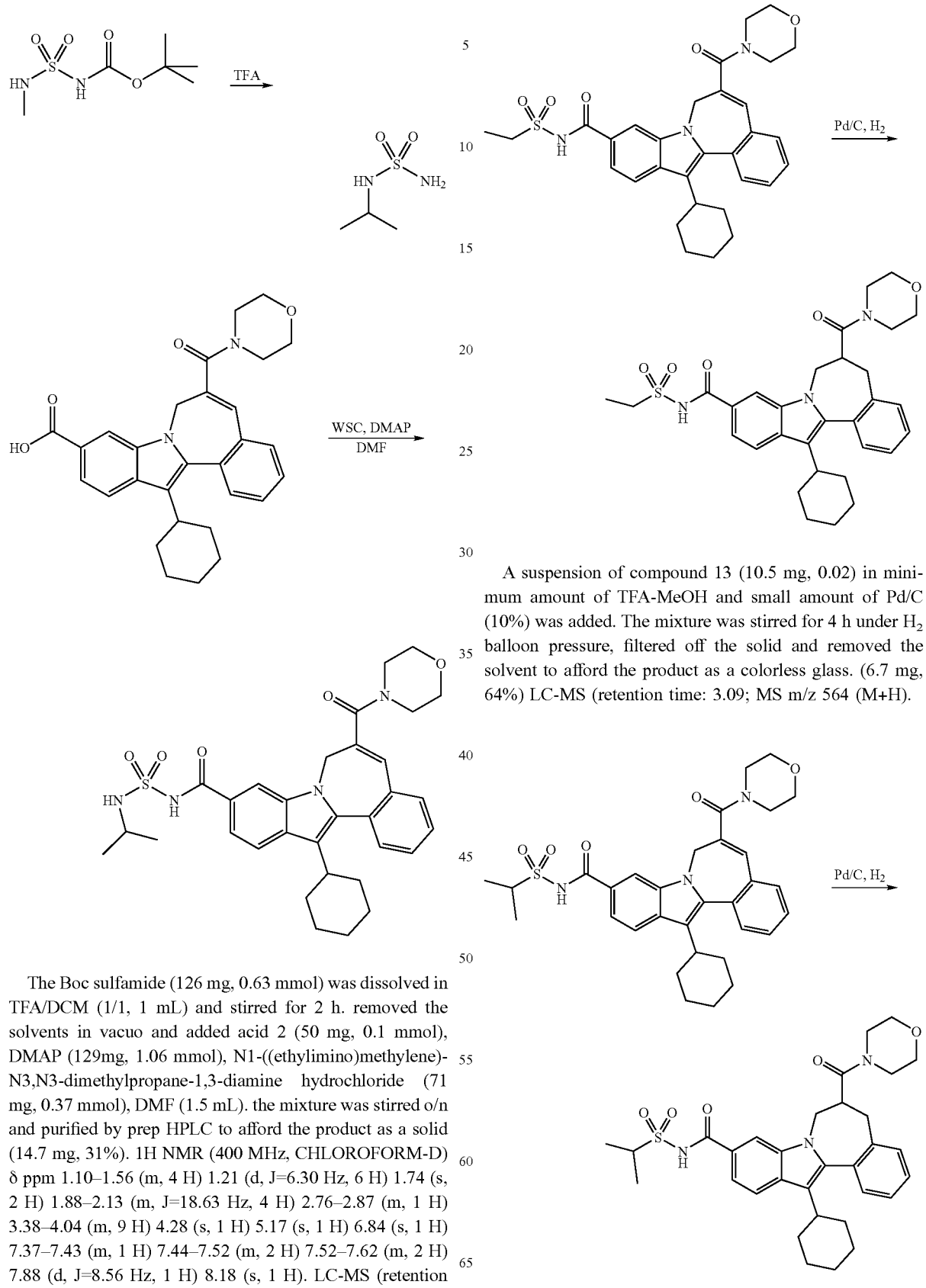

The Boc sulfamide (126 mg, 0.63 mmol) was dissolved in TFA/DCM (1/1, 1 mL) and stirred for 2 h. removed the solvents in vacuo and added acid 2 (50 mg, 0.1 mmol), DMAP (129mg, 1.06 mmol), N1-((ethylimino)methylene)-N3,N3-dimethylpropane-1,3-diamine hydrochloride (71 mg, 0.37 mmol), DMF (1.5 mL). the mixture was stirred o/n and purified by prep HPLC to afford the product as a solid (14.7 mg, 31%). 1H NMR (400 MHz, CHLOROFORM-D) δ ppm 1.10–1.56 (m, 4 H) 1.21 (d, J=6.30 Hz, 6 H) 1.74 (s, 2 H) 1.88–2.13 (m, J=18.63 Hz, 4 H) 2.76–2.87 (m, 1 H) 3.38–4.04 (m, 9 H) 4.28 (s, 1 H) 5.17 (s, 1 H) 6.84 (s, 1 H) 7.37–7.43 (m, 1 H) 7.44–7.52 (m, 2 H) 7.52–7.62 (m, 2 H) 7.88 (d, J=8.56 Hz, 1 H) 8.18 (s, 1 H). LC-MS (retention time: 3.07; MS m/z 591 (M+H).

A suspension of compound 13 (10.5 mg, 0.02) in minimum amount of TFA-MeOH and small amount of Pd/C (10%) was added. The mixture was stirred for 4 h under H$_2$ balloon pressure, filtered off the solid and removed the solvent to afford the product as a colorless glass. (6.7 mg, 64%) LC-MS (retention time: 3.09; MS m/z 564 (M+H).

A suspension of compound 13 (11 mg, 0.02 mmol) in minimum amount of TFA-MeOH and small amount of Pd/C (10%) was added. The mixture was stirred for 4 h under H₂ balloon pressure, filtered off the solid and removed the solvent to afford the product as a colorless glass (7.4 mg, 68%). 1H NMR (500 MHz, CHLOROFORM-D) δ ppm 1.18–1.31 (m, 6 H) 1.32–1.81 (m, 6 H) 1.83–2.20 (m, 4 H) 2.69–2.98 (m, 3 H) 3.06–3.18 (m, 1 H) 3.37–3.94 (m, 9 H) 4.04–4.25 (m, 1 H) 4.64 (d, J=14.65 Hz, 1 H) 7.30–7.47 (m, 4 H) 7.62 (dd, J=8.55, 1.22 Hz, 1 H) 7.86–7.91 (m, 1 H) 7.95–8.04 (m, 1 H) LC-MS (retention time: 3.11; MS m/z 578 (M+H).

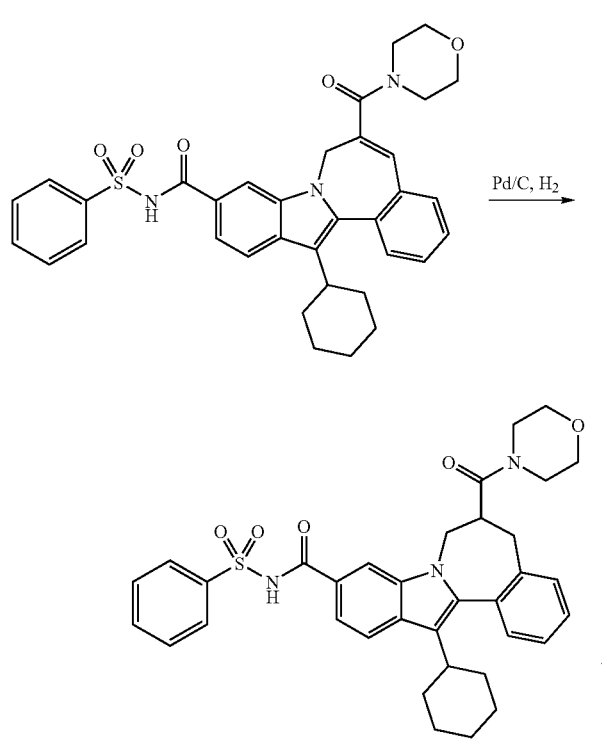

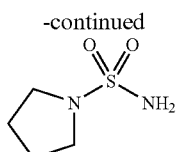

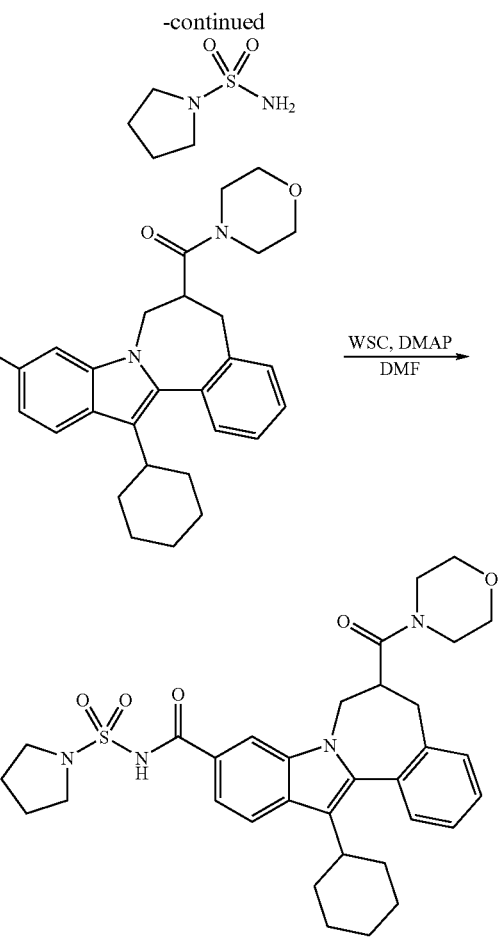

The product (10.8 mg, 77%) was obtained from the same unsaturated compound (13.3 mg), 0.02 mmol) method as in Example 37 compound 39 was used. 10. LC-MS (retention time: 3.17; MS m/z 612 (M+H).

A mixture of pyrrolidine-1-sulfonamide (63 mg, 0.4 mmol), added acid 1 (40 mg, 0.08 mmol), DMAP (103 mg, 0.84 mmol), N1-((ethylimino)methylene)-N3,N3-dimethyl-propane-1,3-diamine hydrochloride (57 mg, 0.3 mmol) in DMF (1.5 mL) was stirred o/n and purified by prep HPLC to afford the product as a solid (13.9 mg, 27%). ¹H NMR (400 MHz, CHLOROFORM-D) δ ppm 1.19–1.50 (m, 4 H) 1.62 (s, 1 H) 1.76 (s, 2 H) 1.84–2.13 (m, 5 H) 2.49 (s, 2 H) 2.69–2.96 (m, 3 H) 3.35–3.92 (m, 12 H) 4.22 (dd, J=14.60, 11.83 Hz, 1 H) 4.30–4.43 (m, 1 H) 4.69 (d, J=14.60 Hz, 1 H) 7.32–7.54 (m, 4 H) 7.81–7.95 (m, 2 H) 8.14 (s, 1 H), LC-MS (retention time: 3.10; MS m/z 605 (M+H).

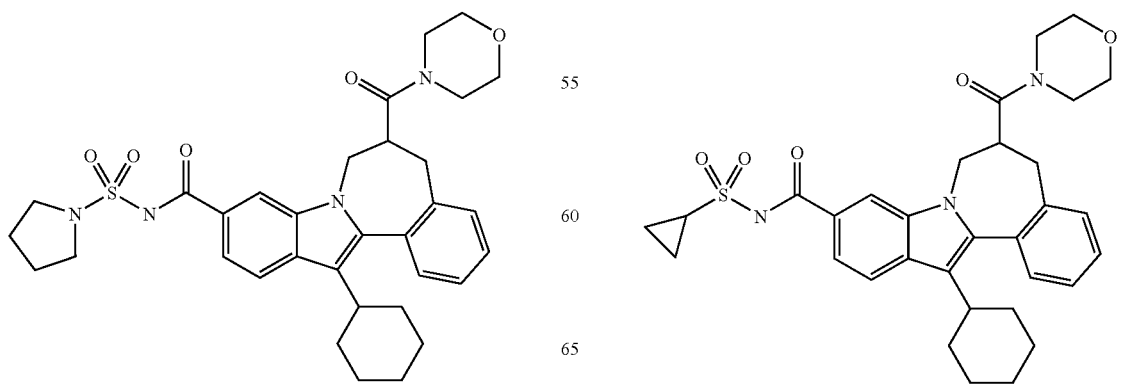

-continued

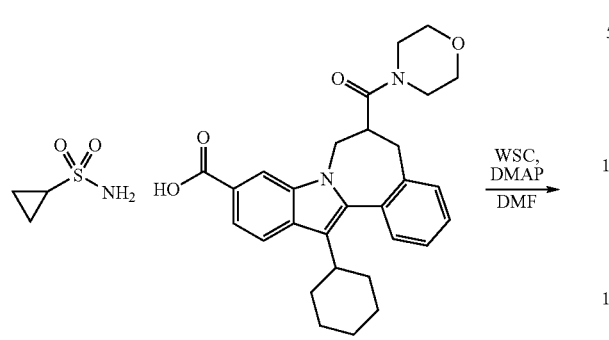

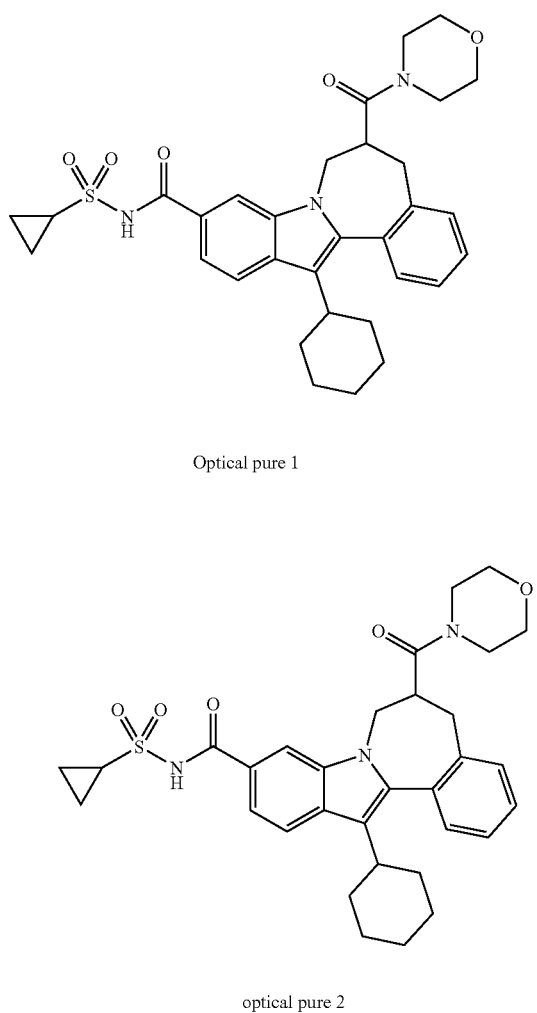

Optical pure 1 optical pure 2

A mixture of cyclopropysulfonamide (64 mg, 0.53 mmol), acid (25 mg, 0.05 mmol), DMAP (100 mg, 0.82 mmol), N1-((ethylimino)methylene)-N3,N3-dimethylpropane-1,3-diamine hydrochloride (80 mg, 0.42 mmol) in DMF (1.5 mL) was stirred o/n and purified by prep HPLC to afford racemate product as a glass (3.7 mg, 13%). 1H NMR (400 MHz, CHLOROFORM-D) δ ppm 1.03–1.57 (m, 6 H) 1.86–2.14 (m, 4 H) 2.65 (d, J=13.60 Hz, 1 H) 2.59–3.27 (m, 6 H) 3.33–3.46 (m, 1 H) 3.51–3.87 (m, 7 H) 4.15–4.26 (m, 1 H) 4.29–4.42 (m, 1 H) 4.66 (none, 1 H) 4.67 (d, J=14.86 Hz, 1 H) 7.32–7.47 (m, 3 H) 7.52 (dd, J=8.18, 1.39 Hz, 1 H) 7.81–7.98 (m, 2 H) 8.13 (s, 1 H) 8.69 (s, 1 H) 9.34 (s, 1 H); LC-MS (retention time: 3.34 MS m/z 576 (M+H).

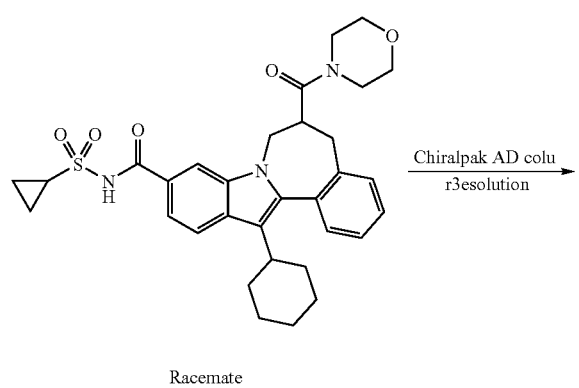

Racemate

Resoluted the racemate (97 mg) on Chiralpak AD column (Chiralpak AD column, 4.6×50 mm, 5 μm, Solvents: 60% CO2—40% Methanol,Temp: 35C, Pressure: 150 bar, Flow rate: 2 mL/min) to supply optcal pure two enantiomers. Enantiomer one peak 1 (23.0 mg); 1H NMR (400 MHz, CHLOROFORM-D) δ ppm 1.06–1.51 (m, 6 H) 1.73 (s, 4 H) 1.81–2.19 (m, 4 H) 2.55–3.00 (m, 4 H) 3.06–3.27 (m, 1 H) 3.49–3.88 (m, 8 H) 4.08–4.43 (m, 1 H) 4.70 (d, J=14.60 Hz, 1 H) 7.30–7.47 (m, 3 H) 7.51–7.62 (m, 1 H) 7.84–7.98 (m, 2 H) 8.16 (d, J=1.01 Hz, 1 H), Chiral HPLC: retention: 6.26 (Chiralpak AD column, 4.6×250 mm, 5 μm, Solvents: 60% CO2—40% Methanol).

Enantiomer two (peak two, 24.1 mg). 1H NMR (400 MHz, CHLOROFORM-D) δ ppm 0.95–1.49 (m, 4 H) 1.58–2.28 (m, 10 H) 2.52–3.00 (m, 4 H) 3.05–3.24 (m, 1 H) 3.30–3.48 (m, 1 H) 3.49–3.90 (m, 7 H) 4.11–4.43 (m, 1 H) 4.72 (d, J=14.60 Hz, 1 H) 7.26–7.59 (m, 5 H) 7.79–7.99 (m, 1 H) 8.17 (d, J=1.01 Hz, 1 H); HPLC: retention: 11.84 (Chiralpak AD column, 4.6×250 mm, 5 μm, Solvents: 60% CO2—40% Methanol).

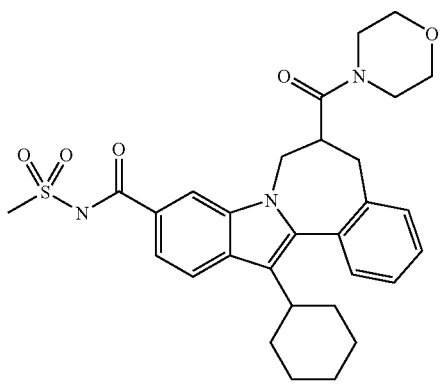

A mixture of methanesulfonamide (45 mg, 0.53 mmol), acid (25 mg, 0.05 mmol), DMAP (100 mg, 0.82 mmol), N1-((ethylimino)methylene)-N3,N3-dimethylpropane-1,3-diamine hydrochloride (80 mg, 0.42 mmol) in DMF (1.5 mL) was stirred o/n and purified by prep HPLC to afford the product as a glass (6.7 mg, 23%). 1H NMR (400 MHz, CHLOROFORM-D) δ ppm 1.12–1.50 (m, 4 H) 1.58–1.83 (m, 2 H) 1.86–2.17 (m, 4 H) 2.57–3.00 (m, 3 H) 3.31–3.52 (m, 4 H) 3.52–3.96 (m, 8 H) 4.10–4.46 (m, 1 H) 4.66 (d, J=14.60 Hz, 1 H) 7.32–7.58 (m, 4 H) 7.78–7.96 (m, 2 H) 8.12 (s, 1 H). LC-MS (retention time: 3.44; MS m/z 550 (M+H). Resoluted the racemate (97 mg) on Chiralpak AD column(Chiralpak AD column, 4.6×50 mm, 5 μm, Solvents: 60% CO2—40% Methanol,Temp: 35C, Pressure: 150 bar, Flow rate: 2 mL/min) to supply optcal pure two enantiomers.

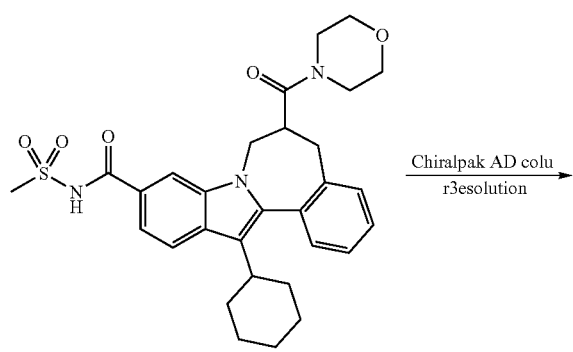

Racemate

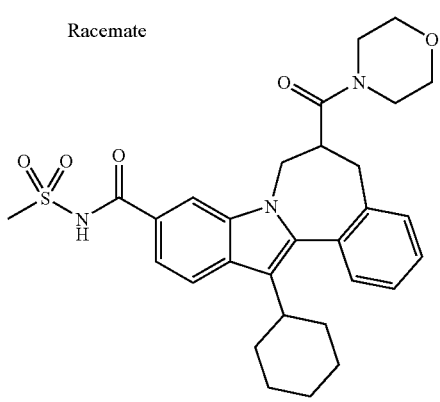

Optical pure 1

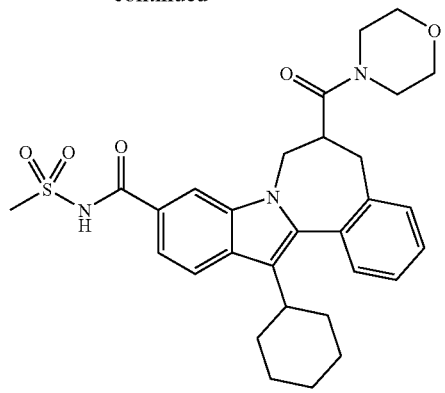

optical pure 2

Resoluted the racemate compound 34 (92 mg) on Chiralpak AD column (Chiralpak AD column, 4.6×250 mm, 5 μm, Solvents: 60% CO2—40% Methanol, Temp: 35C, Pressure: 150 bar, Flow rate: 2 mL/min.) to supply two optcal pure enantiomers.

Enantiomer one: Peak 1 (26.1 mg); 1H NMR (400 MHz, CHLOROFORM-D) δ ppm 1.12–1.54 (m, 4 H) 1.55–1.81 (m, 2 H) 1.87–2.16(m, 4 H) 2.55–3.06 (m, 3 H) 3.36–3.50 (m, 3 H) 3.52–3.92 (m, 8 H) 4.12–4.41 (m, 1 H) 4.72 (d, J=14.60 Hz, 1 H) 7.30–7.64 (m, 4 H) 7.84–8.01 (m, 2 H) 8.18 (s, 1 H); LC-MS (retention time: 3.30; MS m/z 550 (M+H). Chiral HPLC: retention: 5.47 ((Chiralpak AD column, 4.6×250 mm, 5 μm, Solvents: 60% CO2—40% Methanol).

Enantiomer two: peak 2 (25.0 mg); 1H NMR (400 MHz, CHLOROFORM-D) δ ppm 1.03–1.57 (m, 6 H) 1.86–2.14 (m, 4 H) 2.65 (d, J=13.60 Hz, 1 H) 2.59–3.27 (m, 6 H) 3.33–3.46 (m, 1 H) 3.51–3.87 (m, 7 H) 4.15–4.26 (m, 1 H) 4.29–4.42 (m, 1 H) 4.67 (d, J=14.86 Hz, 1 H) 7.32–7.47 (m, 3 H) 7.52 (dd, J=8.18, 1.39 Hz, 1 H) 7.81–7.98 (m, 2 H) 8.13 (s, 1 H) 8.69 (s, 1 H) 9.34 (s, 1 H) Chiral HPLC: retention: 11.13 ((Chiralpak AD column, 4.6×250 mm, 5 μm, Solvents: 60% CO2—40% Methanol).

13-Cyclohexyl-N-[(dimethylamino)carbonyl)]-6-(4-morpholinylcarbonyl)-7H-indolo[2,1-a][2]benzazepine-10-carboxamide

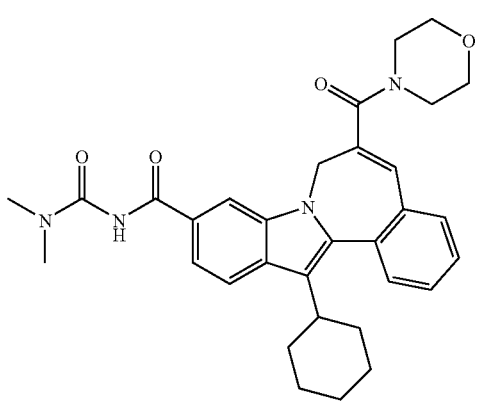

To a stirred cold (−20° C.) solution of 13-cyclohexyl-6-(4-morpholinylcarbonyl)-7H-indolo[2,1-a][2]benzazepine-10-carboxamide (47 mg, 0.1 mmol) in an. DMF (2 mL) dry NaH (10 mg, 0.4 mmol) was added under nitrogen. The mixture was allowed to warm to 0° C. and then a solution of Me₂NCOCl in DMF (0.5 mL) was added at −20° C. Reaction mixture was allowed to warm to rt and kept for 1 h and then quenched with water, acidified with 0.5N HCl, extracted with EtOAc. The crude isolated product (69 mg) was purified by prep. HPLC to afford the designated compound (36 mg; 67%): LC/MS: m/e 541 (MH⁺); 1H NMR (400 MHz, CHLOROFORM-D) □ ppm 1.12–1.50 (m, 3 H) 1.64–2.16 (m, 7 H) 2.78–2.89 (m, 1 H) 3.02–3.17 (m, 6 H) 3.30–3.68 (m, 8 H) 4.38 (s, 1 H) 5.13 (s, 1 H) 6.87 (d, J=2.52 Hz, 1 H) 7.36–7.43 (m, 1 H) 7.44–7.55 (m, 3 H) 7.56–7.62 (m, 1 H) 7.91 (dd, J=8.56, 3.53 Hz, 1 H) 8.08 (s, 1 H).

LCMS data: Stop time: Gradient time+1 minute; Starting conc: 0% B unless otherwise noted. Eluent A: 5% CH3CN/95% H2O with 10 mM NH4OAc (for columns A and D); 10% MeOH/90% H2O with 0.1% TFA (for columns B and C) Eluent B: 95% CH3CN/5% H2O with 10 mM NH4OAc (for columns A and D) 90% MeOH/10% H2O with 0.1% TFA (for columns B and C). Column A: Phenomenex 10□4.6×50 mm C18; Column B: Phenomenex C18 10μ 3.0×50 mm; Column C: Phenomenex 4.6×50 mm C18 10□; Column D: Phenomenex Lina C18 5μ 3.0×50 mm.

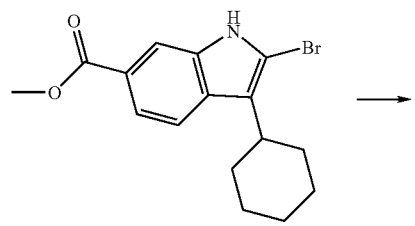

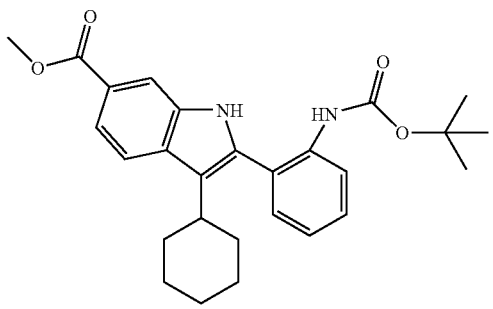

A slurry of methyl 2-bromo-3-cyclohexyl-1H-indole-6-carboxylate (1.75 g, 5.22 mmol), LiCl (880 mg, 21.0 mmol), 1M aqueous Na₂CO₃ (13 mL, 13.0 mmol), Pd(PPh₃)₄ (600 mg, 0.52 mmol) and tert-butyl 2-(4,4,5,5-tetramethyl-1,3,2-dioxaborolan-2-yl)phenylcarbamate (2.5 g, 7.8 mmol) in toluene (19 mL) and EtOH (19 mL) was heated at relfux for 2 h. The reaction mixture was cooled and concentrated to dryness under vacuum. The residue was treated with H₂O (120 mL) and extracted with EtOAc(2×200 mL). The combined organics were washed with brine (2×20 mL), dried (MgSO₄), filtered, concentrated and purified by SiO₂ chromatography (5–25% EtOAc/hexanes) to yield methyl 2-(2-(tert-butoxycarbonyl)phenyl)-3-cyclohexyl-1H-indole-6-carboxylate (1.8 g, 4.0 mmol, 77%) as a yellow-pink solid. ¹HNMR (500 MHz, CDCl₃) δ. 8.26 (d, J=8.5 Hz, 1H), 8.14 (s, 1H), 8.11 (s, 1 H), 7.86 (d, J=8.2 Hz, 1H), 7.82 (dd, J=8.2, 1.5 Hz, 1H), 7.43 (ddd, J=8.5, 7.3, 1.5 Hz, 1H), 7.28 (d, J=7.6, 1.5 Hz, 1H), 7.11 (ddd, J=7.6, 7.3, 1.2 Hz, 1H), 6.67 (br s, 1H), 3.94 (s, 3H), 2.56 (tt, J=12.1, 3.5 Hz, 1H), 1.97–1.22 (m, 10H), 1.45 (s, 9H). LCMS: m/e 449 (M+H)⁺, ret time 2.39 min, column C, 2 minute gradient, start at 0% B.

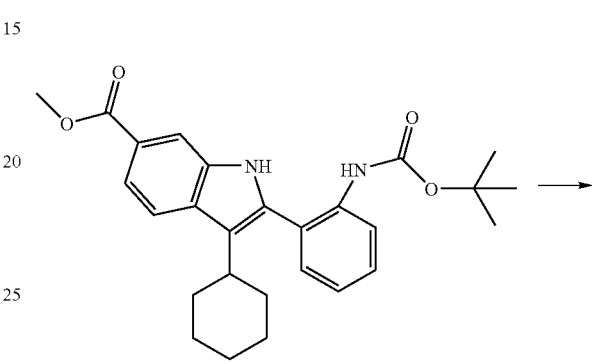

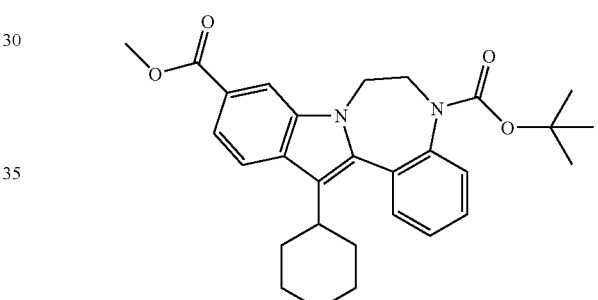

A slurry of methyl 2-(2-(tert-butoxycarbonyl)phenyl)-3-cyclohexyl-1H-indole-6-carboxylate (1.0 g, 2.2 mmol), powdered NaOH (460 mg, 11.5 mmol) and nBu₄N⁺HSO₄⁻ (150 mg, 0.44 mol) in 1,2-dichloroethane (10 mL) was heated in a sealed tube with microwave irradiation at 100° C. for 45 min. The reaction mixture was cooled to rt, diluted with CH₂Cl₂ (20 mL) and the solids were removed. The organics were washed with brine (20 mL) and the solids were dissolved into saturated aqueous NH₄Cl (20 mL) and extracted with EtOAc (2×30 mL). The combined organics were dried (MgSO₄), filtered, concentrated and purified by SiO₂ chromatography (10–20% EtOAc/hexanes, loaded using CH₂Cl₂) to yield methyl 5-[(1,1-dimethylethoxy)carbonyl]-13-cyclohexyl-6,7-dihydro-5H-indolo[1,2-d][1,4]benzodiazepin-10-carboxylate (440 mg, 0.92 mmol, 42% (60% based on recovered starting indole)) as a light yellow solid. ¹HNMR (500 MHz, CDCl₃) δ 8.07 (s, 1H), 7.85 (d, J=8.5 Hz, 1H), 7.75 (dd, J=8.5, 1.2 Hz, 1H), 7.48–7.40 (m, 3H), 7.32–7.27 (m, 1H), 4.74–4.36 (m, 2H), 3.95 (s, 3H), 3.91–3.73 (m, 1H), 3.68–3.47 (m, 1H), 3.01–2.90 (m, 1H), 2.10–1.25 (m, 10H), 1.20 s (9H). LCMS: m/e 475 (M+H)⁺, ret time 2.38 min, column C, 2 minute gradient, start at 0% B.

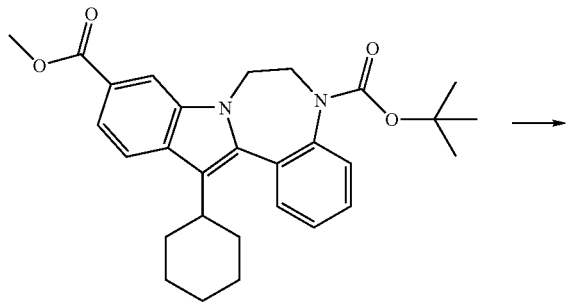

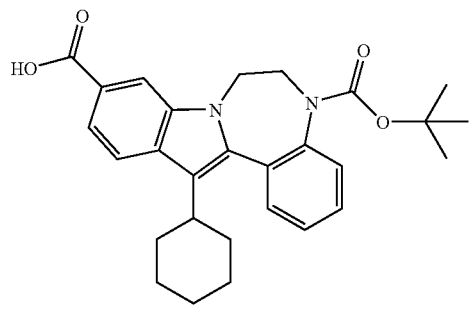

A solution of methyl 5-[(1,1-dimethylethoxy)carbonyl]-13-cyclohexyl-6,7-dihydro-5H-indolo[1,2-d][1,4]benzodiazepin-10-carboxylate (1.08 g, 2.28 mmol) in MeOH (40 mL), THF (30 mL) and 5N aqueous NaOH (2 mL) was heated at 50° C. overnight. Additional 10N aqueous NaOH (6 mL) was added and the reaction mixture was again heated at 50° C. for 5 h. The reaction was cooled, concentrated under vacuum and partitioned between EtOAc (60 mL) and ½ saturated aqueous NH₄Cl (30 mL). The organic layer was washed with brine (10 mL) and the combined aqueous layers were extracted with EtOAc (40 mL). The combined organic layers were dried (MgSO₄), filtered, concentrated to yield 5-[(1,1-dimethylethoxy)carbonyl]-13-cyclohexyl-6,7-dihydro-5H-indolo[1,2-d][1,4]benzodiazepin-10-carboxylic acid (1.01 g, 2.20 mmol, 96%) as a yellow solid. ¹HNMR (500 MHz, Acetone-d₆) δ 8.23 (s, 1H), 7.93 (d, J=8.4 Hz, 1H), 7.75 (d, J=8.4 Hz, 1H), 7.60–7.51 (m, 3H), 7.48–7.41 (m, 1H), 4.81 (br s, 1H), 4.66 (br s, 1H), 3.86 (br s, 1H), 3.59 (br s, 1H), 3.12–2.97 (m, 1H), 2.15–1.67 (m, 6H), 1.52–1.20 (m, 4H), 1.18 (s, 9H). LCMS: m/e 461 (M+H)⁺, ret time 2.26 min, column C, 2 minute gradient, start at 0% B.

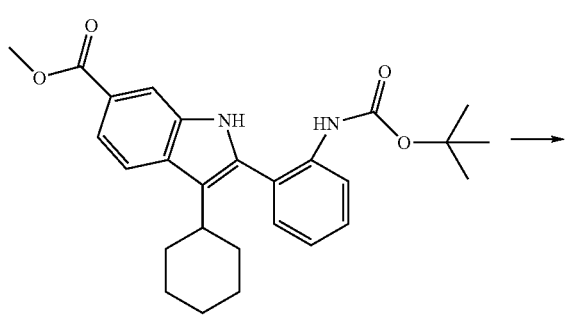

-continued

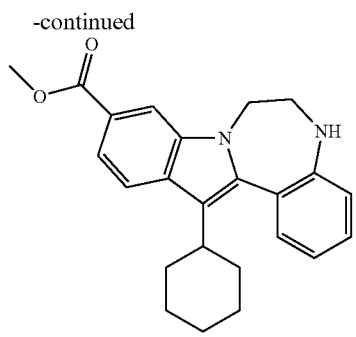

A slurry of methyl 2-(2-(tert-butoxycarbonyl)phenyl)-3-cyclohexyl-1H-indole-6-carboxylate (100 mg, 0.22 mmol), powdered NaOH (53 mg, 1.3 mmol) and nBu₄N⁺HSO₄⁻ (15 mg, 0.044 mol) in 1,2-dichloroethane (2 mL) was heated in a sealed tube with microwave irradiation at 100° C. for 45 min. The reaction mixture was cooled to rt, diluted with saturated aqueous NH₄Cl (20 mL) and extracted with CH₂Cl₂ (2×10 mL). The organics were dried (MgSO₄), filtered, concentrated and the crude residue was dissolved into CH₂Cl₂ (0.5 mL), treated with TFA (0.5 mL) and stirred 10 min. The reaction solution was concentrated to dryness portioned between saturated aqueous NH₄Cl (3 mL) and EtOAc (3 mL). The organic layer was concentrated and purified by SiO₂ chromatography (5–25% EtOAc/hexanes, loaded using CH₂Cl₂) to yield methyl 13-cyclohexyl-6,7-dihydro-5H-indolo[1,2-d][1,4]benzodiazepin-10-carboxylate (24 mg, 0.064 mmol, 29% over two steps) as a white solid. ¹HNMR (500 MHz, MeOD) δ 8.26 (s, 1H), 7.97 (d, J=8.6 Hz, 1H), 7.77 (dd, J=8.6, 1.5 Hz, 1H), 7.64–7.55 (m, 3H), 7.51–7.48 (m, 1H), 4.45 (br s, 2H), 3.96 (s, 3H), 3.92–3.88 (m, 2H), 3.03 (tt, J=12.2, 3.3 Hz, 1H), 2.21–2.10 (m, 2H), 1.98–1.80 (m, 5H), 1.54–1.36 (m, 2H). LCMS: m/e 375 (M+H)⁺, ret time 2.02 min, column C, 2 minute gradient, start at 0% B.

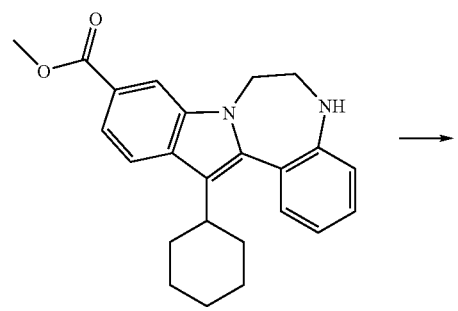

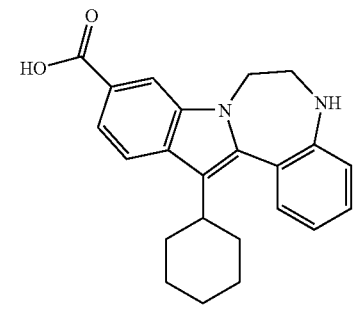

A solution of methyl 13-cyclohexyl-6,7-dihydro-5H-indolo[1,2-d][1,4]benzodiazepin-10-carboxylate (45.8 mg, 0.12 mmol) in THF/MeOH (1:2, 3 mL) and 1N aqueous NaOH (0.5 mL) was heated at 50° C. for 5 h. The reaction solution was concentrated to remove volatile organics, neutralized with TFA (0.04 mL) and purified by preparative HPLC (MeOH/H$_2$O with TFA buffer) to yield 13-cyclohexyl-6,7-dihydro-5H-indolo[1,2-d][1,4]benzodiazepin-10-carboxylic acid (33 mg, 0.092 mmol, 76%) as white solid. $^1$HNMR (500 MHz, MeOD) δ 8.25 (s, 1H), 7.96 (d, J=8.5 Hz, 1H), 7.79 (dd, J=8.5, 1.2 Hz, 1H), 7.63–7.52 (m, 3H), 7.50–7.46 (m, 1H), 4.44 (br s, 2H), 3.92–3.86 (m, 2H), 3.03 (tt, J=12.4, 3.1 Hz, 1H), 2.21–2.10 (m, 2H), 1.97–1.80 (m, 5H), 1.54–1.36 (m, 2H). LCMS: m/e 361 (M+H)$^+$, ret time 1.88 min, column C, 2 minute gradient, start at 0% B.

General procedure for preparation of acylsulfonamides and acylsulfamides: To a solution of 5-[(1,1-dimethylethoxy)carbonyl]-13-cyclohexyl-6,7-dihydro-5H-indolo[1,2-d][1,4]benzodiazepin-10-carboxylic acid (1 equiv.), RSO$_2$Cl (5 equiv.) and DMAP (5 equiv.) in DMA (0.11 M) was added 1-(3-dimethylaminopropyl)-3-ethylcarbodiimide hydrochloride (4 equiv.). The reaction solution was stirred at 50° C. for 3 h, diluted with MeOH/DMSO (1:3, 4 mL), and purified by preparative HPLC (MeOH/H$_2$O with TFA buffer).

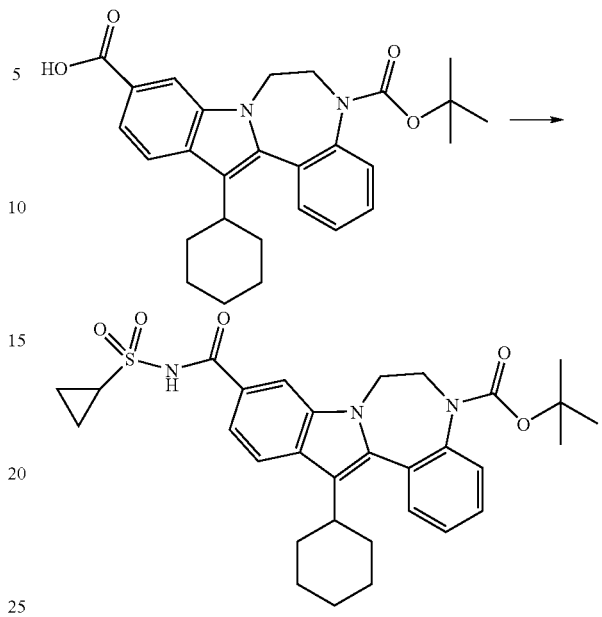

Yielded 5-[(1,1-dimethylethoxy)carbonyl]6,7-dihydro-5H-indolo[1,2-d][1,4]benzodiazepin-10-carboxamide, 13-cyclohexyl-N-[(dimethylamino)sulfonyl](172 mg, 0.303 mmol, 64%) as a white solid. $^1$HNMR (500 MHz, Acetone-d$_6$) δ 10.25 (s, 1H), 8.31 (s, 1H), 7.96 (d, J=8.5 Hz, 1H), 7.71 (d, J =8.5 Hz, 1H), 7.61–7.51 (m, 3H), 7.48–7.41 (m, 1H), 4.78 (br s, 1H), 4.61 (br s, 1H), 3.65 (br s, 1H), 3.59 (br s, 1H), 3.02 (s, 6H), 3.04–2.95 (m, 1H), 2.15–1.20 (m, 10H), 1.18 (s, 9H). LCMS: m/e 567 (M+H)$^+$, ret time 2.21 min, column C, 2 minute gradient, start at 0% B.

Yielded 5-[(1,1-dimethylethoxy)carbonyl]-6,7-dihydro-5H-indolo[1,2-d][1,4]benzodiazepin-10-carboxamide, 13-cyclohexyl-N-[(cyclopropyl)sulfonyl](75.6 mg, 0.134 mmol, 59%) as a light yellow solid. $^1$HNMR (500 MHz, MeOD) δ 8.21 (s, 0.25H), 8.12 (s, 0.75H), 8.02 (d, J=8.5 Hz, 0.25H), 7.92 (d, J=8.5 Hz, 0.75H), 7.69–7.38 (m, 5H), 4.66 (br s, 1H), 4.57 (br s, 1H), 3.79 (br s, 1H), 3.57 (br s, 1H), 3.25–3.17 (m, 1H), 3.06–2.96 (m, 1H), 2.20–1.11 (m, 14H), 1.18 (s, 9H). LCMS: m/e 564 (M+H)$^+$, ret time 2.07 min, column C, 2 minute gradient, start at 30% B.

Yielded 5-[(1,1-dimethylethoxy)carbonyl]-6,7-dihydro-5H-indolo[1,2-d][1,4]benzodiazepin-10-carboxamide, 13-cyclohexyl-N-[methylsulfonyl] (55 mg, 0.102 mmol, 42%) as an orange solid. LCMS: m/e 538 (M+H)+, ret time 2.03 min, column C, 2 minute gradient, start at 30% B.

General procedure for BOC deprotection of acylsulfonamides and acylsulfamides: The BOC-protected substrate was dissolved into CH$_2$Cl$_2$/TFA (2:1, 60 mM) and stirred at rt overnight. The reaction solution was concentrated under vacuum, the residue was diluted with MeOH/DMSO (1:1, 4 mL), and purified by preparative HPLC (MeOH/H$_2$O with TFA buffer).

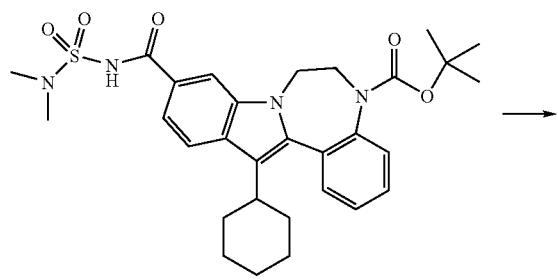

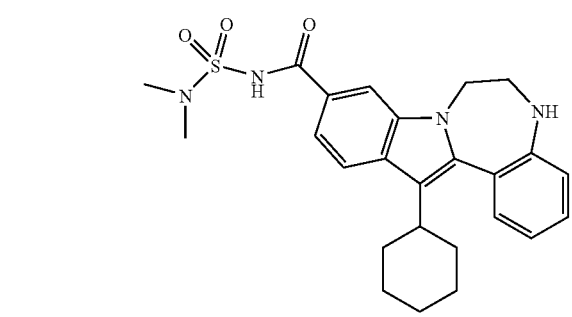

Yielded 6,7-dihydro-5H-indolo[1,2-d][1,4]benzodiazepin-10-carboxamide, 13-cyclohexyl-N-[(dimethylamino)sulfonyl] (161 mg, 0.284 mmol, 94%) as a yellow solid. $^1$HNMR (500 MHz, Acetone-d$_6$) δ 8.26 (s, 1H), 7.97 (d, J=8.5 Hz, 1H), 7.72 (dd, J=8.5, 1.5 Hz, 1H), 7.41 (dd, J=7.6, 1.5 Hz, 1H), 7.30 (ddd, J=7.6, 7.6, 1.5 Hz, 1H), 7.12 (br d, J=7.6 Hz, 1H), 7.05 (ddd, J=7.6, 7.6, 1.5 Hz, 1H), 4.53 (br s, 2H), 3.77–3.72 (m, 2H), 3.02 (s, 6H), 3.02–2.98 (m, 1H), 1.95–1.66 (m, 6H), 1.52–1.30 (m, 4H). LCMS: m/e 467 (M+H)+, ret time 1.83 min, column C, 2 minute gradient, start at 0% B.

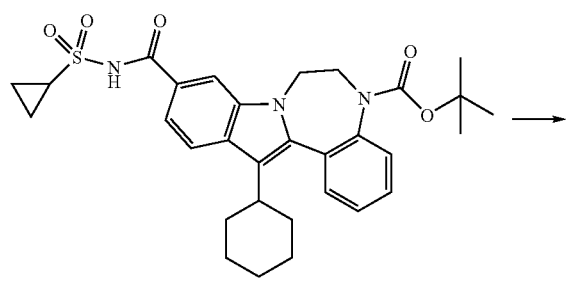

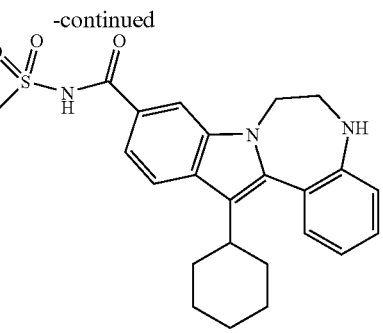

Yielded 6,7-dihydro-5H-indolo[1,2-d][1,4]benzodiazepin-10-carboxamide, 13-cyclohexyl-N-[(cyclopropyl)sulfonyl] (40.8 mg, 0.073 mmol, 81%) as a light pink solid. $^1$HNMR (500 MHz, MeOD) δ 8.19 (s, 1H), 8.01 (d, J=8.5 Hz, 1H), 7.68–7.60 (m, 4H), 7.59–7.55 (m, 1H), 4.46 (br s, 2H), 3.95 (dd, J=5.8, 5.5 Hz, 2H), 3.24–3.17 (m, 1H), 3.08–2.99 (m, 1H), 2.20–2.08 (m, 2H), 1.99–1.80 (m, 2H), 1.54–1.37 (m, 2H), 1.37–1.32 (m, 2H), 1.20–1.14 (m, 2H). LCMS: m/e 464 (M+H)+, ret time 1.52 min, column C, 2 minute gradient, start at 30% B.

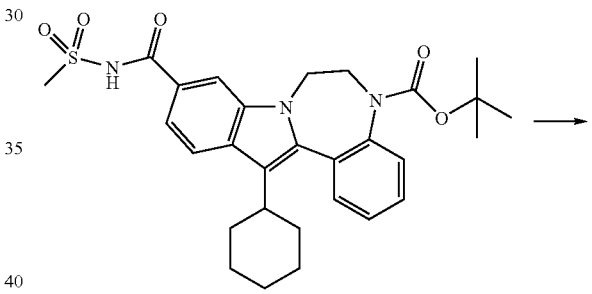

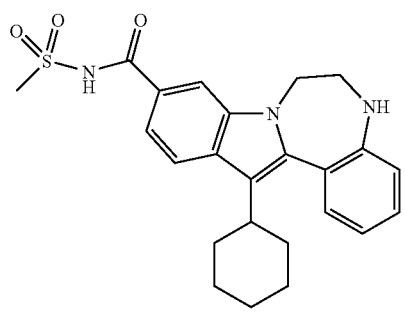

Yielded 6,7-dihydro-5H-indolo[1,2-d][1,4]benzodiazepin-10-carboxamide, 13-cyclohexyl-N-[methylsulfonyl] (28.8 mg, 0.066 mmol, 86%) as an orange solid. $^1$HNMR (500 MHz, DMSO-d$_6$) δ 11.82 (s, 1H), 8.27 (s, 1H), 7.88 (d, J=8.5 Hz, 1H), 7.61 (dd, J=8.5, 1.5 Hz, 1H), 7.24–7.20 (m, 2H), 6.95 (d, J=7.9 Hz, 1H), 6.87 (dd, J=7.9, 7.0 Hz, 1H), 5.85 (br s, 1H), 4.42 (br s, 2H), 3.59 (br s, 2H), 3.59 (br s, 2H), 3.41 (s, 3H), 2.90–2.82 (m, 1H), 2.09–1.99 (m, 2H), 1.86–1.69 (m, 5H), 1.45–1.23 (m, 3H). LCMS: m/e 438 (M+H)+, ret time 1.45 min, column C, 2 minute gradient, start at 30% B.

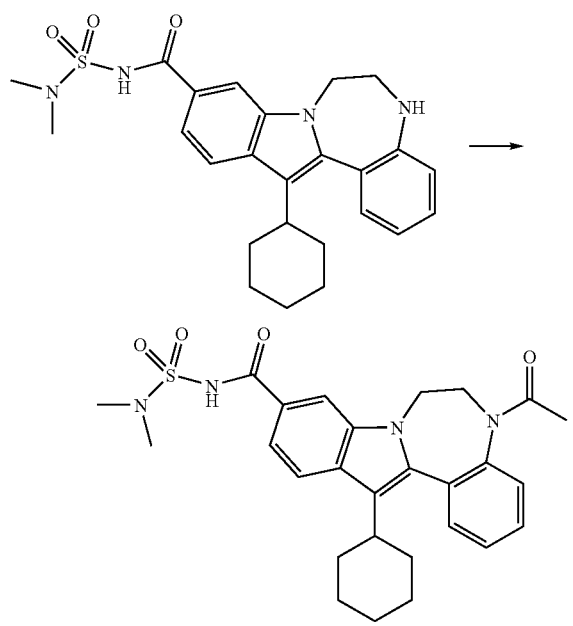

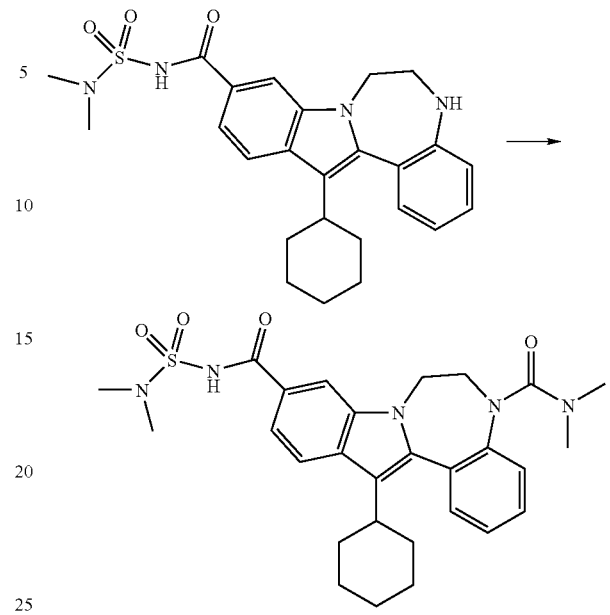

To a stirring solution of 6,7-dihydro-5H-indolo[1,2-d][1,4]benzodiazepin-10-carboxamide, 13-cyclohexyl-N-[(dimethylamino)sulfonyl] (50 mg, 0.11 mmol) in THF (1 mL) was added acetyl chloride (0.05 mL, 0.7 mmol) pyridine (0.009 mL) and DIPEA (0.020 mL, 0.12 mmol) The reaction solution was stirred at rt for 10 min, diluted with MeOH/DMSO 2:1, 3 mL), and purified by preparative HPLC (MeOH/H$_2$O with TFA buffer) to yield 5-acetyl-13-cyclohexyl-N-[(dimethylamino)sulfonyl]-6,7-dihydro-5H-indolo[1,2-d][1,4]benzodiazepin-10-carboxamide (18.3 mg, 0.059 mmol, 34%) as white solid. $^1$HNMR (500 MHz, MeOD) δ 8.12 (s, 1H), 7.93 (d, J=8.6 Hz, 1H), 7.72–7.53 (m, 5H), 5.05–4.97 (m, 1H), 4.75–4.69 (m, 1H), 3.90–3.81 (m, 1H), 3.49–3.44 (m, 1H), 3.03 (s, 6H), 3.05–2.97 (m, 1H), 2.16–1.79 (m, 6H), 1.64 (s, 3H), 1.62–1.30 (m, 4H). LCMS: m/e 509 (M+H)$^+$, ret time 1.86 min, column C, 2 minute gradient, start at 30% B.

To a stirring solution of 6,7-dihydro-5H-indolo[1,2-d][1,4]benzodiazepin-10-carboxamide, 13-cyclohexyl-N-[(dimethylamino)sulfonyl] (59 mg, 0.13 mmol) in THF (1 mL) was added dimethyl carbamyl chloride (0.06 mL, 0.6 mmol) and DIPEA (0.022 mL, 0.13 mmol) The clear orange solution was stirred and heated at 80° C. with microwave irradiation for 6 h. The reaction solution was cooled to rt, diluted with MeOH/DMSO 1:1, 3 mL), and purified by preparative HPLC (MeOH/H$_2$O with TFA buffer) to yield 6,7-dihydro-5H-indolo[1,2-d][1,4]benzodiazepin-10-carboxamide, 13-cyclohexyl-N-[(dimethylamino)sulfonyl], 5-[(dimethylamino)carbonyl] (31.7 mg, 0.059 mmol, 47%) as white solid. $^1$HNMR (500 MHz, CDCl$_3$) δ 8.92 (s, 1H), 8.03 (s, 1H), 7.90 (d, J=8.5 Hz, 1H), 7.52–7.39 (m, 4H), 7.22 (d, J=7.6 Hz, 1H), 4.57 (br s, 1H), 4.12–3.76 (m, 3H), 3.07 (s, 6H), 2.90–2.82 (m, 1H), 2.44 (s, 6H), 2.10–1.15 (m, 10H). LCMS: m/e 538 (M+H)$^+$, ret time 2.00 min, column C, 2 minute gradient, start at 30% B.

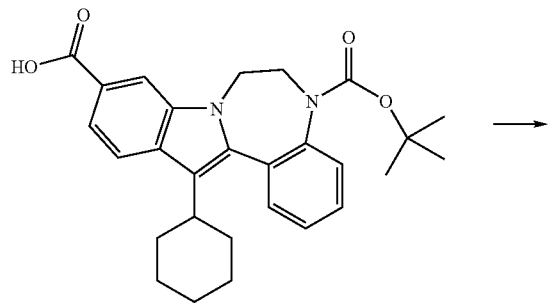

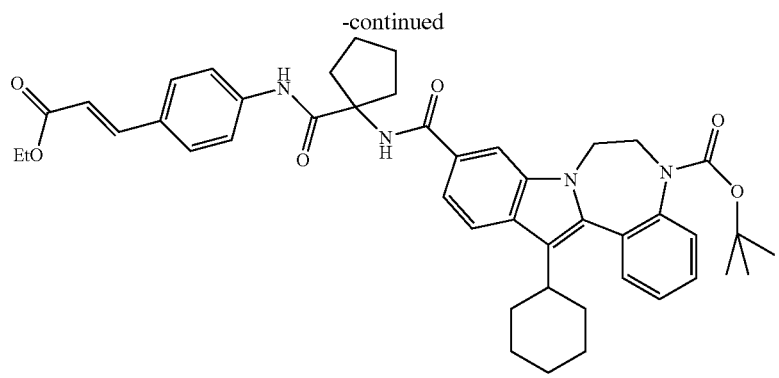

To a stirred solution of 5-[(1,1-dimethylethoxy)carbonyl]-13-cyclohexyl-6,7-dihydro-5H-indolo[1,2-d][1,4]benzodiazepin-10-carboxylic acid (300 mg, 0.65 mmol), (E)-ethyl 3-(4-(1-aminocyclopentanecarboxamido)phenyl)acrylate (217 mg, 0.72 mmol) and triethylamine (0.54 mL, 0.41 mmol) in DMSO (4 mL) was added O-benzotriazol-1-yl-N,N,N',N'-tetramethyluronium tetrafluoroborate (252 mg, 0.79 mmol). The reaction solution was stirred at rt for 1 h. An aliquot (0.5 mL, ~12.5%) was removed, diluted with DMSO (1 mL) and purified by preparative HPLC (MeOH/H$_2$O with TFA buffer) to yield ethyl 2-propenoate, 3-[4-[[[1-[[(5-[(1,1-dimethylethoxy)carbonyl]-13-cyclohexyl-6,7-dihydro-5H-indolo[1,2-d][1,4]benzodiazepin-10-yl)carbonyl]amino]cyclopentyl]carbonyl]amino]phenyl]-, (2E) (15.5 mg, 0.021 mmol, 26%) as a yellow solid. LCMS: m/e 538 (M+H)$^+$, ret time 2.00 min, column C, 3 minute gradient, start at 30% B.

removed, diluted with DMSO and purified by preparative HPLC (MeOH/H$_2$O with TFA buffer) to yield ethyl 2-propenoate, 3-[4-[[[1-[[(13-cyclohexyl-6,7-dihydro-5H-indolo[1,2-d][1,4]benzodiazepin-10-yl)carbonyl]amino]cyclopentyl]carbonyl]amino]phenyl]-, (2E) (11.1 mg, 0.017 mmol, 21%) as a yellow solid. $^1$HNMR (500 MHz, MeOD) δ 8.13 (s, 1H), 7.98 (d, J=8.5 Hz, 1H), 7.70–7.51 (m, 10H), 6.42 (d, J=16.2 Hz, 1H), 4.51–4.16 (m, 2H), 4.24 (q, J=7.0 Hz, 2H), 3.97–3.87 (m, 2H), 3.09–2.98 (m, 1H), 2.56–2.45 (m, 2H), 2.26–2.07 (m, 4H), 2.00–1.78 (m, 9H), 1.53–1.36 (m, 3H), 1.33 (t, J=7.0 Hz, 3H). LCMS: m/e 645 (M+H)$^+$, ret time 1.89 min, column C, 2 minute gradient, start at 30% B.

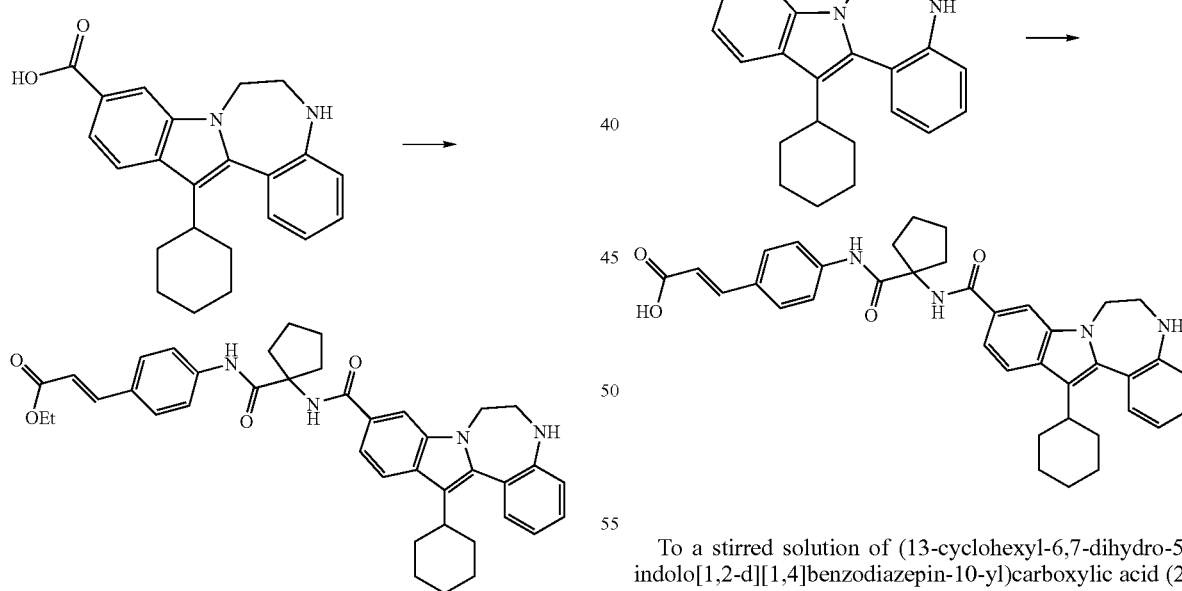

To a stirred solution of (13-cyclohexyl-6,7-dihydro-5H-indolo[1,2-d][1,4]benzodiazepin-10-yl)carboxylic acid (230 mg, 0.65 mmol), (E)-ethyl 3-(4-(1-aminocyclopentanecarboxamido)phenyl)acrylate (217 mg, 0.72 mmol) and triethylamine (0.54 mL, 0.41 mmol) in DMSO (4 mL) was added O-benzotriazol-1-yl-N,N,N',N'-tetramethyluronium tetrafluoroborate (252 mg, 0.79 mmol). The reaction solution was stirred at rt for 1 h. An aliquot (0.5 mL, ~12.5%) was removed. The remaining reaction solution was diluted with H$_2$O (5 mL) and the precipitate (yellow solid) that formed was collected by filtration. This material was diluted with THF (12 mL) and MeOH (12 mL) and then treated with 1M aqueous NaOH (4 mL). The reaction was stirred 6 h at 50° C., and concentrated to remove volatile organic solvents. The solution was diluted with saturated aqueous NH₄Cl (20 mL) and extracted with EtOAc (40 mL). The remaining sticky solid was dissolved into H₂O (50 mL) and extracted with EtOAc (100 mL). The combined organics were dried (MgSO₄), filtered and concentrated. The residue was purified by preparative HPLC (MeOH/H₂O with TFA buffer) to yield an orange solid which was further purified by preparative HPLC (MeOH/H₂O with NH₄OAc buffer) to yield 2-propenoic acid, 3-[4-[[[1-[[(13-cyclohexyl-6,7-dihydro-5H-indolo[1,2-d][1,4]benzodiazepin-10-yl)carbonyl]amino]cyclopentyl]-carbonyl]amino]phenyl]-, (2E)-(104 mg, 0.17 mmol, 30%) as a light yellow solid. ¹HNMR (300 MHz, DMSO-d₆) δ 9.95 (s, 1H), 8.25 (s, 1H), 8.14 (s, 1H), 7.80 (d, J=8.3 Hz, 1H), 7.65 (d, J=8.8 Hz, 2H), 7.61–7.55 (m, 3H), 7.50 (d, J=15.9 Hz, 1H), 7.23–7.15 (m, 2H), 6.92 (d, J=8.0 Hz, 1H), 6.84 (dd, J=7.3, 7.3 Hz, 1H), 6.38 (d, J=15.9 Hz, 1H), 5.80 (br s, 1H), 4.44 (br s, 2H), 3.51 (br s, 2H), 2.92–2.79 (m, 1H), 2.54 (s, 1H), 2.40–2.29 (m, 2H), 2.16–1.96 (m, 4H), 1.87–1.63 (m, 9H), 1.46–1.19 (m, 3H). LCMS: m/e 617 (M+H)⁺, ret time 1.59 min, column A, 3 minute gradient.

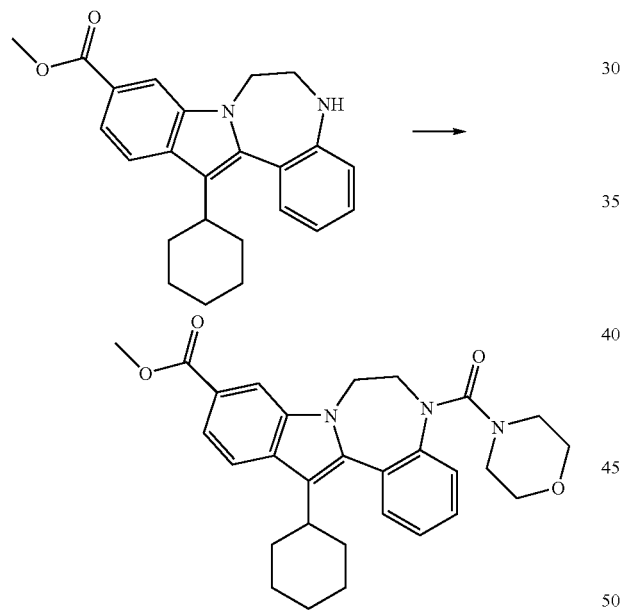

4-Morpholinecarbonyl chloride (0.30 mL, 2.6 mmol) was added to a solution of (methyl (13-cyclohexyl-6,7-dihydro-5H-indolo[1,2-d][1,4]benzodiazepin-10-yl)-carboxylate) (80 mg. 0.16 mmol) in CH₂Cl₂ (3 mL) and triethylamine (0.50 mL). The reaction mixture was sealed, heated at 100° C. for 30 min and then at 110° C. for 30 min (~70% conversion by LCMS) with microwave irradiation, cooled, diluted with CH₂Cl₂ (~3 mL) washed with H₂O (~5 mL), dried (MgSO₄) and concentrated to dryness. The residue was purified by preparative HPLC (MeOH/₂O with NH₄OAc buffer) to yield (methyl (13-cyclohexyl-6,7-dihydro-5H-indolo[1,2-d][1,4]benzodiazepin-10-yl)-carboxylate), 5-(4-morpholinylcarbonyl) (25 mg, 0.51 mmol, 30%) as a light yellow solid.

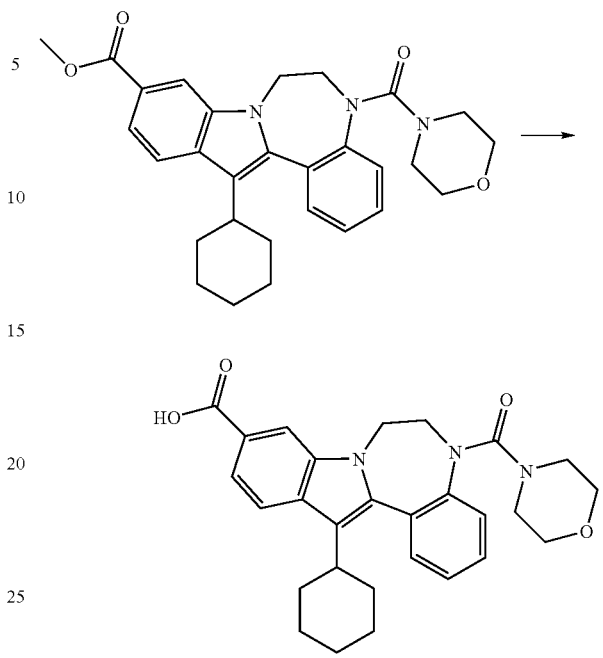

To a solution of (methyl (13-cyclohexyl-6,7-dihydro-5H-indolo[1,2-d][1,4]benzodiazepin-10-yl)-carboxylate), 5-(4-morpholinylcarbonyl) (25 mg, 0.05 mmol) in MeOH//THF (1:1, 1.6 mL) was added 1 M aqueous NaOH (0.80 mL). The reaction mixture was stirred and heated at 90° C. with microwave irradiation for 15 min in a sealed tube. The clear solution was diluted with H₂O (1 mL), neutralized with 1M aqueous HCl (0.80 mL) and concentrated to remove organic solvents. The resultant solids were collected by filtration, washed with H₂O and dried under vacuum to yield (13-cyclohexyl-6,7-dihydro-5H-indolo[1,2-d][1,4]benzodiazepin-10-yl)carboxylic acid, 5-(4-morpholinylcarbonyl) (21 mg, 0.05 mmol, 85%) as a light yellow solid. ¹HNMR (300 MHz, DMSO-d₆) δ 8.19 (s, 1H), 7.87 (d, J=8.4 Hz, 1H), 7.63 (dd, J=8.4, 1.5 Hz, 1H), 7.60–7.47 (m, 3H), 7.29 (dd, J=7.0, 1.5 Hz, 1H), 4.84 (br s, 2H), 3.98–3.55 (m, 4H), 3.23–3.05 (m, 2H), 2.88–2.69 (m, 5H), 2.12–1.63 (m, 6H), 1.51–1.06 (m, 4H). LCMS: m/e 472 (M–H)⁻, ret time 1.39 min, column A, 3 minute gradient.

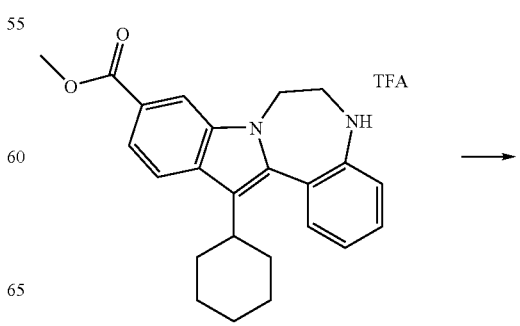

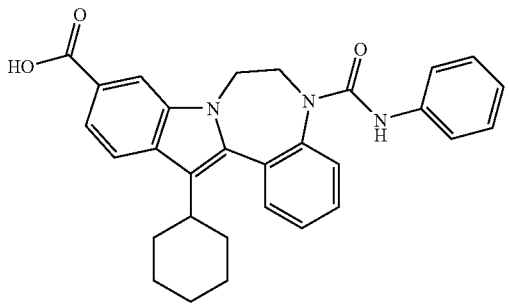

To a solution of methyl (13-cyclohexyl-6,7-dihydro-5H-indolo[1,2-d][1,4]benzodiazepin-10-yl)-carboxylate TFA (80 mg, 0.17 mmol) in triethylamine (0.20 mL) and CH₂Cl₂ (5 mL) which had been stirred for 5 min. was added phenyl isocyanate (0.20 mL, 1.84 mmol). The reaction solution was stirred for 2 h at rt, diluted with CH₂Cl₂ (~10 mL) and MeOH (~2 mL) and washed with ½ saturated aqueous NH₄Cl (10 mL) and brine (10 mL). The organics were concentrated to dryness, dissolved into MeOH/THF (1:1, 3 mL) and treated with 1 M aqueous NaOH (0.80 mL). The reaction mixture was stirred and heated at 80° C. with microwave irradiation for 15 min in a sealed tube. The clear solution was diluted with H₂O (3 mL), neutralized with 1M aqueous HCl (0.80 mL) and concentrated to remove organic solvents. The solids were collected by filtration, washed with water and purified by preparative HPLC (MeOH/H₂O with NH₄OAc buffer) to yield 5H-indolo[1,2-d][1,4]benzodiazepine-10-carboxylic acid, 13-cyclohexyl-6,7-dihydro-5-[(phenylamino)carbonyl] (21 mg, 0.044 mmol, 25%) as an off-white solid. $^1$H NMR (300 MHz, CD₃OD) δ 8.20 (s, 1H), 7.86 (d, J=8.4 Hz, 1H), 7.75–7.59 (m, 5H), 7.19–6.92 (m, 5H), 4.78–4.47 (m, 2H), 4.00–3.51 (m, 2H), 3.10–2.96 (m, 1H), 2.20–1.14 (m, 10H). LCMS: m/e 480 (M+H)$^+$, ret time 1.54 min, column A, 3 minute gradient.

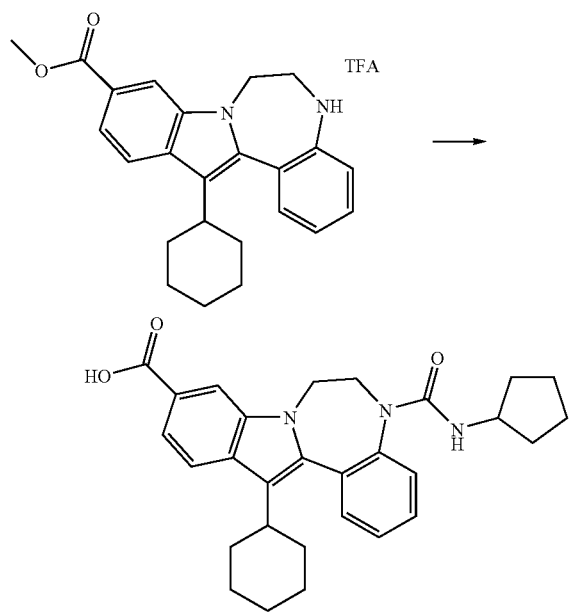

To a solution of methyl (13-cyclohexyl-6,7-dihydro-5H-indolo[1,2-d][1,4]benzodiazepin-10-yl)-carboxylate TFA (80 mg, 0.17 mmol) in triethylamine (0.20 mL) and CH₂Cl₂ (5 mL) which had been stirred for 5 min. was added cyclopentyl isocyanate (0.20 mL, 1.77 mmol). The reaction solution was stirred overnight at rt, concentrated to dryness, dissolved into MeOH/THF (1:1, 3 mL) and treated with 1M aqueous NaOH (0.80 mL). The reaction mixture was stirred and heated at 80° C. with microwave irradiation for 15 min in a sealed tube. The clear solution was diluted with H₂O (3 mL), neutralized with 1M aqueous HCl (0.80 mL) and concentrated to remove organic solvents. The solids were collected by filtration, washed with water and purified by preparative HPLC (MeOH/H₂O with NH₄OAc buffer) to yield 5H-indolo[1,2-d][1,4]benzodiazepine-10-carboxylic acid, 13-cyclohexyl-5-[(cyclopentylamino)carbonyl]-6,7-dihydro (8 mg, 0.02 mmol, 10%) as an off-white solid. $^1$HNMR (300 MHz, CD₃OD) δ 8.14 (s, 1H), 7.84 (d, J=8.4 Hz, 1H), 7.72 (dd, J=8.4, 1.1 Hz, 1H), 7.68–7.59 (m, 3H), 7.52–7.46 (m, 1H), 4.79–4.60 (m, 2H), 4.05–3.46 (m, 3H), 3.06–2.92 (m, 1H), 2.14–1.25 (m, 18H). LCMS: m/e 472 (M+H)$^+$, ret time 2.66 min, column A, 3 minute gradient.

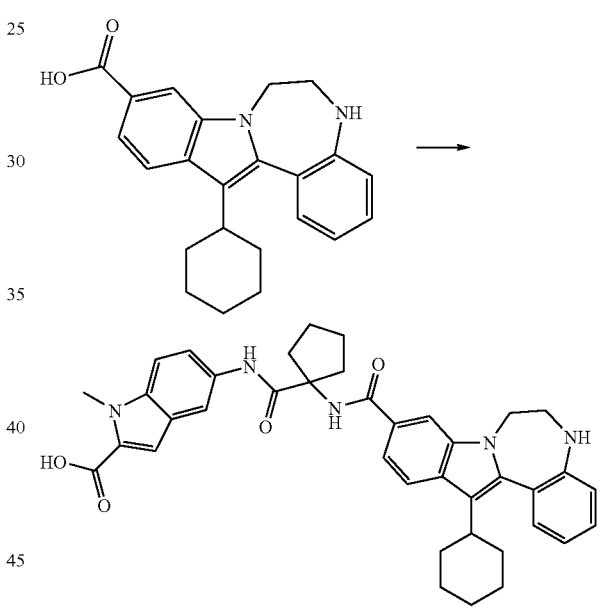

To a stirred solution of (13-cyclohexyl-6,7-dihydro-5H-indolo[1,2-d][1,4]benzodiazepin-10-yl)carboxylic acid (29 mg, 0.081 mmol), ethyl 5-(1-aminocyclopentanecarboxamido)-1-methyl-1H-indole-2-carboxylate (32 mg, 0.097 mmol) and triethylamine (0.060 mL, 0.41 mmol) in DMSO (0.5 mL) was added O-benzotriazol-1-yl-N,N,N',N'-tetramethyluronium tetrafluoroborate (32 mg, 0.097 mmol). The reaction solution was stirred at rt for 2 h, diluted with MeOH and the crude solution was purified by preparative HPLC to give an intermediate ethyl ester as a white solid. This material was diluted with THF (1.5 mL) and MeOH (1.5 mL) and then treated with 1M aqueous NaOH (1.5 mL). The reaction was stirred 3 h at rt, neutralized with 1N aqueous HCl (1.5 mL) and concentrated to remove the organic solvents. The resulting precipitate was collected by filtration and the off-white solid was shown to be 1H-indole-2-carboxylic acid, 5-[[[1-[[(13-cyclohexyl-6,7-dihydro-5H-indolo[1,2-d][1,4]benzodiazepin-10-yl)carbonyl]amino]cyclopentyl]carbonyl]amino]-1-methyl (22 mg, 0.034, 42%)

(10 mg, 18%, of the intermediate ester was held out of the final hydrolysis). $^1$HNMR (300 MHz, DMSO-$d_6$) δ 9.44 (s, 1H), 8.26 (s, 1H), 8.21 (s, 1H), 7.92 (s, 1H), 7.84 (d, J=8.8 Hz, 1H), 7.62 (d, J=8.8 Hz, 1H), 7.58–7.28 (m, 4H), 7.23–7.03 (m, 2H), 4.42 (br s, 2H), 3.98 (s, 3H), 3.62 (s, 2H), 2.93–2.80 (m, 1H), 2.43–2.30 (m, 2H), 2.20–1.96 (m, 4H), 1.89–1.65 (m, 9H), 1.45–1.19 (m, 3H). LCMS: m/e 644 (M+H)$^+$, ret time 2.53 min, column B, 3 minute gradient.

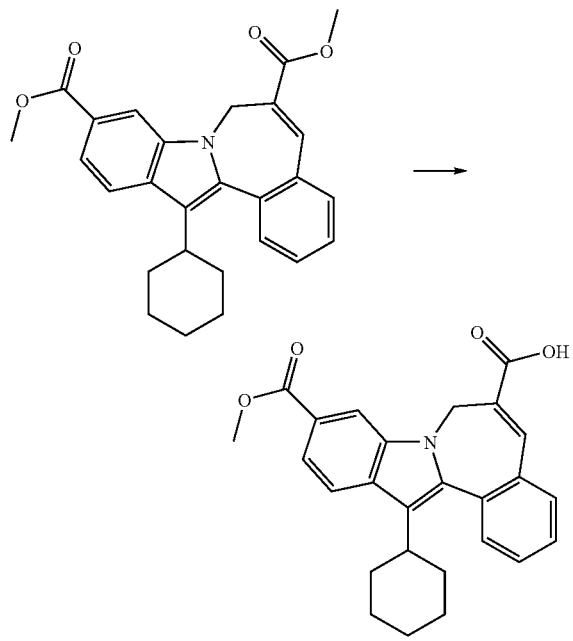

To a stirred solution of dimethyl 13-cyclohexyl-7H-indolo[2,1-a][2]benzazepine-6,10-dicarboxylate (2.6 g, 6.1 mmol) in DMF (60 mL) was added LiOH (1.45 g, 60 mmol) and the reaction mixture was heated at 60° C. for 2d. The reaction mixture was cooled internally with ice, acidified with 1M aqueous HCl (pH<2) and extracted with EtOAc (350 mL). The organics were washed with H$_2$O (~150 mL), brine (~150 mL), dried (MgSO$_4$), filtered and concentrated. The solids were triturated with Et$_2$O/hexanes (1:2) and collected to yield methyl 13-cyclohexyl-7H-indolo[2,1-a][2]benzazepine-10-carboxylate, 6-carboxylic acid (2.06 g, 4.96 mmol. 81%) as a fluffy yellow solid. $^1$HNMR (500 MHz, DMSO-$d_6$) δ 8.18 (s, 1H), 7.94 (d, J=8.5 Hz, 2H), 7.88 (s, 1H), 7.88 (d, J=7.6 Hz, 1H), 7.67–7.55 (m, 4H), 5.58 (br s, 1H), 4.15 (br s, 1H), 3.90 (s, 3H), 2.84–2.75 (m, 1H), 2.10–1.65 (m, 6H), 1.49–1.07 (m, 4H). LCMS: m/e 416 (M+H)$^+$, ret time 1.47 min, column A, 2 minute gradient.

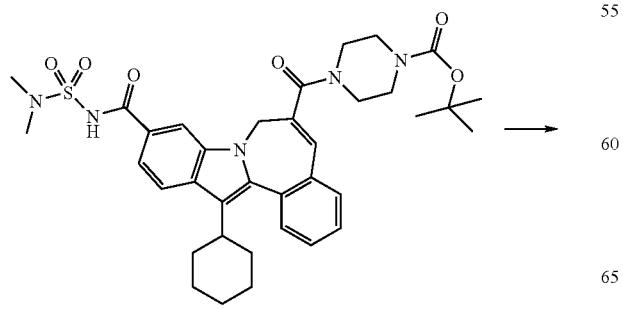

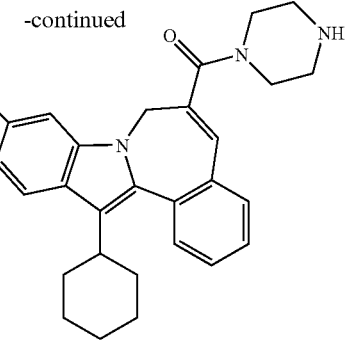

Trifluoroacetic acid (1.5 mL) was added dropwise to a stirred solution of 1-piperazinecarboxylic acid, 4-[[13-cyclohexyl-10-[[[(dimethylamino)sulfonyl]amino]carbonyl]-7H-indolo[2,1-a][2]benzazepin-6-yl]carbonyl]-, 1,1-dimethylethyl ester (77 mg. 0.11 mmol) in CH$_2$Cl$_2$ (1.5 mL). The reaction solution was stirred 2 h, concentrated and the residue was purified by preparative HPLC (MeOH/H$_2$O with TFA buffer) to yield 7H-indolo[2,1-a][2]benzazepine-10-carboxamide, 13-cyclohexyl-N-[(dimethylamino)sulfonyl]-6-(1-piperazinylcarbonyl) (37 mg, 0.06 mmol, 56%) as a yellow solid. $^1$HNMR (500 MHz, CDCl$_3$) δ 9.36 (br s, 1H), 8.25 (s, 1H), 7.87 (d, J=8.2 Hz, 1H), 7.61–7.39 (m, 5H), 6.91 (s, 1H), 5.16 (br s, 1H), 4.31 (br s, 1H), 3.88–3.39 (m, 8H), 2.98 (s, 6H), 2.89–2.75 (m, 1H), 2.11–1.13 (m, 10H). LCMS: m/e 576 (M+H)$^+$, ret time 2.39 min, column B, 3 minute gradient.

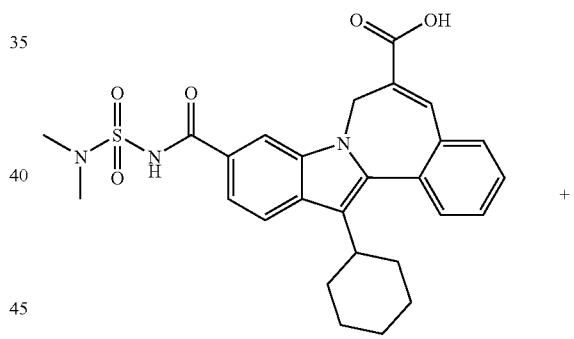

1

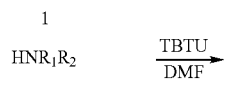

2

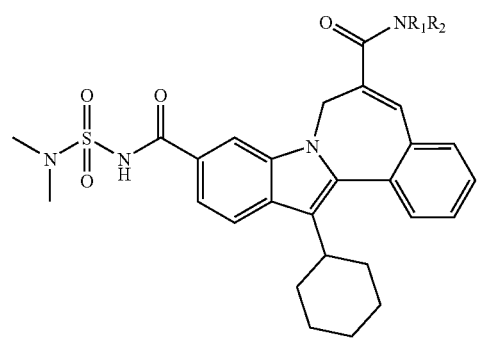

To 0.05 mmol of 1 in 1.0 mL of anhydrous N,N-Dimethylformamide (DMF) in a 3 dram vial equipped with a teflon lined screw cap was added 0.15 mmol (3 eq.) of 2-(1H-Benzotriazole-1-yl)-1,1,3,3,-Tetramethyluronium Tetrafluoroborate (TBTU) in 1.0 mL of anhydrous DMF followed by the addition of 0.1 mmol (2 eq.) of amine 2 in 1.0 mL of anhydrous DMF. The reaction was shaken on an Innova 2000 orbital shaker at 240 rpm overnight at room temperature. The reaction volume was then reduced to a total volume of 2.0 mL in a Savant Speedvac and the crude product was purified using a Dionex ELSD triggered preparative HPLC employing acetonitrile/water and 10 mM ammonium acetate buffer with a Sunfire, C18, 21.2 mm×150 mm, 10 μm column at a focused gradient flow rate of 20 mL/min. Postpurification LC/MS data was obtained on a Waters analytical LC/Micromass Platform LC (ESI+) at 220 nm using the following set of conditions: Sunfire 5 μm C18, 4.6×100 mm column, with a focused gradient of 50–95% B (B=HPLC grade acetonitrile), (A=HPLC grade water with 0.1% ammonium acetate), in 7 minutes with a 1 minute hold.

All NMR spectra were recorded at room temperature using a Bruker DRX500 spectrometer. The NMR solvent used was 1:1 (by volume) methyl alcohol-$d_4$ ($CD_3OD$)/chloroform-d ($CDCl_3$). Chemical shifts were reported in ppm relative to $CD_3OD$. Coupling constants were reported in hertz. Peak multiplicity was reported using the following abbreviations: s (singlet), d (doublet), t (triplet), m (multiplet), br (broad).

7H-indolo[2,1-a][2]benzazepine-10-carboxamide, 13-cyclohexyl-N-[(dimethylamino)sulfonyl]-6-[(3,5-dimethyl-1-piperazinyl)carbonyl]-

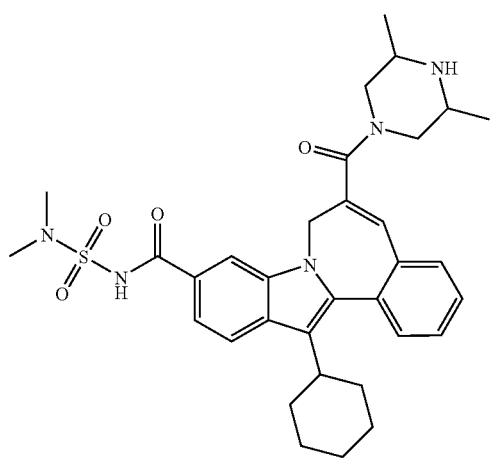

$^1$H NMR: δ 0.84 (m, 1H), 1.23 (m, 6H), 1.38 (m, 2H), 1.47 (m, 2H), 1.74 (m, 2H), 1.98 (m, 5H), 2.73 (m, 2H), 2.84 (m, 2H), 3.00 (s, 6H), 3.10 (m, 1H), 3.73 (s, 1H), 4.44 m, 1H), 5.06 (m, 1H), 6.91 (br s, 1H), 7.46–7.61 (br m, 5H), 7.91 (d, 1H, J=8.48 Hz), 8.07 (br s, 1H). LC/MS: m/z 604.26, Rf 1.8 min., 99.4% purity.

7H-indolo[2,1-a][2]benzazepine-6,10-dicarboxamide, 13-cyclohexyl-$N^{10}$-[(dimethylamino)sulfonyl]-$N^6$-(2-hydroxyethyl)-$N^6$-methyl-

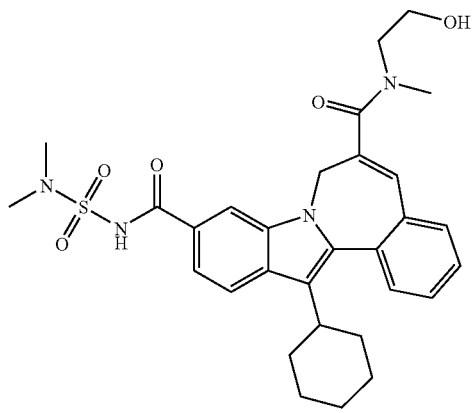

$^1$H NMR: δ 1.29 (m, 1H), 1.50 (m, 3H), 1.80 (m, 2H), 1.98 (m, 1H), 2.08 (m, 3H), 2.92 (m, 1H), 3.10 (m, 8H), 3.58 (m, 1H), 3.71 (m, 3H), 3.78 (s, 1H), 3.82 (m, 1H), 4.43 (m, 1H), 5.17 (m, 1H), 7.11 (s, 1H), 7.53 (m, 3H), 7.66 (m, 2H), 7.95 (d, 1H, J=8.47 Hz), 8.10 (m, 1H). LC/MS: m/z 565.18, Rf 1.9 min., 100% purity.

13-cyclohexyl-N-[4-hydroxy-3-methoxybenzyl]-6-[(N-morpholinyl)carbonyl]-7H-indolo[2,1-a][2]benzazepine-10-carboxamide,

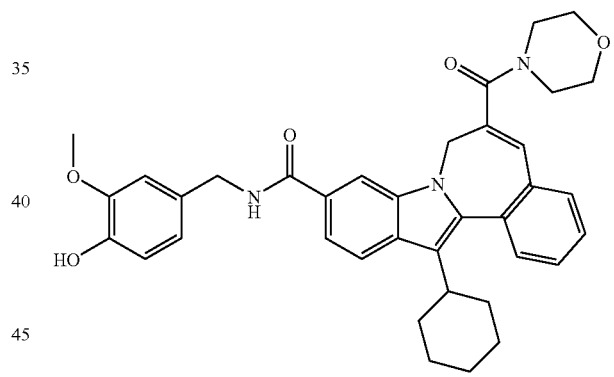

The diversity amines (0.108 mmol, 1.3 equiv) were weighed directly into successive reactor vessels of a multi-position reactor. To each position in the reactor was then added the carboxylic acid template (500 uL of a 0.172 M stock solution in DMF, 0.086 mmol, 1.0 equiv) followed by 500 uL of a three-component stock solution in DMF containing EDC (0.108 mmol, 1.3 equiv), HOBt (0.108 mmol, 1.3 equiv), and N,N-diisoproylethylamine (0.430 mmol, 5.0 equiv). The reactions were capped with a septum and agitated overnight via orbital shaker at room temperature.

Purification was effected by injecting the reaction mixture directly onto a preparative LCMS system using the following conditions:
Analysis Conditions:
  Column: Waters SunFire Prep C18 OBD, 19×100 mm×5 um
    (A) 10:90 methanol:water; (B) 90:10
  Mobile Phase: methanol:water
  Buffer: 0.1% TFA
  Gradient Range: 40–100% B Gradient Time: 10 min
Flow Rate: 20 mL/min
Analysis Time: 15 min
Detection:
Detector 1: UV at 220 nm
Detector 2: MS (ESI+)
Fraction Collection: UV-triggered
Fraction Drying: Savant Speedvac
Analysis and characterization were effected by the following method:
Instrument Name: LVL-L3407-LCMS2
Analysis Conditions:
  Column: Phenomenex Luna C18(2), 4.6×50 mm×5 um
    (A) 10:90 methanol:water; (B) 90:10
  Mobile Phase: methanol:water
  Buffer: 0.1% TFA
  Gradient Range: 0–100% B
  Gradient Time: 4 min
  Flow Rate: 4 mL/min
  Analysis Time: 5 min
Detection:
  Detector 1: UV at 220 nm
  Detector 2: MS (ESI+)
  Detector 3: ELSD

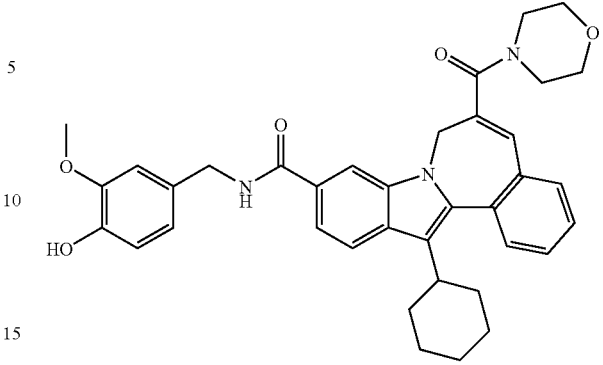

RT = 3.88 min
MS ion = 606.58

(500 MHz, MeOD) δ 1.30–2.30 (m, 18 H), 2.45–2.60 (m, 2H), 3.10 (t, 2H, J=7.0), 3.13 (tt, 1H, J=3.0, 12.0 Hz), 4.30 (m, 2H), 6.38 (d, 1H, J=16.0 Hz), 6.64 (d, 1H, J=2.0 Hz), 7.50–7.65 (m, 7H), 7.80 (d, 1H, J=8.5 Hz), 8.02 (s, 1H), 8.37 (s, 1H, NH), 9.65 (s, 1H, NH).

Examples of methods that can be used to prepare the fused imidazole derivatives of the instant invention, are outlined in the scheme below.

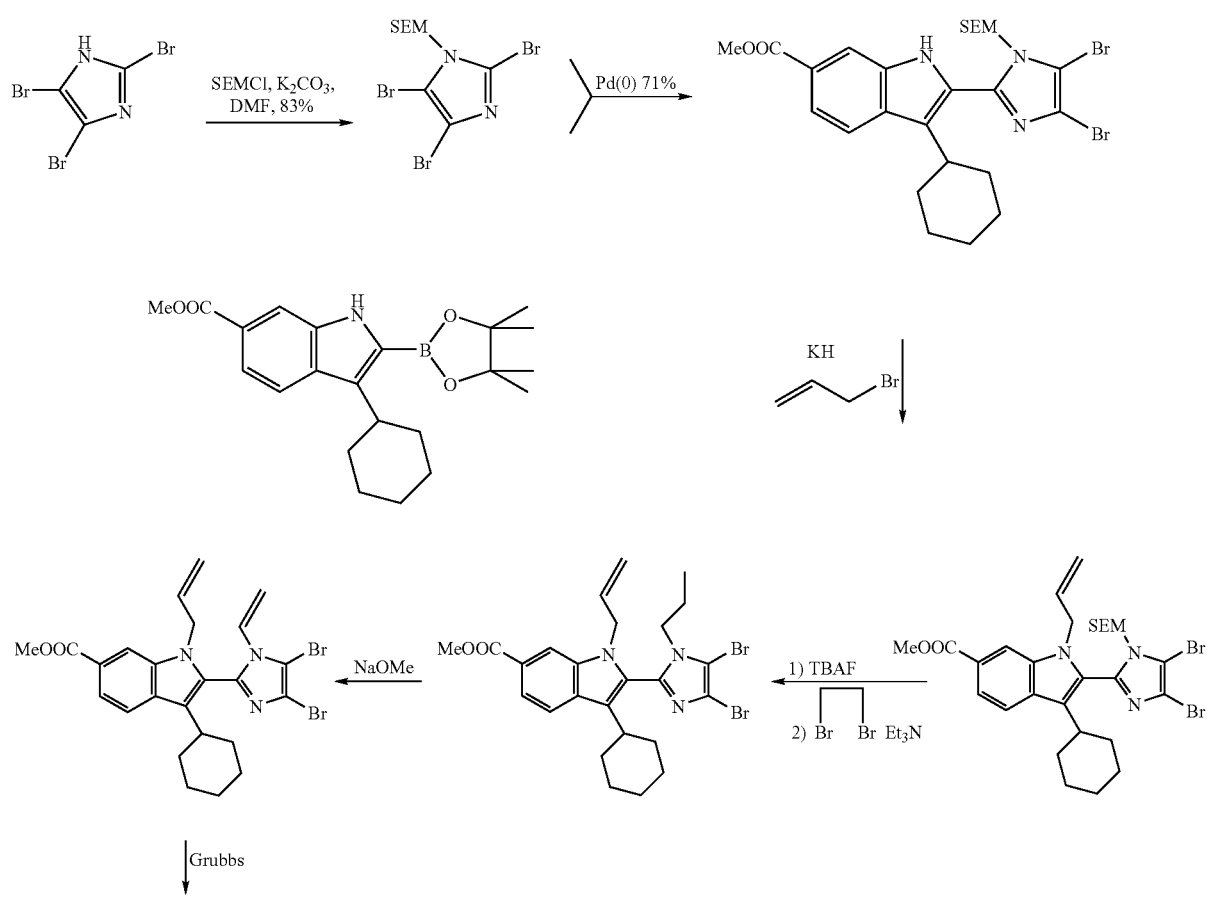

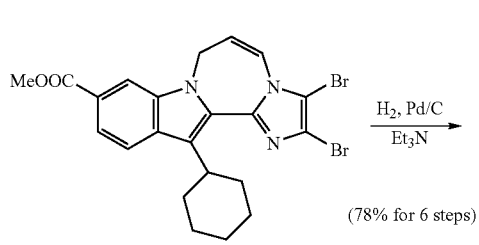
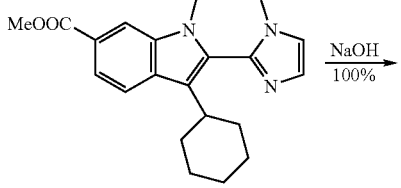

(78% for 6 steps)

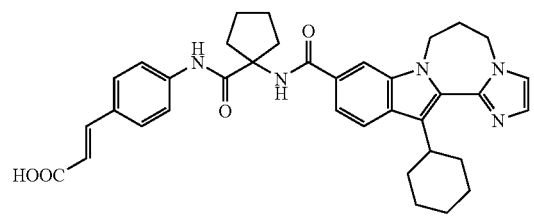
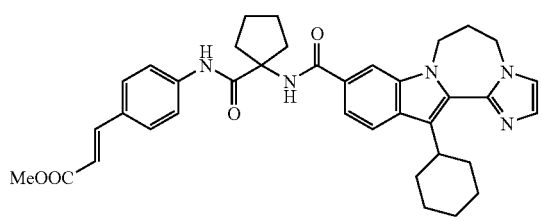

2,4,5-tribromo-1-((2-(trimethylsilyl)ethoxy)methyl)-1H-imidazole

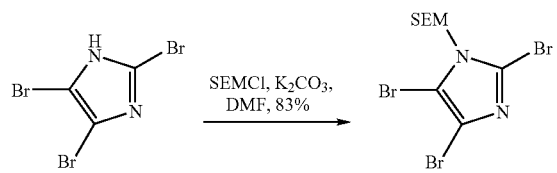

To a solution of 2,4,5-tribromoimidazole (3.05 g, 10 mmol) in anhydrous DMF (50 mL) was added powdered $K_2CO_3$ (19 g, 137 mmol), and the resulting suspension was stirred vigorously and treated dropwise with SEMCl (2.3 g, 13.8 mmol). The suspension was then stirred vigorously overnight. The solid was filtered off and washed with fresh DMF (20 mL). The combined filtrates were then evaporated under reduced pressure. Methylene chloride (30 mL) was then added and the solution washed with 0.1 N $Na_2CO_3$ (3×50 mL), dried ($Na_2SO_4$), filtered and evaporated to give a residue, which was passed through a silica gel pad ($CH_2Cl_2$) and evaporated to give 3.6 g (83%) of the title compound as a colorless oil. $^1H$ NMR (500 MHz, $CDCl_3$) δ 0.01 (s, 9H), 0.93 (t, 2H, J=8.0 Hz), 3.60 (t, 2H, J=8.0 Hz), 5.32 (s, 3H).

Methyl 3-cyclohexyl-2-(4,5-dibromo-1-((2-(trimethylsilyl)ethoxy)methyl)-1H-imidazol-2-yl)-]H-indole-6-carboxylate

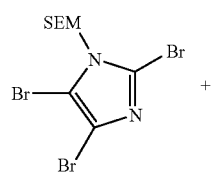 +

1H-indole-6-carboxylic acid, 3-cyclohexyl-2-(4,4,5,5-tetramethyl-1,3,2-dioxaborolan-2-yl)-, methyl ester. (383 mg, 1.0 mmol), 2,4,5-tribromo-1-((2-(trimethylsilyl)ethoxy)methyl)-1H-imidazole (435.2 mg, 1.0 mmol) and LiCl (84 mg, 2.0 mmol) were dissolved in a mixture of ethanol (4 mL) and toluene (4 mL). An aqueous $Na_2CO_3$ solution (1M, 2.5 mL, 2.5 mmol) was added and the mixture degassed with nitrogen for 20 min. $Pd(PPh_3)_4$ (11.5 mg, 0.1 mmol) was then added and the mixture stirred at 80° C. under $N_2$ for 3–4 h. EtOAc (6 mL) was added, followed by 20 mL of water. The organic layer was separated, dried ($Na_2SO_4$), filtered and evaporated under reduced pressure to give a residue. This was subjected to flash chromatography on silica gel ((EtOAc-Hexane 1:3) to afford 435 (71%) of the title compound as a foam. $^1H$ NMR (300 MHz, $CDCl_3$) δ 0.04 (s, 9H), 1.02 (t, 2H, J=8.4 Hz), 1.20–2.00 (m, 10H), 3.31 (m, 1H), 3.76 (t, 2H, J=8.4 Hz), 3.91 (s, 3H), 5.36 (s, 2H), 7.73 (dd, 1H, J=1.5, 8.5 Hz), 7.88 (d, 1H, J=8.5 Hz), 8.07 (s, 1H).

303

Methyl 1-allyl-3-cyclohexyl-2-(4,5-dibromo-1-((2-(trimethylsilyl)ethoxy)methyl)-1H-imidazol-2-yl)-1H-indole-6-carboxylate

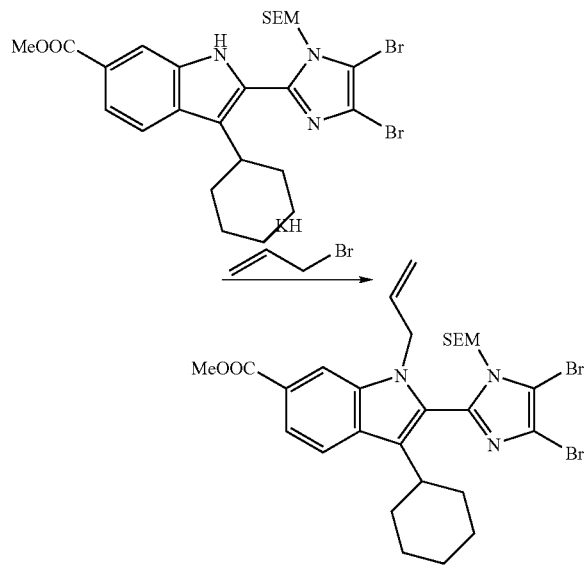

To a solution of methyl 3-cyclohexyl-2-(4,5-dibromo-1-((2-(trimethylsilyl)ethoxy)methyl)-1H-imidazol-2-yl)-1H-indole-6-carboxylate (428 mg, 0.7 mmol) in dry DMF (5 mL) was added KH (30% in oil, 0.8 mmol, 109 mg) proportion-wise at RT. The mixture was stirred at RT for 10 min until no further effervescence was observed. Allyl bromide (420 mg, 3.5 mmol) was added and the resulting mixture was stirred at RT for 15 min. Methylene chloride (10 mL) was added and the solution was washed with 1N HCl (3×10 mL), dried (Na$_2$SO$_4$), filtered and evaporated to give the title compound in a form pure enough for use in the following step (100%). $^1$H NMR (300 MHz, CDCl$_3$) δ 0.04 (s, 9H), 0.80 (m, 2H), 1.00–2.00(m, 10H), 2.45 (m, 1H), 3.43 (dd, 2H, J=7.5, 9.6 Hz), 3.91 (s, 3H), 4.50 (dd, 1H, J=4.8, 15.0), 4.60 (dd, 1H, J=6.0, 15.0), 4.88 (dd, 1H, J=1.2, 17.1 Hz), 5.03 (s, 2H), 5.04 (dd, 1H, J=0.9, 9.0 Hz), 5.78 (m, 1H), 7.75 (dd, 1H, J=1.5, 8.5 Hz), 7.82 (d, 1H, J=8.5 Hz), 8.02 (s, 1H).

Methyl 1-allyl-3-cyclohexyl-2-(4,5-dibromo-1-(2-bromoethyl)-1H-imidazol-2-yl)-1H-indole-6-carboxylate

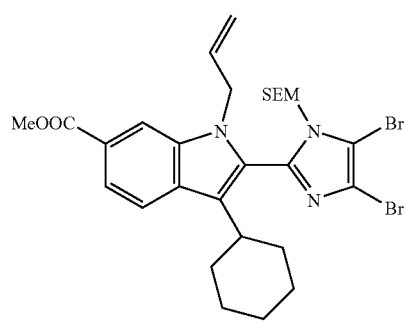

304

-continued

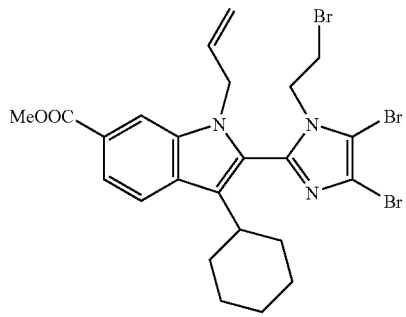

Methyl 1-allyl-3-cyclohexyl-2-(4,5-dibromo-1-((2-(trimethylsilyl)ethoxy)methyl)-1H-imidazol-2-yl)-1H-indole-6-carboxylate generated in the above reaction was dissolved in a solution of TABF (1M in THF, 10 mL) and the resultant mixture stirred at RT for 2 h. Methylene chloride (20 mL) was then added and the solution washed with water (3×50 mL), dried (Na$_2$SO$_4$), filtered and evaporated to give the title compound as an off-white solid, which was also pure enough for next step. The off-white solid was dissolved in 1,2-dibromoethane (3 mL). Triethylamine (300 uL, 2.0 mmol) was added and the resulting mixture stirred at 85° C. for 2 h. The solution was then evaporated under vacuum and the residue was dissolved in CH$_2$Cl$_2$ (10 mL), and then washed sequentially with 1N HCl, water and brine. The mixture was then dried (Na$_2$SO$_4$), filtered, and evaporated to give a solid residue. This material was dissolved in a small amount of CH$_2$Cl$_2$ and passed through a silica gel pad (CH$_2$Cl$_2$) to remove colored by-products. The elutes were concentrated to give the title compound, in a form pure enough for use in the next step. $^1$H NMR (500 MHz, CDCl$_3$) δ 0.80–2.10 (m, 10 H), 2.42 (m, 1 H), 3.30–3.40 (m, 1 H), 3.0–3.50 (m, 1H), 3.94 (s, 3H), 4.10–4.30 (m, 2H), 4.55–4.70 (m, 2H), 4.87 (d, 1H, J=17.0), 5.11 (d, 1H, J=10.5), 5.80–5.90(m, 1H), 7.80 (dd, 1H, J=8.0), 7.85 (d, 1H, J=8.0), 8.08 (s, 1H).

Methyl 1-allyl-3-cyclohexyl-2-(4,5-dibromo-1-vinyl-1H-imidazol-2-yl)-1H-indole-6-carboxylate

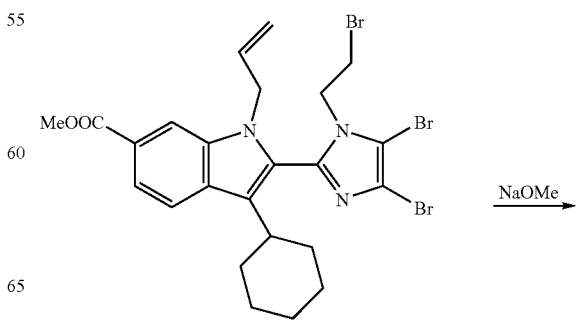

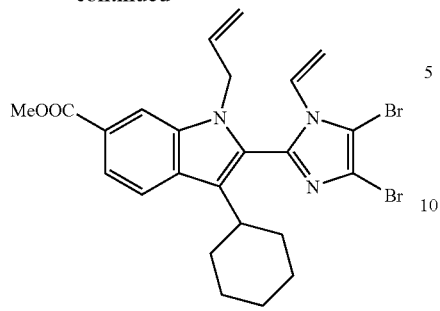

Methyl 1-allyl-3-cyclohexyl-2-(4,5-dibromo-1-(2-bromoethyl)-1H-imidazol-2-yl)-1H-indole-6-carboxylate was dissolved in a solution of sodium methoxide (0.5 M in Methanol from Aldrich, 10 mL) and the light yellow solution was heated to 65° C. for 1h. Methylene chloride (20 mL) was then added, followed by ice-water (50 mL). The aqueous layer was then adjusted to pH 5, and the organic layer was separated, dried (Na$_2$SO$_4$), filtered and evaporated to give the title compound in a form pure enough for use in the next step. $^1$H NMR (500 MHz, CDCl$_3$) δ 0.8–1.90 (m, 10 H), 2.50 (m, 1H), 3.92 (s, 3H), 4.55 (dd, 1H, J=4.5, 16.5 Hz), 4.70 (dd, 1H, J=6.5, 16.5 Hz), 5.85 (dd, 1H, J=6.0, 17.5 Hz), 5.05 (d, 1H, J=10.5 Hz), 5.09 (d, 1H, J=9.0 Hz), 5.26 (d, 1H, J=13.5 Hz), 5.7–5.80 (m, 1H), 6.56 (dd, 1H, J=9.0, 16.0 Hz), 7.77 (d, 1H, J=8.0 Hz), 7.82 (d, 1H, J=8.0 Hz), 8.07 (s, 1H).

7H-imidazo[2',1':3,4][1,4]diazepino[1,2-a]indole-10-carboxylic acid, 2,3-dibromo-13-cyclohexyl-, methyl ester

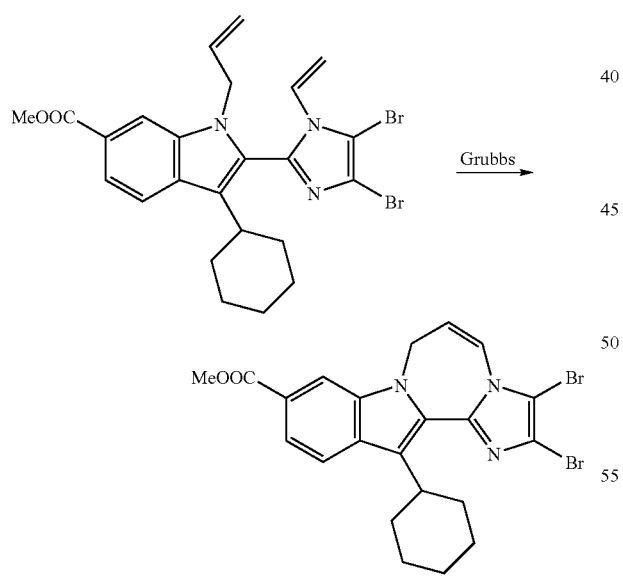

To a solution of methyl 1-allyl-3-cyclohexyl-2-(4,5-dibromo-1-vinyl-1H-imidazol-2-yl)-1H-indole-6-carboxylate in CH$_2$Cl$_2$ (50 mL) was added Grubbs catalyst (2$^{nd}$ generation, 60 mg, 0.07 mmol). The resulting solution was heated under reflux for 10 h. The solvent was removed and the resultant residue passed through a silica gel pad (CH$_2$Cl$_2$) to remove the catalyst. The elutes were then evaporated to give the title compound as an off-white solid that was pure enough for use in subsequent steps. $^1$H NMR (500 MHz, CDCl$_3$) δ 0.8–2.00 (m, 10 H), 3.56 (m, 1H), 3.95 (s, 3H), 4.74 (d, 2H, J=7.0), 6.13 (q, 1H, J=7.0), 6.93 (d, 1H, J=8.0), 7.74 (dd, 1H, J=1.5, 8.5), 7.93 (d, 1H, J=8.5), 8.12 (s, 1H).

5H-imidazo[2'1':3,4][1,4]diazepino[1,2-a]indole-10-carboxylic acid, 13-cyclohexyl-6,7-dihydro-, methyl ester

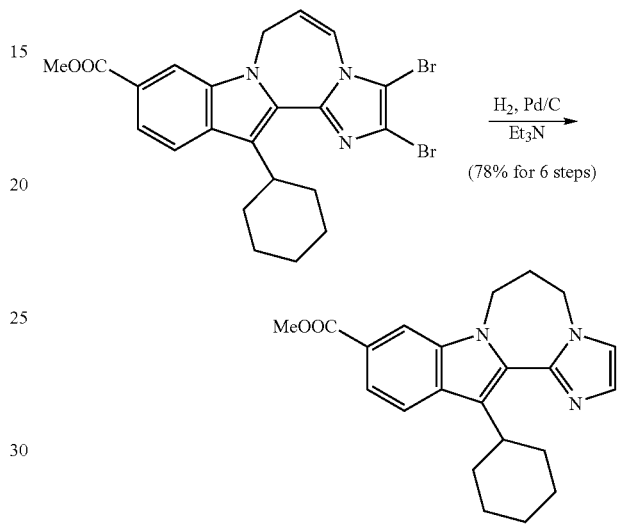

7H-imidazo[2',1':3,4][1,4]diazepino[1,2-a]indole-10-carboxylic acid, 2,3-dibromo-13-cyclohexyl-, methyl ester, generated in the preceding reaction was dissolved in a mixture of EtOAc (10 mL) and methanol (10 mL). Triethylamine (0.5 mL) was then added, followed by Pd—C (10%, 50 mg). The resulting mixture was stirred at RT under hydrogen (1 atm) for 30 min. The catalyst was then removed by filtration, and the filtrate evaporated under reduced pressure to give a solid. Flash chromatography on silica gel (EtOAc-Hexane 1:1) afforded 196 mg (77% for 6 steps) of the title compound as a foam. $^1$H NMR (500 MHz, CDCl$_3$) δ 1.04–2.10 (m, 10 H), 2.43 (m, 2H), 3.34 (m, 1H), 3.95 (s, 3H), 4.08 (t, 2H, J=6.5), 4.12 (t, 1H, J=6.5), 7.11 (s, 1H), 7.31 (s, 1H), 7.75 (dd, 1H, J=1.5, 8.5), 7.90 (d, 1H, J=8.5), 8.08 (s, 1H).

5H-imidazo[2',1':3,4][1,4]diazepino[1,2-a]indole-10-carboxylic acid, 13-cyclohexyl-6,7-dihydro-

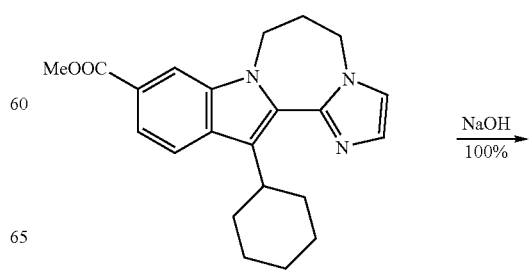

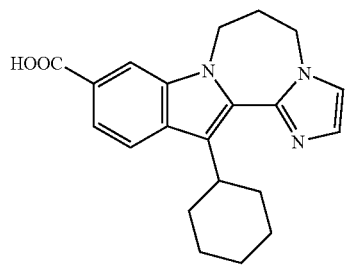

5H-imidazo[2',1':3,4][1,4]diazepino[1,2-a]indole-10-carboxylic acid, 13-cyclohexyl-6,7-dihydro-, methyl ester (90 mg, 0.25 mmol) was dissolved in MeOH (6 mL) and aqueous NaOH (6N, 3 mL) was added. The resulting mixture was stirred at 45° C. for 1h. Methylene chloride was added, followed by water(8 mL). The pH of the aqueous layer was adjusted to 4–5 with solid citric acid. The organic layer was then separated and the aqueous layer was re-extracted with CH$_2$Cl$_2$ (10 mL). The combined extracts were dried (Na$_2$SO$_4$), filtered and evaporated to give 85 mg (100%) the title compound. $^1$H NMR (500 MHz, CDCl$_3$) δ 1.30–2.10 (m, 10 H), 2.45 (m, 2H), 3.36 (m, 1H), 4.07 (t, 2H, J=6.5), 4.20 (t, 1H, J=6.5), 7.09 (dd, 1H, J=1.5), 7.34 (dd, 1H, J=1.5), 7.85 (dd, 1H, J=1.0, 8.5), 7.93 (d, 1H, J=8.5), 8.15 (s, 1H).

2-propenoic acid, 3-[4-[[[1-[[(13-cyclohexyl-6,7-dihydro-5H-imidazo[2',1':3,4][1,4]diazepino[1,2-a]indol-10-yl)carbonyl]amino]cyclopentyl]carbonyl]amino]phenyl]-, methyl ester, (2E)-

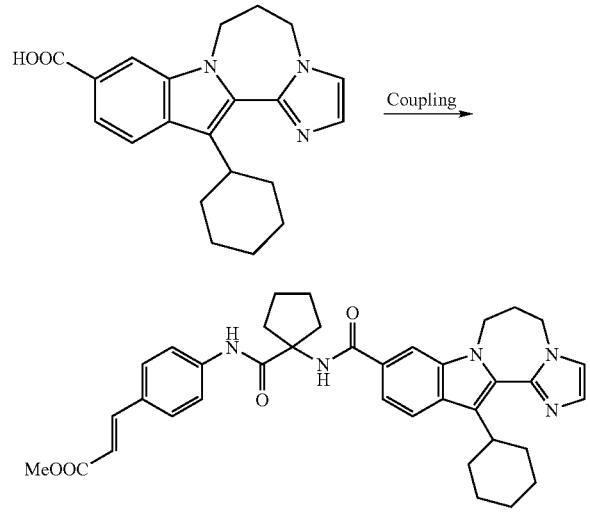

5H-imidazo[2',1':3,4][1,4]diazepino[1,2-a]indole-10-carboxylic acid, 13-cyclohexyl-6,7-dihydro- (18 mg, 0.05 mmol) and TBTU (24 mg, 0.075 mmol) was dissolved in DMSO (1 mL). Diisopropylethylamine (26 uL, 0.15 mmol) was added and the mixture was stirred at RT for 5 min. Then (E)-methyl 3-(4-(1-aminocyclopentanecarboxamido)phenyl)acrylate (20 mg, 0.69 mmol) was added and the solution was stirred at RT overnight. Methylene chloride (3 mL) was added and the solution was washed with aqueous HCl (0.5N, 2×5 ML), dried (Na$_2$SO4) and evaporated to give a residue. Flash chromatography on silica gel (EtOAc-CH$_2$Cl$_2$ 1:3) afforded 25.1 mg (81%) of methyl ester. $^1$H NMR (500 MHz, CDCl$_3$) δ 1.30–2.00 (m, 14 H), 2.20–2.30 (m, 2H), 2.38–2.45 (m, 2H), 2.55–2.63 (m, 2H), 3.38 (m, 1H), 3.78 (s, 3H), 4.04 (t, 2H, J=6.5), 4.17 (t, 2H, J=6.5), 6.34 (d, 1H, J=16.0), 6.49 (s, 1H, NH), 7.06 (d, 1H, J=1.0), 7.24 (d, 1H, J=1.0), 7.32 (dd, 1H, J=1.5, 8.5), 7.46 (d, 2H, J=8.5), 7.62 (d, 1H, J=8.5), 7.63 (d, 1H, J=16.0), 7.88 (d, 1H, J=8.5), 7.93 (s, 1H).

2-propenoic acid, 3-[4-[[[1-[[(13-cyclohexyl-6,7-dihydro-5H-imidazo[2',1':3,4][1,4]diazepino[1,2-a]indol-10-yl)carbonyl]amino]cyclopentyl]carbonyl]amino]phenyl]-(2E)-

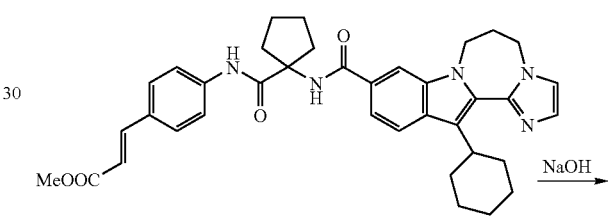

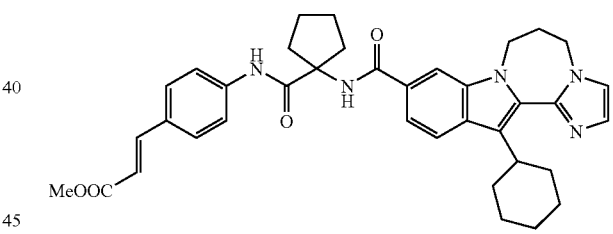

2-propenoic acid, 3-[4-[[[1-[[(13-cyclohexyl-6,7-dihydro-5H-imidazo[2',1':3,4][1,4]diazepino[1,2-a]indol-10-yl)carbonyl]amino]cyclopentyl]carbonyl]amino]phenyl]-, methyl ester, (2E)- (12 mg) was dissolve in methanol (0.5 mL). Aqueous NaOH (6N, 0.3 mL) was added and the solution was stirred at RT for 2 h. Methylene chloride (2 mL) was added and the organic solution was washed with 0.5N HCl, dried (Na$_2$SO$_4$) and evaporated to give 11.2 mg ( ) of acid. $^1$H NMR (500 MHz, MeOD) δ 1.30–2.00 (m, 12 H), 2.00–2.10 (m, 2H), 2.15–2.25 (m, 2H), 2.35–2.55 (m, 4H), 3.30 (m, 1H), 4.09 (t, 2H, J=6.5), 4.21 (t, 2H, J=6.5), 6.45 (d, 1H, J==16.0), 7.18 (d, 1H, J=1.0), 7.34 (d, 1H, J=1.0), 7.35 (d, 1H, J=8.5), 7.45 (d, 2H, J=8.5), 7.56 (d, 1H, J=8.5), 7.63 (dd, 1H, J=1.5, 8.5), 7.91 (d, 1H, J=8.5), 8.14 (s, 1H).

Further examples of methods that can be used to prepare additional isomers of the fused imidazole derivatives of the instant invention, are outlined in the Scheme below.

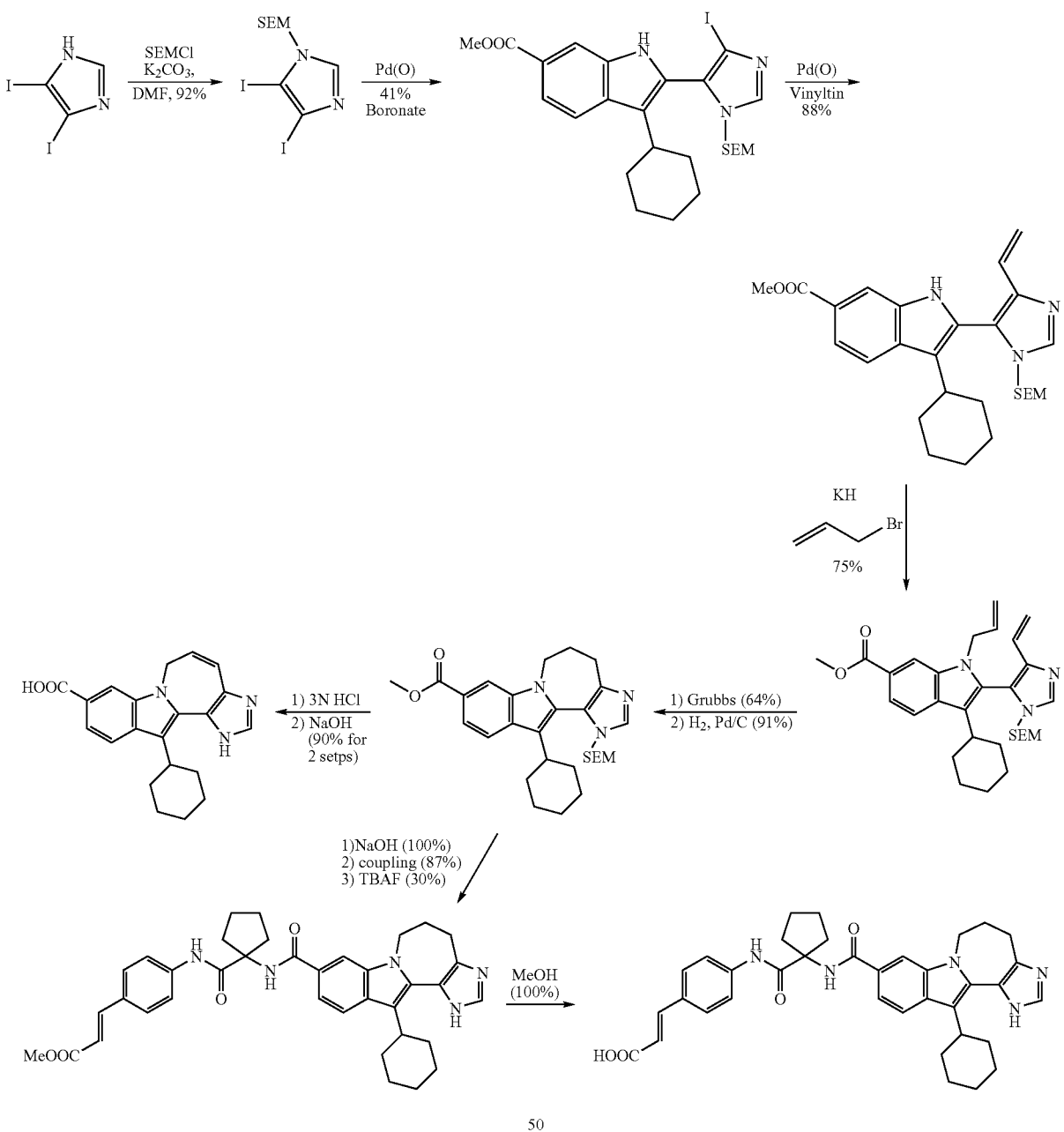

1H-imidazole,
4,5-diiodo-1-[[2-(trimethylsilyl)ethoxy]methyl]-

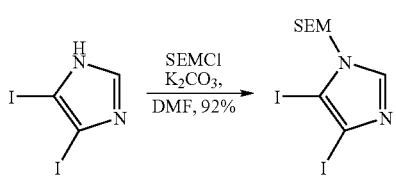

To a solution of 4,5-diiodoimidazole (3.20 g, 10 mmol) in anhydrous DMF (50 mL) was added powdered $K_2CO_3$ (19 g, 137 mmol), and the resulting suspension was stirred vigorously and treated dropwise with SEMCl (1.88 g, 11.3 mmol). The suspension was then stirred vigorously overnight. The solid was filtered off from the resultant mixture and washed with fresh DMF (20 mL). The combined filtrates were then evaporated under reduced pressure, and methylene chloride (30 mL) was then added to the residue and the subsequent solution was washed with 0.1 N $Na_2CO_3$ (3×50 mL), dried ($Na_2SO_4$), filtered and evaporated in vacuo. The residue was dissolved and the solution passed through a silica gel pad ($CH_2Cl_2$) and evaporated to give 4.15 g (92%) of the title compound as a colorless oil (High vacuum was used to remove excess SEMCl). $^1$H NMR (500 MHz, $CDCl_3$) δ 0.00 (s, 9), 0.92(m, 2H), 3.52 (m, 2H), 5.29 (s, 2H).

311

1H-indole-6-carboxylic acid, 3-cyclohexyl-2-[4-iodo-]-[[2-(trimethylsilyl)ethoxy]methyl]-1H-imidazol-5-yl]-, methyl ester

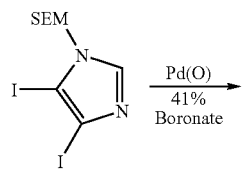

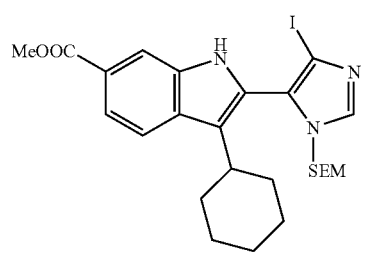

1H-indole-6-carboxylic acid, 3-cyclohexyl-2-(4,4,5,5-tetramethyl-1,3,2-dioxaborolan-2-yl)-, methyl ester (383 mg, 1.0 mmol), 1H-imidazole, 4,5-diiodo-1-[[2-(trimethylsilyl)ethoxy]methyl]- (562 mg, 1.25 mmol) and LiCl (84 mg, 2.0 mmol) were dissolved in a mixture of ethanol (4 mL) and toluene (4 mL). An aqueous Na₂CO₃ solution (1M, 2.5 mL, 2.5 mmol) was added and the mixture was degassed with nitrogen for 20 min. Pd(PPh₃)₄ (11.5 mg, 0.1 mmol) was then added and the mixture stirred at 70° C. under N₂ for 24 h. EtOAc (6 mL) was added, followed by 20 mL of water. The organic layer was separated, dried (Na₂SO₄) filtered and evaporated under reduced pressure to give a residue. Flash chromatography on silica gel ((EtOAc-Hexane 2:3) afforded 240 (41%) of the title compound as a white crystalline solid. ¹H NMR (500 MHz, CDCl₃) δ 0.00 (s,9H), 0.95 (m, 2H), 1.20–2.20 (10 H), 2.62 (m, 1H), 3.47 (m, 1H), 3.54 (m, 1H), 3.94 (s, 3H), 5.00–5.15 (m, 2H), 7.78 (dd, 1H, J=1.5, 8.5), 7.87 (d, 1H, J=8.5), 8.10 (s, 1H), 8.83 (s, 1H, NH).

1H-indole-6-carboxylic acid, 3-cyclohexyl-2-[4-ethenyl-1-[[2-(trimethylsilyl)ethoxy]methyl]-1H-imidazol-5-yl]-, methyl ester

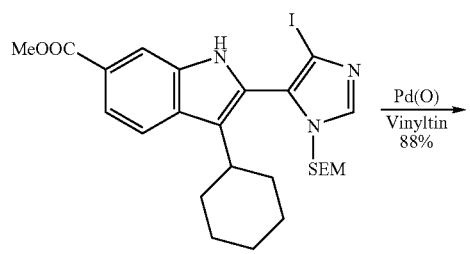

312

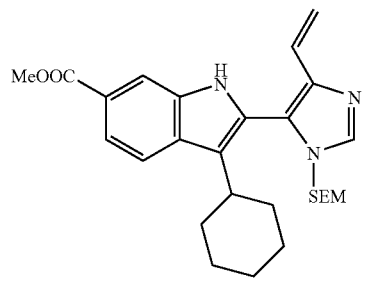

To a solution of 1H-indole-6-carboxylic acid, 3-cyclohexyl-2-[4-iodo-1-[[2-(trimethylsilyl)ethoxy]methyl]-1H-imidazol-5-yl]-, methyl ester (240 mg, 0.4 mmol) in DMF (2.0 mL) was added tributyl(vinyl)tin (190 mg, 0.6 mmol), LiCl (50 mg, 1.2 mmol), and PdCl₂ (PPh₃)₂ (140 mg, 0.02 mmol, 5mmol %). The mixture was stirred at 80° C. for 2 h. Methylene chloride (5 mL) was added and the resultant solution was washed with water (3×5 mL), then dried (Na₂SO₄), filtered and evaporated to give a residue. Flash chromatography on silica gel (CH₂Cl₂-EtOAc 2:1) afforded 168 mg (88%) of title compound as a foam. ¹H NMR (500 MHz, CDCl₃) δ 0.00 (s,9H), 0.95 (br s, 2H), 1.20–2.00 (10 H), 2.62 (m, 1H), 3.55 (br s, 1H), 3.61 (br s, 1H), 3.94 (s, 3H), 5.01 (s, 2H), 5.20 (td, 1H, J=1.5, 8.8), 6.00 (dd, 1H, J=1.5, 17.0), 6.47 (dd, 1H, J=11.0, 17.0), 7.70 (s, 1H), 7.78 (dd, 1H, J=1.5, 8.5), 7.86 (d, 1H, J=8.5), 8.09 (s, 1H), 9.00 (s, 1H, NH).

1H-indole-6-carboxylic acid, 3-cyclohexyl-2-[4-ethenyl-1-[[2-(trimethylsilyl)ethoxy]methyl]-1H-imidazol-5-yl]-1-(2-propenyl)-, methyl ester

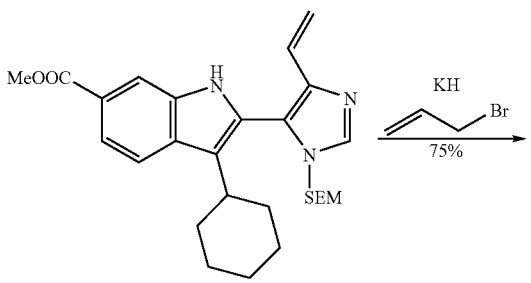

To a solution of 1H-indole-6-carboxylic acid, 3-cyclohexyl-2-[4-ethenyl-1-[[2-(trimethylsilyl)ethoxy]methyl]-

1H-imidazol-5-yl]-, methyl ester (168 mg, 0.35 mmol) in dry DMF (2.5 mL) was added KH (30% in oil, 0.4 mmol, 55 mg) proportion-wise at RT. The mixture was stirred at RT for 10 min until no further effervescence was observed. Allyl bromide (24 mg, 2.0 mmol) was then added and the resulting mixture stirred at RT for 20 min. Methylene chloride (5 mL) was added and the resultant solution was washed with 1N HCl (3×5 mL), dried (Na$_2$SO$_4$), filtered and evaporated to give a residue. Flash chromatography on silica gel (CH$_2$Cl$_2$-EtOAc 10:1) afforded 136 mg (75%) of the title compound as a white crystalline solid. $^1$H NMR (500 MHz, CDCl$_3$) δ 0.00 (s,9H), 0.84 (t, 2H, J=8.5), 1.20–1.90 (10 H), 2.48 (m, 1H), 3.45–3.50 (m, 2H), 3.94 (s, 3H), 4.20 (dd, 1H, J=5.0, 14.0), 4.48 (dd, 1H, J=6.0, 14.0), 4.89 (dd, 1H, J=1.0, 17.0), 4.97 (s, 2H), 5.06 (d, 1H, J=10.5), 5.11 (dd, 1H, J=1.5, 11.0), 5.70–5.80 (m, 1H), 5.83 (dd, 1H, J=1.5, 17.5), 6.27 (dd, 1H, J=11.0, 17.5), 7.78 (s, 1H), 7.79 (dd, 1H, J=1.5, 8.5), 7.83 (d, 1H, J=8.5), 8.07 (s, 1H).

Imidazo[4',5':3,4]azepino[1,2-a]indole-9-carboxylic acid, 12-cyclohexyl-1-[[2-(trimethylsilyl)ethoxy]methyl]-, methyl ester To a solution of 1H-indole-6-carboxylic acid, 3-cyclohexyl-2-[4-ethenyl-1-[[2-(trimethylsilyl)ethoxy]methyl]-1H-imidazol-5-yl]-1-(2-propenyl)-, methyl ester (136 mg, 0.26 mmol) in CH$_2$Cl$_2$ (20 mL) was added Grubbs catalyst (2$^{nd}$ generation, 22 mg, 0.026 mmol). The resulting solution was heated under reflux for 8 h. The solvent was removed in vacuo, and the residue purified by flash chromatography on silica gel (CH$_2$Cl$_2$-EtOAc 10:1) to give 82 mg (64%) of the title compound. $^1$H NMR (500 MHz, CDCl$_3$) δ −0.15 (s,9H), 0.77 (t, 2H, J=8.5), 1.20–2.10 (9 H), 2.15–2.30 (m, 1H), 2.47 (br t, 1H, J=12.0), 3.25–3.35 (m, 2H), 3.94 (s, 3H), 4.10 (ddd, 1H, J=1.5, 5.0, 10.0), 5.06 (dd, 1H, J=7.5, 14.5), 5.35 (d, 1H, J=10.5), 5.55 (d, 1H, J=10.5), 6.08 (m, 1H), 6.89 (d, 1H, J=10.0), 7.73 (dd, 1H, J=1.0, 8.5), 7.84 (d, 1H, J=8.5), 7.90 (s, 1H), 8.14 (s, 1H).

Imidazo[4',5':3,4]azepino[1,2-a]indole-9-carboxylic acid, 12-cyclohexyl-1,4,5,6-tetrahydro-1-[[2-(trimethylsilyl)ethoxy]methyl]-, methyl ester

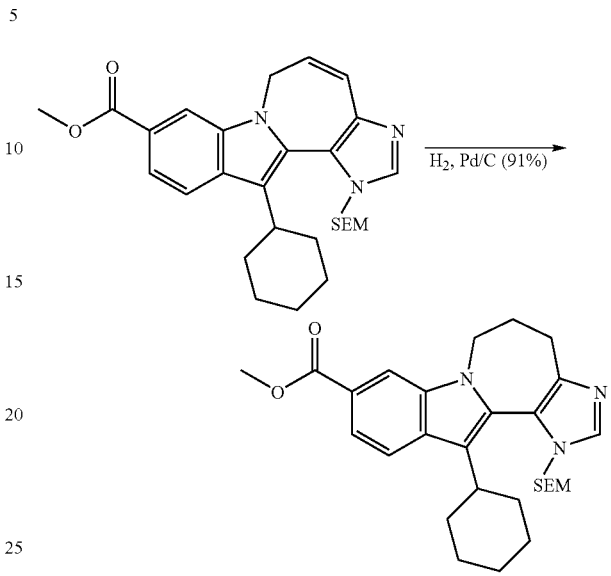

Imidazo[4',5':3,4]azepino[1,2-a]indole-9-carboxylic acid, 12-cyclohexyl-1-[[2-(trimethylsilyl)ethoxy]methyl]-, methyl ester from the previous step was dissolved in methanol (5 mL). Triethylamine (0.15 mL) was added, followed by Pd—C (10%, 15 mg). The resulting mixture was stirred at RT under a hydrogen (1 atm) for 2 h. The catalyst was then removed by filtration and the filtrate evaporated to give 80 mg (100%) of the title compound as a white foam. $^1$H NMR (500 MHz, CDCl$_3$) δ −0.13 (s,9H), 0.77 (t, 2H, J=8.5), 1.20–2.30 (12 H), 2.59 (br tt, 1H, J=1.5, 12.0), 2.70–2.80 (m, 1H), 2.90–3.00 (m, 1H), 3.20–3.30 (m, 1H), 3.30–3.40 (m, 1H), 3.75 (dt 1H, J=4.5, 14.5), 3.94 (s, 3H), 5.25 (d, 1H, J=10.5), 5.40 (d, 1H, J=10.5), 7.74 (dd, 1H, J=1.0, 8.5), 7.77 (s, 1H), 7.84 (d, 1H, J=8.5), 8.02 (s, 1H).

Imidazo[4',5':3,4]azepino[1,2-a]indole-9-carboxylic acid, 12-cyclohexyl-1,4,5,6-tetrahydro-

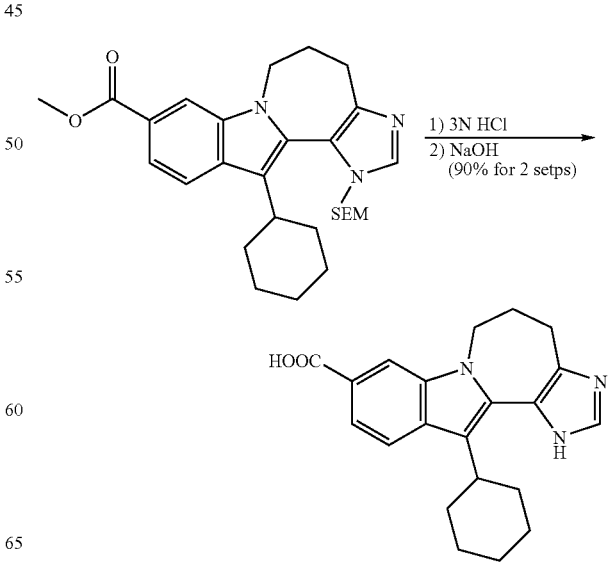

To a solution of imidazo[4',5':3,4]azepino[1,2-a]indole-9-carboxylic acid, 12-cyclohexyl-1,4,5,6-tetrahydro-1-[[2-(trimethylsilyl)ethoxy]methyl]-, methyl ester (5 mg) in methanol (0.5 mL) was added 3N HCl (0.5 mL). The mixture was heated to 65° C. for 8 h. Ethyl acetate (1 mL) was added, followed by water (2 mL). The pH of the aqueous layer was adjusted with solid NaHCO₃ to pH=5. The organic layer was separated and the aqueous layer re-extracted with EtOAc (2×1 mL). The combined extracts were dried (Na₂SO₄), filtered and evaporated to give a deprotected mixture of methyl ester and acid. This mixture was then dissolved in methanol (0.5 mL) and NaOH (3N, 0.5 mL) was added. The solution was heated to 50° C. for 1h. Ethyl acetate (2 mL) was added, followed by water (2 mL). The pH of the aqueous layer was adjusted to 5–6 with solid citric acid. The organic phase was separated and the aqueous phase re-extracted with EtOAc (2×1 mL). The combined extracts were dried (Na₂SO₄), filtered and evaporated to give 3 mg (90%) of the title compound. ¹H NMR (500 MHz, MeOD) δ 1.20–2.10 (m, 10 H), 2.20–2.30 (m, 2H), 3.05 (t, 2H, J=7.0), 3.62 (br t, 1H, J=12.5), 4.30 (m, 2H), 7.67 (dd, 1H, J=1.5, 8.5), 7.84 (d, 1H, J=8.5), 7.86 (s, 1H), 8.11 (s, 1H).

Imidazo[4',5':3,4]azepino[1,2-a]indole-9-carboxylic acid, 12-cyclohexyl-1,4,5,6-tetrahydro-1-[[2-(trimethylsilyl)ethoxy]methyl]-

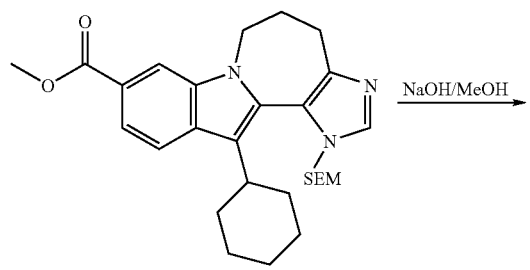

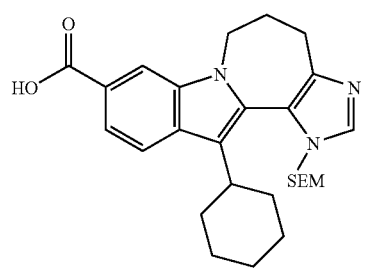

Imidazo[4',5':3,4]azepino[1,2-a]indole-9-carboxylic acid, 12-cyclohexyl-1,4,5,6-tetrahydro-1-[[2-(trimethylsilyl) ethoxy]methyl]-, methyl ester (20 mg, 0.040 mmol) was dissolved in MeOH (1 mL) and aqueous NaOH (6N, 1 mL) was added. The resulting mixture was stirred at 45° C. for 1 h. Methylene chloride was added, followed by water(2 mL). The pH of the aqueous layer was adjusted to 4–5 with solid citric acid. The organic layer was separated and the aqueous layer extracted with CH₂Cl₂ (2 mL). The combined organic layers were dried (Na₂SO₄), filtered and evaporated to give 19.5 mg (100%) of the title compound as a white solid, which was pure enough for use in subsequent steps. 1H NMR (500 MHz, CDCl₃) δ −0.13 (s,9H), 0.77 (t, 2H, J=8.5), 1.20–2.40 (12 H), 2.60 (br t, 1H, J=12.5), 2.70–2.80 (br s, 1H), 3.00–3.10 (br s, 1H), 3.31 (q, 1H, J=8.5), 3.40 (q, 1H, J=8.5), 3.78 (br t, 1H, J=14.5), 4.53 (br d, 1H, J=14.5), 5.32 (d, 1H, J=10.5), 5.45 (d, 1H, J=10.5), 7.85 (dd, 1H, J=1.0, 8.5), 7.89 (d, 1H, J=8.5), 8.02 (br s, 1H), 8.19 (s, 1H).

2-propenoic acid, 3-[4-[[[1-[[[12-cyclohexyl-1,4,5,6-tetrahydro-1-[[2-(trimethylsilyl)ethoxy]methyl] imidazo[4',5':3,4]azepino[1,2-a]indol-9-yl]carbonyl] amino]cyclopentyl]carbonyl]amino]phenyl]-, methyl ester, (2E)-

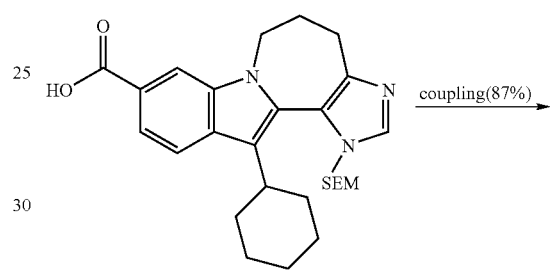

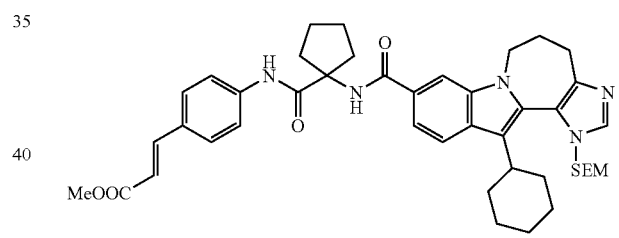

Imidazo[4',5':3,4]azepino[1,2-a]indole-9-carboxylic acid, 12-cyclohexyl-1,4,5,6-tetrahydro-1-[[2-(trimethylsilyl) ethoxy]methyl]- (19.5 mg, 0.40 mmol) and TBTU (25 mg, 0.08 mmol) was dissolved in DMSO (1 mL). Diisopropyl-ethyl amine (21 uL, 0.12 mmol) was added and the mixture was stirred at RT for 5 min. Then (E)-methyl 3-(4-(1-aminocyclopentanecarboxamido)phenyl)acrylate (20 mg, 0.07 mmol) was added and the solution was stirred at RT overnight. Methylene chloride (3 mL) was added and the solution was washed with aqueous HCl (0.5N, 2×3 mL), dried (Na₂SO₄) and evaporated to give a residue. Flash chromatography on silica gel (EtOAc-CH₂Cl₂ 1:1, then MeOH) afforded 26 mg (87%) of the title compound as a white solid. ¹H NMR (500 MHz, CDCl₃) δ −0.13 (s,9H), 0.77 (t, 2H, J=8.5), 1.20–2.65 (21 H), 2.65–2.75 (m, 1H), 2.90–3.00 (m, 1H), 3.26 (q, 1H, J=8.5), 3.36 (q, 1H, J=8.5), 3.75 (br t, 1H, J=14.5), 3.77 (s, 3H), 4.47 (br d, 1H, J=14.5), 5.26 (d, 1H, J=10.5), 5.39 (d, 1H, J=10.5), 6.33 (d, 1H, J=16.0), 6.57 (s, 1H, NH), 7.35 (dd, 1H, J=1.0, 8.5), 7.45 (d, 2H, J=8.5), 7.61 (d, 2H, J=8.5), 7.61 (d, 1H, J=16.0), 7.79 (s, 1H), 7.85 (d, 1H, J=8.5), 7.96 (s, 1H).

2-propenoic acid, 3-[4-[[[1-[[(12-cyclohexyl-1,4,5,6-tetrahydroimidazo[4',5':3,4]azepino[1,2-a]indol-9-yl)carbonyl]amino]cyclopentyl]carbonyl]amino]phenyl]-, methyl ester, (2E)- mg (32%) of deproteced compound as a white solid. $^1$H NMR (500 MHz, CDCl$_3$) δ 1.20–2.75 (m, 18H), 2.50–2.60 (m, 2H), 3.00–3.10 (br s, 2H), 3.78 (s, 3H), 4.00 (br s, 1H), 4.26 (m, 2H), 6.33 (d, 1H, J=16.0), 6.43 (br s, 1H, NH), 7.26 (br d, 1H, J=8.5), 7.46 (d, 2H, J=8.5), 7.61 (d, 1H, J=16.0),

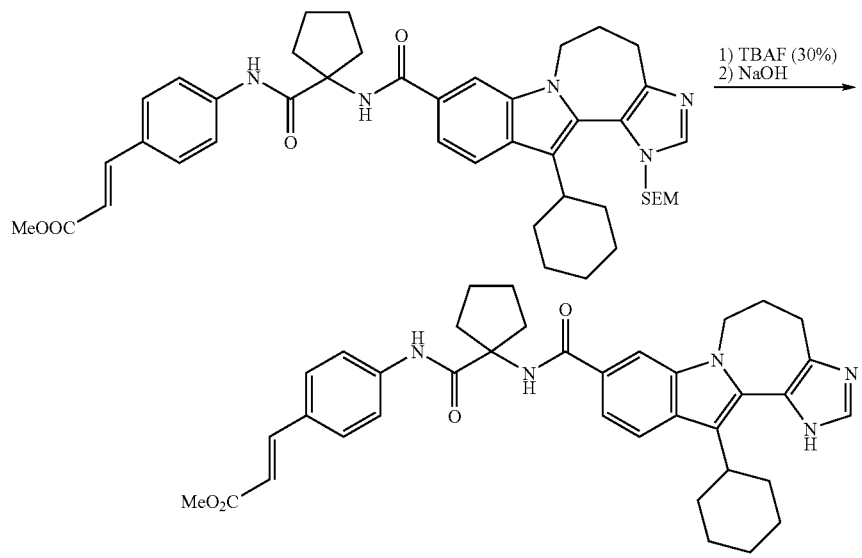

2-propenoic acid, 3-[4-[[[1-[[(12-cyclohexyl-1,4,5,6-tetrahydro-1-[[2-(trimethylsilyl)ethoxy]methyl]-imidazo[4',5':3,4]azepino[1,2-a]indol-9-yl)carbonyl]amino]cyclopentyl]carbonyl]amino]phenyl]-, methyl ester, (2E)- (26 mg, 0.035 mmol) was dissolve in a solution of TABF (1M in THF, 1.0 mL). The solution was stirred at 60 for 1 h. Methylene chloride (2 mL) was added and the solution was washed with aqueous NaHCO$_3$ (0.1N), dried (Na$_2$SO$_4$) and evaporated to give a dark residue. Recrystalization form methanol gave 7.0

7.62 (d, 2H, J=8.5), 7.73 (br s, 1H), 7.83 (br d, 1H, J=8.5), 7.91 (br s, 1H).

2-propenoic acid, 3-[4-[[[1-[[(12-cyclohexyl-1,4,5,6-tetrahydroimidazo[4',5':3,4]azepino[1,2-a]indol-9-yl)carbonyl]amino]cyclopentyl]carbonyl]amino]phenyl]-, (2E)-

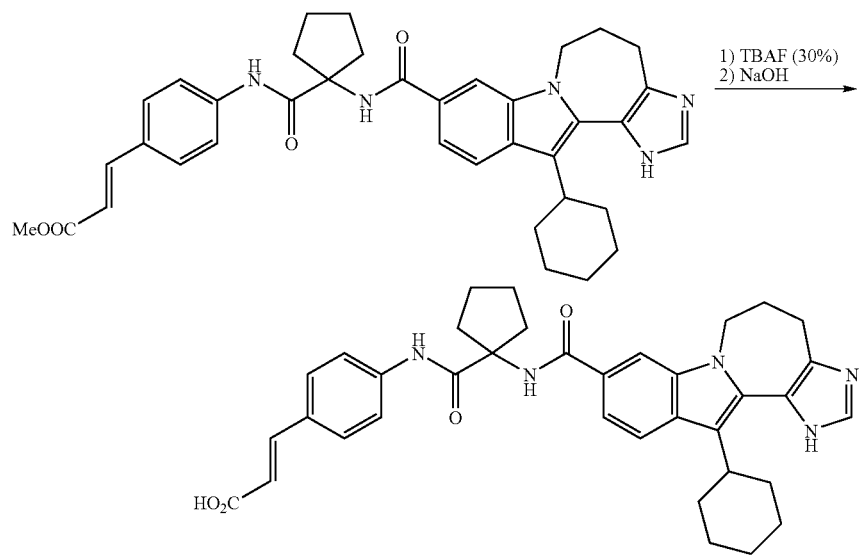

2-propenoic acid, 3-[4-[[[1-[[(12-cyclohexyl-1,4,5,6-tetrahydroimidazo[4',5':3,4]azepino[1,2-a]indol-9-yl)carbonyl]amino]cyclopentyl]carbonyl]amino]phenyl]-, methyl ester, (2E)- (5.0 mg) was dissolve in methanol (0.5 mL). Aqueous NaOH (6N, 0.3 mL) was added and the solution was stirred at RT for 2 h. Ethyl acetate (2 mL) was added and the pH of the aqueous layer was adjusted to 5 with solid citric acid. The organic phase was separated, dried (Na$_2$SO$_4$) and evaporated to give 3.5 mg (70%) of the title acid. $^1$H NMR (500 MHz, MeOD) δ 1.40–2.55 (18 H), 2.45–2.55 (m, 2H), 3.05 (t, 2H, J=7.0), 3.68 (br m, 1H), 4.28–4.35 (m, 2H), 6.42 (d, 1H, J=16.0), 7.48–7.62 (m, 6H), 7.78 (s, 1H), 7.86 (d, 1H, J=8.5), 8.03 (s, 1H).

Examples of some of the methods that can be used to prepare some fused pyrazine derivatives of formula I are outlined in the scheme below.

-continued

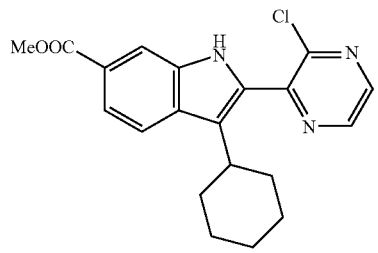

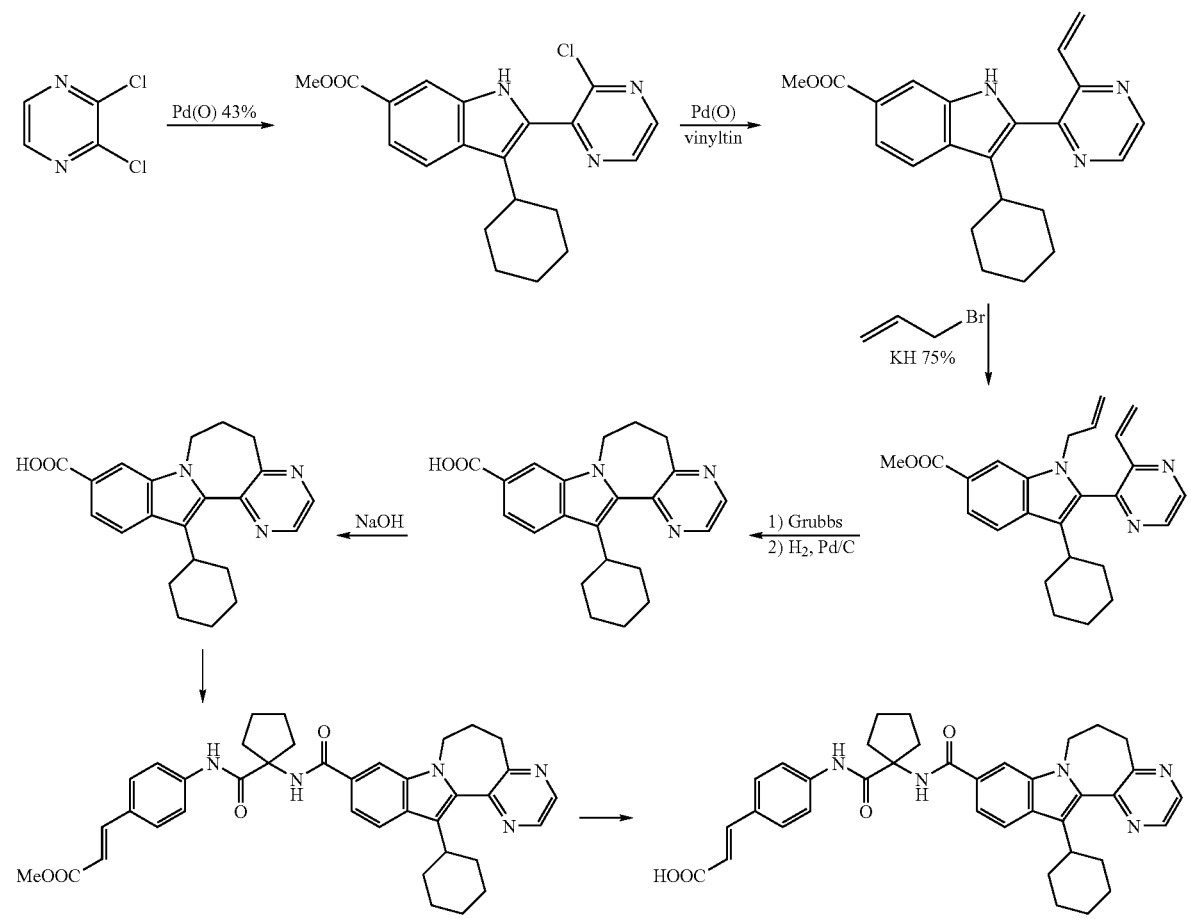

1H-indole-6-carboxylic acid, 2-(3-chloropyrazinyl)-3-cyclohexyl-, methyl ester

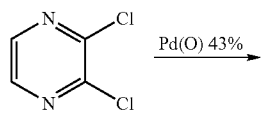

1H-indole-6-carboxylic acid, 3-cyclohexyl-2-(4,4,5,5-tetramethyl-1,3,2-dioxaborolan-2-yl)-, methyl ester (383 mg, 1.0 mmol), 2,3-dichloropyrazine (298 mg, 2.0 mmol) and LiCl (84 mg, 2.0 mmol) were dissolved in a mixture of ethanol (4 mL) and toluene (4 mL). An aqueous Na$_2$CO$_3$ solution (1M, 2.5 mL, 2.5 mmol) was added and the mixture was degassed with nitrogen for 20 min. Pd(PPh$_3$)$_4$ (11.5 mg, 0.1 mmol) was added and the mixture was stirred at 60° C. under N$_2$ for 20 h. EtOAc (10 mL) was added, followed by 25 mL of water. The organic layer was separated, dried (Na$_2$SO$_4$), filtered and evaporated under reduced pressure to give a residue. This material was fractionated using flash chromatography on silica gel (CH$_2$Cl$_2$-EtOAc 10:1) to afford 160 mg (43%) of the title compound as a foam. ¹H NMR (500 MHz, CDCl₃) δ 1.20–2.00 (m, 10H), 2.88 (m, 1H), 3.94 (s, 3H), 7.79 (dd, 1H, J=1.5, 8.5), 7.91 (d, 1H, J=8.5), 8.14 (d, 1H, J=1.5), 8.41 (d, 1H, J=2.5), 8.60 (br s, 1H, NH), 8.63 (d, 1H, J=2.5).

1H-indole-6-carboxylic acid, 3-cyclohexyl-2-(3-methylpyrazinyl)-, methyl ester

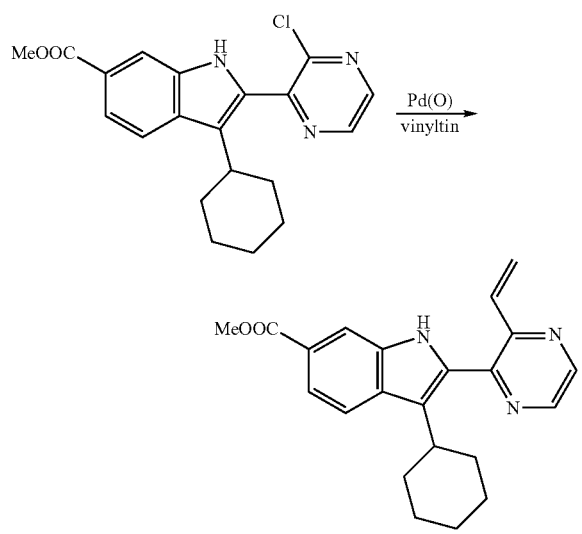

To a solution of 1H-indole-6-carboxylic acid, 2-(3-chloropyrazinyl)-3-cyclohexyl-, methyl ester (160 mg, 0.43 mmol) in DMF (2.0 mL) was added tributyl(vinyl)tin (190 mg, 0.6 mmol), LiCl (50 mg, 1.2 mmol), and PdCl₂ (PPh₃)₂ (140 mg, 0.02 mmol, 5 mmol %). The mixture was stirred at 85° C. for 2 h under nitrogen. Ethyl acetate (5 mL) was added, followed by 10 mL of water. The organic phase was separated, dried (Na₂SO₄), filtered and evaporated to give a dark residue. This material was fractionated using flash chromatography on silica gel (CH₂Cl₂-EtOAc 10:1) to afford 46 mg (29%) of the title compound. ¹H NMR (500 MHz, CDCl₃) δ 1.20–2.00 (m, 10H), 2.64 (tt, 1H, J=3.5, 12.0), 3.91 (s, 3H), 5.54 (dd, 1H, J=1.5, 17.0), 6.82 (dd, 1H, J=8.5, 17.0), 7.75 (dd, 1H, J=1.0, 8.5), 7.85 (d, 1H, J=8.5), 8.09 (s, 1H), 8.49 (d, 1H, J=2.0), 8.55 (d, 1H, J=2.0), 9.02 (s, 1H, NH).

1H-indole-6-carboxylic acid, 3-cyclohexyl-2-(3-ethenylpyrazinyl)-1-(2-propenyl)-, methyl ester

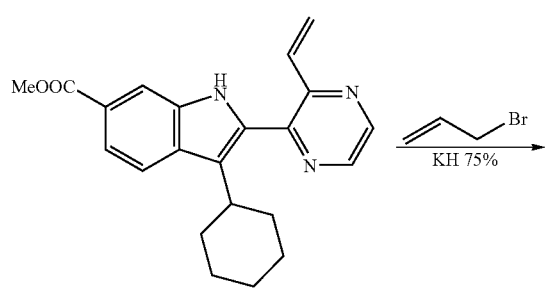

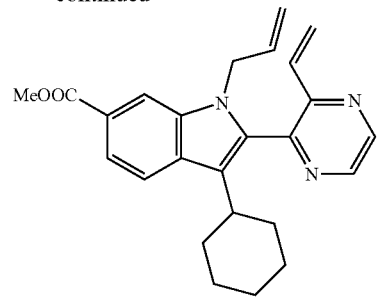

To a solution of 1H-indole-6-carboxylic acid, 3-cyclohexyl-2-(3-methylpyrazinyl)-, methyl ester (46 mg, 0.13 mmol) in dry DMF (2.0 mL) was added KH (30% in oil, 0.2 mmol, 26 mg) proportion wise at RT. The mixture was stirred at RT for 10 min until no more effervescence was observed. Allyl bromide (20 mg, 2.0 mmol) was added, and the resulting mixture stirred at RT for 20 min. Methylene chloride (5 mL) was then added and the solution washed with 1N HCl (3×5 mL), dried (Na₂SO₄), filtered and evaporated to give a residue. This was fractionated using flash chromatography on silica gel (EtOAc-hexane 1:3) to afford 38 mg (75%) of the title compound as a light yellow oil. ¹H NMR (500 MHz, CDCl₃) δ 1.10–1.90 (m, 10H), 2.43 (m, 1H), 3.94(s, 3H), 4.54 (dd, 1H, J=4.5, 10.5), 4.63 (d, 1H, J=6.0, 10.5), 4.76 (d, 1H, J=17.0), 4.95 (d, 1H, J=5.5), 5.50 (dd, 1H, J=2.0, 10.5), 5.65–5.75 (m, 1H), 6.51 (dd, 1H, J=2.0, 17.0), 6.62 (dd, 1H, J=10.5, 17.0), 7.80 (dd, 1H, J=1.0, 8.5), 7.84 (d, 1H, J=8.5), 8.10 (s, 1H), 8.60 (d, 1H, J=2.0), 8.63 (d, 1H, J=2.0).

5H-pyrazino[2',3':3,4]azepino[1,2-a]indole-10-carboxylic acid, 13-cyclohexyl-, methyl ester

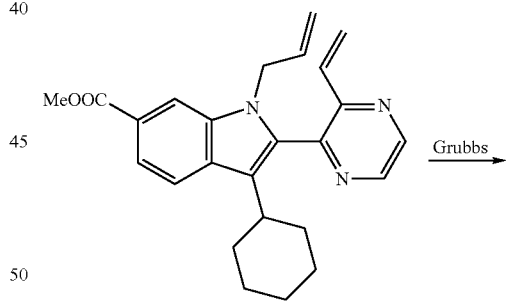

To a solution of 1H-indole-6-carboxylic acid, 3-cyclohexyl-2-(3-ethenylpyrazinyl)-1-(2-propenyl)-, methyl ester (38 mg, 0.095 mmol) in CH₂Cl₂ (6 mL) was added Grubbs catalyst (2ⁿᵈ generation, 8 mg, 0.0095 mmol). The resulting solution was heated to reflux for 4 h. Solvents was removed and the residue was purified by flash chromatography on silica gel (Hexane-EtOAc 3:1) gave 37 mg (100%) of cyclic compound. $^1$H NMR (500 MHz, CDCl$_3$) δ 1.20–2.10 (m, 10H), 3.20 (tt, 1H, J=3.5, 12.0), 3.96 (s, 3H), 4.70 (d, 2H, J=7.0), 6.60–6.70 (m, 1H), 6.96 (d, 1H, J=11.0), 7.75 (dd, 1H, J=1.0, 8.5), 7.95 (d, 1H, J=8.5), 8.17 (s, 1H), 8.58 (d, 1H, J=2.0), 8.63 (d, 1H, J=2.0).

5H-pyrazino[2',3':3,4]azepino[1,2-a]indole-10-carboxylic acid, 13-cyclohexyl-6,7-dihydro-, methyl ester

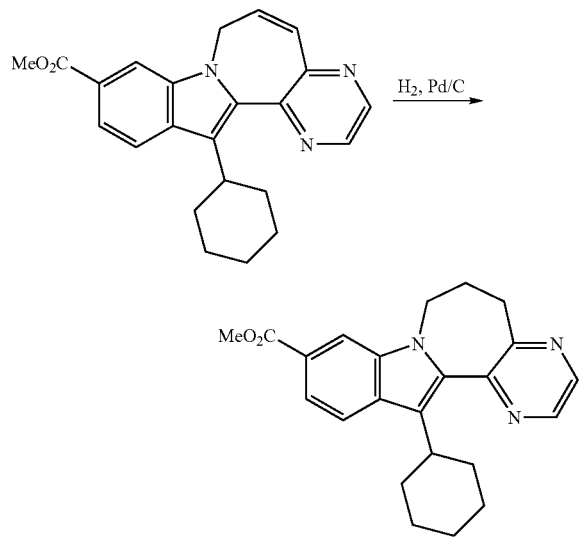

5H-pyrazino[2',3':3,4]azepino[1,2-a]indole-10-carboxylic acid, 13-cyclohexyl- (37 mg, 0.095 mmol) was dissolved in a mixture of ethyl acetate (1 mL) and methanol (1 mL). Pd—C (10%, 7 mg) was added and the resulting mixture was stirred at RT under hydrogen (1 atm) for 1 h. Catalyst was filtered off and the filtration was evaporated to give 30 mg (81%) of the title compound. $^1$H NMR (500 MHz, CDCl$_3$) δ 1.20–2.00 (m, 10H), 2.41 (m, 2H), 2.90 (t, 2H, J=7.0), 3.23 (tt, 1H, J=3.0, 12.0), 3.95 (s, 3H), 4.15 (t, 2H, J=6.0), 7.76 (dd, 1H, J=1.0, 8.5), 7.92 (d, 1H, J=8.5), 8.11 (s, 1H), 8.45 (d, 1H, J=2.0), 8.61 (d, 1H, J=2.0).

5H-pyrazino[2',3':3,4]azepino[1,2-a]indole-10-carboxylic acid, 13-cyclohexyl-6,7-dihydro-

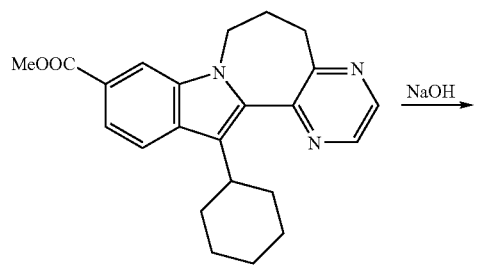

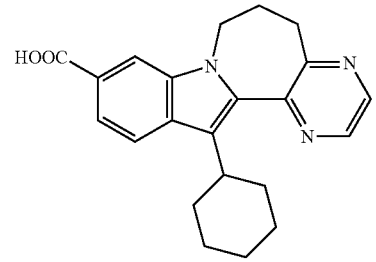

To a solution of 5H-pyrazino[2',3':3,4]azepino[1,2-a]indole-10-carboxylic acid, 13-cyclohexyl-6,7-dihydro-, methyl ester (30 mg, 0.08 mmol) in methanol (1.0 mL) was added aqueous NaOH (6N, 0.5 mL). The solution was heated to 50° C. for 1 h. Ethyl acetate (2 mL) was added, followed by water (2 mL). The pH of aqueous layer was adjusted to 5–6 with solid citric acid. Organic phase was separated and aqueous phase was extracted with EtOAc (2×2 mL). The combined organic phased were dried (Na$_2$SO$_4$) and evaporated to give 29 mg (100%) of the title compound, which was pure enough for the next step. $^1$H NMR (500 MHz, CDCl$_3$) δ 1.30–2.00 (m, 10H), 2.44 (t, 2H, J=7.0), 2.93 (t, 2H, J=7.0), 3.24 (t, 1H, J=11.5), 4.17 (t, 2H, J=6.5), 7.85 (d, 1H, J=8.5), 7.97 (d, 1H, J=8.5), 8.12 (s, 1H), 8.48 (d, 1H, J=2.5), 8.64 (d, 1H, J=2.5).

2-propenoic acid, 3-[4-[[[1-[[(13-cyclohexyl-6,7-dihydro-5H-pyrazino[2',3':3,4]azepino[1,2-a]indol-10-yl)carbonyl]amino]cyclopentyl]carbonyl]amino]phenyl]-, methyl ester, (2E)-

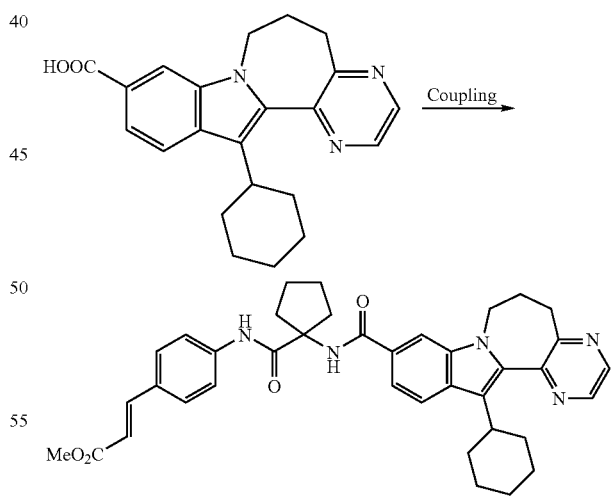

To a solution of the acid (12 mg, 0.033 mmol) in DMSO (1 mL) was added TBTU (16 mg, 0.05 mmol), followed by diisopropylethyl amine (17 uL, 0.1 mmol). The mixture was stirred at RT for 5 min. Then side-chain amine (13 mg, 0.045 mmol) was added and the solution was stirred at RT overnight. Methylene chloride (3 mL) was added and the solution was washed with aqueous HCl (0.5N, 2×3 mL), dried (Na$_2$SO$_4$) and evaporated to give a residue. Flash chromatography on silica gel (EtOAc-CH$_2$Cl$_2$ 2:5) afforded 13 mg (62%) of methyl ester as a white solid. $^1$H NMR (500 MHz, CDCl$_3$) δ 1.30–2.00 (m, 14H), 2.20–2.30 (m, 2H), 2.35–2.45 (m, 2H), 2.50–2.60 (m, 2H), 2.90 (t, 2H, J=7.0), 3.22 (t, 1H, J=11.5), 3.78 9s, 3H), 4.16 (t, 2H, J=6.5), 6.35 (d, 1H, J=16.0), 6.48 (s, 1H, NH), 7.34 (d, 1H, J=8.5), 7.47 (d, 2H, J=8.5), 7.60–7.65 (m, 3H), 7.94 (d, 1H, J=8.5), 7.98 (s, 1H), 8.46 (d, 1H, J=2.5), 8.62 (d, 1H, J=2.5).

2-propenoic acid, 3-[4-[[[1-[[(13-cyclohexyl-6,7-dihydro-5H-pyrazino[2',3':3,4]azepino[1,2-a]indol-10-yl)carbonyl]amino]cyclopentyl]carbonyl]amino]phenyl]-, (2E)-

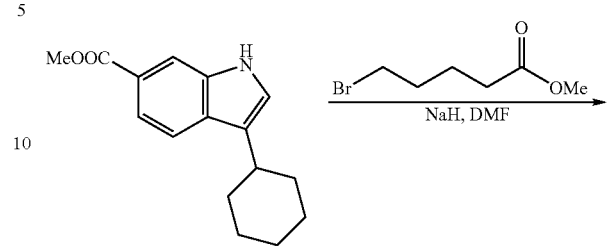

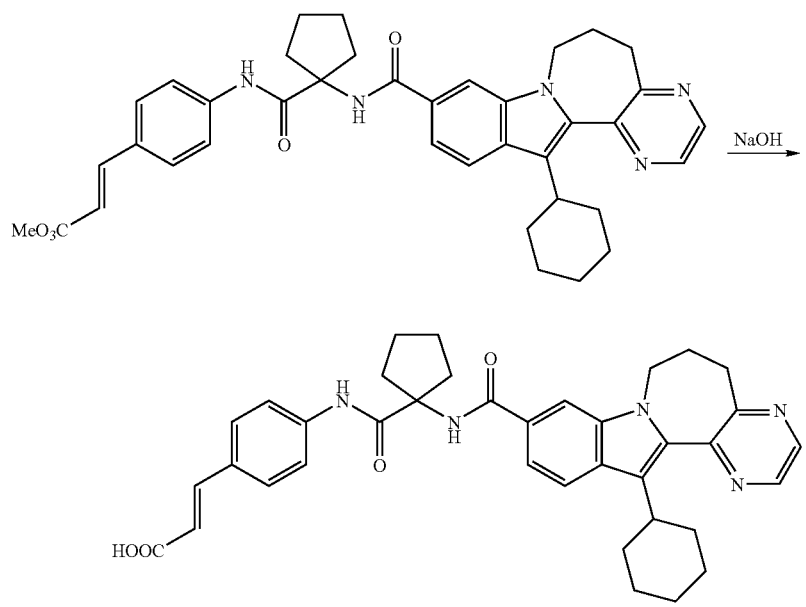

The 2-propenoic acid, 3-[4-[[[1-[[(13-cyclohexyl-6,7-dihydro-5H-pyrazino[2',3':3,4]azepino[1,2-a]indol-10-yl)carbonyl]amino]cyclopentyl]carbonyl]amino]phenyl]-, methyl ester, (2E)- (13 mg, 0.021 mmol) was dissolve in methanol (1.0 mL). Aqueous NaOH (6N, 0.5 mL) was added and the solution was stirred at RT for 2 h. Ethyl acetate (2 mL) was added and the pH of the aqueous layer was adjusted to 5 with solid citric acid. The organic phase was separated, dried (Na$_2$SO$_4$) and evaporated to give 9.0 mg (69%) of the title acid as a white solid. $^1$H NMR (300 MHz, MeOD) δ 1.30–2.60 (m, 20H), 2.87 (t, 2H, J=6.9), 3.28 (m, 1H), 4.16 (t, 2H, J=6.6), 6.43 (d, 1H, J=15.9), 7.40 (d, 1H, J=15.9), 7.47 (d, 2H, J=8.7), 7.58 (d, 2H, J=8.7), 7.63 (dd, 1H, J=1.2, 8.4), 7.95 (d, 1H, J=8.7), 8.15 (d, 1H, J=0.9), 8.49 (d, 1H, J=3.0), 8.68 (d, 1H, J=3.0).

Further examples of methods that can be used to prepare ring-fused five membered hetercocylic derivatives of the instant invention are outlined in the scheme below.

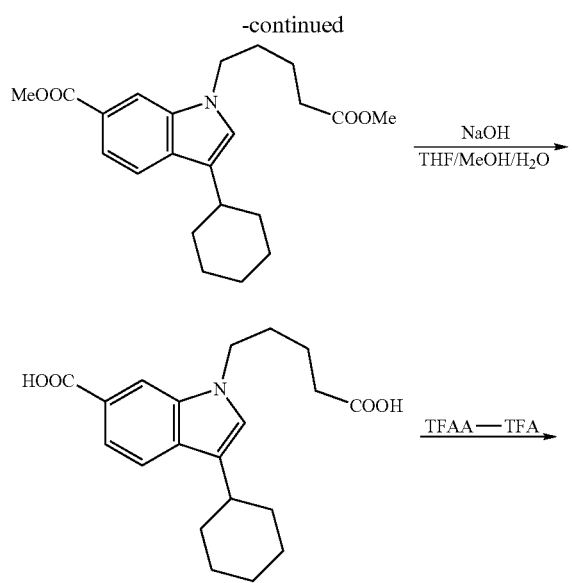

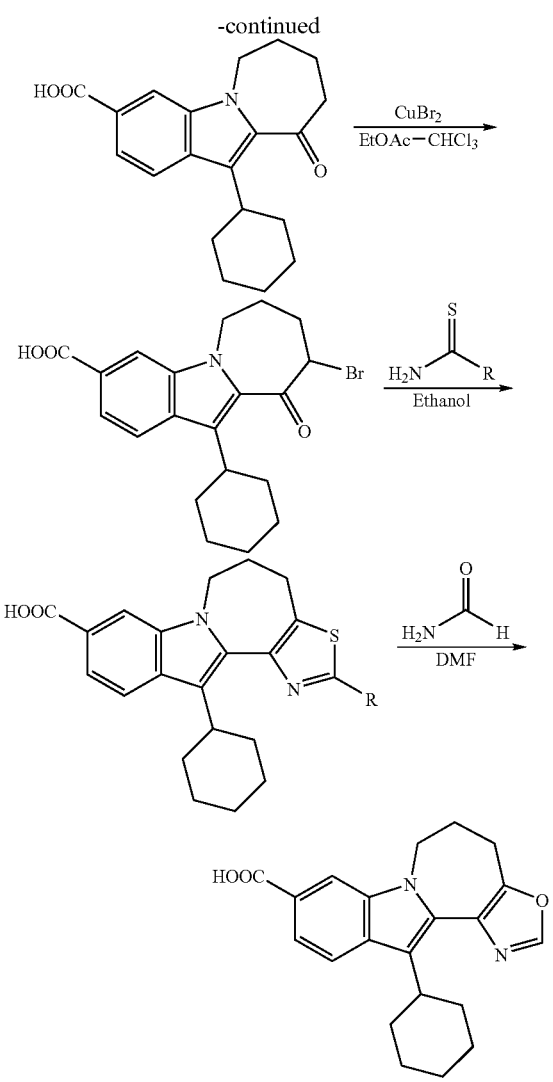

The synthesis of the required bromo ketone intermediate is described below. The target heterocycles are obtained by condensation of this compound with appropriate amide or thioamide derivatives.

Methyl 3-cyclohexyl-1-(5-methoxy-5-oxopentyl)-1H-indole-6-carboxylate

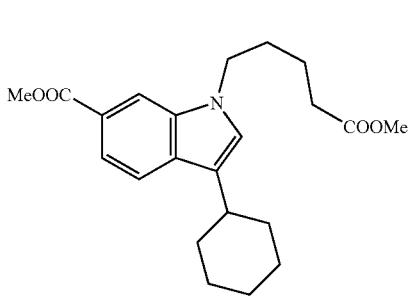

Methyl 3-cyclohexyl-1H-indole-6-carboxylate (500 mg, 1.94 mmol) was added to a suspension of NaH (85.5 mg of 60% dispersion in mineral oil, 2.14 mmol) in DMF (5 mL), and the reaction mixture stirred at RT for 15 min. Methyl 5-bromovalerate (0.305 mL, 2.14 mmol) was then added and the reaction mixture stirred at RT overnight, after which the reaction was quenched with ice and extracted with ethyl acetate (2×50 mL). The extracts were then combined, washed with 1N HCl solution, dried (MgSO$_4$), filtered and concentrated in vacuo. The residue was purified by silica gel flash chromatography using hexanes to 25% ethyl acetate in hexanes as eluant to give the title compound as a colorless thick oil (0.41 g, 57% yield). MS m/z 372(MH$^+$). $^1$H NMR (300 MHz, CDCl$_3$) □ ppm 1.23 (m, 1 H) 1.35–1.48 (m, 5 H) 1.62 (m, 2 H) 1.69–1.89 (m, 6 H) 2.03 (m, 2 H) 2.29 (t, J=7.32 Hz, 2 H) 2.78 (m, 1 H) 3.62 (s, 3 H) 3.90 (s, 3 H) 4.11 (t, J=6.95 Hz, 2 H) 6.97 (s, 1 H) 7.60 (d, J=8.42 Hz, 1 H) 7.72 (d, J=9.51 Hz, 1 H) 8.00 (s, 1 H).

1-(4-carboxybutyl)-3-cyclohexyl-1H-indole-6-carboxylic acid

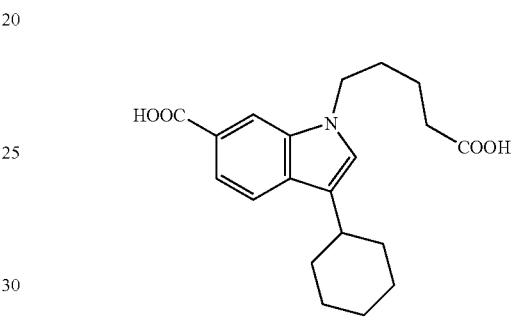

2N NaOH solution (2.0 mL) was added to a solution of methyl 3-cyclohexyl-1-(5-methoxy-5-oxopentyl)-1H-indole-6-carboxylate (410 mg, 1.1 mmol) in THF/Methanol mixture (2.0 mL/2.0 mL). The reaction mixture was heated at 100° C. under microwave condition for 15 min, after which it was concentrated and the pH was adjusted to 4–5 with 1N HCl solution. A precipitate formed which was collected by filtration to give the product as a white powder, (375 mg, 99% yield). MS m/z 344(MH$^+$). $^1$H NMR (300 MHz, CD$_3$OD) δ ppm 1.24–1.98 (m, 10 H) 2.00–2.15 (m, 2 H) 2.25–2.39 (m,2H) 2.84 (m, 1 H) 4.16–4.30 (m, 2 H) 4.56–4.72 (m, 2 H) 7.22 (m, 1H) 7.58–7.78 (m, 2H) 8.10 (m, 1H).

11-Cyclohexyl-10-oxo-7,8,9,10-tetrahydro-6H-azepino[1,2-a]indole-3-carboxylic acid

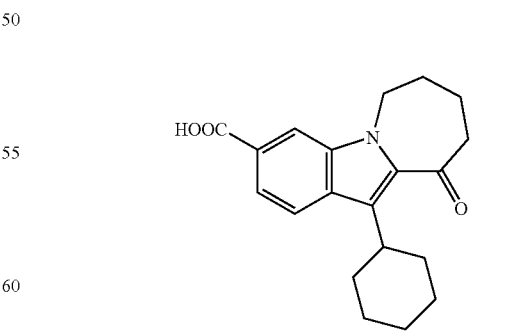

A mixture of TFA (1.0 mL) and TFAA (469 mg, 2.232 mmol) was added dropwise to 1-(4-carboxybutyl)-3-cyclohexyl-1H-indole-6-carboxylic acid (365 mg, 1.063 mmol) at 0° C. The reaction mixture was then warmed to rt. and stirred for 4 hr. Water was then added slowly to quench the reaction and a precipitate formed. This was collected by filtration to provide the product as a yellow-greenish solid, (410 mg, >100% yield). MS m/z 326(MH+); $^1$H NMR (500 MHz, CD$_3$OD) ☐ ppm 1.39–1.50 (m, 3 H) 1.73–2.14 (m, 11 H) 2.88 (m, 2 H) 3.45 (m, 1 H) 4.46 (m, 2 H) 7.73 (dd, J=8.54, 1.22 Hz, 1 H) 7.98 (d, J=8.55 Hz, 1 H) 8.21 (s, 1 H).

9-Bromo-11-cyclohexyl-10-oxo-7,8,9,10-tetrahydro-6H-azepino[1,2-a]indole-3-carboxylic acid

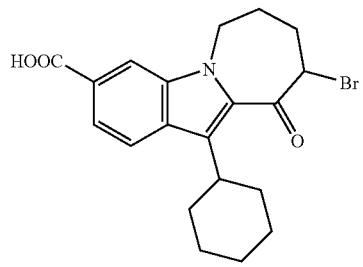

A solution of 11-cyclohexyl-10-oxo-7,8,9,10-tetrahydro-6H-azepino[1,2-a]indole-3-carboxylic acid (100 mg, 0.307 mmol) in chloroform (2.0 mL) was added to a refluxing suspension of CuBr$_2$ (103 mg, 0.461 mmol) in ethyl acetate (2.0 mL). The reaction mixture was heated under reflux for 4 h. It was then cooled and the salt was removed by filtration. The filtrate was concentrated in vacuo to provide the title compound as a dark-green solid, (120 mg, 97% yield). MS m/z 404,406 (MH+).

4H-Thiazolo[4',5':3,4]azepino[1,2-a]indole-9-carboxylic acid, 12-cyclohexyl-5,6-dihydro-2-methyl-

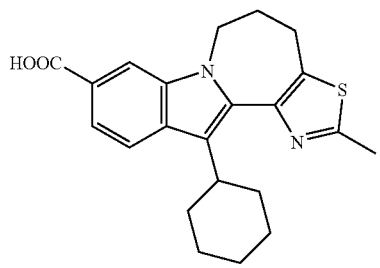

Thioacetamide (7.4 mg, 0.099 mmol) was added to a solution of 9-bromo-11-cyclohexyl-10-oxo-7,8,9,10-tetrahydro-6H-azepino[1,2-a]indole-3-carboxylic acid (40 mg, 0.099 mmol) in ethanol (3.0 mL). The reaction mixture was heated under reflux for 12 hr., after which the solvent was removed in vacuo and the residue suspended in water. A precipitate formed which was collected by filtration to provide the crude product as a greenish solid (30 mg, 80% yield). 8 mg of this crude product was subsequently fractionated by preparative reverse phase HPLC to afford the title compound as a light yellow colored solid. MS m/z 381(MH+); $^1$H NMR (500 MHz, CD$_3$OD) ☐ ppm 1.31 (m, 1 H) 1.40–1.47 (m, 3 H) 1.79–1.91 (m, 4 H) 2.00–2.09 (m, 2 H) 2.32–2.36 (m, 2 H) 2.77 (s, 3 H) 2.98 (t, J=7.17 Hz, 2 H) 3.41 (m, 1 H) 4.25 (d, J=6.10 Hz, 2 H) 7.72 (dd, J=8.39, 1.37 Hz, 1 H) 7.87 (d, J=8.55 Hz, 1 H) 8.15 (s, 1 H.)

4H-Thiazolo[4',5':3,4]-azepino[1,2-a]indole-9-carboxylic acid, 12-cyclohexyl-5,6-dihydro-2-amino-

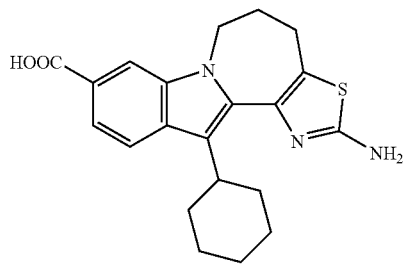

Thiourea (22.6 mg, 0.297 mmol) was added to a solution of 9-bromo-11-cyclohexyl-10-oxo-7,8,9,10-tetrahydro-6H-azepino[1,2-a]indole-3-carboxylic acid (100 mg, 0.247 mmol) in ethanol (5.0 mL). The reaction mixture was heated under reflux for 8 hr. The solvent was then removed in vacuo, and the residue suspended in water. A precipitate formed which was collected by filtration to provide the crude product as a yellow solid, (99 mg, 100% yield). 10 mg of this material was then purified by preparative reverse phase HPLC column to afford the TFA salt of the title compound as a light yellow solid. MS m/z 382 (MH+); $^1$H NMR (500 MHz, CD$_3$OD) ☐ ppm 1.32 (m, 1 H) 1.43–1.53 (m, 3 H) 1.79–1.94 (m, 4 H) 2.00–2.10 (m, 2 H) 2.29–2.35 (m, 2 H) 2.81 (t, J=7.17 Hz, 2 H) 3.06 (m, 1 H) 4.33 (t, J=5.95 Hz, 2 H) 7.74 (d, J=8.55 Hz, 1 H) 7.92 (d, J=8.54 Hz, 1 H) 8.17 (s, 1 H).

2-Propenoic acid, 3-[4-[[[1-[[(12-cyclohexyl-5,6-dihydro-2-methyl-4H-thiazolo[4',5':3,4]azepino[1,2-a]indol-9-yl)carbonyl]amino]cyclopentyl]carbonyl]-amino]phenyl]-, methyl ester, (2E)-

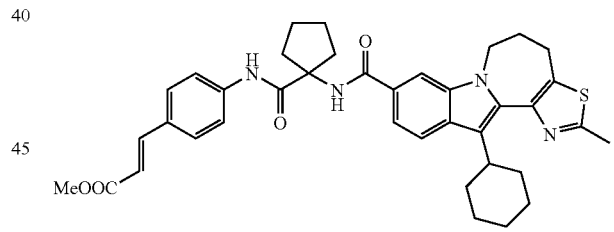

TBTU (27.8 mg, 0.087 mmol) was added to a solution of 4H-thiazolo[4',5':3,4]azepino[1,2-a]indole-9-carboxylic acid, 12-cyclohexyl-5,6-dihydro-2-methyl (22 mg, 0.058 mmol) and DIPEA (0.050 mL, 0.289 mmol) in DMSO (2.0 mL), The reaction mixture was stirred at rt for 15 min., after which (E)-methyl 3-(4-(1-aminocyclopentanecarboxamido) phenyl)acrylate (20 mg, 0.069 mmol) was added. The resultant mixture was stirred at rt overnight. It was then concentrated in vacuo and the residue purified by preparative reverse phase HPLC column to give the title compound as an off-white solid, (18 mg, 48% yield). MS m/z 651(MH+); $^1$H NMR (500 MHz, CDCl$_3$) ☐ ppm 1.32–1.47(m, 3 H) 1.74–2.01 (m, 11 H) 2.21–2.28 (m, 2 H) 2.28–2.35 (m, 2 H) 2.53–2.61 (m, 2 H) 2.74 (s, 3 H) 2.95 (t, J=7.32 Hz, 2 H) 3.44 (m, 1 H) 3.78 (s, 3 H) 4.20 (m, 2 H) 6.35 (d, J=15.87 Hz, 1 H) 6.42 (s, 1 H) 7.28 (m, 1 H) 7.47 (d, J=8.54 Hz, 2 H) 7.60–7.66 (m, 3 H) 7.88 (d, J=8.55 Hz, 1 H) 7.94 (s, 1 H) 10.40 (s, 1 H).

2-Propenoic acid, 3-[4-[[[1-[[(12-cyclohexyl-5,6-dihydro-2-methyl-4H-thiazolo[4',5':3,4]azepino[1,2-a]indol-9-yl)carbonyl]amino]cyclopentyl]carbonyl]amino]phenyl]-, (2E)-

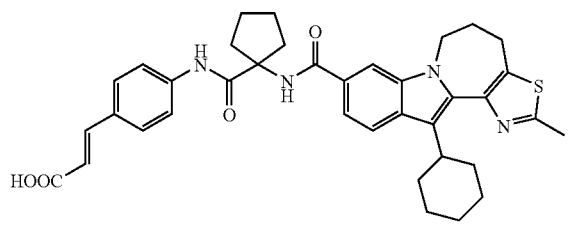

2N NaOH solution (0.5 mL) was added to a solution of 2-propenoic acid, 3-[4-[[[1-[[(12-cyclohexyl-5,6-dihydro-2-methyl-4H-thiazolo[4',5':3,4]azepino[1,2-a]indol-9-yl)carbonyl]amino]cyclopentyl]carbonyl]amino]phenyl]-, methyl ester, (2E)- (15 mg, 0.023 mmol) in a THF/Methanol mixture (2.0 mL/2.0 mL). The reaction mixture was heated at 100° C. under microwave conditions for 15 min. It was cooled, and concentrated in vacuo. The pH of the mixture was adjusted to 4–5 with 1N HCl solution, and then extracted with ethyl acetate. The extracts were combined, dried over MgSO₄, filtered and concentrated under vacuum. The crude yellow residue was then purified by preparative reverse phase. HPLC to afford the title compound as a yellow solid, (7.0 mg, 48% yield). MS m/z 637(MH⁺). ¹H NMR (500 MHz, CD₃OD) δ ppm 1.38–1.47 (m, 3 H) 1.78–1.95 (m, 9 H) 1.98–2.08 (m, 2 H) 2.16–2.24 (m, 2 H) 2.30–2.37 (m, 2 H) 2.45–2.55 (m, 2 H) 2.76 (s, 3 H) 2.97 (t, J=7.17 Hz, 2 H) 3.41 (m, 1 H) 4.25 (m, 2 H) 6.40 (d, J=15.87 Hz, 1 H) 7.52–7.66 (m, 6 H) 7.89 (d, J=8.55 Hz, 1 H) 8.07 (s, 1 H).

2-Propenoic acid, 3-[4-[[[1-[[(12-cyclohexyl-5,6-dihydro-2-amino-4H-thiazolo[4',5':3,4]azepino[1,2-a]indol-9-yl)carbonyl]amino]cyclopentyl]carbonyl]amino]phenyl]-, methyl ester, (2E)-

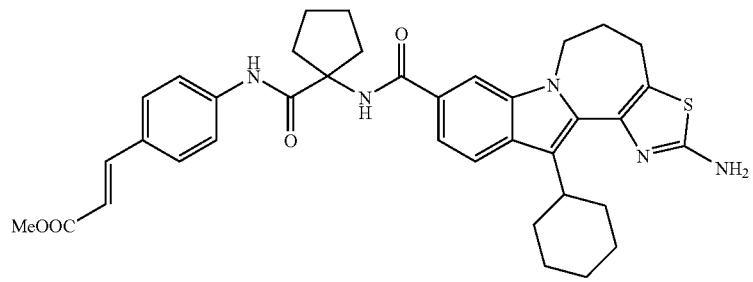

To a solution of 4H-thiazolo[4',5':3,4]azepino[1,2-a]indole-9-carboxylic acid, 12-cyclohexyl-5,6-dihydro-2-amino (17 mg, 0.045 mmol) in DMSO (2.0 mL), TBTU (21.5 mg, 0.067 mmol) and DIPEA (0.039 mL, 0.223 mmol) were added. The reaction mixture was stirred at rt for 15 min. Then (E)-methyl 3-(4-(1-aminocyclopentanecarboxamido)phenyl)acrylate (15.4 mg, 0.054 mmol) was added and the reaction mixture stirred at rt overnight. The reaction mixture was then concentrated in vacuo and the residue purified by preparative reverse phase HPLC column to give the title compound as to give the title compound as a yellow solid, (17 mg, 59% yield). MS m/z 652(MH⁺). ¹H NMR (300 MHz, CD₃OD) δ ppm 1.38–1.50 (m, 3 H) 1.74–2.09 (m, 11 H) 2.13–2.23 (m, 4 H) 2.44–2.55 (m, 2 H) 2.79 (t, J=7.14 Hz, 2 H) 3.45 (m, 1 H) 3.78 (s, 3 H) 4.26 (m, 2 H) 6.45 (d, J=16.10 Hz, 1 H) 7.52–7.68 (m, 6 H) 7.85 (d, J=8.42 Hz, 1 H) 8.03 (s, 1 H)

2-Propenoic acid, 3-[4-[[[1-[[(12-cyclohexyl-5,6-dihydro-2-amino-4H-thiazolo[4',5':3,4]azepino[1,2-a]indol-9-yl)carbonyl]amino]cyclopentyl]carbonyl]amino]phenyl]-, (2E)

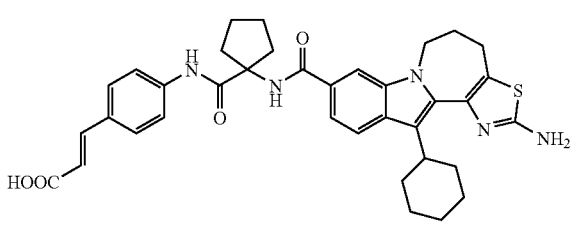

2N NaOH solution (1.0 mL) was added to a solution of 2-propenoic acid, 3-[4-[[[1-[[(12-cyclohexyl-5,6-dihydro-2-amino-4H-thiazolo[4',5':3,4]azepino[1,2-a]indol-9-yl)carbonyl]amino]cyclopentyl]carbonyl]amino]phenyl]-, methyl ester, (2E)- (15 mg, 0.023 mmol) in a THF/Methanol mixture (2.0 mL/2.0 mL). The reaction mixture was heated at 100° C. under microwave conditions for 15 min. It was then concentrated in vacuo, and the pH was adjusted to 4–5 by the addition of 1N HCl solution. The resultant mixture was then extracted with ethyl acetate and the organic layer was dried over MgSO₄.filtered, and evaporated under vacuum to give the crude product that was subsequently purified by Prep. Reverse phase HPLC to afford the TFA salt of the title compound as a yellow solid (5.2 mg, 30% yield). MS m/z 638(MH⁺); ¹H NMR (300 MHz, CD₃OD) δ ppm 1.40–1.53 (m, 3 H) 1.77–2.37 (m, 14 H) 2.44–2.56 (m, 2 H) 2.79 (t, J=7.32 Hz, 2 H) 2.97 (m, 1 H) 4.32 (m, 2 H) 6.40 (d, J=16.10 Hz, 1 H) 7.50–7.65 (m, 6 H) 7.93 (d, J=8.42 Hz, 1 H) 8.09 (s, 1 H) 9.66 (s, 1 H).

333

4H-Oxazolo[4',5':3,4]azepino[1,2-a]indole-9-carboxylic acid, 12-cyclohexyl-5,6-dihydro-

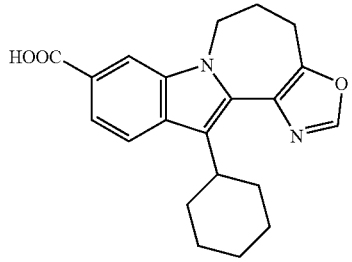

Formamide (2.0 mL) was added to a solution of 9-bromo-11-cyclohexyl-10-oxo-7,8,9,10-tetrahydro-6H-azepino[1,2-a]indole-3-carboxylic acid (30 mg, 0.0742 mmol) in DMF (1.0 mL). The reaction mixture was heated at 125° C. for 8 hr, after which it was cooled, water was added and the mixture was extracted with ethyl acetate (2×20 mL). The organic layers were combined, dried (MgSO$_4$), filtered and concentrated in vacuo. The residue was then purified by preparative reverse phase HPLC column to afford the title compound as an orange colored solid (3.5 mg, 13% yield). MS m/z 351(MH$^+$); $^1$H NMR (300 MHz, CD$_3$OD) δ ppm 1.31 (m, 1 H) 1.38–1.55 (m, 3 H) 1.79–1.93 (m, 4 H) 1.99–2.13 (m, 2 H) 2.19–2.29 (m, 2 H) 3.17 (t, J=6.77 Hz, 2 H) 4.03 (m, 1 H) 4.33–4.39 (m, 2 H) 7.67 (m, 1 H) 7.86 (d, J=8.42 Hz, 1 H) 8.12 (s, 1 H) 8.16 (s, 1 H)

2-Propenoic acid, 3-[4-[[[1-[[(12-cyclohexyl-5,6-dihydro-4H-oxazolo[4',5':3,4]azepino[1,2-a]indol-9-yl)carbonyl]amino]cyclopentyl]carbonyl]amino]phenyl]-, methyl ester, (2E)-

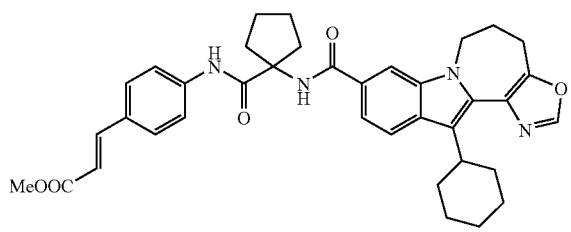

TBTU (20.6 mg, 0.064 mmol) was added to a solution of 4H-oxazolo[4',5':3,4]azepino[1,2-a]indole-9-carboxylic acid, 12-cyclohexyl-5,6-dihydro-(15 mg, 0.043 mmol) and DIPEA (0.037 mL, 0.214 mmol) in DMSO (2.0 mL). The reaction mixture was stirred at rt for 15 min., after which (E)-methyl 3-(4-(1-aminocyclopentanecarboxamido)phenyl)acrylate (14.8 mg, 0.051 mmol) was added and the reaction mixture was stirred at rt overnight. The resultant mixture was then concentrated in vacuo, and the residue purified by Prep. reverse phase HPLC column to give the title compound as a light yellow solid (12 mg, 45% yield). MS m/z 621(MH$^+$); $^1$H NMR (300 MHz, CDCl$_3$) ☐ ppm 1.12–2.08 (m, 14 H) 2.16–2.27 (m, 4 H) 2.48–2.62 (m, 2 H) 3.03–3.13 (m, 2 H) 3.76 (s, 3 H) 3.92 (m, 1 H) 4.24–4.32 (m, 2 H) 6.32 (d, J=16.47 Hz, 1 H) 6.38 (m, 1 H) 7.25 (m, 1 H) 7.44 (d, J=8.42 Hz, 2 H) 7.56–7.63 (m, 3 H) 7.84–7.98 (m, 3 H) 10.38 (s, 1 H).

334

2-Propenoic acid, 3-[4-[[[1-[[(12-cyclohexyl-5,6-dihydro-4H-oxazolo[4',5':3,4]azepino[1,2-a]indol-9-yl)carbonyl]amino]cyclopentyl]carbonyl]amino]phenyl]-, (2E)-

2N NaOH solution (0.5 mL) was added to a solution of 2-propenoic acid, 3-[4-[[[1-[[(12-cyclohexyl-5,6-dihydro-4H-oxazolo[4',5+:3,4]azepino[1,2-a]indol-9-yl)carbonyl]amino]cyclopentyl]carbonyl]amino]phenyl]-, methyl ester, (2E)- (10 mg, 0.016 mmol) in a THF/Methanol mixture (1.5 mL/1.0 mL). The reaction mixture was heated at 100° C. under microwave conditions for 15 min. It was then cooled, and concentrated in vacuo. The pH of the solution was then adjusted to 4–5 by the dropwise addition of 1N HCl solution. The resultant mixture was then extracted with ethyl acetate and the organic layer was dried with MgSO$_4$, filtered, and the solvent was evaporated under vacuum. The residue was then purified by Prep. reverse phase HPLC to afford the title compound as a light yellow solid, (2.5 mg, 26% yield). MS m/z 607(MH$^+$); $^1$H NMR (500 MHz, CD$_3$OD) δ ppm 1.40–1.54 (m, 3 H) 1.80–2.28 (m, 15 H) 2.46–2.54 (m, 2 H) 3.17 (t, J=6.87 Hz, 2 H) 4.02 (m, 1 H) 4.38 (m, 2 H) 6.41 (d, J=15.87 Hz, 1 H) 7.51–7.65 (m, 6 H) 7.89 (d, J=8.55 Hz, 1 H) 8.04 (s, 1 H) 8.16 (s, 1 H).

Examples of some of the methods that can be used to prepare some fused pyridine compounds of Formula I are outlined in the scheme below.

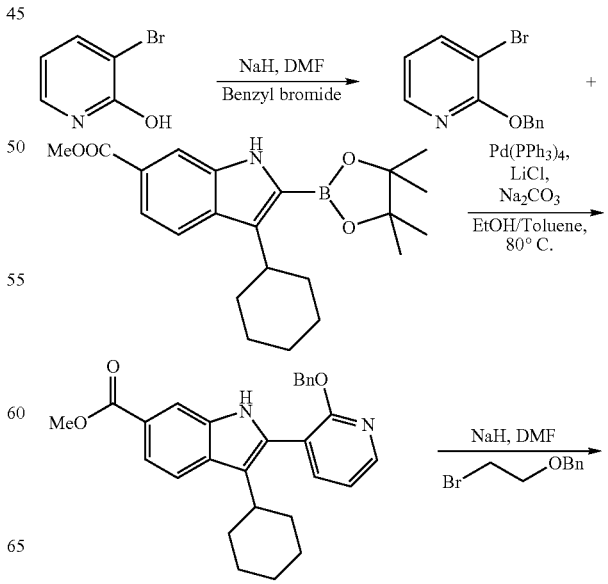

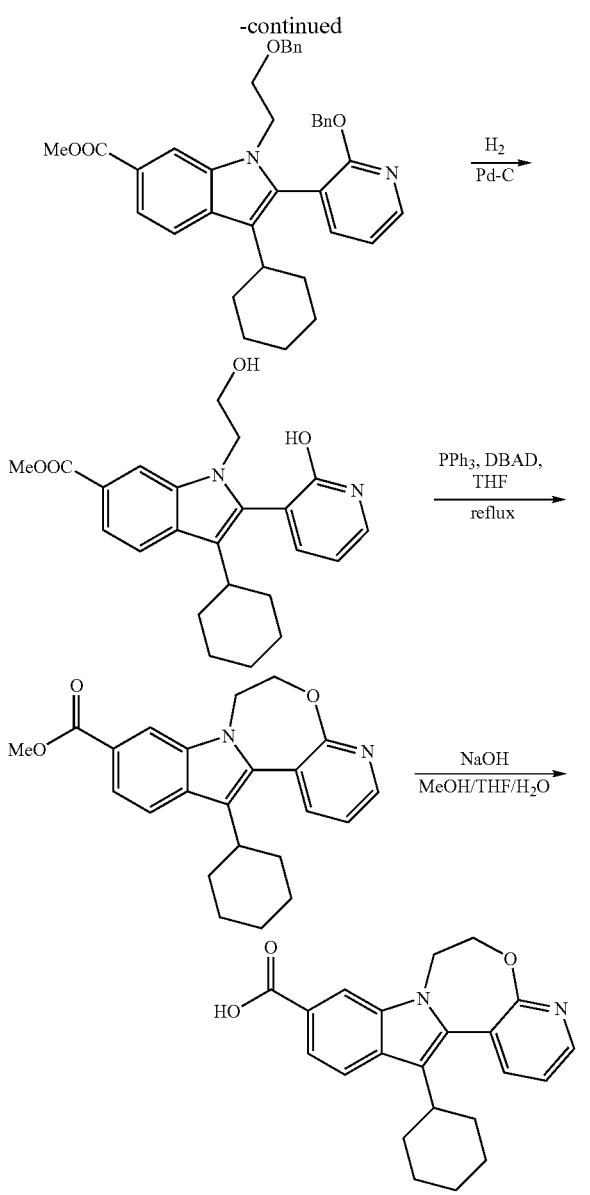

The indole-9-carboxylic acid derivatives described in the above section can be subsequently coupled to a variety of amines using methodology known in the art to provide further examples of Formula I compounds.

2-(Benzyloxy)-3-bromopyridine

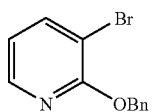

3-bromo-2-hydroxypyridine (1.74 g, 10 mmol) was added to a suspension of NaH (440 mg of 60% dispersion in mineral oil, 11 mmol) in DMF (10 mL), and the resultant mixture was stirred at rt for 30 min. Benzyl bromide (1.3 mL, 11 mmol) was then added, and the reaction was stirred at rt overnight. It was then quenched by the addition of water, and the product extracted with ethyl acetate (2×50 mL). The extracts were combined, washed with 1N HCl solution, then dried (MgSO$_4$), filtered and concentrated in vacuo. The residue was purified by silica gel flash chromatography using hexanes to 100% ethyl acetate in hexanes as eluent to give the title compound as a colorless thick oil, (1.37 g, 52% yield). MS m/z 264, 266(MH$^+$); $^1$H NMR (500 MHz, CDCl$_3$) δ ppm 5.17 (s, 2 H) 6.05 (t, J=7.02 Hz, 1 H) 7.27–7.88 (m, 6 H) 7.70 (dd, J=7.17, 1.98 Hz, 1 H)

Methyl 2-(2-(benzyloxy)pyridin-3-yl)-3-cyclohexyl-1H-indole-6-carboxylate

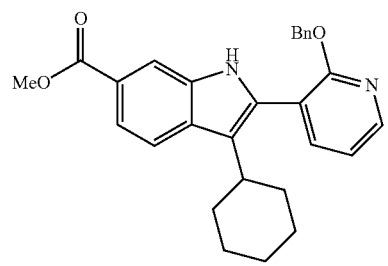

2M Na$_2$CO$_3$ (1.25 mL, 2.5 mmol) aqueous solution was added to a suspension of methyl 3-cyclohexyl-2-(4,4,5,5-tetramethyl-1,3,2-dioxaborolan-2-yl)-1H-indole-6-carboxylate (383 mg, 1.0 mmol), 2-(benzyloxy)-3-bromopyridine (317 mg, 1.2 mmol) and LiCl (84.8 mg, 2.0 mmol), in ethanol (3 mL) and toluene (3 mL). The mixture was degassed by evacuating the reaction flask and then flushing with N$_2$. Pd(PPh$_3$)$_4$ (58 mg, 0.05 mmol) was then added, and the reaction mixture was heated at 80° C. for 6 hr. The reaction mixture was then filtered and concentrated in vacuo, and the resultant residue was purified by silica gel flash chromotagraphy using hexanes to 50% ethyl acetate in hexanes as eluent to afford the title compound as a yellowish solid, (310 mg, 70% yield). MS m/z 441(MH$^+$); $^1$H NMR (500 MHz, CDCl$_3$) δ ppm 1.32–1.46 (m, 3 H) 1.78–1.93 (m, 5 H) 2.05–2.16 (m, 2 H) 2.96 (m, 1 H) 3.92 (s, 3 H) 5.25 (s, 2 H) 6.39 (t, J=6.87 Hz, 1 H) 7.31–7.41 (m, 6 H) 7.60 (dd, J=7.17, 1.98 Hz, 1 H) 7.71 (d, J=8.55 Hz, 1 H) 7.84 (d, J=8.55 Hz, 1 H) 8.07 (s, 1 H) 10.32 (s, 1 H).

Methyl 1-(2-(benzyloxy)ethyl)-2-(2-(benzyloxy)pyridin-3-yl)-3-cyclohexyl-1H-indole-6-carboxylate To a suspension of NaH (14 mg of 60% dispersion in mineral oil, 0.354 mmol) in DMF (2 mL), methyl 2-(2-

(benzyloxy)pyridin-3-yl)-3-cyclohexyl-1H-indole-6-carboxylate (130 mg, 0.295 mmol) was added and the reaction mixture was stirred at rt for 15 min. Benzyl 2-bromoethyl ether (0.052 mL, 0.325 mmol) was then added, and the reaction mixture was stirred at rt overnight before being quenched by the addition of water. The resultant mixture was extracted with ethyl acetate (2×20 mL) and the organic layers were combined, washed with 1N HCl solution, and then dried (MgSO$_4$), filtered and concentrated under vacuum. The residue was then purified by Prep. reverse phase HPLC to give the title compound as light yellow solid (83.5 mg, 49% yield). MS m/z 575(MH$^+$); $^1$H NMR (500 MHz, CDCl$_3$) δ ppm 1.21–1.31 (m, 3 H) 1.69–1.90 (m, 7 H) 2.53 (m, 1 H) 3.65 (m, 1 H) 3.72 (m, 1 H) 3.92 (s, 3 H) 4.17 (m, 1 H) 4.27 (m, 1 H) 4.32 (s, 2 H) 5.21 (s, 2 H) 6.18 (t, J=6.87 Hz, 1 H) 7.07–7.12 (m, 2 H) 7.21–7.36 (m, 9 H) 7.41 (dd, J=6.71, 2.14 Hz, 1 H) 7.74 (dd, J=8.54, 1.22 Hz 1 H) 7.78 (m, J=8.55 Hz, 1 H) 8.12 (s, 1 H).

Methyl 3-cyclohexyl-1-(2-hydroxyethyl)-2-(2-hydroxypyridin-3-yl)-1H-indole-6-carboxylate

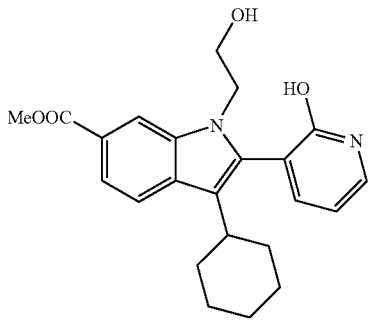

To a solution of methyl 1-(2-(benzyloxy)ethyl)-2-(2-(benzyloxy)pyridin-3-yl)-3-cyclohexyl-1H-indole-6-carboxylate (57 mg, 0.099 mmol) in ethyl acetate (10 mL), 10% Pd on carbon (10 mg) was added. The reaction mixture was stirred under an hydrogen atmosphere (1 atmos.) for three days. It was filtered through celite, and the filtrate concentrated to give the title compounds as an off-white solid, (35 mg, 90% yield). MS m/z 395(MH$^+$); $^1$H NMR (300 MHz, CD$_3$OD) □ ppm 1.24–1.40 (m, 3 H) 1.70–1.98 (m, 7 H) 2.58 (m, 1 H) 3.71 (t, J=6.04 Hz, 2 H) 3.94 (s, 3 H) 4.11 (m, 1 H) 4.22 (m, 1 H) 6.58 (t, J=6.59 Hz, 1 H) 7.58–7.76 (m, 3 H) 7.82 (d, J=8.78 Hz 1 H) 8.19 (s, 1 H).

Pyrido[3',2':6,7][1,4]oxazepino[4,5-a]indole-10-carboxylic acid, 13-cyclohexyl-6,7-dihydro-, methyl ester.

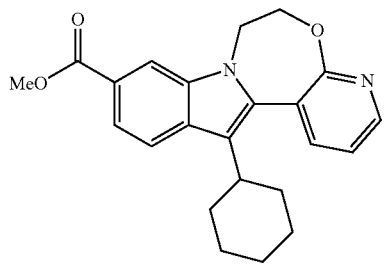

To a solution of methyl 3-cyclohexyl-1-(2-hydroxyethyl)-2-(2-hydroxypyridin-3-yl)-1H-indole-6-carboxylate (49 mg, 0.124 mmol) in THF (8 mL), PPh$_3$ (130 mg, 0.497 mmol) and DBAD (114 mg, 0.497 mmol) were added. The reaction mixture was heated at 85° C. under microwave conditions for 3.5 hr. It was then concentrated under vacuum and the residue purified by Prep. reverse phase HPLC to afford the title compound as a yellowish solid, (27 mg, 58% yield). MS m/z 377(MH$^+$); $^1$H NMR (500 MHz, CD$_3$OD) □ ppm 1.31 (m, 1 H) 1.35–1.51 (m, 3 H) 1.78–1.95 (m, 4 H) 2.06–2.19 (m, 2 H) 2.92 (m, 1 H) 3.96 (s, 3 H) 4.51 (m, 2 H) 4.66 (m, 2 H) 7.45 (m, 1 H) 7.76 (d, J=7.63 Hz, 1 H) 7.91–7.99 (m, 2 H) 8.23 (s, 1 H) 8.37 (d, J=2.44 Hz, 1 H).

Pyrido[3',2':6,7][1,4]oxazepino[4,5-a]indole-10-carboxylic acid, 13-cyclohexyl-6,7-dihydro-

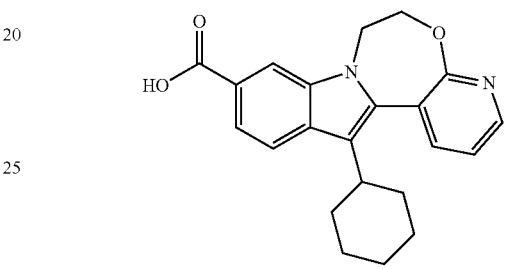

2N aqueous NaOH (0.5 mL) was added to a solution of pyrido[3',2':6,7][1,4]oxazepino[4,5-a]indole-10-carboxylic acid, 13-cyclohexyl-6,7-dihydro-, methyl ester (5.5 mg, 0.0146 mmol) in a THF/Methanol mixture (1.5 mL/1.5 mL). The reaction was heated at 100° C. under microwave conditions for 15 min, after which it was concentrated in vacuo and the pH of the resultant mixture adjusted to 4–5 using 1N HCl solution. The mixture was then extracted with ethyl acetate and the organic layer dried with MgSO$_4$, filtered, and concentrated in vacuo. The residue was purified by Prep. reverse phase HPLC to afford the TFA salt of the title compound as a yellow solid, (4.5, 65% yield). MS m/z 363(MH$^+$); $^1$H NMR (500 MHz, CD$_3$OD) δ ppm 1.31 (m, 1 H) 1.36–1.63 (m, 3 H) 1.79–1.96 (m, 4 H) 2.09–2.21 (m, 2 H) 2.91 (m, 1 H) 4.57 (t, J=5.19 Hz, 2 H) 4.72 (t, J=5.19 Hz, 2 H) 7.51 (dd, J=7.63, 5.19 Hz, 1 H) 7.78 (d, J=8.55 Hz, 1 H) 7.96 (d, J=8.55 Hz, 1 H) 8.08 (dd, J=7.63, 1.83 Hz, 1 H) 8.23 (s, 1 H) 8.40 (d, J=4.58 Hz, 1 H).

2-Propenoic acid, 3-[4-[[[1-[[(13-cyclohexyl-6,7-dihydropyrido[3',2':6,7][1,4]oxazepino[4,5-a]indol-10-yl)carbonyl]amino]cyclopentyl]carbonyl]amino]phenyl]-, (2E)-

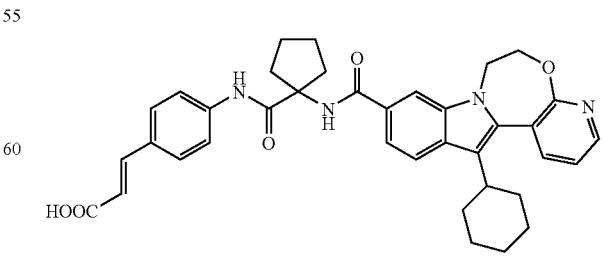

To a solution of pyrido[3',2':6,7][1,4]oxazepino[4,5-a]indole-10-carboxylic acid, 13-cyclohexyl-6,7-dihydro- (23 mg, 0.064 mmol) in DMSO (2.0 mL), TBTU (30.6 mg, 0.095 mmol) and DIPEA (0.055 mL, 0.318 mmol) were added. The reaction mixture was stirred at rt for 15 min. Then (E)-methyl 3-(4-(1-aminocyclopentanecarboxamido)phenyl)acrylate (22 mg, 0.076 mmol) was added and the reaction mixture was stirred at rt overnight. It was then concentrated and the residue was purified by Prep. reverse phase HPLC to give the ester intermediate. To a solution of the this material in a THF/Methanol mixture (1.5 mL/5 mL), 2N NaOH solution (0.5 mL) was added. The reaction mixture was heated at 100° C. under microwave conditions for 15 min. It was concentrated and the pH was adjusted to 4–5 using 1N HCl solution. This mixture was extracted using ethyl acetate. The organic layer was dried with MgSO$_4$, filtered and the solvent evaporated to give a crude product which was purified by Prep. reverse phase HPLC to afford the title compound as a yellow solid. (4.0 mg, 8.6% yield two steps). MS m/z 619(MH$^+$); $^1$H NMR (500 MHz, CD$_3$OD) ☐ ppm 1.31 (m, 1 H) 1.38–1.60 (m, 3 H) 1.79–1.96 (m, 8 H) 2.08–2.24 (m, 4 H) 2.47–2.56 (m, 2 H) 2.92 (m, 1 H) 4.55 (t, J=5.04 Hz, 2 H) 4.70 (t, J=5.19 Hz, 2 H) 6.41 (d, J=16.17 Hz, 1 H) 7.49 (dd, J=7.63, 5.19 Hz, 1 H) 7.56 (d, J=8.55 Hz, 2 H) 7.60–7.69 (m, 4 H) 7.97 (d, J=8.55 Hz, 1 H) 8.05 (dd, J=7.63, 1.83 Hz, 1 H) 8.12 (s, 1 H) 8.39 (m, 1 H).

Some representative examples of methods that can be used to prepare some hydroxylated derivatives of the proprano bridged compounds are outlined in the scheme below.

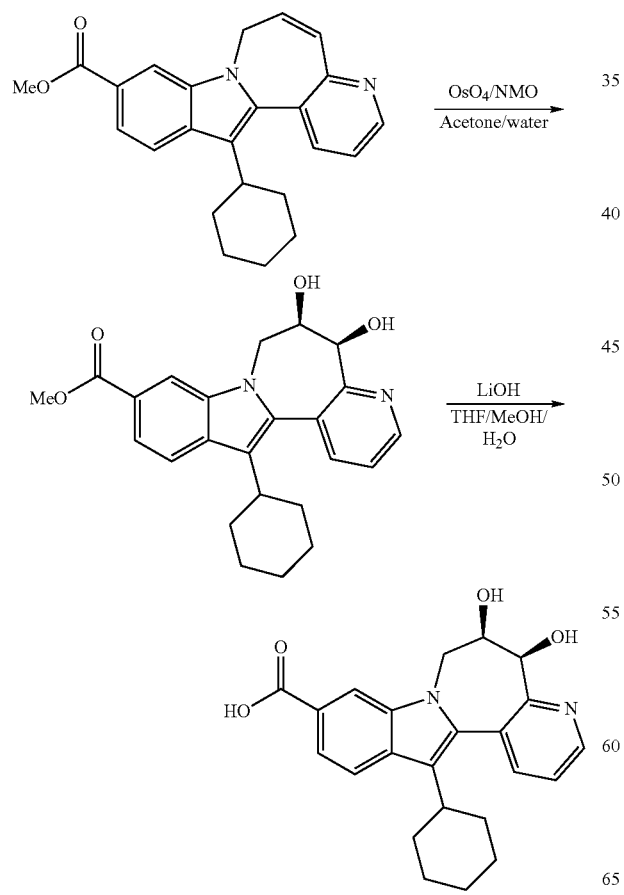

(5S,6R) and (5R,6S)-5H-pyrido[3',2':3,4]azepino[1,2-a]indole-10-carboxylic acid, 13-cyclohexyl-6,7-dihydro-5,6-dihydroxy-, methyl ester

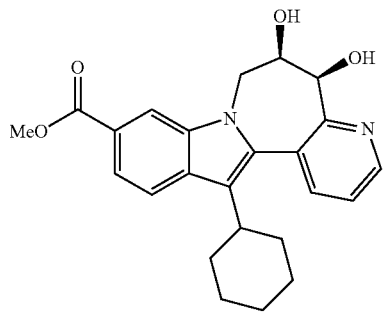

OsO$_4$ (2.7 mg, 0.0107 mmol) was added to a solution of 7H-pyrido[3',2':3,4]azepino[1,2-a]indole-10-carboxylic acid, 13-cyclohexyl-, methyl ester (40 mg, 0.107 mmol) and N-methylmorpholine oxide (38 mg, 0.322 mmol) in a mixture of acetone and water (9 mL-1 mL). The resultant solution was stirred at rt overnight, after which it was concentrated in vacuo and the residue purified by Prep. reverse phase HPLC to give a racemic mixture of title compounds as a light yellow, (25 mg, 57% yield). MS m/z 407(MH$^+$); $^1$H NMR (500 MHz, CD$_3$OD) δ ppm 1.31 (m, 1 H) 1.39–1.55 (m, 2 H) 1.66 (m, 1 H) 1.76–1.86 (m, 2 H) 1.92–2.17 (m, 4 H) 2.88 (m, 1 H) 3.39 (m, 1 H) 3.96 (s, 3 H) 4.49 (m, 1 H) 4.66 (m, 2 H) 7.58 (dd, J=7.48, 5.04 Hz, 1 H) 7.75 (d, J=8.24 Hz, 1 H) 7.88–7.96 (m, 2 H) 8.24 (s, 1 H) 8.69 (d, J=1.83 Hz, 1 H)

(5S,6R) and (5R,6S)-5H-pyrido[3',2':3,4]azepino[1,2-a]indole-10-carboxylic acid, 13-cyclohexyl-6,7-dihydro-5,6-dihydroxy-

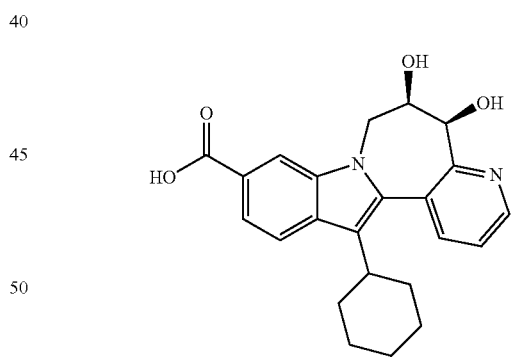

LiOH (14.7 mg, 0.615 mmol) and water (0.5 mL) were added to a solution of racemic (5S,6R) and (5R,6S)-5H-pyrido[3',2':3,4]azepino[1,2-a]indole-10-carboxylic acid, 13-cyclohexyl-6,7-dihydro-5,6-dihydroxy-, methyl ester (25 mg, 0.0615 mmol) in a THF/Methanol mixture (1.5 mL/1.5 mL). The reaction was stirred at rt. for three days. It was then concentrated in vacuo, and the pH was adjusted to 4–5 using 1N HCl solution. The resultant mixture was extracted with ethyl acetate. The organic layer was dried (MgSO$_4$), filtered and the solvent evaporated. The residue was purified by Prep. reverse phase HPLC to afford the TFA salts of a racemic mixture of the title compounds, (15 mg, 48% yield). MS m/z 393(MH$^+$); $^1$H NMR (500 MHz, CD$_3$OD) ☐ ppm 1.32 (m, 1 H) 1.42–1.61 (m, 2 H) 1.68 (m, 1 H) 1.79–1.89

(m, 2 H) 1.99 (m, 1 H) 2.07–2.22 (m, 3 H) 2.87 (m, 1 H) 3.44 (m, 1 H) 4.79–4.89 (m, 3 H) 7.81 (d, J=8.24 Hz, 1 H) 8.01 (d, J=8.55 Hz, 1 H) 8.21 (dd, J=7.93, 6.10 Hz, 1 H) 8.30 (s, 1 H) 8.63 (d, J=7.93 Hz, 1 H) 8.85 (d, J=5.80 Hz, 1 H).

The above derivatives may be coupled to a variety of amines and related compounds through the acid functionality of these intermediates using methodology described herein or other common methods known to those skilled in the art to generate products of the type described below.

(5S,6R) and (5R,6S)-2-propenoic acid, 3-[4-[[[1-[[[13-cyclohexyl-6,7-dihydro-5,6-dihydroxy-5H-pyrido[3',2':3,4]azepino[1,2-a]indol-10-yl]carbonyl]amino]cyclopentyl]carbonyl]amino]phenyl]-, methyl ester, (2E)-

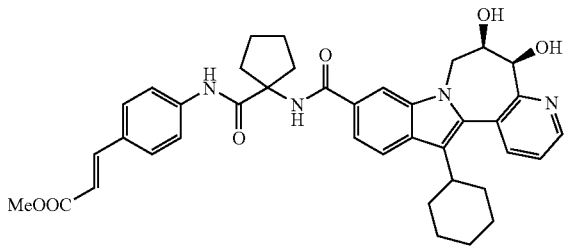

To a solution of racemic (5S,6R) and (5R,6S)-5H-pyrido[3',2':3,4]azepino[1,2-a]indole-10-carboxylic acid, 13-cyclohexyl-6,7-dihydro-5,6-dihydroxy- (31 mg, 0.079 mmol) in DMF (1.5 mL), HATU (45 mg, 0.119 mmol) and DIPEA (0.069 mL, 0.395 mmol) were added. The reaction mixture was stirred at rt for 15 min. Then (E)-methyl 3-(4-(1-aminocyclopentanecarboxamido)phenyl)acrylate (30 mg, 0.103 mmol) was added and the reaction mixture stirred at rt overnight. It was then concentrated in vacuo, and the residue purified by Prep. reverse phase HPLC to give a racemic mixture of the title compounds as a light yellow solid, (26 mg, 50% yield). MS m/z 663(MH+); 1H NMR (500 MHz, CD3OD) δ ppm 1.22–1.53 (m, 3 H) 1.62 (m, 1 H) 1.75–2.15 (m, 10 H) 2.17–2.26 (m, 2 H) 2.47–2.55 (m, 2 H) 2.86 (m, 1 H) 3.38 (m, 1 H) 3.78 (s, 3 H) 4.47 (m, 1 H) 4.86 (m, 2 H) 6.44 (d, J=15.87 Hz, 1 H) 7.53 (d, J=8.55 Hz, 2 H) 7.57 (dd, J=7.48, 5.04 Hz, 1 H) 7.60–7.66 (m, 4 H) 7.89 (d, J=7.32 Hz, 1 H) 7.92 (d, J=8.55 Hz, 1 H) 8.18 (s, 1 H) 8.68 (d, J=4.27 Hz, 1 H).

(5S,6R) and (5R,6S)-2-propenoic acid, 3-[4-[[[1-[[[13-cyclohexyl-6,7-dihydro-5,6-dihydroxy-5H-pyrido[3',2':3,4]azepino[1,2-a]indol-10-yl]carbonyl]amino]cyclopentyl]carbonyl]amino]phenyl]-, (2E)-

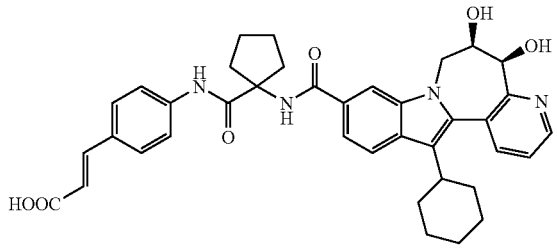

LiOH (6.1 mg, 0.256 mmol) in water (0.5 mL) was added to a solution of racemic (5R,6S) and (5S,6R)-2-propenoic acid, 3-[4-[[[1-[[[13-cyclohexyl-6,7-dihydro-5,6-dihydroxy-5H-pyrido[3',2':3,4]azepino[1,2-a]indol-10-yl]carbonyl]amino]cyclopentyl]carbonyl]amino]phenyl]-, methyl ester, (2E)- (17 mg, 0.0256 mmol) in a THF/Methanol mixture (2.0 mL/2.0 mL). The reaction was stirred at rt. for two days. It was then concentrated in vacuo, and the pH of the resultant solution adjusted to 4–5 using 1N HCl solution. This mixture was then extracted using ethyl acetate and the organic layer was dried with MgSO4, filtered and evaporated to give the crude product which was purified by Prep. reverse phase HPLC to afford a racemic mixture of the TFA salts of the title compounds as a yellow solid, (10 mg, 51% yield). MS m/z 649(MH+); 1H NMR (300 MHz, CD3OD) □ ppm 1.20–1.72 (m, 4 H) 1.76–2.29 (m, 12 H) 2.44–2.60 (m, 2 H) 2.87 (m, 1 H) 3.43 (m, 1 H) 4.81 (m, 2 H) 4.97 (m, 1 H) 6.40 (d, J=15.74 Hz, 1 H) 7.51–7.73 (m, 6 H) 8.01 (d, J=8.42 Hz, 1 H) 8.16 (dd, J=7.87, 6.04 Hz, 1 H) 8.22 (s, 1 H) 8.57 (d, J=6.59 Hz, 1 H) 8.82 (d, J=5.86 Hz, 1 H) 9.66 (s, 1 H).

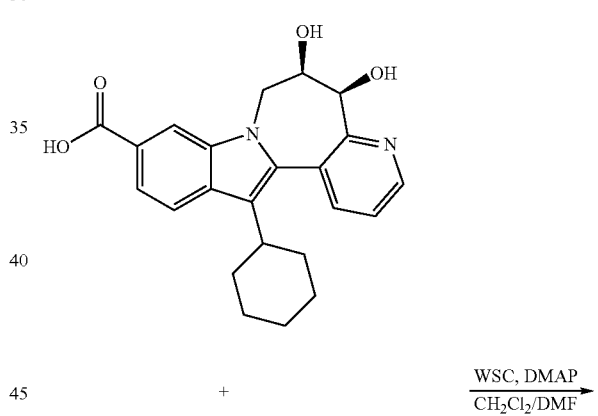

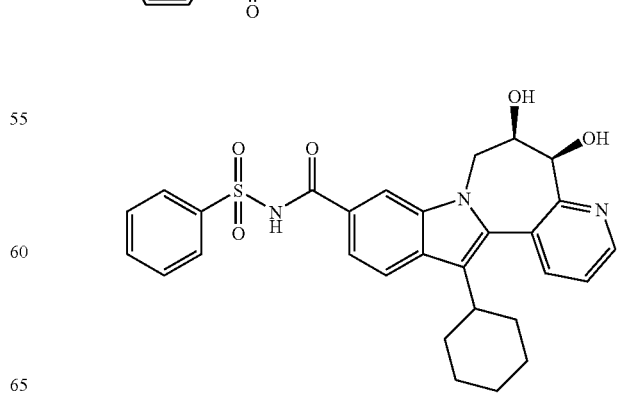

(5S,6R) and (5R,6S)-5H-pyrido[3',2':3,4]azepino[1,2-a]indole-10-carboxamide, 13-cyclohexyl-6,7-dihydro-5,6-dihydroxy-N-(phenylsulfonyl)-

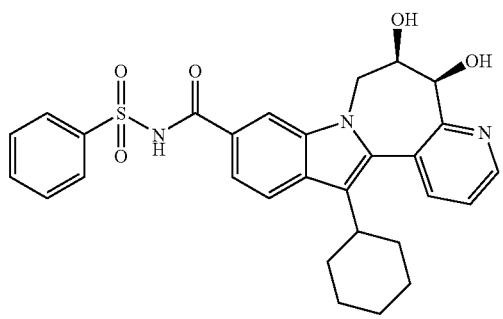

To a solution of racemic (5S,6R) and (5R,6S)-5H-pyrido[3',2':3,4]azepino[1,2-a]indole-10-carboxylic acid, 13-cyclohexyl-6,7-dihydro-5,6-dihydroxy- (15 mg, 0.038 mmol) in $CH_2Cl_2$/DMF(1 mL/1 mL); N-3-dimethylaminopropyl)-N'-ethylcarbodiimide hydrochloride (14.6 mg, 0.0764 mmol), DMAP(9.3 mg, 0.0764 mmol) and benzensulfonamide (12 mg, 0.0764 mmol) were added. The reaction mixture was heated at 120° C. under microwave conditions for 15 min. It was then concentrated under vacuum and the residue purified by Prep reverse phase HPLC to afford a racemic mixture of the TFA salts of the title compounds as a yellow solid, (1.3 mg, 5% yield). MS m/z 532(MH+); $^1$H NMR (500 MHz, $CD_3OD$) δ ppm 1.31 (m, 1 H) 1.40–1.60 (m, 2 H) 1.65 (m, 1 H) 1.79–1.88 (m, 2 H) 1.98 (m, 1 H) 2.03–2.18 (m, 3 H) 2.86 (m, 1 H) 3.44 (m, 1 H) 4. 74–4.89 (m,3 H) 7.57–7.67 (m, 3 H) 7.73 (m, 1 H) 8.01 (d, J=8.54 Hz, 1 H) 8.09 (m, 1 H) 8.14–8.19 (m, 3 H) 8.52 (s, 1 H) 8.82 (d, J=5.49 Hz, 1 H).

Additional examples of some of the methods that can be used to prepare some fused pyridine derivatives of compounds of Formula I are outlined in the scheme below.

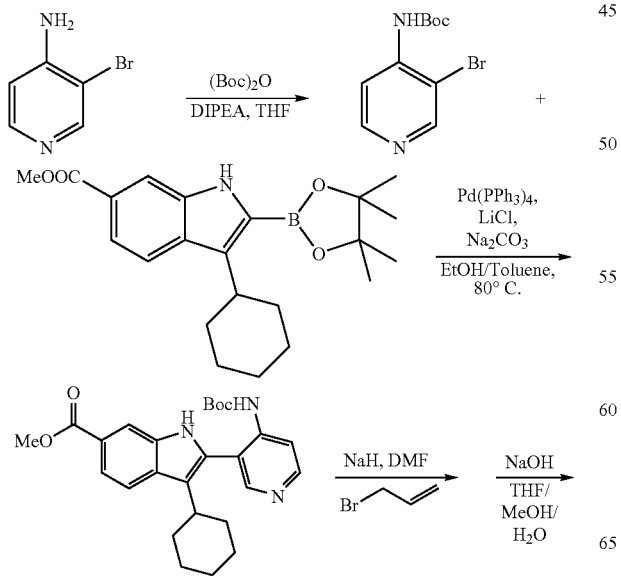

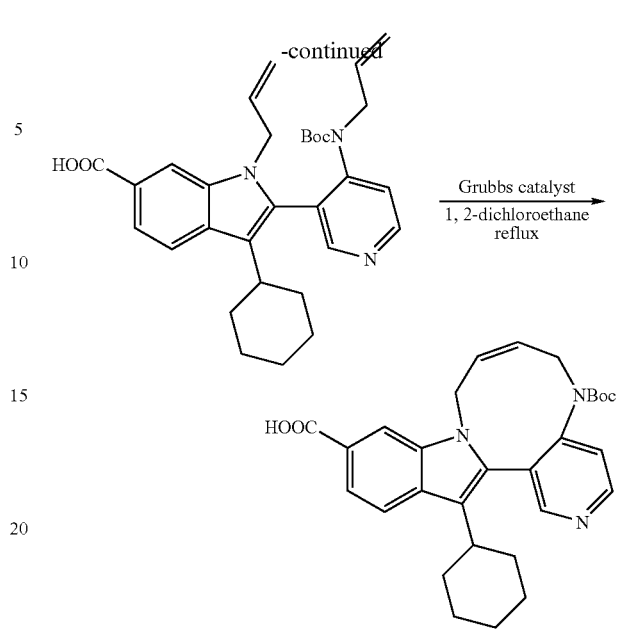

tert-Butyl 3-bromopyridin-4-ylcarbamate

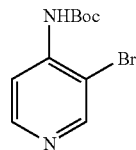

To a solution of 4-amino-3-bromopyridine (1.0 g, 5.78 mmol) in THF (10 mL), DIPEA (1.1 mL, 6.36 mmol) and $(Boc)_2O$ (1.39 g, 6.36 mmol) were added. The reaction mixture was stirred at rt. for two days. It was then quenched with 1N HCl solution and extracted with ethyl acetate (2×50 mL). The organic layers were combined, dried ($MgSO_4$), filtered and concentrated to give tert-butyl 3-bromopyridin-4-ylcarbamate as a yellowish thick oil, (1.1 g, 70% yield). MS m/z 273,275(MH+); $^1$H NMR (300 MHz, $CDCl_3$)δ ppm 1.51 (s, 9 H) 7.14 (s, 1 H) 8.12 (d, J=5.49 Hz, 1 H) 8.34 (d, J=5.86 Hz, 1 H) 8.55 (s, 1 H).

Methyl 2-(4-(tert-butoxycarbonyl)pyridin-3-yl)-3-cyclohexyl-1H-indole-6-carboxylate

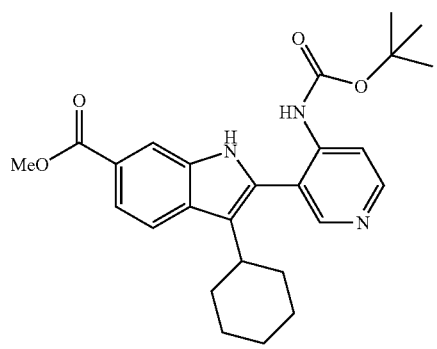

To a mixture of methyl 3-cyclohexyl-2-(4,4,5,5-tetramethyl-1,3,2-dioxaborolan-2-yl)-1H-indole-6-carboxylate (383 mg, 1.0 mmol), tert-butyl 3-bromopyridin-4-ylcarbamate (328 mg, 1.2 mmol) and LiCl (84.8 mg, 2.0 mmol), in ethanol (3 mL) and toluene (3 mL) was added, 2M aqueous $Na_2CO_3$ (1.25 mL, 2.5 mmol) solution. The mixture was then degassed by the application of vacuum followed by flushing with $N_2$.Pd(PPh$_3$)$_4$ (58 mg, 0.05 mmol) was then added and the reaction was heated at 80° C. overnight. The resultant mixture was then filtered and concentrated under vacuum, and the product residue was purified by Prep. reverse phase HPLC to afford the title compound as an off-white solid, (170 mg, 38% yield). MS m/z 450(MH$^+$); $^1$H NMR (300 MHz, CDCl$_3$) δ ppm 1.15–1.33 (m, 13 H) 1.63–1.98 (m, 6 H) 2.45 (m, 1 H) 3.92 (s, 3 H) 6.94 (s, 1 H) 7.75–7.89 (m, 2 H) 8.17 (s, 1 H) 8.21 (d, J=5.86 Hz, 1 H) 8.37 (s, 1 H) 8.45 (d, J=5.86 Hz, 1 H) 9.45 (s, 1 H).

1-Allyl-2-(4-(tert-butoxycarbonyl)pyridin-3-yl)-3-cyclohexyl-1H-indole-6-carboxylic acid

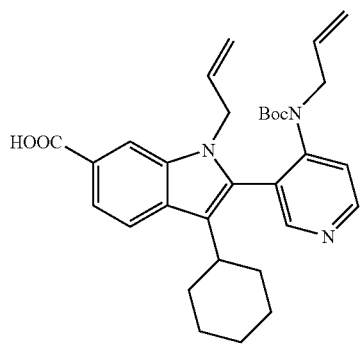

To a suspension of NaH (19.5 mg of 60% dispersion in mineral oil, 0.488 mmol) in DMF (2 mL), methyl 2-(4-(tert-butoxycarbonyl)pyridin-3-yl)-3-cyclohexyl-1H-indole-6-carboxylate (100 mg, 0.222 mmol) was added and the reaction mixture was stirred at rt for 10 min. Allyl bromide (0.040 mL, 0.466 mmol) was then added, and the reaction mixture was stirred at rt for 3 hr. It was then quenched by the addition of water and acidified using 1N HCl solution. A yellowish precipitate formed which was collected by filtration to give the crude ester product in sufficient purity to proceed to the next step. This material was then dissolved in a THF/Methanol mixture (3 mL/3 mL) and 2N NaOH solution (2 mL) was added. The reaction mixture was heated at 100° C. under microwave conditions for 15 min. It was then concentrated and the pH was adjusted to 4–5 using 1N HCl solution. This mixture was then extracted using ethyl acetate and the organic layer was dried with MgSO$_4$, filtered and evaporated and the resultant residue was purified using Prep. reverse phase HPLC to afford the title compound as a yellow solid, (50 mg, 44% yield two steps). MS m/z 516(MH$^+$); $^1$H NMR (500 MHz, CD$_3$OD) □ ppm 1.22–1.48 (m, 13 H) 1.70–2.02 (m, 5 H) 2.15 (m, 1 H) 2.37 (m, 1 H) 3.88 (dd, J=16.63, 5.04 Hz, 1 H) 4.13 (m, 1 H) 4.51 (m, 1 H) 4.76 (m, 1 H) 4.87 (m, 1 H) 5.04–5.21 (m, 3 H) 5.79 (m, 1 H) 5.97 (m, 1 H) 7.58 (d, J=5.80 Hz, 1 H) 7.78 (m, 1 H) 7.90 (d, J=8.24 Hz, 1 H) 8.13 (s, 1 H) 8.50 (s, 1 H) 8.67 (d, J=5.80 Hz, 1 H).

5H-pyrido[3',4':3,4][1,5]diazonino[1,2-a]indole-5,12-dicarboxylic acid, 15-cyclohexyl-6,9-dihydro-, 5-(1,1-dimethylethyl) ester, (7Z)-

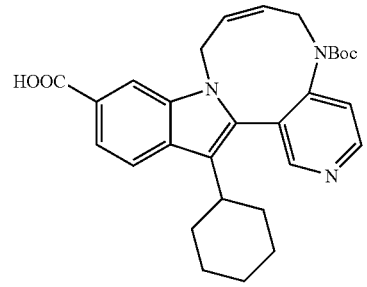

To a solution of 1-allyl-2-(4-(tert-butoxycarbonyl)pyridin-3-yl)-3-cyclohexyl-1H-indole-6-carboxylic acid (45 mg, 0.087 mmol) in 1,2-dichloroethane (15 mL), Grubbs Catalyst 2$^{nd}$ generation (7.4 mg, 0.0087 mmol) was added. The reaction mixture was heated under reflux for overnight. The solvent was evaporated and the residue was purified by Prep.HPLC column to give a yellow solid as 5H-pyrido[3',4':3,4][1,5]diazonino[1,2-a]indole-5,12-dicarboxylic acid, 15-cyclohexyl-6,9-dihydro-, 5-(1,1-dimethylethyl) ester, (7Z)-. (15 mg, 35% yield). MS m/z 488(MH$^+$); $^1$H NMR (300 MHz, CD$_3$OD) □ ppm 1.29–1.44 (m, 13 H) 1.67–1.92 (m, 6 H) 2.45 (m, 1 H) 4.11 (m, 1 H) 4.36 (m, 1 H) 4.62 (m, 1 H) 5.05 (m, 1 H) 5.67 (m, 1 H) 5.94 (m, 1 H) 7.82 (dd, J=8.42, 1.46 Hz, 1 H) 7.91 (m, 1 H) 8.02 (d, J=6.22 Hz, 1 H) 8.25 (s, 1 H) 8.79–8.89 (m, 2 H).

5H-pyrido[3',4':3,4][1,5]diazonino[1,2-a]indole-5,12-dicarboxylic acid, 15-cyclohexyl-6,7,8,9-tetrahydro-, 5-(1,1-dimethylethyl) ester

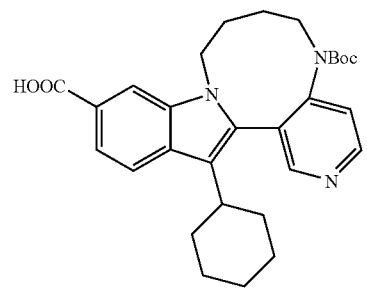

To a solution of 5H-pyrido[3',4':3,4][1,5]diazonino[1,2-a]indole-5,12-dicarboxylic acid, 15-cyclohexyl-6,9-dihydro-, 5-(1,1-dimethylethyl) ester, (7Z)- (12 mg, 0.0246 mmol) in methanol (5 mL), 10% Pd on carbon (5 mg) was added. The reaction mixture was stirred under a hydrogen atmosphere (1 atmos.) for 2 hr. It was then filtered through celite and concentrated to give the desired product as a yellow solid, (7.3 mg, 60% yield). MS m/z 490(MH$^+$); $^1$H NMR (500 MHz, CD$_3$OD) □ ppm 1.22–1.44 (m, 13 H) 1.55–2.04 (m, 9 H) 2.23 (m, 1 H) 2.51 (m, 1 H) 3.47 (m, 1 H) 3.59 (m, 1 H) 3.78 (m, 1 H) 4.33 (m, 1 H) 7.73–7.81 (m, 2 H) 7.90 (d, J=8.55 Hz, 1 H) 8.15 (s, 1 H) 8.63 (s, 1 H) 8.84 (d, J=4.88 Hz, 1 H).

Representative methodologies for the synthesis of some of the sulfonylated carboxamide derivatives of the instant invention are outlined below.

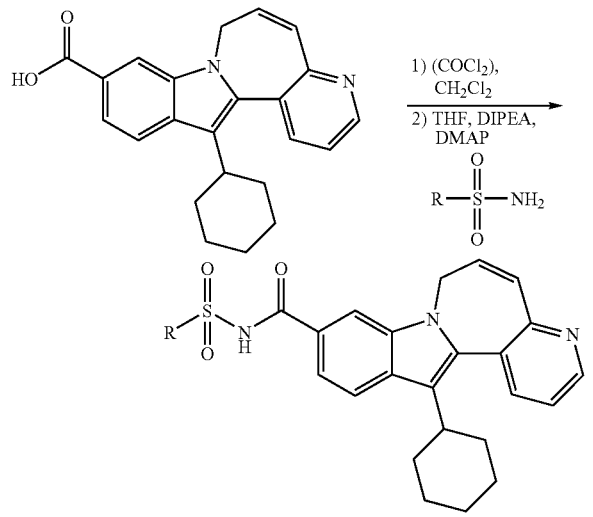

7H-pyrido[3',2':3,4]azepino[1,2-a]indole-10-carboxamide, 13-cyclohexyl-N-[(dimethylamino)sulfonyl]-

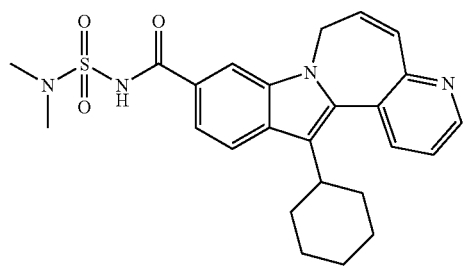

To a solution of 7H-pyrido[3',2':3,4]azepino[1,2-a]indole-10-carboxylic acid, 13-cyclohexyl- (20 mg, 0.056 mmol) in CH$_2$Cl$_2$ (5 mL), one drop of DMF was added. Then a 2M solution of oxalyl chloride (0.036 mL, 0.072 mmol) in CH$_2$Cl$_2$ was added dropwise. The reaction mixture was then stirred at rt. for 2 hr after which it was concentrated and dried under high vacuum. The residue was dissolved in THF(5 mL) and a solution of N,N-dimethylsulfonamide (10.4 mg, 0.084 mmol) and DIPEA (0.020 mL, 0.112 mmol)) in THF (2 mL) was added. DMAP (10 mg) was then added after the reaction mixture had been stirred at rt. for 10 min., and stirring was continued for a further 2 hr. The resultant mixture was then concentrated under vacuum and the residue purified by Prep. reverse phase HPLC to afford the TFA salt of the desired product as a yellow solid, (13 mg, 40% yield). MS m/z 465(MH$^+$); $^1$H NMR (500 MHz, CD$_3$OD) δ ppm 1.25–1.58 (m, 3 H) 1.80–2.30 (m, 7 H) 2.97 (m, 1 H) 3.03 (s, 6 H) 3.67 (s, 2 H) 6.05 (m, 1 H) 7.41 (d, J=7.63 Hz, 1 H) 7.79 (m, 1 H) 7.87 (dd, J=7.93, 5.80 Hz, 1 H) 8.10 (d, J=8.55 Hz, 1 H) 8.21 (s, 1 H) 8.31 (d, J=7.94 Hz, 1 H) 8.65 (d, J=5.49 Hz, 1 H).

7H-pyrido[3',2':3,4]azepino[1,2-a]indole-10-carboxamide, 13-cyclohexyl-N-(methylsulfonyl)-

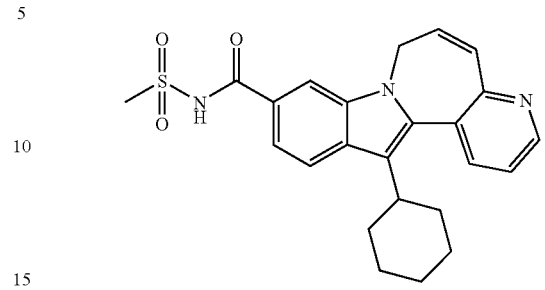

To a solution of 7H-pyrido[3',2':3,4]azepino[1,2-a]indole-10-carboxylic acid, 13-cyclohexyl- (36 mg, 0.1 mmol) in CH$_2$Cl$_2$ (5 mL), one drop of DMF was added. Then a 2M solution of oxalyl chloride (0.075 mL, 0.15 mmol) in CH$_2$Cl$_2$ was added dropwise. The reaction mixture was stirred at rt. for 2 hr. It was then concentrated and dried under high vacuum. This material was then dissolved in THF(5 mL) and a solution of methanesulfonamide (14.3 mg, 0.15 mmol) and DIPEA (0.025 mL, 0.15 mmol)) in THF (2 mL) were added. DMAP (10 mg) was added after the reaction mixture was stirred at rt. for 10 min. Stirring was continued at 50° C. overnight. The reaction mixture was then concentrated under vacuum and the residue purified by Prep. reverse phase HPLC to afford the title compound as a light yellow solid, (24 mg, 55% yield). MS m/z 436(MH$^+$); $^1$H NMR (500 MHz, CD$_3$OD) □ ppm 1.22–2.32 (m, 10 H) 2.97 (m, 1 H) 3.36 (s, 3 H) 3.50 (m, 2 H) 6.04 (m, 1 H) 7.29 (d, J=7.32 Hz, 1 H) 7.49 (dd, J=7.78, 5.04 Hz, 1 H) 7.81 (d, J=8.54 Hz, 1 H) 7.90 (d, J=7.93 Hz, 1 H) 8.02 (d, J=8.54 Hz, 1 H) 8.22 (s, 1 H) 8.47 (d, J=5.19 Hz, 1 H).

7H-pyrido[3',2':3,4]azepino[1,2-a]indole-10-carboxamide, 13-cyclohexyl-N-(phenylsulfonyl)-

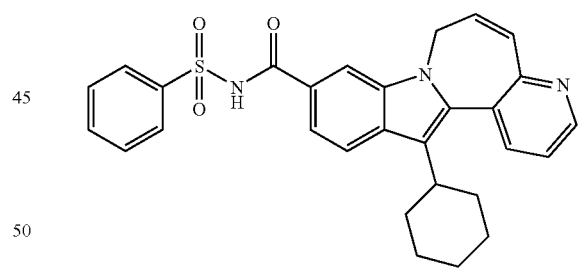

To a solution of 7H-pyrido[3',2':3,4]azepino[1,2-a]indole-10-carboxylic acid, 13-cyclohexyl- (36 mg, 0.1 mmol) in CH$_2$Cl$_2$ (5 mL), was added one drop of DMF. 2M solution of oxalyl chloride (0.075 mL, 0.15 mmol) in CH$_2$Cl$_2$ was then added dropwise. The reaction mixture was stirred at rt. for 2 hr. It was then concentrated and dried under high vacuum. The residue was then dissolved in THF(5 mL) and a solution of benzenesulfonamide (23.6 mg, 0.15 mmol) and DIPEA (0.025 mL, 0.15 mmol)) in THF (2 mL) was added. DMAP (10 mg) was added after the reaction mixture was stirred at rt. for 10 min. Stirring was continued at rt. Overnight, after which the reaction mixture was concentrated under vacuum and the residue purified by Prep. reverse phase HPLC to afford the TFA salt of the title compound as a light yellow solid, (18 mg, 29% yield). MS m/z 498(MH$^+$); $^1$H NMR (500 MHz, CD$_3$OD) δ ppm 1.24–2.28(m, 10 H) 2.93 (m, 1 H) 3.66 (s, br, 2 H) 6.03 (m, 1 H) 7.36 (d, J=7.63 Hz, 1 H) 7.60–7.66 (m, 2 H) 7.69–7.74 (m, 2 H) 7.88 (dd, J=7.78, 5.65 Hz, 1 H) 8.06 (d, J=8.54 Hz, 1 H) 8.12–8.17 (m, 3 H) 8.31 (d, J=7.94 Hz, 1 H) 8.65 (d, J=5.49 Hz, 1 H).

7H-pyrido[3',2':3,4]azepino[1,2-a]indole-10-carboxamide, 13-cyclohexyl-N-[(1-methyl-1H-imidazol-4-yl)sulfonyl]-

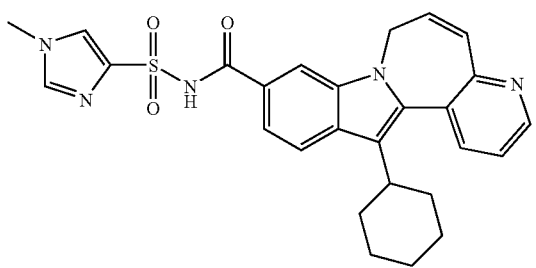

To a solution of 7H-pyrido[3',2':3,4]azepino[1,2-a]indole-10-carboxylic acid, 13-cyclohexyl- (31 mg, 0.0865 mmol) in CH$_2$Cl$_2$ (5 mL), was added one drop of DMF. A 2M solution of oxalyl chloride (0.056 mL, 0.112 mmol) in CH$_2$Cl$_2$ was then added dropwise, and the reaction mixture was stirred at rt. for 2 hr. It was then concentrated and dried under high vacuum. The resultant residue was then dissolved in THF(5 mL) and a solution of 1-methyl-imidazole-4-sulfonamide(21 mg, 0.13 mmol) and DIPEA (0.023 mL, 0.13 mmol) in DMF (2 mL) was added. DMAP (10 mg) was added after the reaction mixture was stirred at rt. for 10 min. Stirring was continued at 50° C. overnight, after which the reaction mixture was concentrated under vacuum to give a residue that was purified by Prep. reverse phase HPLC to afford the title compound as a light yellow solid, (13 mg, 30% yield). MS m/z 502 (MH$^+$); $^1$H NMR (500 MHz, CD$_3$OD) □ ppm 1.28–2.28 (m, 10 H) 2.95 (m, 1 H) 3.42–3.55 (m, 2 H) 3.84 (s, 3 H) 6.02 (m, 1 H) 7.25 (m, 1 H) 7.48 (dd, J=7.78, 5.04 Hz, 1 H) 7.73–7.80 (m, 2 H) 7.87–7.95 (m, 2 H) 7.99 (m, 1 H) 8.20 (s, 1 H) 8.46 (dd, J=5.04, 1.37 Hz, 1 H)

7H-pyrido[3',2':3,4]azepino[1,2-a]indole-10-carboxamide, 13-cyclohexyl-N-(cyclopropylsulfonyl)-

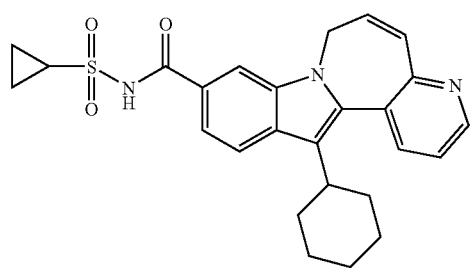

To a solution of 7H-pyrido[3',2':3,4]azepino[1,2-a]indole-10-carboxylic acid, 13-cyclohexyl- (14 mg, 0.039 mmol) in CH$_2$Cl$_2$ (5 mL), was added one drop of DMF. A 2M solution of oxalyl chloride (0.039 mL, 0.078 mmol) in CH$_2$Cl$_2$ was then added dropwise, and the reaction mixture was stirred at rt. for 2 hr. It was concentrated and dried under high vacuum. The residue was then dissolved in THF(5 mL) and a solution of cyclopropanesulfonamide (9.5 mg, 0.078 mmol) and DIPEA (0.014 mL, 0.078 mmol)) in THF (2 mL) was added. DMAP (10 mg) was added after the reaction mixture was stirred at rt. for 10 min. Stirring was continued at 50° C. for overnight, after which the reaction mixture was concentrated under vacuum to give a residue that was then fractionated by Prep. reverse phase HPLC to afford the TFA salt of the title compound as a yellow solid, (4.2 mg, 19% yield). MS m/z 462 (MH$^+$); $^1$H NMR (300 MHz, CD$_3$OD) δ ppm 1.18 (m, 2 H) 1.34 (m, 2 H) 1.28–1.60 (m, 4 H) 1.76–2.34 (m, 6 H) 2.96 (m, 1 H) 3.21 (m, 1 H) 3.68 (s, 2 H) 6.05 (m, 1 H) 7.42 (d, J=7.68 Hz, 1 H) 7.81 (dd, J=8.42, 1.46 Hz, 1 H) 7.91 (dd, J=7.87, 5.67 Hz, 1 H) 8.12 (d, J=8.78 Hz, 1 H) 8.23 (s, 1 H) 8.36 (dd, J=8.05, 1.46 Hz, 1 H) 8.67 (d, J=5.49 Hz, 1 H).

Examples the unsaturated propeno-bridged intermediates described above may be converted to the corresponding propano-bridged derivatives using a variety of methods, a representative one being shown in the scheme below.

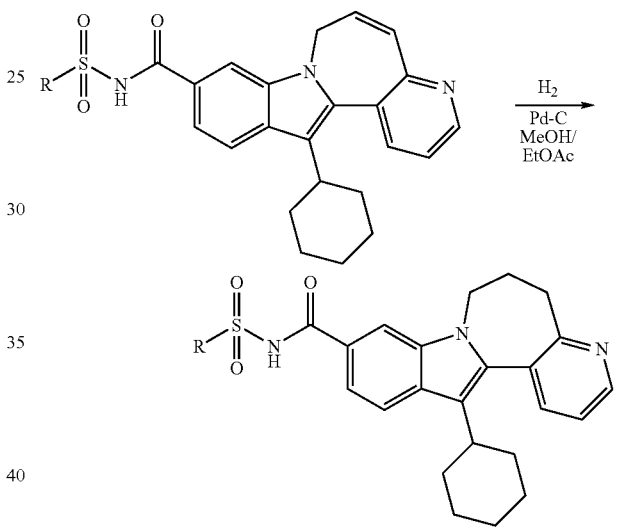

5H-pyrido[3',2':3,4]azepino[1,2-a]indole-10-carboxamide, 13-cyclohexyl-6,7-dihydro-N-(methylsulfonyl)-

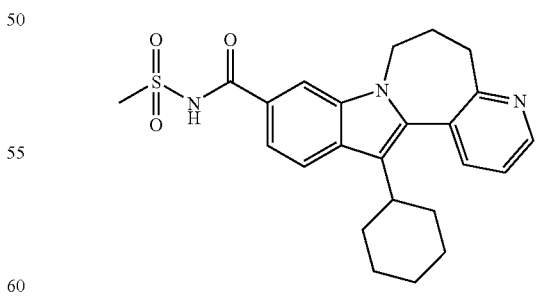

To a solution of 7H-pyrido[3',2':3,4]azepino[1,2-a]indole-10-carboxamide, 13-cyclohexyl-N-(methylsulfonyl)- (7.5 mg, 0.0137 mmol) in methanol (5 mL), 10% Pd on carbon (2 mg) was added. The reaction mixture was stirred under a hydrogen atmosphere (1 atm.) for three days. It was then filtered through celite and the filtrate concentrated under reduced pressure. The resultant residue was then purified by Prep. reverse phase HPLC to give the TFA salt of the title compound as a yellow solid, (4.7 mg, 62% yield). MS m/z 438 (MH+); $^1$H NMR (300 MHz, CD$_3$OD) ☐ ppm 1.15–2.21 (m, 10 H) 2.21–2.71 (m, 2 H) 2.75–3.20 (m, 3 H) 3.39 (s, 3 H) 3.82 (m, 1 H) 4.68 (m, 1 H) 7.64 (d, J=8.42 Hz, 1 H) 7.91–8.04 (m, 2 H) 8.16 (s, 1 H) 8.37 (d, J=8.05 Hz, 1 H) 8.73 (d, J=5.49 Hz, 1 H).

Alternatively, analogs of the above type may be accessed by directly coupling appropriate proprano-bridged carboxylate intermediates with the suitable derivitized amines to generate the fictionalized carboxamides of the instant invention, as shown in the scheme below.

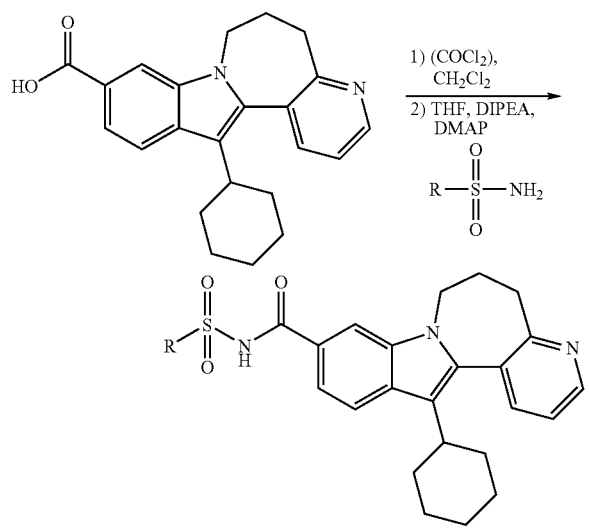

5H-pyrido[3',2':3,4]azepino[1,2-a]indole-10-carboxamide, 13-cyclohexyl-6,7-dihydro-N-(cyclopropylsulfonyl)-

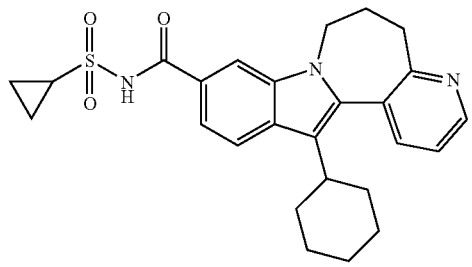

To a solution of 5H-pyrido[3',2':3,4]azepino[1,2-a]indole-10-carboxylic acid, 13-cyclohexyl-6,7-dihydro- (40 mg, 0.111 mmol) in CH$_2$Cl$_2$ (5 mL), was added one drop of DMF. A 2M solution of oxalyl chloride (0.11 mL, 0.22 mmol) in CH$_2$Cl$_2$ was then added dropwise. The reaction mixture was stirred at rt. for 2 hr. It was then concentrated and dried under high vacuum. The resultant residue was dissolved in THF(5 mL) and a solution of cyclopropanesulfonamide (26.9 mg, 0.222 mmol) and DIPEA (0.039 mL, 0.222 mmol)) in THF (2 mL) was added. DMAP (10 mg) was added after the reaction mixture was stirred at rt. for 10 min. Stirring was continued at 50° C. for 10 hr., after which the reaction mixture was concentrated under vacuum and the resultant residue was purified by Prep. reverse phase HPLC to afford the TFA salt of the title compound as a yellow solid, (31 mg, 50% yield). MS m/z 464 (MH+); $^1$H NMR (500 MHz, CD$_3$OD) ☐ppm 1.18 (m, 2 H) 1.23–2.21 (m, 12 H) 2.40 (s, br, 1 H) 2.64 (s, br, 1 H) 2.80–2.99 (m, 2 H) 3.10–3.25 (m, 2 H) 3.84 (s, br, 1 H) 4.71 (s, br, 1 H) 7.66 (d, J=8.55 Hz, 1 H) 8.00–8.07 (m, 2 H) 8.18 (s, 1 H) 8.44 (m, 1 H) 8.78 (m, 1H).

5H-pyrido[3',2':3,4]azepino[1,2-a]indole-10-carboxamide, 13-cyclohexyl-6,7-dihydro-N-(phenylsulfonyl)-

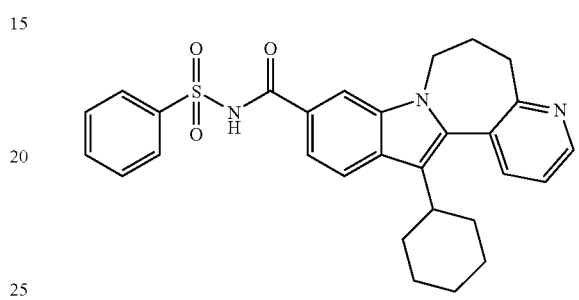

To a solution of 5H-pyrido[3',2':3,4]azepino[1,2-a]indole-10-carboxylic acid, 13-cyclohexyl-6,7-dihydro- (40 mg, 0.111 mmol) in CH$_2$Cl$_2$ (5 mL), one drop of DMF was added. A 2M solution of oxalyl chloride (0.11 mL, 0.22 mmol) in CH$_2$Cl$_2$ was then added dropwise. The reaction mixture was stirred at rt. for 2 hr. It was then concentrated and dried under high vacuum. The resultant residue was then dissolved in THF(5 mL) and a solution of benzenesulfonamide (34.9 mg, 0.222 mmol) and DIPEA (0.039 mL, 0.222 mmol)) in THF (2 mL) was added. DMAP (10 mg) was added after the reaction mixture was stirred at rt. for 10 min. Stirring was continued at 50° C. for 10 hr. The reaction mixture was then concentrated under reduced pressure and the resultant residue purified by Prep. reverse phase HPLC to afford the TFA salt of the title compound as a yellow solid, (49 mg, 72% yield). MS m/z 500 (MH+); $^1$H NMR (500 MHz, CD$_3$OD) δ ppm 1.21–2.17 (m, 10 H) 2.38 (s, br, 1 H) 2.61 (s, br, 1 H) 2.78–2.96 (m, 2 H) 3.19 (s, br, 1 H) 3.81 (s, br, 1 H) 4.68 (s, br, 1 H) 7.56 (d, J=8.55 Hz, 1 H) 7.60–7.66 (m, 2 H) 7.71 (m, 1 H) 7.98 (d, J=8.55 Hz, 1 H) 8.07 (m, 1 H) 8.10 (s, 1 H) 8.12–8.17 (m, 2 H) 8.47 (m, 1 H) 8.79 (dd, J=3.51, 1.98 Hz, 1 H).

5H-pyrido[3',2':3,4]azepino[1,2-a]indole-10-carboxamide, 13-cyclohexyl-6,7-dihydro-N-[(dimthylamino)sulfonyl]-

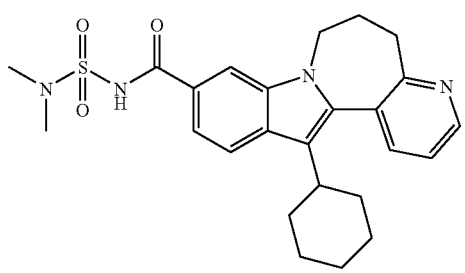

To a solution of 5H-pyrido[3',2':3,4]azepino[1,2-a]indole-10-carboxylic acid, 13-cyclohexyl-6,7-dihydro- (40 mg, 0.111 mmol) in CH$_2$Cl$_2$ (5 mL), was added one drop of DMF. A 2M solution of oxalyl chloride (0.11 mL, 0.22 mmol) in CH$_2$Cl$_2$ was then added dropwise. The reaction mixture was stirred at rt. for 2 hr. It was then concentrated and dried under high vacuum. The resultant residue was then dissolved in THF(5 mL) and a solution of N,N-dimethyl-sulfonamide (27.6 mg, 0.222 mmol) and DIPEA (0.039 mL, 0.222 mmol)) in THF (2 mL) was added. DMAP (10 mg) was added after the reaction mixture was stirred at rt. for 10 min. Stirring was continued at 50° C. for 10 hr., after which the reaction mixture was concentrated under vacuum and the product residue was then purified by Prep. reverse phase HPLC column to afford the TFA salt of the title compound as a yellow solid, (29 mg, 45% yield). MS m/z 467 (MH$^+$); $^1$H NMR (500 MHz, CD$_3$OD) □ ppm 1.21–2.21 (m, 10 H) 2.40 (s, br, 1 H) 2.64 (s, br, 1 H) 2.80–2.97 (m, 2 H) 3.04 (s, 6 H) 3.17 (m, 1 H) 3.84 (s, br, 1 H) 4.72 (m, 1 H) 7.65 (dd, J=8.39, 1.37 Hz, 1 H) 8.00–8.07 (m, 2 H) 8.17 (s, 1 H) 8.44 (m, 1 H) 8.78 (d, J=5.80 Hz, 1 H)

5H-pyrido[3',2':3,4]azepino[1,2-a]indole-10-carboxamide, 13-cyclohexyl-6,7-dihydro-N-[(1-methyl-1H-imidazol-4-yl)sulfonyl]-

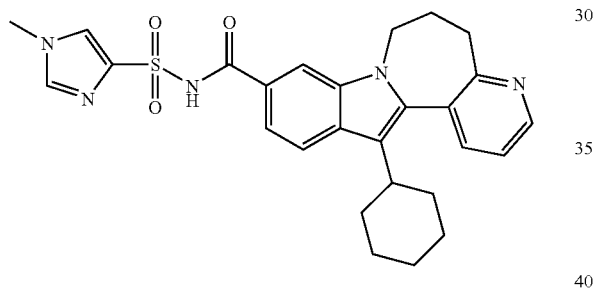

To a solution of 5H-pyrido[3',2':3,4]azepino[1,2-a]indole-10-carboxylic acid, 13-cyclohexyl-6,7-dihydro- (40 mg, 0.111 mmol) in CH$_2$Cl$_2$ (5 mL), one drop of DMF was added. A 2M solution of oxalyl chloride (0.11 mL, 0.22 mmol) in CH$_2$Cl$_2$ was then added dropwise. The reaction mixture was stirred at rt. for 2 hr. It was then concentrated and dried under high vacuum. The resultant residue was then dissolved in THF(5 mL) and a solution of 1-methyl-imidazole-4-sulfonamide (35.8 mg, 0.222 mmol) and DIPEA (0.039 mL, 0.222 mmol)) in DMF (2 mL) was added. DMAP (10 mg) was added after the reaction mixture was stirred at rt. for 10 min. Stirring was continued stirring at 50° C. for 10 hr. The reaction mixture was then concentrated under reduced pressure and the product residue was then purified by Prep. reverse phase HPLC to afford the TFA salt of the title compound as a yellow solid, (36 mg, 53% yield). MS m/z 504 (MH$^+$); $^1$H NMR (500 MHz, CD$_3$OD) □ ppm 1.21–2.18 (m, 10 H) 2.41 (s, br, 1 H) 2.65 (s, br, 1 H) 2.79–2.99 (m, 2 H) 3.22 (m, 1 H) 3.74–3.96 (m, 4 H) 4.71 (s, br, 1 H) 7.60 (d, J=8.55 Hz, 1 H) 7.82 (s, 1 H) 7.98–8.03 (m, 2 H) 8.09 (m, 1 H) 8.17 (s, 1 H) 8.50 (d, J=7.94 Hz, 1 H) 8.81 (d, J=5.80 Hz, 1 H).

Some representative methodology that can be applied to the syntheses of some bridged indole tetrazole derivatives of the instant invention is described in the scheme below.

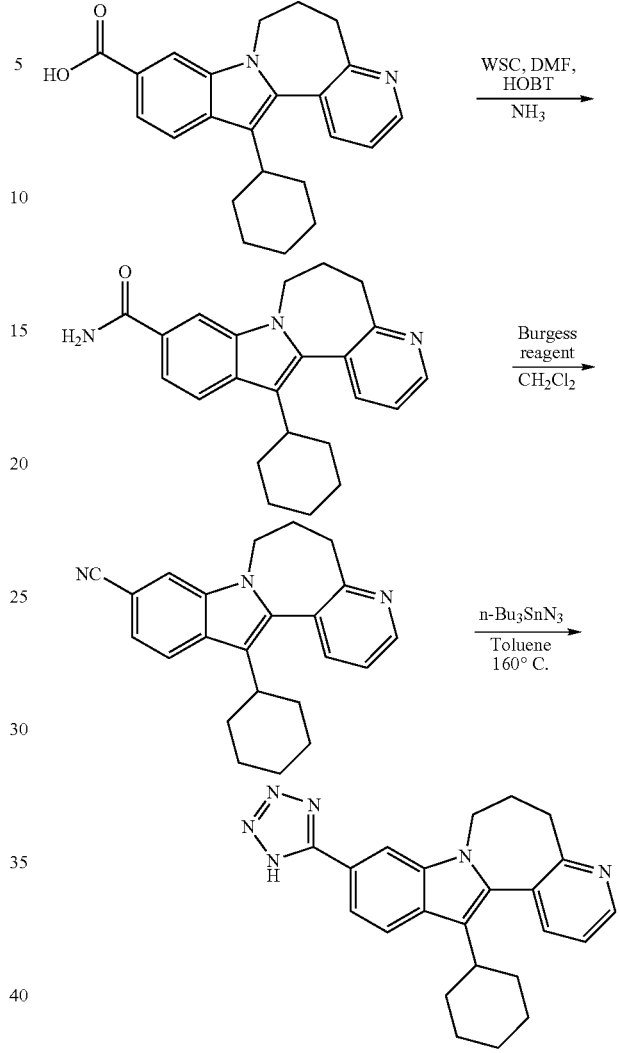

5H-pyrido[3',2':3,4]azepino[1,2-a]indole-10-carboxamide, 13-cyclohexyl-6,7-dihydro-

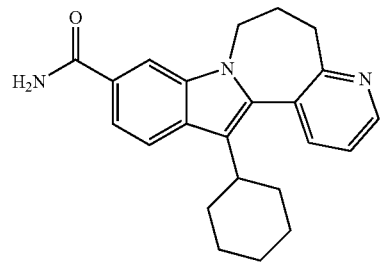

To a solution of 5H-pyrido[3',2':3,4]azepino[1,2-a]indole-10-carboxylic acid, 13-cyclohexyl-6,7-dihydro- (100 mg, 0.277 mmol) in DMF (2.0 mL), N-3-dimethylaminopropyl)-N'-ethylcarbodiimide hydrochloride (80 mg, 0.416 mmol) and HOBt (56.2 mg, 0.416 mmol) were added. The reaction mixture was stirred at rt. for 1 hr. A 0.5M solution of ammonia in dioxane (2.0 mL, 1.0 mmol) was then added.

The reaction mixture was then stirred at rt. overnight, after which it was concentrated and then diluted with water. The mixture was then extracted using ethyl acetate (2×30 mL) and the combined extracts were dried (MgSO$_4$), filtered and concentrated to give the title compound as a yellowish solid, (100 mg, 100% yield). MS m/z 360 (MH$^+$); $^1$H NMR (300 MHz, CD$_3$OD) □ ppm 1.31 (m, 1 H) 1.39–1.56 (m, 2 H) 1.67 (m, 1 H) 1.77–2.18 (m, 6 H) 2.26 (m, 1 H) 2.51 (m, 1 H) 2.72 (m, 1 H) 2.87 (m, 1 H) 2.95 (m, 1 H) 3.70 (m, 1 H) 4.62 (m, 1 H) 7.53 (dd, J=7.63, 4.88 Hz, 1 H) 7.61 (dd, J=8.55, 1.53 Hz, 1 H) 7.88 (dd, J=7.78, 1.37 Hz, 1 H) 7.92 (d, J=8.54 Hz, 1 H) 8.08 (s, 1 H) 8.54 (dd, J=5.04, 1.37 Hz, 1 H).

5H-pyrido[3',2':3,4]azepino[1,2-a]indole-10-carbonitrile, 13-cyclohexyl-6,7-dihydro-

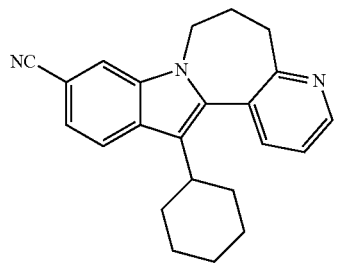

To a solution of 5H-pyrido[3',2':3,4]azepino[1,2-a]indole-10-carboxamide, 13-cyclohexyl-6,7-dihydro- (50 mg, 0.139 mmol) in CH$_2$Cl$_2$ (3 mL), Burgess reagent (132 mg, 0.556 mmol) was added. The reaction mixture was stirred at rt for 5 hr. It was then concentrated under vacuum and the residue was purified by flash column chromatography (silica gel, ethyl acetate) to afford the title compound as a white solid, (42 mg, 88% yield). MS m/z 342 (MH$^+$); $^1$H NMR (500 MHz, CD$_3$OD) δ ppm 1.31 (m, 1 H) 1.41–1.53 (m, 2 H) 1.65 (m, 1 H) 1.77–1.87 (m, 2 H) 1.92–2.16 (m, 4 H) 2.24 (m, 1 H) 2.51 (m, 1 H) 2.69 (m, 1 H) 2.88 (m, 1 H) 2.95 (m, 1 H) 3.69 (m, 1 H) 4.63 (m, 1 H) 7.33 (dd, J=8.24, 1.22 Hz, 1 H) 7.54 (dd, J=7.63, 5.19 Hz, 1 H) 7.89 (dd, J=7.63, 1.53 Hz, 1 H) 7.97 (s, 1 H) 8.01 (d, J=8.24 Hz, 1 H) 8.56 (dd, J=4.88, 1.53 Hz, 1 H)

5H-pyrido[3',2':3,4]azepino[1,2-a]indole, 13-cyclohexyl-6,7-dihydro-10-(1H-tetrazol-5-yl)-

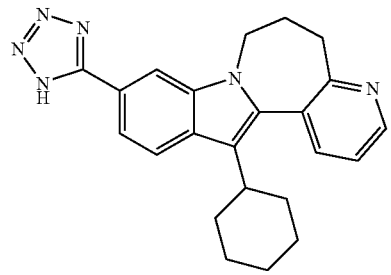

To a solution of 5H-pyrido[3',2':3,4]azepino[1,2-a]indole-10-carbonitrile, 13-cyclohexyl-6,7-dihydro- (23.5 mg, 0.0688 mmol) in toluene (1.5 mL), tributyltin azide (0.056 mL, 0.206 mmol) was added. The reaction mixture was heated in a sealed tube at 160° C. under microwave conditions for 1.5 hr. It was then concentrated under vacuum and the residue was purified by sequential use of Prep. reverse phase HPLC and flash column chromatography (silica gel, ethyl acetate to methanol) to afford the title compound as a light yellow solid, (14 mg, 52% yield). MS m/z 385 (MH$^+$); $^1$H NMR (500 MHz, CD$_3$OD) δ ppm 1.31 (m, 1 H) 1.40–1.55 (m, 2 H) 1.69 (m, 1 H) 1.78–1.90 (m, 2 H) 1.93–2.33 (m, 5 H) 2.54 (m, 1 H) 2.77 (m, 1 H) 2.87 (m, 1 H) 2.95 (m, 1 H) 3.70 (m, 1 H) 4.63 (m, 1 H) 7.51 (dd, J=7.63, 4.88 Hz, 1 H) 7.79 (d, J=8.24 Hz, 1 H) 7.87 (dd, J=7.63, 1.53 Hz, 1 H) 7.93 (d, J=8.55 Hz, 1 H) 8.14 (s, 1 H) 8.51 (dd, J=5.19, 1.53 Hz, 1 H).

Some representative methodology for the synthesis of N-alkylated amide derivatives of the instant invention is outlined in the scheme depicted below.

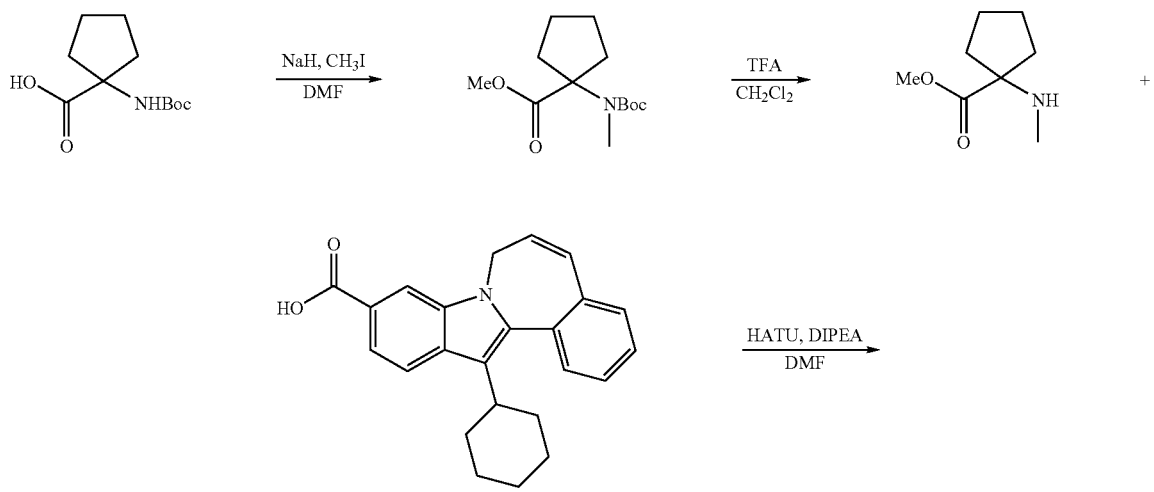

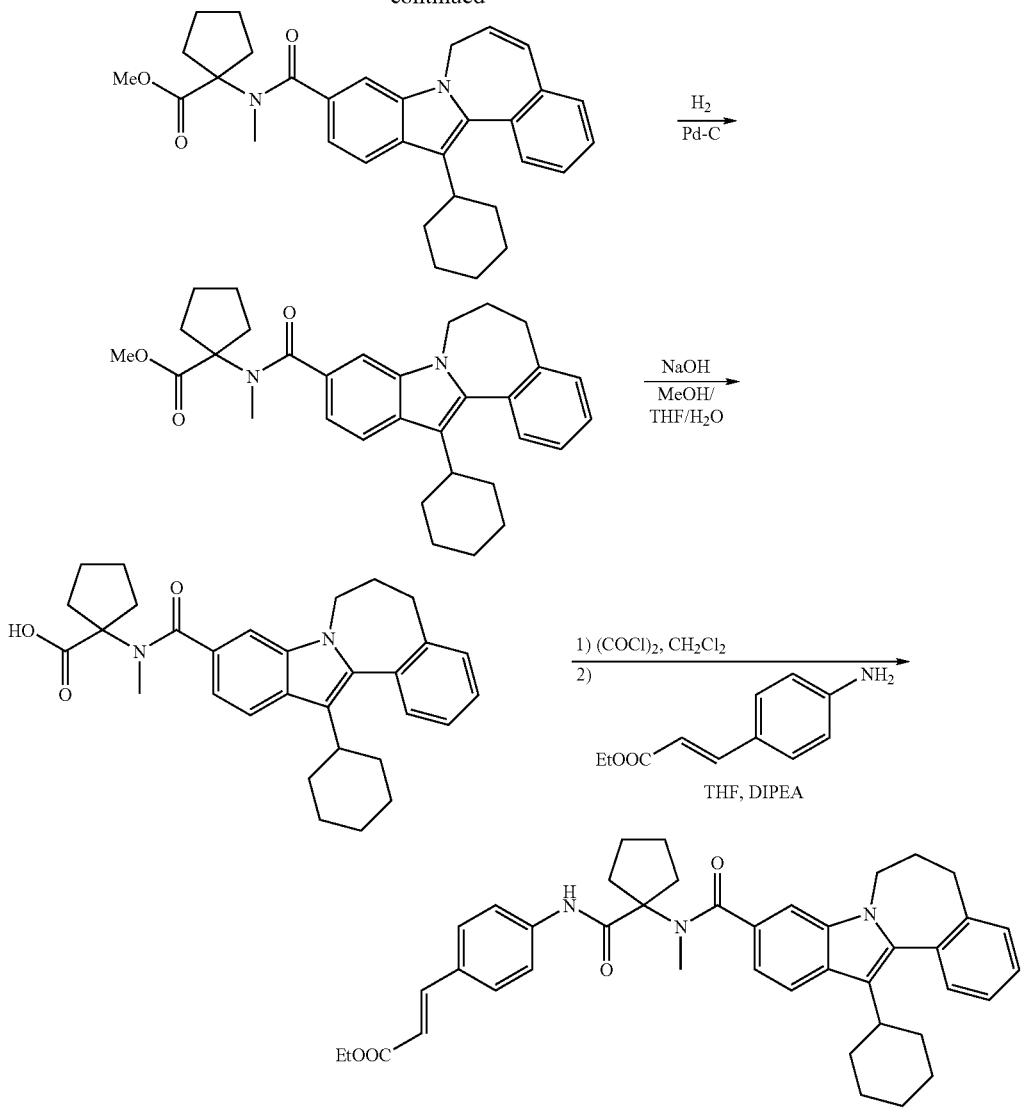

Methyl 1-(tert-butoxycarbonyl)cyclopentanecarboxylate

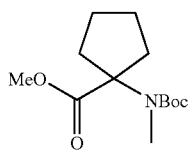

To a solution of 1-(boc-amino)cyclopentane carboxylic acid (2.29 g, 10 mmol) in DMF (20 mL), NaH (0.92 g in 60% oil dispersion, 23 mmol) was added at 0° C. The reaction mixture was stirred at 0° C. for 15 min. Methyl iodide (1.37 mL, 22 mmol) was then added, and the reaction mixture was allowed to warm to rt. and stirring was continued overnight. The reaction was then quenched by the addition of water, and the solution acidified by the addition of 1N HCl solution. The resultant mixture was then extracted with ethyl acetate (2×50 mL). The organic layers were combined, washed with water, brine, dried (MgSO$_4$), and then filtered. Evaporation of the solvent gave the title compound as a brown-reddish oil, (2.5 g, 97% yield). MS m/z 280(M+Na$^+$); $^1$H NMR (500 MHz, CD$_3$OD) δ ppm 1.43 (s, 9 H) 1.71–1.78 (m, 4 H) 2.01 (m, 2 H) 2.29 (m, 2 H) 2.98 (s, 3 H) 3.70 (s, 3 H).

Methyl 1-(methylamino)cyclopentanecarboxylate

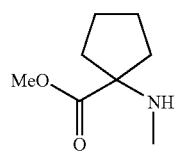

To a solution of methyl 1-(tert-butoxycarbonyl)cyclopentanecarboxylate (0.5 g, 1.944 mmol) in CH$_2$Cl$_2$ (10 mL), TFA(1.5 mL) was added. The reaction mixture was stirred at rt. for 2 hr. It was then concentrated down to give the TFA of the title compound as a brownish colored oil, (0.68 g, >100% yield). MS m/z 158 (MH⁺); ¹H NMR (300 MHz, CD₃OD) δ ppm 1.85–2.05 (m, 6 H) 2.34 (m, 2 H) 2.72 (s, 3 H) 3.88 (s, 3 H).

Cyclopentanecarboxylic acid, 1-[[(13-cyclohexyl-7H-indolo[2,1-a][2]benzazepin-10-yl)carbonylmethylamino]-, methyl ester

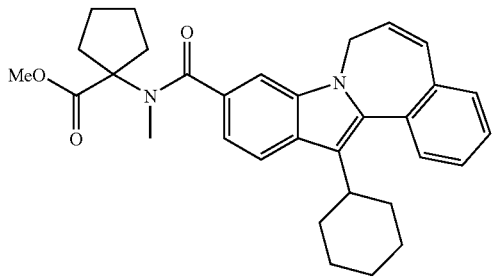

To a solution of 7H-indolo[2,1-a][2]benzazepine-10-carboxylic acid, 13-cyclohexyl- (36 mg, 0.1007 mmol) in DMF (1.0 mL), HATU (57.5 mg, 0.1511 mmol) and DIPEA (0.088 mL, 0.5035 mmol) were added. The reaction mixture was stirred at rt for 15 min. Methyl 1-(methylamino)cyclopentane carboxylate TFA salt (41 mg, 0.1511 mmol) was then added and the reaction mixture was stirred at rt for five days. It was then concentrated under vacuum and the residue was purified by Prep. reverse phase HPLC to give the title compound as a yellowish solid, (15 mg, 30% yield). MS m/z 497 (MH⁺); ¹H NMR (500 MHz, CDCl₃) ☐ ppm 1.06–1.58 (m, 4 H) 1.65–2.07 (m, 12 H) 2.39 (m, 2 H) 2.79 (m, 1 H) 3.08 (s, 3 H) 3.68 (s, 3 H) 4.12 (s, br, 1 H) 4.78 (s, br, 1 H) 6.22 (m, 1 H) 6.75 (d, J=10.38 Hz, 1 H) 7.03 (dd, J=8.39, 1.37 Hz, 1 H) 7.29 (m, 1 H) 7.33–7.36 (m, 2 H) 7.46 (m, 1 H) 7.49 (s, 1 H) 7.79 (d, J=8.24 Hz, 1 H)

Cyclopentanecarboxylic acid, 1-[[(13-cyclohexyl-6,7-dihydro-5H-indolo[2,1-a][2]benzazepin-10-yl)carbonyl]methylamino]-, methyl ester

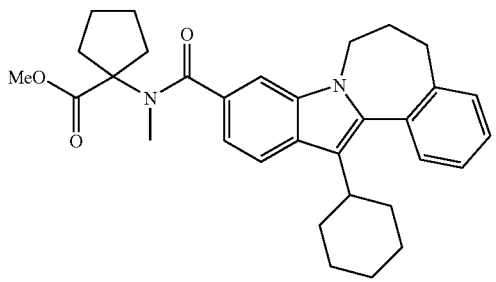

To a solution of 7H-indolo[2,1-a][2]benzazepine-10-carboxylic acid, 13-cyclohexyl- (150 mg, 0.42 mmol) in DMF (3.0 mL), HATU (240 mg, 0.63 mmol) and DIPEA (0.37 mL, 2.1 mmol) were added. The reaction mixture was stirred at rt for 15 min. Methyl 1-(methylamino)cyclopentane carboxylate TFA salt (171 mg, 0.63 mmol) was then added and the reaction mixture was stirred at rt for three days. It was then quenched by the addition of 1N HCl solution and then extracted using ethyl acetate (2×30 mL). The organic layers were combined, dried (MgSO₄), filtered and concentrated in vacuo. The resultant residue was dissolved in methanol/ethyl acetate (30 mL/30 mL) and 10% Pd on carbon (10 mg) was added. The reaction mixture was stirred under a hydrogen atmosphere (1 atm.) overnight. It was then filtered through celite and the filtrand washed with methanol/ethyl acetate. The combined filtrates and washings were concentrated under vacuum and the residue was purified by Prep. reverse phase HPLC to give the title compound as a light yellow solid, (70 mg, 33% yield). MS m/z 499 (MH); ¹H NMR (500 MHz, CD₃OD) δ ppm 1.27 (m, 1 H) 1.36–1.53 (m, 2 H) 1.61 (m, 1 H) 1.73–1.89 (m, 6 H) 1.94 (m, 1 H) 1.97–2.19 (m, 6 H) 2.36 (m, 1 H) 2.42–2.54 (m, 3 H) 2.71 (dd, J=13.43, 6.41 Hz, 1 H) 2.94 (m, 1 H) 3.18 (s, 3 H) 3.62 (m, 1 H) 3.75 (s, 3 H) 4.47 (dd, J=14.50, 6.56 Hz, 1 H) 7.11 (m, 1 H) 7.33–7.43 (m, 4 H) 7.54 (s, 1 H) 7.88 (d, J=8.24 Hz, 1 H).

Cyclopentanecarboxylic acid, 1-[[(13-cyclohexyl-6,7-dihydro-5H-indolo[2,1-a][2]benzazepin-10-yl)carbonyl]methylamino]-

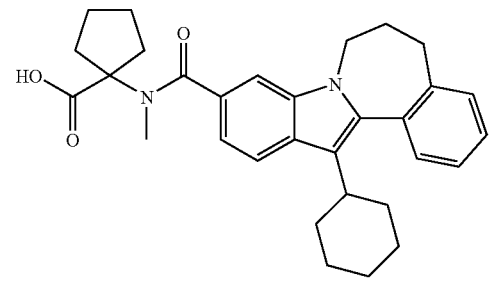

A 2N NaOH solution (1.0 mL) was added to a solution of cyclopentanecarboxylic acid, 1-[[(13-cyclohexyl-6,7-dihydro-5H-indolo[2,1-a][2]benzazepin-10-yl)carbonyl]methylamino]-, methyl ester (65 mg, 0.13 mmol) in a THF/Methanol mixture (2.0 mL/2.0 mL) in a sealed tube. The reaction was heated at 100° C. under microwave conditions for 15 min. It was then concentrated under reduced pressure and the pH was adjusted to 4–5 using 1N HCl solution. The resultant mixture was then extracted with ethyl acetate and the organic layer was dried with MgSO₄, filtered and concentrated in vacuo to give the crude title compound as a yellow colored solid, (58 mg, 92% yield). 5 mg of this material was then purified by Prep. reverse phase HPLC to afford the pure title compound as a yellow solid. MS m/z 485 (MH⁺); ¹H NMR (500 MHz, CD₃OD) ☐ ppm 1.30 (m, 1 H) 1.38–1.55 (m, 2 H) 1.64 (m, 1 H) 1.77–2.22 (m, 13 H) 2.39 (m, 1 H) 2.44–2.55 (m, 3 H) 2.74 (dd, J=13.43, 6.71 Hz, 1 H) 2.95 (m, 1 H) 3.20 (s, 3 H) 3.65 (m, 1 H) 4.50 (dd, J=14.50, 6.87 Hz, 1 H) 7.13 (d, J=8.24 Hz, 1 H) 7.36–7.44 (m, 4 H) 7.56 (s, 1 H) 7.89 (d, J=8.24 Hz, 1 H)

2-propenoic acid, 3-[4-[[[1-[[(13-cyclohexyl-6,7-dihydro-5H-indolo[2,1-a][2]benzazepin-10-yl)carbonyl]methylamino]cyclopentyl]carbonyl]amino]phenyl]-, ethyl ester, (2E)-

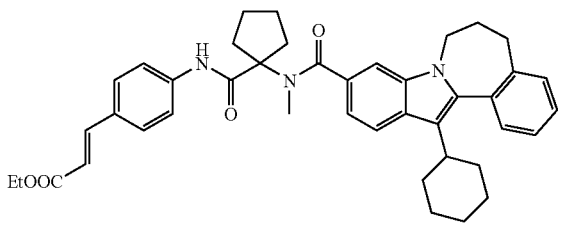

To a solution of cyclopentanecarboxylic acid, 1-[[(13-cyclohexyl-6,7-dihydro-5H-indolo[2,1-a][2]benzazepin-10-yl)carbonyl]methylamino]- (36 mg, 0.0741 mmol) in CH₂Cl₂ (5 mL), one drop of DMF was added. A 2M solution of oxalyl chloride (0.048 mL, 0.096 mmol) in CH₂Cl₂ was then added dropwise. The reaction mixture was stirred at rt. for 2 hr. It was then concentrated and dried under high vacuum. The residue was then dissolved in THF(5 mL) and a solution of ethyl 4-aminocinnamate (21 mg, 0.111 mmol) and DIPEA (0.026 mL, 0.149 mmol)) in THF (2 mL) was added. The reaction mixture was stirred at rt. overnight. It was concentrated under vacuum and the residue was purified sequentially using silica gel flash chromatography using hexanes to ethyl acetate as eluent and Prep. reverse phase HPLC to afford the title compound as an off-white solid, (8 mg, 16% yield). MS m/z 658 (MH⁺); ¹H NMR (500 MHz, CD₃OD) ☐ ppm 1.29–1.52 (m, 6 H) 1.64 (m, 1 H) 1.77–2.23 (m, 13 H) 2.33–2.53 (m, 2 H) 2.63–2.70 (m, 2 H) 2.73 (m, 1 H) 2.95 (m, 1 H) 3.23 (s, 3 H) 3.65 (m, 1 H) 4.25 (q, J=7.12 Hz, 2 H) 4.50 (dd, J=14.65, 6.71 Hz, 1 H) 6.46 (d, J=15.87 Hz, 1 H) 7.25 (d, J=8.24 Hz, 1 H) 7.36–7.44 (m, 4 H) 7.57–7.61 (m, 2 H) 7.63–7.69 (m, 4 H) 7.90 (d, J=8.55 Hz, 1 H).

2-propenoic acid, 3-[4-[[[1-[[(13-cyclohexyl-6,7-dihydro-5H-pyrido[3',2':3,4]azepino[1,2-a]indol-10-yl)carbonyl]amino]cyclopentyl]carbonyl]amino]phenyl]-, methyl ester, (2E)-

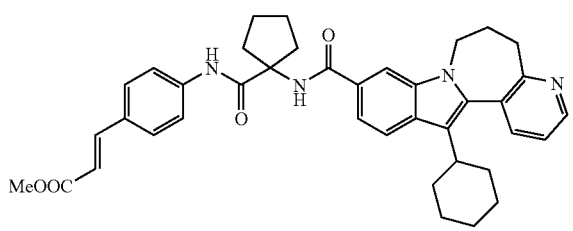

To a solution of 5H-pyrido[3',2':3,4]azepino[1,2-a]indole-10-carboxylic acid, 13-cyclohexyl-6,7-dihydro- (135 mg, 0.375 mmol) in DMSO (5.0 mL), TBTU (180 mg, 0.5625 mmol) and DIPEA (0.33 mL, 1.875 mmol) were added. The reaction mixture was stirred at rt for 15 min. Then (E)-methyl 3-(4-(1-aminocyclopentanecarboxamido)phenyl)acrylate (130 mg, 0.449 mmol) was added and the reaction mixture was stirred at rt overnight. It was then concentrated and the residue purified by Prep. reverse phase HPLC to give the title compound as an off-white solid, (90 mg, 38% yield). MS m/z 631(MH⁺); ¹H NMR (500 MHz, CD₃OD) ☐ ppm 1.27 (m, 1 H) 1.36–1.55 (m, 2 H) 1.63 (m, 1 H) 1.73–2.27 (m, 13 H) 2.43–2.55 (m, 3 H) 2.68 (m, 1 H) 2.85 (m, 1 H) 2.92 (m, 1 H) 3.67 (m, 1 H) 3.76 (s, 3 H) 4.64 (m, 1 H) 6.44 (d, J=16.17 Hz, 1 H) 7.47–7.67 (m, 7 H) 7.84 (m, 1 H) 7.91 (d, J=8.55 Hz, 1 H) 8.10 (s, 1 H) 8.51 (d, J=1.83 Hz, 1 H).

As described in other sections of this document, certain fused heterocyclic examples of the instant invention may be accessed using the methodology described in the scheme outlined below.

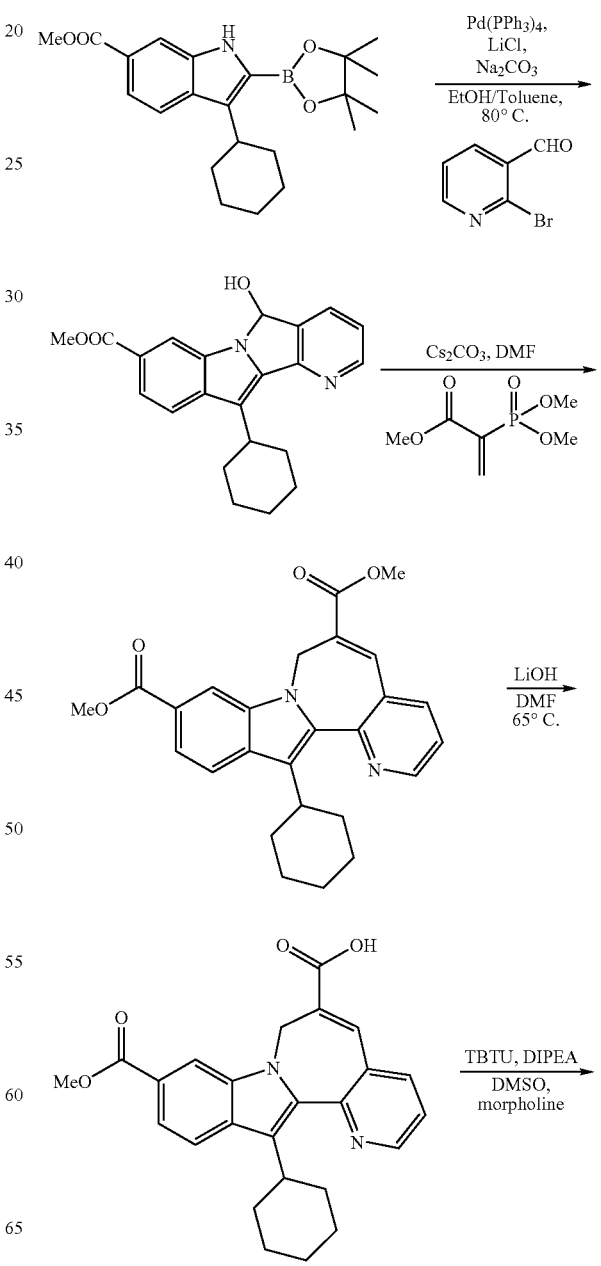

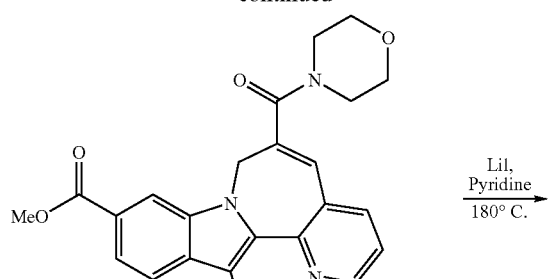

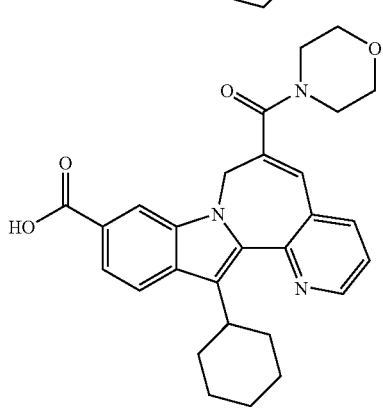

5H-pyrido[2',3':3,4]pyrrolo[1,2-a]indole-8-carboxylic acid, 11-cyclohexyl-5-hydroxy-, methyl ester

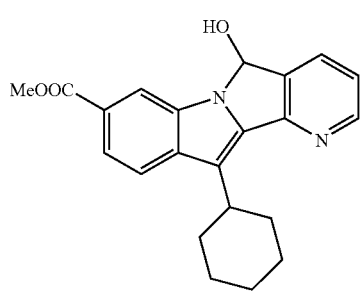

A 2M aqueous solution of $Na_2CO_3$ (3.75 mL, 7.5 mmol) was added to a mixture of; methyl 3-cyclohexyl-2-(4,4,5,5-tetramethyl-1,3,2-dioxaborolan-2-yl)-1H-indole-6-carboxylate (1150 mg, 3.0 mmol), 2-bromo-3-pyridinecarboxaldehyde (670 mg, 3.6 mmol) and LiCl (254 mg, 6.0 mmol), in ethanol (10 mL) and toluene (10 mL). The resultant mixture was degassed by the application of vacuum followed by flushing with $N_2$. Pd(PPh$_3$)$_4$ (173 mg, 0.15 mmol) was then added, and the reaction mixture was heated at 80° C. for 14 hr. It was then filtered and concentrated under reduced pressure. The residue was triturated with ether to give the title compound as a light yellow solid, (800 mg, 74% yield). MS m/z 363(MH$^+$); $^1$H NMR (300 MHz, DMSO-D6) δ ppm 1.35–1.55 (m, 3 H) 1.69–1.92 (m, 5 H) 2.05–2.23 (m, 2 H) 3.31 (m, 1 H) 3.88 (s, 3 H) 6.73 (s, 1 H) 7.35 (dd, J=7.68, 5.12 Hz, 1 H) 7.44 (s, 1 H) 7.66 (dd, J=8.42, 1.46 Hz, 1 H) 7.84 (d, J=8.42 Hz, 1 H) 7.97 (d, J=6.59 Hz, 1 H) 8.25 (s, 1 H) 8.66 (d, J=3.66 Hz, 1 H)

7H-pyrido[2',3':3,4]azepino[1,2-a]indole-6,10-dicarboxylic acid, 13-cyclohexyl-, dimethyl ester

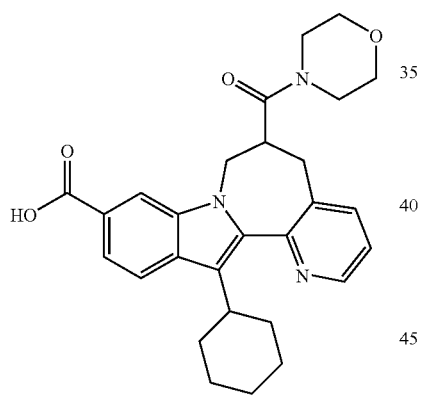

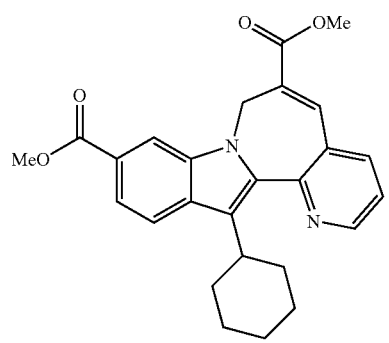

To a solution of 5H-pyrido[2',3':3,4]pyrrolo[1,2-a]indole-8-carboxylic acid, 11-cyclohexyl-5-hydroxy-, methyl ester (500 mg, 1.38 mmol) in DMF (8 mL), $Cs_2CO_3$ (674 mg, 2.07 mmol) and trimethyl-2-phosphonoacrylate (348 mg, 1.79 mmol) were added. The reaction mixture was heated at 60° C. for 4 hr. It was then diluted with water after which a yellow precipitate formed. This was collected by filtration and dried under vacuum to give the title compound as a yellow powder, (500 mg, 84% yield). MS m/z 431 (MH$^+$); $^1$H NMR (300 MHz, DMSO-D6) □ ppm 1.18–1.42 (m, 3 H) 1.66–1.83 (m, 5 H) 1.85–2.04 (m, 2 H) 3.30 (m, 1 H) 3.80 (s, 3 H) 3.90 (s, 3 H) 4.98 (s, 2 H) 7.57 (dd, J=7.87, 4.57 Hz, 1 H) 7.64 (d, J=8.42 Hz, 1 H) 7.92 (s, 1 H) 7.96 (d, J=8.78 Hz, 1 H) 8.13 (dd, J=8.23, 1.65 Hz, 1 H) 8.21 (s, 1 H) 8.84 (dd, J=4.76, 1.83 Hz, 1 H).-

7H-pyrido[2',3':3,4]azepino[1,2-a]indole-6,10-dicarboxylic acid, 13-cyclohexyl-, 10-methyl ester

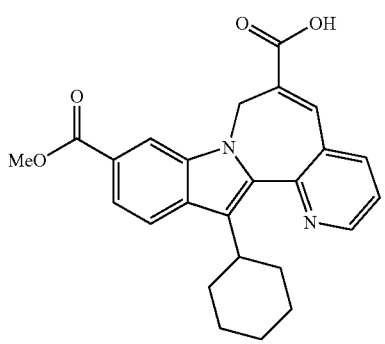

To a solution of 7H-pyrido[2',3':3,4]azepino[1,2-a]indole-6,10-dicarboxylic acid, 13-cyclohexyl-, dimethyl ester (150 mg, 0.348 mmol) in DMF (4 mL), LiOH (50 mg, 2.091 mmol) was added. The reaction mixture was heated in a sealed tube under microwave conditions at 65° C. for 1 hr 15 min. Water was then added and the mixture acidified to pH 4–5 using 1N HCl solution. A precipitate formed which was collected by filtration to give the title compound as a yellow solid, (150 mg, >100% yield). MS m/z 417(MH$^+$); $^1$H NMR (500 MHz, DMSO-D6) δ ppm 1.21–1.43 (m, 3 H) 1.66–1.82 (m, 5 H) 1.88–2.00 (m, 2 H) 3.29 (m, 1 H) 3.90 (s, 3 H) 4.97 (s, 2 H) 7.57 (dd, J=7.93, 4.58 Hz, 1 H) 7.65 (dd, J=8.55, 1.53 Hz, 1 H) 7.88 (s, 1 H) 7.96 (d, J=2.44 Hz, 1 H) 8.11 (dd, J=8.09, 1.37 Hz, 1 H) 8.20 (s, 1 H) 8.83 (dd, J=4.73, 1.68 Hz, 1 H)

7H-pyrido[2',3':3,4]azepino[1,2-a]indole-10-carboxylic acid, 13-cyclohexyl-6-(4-morpholinylcarbonyl)-, methyl ester

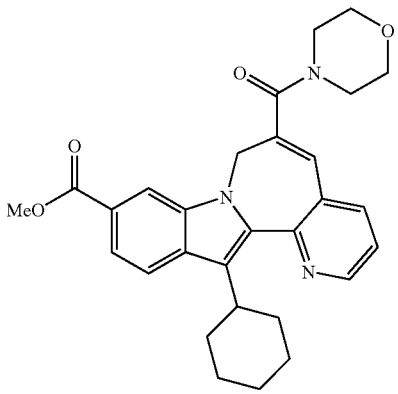

To a solution of 7H-pyrido[2',3':3,4]azepino[1,2-a]indole-6,10-dicarboxylic acid, 13-cyclohexyl-, 10-methyl ester (150 mg, 0.36 mmol) in DMSO (3.0 mL), TBTU (173 mg, 0.54 mmol) and DIPEA (0.314 mL, 1.8 mmol) were added. The reaction mixture was stirred at rt for 15 min. Then morpholine (0.047 mL, 0.54 mmol) was added and the reaction mixture was stirred at rt overnight. It was then concentrated and the residue was purified by Prep. reverse phase HPLC to provide the desired material as a light yellow solid, (105 mg, 60% yield). MS m/z 486(MH$^+$); $^1$H NMR (500 MHz, CD$_3$OD) ☐ ppm 1.26–1.51 (m, 3 H) 1.72–1.92 (m, 5 H) 1.93–2.13 (m, 2 H) 3.31 (m, 1H) 3.41–3.77 (m, 8 H) 3.97 (s, 3 H) 4.89 (s, 2H) 7.02 (s, 1 H) 7.52 (dd, J=7.93, 4.88 Hz, 1 H) 7.74 (dd, J=8.55, 1.22 Hz, 1 H) 7.88–8.05 (m, 2 H) 8.29 (s, 1 H) 8.77 (dd, J=4.73, 1.68 Hz, 1 H)

7H-pyrido[2',3':3,4]azepino[1,2-a]indole-10-carboxylic acid, 13-cyclohexyl-6-(4-morpholinylcarbonyl)-

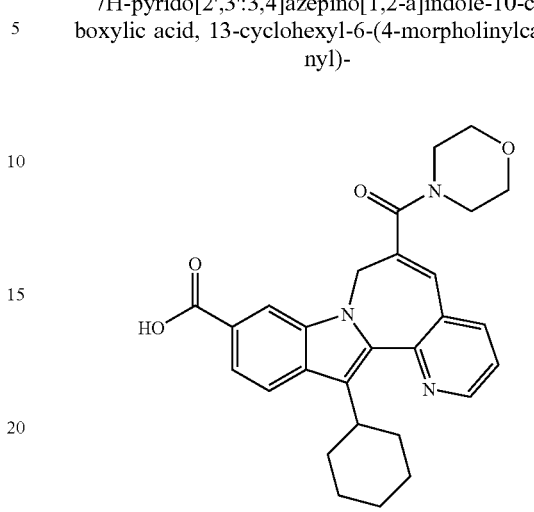

LiI (69.5 mg, 0.519 mmol) was added to a solution of 7H-pyrido[2',3':3,4]azepino[1,2-a]indole-10-carboxylic acid, 13-cyclohexyl-6-(4-morpholinylcarbonyl)-, methyl ester (84 mg, 0.173 mmol) in pyridine (4 mL) in a sealed tube. The reaction mixture was then heated at 180° C. under microwave conditions for 2 hr. Water was added, and the pH of the resultant mixture was adjusted to 4–5 using 1N HCl solution. This mixture was then extracted with ethyl acetate (2×20 mL) and the organic layers were combined, dried (MgSO$_4$), filtered and concentrated in vacuo. The resultant residue was purified by Prep. reverse phase HPLC to afford the TFA salt of the desired product as a yellow solid, (66 mg, 65% yield). MS m/z 472(MH$^+$); $^1$H NMR (500 MHz, CD$_3$OD) ☐ ppm 1.29–1.48 (m, 3 H) 1.73–1.93 (m, 5 H) 1.99–2.10 (m, 2 H) 3.26 (m, 1 H) 3.37–3.70 (m, 8 H) 4.91 (s, 2H) 7.03 (s, 1 H) 7.59 (dd, J=7.93, 4.88 Hz, 1 H) 7.77 (dd, J=8.55, 1.53 Hz, 1 H) 7.98 (d, J=8.55 Hz, 1 H) 8.01–8.06 (m, 1 H) 8.30 (s, 1 H) 8.80 (dd, J=4.88, 1.53 Hz, 1 H)

5H-pyrido[2',3':3,4]azepino[1,2-a]indole-10-carboxylic acid, 13-cyclohexyl-6,-7-dihydro-6-(4-morpholinylcarbonyl)-

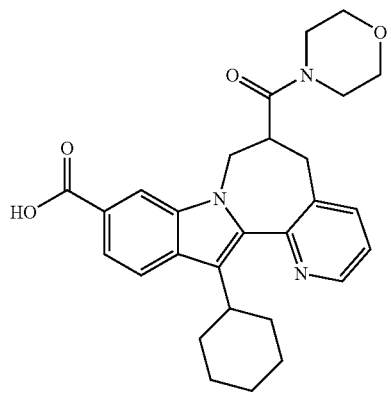

To a solution of 7H-pyrido[2',3':3,4]azepino[1,2-a]indole-10-carboxylic acid, 13-cyclohexyl-6-(4-morpholinylcarbonyl)- (10 mg, 0.017 mmol) in methanol (5 mL), 10% Pd on carbon (3 mg) was added. The reaction mixture was then stirred under a hydrogen atmosphere (1 atm.) for 2 days. It was filtered through celite and the filtrand washed with methanol. The combined filtrates and washings were concentrated under vacuum and the residue was purified by Prep. reverse phase HPLC to give the TFA salt of the title compound as yellow solid, (5.0 mg, 50% yield). MS m/z 474(MH+); $^1$H NMR (500 MHz, CD$_3$OD) ☐ ppm 1.36–1.48 (m, 3 H) 1.77–1.96 (m, 5 H) 2.00–2.11 (m, 2 H) 2.82 (dd, J=14.04, 6.71 Hz, 1 H) 2.94 (m, 1 H) 3.10 (m, 1 H) 3.58 (m, 1 H) 3.65–3.91 (m, 8 H) 4.21–4.45 (m, 2 H) 7.72 (dd, J=7.63, 5.49 Hz, 1 H) 7.78 (d, J=8.55 Hz, 1 H) 7.99 (d, J=8.55 Hz, 1 H) 8.19–8.24 (m, 2 H) 8.78 (dd, J=5.19, 1.53 Hz, 1 H).

As described elsewhere in this document, the intermediate acids shown above may be coupled to a variety of amines or other nucleophiles using a variety of methods known to those skilled in the art, to give additional examples of the instant invention, as outlined in the scheme below.

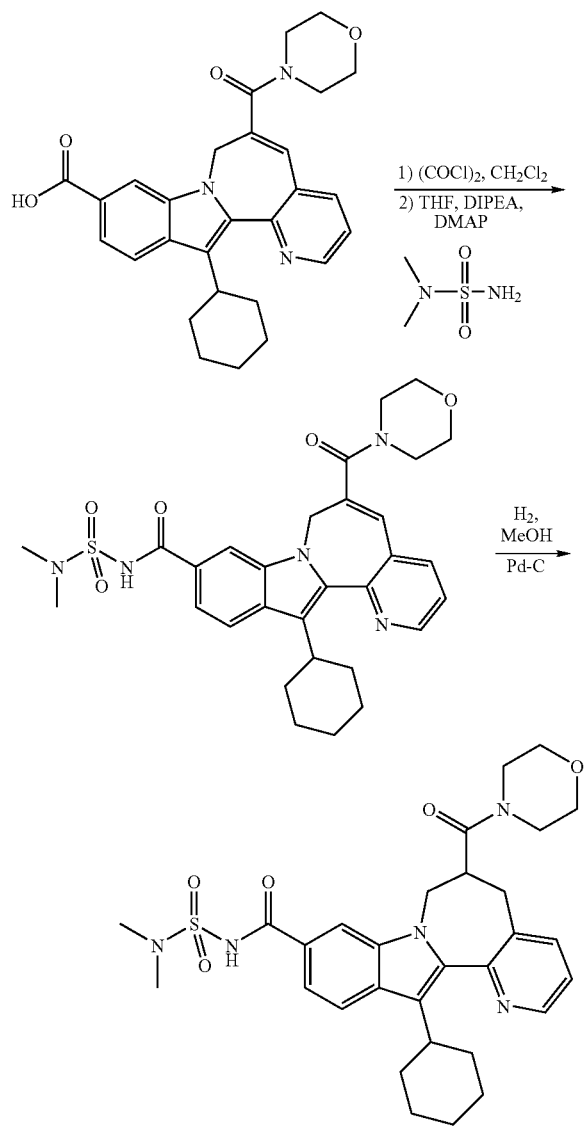

7H-pyrido[2',3':3,4]azepino[1,2-a]indole-10-carboxamide, 13-cyclohexyl-N-[(dimethylamino)sulfonyl]-6-(4-morpholinylcarbonyl)-

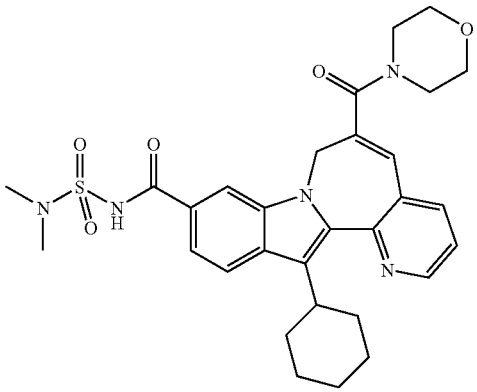

To a solution of 7H-pyrido[2',3':3,4]azepino[1,2-a]indole-10-carboxylic acid, 13-cyclohexyl-6-(4-morpholinylcarbonyl)- (56 mg, 0.096 mmol) in CH$_2$Cl$_2$ (10 mL), one drop of DMF was added. A 2M solution of oxalyl chloride (0.096 mL, 0.191 mmol) in CH$_2$Cl$_2$ was then added dropwise. The reaction mixture was stirred at rt. for 2 hr. It was concentrated and dried under high vacuum. The resultant residue was dissolved in THF (10 mL) and a solution of N,N-dimethylsulfonamide (23.7 mg, 0.191 mmol) and DIPEA (0.033 mL, 0.191 mmol)) in THF (2 mL) was added. DMAP (10 mg) was added after the reaction mixture was stirred at rt. for 10 min. Stirring was continued at 50° C. for 2 hr. after which the reaction mixture was concentrated under reduced pressure, and the resultant residue was purified by Prep. reverse phase HPLC to afford the title compound as a yellow solid, (0 mg, 36% yield). MS m/z 578(MH+); $^1$H NMR (500 MHz, CD$_3$OD) δ ppm 1.32–1.47 (m, 3 H) 1.75–1.90 (m, 5 H) 1.98–2.08 (m, 2 H) 3.04 (s, 6 H) 3.32 (m, 1H) 3.46–3.79 (m, 8 H) 4.88 (s, 2H) 7.03 (s, 1 H) 7.53 (dd, J=7.93, 4.58 Hz, 1 H) 7.62 (dd, J=8.55, 1.53 Hz, 1 H) 7.95 (m, 1 H) 8.00 (d, J=8.55 Hz, 1 H) 8.19 (s, 1 H) 8.78 (dd, J=4.73, 1.68 Hz, 1 H)

5H-pyrido[2',3':3,4]azepino[1,2-a]indole-10-carboxamide, 13-cyclohexyl-N-[(dimethylamino)sulfonyl-6,7-dihydro-6-(4-morpholinylcarbonyl)-

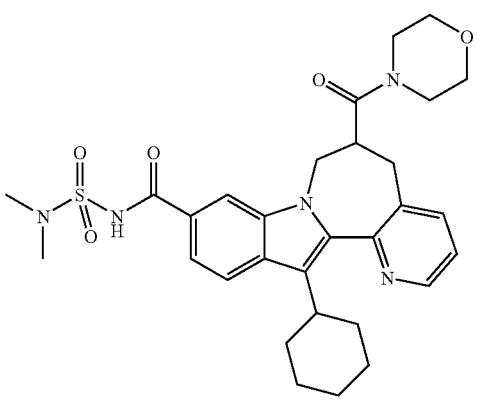

To a solution of 7H-pyrido[2',3':3,4]azepino[1,2-a]indole-10-carboxamide, 13-cyclohexyl-N-[(dimethylamino)sulfonyl]-6-(4-morpholinylcarbonyl)- (12 mg, 0.021 mmol) in methanol (10 mL), 10% Pd on carbon (5 mg) was added. The reaction mixture was stirred under a hydrogen atmosphere (1 atm.) for 3 days. It was filtered through celite and the filtrand washed with methanol. The combined filtrates and washings were concentrated under reduced pressure and the residue was purified by Prep. reverse phase HPLC to give the TFA salt of the title compound as a yellow solid, (7.5 mg, 52% yield). MS m/z 580(MH$^+$); $^1$H NMR (500 MHz, CD$_3$OD) δ ppm 1.36–1.49 (m, 3 H) 1.77–1.98 (m, 5 H) 2.00–2.11 (m, 2 H) 2.84–2.94 (m, 2 H) 3.04 (s, 6 H) 3.08 (m, 1 H) 3.57–3.92 (m, 9 H) 4.32 (m, 1 H) 4.44 (m, 1 H) 7.64 (d, J=8.55 Hz, 1 H) 7.76 (dd, J=7.78, 5.65 Hz, 1 H) 8.05 (d, J=8.55 Hz, 1 H) 8.13 (s, 1 H) 8.28 (d, J=7.63 Hz, 1 H) 8.79 (d, J=5.19 Hz, 1 H).

Alternative pyridine fused derivatives of the instant invention may be prepared using the methodology shown in the scheme below.

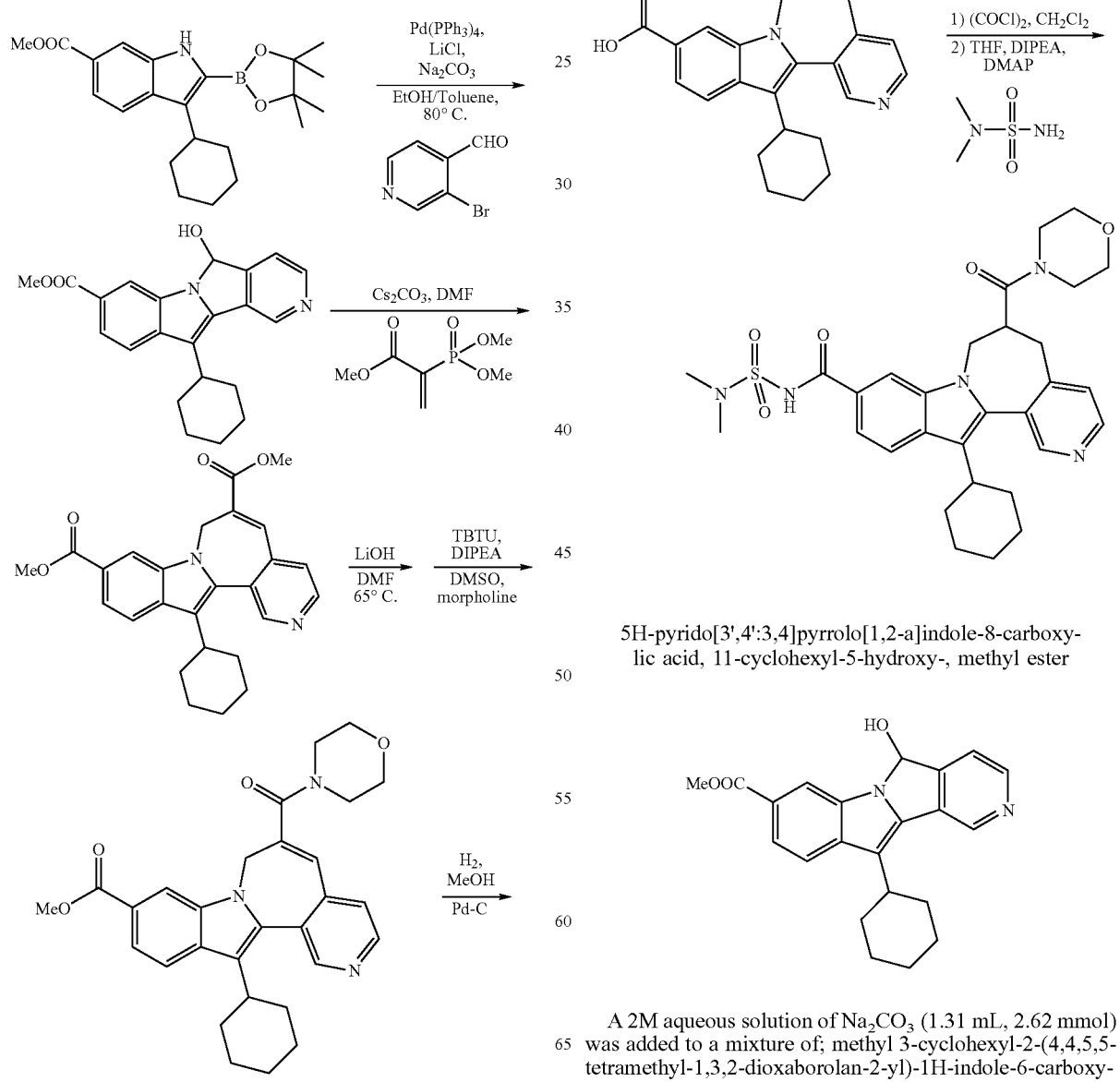

5H-pyrido[3',4':3,4]pyrrolo[1,2-a]indole-8-carboxylic acid, 11-cyclohexyl-5-hydroxy-, methyl ester A 2M aqueous solution of Na$_2$CO$_3$ (1.31 mL, 2.62 mmol) was added to a mixture of; methyl 3-cyclohexyl-2-(4,4,5,5-tetramethyl-1,3,2-dioxaborolan-2-yl)-1H-indole-6-carboxylate (400 mg, 1.05 mmol), 3-bromo-4-pyridinecarboxaldehyde (214 mg, 1.15 mmol) and LiCl (89 mg, 2.1 mmol), in ethanol (5 mL) and toluene (5 mL). The resultant mixture was degassed by the application of vacuum followed by flushing with N₂. Pd(PPh₃)₄ (60.7 mg, 0.0525 mmol) was added and the reaction mixture was heated at 80° C. for 5 hr. It was then filtered and concentrated under reduced pressure. The residue was triturated with CH₂Cl₂ to give the title compound as a light yellow solid, (295 mg, 78% yield). MS m/z 363(MH⁺); ¹H NMR (500 MHz, DMSO-D6) δ ppm 1.40–1.51 (m, 3 H) 1.75–1.97 (m, 7 H) 3.24 (m, 1 H) 3.89 (s, 3 H) 6.75 (d, J=8.85 Hz, 1 H) 7.55 (d, J=8.85 Hz, 1 H) 7.63–7.68 (m, 2 H) 7.68 (d, J=8.55 Hz, 1 H) 8.23 (s, 1 H) 8.63 (d, J=4.88 Hz, 1 H) 9.12 (s, 1 H).

7H-pyrido[3',4':3,4]azepino[1,2-a]indole-6,10-dicarboxylic acid, 13-cyclohexyl-, dimethyl ester

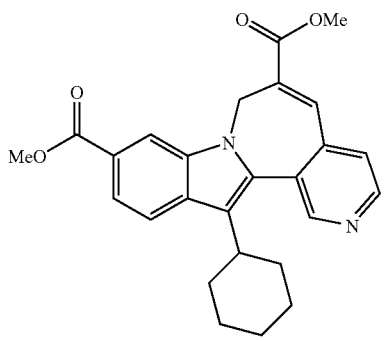

To a solution of 5H-pyrido[3',4':3,4]pyrrolo[1,2-a]indole-8-carboxylic acid, 11-cyclohexyl-5-hydroxy-, methyl ester (290 mg, 0.8 mmol) in DMF (5 mL), Cs₂CO₃ (391 mg, 1.2 mmol) and trimethyl-2-phosphonoacrylate (202 mg, 1.04 mmol) were added. The reaction mixture was heated at 60° C. for 3 hr. It was then quenched with water and the solid that precipitated was collected by filtration. This material was dried in vacuo to give the title compound as a yellow solid, (230 mg, 67% yield). MS m/z 431(MH⁺); ¹H NMR (500 MHz, CD₃OD) □ ppm 1.39–1.59 (m, 3 H) 1.75–2.03 (m, 5 H) 2.09–2.28 (m, 2 H) 2.86 (m, 1 H) 3.89 (s, 3 H) 3.98 (s, 3 H) 4.89 (s, 2H) 7.65 (d, J=4.88 Hz, 1 H) 7.76 (d, J=8.54 Hz, 1 H) 7.92 (s, 1 H) 7.97 (d, J=8.55 Hz, 1 H) 8.33 (s, 1 H) 8.69 (d, J=5.19 Hz, 1 H) 8.84 (s, 1 H).

7H-pyrido[3',4':3,4]azepino[1,2-a]indole-10-carboxylic acid, 13-cyclohexyl-6-(4-morpholinylcarbonyl)-, methyl ester

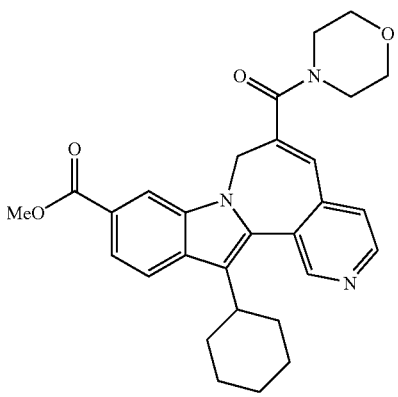

LiOH (45 mg, 1.882 mmol) was added to a solution of 7H-pyrido[3',4':3,4]azepino[1,2-a]indole-6,10-dicarboxylic acid, 13-cyclohexyl-, dimethyl ester (135 mg, 0.314 mmol) in DMF (4 mL) in a sealed tube. The reaction mixture was heated under microwave conditions at 65° C. for 1 hr. Water was then added and the mixture was acidified (pH ~4) using 1N HCl solution. This mixture was extracted using ethyl acetate (4×20 mL), and the organic layers were combined, dried (MgSO₄), filtered and concentrated in vacuo to give the intermediate acid as an orange oil. This material was dissolved in DMSO (1.0 mL), and TBTU (151 mg, 0.47 mmol) and DIPEA (0.273 mL, 1.57 mmol) were added. The reaction mixture was stirred at rt for 15 min. Then morpholine (0.041 mL, 0.47 mmol) was added and the reaction mixture was stirred at rt overnight. It was then concentrated under reduced pressure and the residue was purified by Prep. reverse phase HPLC to give the title compound as a light yellow solid, (48 mg, 32% yield two steps). MS m/z 486(MH⁺); ¹H NMR (500 MHz, CD₃OD) δ ppm 1.37–1.59 (m, 4 H) 1.72–2.06 (m, 4 H) 2.07–2.29 (m, 2 H) 2.87 (m, 1 H) 3.38–3.86 (m, 8 H) 3.97 (m, 3 H) 4.35–4.68 (m, br, 1 H) 5.14–5.38 (m, br, 1 H) 7.04 (s, 1 H) 7.59 (d, J=5.19 Hz, 1 H) 7.77 (dd, J=8.55, 1.22 Hz, 1 H) 7.98 (d, J<8.54 Hz, 1 H) 8.31 (s, 1 H) 8.66 (d, J=5.19 Hz, 1 H) 8.81 (s, 1 H).

5H-pyrido[3',4':3,4]azepino[1,2-a]indole-10-carboxylic acid, 13-cyclohexyl-6,7-dihydro-6-(4-morpholinylcarbonyl)-, methyl ester

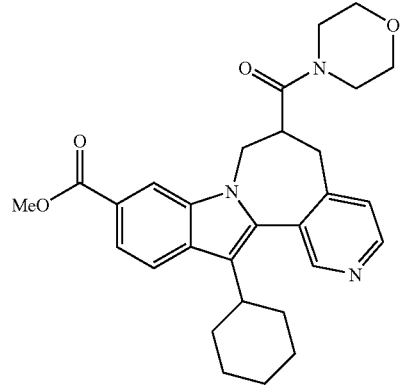

To a solution of 7H-pyrido[3',4':3,4]azepino[1,2-a]indole-10-carboxylic acid, 13-cyclohexyl-6-(4-morpholinylcarbonyl)-, methyl ester (35 mg, 0.072 mmol) in methanol (10 mL), 10% Pd on carbon (5 mg) was added. The reaction mixture was stirred under a hydrogen atmosphere (1 atm.) overnight. It was then filtered through celite and the filtrand washed with methanol. The combined filtrates and washings were concentrated under reduced pressure and the resultant residue was purified by Prep. reverse phase HPLC to give the TFA salt of the title compound as a yellow solid, (19 mg, 44% yield). MS m/z 488(MH⁺); ¹H NMR (500 MHz, CD₃OD) δ ppm 1.23–1.58 (m, 3 H) 1.65 (m, 1 H) 1.75–1.86 (m, 2 H) 1.90–2.18 (m, 4 H) 2.80–3.12 (m, 3 H) 3.41–4.18 (m, 13 H) 4.66 (m, 1 H) 7.74 (m, 1 H) 7.91–8.03 (m, 2 H) 8.19 (m, 1 H) 8.70–8.78 (m, 2 H).-

5H-pyrido[3',4':3,4]azepino[1,2-a]indole-10-carboxylic acid, 13-cyclohexyl-6,7-dihydro-6-(4-morpholinylcarbonyl)-

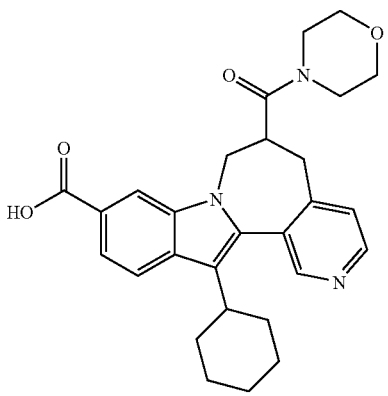

LiI (10 mg, 0.075 mmol) was added to a solution of 5H-pyrido[3',4':3,4]azepino[1,2-a]indole-10-carboxylic acid, 13-cyclohexyl-6,7-dihydro-6-(4-morpholinylcarbonyl)-, methyl ester (16 mg, 0.027 mmol) in pyridine (2 mL) in a sealed tube. The reaction mixture was heated at 180° C. under microwave conditions for 1.5 hr. Water was then added and the pH of the reaction mixture was adjusted to 4–5 with 1N HCl solution. This mixture was extracted with ethyl acetate (2×20 mL) and the organic layers were combined, dried (MgSO$_4$), filtered and concentrated under reduced pressure. The residue was purified by Prep. reverse phase HPLC to afford the TFA salt of the title compound as a yellow solid, (11.7 mg, 75% yield). MS m/z 474(MH$^+$); $^1$H NMR (500 MHz, CD$_3$OD) □ ppm 1.28–1.62 (m, 3 H) 1.69 (m, 1 H) 1.79–1.90 (m, 2 H) 1.99 (m, 1 H) 2.07–2.21 (m, 3 H) 2.83–3.09 (m, 2 H) 3.17 (m, 1 H) 3.46–4.23 (m, 10 H) 4.69 (m, 1 H) 7.78 (m, 1 H) 7.98 (m, 1 H) 8.08 (m, 1 H) 8.23 (m, 1 H) 8.75–8.83 (m, 2 H).

5H-pyrido[3',4':3,4]azepino[1,2-a]indole-10-carboxamide, 13-cyclohexyl-N-[(dimethylamino)sulfonyl]-6,7-dihydro-6-(4-morpholinylcarbonyl)-

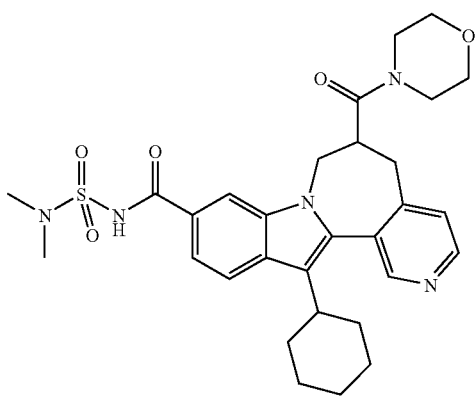

To a solution of 5H-pyrido[3',4':3,4]azepino[1,2-a]indole-10-carboxylic acid, 13-cyclohexyl-6,7-dihydro-6-(4-morpholinylcarbonyl)- (40 mg, 0.084 mmol) in CH$_2$Cl$_2$ (10 mL), one drop of DMF was added. A 2M solution of oxalyl chloride (0.085 mL, 0.169 mmol) in CH$_2$Cl$_2$ was then added dropwise. The reaction mixture was stirred at rt. for 2 hr. It was then concentrated and dried under high vacuum. The resultant residue was then dissolved in THF(10 mL) and a solution of N,N-dimethylsulfonamide (21 mg, 0.169 mmol) and DIPEA (0.044 mL, 0.1252 mmol)) in THF (2 mL) was added. DMAP (10 mg) was added after the reaction mixture was stirred at rt. for 10 min. Stirring was continued at 50° C. for 2 hr after which the mixture was concentrated under reduced pressure and the residue was purified by Prep. reverse phase HPLC to afford the TFA salt of the title compound as a yellow solid, (9.0 mg, 15% yield). MS m/z 580(MH$^+$); $^1$H NMR (300 MHz, CD$_3$OD) □ ppm 1.18–1.74 (m, 4 H) 1.77–1.90 (m, 2 H) 1.90–2.23 (m, 4 H) 2.83–3.13 (m, 9 H) 3.52–4.25 (m, 10 H) 4.70 (m, 1 H) 7.63 (m, 1 H) 7.91–8.24 (m, 3 H) 8.69–8.77 (m, 2 H).

Isomeric propeno-bridged carboxamides of the instant invention may be accessed by a number of methods known to those skilled in the art, one example of which is shown in the scheme depicted below.

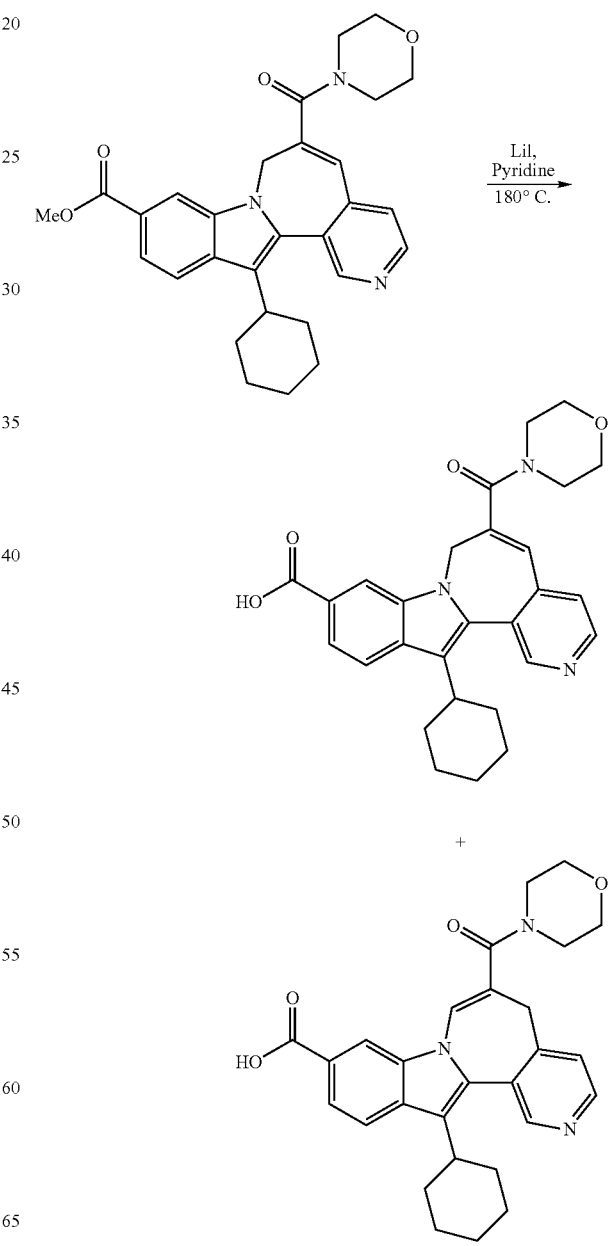

7H-pyrido[3',4':3,4]azepino[1,2-a]indole-10-carboxylic acid, 13-cyclohexyl-6-(4-morpholinylcarbonyl)-

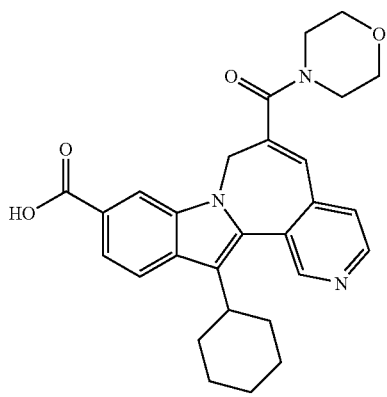

LiI (37 mg, 0.278 mmol) was added to a solution of 7H-pyrido[3',4':3,4]azepino[1,2-a]indole-10-carboxylic acid, 13-cyclohexyl-6-(4-morpholinylcarbonyl)-, methyl ester (45 mg, 0.093 mmol) in pyridine (4 mL) in a sealed tube. The reaction mixture was heated at 180° C. under microwave conditions for 2 hr. Water was then added and the reaction mixture pH adjusted to 4–5 with 1N HCl solution. The resultant solution was then extracted with ethyl acetate (2×20 mL). The extracts were combined, dried (MgSO$_4$), filtered and concentrated under reduced pressure. The resultant residue was purified by Prep.reverse phase HPLC to afford the TFA salt of the title compound as a yellow solid. (23 mg, 43% yield). MS m/z 472(MH$^+$); $^1$H NMR (300 MHz, CD$_3$OD) □ ppm 1.18–2.23 (m, 10 H) 2.81 (m, 1 H) 3.35–3.79 (m, 8 H) 4.56 (m, br, 1 H) 5.30 (m, br, 1 H) 7.10 (s, 1 H) 7.77 (dd, J=8.48, 1.37 Hz, 1 H) 7.84 (d, J=5.73 Hz, 1 H) 7.98 (d, J=8.48 Hz, 1 H) 8.31 (s, 1 H) 8.74 (d, J=5.73 Hz, 1 H) 8.84 (s, 1 H).

Also isolated from the above reaction mixture as a minor component was the compound characterized below.

5H-pyrido[3',4':3,4]azepino[1,2-a]indole-10-carboxylic acid, 13-cyclohexyl-6-(4-morpholinylcarbonyl)-

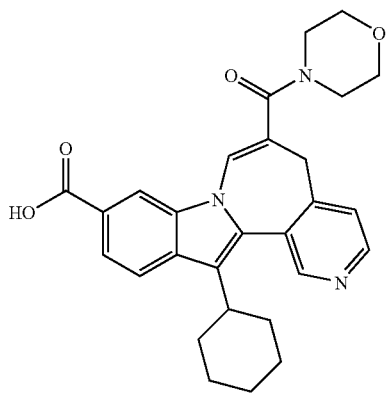

MS m/z 472(MH$^+$); $^1$H NMR (300 MHz, CD$_3$OD) □ ppm 1.32 (m, 1 H) 1.45–1.62 (m, 2 H) 1.67–2.07 (m, 4 H) 2.11–2.35 (m, 3 H) 3.00 (m, 1 H) 3.60–3.78 (m, 9 H) 3.85 (m, 1 H) 7.73 (s, 1 H) 7.95 (dd, J=8.48, 1.37 Hz, 1 H) 7.98 (d, J=5.73 Hz, 1 H) 8.09 (d, J=8.48 Hz, 1 H) 8.31 (s, 1 H) 8.70 (s, 1 H) 8.76 (d, J=5.73 Hz, 1 H).

Further examples of the instant invention in which the propeno bridge is poly functionalized may be accessed by a number of methodologies, one example of which is that shown in the Scheme below.

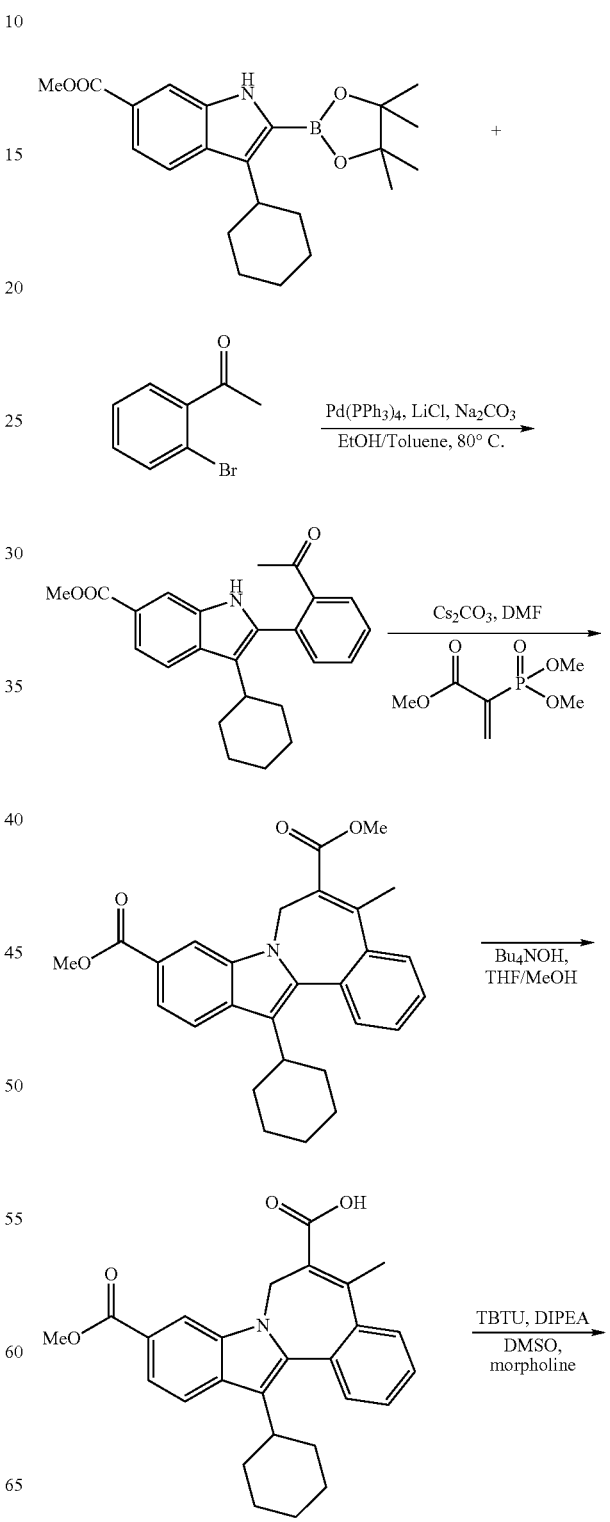

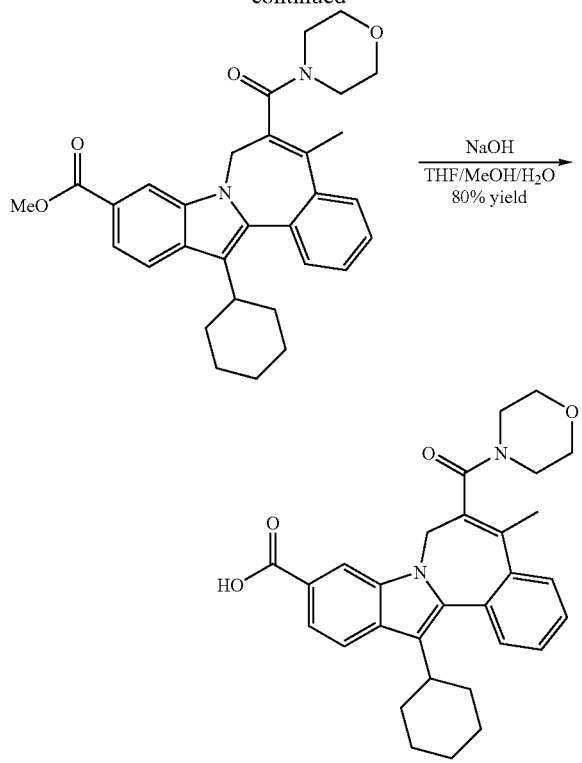

Methyl 2-(2-acetylphenyl)-3-cyclohexyl-]H-indole-6-carboxylate

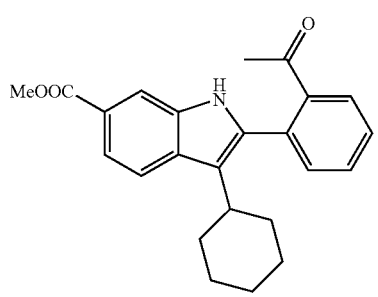

A 2M aqueous solution of Na₂CO₃ (2.5 mL, 5.0 mmol) was added to a mixture of; methyl 3-cyclohexyl-2-(4,4,5,5-tetramethyl-1,3,2-dioxaborolan-2-yl)-1H-indole-6-carboxylate (766 mg, 2.0 mmol), 2'-bromoacetophenone (478 mg, 2.4 mmol) and LiCl (170 mg, 4.0 mmol), in ethanol (5 mL) and toluene (5 mL). The mixture was then degassed by sequentially applying vacuum followed by flushing with N₂. Pd(PPh₃)₄ (115 mg, 0.1 mmol) was then added and the reaction heated at 80° C. for 4 hr. The reaction mixture was then filtered and concentrated under reduced pressure. The resultant residue was purified by silica gel flash chromatography using hexanes to 20% ethyl acetate in hexanes as eluent to give the title compound as a white foam which could be crushed to a powder, (686 mg, 91% yield). MS m/z 374(M-H⁻); ¹H NMR (500 MHz, CD₃OD) ☐ ppm 1.30 (m, 1 H) 1.41–1.64 (m, 3 H) 1.82–2.21 (m, 9 H) 3.26 (m, 1 H) 3.95 (s, 3 H) 7.40 (m, 1 H) 7.49 (m, 1 H) 7.61 (m, 1 H) 7.69 (m, 1 H) 7.79 (m, 1 H) 7.84 (m, 1 H) 8.29 (s, 1 H).

7H-indolo[2,1-a][2]benzazepine-6,10-carboxylic acid, 13-cyclohexyl-5-methyl-, dimethyl ester

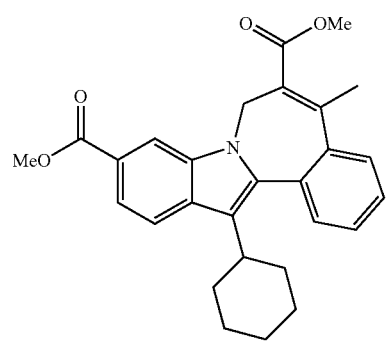

To a solution of methyl 2-(2-acetylphenyl)-3-cyclohexyl-1H-indole-6-carboxylate (400 mg, 1.065 mmol) in DMF (10 mL), Cs₂CO₃ (521 mg, 1.6 mmol) and trimethyl-2-phosphonoacrylate (310 mg, 1.6 mmol) were added. The reaction mixture was heated at 60° C. overnight. It was then quenched by the addition of water after which a precipitate formed. This was collected by filtration, and dried under vacuum to give the crude product as a light yellow solid (380mg, 80% yield). 10 mg of this material was purified by Prep. reverse phase HPLC to provide pure, 7H-indolo[2,1-a][2]benzazepine-6,10-carboxylic acid, 13-cyclohexyl-5-methyl-, dimethyl ester. MS m/z 444(MH⁺); ¹H NMR (500 MHz, CD₃OD) δ ppm 1.15–1.66 (m, 4 H) 1.76–1.87 (m, 2 H) 1.97 (m, 1 H) 2.02–2.22 (m, 3 H) 2.49 (s, 3H) 2.95 (m, 1 H) 3.83 (s, 3 H) 3.97 (s, 3 H) 4.09 (d, J=14.65 Hz, 1 H) 5.49 (d, J=14.65 Hz, 1 H) 7.55–7.61 (m, 3 H) 7.70 (dd, J=8.39, 1.37 Hz, 1 H) 7.76 (m, 1 H) 7.88 (d, J=8.55 Hz, 1 H) 8.33 (s, 1 H).

7H-indolo[2,1-a][2]benzazepine-6,10-dicarboxylic acid, 13-cyclohexyl-5-methyl-, 10-methyl ester

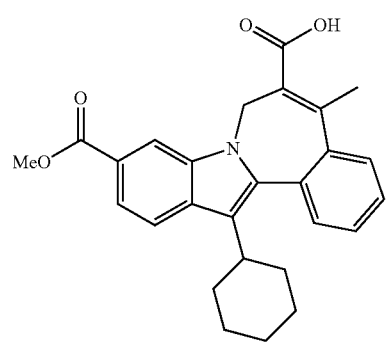

To a solution of 7H-indolo[2,1-a][2]benzazepine-6,10-carboxylic acid, 13-cyclohexyl-5-methyl-, dimethyl ester (179, 0.4 mmol) in THF (10 mL), 1M solution of Bu₄NOH (0.6 mL, 0.6 mmol) in methanol was added. The reaction mixture was stirred at rt. for two days. It was then concentrated, acidified with 1N HCl solution and extracted with ethyl acetate (2×30 mL). The organic layers were combined, dried (MgSO₄), filtered and concentrated in vacuo. The resultant residue was purified by Prep. reverse phase HPLC column to give the title compound as a yellow solid, (90 mg, 52% yield). MS m/z 430(MH⁺); ¹H NMR (300 MHz, DMSO-D6) ☐ ppm 1.10–1.27 (m, 1H) 1.32–1.59 (m, 3 H) 1.64–1.79 (m, 2 H) 1.81–1.94 (m, 1 H) 1.94–2.13 (m, 3 H) 2.41 (s, 3 H) 2.86 (m, 1 H) 3.87 (s, 3 H) 3.98 (d, J=14.64 Hz, 1 H) 5.43 (d, J=14.64 Hz, 1 H) 7.49–7.67 (m, 4 H) 7.74–7.83 (m, 1 H) 7.91 (d, J=8.42 Hz, 1 H) 8.22 (s, 1 H) 13.00 (s, 1 H).

7H-indolo[2,1-a][2]benzazepine-10-carboxylic acid, 13-cyclohexyl-5-methyl-6-(4-morpholinylcarbonyl)-, methyl ester

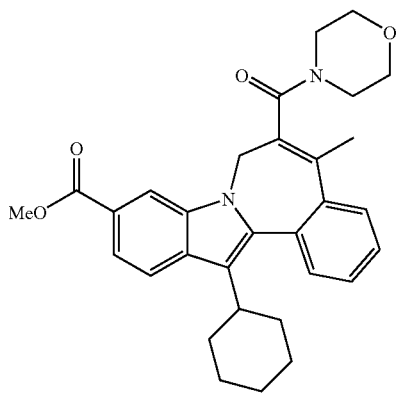

To a solution of 7H-indolo[2,1-a][2]benzazepine-6,10-dicarboxylic acid, 13-cyclohexyl-5-methyl-, 10-methyl ester (120 mg, 0.28 mmol) in DMSO (3.0 mL), TBTU (135 mg, 0.42 mmol) and DIPEA (0.244 mL, 1.4 mmol) were added. The reaction mixture was stirred at rt for 15 min. Then morpholine (0.037 mL, 0.42 mmol) was added and the reaction mixture was stirred at rt for overnight. It was then concentrated under reduced pressure and the residue was purified by Prep. reverse phase HPLC to give the title compound as a white solid, (115 mg, 82% yield). MS m/z 499(MH⁺); ¹H NMR (500 MHz, CD₃OD) ☐ ppm Compound exists as a complex mixture of rotamers.

7H-indolo[2,1-a][2]benzazepine-10-carboxylic acid, 13-cyclohexyl-5-methyl-6-(4-morpholinylcarbonyl)-

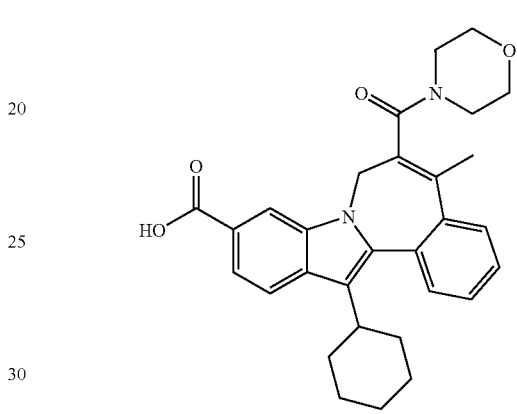

2N NaOH solution (1.0 mL) was added to a solution of 7H-indolo[2,1-a][2]benzazepine-10-carboxylic acid, 13-cyclohexyl-5-methyl-6-(4-morpholinylcarbonyl)-, methyl ester (100 mg, 0.2 mmol)in a THF/Methanol mixture (2.0 mL/2.0 mL) in a sealed tube. The reaction mixture was heated at 90° C. under microwave conditions for 10 min. It was then concentrated and acidified with 1N HCl solution after which a precipitate formed. This was collected by filtration and dried under vacuum to provide the title compound as an off-white solid, (75 mg, 77% yield). MS m/z 485(MH⁺); ¹H NMR (300 MHz, CD₃OD) ☐ ppm exists as rotamers.

Libraries of carboxamides of the instant invention can be rapidly prepared using the methodology shown in the scheme depicted below.

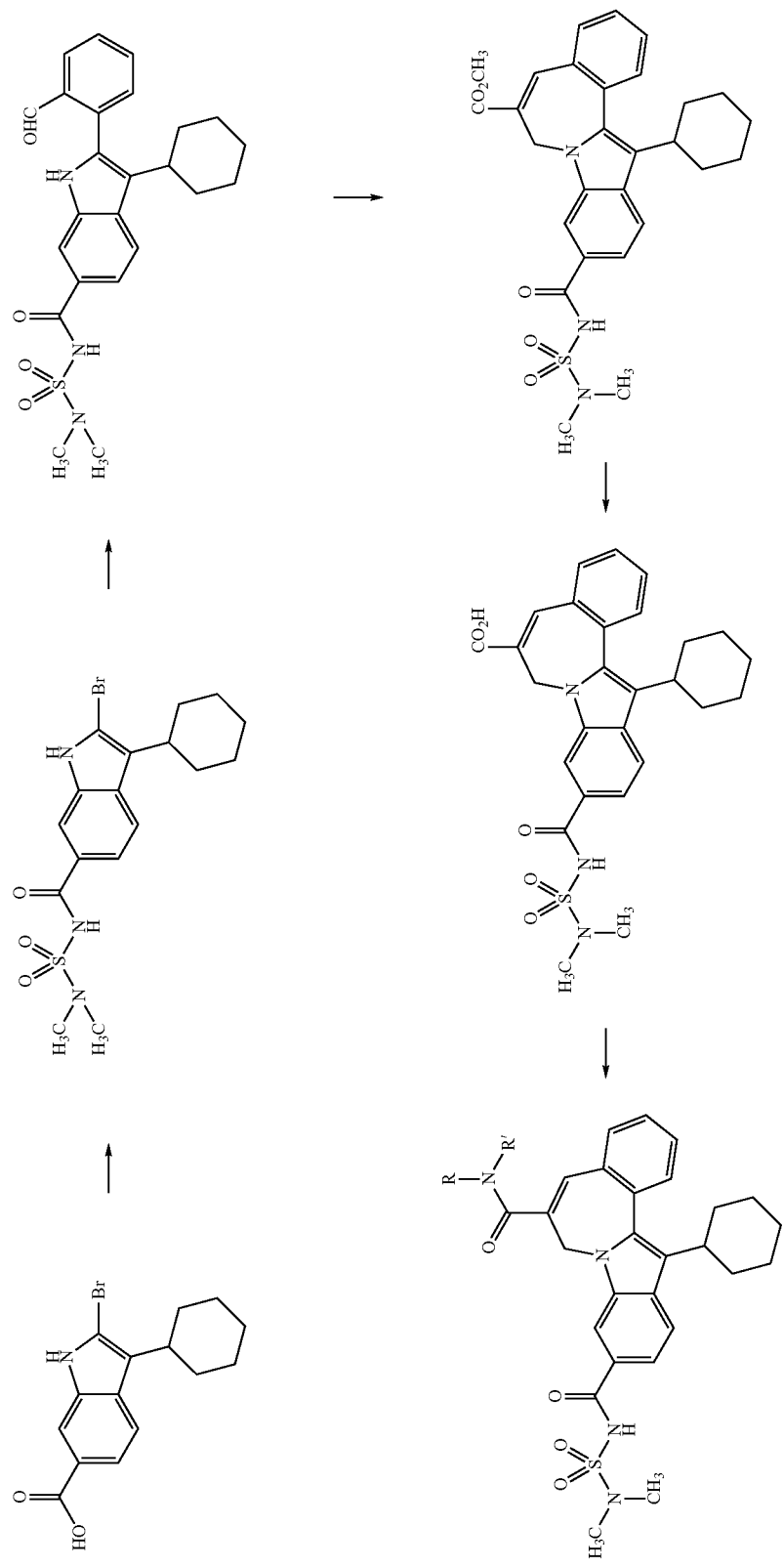

2-Bromo-3-cyclohexyl-1H-indole-6-carboxylic Acid

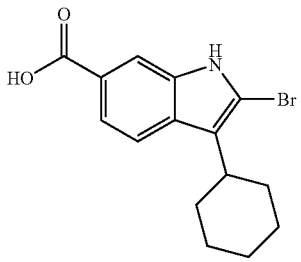

A mixture of methyl 2-bromo-3-cyclohexyl-1H-indole-6-carboxylate (2.0 g, 5.95 mmol) in THF (10 mL), methanol (10 mL), and water (10.5 mL) in which LiOH (690 mg) was dissolved was stirred under reflux for 1.5 hr. The solution was cooled in ice and diluted with water. Acidification with 37% HCl (3mL) resulted in precipitation of the titled acid. The acid was collected, washed with cold water and air dried to afford the product as a pale yellow granular solid (2.1 g, 90 5) solvated with one molar equivalent of THF. $^1$H NMR (500 MHz, CHLOROFORM-D) ☐ ppm 1.25–1.55 (m, 3 H) 1.68–2.07 (m, 11 H) 2.72–2.96 (m, 1 H) 3.60–3.82 (m, 4 H) 7.70–7.77 (m, 1 H) 7.80–7.85 (m, 1 H) 8.06–8.10 (m, 1 H) 8.26–8.31 (m, 1 H) 11.21–12.62 (br. S., 1 H).

2-Bromo-3-cyclohexyl-N-[(dimethylamino)sulfonyl]-1H-indole-6-carboxamide

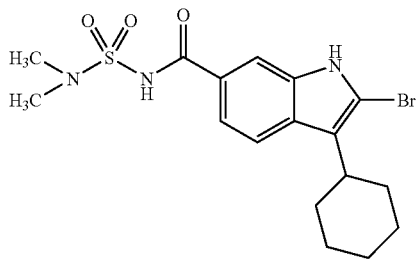

1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22☐ C. The evolution of $CO_2$ was instantaneous and when it slowed the solution was heated at 50° C. for 1 hr and then cooled to 22☐ C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer was washed with water followed by brine and dried over $Na_2SO_4$. The extract was concentrated to dryness to leave the titled product as a pale yellow friable froth (2.0 g, 74%) of substantial purity (90%). $^1$H NMR (300 MHz, DMSO-D6) ☐ ppm 1.28–1.49 (m, 3 H) 1.59–2.04 (m, 7 H) 2.74–2.82 (m, 1 H) 2.88 (s, 6 H) 7.57 (dd, J=8.42, 1.46 Hz, 1 H) 7.74 (d, J=8.78 Hz, 1 H) 7.91 (s, 1 H) 11.71 (s, 1 H) 12.08 (s, 1 H).

3-Cyclohexyl-N-[(dimethylamino)sulfonyl-1-2-(2-formylphenyl)-]H-indole-6-carboxamide

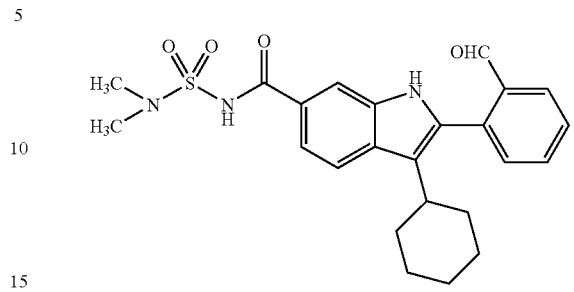

A mixture of 2-bromo-3-cyclohexyl-N-[(dimethylamino)sulfonyl]-1H-indole-6-carboxamide (950 mg, 2.22 mmol), LiCl (370 mg, 4.44 mmol), tetrakis(triphenylphosphine)palladium(0) (130 mg, 0.11 mmol) in toluene (30 mL) and ethanol (30 mL) containing aqueous 1 N $Na_2CO_3$ (15 mL, 15 mmol) was stirred under reflux for 18 hr. The mixture was diluted with ethyl acetate and washed with 1 N HCl (3×) followed by brine (3×). The solution was dried over $Na_2SO_4$ and concentrated to dryness to afford the titled compound as a yellow solid (1.06 g, 106%) which contained some triphenyl oxide . The product was used in the following step without additional purification. MS m/z 454 (MH$^+$).

6-Carbomethoxy-13-cyclohexyl-N-[(dimethylamino)sulfonyl]-5H-indolo[2,1-a][2]benzazepine-10-carboxamide

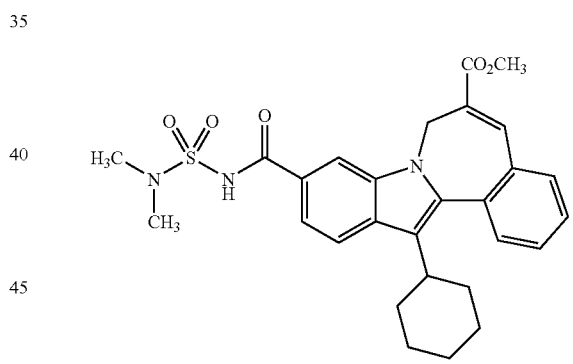

A mixture of 3-cyclohexyl-N-[(dimethylamino)sulfonyl]-2-(2-formylphenyl)-1H-indole-6-carboxamide (1.06 g, 2.1 mmol), methyl 2-(dimethoxyphosphoryl)acrylate (0.4 mL, 3.2 mmol), and $Cs_2CO_3$ (1.04 g, 3.2 mmol) in DMF (4 mL) was stirred at 60° C. for 18 hr, at which time additional $Cs_2CO_3$ 4 g, 0.32 mmol) and methyl dimethoxyphosphoryl)acrylate (0.4 mL, 3.2 mmol) were added. The mixture was stirred for an additional 8 hr, cooled and diluted with ethyl acetate. The resulting mixture was washed with dilute HCl (3×) followed by brine (3×). The solution was concentrated to leave the crude product as a yellow solid (1.2 g). The crude product was purified utilizing a Biotage apparatus with a prepacked silicic acid column and using gradients of hexanes: ethyl acetate:acetic acid of from (100:2:.0.5) to (64:36:0.5). The product containing fractions were combined and concentrated to dryness to afford the titled compound as a pale yellow solid (640 mg, 59%). MS m/z 522 (MH$^+$).

385

6-Carboxy-13-cyclohexyl-N-[(dimethylamino)sulfonyl]-5H-indolo[2,1-a][2]benzazepine-10-carboxamide

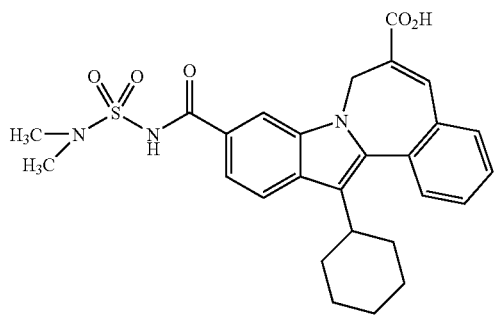

Sodium hydroxide (2.0 mL of 1.0 N, 2.0 mmol) was added to a solution of the preceding methyl ester (640 mg, 1.23 mmol) in methanol (2 mL) and THF (2 mL) in a microwave vial. The vial was sealed and the contents heated at 90° C. for 15 minutes in a microwave apparatus. The solution was acidified with dilute hydrochloric acid and extracted with ethyl acetate. The ethyl acetate solution was washed with dilute hydrochloric acid (1×) and brine (1×), dried (NaSO$_4$), and concentrated on a rotary evaporator to afford the product as a light yellow solid (570 mg, 91%). ESI-MS m/z 508 (MH$^+$); $^1$H NMR (500 MHz, MeOD) □ 1.14–1.27 (m, 1 H) 1.35–1.56 (m, 3 H) 1.71–1.81 (m, 2 H) 1.89–1.99 (m, 1 H) 2.00–2.19 (m, 3 H) 2.83–2.91 (m, 1 H) 3.01 (s, 6 H) 4.11–4.22 (m, 1 H) 5.64–5.75 (s, 1 H) 7.51–7.61 (m, 4 H) 7.61–65 (m, 1 H) 7.91 (s, 1 H) 7.91–7.95 (m, 1 H) 8.18 (s, 1 H).

386

13-Cyclohexyl-N-[(dimethylamino)sulfonyl]-6-(homomorpholinylcarbonyl)-5H-indolo[2,1-a][2]benzazepine-10-carboxamide

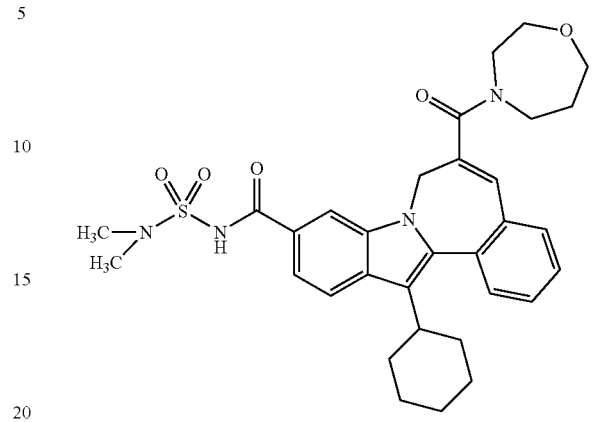

TBTU (22 mg, 0.069 mmol) was added to a stirred solution of 6-carboxy-13-cyclohexyl-N-[(dimethylamino)sulfonyl]-5H-indolo[2,1-a][2]benzazepine-10-carboxamide (25 mg, 0.049 mmol), homomorpholine hydrochloride (8.1 mg, 0.059 mmol), and N,N-diisopropylethylamine (0.3 mL, 1.74 mmol) in DMF (3 mL). The mixture was stirred at 22° C. for 20 min. The resulting solution was concentrated down to the volume of 2 mL on a Speed Vac® and filtered. The filtrate was injected on the Shimadzu preparative liquid chromatograph. The product containing fraction was concentrated on a Speed Vac® to leave the titled compound as a white solid (28 mg, 97%). ESI-MS m/z 591 (MH$^+$); $^1$H NMR (500 MHz, Solvent) □ 1.16–1.32 (m, 1 H) 1.38–1.55 (m, 4 H) 1.75–1.86 (m, 2 H) 1.90–2.21 (m, 5 H) 2.90 (m, 1 H) 3.04 (s, 6 H) 3.39–3.93 (m, 8 H) 4.42 (m, 1 H) 5.20 (m, 1 H) 7.05 (s, 1 H) 7.57 (m, 3 H) 7.63 (m, 2 H) 7.96 (d, J<8.55 Hz, 1 H) 8.15 (s, 1 H).

The following library of 13-Cyclohexyl-N-[(dimethylamino)sulfonyl]-6-(substituted-aminocarbonyl)-5H-indolo[2,1-a][2]benzazepine-10-carboxamides was synthesized using the protocols described in the preceding section.

| Table of Bridged Carboxamides. | | |
|---|---|---|
| Structure | Physiochemical Data | IC$_{50}$ EC$_{50}$ |
| | ESI-MS m/z 631 (MH$^+$); Rt 1.71 min | |

Table of Bridged Carboxamides.
| Structure | Physiochemical Data | IC$_{50}$ | EC$_{50}$ |
|---|---|---|---|
| 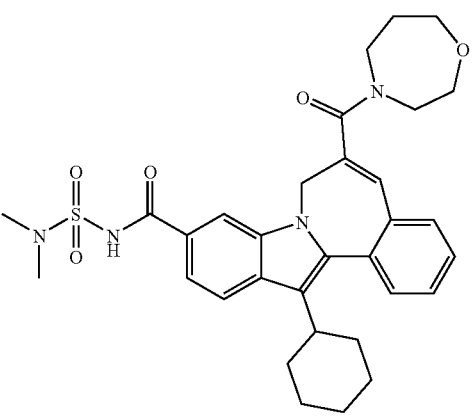 | ESI-MS m/z 591 (MH$^+$); Rt 1.94 min<br>NMR data reported above | | |
| 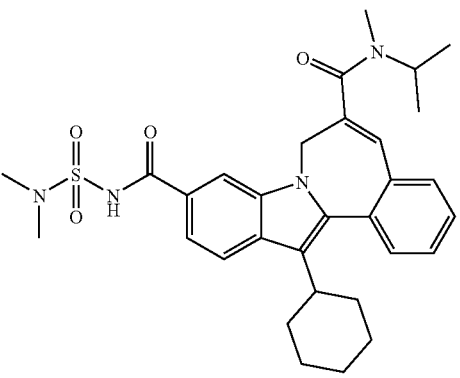 | ESI-MS m/z 563 (MH$^+$); Rt 2.64 min | | |
| 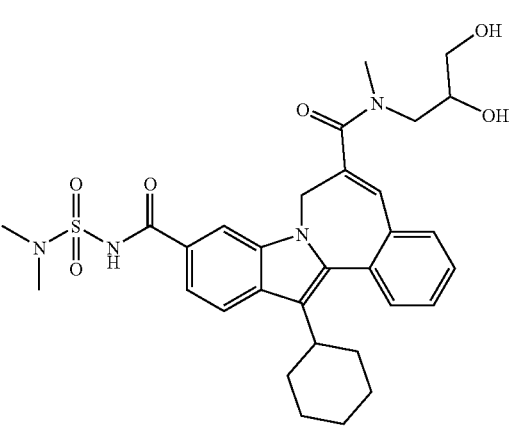 | ESI-MS m/z 595 (MH$^+$); Rt 2.52 min | | |

| Table of Bridged Carboxamides. | | | |
|---|---|---|---|
| Structure | Physiochemical Data | IC$_{50}$ | EC$_{50}$ |
| | ESI-MS m/z 591 (MH$^+$); Rt 2.69 min | | |
| | ESI-MS m/z 563 (MH$^+$); Rt 2.66 min | | |

Benzyl 1-aminocyclopentanecarboxylate

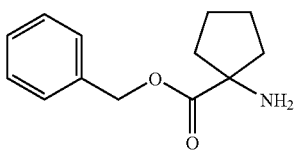

Benzyl chloride (634 mg, 5.0 mmol) was added to an ice-cold stirred mixture of 1-(tert-butoxycarbonylamino)cyclopentanecarboxylic acid (1.0 g, 4.36 mmol) and Cs$_2$CO$_3$ (1.42 g, 5.0 mmol) in DMF (8 mL). After the ice melted the mixture was stirred for 2 hr at 60° C. The mixture was poured into ice-water and extracted with ethyl acetate. The extract was washed with water followed by brine and dried over sodium sulfate. Concentration of the solution left benzyl 1-(tert-butoxycarbonylamino)cyclopentanecarboxylate as an oil which crystallized on standing. MS m/z 320 (MH$^+$).

TFA (8 mL) was then added to a stirred solution of the above ester (1 g) in methylene chloride (8 mL). The solution was stirred for 35 min at 22° C. and then concentrated. The residue was partitioned between ethyl acetate and dilute aqueous K$_2$CO$_3$. The ethyl acetate layer was washed (water, brine), dried (Na$_2$SO$_4$), and concentrated to leave the titled compound as an oil. 1H NMR (300 MHz, CHLOROFORM-D) δ ppm 1.56–1.92 (m, 6 H) 2.08 (dd, J=12.63, 6.77 Hz, 2 H) 2.55 (s, 2 H) 5.12 (s, 2 H) 7.25–7.32 (m, 5 H).

This product was coupled to the indole derivative shown in the scheme above using methodology described in previous sections of this document, to provide the intermediate characterized below.

Phenylmethyl 1-[[[3-hydroxy-13-cyclohexyl-6,7,13,13a-tetrahydro-5H-indolo[2,1-a][2]benzazepin-10-yl]carbonyl]amino]cyclopentanecarboxylate

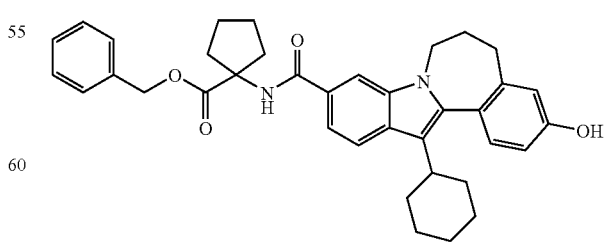

MS m/z 577 (MH$^+$); 1H NMR (300 MHz, CHLOROFORM-D) δ ppm 1.17–2.13 (m, 22 H) 2.81–2.92 (m, 1 H) 4.39–4.51 (m, 1 H) 4.59 (s, 2 H) 4.90–5.06 (m, 1 H)

6.55–6.68 (m, 1 H) 7.15 (d, J=7.32 Hz, 1 H) 7.35 (t, J=6.95 Hz, 1 H) 7.40–7.48 (m, 2 H) 7.52 (d, J=7.68 Hz, 1 H) 7.87 (d, J=8.42 Hz, 1 H) 8.00 (s, 1 H) 8.15 (s, 1 H).

Additional examples of the instant invention were prepared by coupling 13-cyclohexyl-6,7-dihydro-6-oxo-5H-indolo[1,2-d][1,4]benzodiazepine-10-carboxylic acid with a diversity of functionalized amines as shown in the scheme and described in the examples provided below. Certain ester derivatives generated using these protocols were subsequently hydrolyzed to provide the related acids, providing further examples of the instant invention.

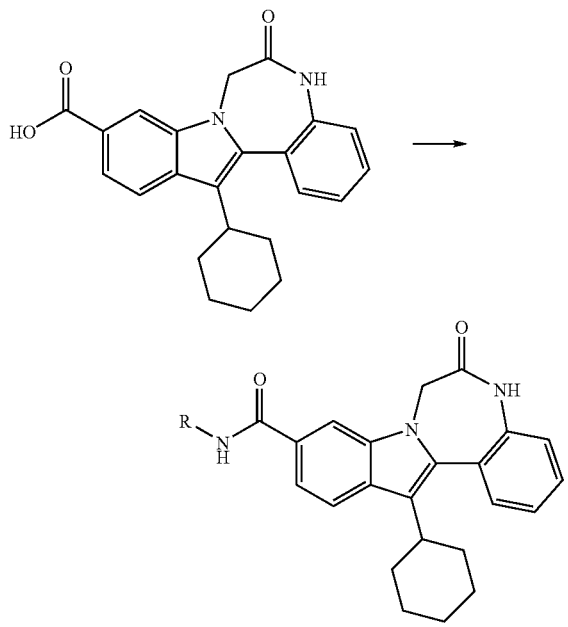

Ethyl 5-[[[1-[[(13-cyclohexyl-6,7-dihydro-6-oxo-5H-indolo[1,2-d][1,4]benzodiazepine-10-yl)carbonyl]amino]cyclopentyl]carbonyl]amino]-1-methyl-1H-indole-2-carboxylate TBTU (94 mg, 0.29 mmol) was added to a stirred solution of ethyl 5-(1-aminocyclopentanecarboxamido)-1-methyl-1H-indole-2-carboxylate¹ (88 mg, 0.27 mmol, 13-cyclohexyl-6,7-dihydro-6-oxo-5H-indolo[1,2-d][1,4]benzodiazepine-10-carboxylic acid (100 mg, 0.27 mmol), and TEA (148 □L, 1.1 mmol) in DMSO (1 mL) at 22° C. The mixture was stirred for 2 hr and then diluted with water to precipitate the product as a colorless solid. The solid was washed with cold water and dried. A portion (30 mg) was purified on a silicic acid thick layer plate. The plate was eluted with methylene chloride:ethyl acetate (100:30). The major band was extracted with methylene chloride-10% methanol. Concentration of the extracts left the product as a colorless solid. MS m/z 686 (MH⁺); ¹H NMR (500 MHz, CHLOROFORM-D) δ ppm 1.18–1.30 (m, 1 H) 1.39 (t, 3 H) 1.54–2.14 (m, 13 H) 2.34 (s, 2 H) 2.54–2.67 (m, 2 H) 2.85–2.97 (m, 1 H) 4.02 (s, 3 H) 4.35 (q, 2 H) 4.40–4.50 (m, 1 H) 5.02–5.13 (m, 1 H) 7.92 (d, J=8.55 Hz, 1 H) 8.11–8.21 (m, 2 H) 8.15 (s, 1 H) 8.18 (s, 1 H).

5-[[[1-[[(13-Cyclohexyl-6,7-dihydro-6-oxo-5H-indolo[1,2-d][1,4]benzodiazepine-10-yl)carbonyl]amino]cyclopentyl]carbonyl]amino]-1-methyl-1H-indole-2-carboxylic Acid

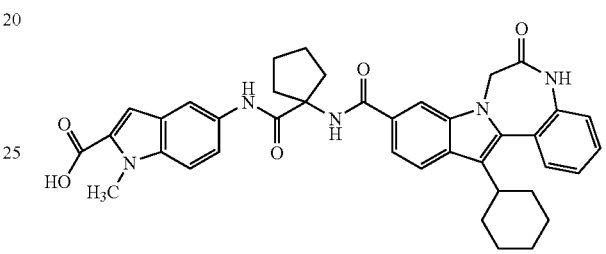

Sodium hydroxide (400 mL of 10 N, 4 mmol) was added to a solution of the preceding ester in THF (2 mL) and methanol (1.5 mL) in a microwave vial. The vial was sealed and the contents heated in a microwave apparatus for 10 min at 100° C. The mixture was cooled and diluted with water. The organics were removed on a rotating evaporator. The aqueous solution was cooled and acidified with 37% HCl to precipitate the mixture of acids. The solids were collected, washed with cold water and dried. The resulting solid (192 mg) was dissolved in acetic acid (4 mL) and the solution heated to boiling. The solution was concentrated to dryness on a rotating evaporator. The residue was diluted with toluene and partially concentrated whereupon the product precipitated. The solid was collected, washed with toluene followed by diethyl ether and dried to afford the titled compound as a colorless solid (70 mg). MS m/z 658 (MH⁺); ¹H NMR (500 MHz, DMSO-D6) δ ppm 1.16–1.26 (m, J=5.49 Hz, 1 H) 1.37–1.56 (m, 3 H) 1.66–1.84 (m, 6 H) 1.87–1.95 (m, J=8.24 Hz, 1 H) 1.99–2.20 (m, 5 H) 2.33–2.45 (m, 2 H) 2.81–2.94 (m, 1 H) 3.97–3.98 (m, 3 H) 4.62 (d, J=14.65 Hz, 1 H) 5.11 (d, J=14.34 Hz, 1 H) 7.06–7.56 (m,

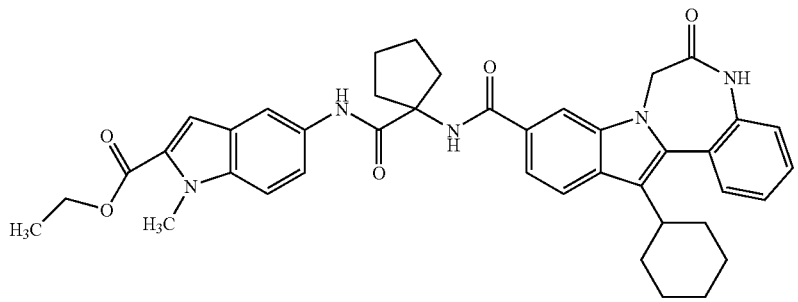

6 H) 7.60–7.72 (m, 1 H) 7.84–7.96 (m, 2 H) 8.38 (d, J=7.63 Hz, 2 H) 9.49 (s, 1 H) 10.36 (s, 1 H).

Methyl 3-[2-[1-[[13-cyclohexyl-6,7,13,13a-tetrahydro-6-oxo-5H-indolo[1,2-d][1,4]benzodiazepine-10-yl)carbonyl]amino]cyclopentyl]-1H-benzimidazol-5-yl]-(2E)-2-propenoate

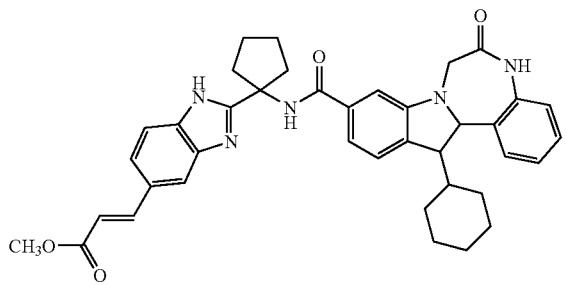

The TBTU mediated coupling of (E)-methyl 3-(2-(1-aminocyclopentyl)-1H-benzo[d]imidazol-5-yl)acrylate[1] with 13-cyclohexyl-6,7-dihydro-6-oxo-5H-indolo[1,2-d][1,4]benzodiazepine-10-carboxylic acid afforded the titled product as a colorless solid. MS m/z 642 (MH$^+$).

3-[2-[1-[[13-Cyclohexyl-6,7,13,13a-tetrahydro-6-oxo-5H-indolo[1,2-d][1,4]benzodiazepine-10-yl)carbonyl]amino]cyclopentyl]-1H-benzimidazol-5-yl]-(2E)-2-propenoic Acid and 3-[2-[1-[[(12-Cyclohexyl-12,12a-dihydroindolo[1,2-c]quinazolin-9-yl)carbonyl)amino]cyclopentyl]-1H-benzimidazol-5-yl]-(2E)-2-propenoic Acid

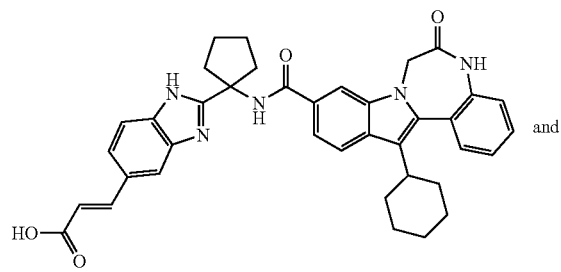

and

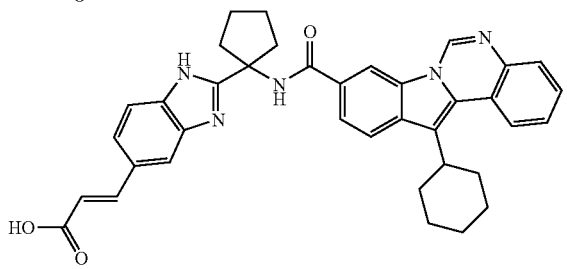

The preceding ester was dissolved in a mixture of THF (1.5 mL) and methanol (1 mL) in a microwave vial to which sodium hydroxide (250 μL of 10 N) was added. The vial was sealed and the contents heated at 100° C. in a microwave apparatus. The mixture was diluted with water and acidified with 37% HCl resulting in the precipitation of a gum. The gum was extracted with ethyl acetate. The extract was washed (water, brine), dried over sodium sulfate and concentrated. The residue was boiled with acetic acid and concentrated to dryness. It was concentrated a second time with acetic acid on a rotary evaporator. The residue was purified on a Shimadzu preparative reverse phase HPLC to afford two major products:

The cyclic lactam (14.9 mg) isolated as a TFA salt by lyophilization of the major fraction. MS m/z 628 (MH$^+$); $^1$H NMR (500 MHz, MeOD) □ ppm 1.25–1.53 (m, 4 H) 1.64–1.76 (m, 2 H) 1.83–2.09 (m, 8 H) 2.36–2.46 (m, 2 H) 2.48–2.58 (m, 2 H) 2.82–2.92 (m, 1 H) 4.49 (d, J=14.95 Hz, 1 H) 4.88–4.95 (m, 1 H) 6.51 (d, J=15.87 Hz, 1 H) 7.20 (d, J=7.93 Hz, 1 H) 7.31 (t, J=7.63 Hz, 1 H) 7.42 (t, J=7.78 Hz, 1 H) 7.51 (dd, J=13.43, 8.24 Hz, 2 H) 7.65 (d, J=8.55 Hz, 1 H) 7.69–7.78 (m, 2 H) 7.81–7.88 (m, 2 H) 8.12 (s, 1 H). And the des carbonyl (3.5 mg) isolated as a yellow solid in the form of a TFA salt. MS m/z 598 (MH$^+$); $^1$H NMR (500 MHz, MeOD) □ ppm 1.66 (d, J=13.12 Hz, 4 H) 1.84–2.29 (m, 11 H) 2.47–2.71 (m, 4 H) 3.70–3.78 (m, 1 H) 6.59–6.64 (m, 1 H) 7.54–8.01 (m, 10 H) 8.21 (d, J=8.85 Hz, 1 H) 8.34–8.42 (m, 1 H) 8.80 (s, 1 H) 9.30 (s, 1 H).

13-Cyclohexyl-6,7-dihydro-6-oxo-N-[1-[[[4-(4-thiazolyl)phenyl]amino]carbonyl]cyclopentyl]-5H-indolo[1,2-d][1,4]benzodiazepine-10-carboxamide

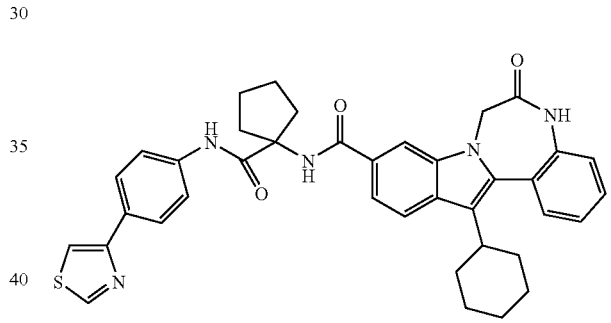

TBTU (65 mg, 0.20 mmol) was added to a stirred mixture of ethyl 4-(4-(1-aminocyclopentanecarboxamido)phenyl)thiazole-2-carboxylate[1] (53.5 mg, 0.15 mmol), 13-cyclohexyl-6,7-dihydro-6-oxo-5H-indolo[1,2-d][1,4]benzodiazepine-10-carboxylic acid (50.7 mg, 0.14 mmol), and TEA (75 μL, 0.54 mmol) in DMSO (800 μL). The mixture was stirred for 1 hr at 22° C. and the was diluted with water to precipitate ethyl 4-[4-[[[1-[[(13-cyclohexyl-6,7-dihydro-6-oxo-5H-indolo[1,2-d][1,4]benzodiazepine-10-yl)carbonyl]amino]phenyl-2-thiazolecarboxylate. The colorless solid was collected, washed with water and dried. A microwave vial containing a mixture of the solid in THF (1 mL), methanol (1 mL), and 10 N NaOH (200 μL) was sealed and heated at 100° C. in a microwave apparatus for 10 min. The solution was cooled and acidified with 1 N HCl to precipitate a solid which was collected, washed with cold water and dried. The solid was boiled in acetic acid for 3 min and then concentrated to dryness. A solution of the residue in DMF was purified on the Shimadzu preparative liquid chromatograph to afford the decarboxylated product with the structure shown as a brown solid. MS m/z 644 (MH$^+$); $^1$H NMR (500 MHz, MeOD) □ ppm 1.15–2.14 (m, 14 H) 2.24–2.39 (m, 2

H) 2.48–2.65 (m, J=13.1.7 Hz, 2 H) 2.79–2.98 (m, 1 H) 4.45 (s, 1 H) 4.96–5.12 (m, 1 H) 6.87 (s, 1 H) 7.18 (d, J=7.32 Hz, 1 H) 7.29–7.46 (m, 3 H) 7.51 (d, J=8.78 Hz, 2 H) 7.66 (d, J=8.78 Hz, 2 H) 7.83 (d, J=8.78 Hz, 2 H) 7.90 (d, J=8.42 Hz, 1 H) 8.13 (d, J=8.42 Hz, 1 H).

13-Cyclohexyl-6,7-dihydro-N-[(1-carboxamidocyclopent-1-yl)1–6-oxo-5H-indolo[1,2-d][1,4]benzodiazepine-10-carboxamide

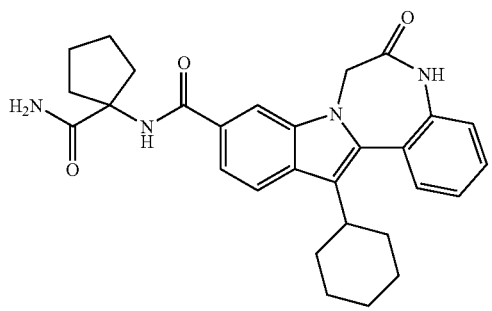

A solution of 2 M methanolic ammonia (3.3 mL) was added to a stirred solution of 1-(tert-butoxycarbonyl)cyclopentanecarboxylic acid (1.0 g, 4.36 mmol), TEA (3.65 mL, 0.0262 mol), and TBTU (1.61 g, 5 mmol) in DMSO (5 mL) at 22° C. After stirring for 1 hr the solution was poured into ice cold water. The mixture was extracted with ethyl acetate. The extract was washed with brine (2×), dried over MgSO$_4$ and concentrated to leave a colorless solid. Recrystallization from ethyl acetate-hexanes afforded 1-(tert-butoxycarbonyl)cyclopentanecarboxamide (660 mg, 66%). TFA (2.5 mL) was added to a stirred solution of the amide (445 g) in methylene chloride (2.5 mL). The solution was stirred for 1 hr at 22° C. and then concentrated to an oil. Trituration with diethyl ether afforded the TFA salt of 1-aminocyclopentanecarboxamide as a colorless solid. Coupling of the amine with, 13-cyclohexyl-6,7-dihydro-6-oxo-5H-indolo[1,2-d][1,4]benzodiazepine-10-carboxylic acid afforded the titled compound. MS m/z 486 (MH$^+$); $^1$H NMR (300 MHz, DMSO-D6) δ ppm 1.09–2.29 (m, 8 H) 2.42–2.56 (m, 2 H) 2.86 (s, 1 H) 4.61 (s, 1 H) 4.97–5.17 (m, 1 H) 6.73 (s, 1 H) 7.03 (s, 1 H) 7.29 (d, J=7.68 Hz, 1 H) 7.38 (t, J=7.50 Hz, 1 H) 7.50 (t, J=7.50 Hz, 2 H) 7.61 (d, J=9.51 Hz, 1 H) 7.88 (d, J=8.78 Hz, 1 H) 8.28 (s, 1 H).

Using methodology similar to that just described the following examples of the instant invention were also prepared.

13-Cyclohexyl-6,7-dihydro-N-[(4-hydroxy-3-methoxyphenyl)methyl-6-oxo-5H-indolo[1,2-d][1,4]benzodiazepine-10-carboxamide

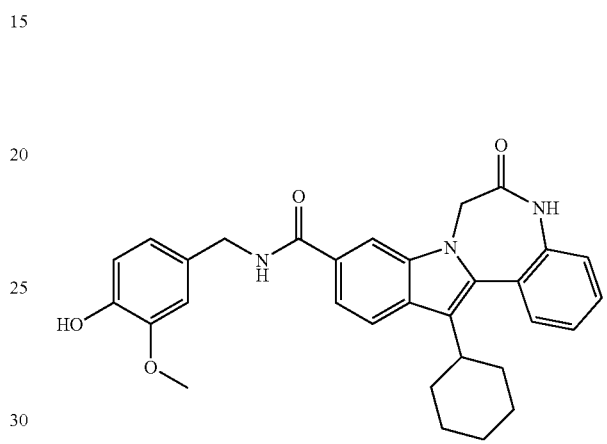

MS m/z 510 (MH$^+$); 1H NMR (300 MHz, CHLOROFORM-D) □ ppm 1.04–2.14 (m, 10 H) 2.78–2.93 (m, 1 H) 4.33–4.49 (m, 1 H) 4.59 (s, 2 H) 4.86–5.07 (m, 1 H) 6.61 (s, 1 H) 6.82–6.93 (m, 3 H) 7.15 (d, J=7.32 Hz, 1 H) 7.35 (t, J=6.95 Hz, 1 H) 7.39–7.47 (m, 2 H) 7.52 (d, J=7.68 Hz, 1 H) 7.87 (d, J=8.42 Hz, 1 H) 8.00 (s, 1 H) 8.15 (s, 1 H).

In addition to the methodology discussed in other sections of this document, examples of the N-(1-(diarylcarbamoyl)-, N-(1-(diheteroarylcarbamoyl)-, N-(1-(arylheteroarylcarbamoyl)-, and N-(1-(heteroarylarylcarbamoyl)cyclopentyl) indole carboxamides of the instant invention can be accessed using the methodology depicted in the scheme below.

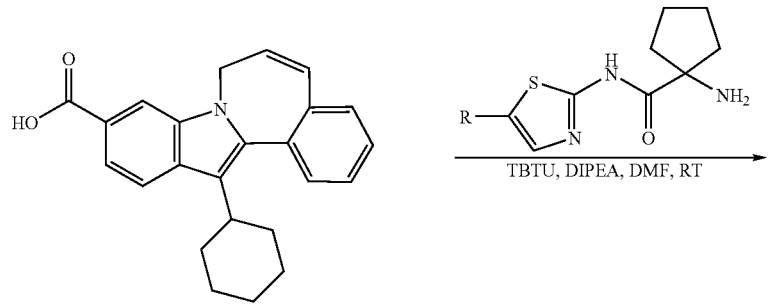

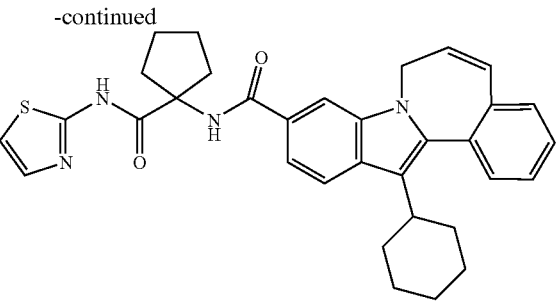

Where R = Br
Pd(PPh₃)₄, NaHCO₃,
THF, 130° C.

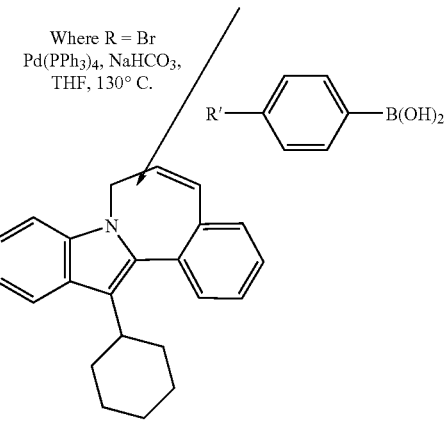

R'—⟨ ⟩—B(OH)₂

7H-indolo[2,1-a][2]benzazepine-10-carboxamide, 13-cyclohexyl-N-[1-[(2-thiazolylamino)carbonyl]cyclopentyl]

7H-indolo[2,1-a][2]benzazepine-10-carboxamide, 13-cyclohexyl-N-(1-((5-bromothiazol-2-yl)carbamoyl)cyclopentyl)

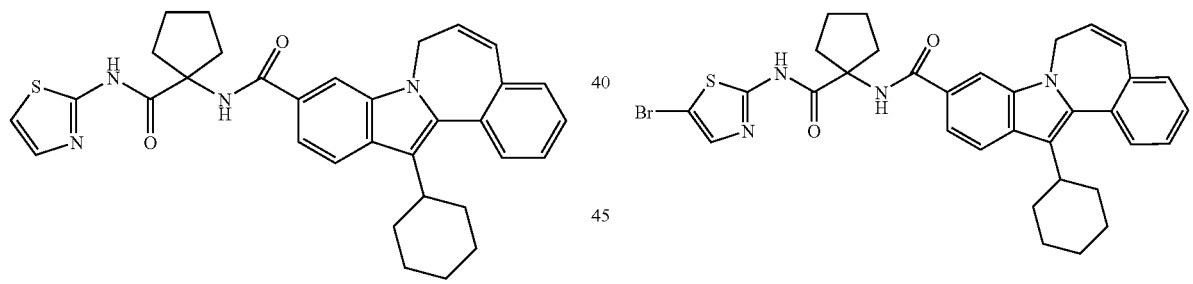

To a solution of 13-cyclohexyl-7H-indolo[2,1-a][2]benzazepine-10-carboxylic acid (19 mg, 0.053 mmol) in DMF (0.2 mL) and DIPEA (0.056 mL, 0.32 mmol) was added TBTU (19 mg, 0.059 mmol). The resulting solution was stirred at 22° C. for 15 min. 1-amino-N-(thiazol-2-yl)cyclopentanecarboxamide (23 mg, 0.11 mmol) was added and this solution was stirred at 22° C. for 18 hr. 1M HCl (20 mL) was added and the aqueous layer was extracted with CHCl₃ (2×40 mL). The organic phase was dried over Na₂SO₄, filtered, and concentrated under reduced pressure. Silica gel chromatography (1:3 EtOAc:hexanes) of the concentrate afforded the title compound (25 mg, 85%) as a clear oil. MS m/z 551 (MH⁺), ¹H NMR (300 MHz, CDCl₃) ☐ ppm 1.15–1.23 (m, 2H), 1.26–1.34 (m, 2H), 1.49–1.62 (m, 6H), 1.68–1.80 (m, 4H), 2.24–2.39 (m, 4H), 2.60–2.77 (m, 3H), 6.07 (m, 1 H), 6.48 (d, J=11.3 Hz, 1H), 6.60 (d, J=10.9 Hz, 1H), 7.22 (dd, J=10.9, 6.3 Hz, 1H), 7.24 (m, 2H), 7.40 (m, 2H), 7.48 (d, J=3.1 Hz, 1 H), 7.56 (d, J=6.3 Hz, 1 H), 7.87 (s, 1 H), 8.34 (d, J=9.1 Hz, 1H).

To a solution of 13-cyclohexyl-7H-indolo[2,1-a][2]benzazepine-10-carboxylic acid (191 mg, 0.534 mmol) in DMF (2 mL) and DIPEA (0.558 mL, 3.21 mmol) was added TBTU (189 mg, 0.588 mmol). The resulting solution was stirred at 22° C. for 15 min. 1-1-amino-N-(5-bromothiazol-2-yl)cyclopentanecarboxamide (431 mg, 1.07 mmol) was added and this solution was stirred at 22° C. for 18 hr. 1 M HCl (20 mL) was added and the aqueous layer was extracted with CHCl₃ (2×40 mL). The organic phase was dried over Na₂SO₄, filtered, and concentrated under reduced pressure. Silica gel chromatography (1:3 EtOAc:hexanes) of the concentrate afforded the title compound (276 mg, 82%) as a yellow oil. MS m/z 630 (MH⁺), ¹H NMR (300 MHz, CDCl₃) δ ppm 1.14–1.21 (m, 2H), 1.24–1.33 (m, 2H), 1.48–1.60 (m, 6H), 1.69–1.80 (m, 4H), 2.24–2.38 (m, 4H), 2.59–2.75 (m, 3H), 6.08 (m, 1H), 6.49 (d, J=11.3 Hz, 1H), 6.62 (d, J=10.9 Hz, 1H), 7.22 (dd, J=1.9, 5.6 Hz, 1H), 7.24 (dd, J=10.9, 6.3 Hz, 1H), 7.42 (m, 2H), 7.54 (s, 1H), 7.57 (d, J=6.3 Hz, 1 H), 7.87 (s, 1 H), 8.33 (d, J=9.1 Hz, 1H).

Benzoic acid, 4-[2-[[[1-[[(13-cyclohexyl-7H-indolo[2,1-a][2]benzazepin-10-yl)carbonyl]amino]cyclopentyl]carbonyl]amino]-5-thiazolyl]

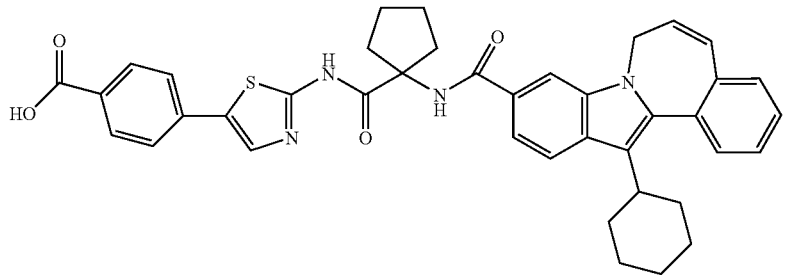

To a solution of 7H-indolo[2,1-a][2]benzazepine-10-carboxamide, 13-cyclohexyl-N-(1-((5-bromothiazol-2-yl)carbamoyl)cyclopentyl)- (60 mg, 0.095 mmol) in THF (2.0 mL) was added 4-boronobenzoic acid (32 mg, 0.19 mmol), sodium bicarbonate (32 mg, 0.38 mmol) and tetrakis(triphenylphosphine)palladium(0) (10 mg, 0.01 mmol). The resulting mixture was stirred in a sealed tube in a microwave at 130° C. for 5 min. 1M HCl (10 mL) was added and the aqueous layer was extracted with CHCl$_3$ (2×20 mL). The organic phase was dried over Na$_2$SO$_4$, filtered, and concentrated under reduced pressure. Silica gel chromatography (1:1 EtOAc:hexanes) of the concentrate afforded the title compound (27 mg, 43%) as a yellow oil. MS m/z 671 (MH$^+$), $^1$H NMR (300 MHz, CDCl$_3$) δ ppm 1.15–1.23 (m, 2H), 1.26–1.34 (m, 2H), 1.49–1.62 (m, 6H), 1.68–1.80 (m, 4H), 2.24–2.39 (m, 4H), 2.60–2.77 (m, 3H), 5.92 (s, 1H) 6.07 (m, 1H), 6.48 (d, J=11.3 Hz, 1H), 6.60 (d, J=10.9 Hz, 1H), 7.23 (dd, J=10.9, 6.3 Hz, 1H), 7.29 (d, J=8.8 Hz, 2H), 7.40 (m, 2H), 7.56 (d, J=6.3 Hz, 1 H), 7.84 (d, J=8.8 Hz, 2H), 7.78 (s, 1 H), 8.34 (d, J=9.1 Hz, 1H).

In a similar fashion, this methodology could be applied to related examples in the indolo[1,2-d][1,4]benzodiazepine class on inhibitors of the instant invention, as depicted in the scheme and examples described below.

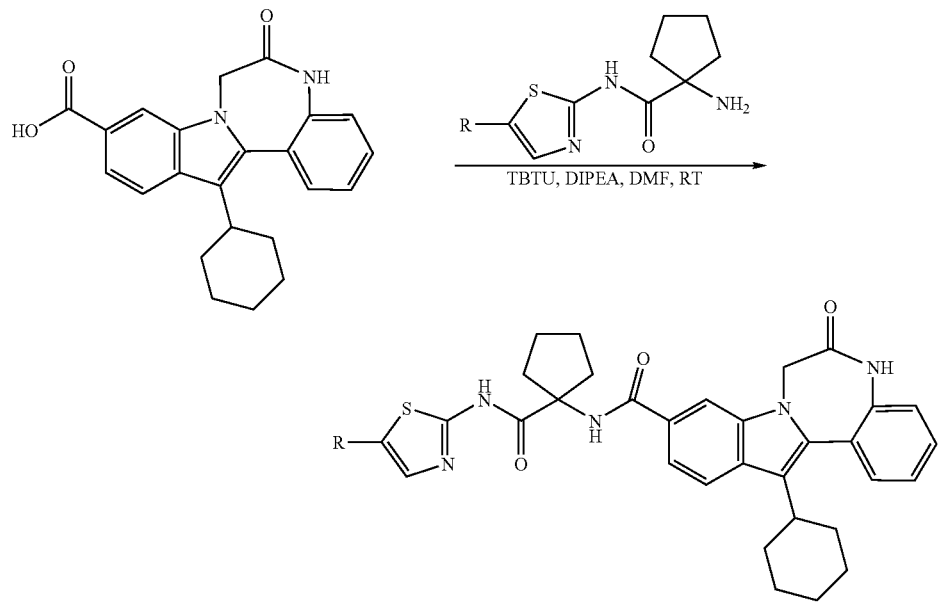

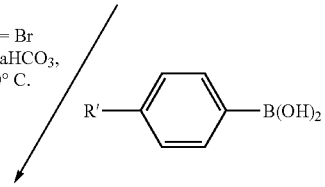

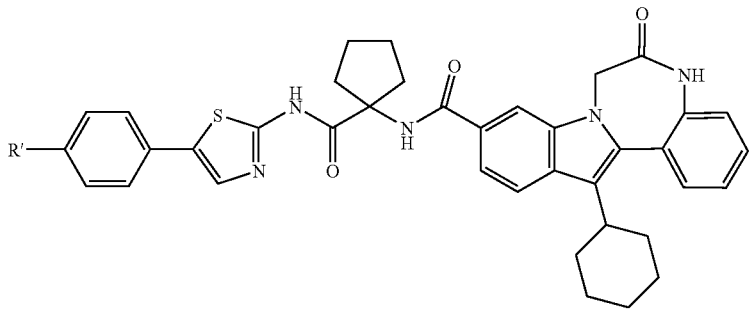

5H-indolo[1,2-d][1,4]benzodiazepine-10-carboxamide, 13-cyclohexyl-6,7-dihydro-6-oxo-N-[1-[(2-thiazolylamino)carbonyl]cyclopentyl]- (Z)

5H-indolo[1,2-d][1,4]benzodiazepine-10-carboxamide, 13-cyclohexyl-6,7-dihydro-6-oxo-N-(1-((5-bromothiazol-2-yl)carbamoyl)cyclopentyl)]-

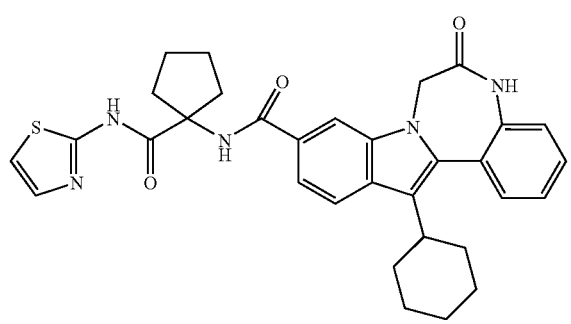

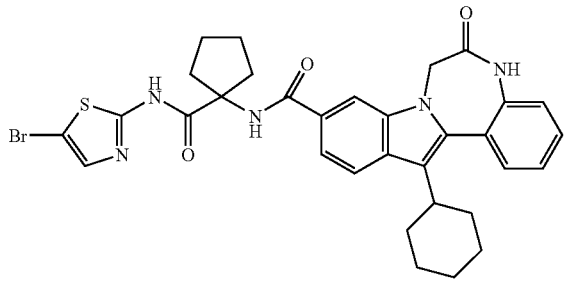

To a solution of 13-cyclohexyl-6,7-dihydro-6-oxo-5H-indolo[1,2-d][1,4]benzodiazepine-10-carboxylic acid (20 mg, 0.053 mmol) in DMF (0.2 mL) and DIPEA (0.056 mL, 0.32 mmol) was added TBTU (19 mg, 0.059 mmol). The resulting solution was stirred at 22° C. for 15 min. 1-amino-N-(thiazol-2-yl)cyclopentanecarboxamide (23 mg, 0.11 mmol) was added and this solution was stirred at 22° C. for 18 hr. 1 M HCl (10 mL) was added and the aqueous layer was extracted with CHCl$_3$ (2×20 mL). The organic phase was dried over Na$_2$SO$_4$, filtered, and concentrated under reduced pressure. Silica gel chromatography (1:3 EtOAc:hexanes) of the concentrate afforded the title compound (25 mg, 83%) as a clear oil. MS m/z 568 (MH$^+$), $^1$H NMR (300 MHz, CDCl$_3$) δ ppm 1.16–1.25 (m, 2H), 1.27–1.35 (m, 2H), 1.49–1.61 (m, 6H), 1.66–1.78 (m, 4H), 2.25–2.40 (m, 2H), 2.61–2.75 (m, 3H), 4.89 (broad m, 1H), 5.41 (broad m, 1H), 7.05 (dd, J=10.9, 6.3 Hz, 1H), 7.24 (d, J=3.1 Hz, 1H), 7.48 (m, 2H), 7.51 (d, J=3.1 Hz, 1H), 7.63 (d, J=9.1 Hz, 1H), 7.66 (d, J=9.0 Hz, 1H), 7.93 (s, 1H), 8.20 (d, J=9.1 Hz, 1H).

To a solution of 13-cyclohexyl-6,7-dihydro-6-oxo-5H-indolo[1,2-d][1,4]benzodiazepine-10-carboxylic acid (200 mg, 0.534 mmol) in DMF (2 mL) and DIPEA (0.558 mL, 3.21 mmol) was added TBTU (189 mg, 0.588 mmol). The resulting solution was stirred at 22° C. for 15 min. 1-1-amino-N-(5-bromothiazol-2-yl)cyclopentanecarboxamide (431 mg, 1.07 mmol) was added and this solution was stirred at 22° C. for 18 hr. 1 M HCl (20 mL) was added and the aqueous layer was extracted with CHCl$_3$ (2×40 mL). The organic phase was dried over Na$_2$SO$_4$, filtered, and concentrated under reduced pressure. Silica gel chromatography (1:3 EtOAc:hexanes) of the concentrate afforded the title compound (269 mg, 78%) as a yellow oil. MS m/z 647 (MH$^+$), $^1$H NMR (300 MHz, CDCl$_3$) □ ppm 1.18–1.26 (m, 2H), 1.28–1.36 (m, 2H), 1.49–1.61 (m, 6H), 1.67–1.78 (m, 4H), 2.25–2.39 (m, 2H) 2.61–2.76 (m, 3H), 4.84 (broad m, 1H), 5.42 (broad m, 1H), 7.04 (dd, J=10.9, 6.3 Hz, 1H), 7.46 (m, 2H), 7.50 (s, 1H), 7.63 (d, J=9.1 Hz, 1H), 7.68 (d, J=9.0 Hz, 1H), 7.95 (s, 1H), 8.17 (d, J=9.1 Hz, 1H). benzoic acid, 4-[2-[[[1-[[(13-cyclohexyl-6,7-dihydro-6-oxo-5H-indolo[1,2-d][1,4]benzodiazepin-10-yl)carbonyl]amino]cyclopentyl]carbonyl]amino]-5-thiazolyl]-

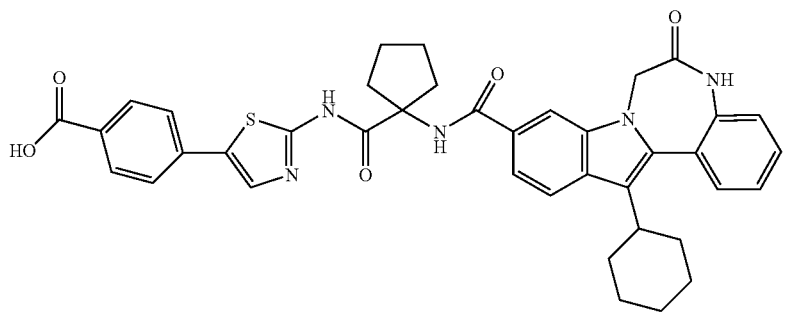

To a solution of 5H-indolo[1,2-d][1,4]benzodiazepine-10-carboxamide, 13-cyclohexyl-6,7-dihydro-6-oxo- N-(1-((5-bromothiazol-2-yl)carbamoyl)cyclopentyl)]- (40 mg, 0.062 mmol) in THF (1.5 mL) was added 4-boronobenzoic acid (21 mg, 0.12 mmol), sodium bicarbonate (21 mg, 0.25 mmol) and tetrakis(triphenylphosphine)palladium(0) (10 mg, 0.01 mmol). The resulting mixture was stirred in a sealed tube in a microwave at 130° C. for 5 min. 1M HCl (10 mL) was added and the aqueous layer was extracted with $CHCl_3$ (2×20 mL). The organic phase was dried over $Na_2SO_4$, filtered, and concentrated under reduced pressure. Silica gel chromatography (1:1 EtOAc:hexanes) of the concentrate afforded the title compound (26 mg, 62%) as a yellow oil. MS m/z 688 (MH+), $^1$H NMR (300 MHz, $CDCl_3$) δ ppm 1.19–1.26 (m, 2H), 1.28–1.37 (m, 2H), 1.50–1.62 (m, 6H), 1.67–1.78 (m, 4H), 2.25–2.39 (m, 2H), 2.61–2.76 (m, 3H), 4.88 (broad m, 1H), 5.41 (broad m, 1H), 5.98 (s, 1H), 7.02 (dd, J=10.9, 6.3 Hz, 1H), 7.28 (d, J=8.8 Hz, 2H), 7.48 (m, 2H), 7.28 (d, J=8.8 Hz, 2H), 7.64 (d, J=9.1 Hz, 1H), 7.71 (d, J=9.0 Hz, 1H), 7.95 (s, 1H), 8.21 (d, J=9.1 Hz, 1H).

Examples of the N-(1-(5-aryl-1H-1,2,4-triazol-3-yl)cyclopentyl)-indole-6-carboxamide class of inhibitors of the instant invention, may be accessed using the methodology shown in the schemes and described in the examples given below.

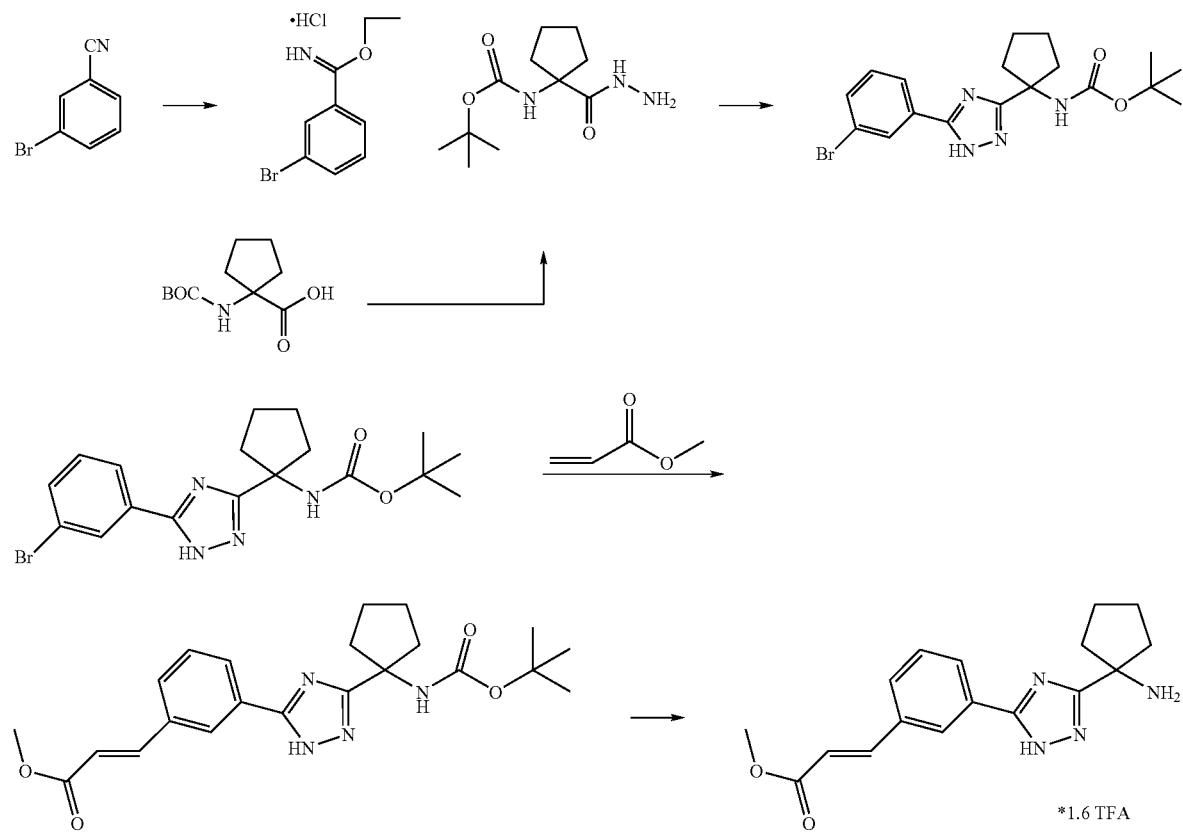

405
Ethyl 3-bromobenzimidate hydrochloride

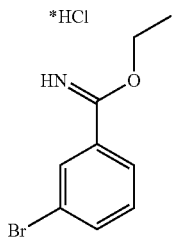

3-bromobenzonitrile (5 g, 27.5 mMol) was dissolved in 130 ml of absolute ethanol and cooled to 0 C under N2. Hydrogen chloride gas was bubbled into the ethanol solution for 3 hrs at 0 C and the reaction capped and placed in a freezer at −7 C for 4 days. A 25 ml aliquot of the reaction mixture was concentrated to dryness in vaccuo and 932 mg the pale pink crystalline solid vacuum dried and placed under nitrogen for storage. $^1$H NMR (300 MHz, CHLOROFORM-D) δ ppm 12.78 (s, 1 H) 12.09 (s, 1 H) 8.55 (d, J=8.05 Hz, 1 H) 8.35 (t, J=1.83 Hz, 1 H) 7.82 (dd, J=8.05, 1.10 Hz, 1 H) 7.47 (t, J=8.05 Hz, 1 H) 4.94 (q, J=7.07 Hz, 2 H) 1.62 (t, J=6.95 Hz, 4 H).

Cyclopentanecarboxylic acid,
1-[[(1,1-dimethylethoxy)carbonyl]amino]-,
hydrazide

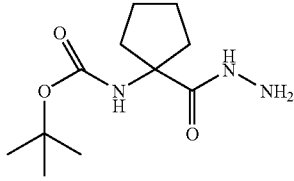

1-[[(1,1-dimethylethoxy)carbonyl]amino]cyclopentanecarboxylic acid, (5.04 g, 22 mMol) was dissolved in 150 ml of THF with 5.8 ml (33 mMol) diisopropylethyl amine. TBTU (9.88 g, 30.8 mMol) was added to the reaction and stirred for 25 minutes prior to the all at once addition of 7 ml (223 mMol) anhydrous hydrazine. The reaction was stirred overnight at room temperature under nitrogen, and volatiles removed in vaccuo. The residue was dissolved in ethyl acetate and diethyl ether, washed with 1N sodium hydroxide, brine and dried over magnesium sulfate. The filtrate concentrated in vaccuo and a reddish oil dried in vaccuo which crystallized upon standing to obtain 1.3 g of a pink solid. $^1$H NMR (300 MHz, CHLOROFORM-D) δ ppm 7.89 (s, 1 H) 4.78 (s, 1 H) 3.33 (s, 2 H) 2.06–2.33 (m, 2 H) 1.60–1.95 (m, 6 H) 1.42 (s, 9 H).

406
tert-Butyl 1-(5-(3-bromophenyl)-1H-1,2,4-triazol-3-yl)cyclopentylcarbamate

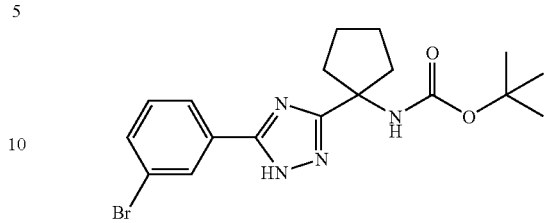

Ethyl 3-bromobenzimidate hydrochloride (905 mg, 3.42 mMol) was suspended in 10.4 ml of isopropanol and 8.9 ml (51 mMol) of diisopropylethyl amine added along with 1-BOC-aminocyclopentane carboxylic acid hydrazide (885 mg, 3.62 mMol). The reaction was stirred for 10 minutes at room temperature and then immersed in an oil bath preheated to 65 C. The reaction was heated at 65 C for 5 days, cooled and volatiles removed in vacuuo. The residue was dissolved in ethyl acetate and washed with citric acid, sodium bicarbonate and brine, dried over magnesium sulfate and the filtrate concentrated to provide 1.29 g (93%) of product. $^1$H NMR (500 MHz, CHLOROFORM-D) δ ppm 12.04 (s, 1 H) 8.25 (d, J=1.53 Hz, 1 H) 8.01 (d, J=7.63 Hz, 1 H) 7.48 (t, J=8.55 Hz, 1 H) 7.28 (t, J=7.78 Hz, 1 H) 5.03 (s, 1 H) 2.41–2.51 (m, 2 H) 2.18–2.26 (m, 2 H) 1.80–1.89 (m, 4 H) 1.43 (s, 9 H) MS m/z 407(MH$^+$); MS m/z 405(M-H)$^-$.

(E)-Methyl 3-(3-(5-(1-(tert-butoxycarbonyl)cyclopentyl)-2H-1,2,4-triazol-3-yl)phenyl)acrylate

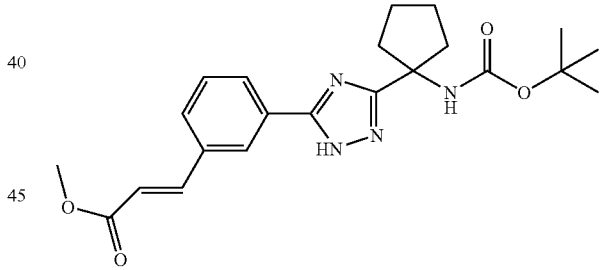

tert-Butyl 1-(5-(3-bromophenyl)-1H-1,2,4-triazol-3-yl) cyclopentylcarbamate (585 mg, 1.44 mMol) was dissolved in 10 ml of acetonitrile and tri(o-tolyl)phosphine (88 mg, 0.29 mMol), palladium(II) acetate (33 mg, 0.15 mMol), and diisopropylethyl amine (0.50 ml, 2,87 mMol) added to the reaction in a 20 ml microwave vessel containing a magnetic stir bar. The reaction was sparged with nitrogen for 5 minutes then heated in a microwave for 5 minutes at 120 C and stepped up in temperature to 170 C for an additional 10 minutes. The reaction cooled, filtered through a ceilite plug, rinsed with acetonitrile. Volatiles were removed from the filtrate to yield a solid of 962 mg which was purified on a 40 g Silica Gel Biotage 25M column. A step gradient elution of 7% ethyl acetate to 60% ethyl acetate yielded 435 mg (73%) of product as a colorless solid. $^1$H NMR (300 MHz, CHLOROFORM-D) δ ppm 8.24 (s, 1 H) 8.07 (d, J=7.68 Hz, 1 H) 7.72 (d, J=16.47 Hz, 1 H) 7.34–7.57 (m, 2 H) 7.23 (s, 1 H) 6.51 (d, J=16.10 Hz, 1 H) 4.99 (s, 1 H) 3.78 (s, 3 H)

2.34–2.58 (m, J=10.25 Hz, 2 H) 2.13–2.31 (m, 2 H) 1.75–1.97 (m, 4 H) 1.41 (s, 9 H); MS m/z 413(MH+); MS m/z 411(M-H)−.

(E)-Methyl 3-(3-(5-(1-aminocyclopentyl)-2H-1,2,4-triazol-3-yl)phenyl)acrylate Trifluoroacetic acid salt

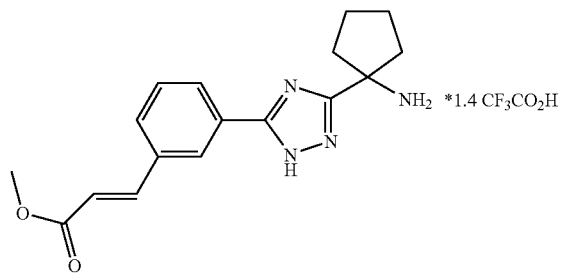

(E)-Methyl 3-(3-(5-(1-(tert-butoxycarbonyl)cyclopentyl)-2H-1,2,4-triazol-3-yl)phenyl)acrylate (429 mg, 1.04 mMol) was dissolved in 10 ml of anhydrous dichloromethane. Trifluoroacetic Acid (10 ml) was added to the reaction and the mixture stirred under nitrogen at room temperature for 1.5 hours. The volatiles were removed in vacuuo and the residual trifluoromethyl acetic acid removed by azeotroping from benzene/dichloromethane. The colorless solid was dried in vacuum at room temperature. $^1$H NMR (300 MHz, DMSO-D6) δ ppm 14.67 (s, 1 H) 8.58 (s, 3 H) 8.31 (s, 1 H) 8.03 (d, J=7.69 Hz, 1 H) 7.87 (d, J=7.68 Hz, 1 H) 7.73 (d, J=15.74 Hz, 1 H) 7.61 (t, J=7.68 Hz, 1 H) 6.71 (d, J=16.10 Hz, 1 H) 3.75 (s, 3 H) 2.26–2.41 (m, 2 H) 1.97–2.14 (m, 2 H) 1.77–1.94 (m, 4 H); MS m/z 313(MH+); MS m/z 311(M-H)−.

The 1-(5-aryl-1H-1,2,4-triazol-3-yl)cyclopentanamine intermediates generated by the above methodology can subsequently be coupled to suitable indole derivatives to generate further examples of the instant invention, as shown in the scheme below.

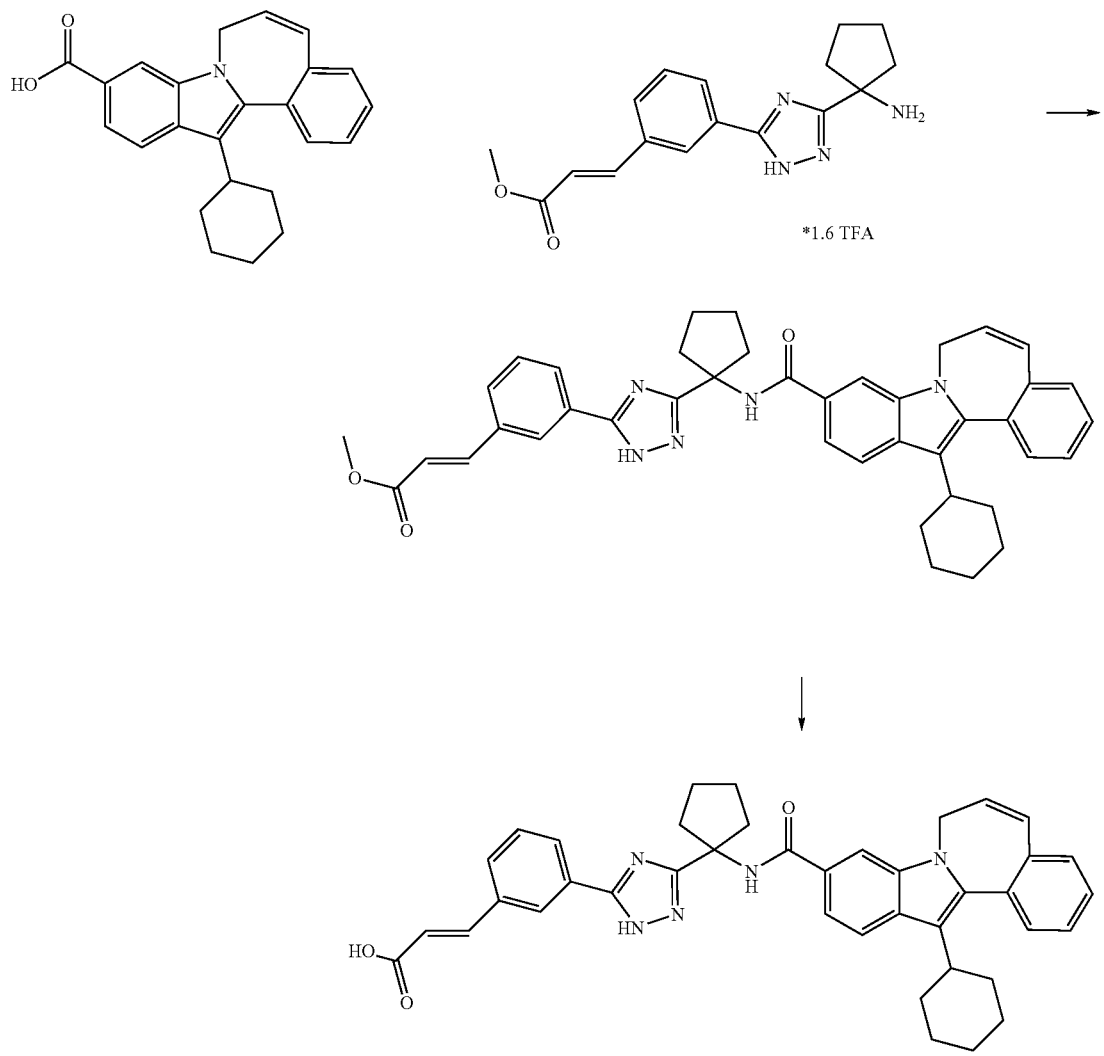

2-propenoic acid, 3-[3-[3-[1-[[(13-cyclohexyl-7H-indolo[2,1-a][2]benzazepin-10-yl)carbonyl]amino]cyclopentyl]-1H-1,2,4-triazol-5-yl]phenyl]-, methyl ester, (2E)-

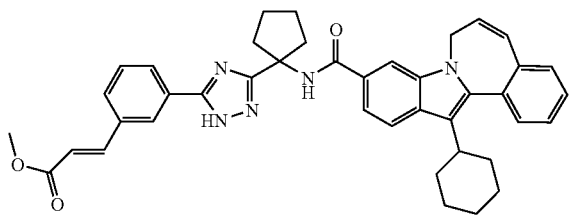

7H-indolo[2,1-a][2]benzazepine-10-carboxylic acid, 13-cyclohexyl- (200 mg, 0.56 mMol) and (E)-methyl 3-(3-(5-(1-aminocyclopentyl)-2H-1,2,4-triazol-3-yl)phenyl)acrylate Trifluoroacetic acid salt (200 mg, 0.41 mMol) was dissolved in 5 ml of DMF along with HOAt (82 mg, 0.60 mMol). Diisopropylethyl amine (390 uL, 2.24 mMol) was added to the reaction mixture followed by HATU (230 mg, 0.60 mMol). The reaction was capped under nitrogen and stirred at room temperature for 5 hours. Water was added to quench the reaction and the volatiles removed in vacuuo, and the residue dissolved in ethyl acetate, washed with 0.1 N hydrochloric acid, saturated aqueous sodium bicarbonate, brine and then dried over magnesium sulfate. The filtrate concentrated to dryness to yield an orange solid which was purified on 20 g of silica gel, eluting with a gradient of 1% ethyl acetate to 20% ethyl acetate in dichloromethane. Product fractions were concentrated to give a total of 178 mg (68%). $^1$H NMR (500 MHz, CHLOROFORM-D) δ ppm 8.28 (s, 1 H) 8.11 (d, J=7.63 Hz, 1 H) 8.01 (s, 1 H) 7.87 (d, J=8.55 Hz, 1 H) 7.73 (d, J=16.17 Hz, 1 H) 7.47–7.59 (m, 2 H) 7.39–7.45 (m, 3 H) 7.33–7.38 (m, 1 H) 7.30 (d, J=8.55 Hz, 2 H) 6.81 (d, J=10.07 Hz, 1 H) 6.62 (s, 1 H) 6.53 (d, J=15.87 Hz, 1 H) 6.20–6.33 (m 1 H) 4.88 (s, 1 H) 4.20 (s, 1 H) 3.80 (s, 3 H) 2.85 (t, J=11.44 Hz, 1 H) 2.64–2.77 (m, 2 H) 2.43–2.58 (m, 2 H) 1.97–2.14 (m, 3 H) 1.85–1.98 (m, 6 H) 1.76 (d, J=6.41 Hz, 2 H) 1.29–1.43 (m, 3 H); MS m/z 652(MH$^+$); MS m/z 650(M-H)$^-$; CHN Analysis: Calculated for $C_{41}H_{41}N_5O_3 \cdot 0.85$ $H_2O$; Calc: C, 73.82; H, 6.45; N, 10.50. Found: C, 73.82; H, 6.48; N, 10.38.

2-propenoic acid, 3-[3-[3-[1-[[(13-cyclohexyl-7H-indolo[2,1-a][2]benzazepin-10-yl)carbonyl]amino]cyclopentyl]-1H-1,2,4-triazol-5-yl]phenyl]-, (2E)-

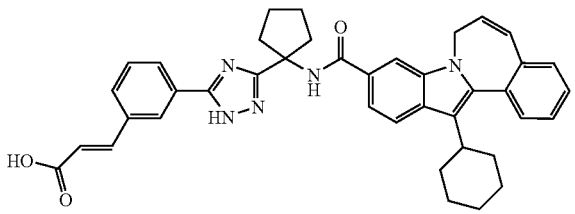

2-propenoic acid, 3-[3-[3-[1-[[(13-cyclohexyl-7H-indolo[2,1-a][2]benzazepin-10-yl)carbonyl]amino]cyclopentyl]-1H-1,2,4-triazol-5-yl]phenyl]-, methyl ester, (2E)- (133 mg, 2.04 mMol) was dissolved in 0.9 ml of THF and 0.9 ml of methanol added along with 250 ul of 1.0N sodium hydroxide (0.25 mMol). The reaction was heated to 65 C for 2 hrs and then an additional 60 uL of 1.0N sodium hydroxide added to the reaction with continued heating for 3 hrs. Volatiles were removed in vacuuo and the residue dissolved in 2 ml of hot water, the solution allowed to cool overnight, did not yield any crystallization or precipitate. To the aqueous solution, 0.5 ml of methanol and 50 uL of 1.0 N sodium hydroxide were added and the reaction heated to 65 C for 2 hours. The reaction was concentrated in vacuuo to remove methanol and the solution acidified with 1N hydrochloric acid. A fine precipitate was removed by filtration and dried in vacuum to yield 96 mg of a fine yellow amorphous powder. Analysis of the solid by TLC (SiO2, 5% ethyl acetate, 2% acetic acid in dichloromethane) indicated further purification was desirable. The crude product (67 mg) was purified by column chromatography on silica gel, eluted with a gradient of 2% ethyl acetate to 5% ethyl acetate in mixture of 2% acetic acid in dichloromethane to yield 35 mg of pure product. $^1$H NMR (500 MHz, MeOD) δ ppm 8.43 (s, 1 H) 8.25 (s, 1 H) 8.09 (s, 1 H) 8.03 (d, J=7.02 Hz, 1 H) 7.86 (d, J=8.54 Hz, 1 H) 7.70 (d, J=15.87 Hz, 1 H) 7.64 (d, J=7.63 Hz, 1 H) 7.47–7.58 (m, 3 H) 7.36–7.46 (m, 3 H) 6.85 (d, J=10.38 Hz, 1 H) 6.57 (d, J=15.87 Hz, 1 H) 6.26–6.38 (m, 1 H) 5.05 (s, 1 H) 4.15 (s, 1 H) 2.79–2.97 (m, 1 H) 2.51 (d, J=5.19 Hz, 4 H) 1.68–2.03 (m, 10 H) 1.17–1.52 (m, 5 H); MS m/z 638 (MH$^+$); MS m/z 636(M-H)$^-$.

6,7-Dihydro-5,6-dihydroxy-5H-indolo[2,1-a][2]benzazepines

Examples of the 6,7-Dihydro-5,6-dihydroxy-5H-indolo[2,1-a][2]benzazepines class of inhibitors of the instant invention may be accessed using the methodology depicted in the schemes and described in the examples given below.

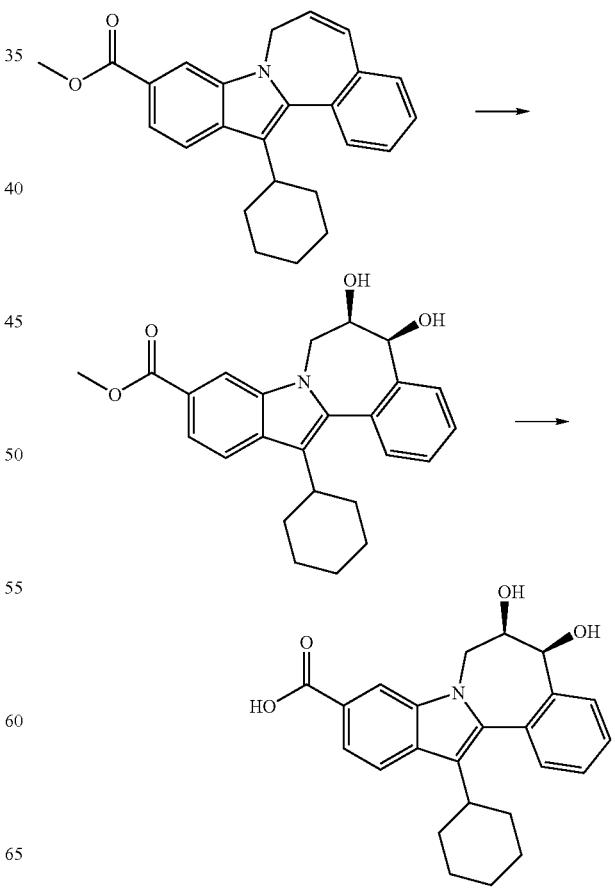

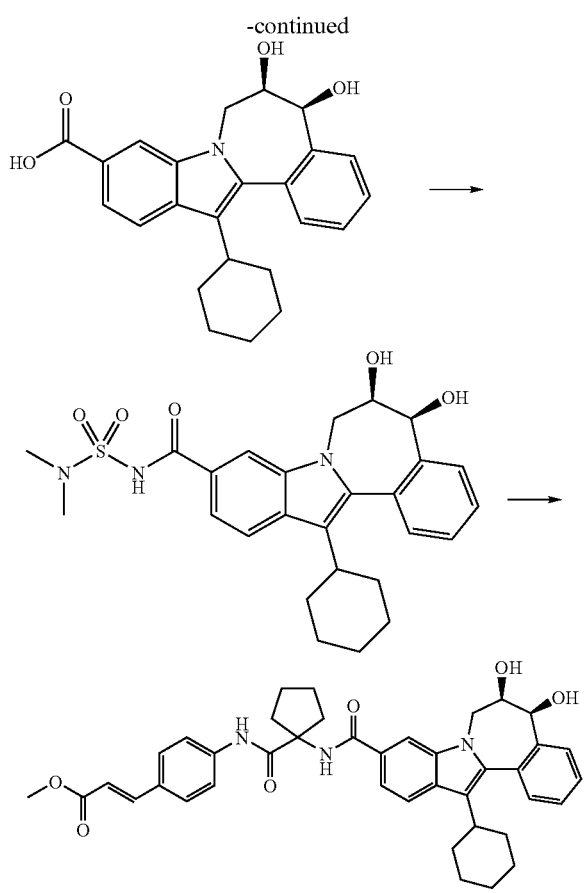

Methyl (5R,6S)-rel-13-cyclohexyl-6,7-dihydro-5,6-dihydroxy-5H-indolo[2,1-a][2]benzazepine-10-carboxylate

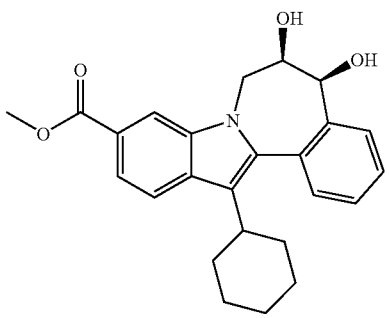

OsO₄ (23 mg, 0.09 mmol) was added to a stirred solution of methyl 13-cyclohexyl-7H-indolo{2,1-a][2]benzazepine-10-carboxylate (341 mg, 0.92 mmol) and 4-methyl-morpholine N-oxide(430 mg, 3.68 mmol) in acetone-water (50 mL-6 mL) at rt. The reaction mixture was stirred at rt for 18 hr and then diluted with aqueous sodium thiosulfate. The mixture was extracted with ethyl acetate. The organic layer was washed with brine (3×) and dried over sodium sulfate, filtered and evaporated under reduced pressure. The crude product was purified utilizing a Biotage apparatus with a prepacked silica column and using gradients of hexanes:ethyl acetate of from (98:2) to (80:20) to afford the product as a light yellow solid (340 mg, 91%). ESI-MS m/z 406 (MH⁺); 1H NMR (500 MHz, MeOD) δ 1.25 (m, 1 H) 1.43 (m, 2 H) 1.58 (d, J=13.12 Hz, 1 H) 1.77 (d, J=8.85 Hz, 2 H) 2.02 (m, 4 H) 2.93 (m, 1 H) 3.31 (m, 1 H) 3.93 (s, 3 H) 4.40. (d, J=4.58 Hz, 1 H) 4.52 (m, 1 H) 4.68 (dd, J=14.19, 7.17 Hz, 1 H) 7.40 (t, J=7.32 Hz, 1 H) 7.44 (t, J=7.32 Hz, 1 H) 7.51 (t, J=7.48 Hz, 1 H) 7.70 (d, J=8.55 Hz, 1 H) 7.78 (d, J=7.63 Hz, 1 H) 7.86 (d, J=8.55 Hz, 1 H) 8.15 (s, 1 H).

(5R,6S)-rel-13-Cyclohexyl-6,7-dihydro-5,6-dihydroxy-5H-indolo[2,1-a][2]benzazepine-10-carboxylic acid

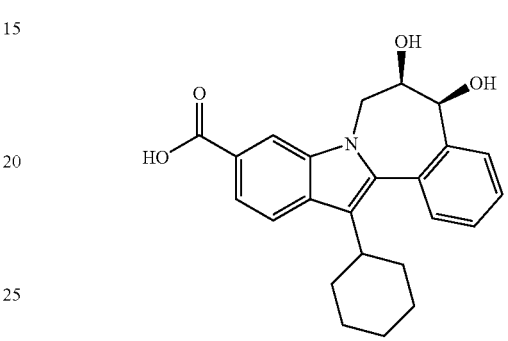

Sodium hydroxide (0.2' 1 mL of 1 N, 0.2 mmol) was added to a solution of methyl (5R,6S)-rel-13-cyclohexyl-6,7-dihydro-5,6-dihydroxy-5H-indolo[2,1-a][2]benzazepine-10-carboxylate (20 mg, 0.049 mmol) in methanol (0.5 mL) and tetrahydrofuran (0.5 mL) in a microwave vial. The vial was sealed and the contents heated at 90° C. for 7 min in a microwave apparatus. The solution was acidified with dilute hydrochloric acid and a precipitate was observed to form. The solid was collected by filtration and purified on the Prep. reverse phase HPLC. The product containing fraction was concentrated on a Speed Vac® to leave the titled compound as a white solid (18 mg, 94%). ESI-MS m/z 392 (MH⁺) 1H NMR (500 MHz, MeOD) δ 1.25–1.34 (m, 1 H) 1.39–1.54 (m, 2 H) 1.60–1.67 (m, 1 H) 1.77–1.86 (m, 2 H) 1.93–2.00 (m, 1 H) 2.01–2.17 (m, 3 H) 2.93–3.02 (m, 1 H) 3.36 (m, 1 H) 4.43 (d, J=4.27 Hz, 1 H) 4.54 (m, 1 H) 4.72 (dd, J=14.19, 7.17 Hz, 1 H) 7.46 (m, 2 H) 7.53 (m, 1 H) 7.74 (dd, J=8.39, 1.37 Hz, 1 H) 7.79 (d, J=7.63 Hz, 1 H) 7.90 (d, J=8.24 Hz, 1 H) 8.19 (s, 1 H).

13-Cyclohexyl-N-[(dimethylamino)sulfonyl]-6,7-dihydro-(5R,6S)-rel-5,6-dihydroxy-5H-Indolo[2,1-a][2]benzazepine-10-carboxamide

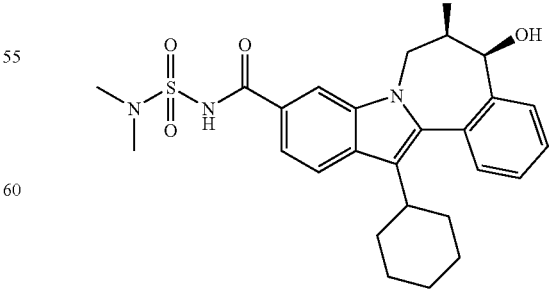

1-[3-(Dimethylamino)propyl]-3-ethylcarbodiimide hydrochloride (12.6 mg, 0.066 mmol) was added to a solution of 13-cyclohexyl-6,7-dihydro-(5R,6S)-rel-5,6-dihydroxy-5H-indolo[2,1-a][2]benzazepine-10-carboxylic acid (8.7 mg, 0.022 mmol) and DMAP (8.1 mg, 0.066 mmol) in DMF (0.3 mL) and CH$_2$Cl$_2$ (0.3 mL) at 22° C. The vial was shaken for a minute at 22° C. then N,N-dimethylsulfamide (5.5 mg, 0.044 mmol) was added. Stirring was continued for 18 hr. The solution was then filtered and purified by Prep. reverse phase chromatography. The product containing fraction was concentrated on a Speed Vac® to leave the title compound as a white film (1.2 mg, 11%). ESI-MS m/z 498 (MH$^+$) 1H NMR (500 MHz, MeOD) δ 1.23–1.33 (m, 1 H) 1.39–1.54 (m, 2 H) 1.62 (m, 1 H) 1.77–1.87 (m, 2 H) 1.93–2.18 (m, 4 H) 2.99 (d, J=11.29 Hz, 1 H) 3.04 (s, 6 H) 3.35 (m, 1 H) 4.42 (d, J=4.58 Hz, 1 H) 4.56 (m, 1 H) 4.75 (dd, J=14.50, 7.17 Hz, 1 H) 7.47 (m, 2 H) 7.54 (m, 1 H) 7.61 (dd, J=8.55, 1.53 Hz, 1 H) 7.80 (d, J=7.63 Hz, 1 H) 7.94 (d, J=8.85 Hz, 1 H) 8.13 (s, 1 H).

Methyl 3-[4-[[[1-[[13-cyclohexyl-6,7-dihydro-(5R,6S)-rel-5,6-dihydroxy-5H-indolo[2,1-a][2]benzazepin-10-yl]carbonyl]amino]cyclopentyl]carbonyl]amino]phenyl]-(2E)-propenoate TBTU (30 mg, 0.092 mmol) was added to a stirred solution of 13-cyclohexyl-6,7-dihydro-(5R,6S)-rel-5,6-dihydroxy-5H-indolo[2,1-a][2]benzazepine-10-carboxylic acid (30 mg, 0.077 mmol), (E)-ethyl (3-(4-(1-aminocyclopentanecarboxamido)phenyl)acrylate (25 mg, 0.085 mmol), and N,N-diisopropylethylamine (0.1 mL, 0.58 mmol) in DMF (1 mL). The mixture was stirred at 22° C. for 20 min. The resulting solution was filtered and fractionated using Prep. reverse phase chromatography. The product containing fraction was concentrated on a Speed Vac® to leave the product as a white solid (90%). ESI-MS m/z 662 (MH$^+$); 1H NMR (500 MHz, MeOD) δ 1.20–1.34 (m, 1 H) 1.35–1.54 (m, 2 H) 1.55–1.66 (m, 1 H) 1.75–1.83 (m, 2 H) 1.83–1.98 (m, 5 H) 1.97–2.16 (m, 3 H) 2.16–2.27 (m, 2 H) 2.46–2.56 (m, 2 H) 2.96 (m, 1 H) 3.30 (d, J=10.07 Hz, 1 H) 3.78 (s, 3 H) 4.41 (d, J=4.58 Hz, 1 H) 4.54 (d, J=4.58 Hz, 1 H) 4.74 (dd, J=14.19, 7.17 Hz, 1 H) 6.44 (d, J=16.17 Hz, 1 H) 7.38–7.56 (m, 5 H) 7.58–7.67 (m, 4 H) 7.78 (d, J=7.63 Hz, 1 H) 7.89 (d, J=8.54 Hz, 1 H) 8.12 (s, 1 H).

In further examples of derivitization of the bridge in the inhibitors of the instant invention, the previously described dihydroxy derivatives can be converted to the corresponding ketone analogs shown below. This provides a synthetic handle for additional modifications to be made to the struc-

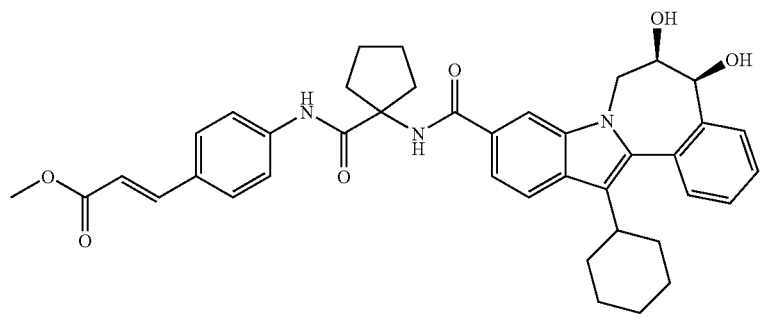

ture by methods known to those skilled in the art. Some examples of such derivitizations are provided for illustrative purposes in the schemes and examples provided below, and are not intended to limit the scope of the current invention.

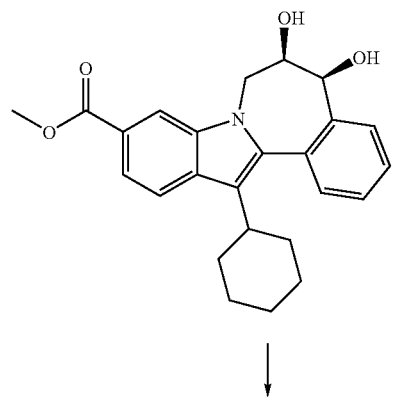

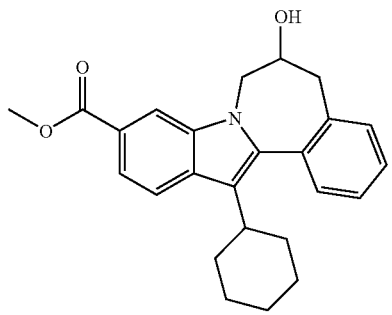

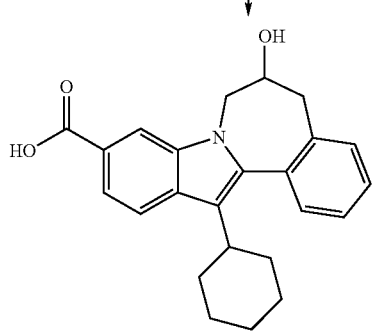

Methyl 13-cyclohexyl-6,7-dihydro-6-oxo-5H-indolo
[2,1-a][2]benzazepine-10-carboxylate

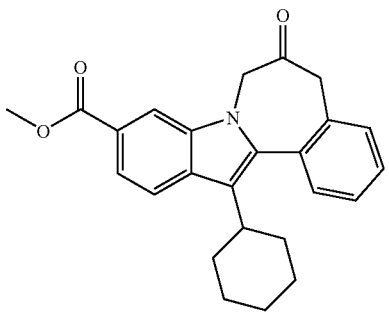

p-Toluenesulfonic acid (50 mg, 0.29 mmol) was added to methyl 13-cyclohexyl-6,7-dihydro-(5R,6S)-rel-5,6-dihydroxy-5H-indolo[2,1-a][2]benzazepine-10-carboxylate (100 mg, 0.25 mmol) in 50 mL of dry toluene. The solution was heated under reflux for 18 hr with removal of water using a Dean-Stark trap. The solution was diluted with ethyl acetate and washed with brine (3×) and dried over sodium sulfate, filtered and concentrated in vacuo. The crude product was purified utilizing a Biotage apparatus with a prepacked silica column and using gradients of hexanes:ethyl acetate of from (98:2) to (85:15) to afford the product as a light yellow solid (60 mg, 62%). ESI-MS m/z 388 (MH$^+$); 1H NMR (500 MHz, CHLOROFORM-D) □ 1.22–1.68 (m, 4 H) 1.73–1.83 (m, 2 H) 1.91–1.99 (m, 1 H) 2.02–2.15 (m, 3 H) 2.95 (m, 1 H) 3.57 (d, J=14.04 Hz, 1 H) 3.84 (d, J=14.04 Hz, 1 H) 3.95 (s, 3 H) 4.44 (d, J=18.01 Hz, 1 H) 4.96 (d, J=18.01 Hz, 1 H) 7.35 (d, J=7.63 Hz, 1 H) 7.43 (m, 1 H) 7.48 (t, J=7.32 Hz, 1 H) 7.54 (m, 1 H) 7.81 (d, J=8.55 Hz, 1 H) 7.92 (d, J=8.55 Hz, 1 H) 8.09 (s, 1 H).

13-Cyclohexyl-6,7-dihydro-6-oxo-5H-indolo[2,1-a]
[2]benzazepine-10-carboxylic acid Sodium hydroxide (0.2 mL of 1 N, 0.2 mmol) was added to a solution of the Methyl 13-cyclohexyl-6,7-dihydro-6-oxo -5H- indolo[2,1-a][2]benzazepine-10-carboxylate (20 mg, 0.052 mmol) in methanol (0.5 mL) and tetrahydrofuran (0.5 mL) in a microwave vial. The vial was sealed and the contents heated at 90° C. for 5 min in a microwave apparatus. The solution was acidified with dilute hydrochloric acid to precipitate the crude acid. The solid was collected and purified on the Shimadzu preparative liquid chromatograph. The product containing fraction was concentrated on a Speed Vac® to leave the titled compound as a white solid (18 mg, 92%). ESI-MS m/z 374 (MH$^+$); 1H NMR (500 MHz, ACETONE-D6) δ 1.22–1.35 (m, 1 H) 1.41–1.58 (m, 2 H) 1.59–1.70 (m, 1 H) 1.73–1.85 (m, 2 H) 1.92–2.00 (m, 1 H) 2.11–2.26 (m, 3 H) 3.04 (m, 1 H) 3.60 (d, J=14.04 Hz, 1 H) 3.97 (d, J=13.73 Hz, 1 H) 4.56 (d, J=18.31 Hz, 1 H) 5.19 (d, J=18.31 Hz, 1 H) 7.51 (m, 2 H) 7.57 (t, J=7.32 Hz, 1 H) 7.66 (d, J=7.63 Hz, 1 H) 7.81 (dd, J=8.39, 1.37 Hz, 1 H) 8.03 (d, J=8.24 Hz, 1 H) 8.23 (s, 3 H).

Methyl (±)-13-cyclohexyl-6,7-dihydro-6-hydroxy-5H-indolo[2,1-a][2]benzazepine-10-carboxylate

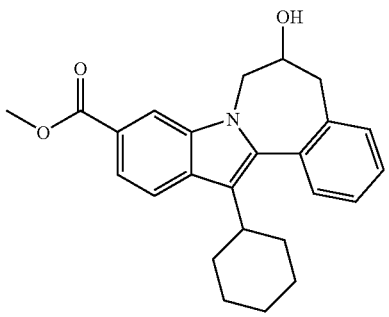

Sodium borohydride (50 mg, 1.3 mmol) was added to a solution of methyl 13-cyclohexyl-6,7-dihydro-6-oxo-5H-indolo[2,1-a][2]benzazepine-10-carboxylate (29 mg, 0.074 mmol) in methanol (4 mL) and tetrahydrofuran (2 mL) at rt. The evolution of $H_2$ was instantaneous and stirring was continued for 30 min at rt. The mixture was concentrated on a rotary evaporator and and the residue purified on the Shimadzu preparative liquid chromatograph. The product containing fraction was concentrated on a Speed Vac® to leave the titled compound as a white solid (27.5 mg, 96%). ESI-MS m/z 390 (MH$^+$); 1H NMR (500 MHz, CHLOROFORM-D) □ 1.18–1.31 (m, 1 H) 1.32–1.53 (m, 2 H) 1.60–1.70 (m, 1 H) 1.71–1.84 (m, 2 H) 1.86–2.18 (m, 4 H) 2.38–3.12 (m, 3 H) 3.36–3.83 (m, 1 H) 3.94 (m, 3 H) 4.39–4.68 (m, 2 H) 7.32–7.48 (m, 4 H) 7.76 (t, J=8.39 Hz, 1 H) 7.88 (t, J=8.09 Hz, 1 H) 8.14 (m, 1 H).

(±)-13-cyclohexyl-6,7-dihydro-6-hydroxy-5H-indolo[2,1-a][2]benzazepine-10-carboxylate

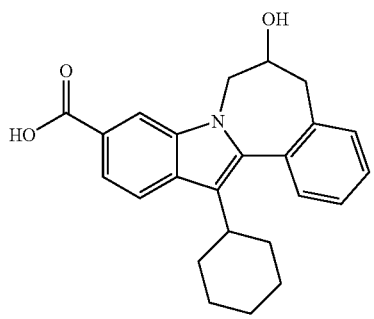

Sodium hydroxide (0.5 mL of 1 N, 0.5 mmol) was added to a solution of the preceding methyl ester (27.5 mg, 0.071 mmol) in methanol (0.5 mL) and tetrahydrofaran (0.5 mL) in a microwave vial. The vial was sealed and the contents heated at 90° C. for 10 min in a microwave apparatus. The solution was acidified with dilute hydrochloric acid to precipitate the crude acid. The solid was collected and purified on the Shimadzu preparative liquid chromatograph. The product containing fraction was concentrated on a Speed Vac® to leave the titled compound as a white solid (13.0 mg, 49%). ESI-MS m/z 376 (MH$^+$); 1H NMR (500 MHz, MeOD) δ 1.22–1.35 (m, 1 H) 1.38–1.55 (m, 2 H) 1.57–1.69 (m, 1 H) 1.74–1.87 (m, 2 H) 1.91–2.22 (m, 4 H) 2.35–2.71 (m, 1 H) 2.75–3.06 (m, 2 H) 3.35–3.77 (m, 1 H) 4.37–4.65 (m, 2 H) 7.33–7.50 (m, 4 H) 7.73 (d, J=8.55 Hz, 1 H) 7.89 (d, J=8.24 Hz, 1 H) 8.20 (m, 1 H).

(±)-13-Cyclohexyl-N-[(dimethylamino)sulfonyl]-6,7-dihydro-6-hydroxy-5H-indolo[2,1-a][2]benzazepine-10-carboxamide

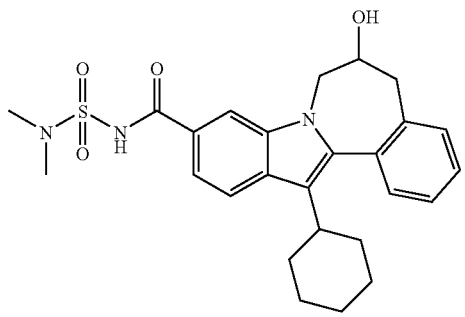

1-[3-(Dimethylamino)propyl]-3-ethylcarbodiimide hydrochloride (11.5 mg, 0.06 mmol) was added to a solution of (±)13-cyclohexyl-6,7-dihydro-6-hydroxy-5H-indolo[2,1-a][2]benzazepine-10-carboxylic acid (7.5 mg, 0.02 mmol) and DMAP (7.4 mg, 0.06 mmol) in DMF (0.5 mL) and $CH_2Cl_2$ (0.5 mL) at 22° C. The vial was shaken for a minute at 22° C. N,N-Dimethylsulfamide (4.9 mg, 0.04 mmol) was then added. Stirring was continued for 18 hr. The solution was filtered and purified on the Shimadzu preparative liquid chromatograph. The product containing fraction was concentrated on a Speed Vac® to leave the titled compound as a white film (3.0 mg, 30%). ESI-MS m/z 482 (MH$^+$); 1H NMR (500 MHz, MeOD) δ 1.26–1.34 (m, 1 H) 1.40–1.55 (m, 2 H) 1.63 (m, 1 H) 1.82 (m, 2 H) 1.96 (m, 1 H) 2.01–2.19 (m, 3 H) 2.36 (m, 1 H) 2.95–3.08 (m, 2 H) 3.03 (s, 6 H) 3.76 (dd, J=15.26, 3.36 Hz, 1 H) 4.41–4.69 (m, 2 H) 7.40–7.50 (m, 4 H) 7.60 (m, 1 H) 7.93 (m, 1 H) 8.11 (m, 1 H).

Another variation for generating additional examples of the instant invention involves performing reductive aminations with either cyclic or acyclic 1° or 2° amines to generate products of the type shown below.

(±)-Methyl 13-cyclohexyl-6,7-dihydro-6-(morpholin-4-yl)-5H-indolo[2,1-a][2]benzazepine-10-carboxylate

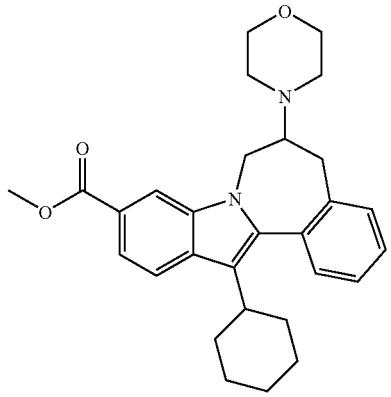

Zinc chloride (21 mg, 0.15 mmol) and morpholine (40 μL, 0.46 mmol) were added to methyl 13-cyclohexyl-6,7-dihydro-6-oxo-5H-indolo[2,1-a][2]benzazepine-10-carboxylate (30 mg, 0.078 mmol) in MeOH (3 mL). The mixture was heated at 60° C. for 3 hr when sodium cyanoborohydride (29 mg, 0.46 mmol) was added. Heating was continued for another hr. The mixture was concentrated and the crude product purified by chromatography on a SiO$_2$ preparative plate using dichloromethane containing 2 N methanolic ammonia (100:1). to afford the product as a light yellow solid (25 mg, 70%). ESI-MS m/z 806 (MH$^+$); 1H NMR (500 MHz, MeOD) □ 1.28–1.36 (m, 1 H) 1.36–1.53 (m, 2 H) 1.59–1.71 (m, 1 H) 1.74–1.86 (m, 2 H) 1.92–2.19 (m, 4 H) 2.36–2.53 (m, 1 H) 2.58 (m, 1 H) 2.73 (m, 2 H) 2.89 (m, 1 H) 2.99 (m, 1 H) 3.12 (m, 1 H) 3.38 (m, 1 H) 3.58–3.77 (m, 4 H) 3.86–4.00 (m, 3 H) 4.04–4.17 (m, 1 H) 4.51–4.66 (m, 1 H) 7.35–7.50 (m, 4 H) 7.71 (d, J=8.55 Hz, 1 H) 7.88 (m, 1 H) 8.13 (m, 1 H).

(±)-Methyl 13-cyclohexyl-6,7-dihydro-6-(morpholin-4-yl)-5H-indolo[2,1-a][2]benzazepine-10-carboxylate

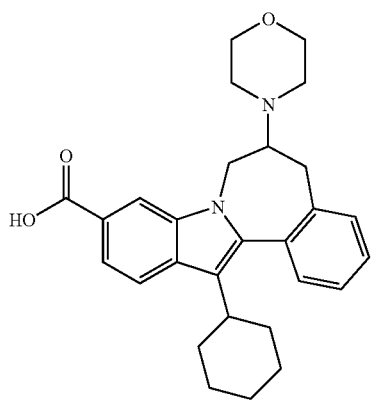

1-[3-(Dimethylamino)propyl]-3-ethylcarbodiimide hydrochloride (11.5 mg, 0.06 mmol) was added to a solution of (±)13-cyclohexyl-6,7-dihydro-6-hydroxy-5H-indolo[2,1-a][2]benzazepine-10-carboxylic acid (7.5 mg, 0.02 mmol) and DMAP(7.4 mg, 0.06 mmol) in DMF (0.5 mL) and CH$_2$Cl$_2$ (0.5 mL) at 22° C. The vial was shaken for a minute at 22° C. N,N-Dimethylsulfamide (4.9 mg, 0.04 mmol) was then added. Stirring was continued for 18 hr. The solution was filtered and purified on the Shimadzu preparative liquid chromatograph. The product containing fraction was concentrated on a Speed Vac® to leave the titled compound as a white film (3.0 mg, 30%). ESI-MS m/z 445 (MH$^+$); 1H NMR (500 MHz, MeOD) δ 1.26–1.38 (m, 1 H) 1.42–1.56 (m, 2 H) 1.58–1.72 (m, 1 H) 1.79–1.89 (m, 2 H) 1.95–2.02 (m, 1 H) 2.03–2.23 (m, 3 H) 2.84–3.08 (m, 2 H) 3.34–3.67 (m, 6 H) 3.89–4.01 (m, 5 m) 4.08–4.18 (m, 1 H) 7.48–7.66 (m, 4 H) 7.78–7.85 (m, 8.39 Hz, 1 H) 7.93–8.01 (m, 1 H) 8.22–8.31 (m, 1 H).

Yet another method for the introduction of additional functionality onto the bridging element of select examples of the instant invention, involves the chemoselective reduction of the bridge carboxylate functionality in the di-ester examples shown below. This results in the generation of hydroxyl methyl derivatives of the type described below.

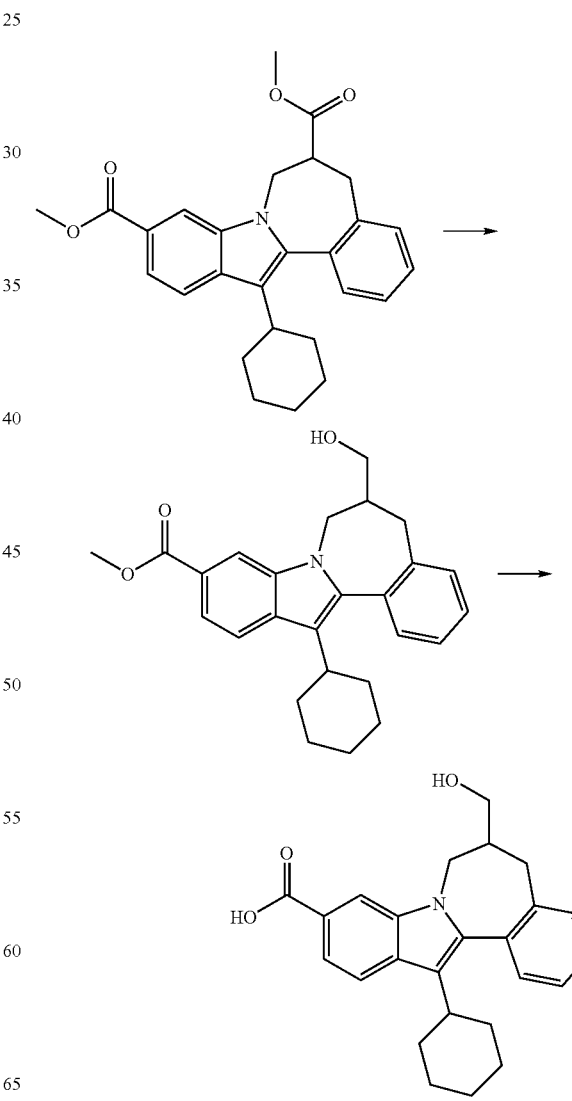

Methyl (±)-13-cyclohexyl-6,7-dihydro-6-hydroxymethyl-5H-indolo[2,1-a][2]benzazepine-10-carboxylate

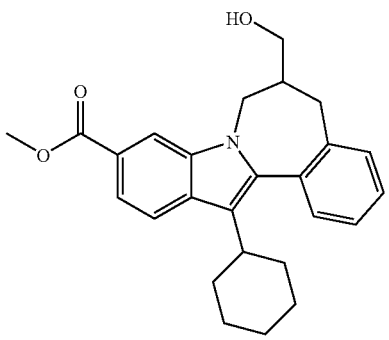

A solution of borane in THF (0.18 mL of 1 N, 0.18 mmol) was added to a solution of methyl (±)-6-carboxy-13-cyclohexyl-6,7-dihydro-5H-indolo[2,1-a][2]benzazepine-10-carboxylate (50 mg, 0.12 mmol) in THF (5 mL) at 0° C. The cooling bath was removed and stirring continued at ambient temperatures for 18 hr. The solution was diluted with ethyl acetate and washed with dilute HCl (1×), brine (3×), and then dried (Na$_2$SO$_4$). The crude product was purified on the Shimadzu preparative liquid chromatograph. The product containing fraction was concentrated on a Speed Vac® to leave the titled compound as a white film (25 mg, 52%). ESI-MS m/z 404 (MH$^+$); 1H NMR (300 MHz, MeOD) δ 1.14–2.19 (m, 11 H) 2.34–2.80 (m, 2 H) 2.82–3.26 (m, 2 H) 3.25–3.38 (m, 1 H) 3.44–3.82 (m, 1 H) 3.92 (s, 3 H) 4.48–4.61 (m, 1 H) 7.35–7.46 (m, 4 H) 7.68 (m, 1 H) 7.85 (m, 1 H) 8.17 (m, 1 H).

(±)-13-Cyclohexyl-6,7-dihydro-6-hydroxymethyl-5H-indolo[2,1-a][2]benzazepine-10-carboxylic acid

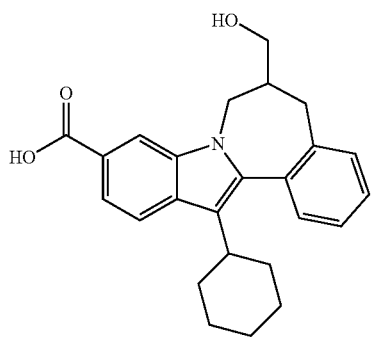

Sodium hydroxide (0.2 mL of 1 N, 0.2 mmol) was added to a solution of methyl (±)-13-cyclohexyl-6,7-dihydro-6-hydroxymethyl-5H-indolo[2,1-a][2]benzazepine-10-carboxylate (15.0 mg, 0.037 mmol) in methanol (0.5 mL) and tetrahydrofuran (0.5 mL) in a microwave vial. The vial was sealed and the contents heated at 100° C. for 10 min in a microwave apparatus. The solution was acidified with dilute hydrochloric acid to precipitate the crude acid. The solid was collected and purified on the Shimadzu preparative liquid chromatograph. The product containing fraction was concentrated on a Speed Vac® to leave the titled compound as a white solid (10.0 mg, 69%). ESI-MS m/z 390 (MH$^+$); 1H NMR (500 MHz, MeOD) δ 1.19–1.34 (m, 1 H) 1.36–1.56 (m, 2 H) 1.63 (m, 1 H) 1.74–1.87 (m, 2 H) 1.91–2.21 (m, 5 H) 2.37–2.60 (m, 1 H) 2.74 (m, 1 H) 2.97 (m, 1 H) 3.36 (m, 1 H) 3.47–3.67 (m, 2 H) 4.59 (m, 1 H) 7.38–7.50 (m, 4 H) 7.72 (m, 1 H) 7.88 (m, 1 H) 8.18 (m, 1 H).

Many examples of the instant invention are composed of racemic mixtures of enantiomers. In addition to the methodology discussed previously, such mixtures can be resolved using preparative HPLC involving a chiral stationary phase. An illustrative example of this procedure is provided below.

Resolution of (±)-13-Cyclohexyl-6,7-dihydro-6-(morpholinylcarbonyl)-5H-indolo[2,1-a][2]benzazepine-10-carboxylic acid

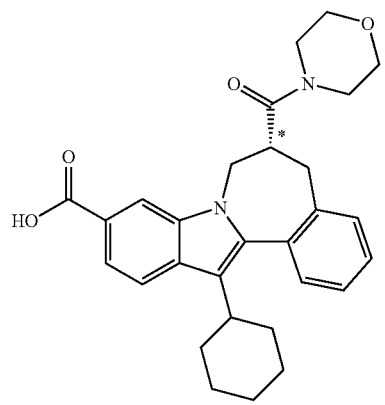

A solution of racemic 13-Cyclohexyl-6,7-dihydro-6-(morpholinylcarbonyl)-5H-indolo[2,1-a][2]benzazepine-10-carboxylic acid (20 mg) in ethanol (1 mL) was injected on a Chiralpak® AD column (20×250 mm, 5 μm). The column was eluted with a mixture of 70% heptane and 30% ethanol at a flow rate of 10 mL/min for 60 min to give a complete separation of the enantiomers.

Enantiomer 1 (10 mg), retention time 14.5 min ESI-MS m/z 487 (MH$^+$), $^1$H NMR (500 MHz, CD$_3$OD) δ 1.24–1.35 (m, 1 H), 1.40–1.55 (m, 2 H), 1.60–1.68 (m, 1 H), 1.76–1.87 (m, 2 H), 1.93–2.20 (m, 4 H), 2.76 (m, 1 H), 2.87–3.02 (m, 1 H), 3.44–3.51 (m, 1 H), 3.59–3.92 (m, 9 H), 4.47–4.59 (m, 1 H), 4.90 (m, 1 H), 7.31–7.42 (m, 1 H), 7.48 (m, 3 H), 7.72 (m, 1 H), 7.88 (m, 1 H), 8.16 (m, 1 H).

Enantiomer 2 (10 mg), retention time 42.8 min. ESI-MS m/z 487 (MH$^+$), $^1$H NMR (500 MHz, CD$_3$OD) δ 1.24–1.35 (m, 1 H), 1.40–1.55 (m, 2 H), 1.60–1.68 (m, 1 H), 1.76–1.87 (m, 2 H), 1.93–2.20 (m, 4 H), 2.76 (m, 1 H), 2.87–3.02 (m, 1 H), 3.44–3.51 (m, 1 H), 3.59–3.92 (m, 9 H), 4.47–4.59 (m, 1 H), 4.90 (m, 1 H), 7.31–7.42 (m, 1 H), 7.48 (m, 3 H), 7.72 (m, 1 H), 7.88 (m, 1 H), 8.16 (m, 1 H).

13-Cyclohexyl-N-[(dimethylamino)sulfonyl]-6,7-dihydro-6-(morpholinylcarbonyl)-5H-indolo[2,1-a][2]benzazepine-10-carboxamide

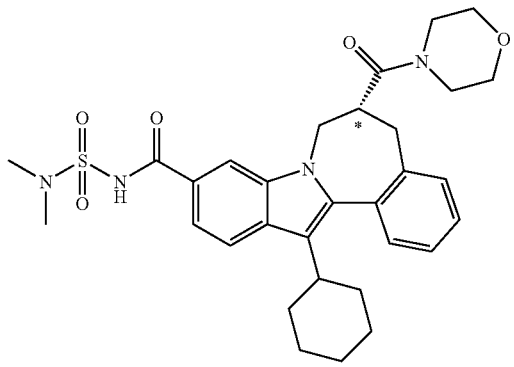

1-[3-(Dimethylamino)propyl]-3-ethylcarbodiimide hydrochloride (11.8 mg, 0.06 mmol) was added to a solution of Enantiomer 2 (10 mg, 0.02 mmol) and DMAP(25.1 mg, 0.21 mmol) in DMA (1.0 mL) and $CH_2Cl_2$ (1.0 mL) at 22° C. The vial was shaken for a minute at 22° C. N,N-Dimethylsulfamide (7.5 mg, 0.06 mmol) was then added. Stirring was continued at 40° C. for 18 hr. The solution was filtered and purified on the Shimadzu preparative liquid chromatograph. The product containing fraction was concentrated on a Speed Vac® to leave the titled compound as a white film (4.0 mg, 35%). ESI-MS m/z 579 (MH+); $^1$H NMR (500 MHz, $CD_3OD$) δ 1.24–1.35 (m, 1 H) 1.42–1.54 (m, 2 H) 1.60–1.68 (m, 1 H) 1.82 (m, 2 H) 1.97 (m, 1 H) 2.02–2.18 (m, 3 H) 2.74–2.86 (m, 1 H) 2.94–3.01 (m, 1 H) 3.04 (s, 6 H) 3.51–3.57 (m, 1 H) 3.60–3.90 (m, 9 H) 4.49–4.66 (m, 1 H) 4.81–4.97 (m, 1 H) 7.31–7.43 (m, 1 H) 7.45–7.53 (m, 3 H) 7.59 (m, 1 H) 7.92 (m, 1 H) 8.07 (m, 1 H).

An additional methodology for the generation of the fused heterocyclic ring systems of the instant invention involves a Michael reaction between acrylonitrile and a suitably functionalized indole derivative, as shown in the scheme provided below.

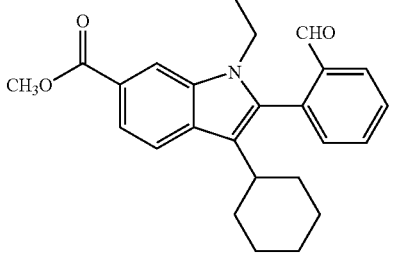

a

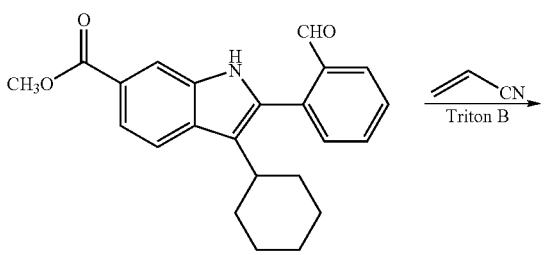

b

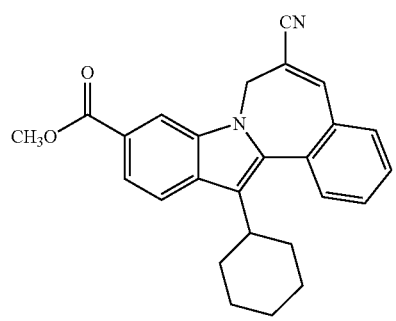

c d e f

Alkylation of the bromoindole shown provided the alkylated product in good yield. Subsequent Suzuki reaction of this compound with 2-formylboronic acid provided the indole formyl intermediate as the major product, with an additional minor product being identified as the indolobenzazepine shown. Alternatively, alkylation of indole aryl aldehyde derivative shown in the above scheme with acrylonitrile using the strong base, benzyltrimethylammonium hydroxide, resulted in formation of the isomeric indolobenzazepine shown at the bottom of the scheme.

Methyl 2-bromo-1-(2-cyanoethyl)-3-cyclohexyl-1H-indole-6-carboxylate

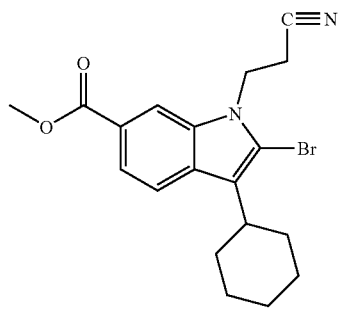

Acrylonitrile (10 mL of 1.52 M in 1,4-dioxane, 30.4 mmol) was added to methyl 2-bromo-3-cyclohexyl-1H-indole-6-carboxylate (840 mg, 2.5 mmol) in a microwave vial. The vial was sealed and Triton® B (500 □L1.1□mol) was added via syringe. The vial was heated in a microwave apparatus for 1 hr at 100° C. The solution was cooled and poured to precipitate the crude product. The granular solid was collected, washed with water and dried. Recrystallization from ethanol gave the product as a colorless solid (696 mg, 74%). MS m/z 390 (MS+); 1H NMR (300 MHz, DMSO-D6) δ ppm 1.27–1.49 (m, 3 H) 1.60–2.01 (m, 7 H) 2.77–2.90 (m, 1 H) 2.98 (t, J=6.40 Hz, 2 H) 3.87 (s, 3 H) 4.62 (t, J=6.59 Hz, 2 H) 7.67 (dd, J=8.42, 1.46 Hz, 1 H) 7.83 (d, J=8.42 Hz, 2 H) 8.25 (s, 1 H).

Methyl 6-cyano-13-cyclohexyl-7H-indolo[2,1-a][2]benzazepine-10-carboxylate

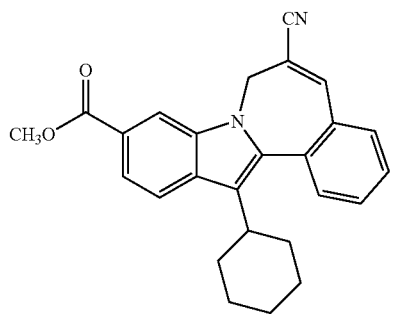

Tetrakis(triphenylphosphine)palladium(0) (207 mg, 0.18 mmol) was added to a stirred and degassed mixture of methyl 2-bromo-1-(2-cyanoethyl)-3-cyclohexyl-1H-indole-6-carboxylate (695 mg, 1.8 mmol), 2-formylphenyl boronic acid (233 mg, 1.56 mmol), LiCl (151 mg, 3.57 mmol) in ethanol (5.8 mL) and toluene (5.8 mL) containing 1M aqueous sodium carbonate (5 mL, 5 mmol). The mixture was stirred under reflux for 2 hr. The mixture was cooled and diluted with ethyl acetate. The organic layer was washed with water (2×), followed by brine, and dried over sodium sulfate. The extract was concentrated and partially purified by chromatography on $SiO_2$ (35 g) using the flash technique and eluting with methylene chloride with between 10–20% ethyl acetate. A solution of the residue when stood in methanol deposited yellow needles of the titled compound. MS m/z 397 (MH+); (500 MHz, CHLOROFORM-D) δ ppm 1.31–2.16 (m, 10 H) 2.73–2.89 (m, 1 H) 3.97 (s, 3 H) 4.46 (s, 1 H) 5.00–5.17 (m, 1 H) 7.41–7.47 (m, 1 H) 7.49–7.53 (m, 1 H) 7.55 (s, 1 H) 7.57–7.61 (m, 1 H) 7.79 (d, J=8.55 Hz, 1 H) 7.91 (d, J=8.55 Hz, 1 H) 8.18 (s, 1 H).

Methyl 6-cyano-13-cyclohexyl-5H-indolo[2,1-a][2]benzazepine-10-carboxylate

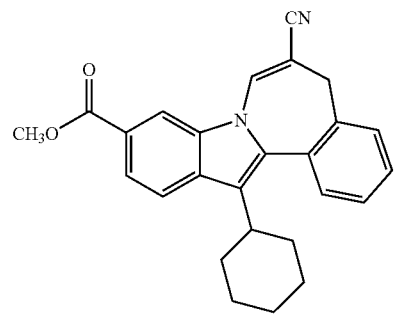

Acrylonitrile (2 mL of 1.52 M in 1,4-dioxane, 3.04 mmol) was added to methyl 3-cyclohexyl-2-(2-formylphenyl)-1H-indole-6-carboxylate (200 mg, 0.55 mmol) in a microwave vial. The vial was sealed and Triton® B (50□L, 0.11□mol) was added via syringe. The vial was heated in a microwave apparatus for 1 hr at 100° C. The solution was concentrated and the residue dissolved in methylene chloride. The solution was applied to a silica gel thick layer plate. The plated was eluted with hexanes-ethyl acetate (8:2). The product containing band was extracted with methylene chloride-methanol (3×). The combined extracts were concentrated and the residue recrystallized from methanol to afford the titled compound as a tan solid. MS m/z 397 (MH); 1H NMR (300 MHz, CHLOROFORM-D) □ ppm 1.16–2.25 (m, 10 H) 2.90–3.10 (m, 1 H) 3.20–3.34 (m, 1 H) 3.60–3.75 (m, 1 H) 3.95 (s, 3 H) 7.28–7.49 (m, 4 H) 7.76 (s, 1 H) 7.86–7.97 (m, 2 H) 8.13 (s, 1 H).

Additional examples of compounds of Formula I are compiled in the following table, and are provided for illustrative purposes only, and are not intended to limit the scope of the current invention. All of these examples can be prepared using one or more, or some combination of the methods and procedures described in the preceding sections of this document.

Table of additional Examples.
| Structure | Physiochemical Properties | IC₅₀ | EC₅₀ |
|---|---|---|---|
| 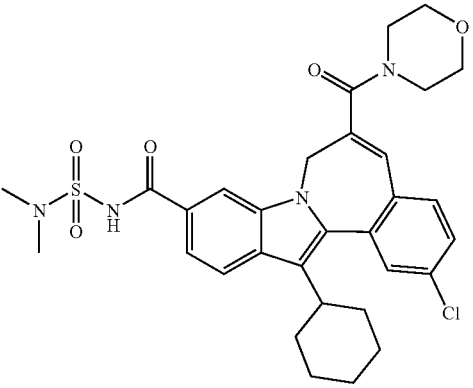 | ESI-MS m/z 612 (MH⁺); ¹H NMR (500 MHz, MeOD) δ 1.20–1.39 (m, 1 H) 1.39–1.57 (m, 3 H) 1.75–1.88 (m, 2 H) 1.97–2.24 (m, 4H) 2.82–2.93 (m, 1 H) 3.04 (s, 6 H) 3.46–3.71 (m, 8 H) 4.45 (br s, 1 H) 5.21 (br s, 1 H) 7.01 (s, 1 H) 7.54–7.59 (m, 2 H) 7.59–7.67 (m, 2 H) 7.97 (d, J=8.55 Hz, 1 H) 8.17 (m, 1 H) | | |
| 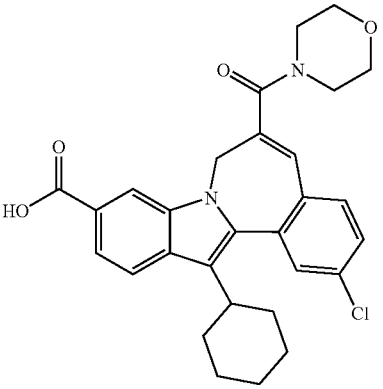 | ESI-MS m/z 506 (MH⁺); 1H NMR (500 MHz, MeOD) δ 1.24–1.39 (m, 1 H) 1.40–1.57 (m, 3 H) 1.73–1.89 (m, 2 H) 1.95–2.06 (m, 1 H) 2.06–2.23 (m, 3 H) 2.85–2.91 (m, 1 H) 3.35–3.71 (m, 8 H) 4.46 (br s, 1 H) 5.21 (br s, 1 H) 7.00 (s, 1 H) 7.56 (m, 2 H) 7.61 (s, 1 H) 7.76 (d, J=8.24 Hz, 1 H) 7.94 (d, =8.55 Hz, 1 H) 8.27 (s, 1 H) | | |
| 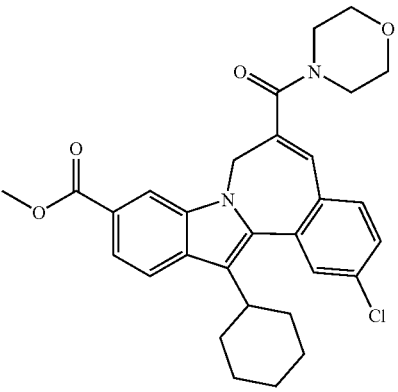 | ESI-MS m/z 520 (MH⁺); 1H NMR (500 MHz, MeOD) δ 1.26–1.39 (m, 1 H) 1.41–1.58 (m, 3 H) 1.78–1.86 (m, 2 H) 1.93–2.04 (m, 1 H) 2.04–2.22 (m, 3 H) 2.80–2.93 (m, 1 H) 3.39–3.71 (m, 8 H) 3.96 (s, 3 H) 4.43 (brs, 1 H) 5.20 (br s, 1 H) 6.99 (s, 1 H) 7.55 (s, 2 H) 7.60 (s, 1 H) 7.75 (d, J=8.54 Hz, 1 H) 7.94 (d, J=8.55 Hz, 1 H) 8.26 (s, 1 H) | | |
| 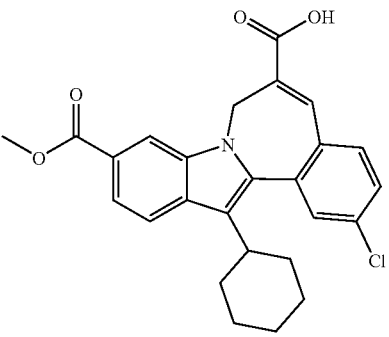 | ESI-MS m/z 450 (MH⁺) | | |

-continued

| Structure | Physiochemical Properties | IC$_{50}$ | EC$_{50}$ |
|---|---|---|---|
| 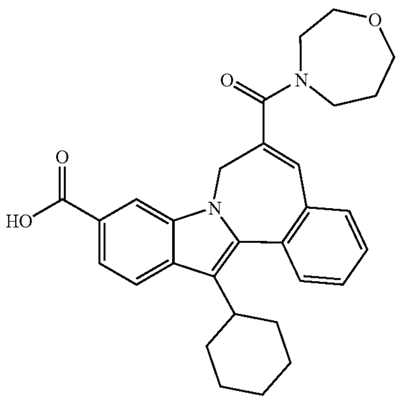 | ESI-MS m/z 485 (MH$^+$); 1H NNR (500 MHz, MeOD) δ 1.62–2.14 (m, 6 H) 2.18–2.31 (m, 2 H) 2.31–2.48 (m, 2 H) 2.48–2.69 (m, 2 H) 3.28–3.42 (m, 1 H) 3.81–4.00 (m, 3 H) 4.01–4.14 (m, 2 H) 4.14–4.37 (m, 3 H) 4.80–4.96 (m, 1 H) 5.59–5.72 (m, 1 H) 7.49 (s, 1 H) 7.96–8.07 (m, 3 H) 8.10 (d, J= 7.32 Hz, 1 H) 8.19 (d, J=8.55 Hz, 1 H) 8.37 (d, J=8.55 Hz, 1 H) 8.69 (s, 1 H) | | |
| 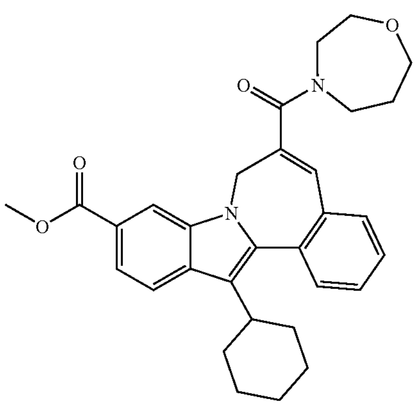 | ESI-MS m/z 499 (MH$^+$); 1H NMR (500 MHz, MeOD) δ 1.20–1.58 (m, 5 H) 1.79–1.86 (m, 2 H) 1.94–2.05 (m, 2 H) 2.08–2.23 (m, 3 H) 2.88–2.98 (m, 1 H) 3.40–3.56 (m, 3 H) 3.62–3.91 (m, 5 H) 3.98 (s, 3 H) 4.41–4.51 (m, 1 H) 5.19–5.29 (m, 1 H) 7.07 (s, 1 H) 7.56–7.63 (m, 3 H) 7.68 (m, 1 H) 7.76 (d, J=8.54 Hz, 1 H) 7.96 (d, J=8.55 Hz, 1 H) 8.26 (s, 1 H) | | |
| 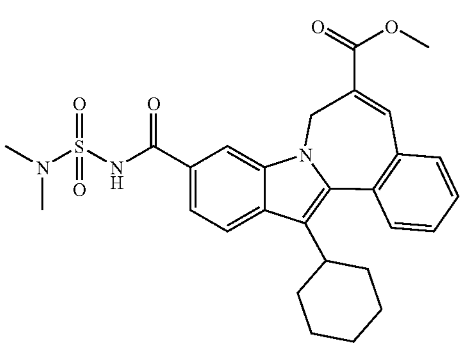 | ESI-MS m/z 522 (MH$^+$); 1H NMR (500 MHz, MeOD) δ 1.20–1.35 (m, 1 H) 1.42–1.62 (m, 3 H) 1.77–1.89 (m, 2 H) 1.97–2.05 (d, 1 H) 2.06–2.05 (m, 3 H) 2.93 (m, 1 H) 3.08 (s, 6 H) 3.91 (s, 3 H) 4.28 (m, 1 H) 5.75 (m, 1 H) 7.59–7.69 (m, 4 H) 7.68–7.75 (m, 1 H) 7.97 (m, 2 H) 8.26 (s, 1 H) | | |
| 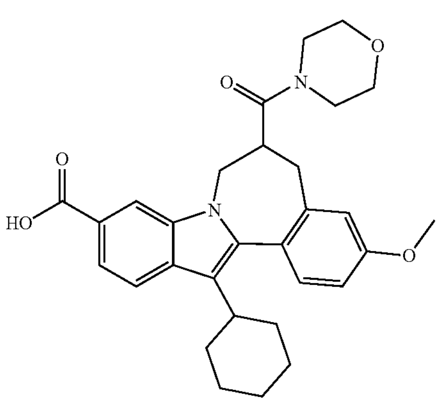 | ESI-MS m/z 503 (MH$^+$); 1H NMR (500 MHz, MeOD) δ 1.34–1.44 (m, 1 H) 1.49–1.62 (m, 2 H) 1.68–1.77 (m, 1 H) 1.84–1.94 (m, 2 H) 2.00–2.25 (m, 4 H) 2.78 (m, 1 H) 2.93–3.01 (m, 2 H) 3.50–3.60 (m, 1 H) 3.66–3.94 (m, 9 H) 3.99 (s, 3 H) 6.96–7.17 (m, 2 H) 7.47 (m, 1 H) 7.78 (m, 1 H) 7.93 (m, 1 H) 8.22 (m, 1 H) | | |

| Structure | Physiochemical Properties | IC$_{50}$ | EC$_{50}$ |
|---|---|---|---|
| 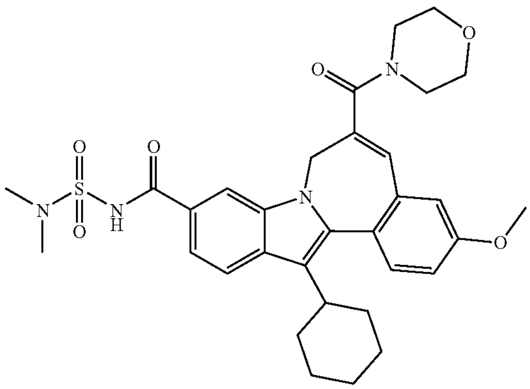 | ESI-MS m/z 607 (MH$^+$); 1H NMR (500 MHz, MeOD) δ 1.27–1.41 (m, 1 H) 1.47–1.65 (m, 3 H) 1.82–1.91 (m, 2 H) 2.08–2.26 (m, 4 H) 2.96 (m, 1 H) 3.05 (s, 6 H) 3.46–3.76 (m, 8 H) 4.02 (s, 3 H) 4.49 (br s, 1 H) 5.21 (br s, 1 H) 7.06 (s, 1 H) 7.19 (m, 1 H) 7.24 (m, 1 H) 7.64 (m, 1 H) 7.76 (dd, J=8.55, 1.53 Hz, 1 H) 7.95 (d, J=8.55 Hz, 1 H) 8.26 (s, 1 H) | | |
| | ESI-MS m/z 501 (MH$^+$); 1H NMR (500 MHz, MeOD) δ 1.20–1.34 (m, 1 H) 1.38–1.53 (m, 3 H) 1.73–1.85 (m, 2 H) 1.91–2.17 (m, 4 H) 2.85 (m, 1 H) 3.35–3.71 (m, 8 H) 3.91 (s, 3 H) 4.38 (br s, 1 H) 5.13 (br s, 1 H) 6.95 (s, 1 H) 7.08 (d, J=2.75 Hz, 1 H) 7.14 (dd, J=8.70, 2.59 Hz, 1 H) 7.55 (d, J=8.54 Hz, 1 H) 7.71 (dd, J=8.39, 1.37 Hz, 1 H) 7.86 (d, J=.18.55 Hz, 1 H) 8.20 (s, 1 H) | | |
| | ESI-MS m/z 515 (MH$^+$); 1H NMR (500 MHz, MeOD) δ 1.21–1.31 (m, 1 H) 1.39–1.56 (m, 3 H) 1.76–1.85 (m, 2 H) 1.93–2.18 (m, 4 H) 2.87 (m, 1 H) 3.35–3.71 (m, 8 H) 3.93 (s, 3 H) 3.96 (s, 3 H) 4.39 (br s, 1 H) 5.17 (br s, 1 H) 6.98 (s, 1 H) 7.11 (d, J=2.75 Hz, 1 H) 7.16 (dd, J=8.70, 2.59 Hz, 1 H) 7.57 (d, J=8.55 Hz, 1 H) 7.72 (dd, J=8.54, 1.53 Hz, 1 H) 7.90 (d, J=8.24 Hz, 1 H) 8.22 (s, 1 H) | | |
| 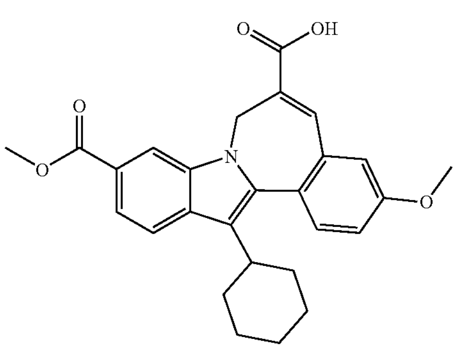 | ESI-MS m/z 446 (MH$^+$); 1H NMR (500 MHz, MeOD) δ 1.15–1.34 (m, 1 H) 1.39–1.58 (m, 3 H) 1.72–1.89 (m, 2 H) 1.98–2.22 (m, 4H) 2.89 (m, 1 H) 3.94 (s, 3H) 3.96 (s, 3H) 4.21 (m, 1 H) 5.67 (m, 1 H) 7.17 (d, J=2.44 Hz, 1 H) 7.20 (m, 1 H) 7.60 (d, J=8.55 Hz, 1 H) 7.70 (d, J=8.55 Hz, 1 H) 7.89 (d, J=8.55 Hz, 1 H) 7.91 (s, 1 H) 8.28 (s, 1 H) | | |

-continued

| Structure | Physiochemical Properties | IC$_{50}$ | EC$_{50}$ |
|---|---|---|---|
| 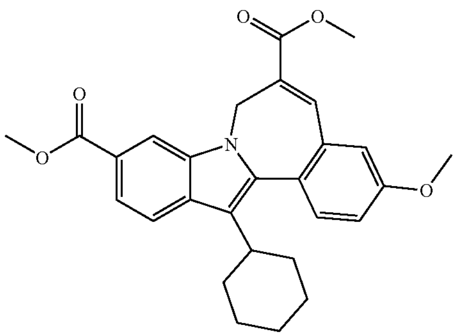 | ESI-MS m/z 460 (MH$^+$); 1H NMR (500 MHz, DMSO-D6) δ 1.07–1.22 (m, 1 H) 1.32–1.48 (m, 3 H) 1.66–1.77 (m, 2 H) 1.83–1.94 (m, 1 H) 1.94–2.11 (m, 3 H) 2.73–2.82 (m, 1 H) 3.79 (s, 3 H) 3.89 (s, 3 H) 3.91 (s, 3 H) 4.18 (br s, 1H) 5.58 (br s, 1 H) 7.26 (dd, J=8.85, 2.75 Hz, 1 H) 7.34 (d, J=2.44 Hz, 1 H) 7.54 (d, J=8.55 Hz, 1 H) 7.63 (dd,18.55, 1.53 Hz, 1 H) 7.91 (m, 2 H) 8.18 (s, 1 H) | | |
| 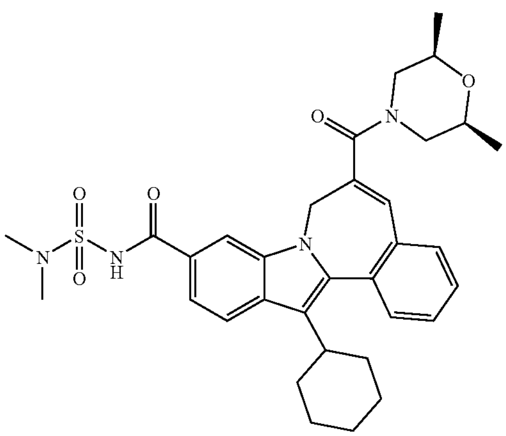 | ESI-MS m/z 605 (MH$^+$); 1H NMR (500 MHz, MeOD) δ 0.93–1.30 (m, 6 H) 1.34–1.55 (m, 4 H) 1.70–1.84 (m, 2 H) 1.90–2.01 (m, 1 H) 2.00–2.21 (m, 3 H) 2.45–2.63 (m, 2 H) 2.79–2.92 (m, 2 H) 3.01 (s, 6 H) 3.06–3.20 (m, 1 H) 3.40–3.55 (m, 1 H) 4.37 (m, 1 H) 5.14 (m, 1 H) 6.94 (s, 1 H) 7.47–7.58 (m, 4 H) 7.62 (d, J=7.02 Hz, 2 H) 7.95 (d, J=8.55 Hz, 1 H) 8.16 (s, 1 H) | | |
| | ESI-MS m/z 499 (MH$^+$); 1H NMR (500 MHz, MeOD) δ 1.03–1.36 (m, 4 H) 1.38–1.58 (m, 4 H) 1.76–1.86 (m, 2 H) 1.94–2.03 (m, 1 H) 2.05–2.24 (m, 3 H) 2.43–2.62 (m, 2 H) 2.90 (m, 1 H) 3.30–3.38 (m, 4 H) 3.47 (m, 2 H) 4.46 (m, 1 H) 5.15 (m, 1 H) 6.93 (br s, 1 H) 7.52–7.60 (m, 3 H) 7.65 (m, 1 H) 7.77 (d,J=8.55 Hz, 1 H) 7.94 (d, J=8.55 Hz, 1 H) 8.25 (s, 1 H) | | |

| Structure | Physiochemical Properties | IC₅₀ EC₅₀ |
|---|---|---|
| 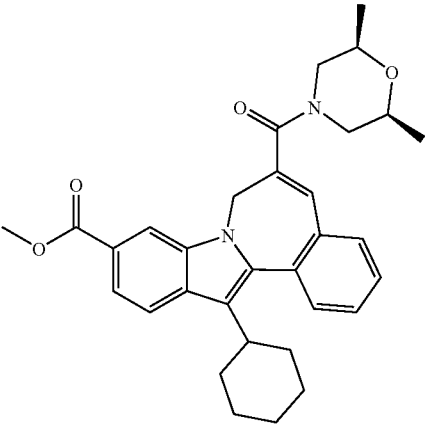 | ESI-MS m/z 513 (MH⁺); 1H NMR (500 Mhz, CHLOROFORM-D) δ 0.98–1.58 (m, 8 H) 1.68–1.84 (m, 2 H) 1.87–2.16 (m, 4 H) 2.28–2.52 (m, 2 H) 2.83 (m, 1 H) 3.30–3.81 (m, 6H) 3.96 (s, 3H) 4.46 (m, 1H) 5.03 (m, 1 H) 6.81 (br s, 1 H) 7.41 (m, 1H) 7.49 (m, 2 H) 7.56 (m, 1 H) 7.76 (dd, J=8.39, 1.37 Hz, 1 H) 7.89 (d, J=8.55 Hz, 1 H) 8.13 (s, 1 H) | |
| 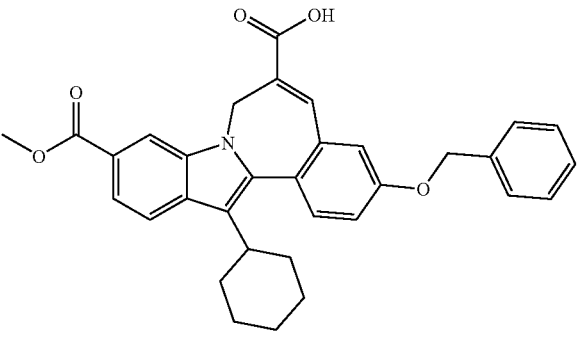 | ESI-MS m/z 522 (MH⁺); 1H NMR (500 MHz, DMSO-D6) δ 1.11–1.20 (m, 1 H) 1.34–1.48 (m, 3 H) 1.66–1.77 (m, 2 H) 1.84–1.94 (m, 1 H) 1.96–2.09 (m, 3 H) 2.78 (m, 1 H) 3.89 (s, 3H) 4.14 (m, 1 H) 5.23 (s, 2H) 5.57 (m, 1H) 7.32 (m, 1H) 7.39 (m, 2 H) 7.44 (t, J=7.48 Hz, 2 H) 7.53 (m, 3 H) 7.63 (d, ft8.24 Hz, 1 H) 7.85 (s, 1 H) 7.91 (d, J=8.55 Hz, 1 H) 8.16 (s, 1 H) | |
| 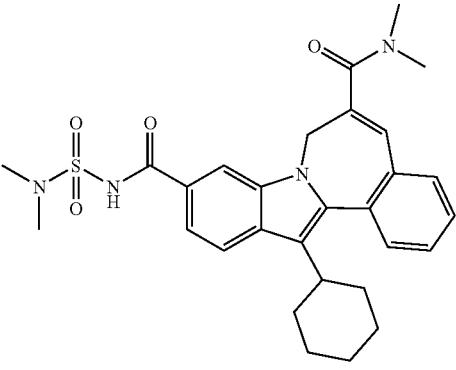 | ESI-MS m/z 535 (MH⁺); 1H NMR (500 MHz, MeOD) δ 1.17–1.30 (m, 1 H) 1.39–1.58 (m, 3 H) 1.75–1.87 (m, 2 H) 1.94–2.25 (m, 4H) 2.91 (m, 1 H) 3.04 (s, 6H) 3.06 (s, 6H) 4.38 (m, 1 H) 5.21 (m, 1H) 7.09 (br s, 1 H) 7.57 (m, 3 H) 7.62 (dd, J=8.55, 1.53 Hz, 1 H) 7.65 (m, 1 H) 7.96 (d, J=8.55 Hz, 1 H) 8.14 (s, 1 H) | |
| 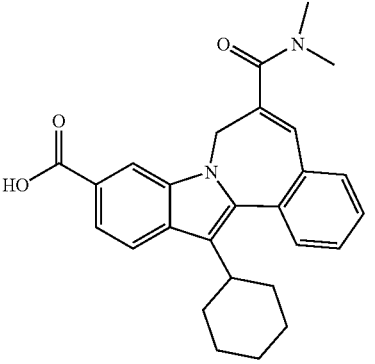 | ESI-MS m/z 429 (MH⁺); 1H NMR (500 MHz, MeOD) δ 1.17–1.34 (m, 1 H) 1.38–1.59 (m, 3 H)1.76–1.85 (m, 2 H) 1.92–2.05 (m, 1 H) 2.05–2.23 (m, 3 H) 2.87–3.09 (m, 7 H), 4.39 (m, 1 H) 5.20 (m, 1 H) 7.07 (s, 1 H) 7.52–7.61 (m, 3 H) 7.66 (d, J=7.02 Hz, 1 H) 7.74 (dd, J=8.55, 1.22 Hz, 1 H) 7.92 (d, J=8.55 Hz, 1 H) 8.23 (s, 1 H) | |

-continued

| Structure | Physiochemical Properties | IC$_{50}$ | EC$_{50}$ |
|---|---|---|---|
| 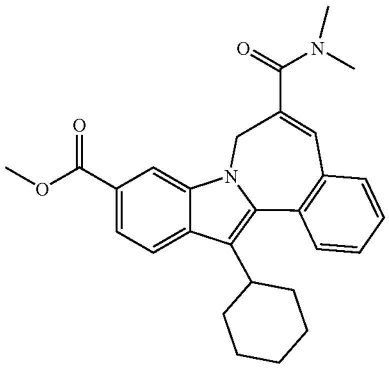 | ESI-MS m/z 443 (MH$^+$); 1H NMR (500 MHz, MeOD) δ 1.20–1.31 (m, 1 H) 1.38–1.56 (m, 3 H) 1.76–1.87 (m, 2 H) 1.95–2.24 (m, 4 H) 2.88–3.10 (m, 7 H) 3.95 (s, 3 H) 4.39 (m, 1H) 5.19 (m, 1H) 7.07 (s, 1H) 7.51–7.60 (m, 3 H) 7.65 (ci, J=6.71 Hz, 1 H) 7.73 (dd, J=8.54, 1.53 Hz, 1 H) 7.93 (d, J=8.55 Hz, 1 H) 8.23 (s, 1 H) | | |
| | ESI-MS m/z 579 (MH$^+$); 1H NMR (500 MHz, CD$_3$OD) δ 1.24–1.35 (m, 1 H) 1.42–1.54 (m, 2 H) 1.60–1.68 (m, 1 H) 1.82 (m, 2 H) 1.97 (m, 1 H) 2.02–2.18 (m, 3 H) 2.74–2.86 (m, 1 H) 2.94–3.0 1 (m, 1 H) 3.04 (s, 6 H) 3.51–3.57 (m, 1 H) 3.60–3.90 (m, 9 H) 4.49–4.66 (m, 1 H) 4.81–4.97 (m, 1 H) 7.31–7.43 (m, 1 H) 7.45–7.53 (m, 3 H) 7.59 (m, 1 H) 7.92 (m, 1 H) 8.07 (m, 1 H) | | |
| 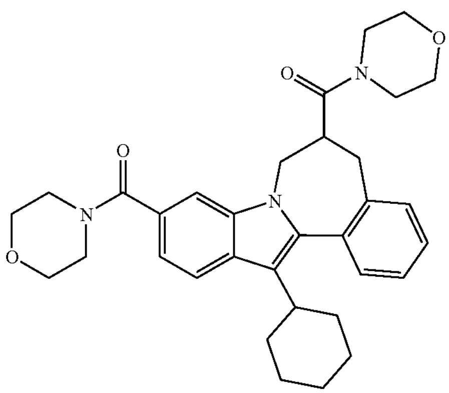 | ESI-MS m/z 542 (MH$^+$); 1H NMR (500 MHz, CHLOROFORM-D) δ 1.17–1.51 (m, 3 H) 1.57–1.71 (m, 1 H) 1.72–1.82 (m, 2 H) 1.87–1.96 (m, 1 H) 1.96–2.11 (m, 3 H) 2.61–2.99 (m, 3 H) 3.48–3.96 (m, 16 H) 4.08–4.34 (m, 1 H) 4.60 (m, 1 H) 7.00–7.14 (m, 1 H) 7.29–7.47 (m, 4 H) 7.52–7.79 (m, 1 H) 7.86 (m, 1 H) | | |
| | ESI-MS m/z 646 (MH$^+$); 1H NMR (500 MHz, MeOD) δ 1.12–2.42 (m, 18 H) 2.67–3.01 (m, 5 H) 3.03 (s, 6 H) 3.16–3.29 (m, 2 H) 3.39–3.58 (m, 2 H) 3.59–3.78 (m, 3 H) 3.81–3.94 (m, 1 H) 4.56 (m, 1 H) 7.39–7.54 (m, 4 H) 7.58 (m, 1 H) 7.93 (m, 1 H) 7.99 (m, 1H) | | |

| Structure | Physiochemical Properties | IC₅₀ | EC₅₀ |
|---|---|---|---|
| | ESI-MS m/z 646 (MH⁺); 1H NMR (500 MHz, MeOD) δ 1.13–2.42 (m, 18 H) 2.65– 3.01 (m, 5 H) 3.03 (s, 6 H) 3.11–3.22 (m, 2 H) 3.44–3.58 (m, 2 H) 3.62–3.78 (m, 3 H) 3.81–3.95 (m, 1 H) 4.55–4.75 (m, 1 H) 7.43–7.54 (m, 4 H) 7.60 (m, 1 H) 7.93 (m, 1 H) 7.99 (m, 1 H) | | |
| | MSI-MS m/z 498 (MH⁺); 1H NMR (300 MHz, MeOD) δ 1.26–1.36 (m, 1 H) 1.38– 1.57 (m, 3 H) 1.71–1.88 (m, 2 H) 1.90–2.23 (m, 4 H) 2.89 (m, 1 H) 3.03 (s, 6 H) 3.36– 3.81 (m, 8H) 4.37 (m, 1H) 5.18 (m, 1H) 7.03 (s, 1 H) 7.49–7.69 (m, 5 H) 7.95 (d, J=8.42 Hz, 1 H) 8.15 (d, J=1.46 Hz, 1 H) | | |
| | ESI-MS m/z 653 (MH⁺); 1H NMR (500 MHz, MeOD) δ 1.20–1.34 (m, 1 H) 1.41– 1.59 (m, 3 H) 1.78–1.87 (m, 2 H) 1.93–2.23 (m, 4 H) 2.93 (m, 1 H) 3.02 (s, 6 H) 3.50– 3.94 (m, 8 H) 4.42 (m, 1 H) 5.25 (m, 1 H) 7.10 (d, J=6.41 Hz, 2 H) 7.14 (s, 1 H) 7.60 (m, 4 H) 7.68 (d, J=7.63 Hz, 1 H) 7.98 (d, J=8.55 Hz, 1 H) 8.17 (m, 3 H) | | |

| Structure | Physiochemical Properties | IC$_{50}$ | EC$_{50}$ |
|---|---|---|---|
| 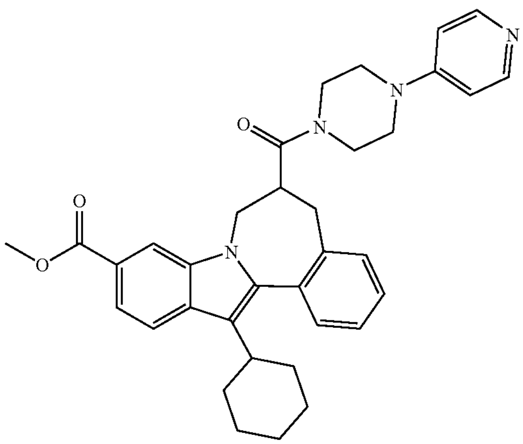 | ESI-MS m/z 563 (MH$^+$); 1H NMR (500 MHz, CHLOROFORM-D) δ 1.17–1.32 (m, 1 H) 1.32–1.51 (m, 2 H) 1.61–1.71 (m, 2.65–3.09 (m, 3 H) 3.61–4.07 (m, 11 H) 4.18 (m, 1H) 4.39 (m, 1 H) 4.58 (m, 1 H) 6.94 (m, 2 H) 7.27 (m, 1 H) 7.39 (m, 1 H) 7.44 (m, 2 H) 7.74 (m, 1 H) 7.87 (m, 1 H) 8.10 (m, 1 H) 8.35 (m, 2 H) | | |
| 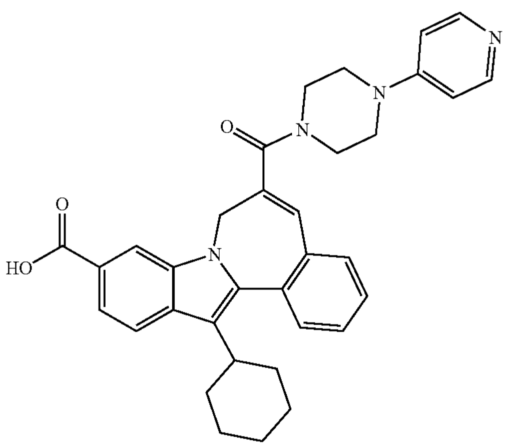 | ESI-MS m/z 547 (MH$^+$); 1H NMR (300 MHz, MeOD) δ 1.11–1.63 (m, 4 H) 1.69–2.28 (m, 6 H) 2.89 (m, 1 H) 3.45–3.99 (m, 8 H) 4.43 (m, 1H) 5.22 (m, 1 H) 7.07 (d, J=7.68 Hz, 2 H) 7.11 (s, 1 H) 7.59 (m, 3 H) 7.69 (m, 2 H) 7.93 (d, J=8.78 Hz, 1 H) 8.15 (d, J=7.69 Hz, 1 H) 8.24 (s, 1 H) | | |
| 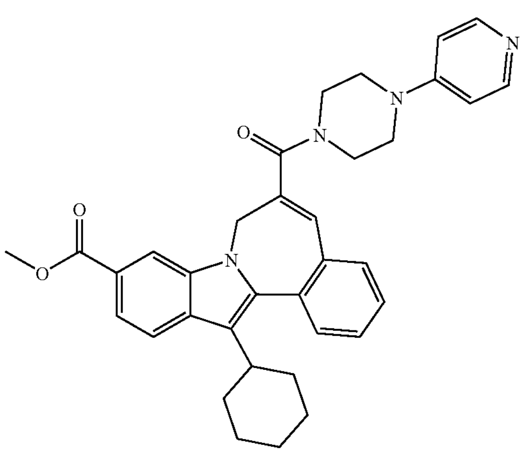 | ESI-MS m/z 561 (MH$^+$); 1H NMR (500 MHz, CHLOROFORM-D) δ 1.12–1.61 (m, 4 H) 1.70–1.86 (m, 2H) 1.88–2.21 (m, 4H) 2.85 (t, J=1 1.44 Hz, 1 H) 3.27–3.87 (m, 8 H) 3.90 (s, 3 H) 4.43 (m, 1 H) 5.14 (m, 1 H) 6.74 (m, 2 H) 6.97 (s, 1 H) 7.42 (d, 7.63 Hz, 1 H) 7.51 (m, 2H) 7.59 (m, 1 H) 7.72 (d, J=8.55 Hz, 1 H) 7.91 (d, J=8.55 Hz, 1 H) 8.15 (s, 1 H) 8.19 (m, 2 H) | | |

| Structure | Physiochemical Properties | IC$_{50}$ | EC$_{50}$ |
|---|---|---|---|
| 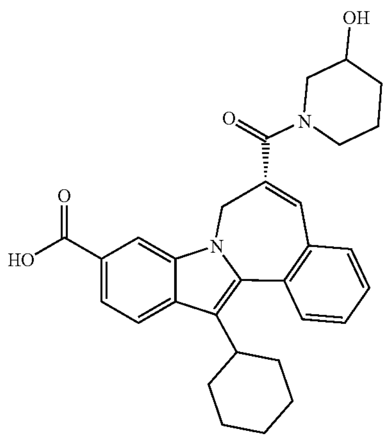 | ESI-MS m/z 487 (MH$^+$); 1H NMR (500 MHz, MeOD) δ 1.27–2.20 (m, 14 H) 2.87 (m, 3 H) 3.17–3.42 (m, 1 H) 3.51–4.00 (m, 5 H) 4.03–4.27 (m, 1 H) 4.43–4.65 (m, 1 H) 7.33–7.51 (m, 4 H) 7.72 (m, 1 H) 7.87 (m, 1 H) 8.21 (m, 1 H) | | |
| 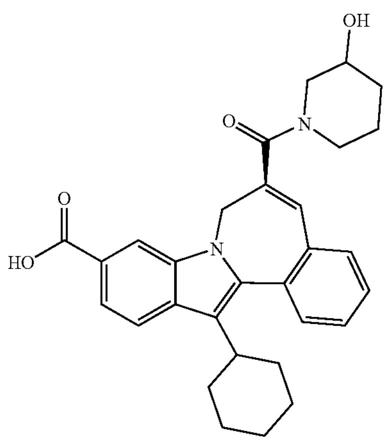 | ESI-MS m/z 487 (MH$^+$); 1H NMR (500 MHz, MeOD) δ 1.22–2.19 (m, 14 H) 2.87 (m, 3 H) 3.17–3.42 (m, 1 H) 3.52–3.98 (m, 5 H) 4.01–4.26 (m, 1 H) 4.42–4.65 (m, 1 H) 7.33–7.51 (m, 4 H) 7.72 (m, 1 H) 7.87 (m, 1 H) 8.21 (m, 1 H | | |
| 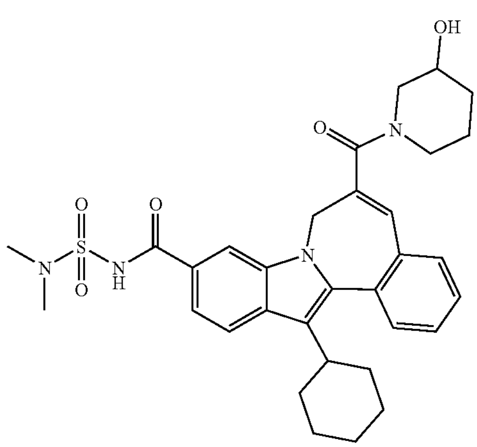 | ESI-MS m/z 593 (MH$^+$); 1H NMR (500 MHz, MeOD) δ 1.25–2.17 (m, 14 H) 2.74– 3.01 (m, 3 H) 3.04 (s, 6 H) 3.13–3.21 (m, 1 H) 3.37–3.95 (m, 7 H) 7.39–7.5 1 (m, 4 H) 7.59 (m, 1 H) 7.91 (m, 1 H) 7.98–8.12 (m, 1 H) | | |

-continued
| Structure | Physiochemical Properties | IC$_{50}$ | EC$_{50}$ |
|---|---|---|---|
| 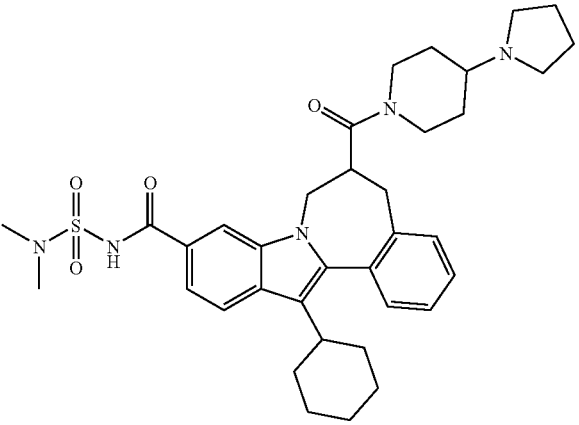 | ESI-MS m/z 646 (MH$^+$); 1H NMR (500 MHz, MeOD) δ 1.07–2.50 (m, 19 H) 2.68–3.01 (m, 4 H) 3.02 (s, 6 H) 3.16–3.32 (m, 3 H) 3.36–3.84 (m, 5 H) 4.19–4.39 (m, 1 H) 4.50–4.74 (m, 1 H) 7.38–7.51 (m, 4 H) 7.55–7.69 (m, 1 H) 7.86–8.09 (m, 2 H) | | |
| 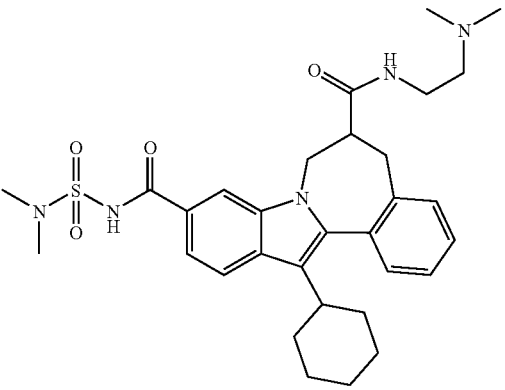 | ESI-MS m/z 580 (MH$^+$); 1H NMR (500 MHz, MeOD) δ 1.25–1.35 (m, 1 H) 1.40–1.56 (m, 2 H) 1.61–1.68 (m, 1 H) 1.78–1.87 (m, 2 H) 1.94–2.18 (m, 4 H) 2.79 (m, 1 H) 2.88–3.01 (m, 8 H) 3.03 (s, 6 H) 3.14–3.21 (m, 1 H) 3.24–3.31 (m, 2 H) 3.36–3.48 (m, 1 H) 3.50–3.67 (m, 2 H) 3.85 (dd, J=14.95, 6.10 Hz, 1 H) 4.80 (m, 1 H) 7.42–7.52 (m, 4 H) 7.59 (m, 1 H) 7.94 (m, 1 H) 8.07 (m, 1 H) | | |
| 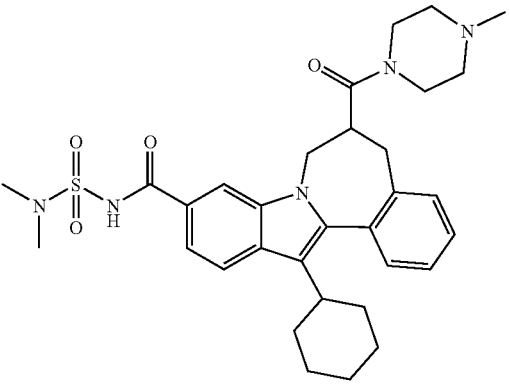 | ESI-MS m/z 592 (MH$^+$); 1H NMR (500 MHz, MeOH) δ 1.22–1.34 (m, 1 H) 1.37–1.67 (m, 3 H) 1.77–1.85 (m, 2 H) 1.92–2.00 (m, 1 H) 1.99–2.19 (m, 3 H) 2.72–2.87 (m, 2 H) 2.92–3.14 (m, 11 H) 3.39–3.75 (m, 4 H) 3.76–4.13 (m, 3 H) 4.14–4.75 (m, 3 H) 7.39–7.54 (m, 4 H) 7.55–7.63 (m, 1 H) 7.89–7.97 (m, 1 H) 7.99–8.08 (m, 1 H) | | |

-continued

| Structure | Physiochemical Properties | IC$_{50}$ | EC$_{50}$ |
|---|---|---|---|
| 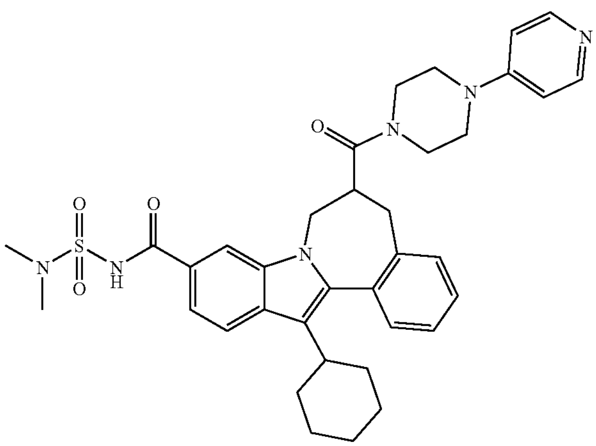 | ESI-MS m/z 655 (MH$^+$) 1H NMR (500 MHz, MeOD) δ 1.20–1.71 (m, 4 H) 1.78–1.88 (m, 2 H) 1.93–2.22 (m, 4 H) 2.74–2.94 (m, 2 H) 2.96–3.07 (m, 7 H) 3.65–3.77 (m, 2 H) 3.81–4.05 (m, 7 H) 4.07–4.20 (m, 1 H) 4.51–4.70 (m, 1 H) 7.19–7.29 (m, 2 H) 7.32–7.44 (m, 1 H) 7.44–7.55 (m, 3 H) 7.55–7.65 (m, 1 H) 7.89 (m, 1 H) 7.97–8.11 (m, 1 H) 8.15–8.28 (m, 2 H) | | |
| 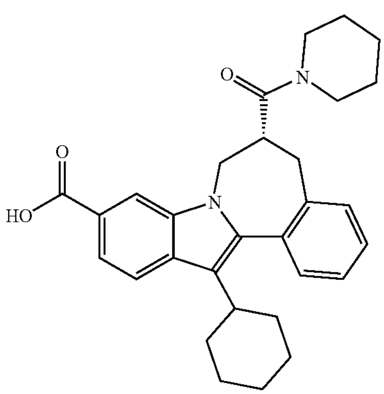 | ESI-MS m/z 471 (MH$^+$) 1H NMR (500 MHz, MeOH) δ 1.40–1.56 (m, 3 H) 1.57–1.69 (m, 2 H) 1.70–1.90 (m, 7 H) 1.94–2.21 (m, 4 H) 2.70–3.03 (m, 3 H) 3.37 (s, 4 H) 3.73–4.06 (m, 2 H) 4.43–4.62 (m, 1 H) 7.36–7.51 (m, 4 H) 7.66–7.76 (m, 1 H) 7.83–7.91 (m, 1 H) 8.09–8.19 (m, 1 H) | | |
| 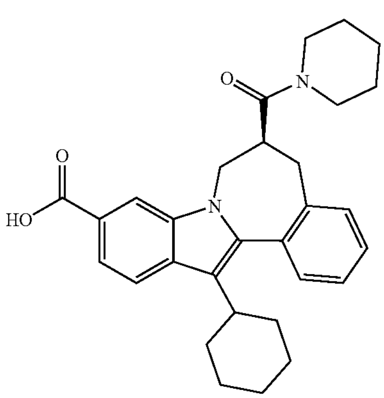 | ESI-MS m/z 471 (MH$^+$); 1H NMR (500 MHz, MeOH) δ 1.40–1.56 (m, 3 H) 1.57–1.69 (m, 2 H) 1.70–1.90 (m, 7 H) 1.94–2.21 (m, 4 H) 2.68–3.04 (m, 3 H) 3.37 (s, 4 H) 3.73–4.06 (m, 2 H) 4.43–4.62 (m, 1 H) 7.36–7.51 (m, 4 H) 7.69–7.75 (m, 1 H) 7.85–7.91 (m, 1 H) 8.15 (m, 1 H) | | |

-continued

| Structure | Physiochemical Properties | IC$_{50}$ | EC$_{50}$ |
|---|---|---|---|
| 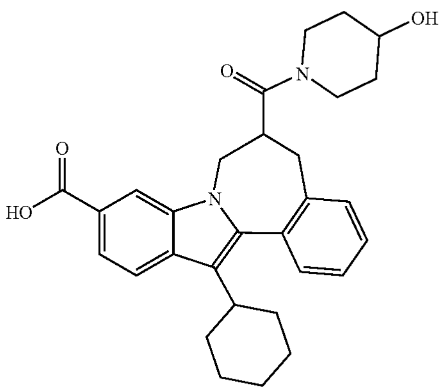 | ESI-MS m/z 487 (MH$^+$); 1H NMR (300 MHz, ACETONE-D6) δ 1.16–2.23 (m, 14 H) 2.73–2.90 (m, 2 H) 2.92–3.07 (m, 1 H) 3.15–3.62 (m, 2 H) 3.64–4.22 (m, 5 H) 4.59 (m, 1 H) 7.27–7.56 (m, 4 H) 7.74 (t, J= 7.87 Hz, 1 H) 7.93 (m, 1 H) 8.26 (m, 1 H) | | |
| 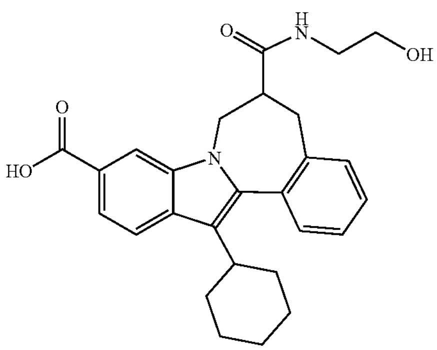 | ESI-MS m/z 447 (MH$^+$); 1H NMR (500 MHz, ACETONE-D6) δ 1.12–1.24 (m, 1 H) 1.32–1.44 (m, 2 H) 1.51–1.60 (m, 1 H) 1.64–1.75 (m, 2 H) 1.81–1.88 (m, 1 H) 2.00–2.12 (m, 3 H) 2.53–2.63 (m, 1 H) 2.72–2.81 (m, 2 H) 2.85–3.00 (m, 2 H) 3.10–3.20 (m, 1 H) 3.20–3.61 (m, 4 H) 3.65–3.90 (m, 1 H) 4.65–4.83 (m, 1 H) 7.37 (m, 4 H) 7.65 (t, J=9.00 Hz, 1 H) 7.84 (m, 1 H) 8.18 (m, 1H) | | |
| 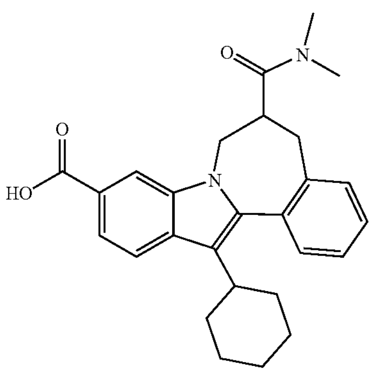 | ESI-MS m/z 431 (MH$^+$); 1H NMR (300 MHz, ACETONE-D6) δ 1.17–1.35 (m, 1 H) 1.41–1.55 (m, 2 H) 1.56–1.69 (m, 1 H) 1.70–1.86 (m, 2 H) 1.88–1.99 (m, 1 H) 2.07–2.22 (m, 4 H) 2.73–2.87 (m, 2 H) 2.96 (m, 3H) 3.27 (m, 3H) 3.68 (m, 1H) 3.96 (m, 1 H) 4.11 (dd, J=14.27, 11.71 Hz, 1 H) 4.60 (m, 1 H) 7.26–7.57 (m, 4 H) 7.74 (m, 1 H) 7.93 (m, 1 H) 8.23 (d, J=21.96 Hz, 1 H) | | |
| | ESI-MS m/z 806 (MH$^+$); 1H NMR (500 MHz, MeOD) δ 1.24–1.39 (m, 1 H) 1.39–1.57 (m, 2 H) 1.62–1.71 (m, 1 H) 1.78–2.26 (m, 14 H) 2.32–2.68 (m, 1 H) 2.69–2.81 (m, 1 H) 2.93–3.05 (m, 2 H) 3.36–3.49 (m, 1 H) 3.59–3.77 (m, 2 H) 3.79–3.98 (m, 5 H) 4.04–4.15 (m, 1 H) 4.50–4.61 (m, 1 H) 6.41 (m, 1 H) 7.15 (m, 2 H) 7.33–7.52 (m, 4 H) 7.53–7.68 (m, 5 H) 7.71 (m, 1 H) 7.87 (m, 1 H) 7.92 (m, 1 H) 8.20 (m, 2 H) | | |

| Structure | Physiochemical Properties | IC$_{50}$ | EC$_{50}$ |
|---|---|---|---|
| 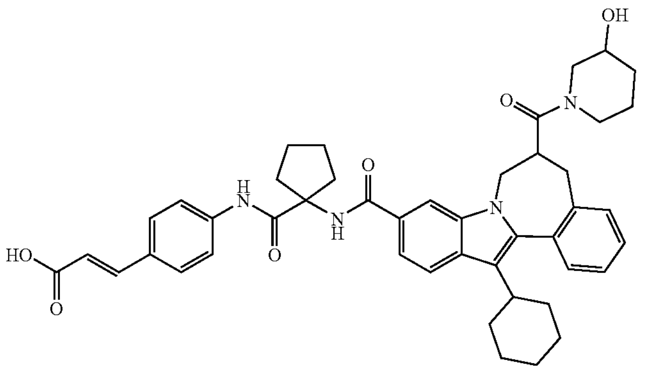 | ESI-MS m/z 743 (MH$^+$); 1H NMR (500 MHz, MeOD) δ 1.21–1.35 (m, 1 H) 1.37–1.55 (m, 3 H) 1.57–1.69 (m, 1 H) 1.76–2.27 (m, 17 H) 2.41–2.60 (m, 2 H) 2.67–3.03 (m, 3 H) 3.53–3.93 (m, 5 H) 4.44–4.69 (m, 1 H) 6.40 (d, J=15.87 Hz, 1 H) 7.39–7.50 (m, 4 H) 7.51–7.59 (m, 3 H) 7.60–7.68 (m, 3 H) 7.89 (m, 1H) 8.08 (m, 1 H) | | |
| 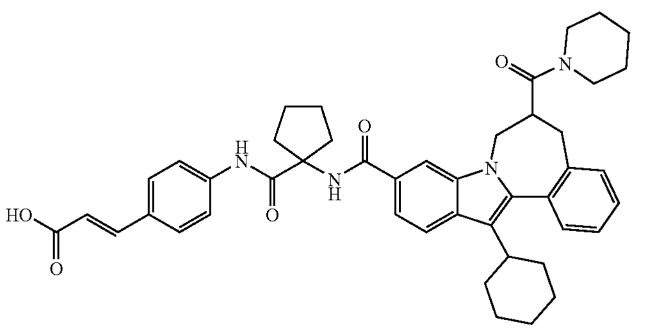 | ESI-MS m/z 727 (MH$^+$); 1H NMR (500 MHz, MeOD) δ 1.19–1.34 (m, 1 H) 1.35–1.56 (m, 3 H) 1.56–2.26 (m, 20 H) 2.41–2.60 (m, 2 H) 2.70–2.85 (m, 2 H) 2.91–3.02 (m, 1 H) 3.36–3.85 (m, 5 H) 4.39–4.62 (m, 1 H) 6.40 (d, J=15.87 Hz, 1 H) 7.35–7.50 (m, 4 H) 7.50–7.59 (m, 3 H) 7.59–7.68 (m, 3 H) 7.85–7.93 (m, 1 H) 7.97–8.11 (m, 1 H) | | |
| 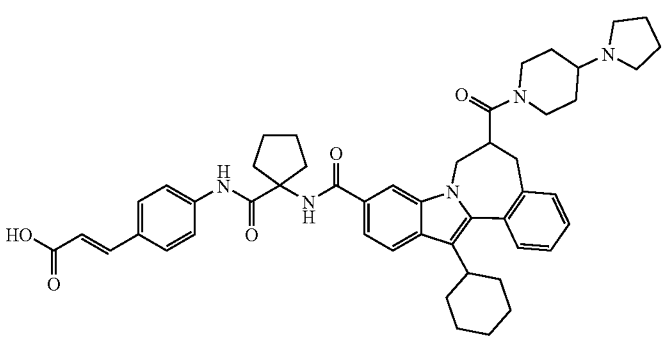 | ESI-MS m/z 797 (MH$^+$); 1H NMR (500 MHz, MeOD) δ 1.28–1.38 (m, 1 H) 1.42–1.55 (m, 3 H) 1.59–1.73 (m, 2 H) 1.78–2.40 (m, 20 H) 2.41–2.50 (m, 1 H) 2.63–2.74 (m, 2 H) 2.97–3.27 (m, 4 H) 3.36–3.45 (m, 1 H) 3.59–3.68 (m, 2 H) 3.71–3.78 (m, 1 H) 3.92–4.00 (m, 1 H) 4.26–4.39 (m, 2 H) 4.44 (d, J=14.95 Hz, 1 H) 6.42 (d, J=16.17 Hz, 1 H) 7.43–7.51 (m, 4 H) 7.56–7.70 (m, 5 H) 7.75 (d, J=8.55 Hz, 1 H) 7.90 (s, 1 H) 7.95 (d, J=8.54 Hz, 1 H) | | |
| 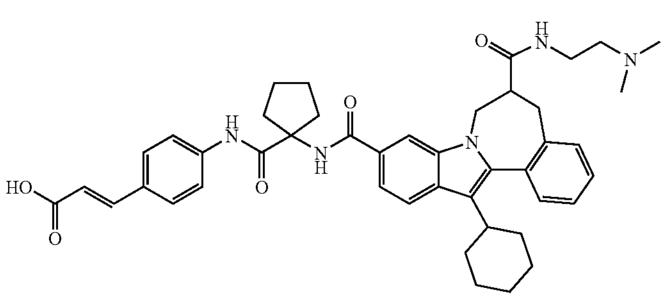 | ESI-MS m/z 730 (MH$^+$); 1H NMR (500 MHz, MeOD) δ 1.24–1.36 (m, 1 H) 1.39–1.58 (m, 2 H) 1.59–1.69 (m, 1 H) 1.76–2.25 (m, 14 H) 2.42–2.59 (m, 2 H) 2.72–2.86 (m, 6 H) 2.93–3.01 (m, 2 H) 3.06–3.18 (m, 1 H) 3.23 (t, J=6.26 Hz, 1 H) 3.35–3.45 (m, 1 H) 3.55–3.64 (m, 1 H) 3.81 (dd, J=14.95, 6.10 Hz, 1 H) 4.71 (d, J=14.95 Hz, 1 H) 6.34–6.47 (m, 1 H) 7.41–7.51 (m, 4H) 7.55 (dd, J=13.89, 8.70 Hz, 2 H) 7.59–7.71 (m, 4 H) 7.91 (d, J=8.24 Hz, 1 H) 7.98 (s, 1 H) | | |

-continued

| Structure | Physiochemical Properties | IC$_{50}$ EC$_{50}$ |
|---|---|---|
| 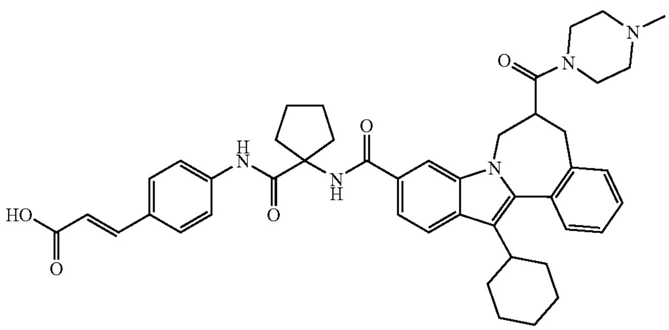 | ESI-MS m/z 742 (MH$^+$); 1H NMR (500 MHz, MeOD) δ 1.19–1.38 (m, 1 H) 1.38–1.56 (m, 2 H)1.58–1.69 (m, 1 H) 1.74–2.27 (m, 14 H) 2.40 (m, 1 H) 2.59 (m, 1 H) 2.70 (m, 1H) 2.93 (m, 6 H) 3.38–4.10 (m, 6 H) 4.29–4.46 (m, 1H) 4.54 (d, J=14.95 Hz, 1 H) 6.40 (m, 1 H) 7.40–7.5 1 (m, 4 H) 7.50–7.60 (m, 2 H) 7.59–7.72 (m, 4 H) 7.86–8.03 (m, 2 H) | |
| 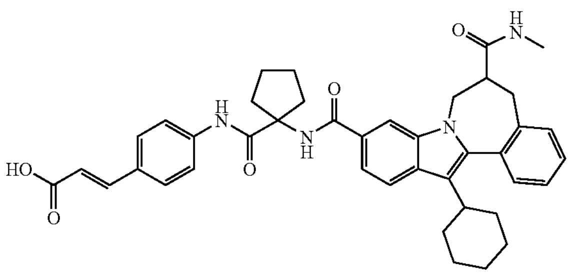 | ESI-MS m/z 673 (MH$^+$); 1H NMR (500 MHz, MeOD) δ 1.19–1.36 (m, 1 H) 1.36–1.55 (m, 2 H) 1.58–1.72 (m, 1 H)1.74–2.29 (m, 12 H) 2.33–2.59 (m, 2 H) 2.63–2.85 (m, 4 H) 2.90 (m, 2 H) 3.10 (m, 1 H) 3.74 (m, 1 H) 4.76 (m, 1H) 6.39 (d, J=15.87 Hz, 1 H) 7.33–7.52 (m, 4 H) 7.50–7.60 (m, 2 H) 7.59–7.73 (m, 3 H) 7.88 (dd, J=14.65, 8.85 Hz, 1 H) 8.05 (m, 1 H) | |
| 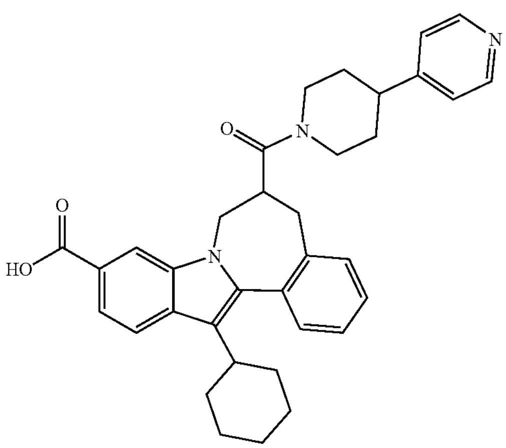 | ESI-MS m/z 549 (MH$^+$); 1H NMR (500 MHz, MeOD) δ 1.22–1.36 (m, 1 H) 1.39–1.56 (m, 2 H) 1.59–1.70 (m, 1 H) 1.77–1.87 (m, 2 H) 1.94–2.22 (m, 4 H) 2.75–3.04 (m, 3 H) 3.69 (m, 1 H) 3.80–4.03 (m, 8 H) 4.12 (m, H) 4.64 (m, H) 7.23 (t, J=8.70 Hz, 2 H) 7.31–7.45 (m, 1 H) 7.49 (m, 3 H) 7.73 (m, 1 H) 7.89 (m, 1 H) 8.12–8.20 (m, 1 H) 8.22 (m, 2 H) | |
| 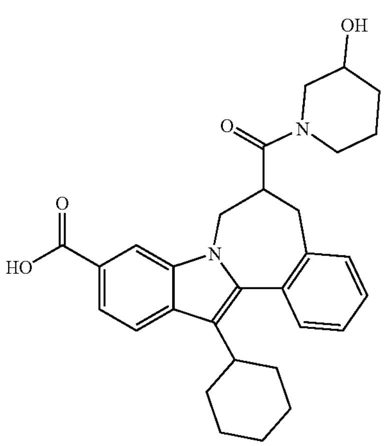 | ESI-MS m/z 487 (MH$^+$); 1H NMR (500 MHz, MeOD) δ 1.18–2.18 (m, 14 H) 2.80 (m, 3 H) 3.08–3.30 (m, 1 H) 3.36–3.98 (m, 5 H) 3.98429 (m, 1 H) 4.34–4.60 (m, 1 H) 7.23–7.52 (m, 4 H) 7.67–7.77 (m, 1 H) 7.86 (m, 1 H) 8.20 (m, 1 H) | |

-continued
| Structure | Physiochemical Properties | IC$_{50}$ | EC$_{50}$ |
|---|---|---|---|
| 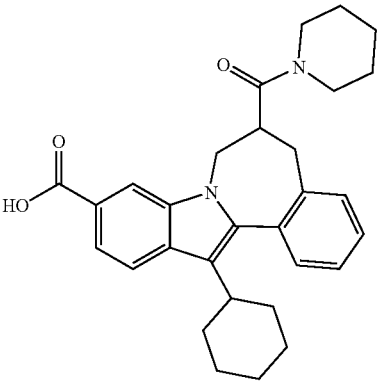 | ESI-MS m/z 471 (MH$^+$); 1H NMR (500 MHz, MeOD) δ 1.17–2.17 (m, 16 H) 2.53– 2.71 (m, 1 H) 2.84 (t, J=12.67 Hz, 1 H) 2.88–3.03 (m, 1 H) 3.38 (m, 1 H) 3.54 (m, 2 H) 3.69–3.84 (m, 2 H) 3.99–4.17 (m, 1 H) 4.33–4.53 (m, 1 H) 7.23–7.46 (m, 4 H) 7.72 (m, 1 H) 7.85 (m, 1 H) 8.13 (m, 1 H) | | |
| 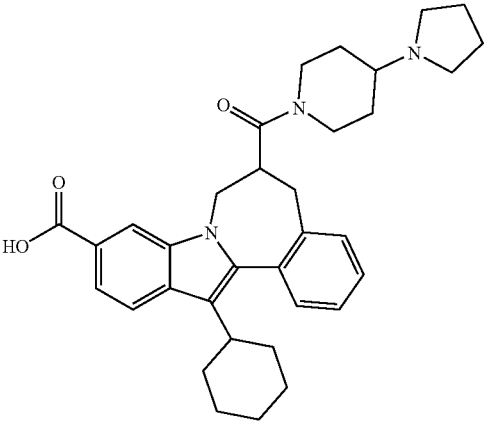 | ESI-MS m/z 540 (MH$^+$); 1H NMR (500 MHz, MeOD) δ 1.27 (m, 1 H) 1.34–1.67 (m, 4 H) 1.67–2.14 (m, 9 H) 2.16–2.40 (m, 4 H) 2.56–3.00 (m, 4 H) 3.13–3.32 (m, 3 H) 3.37–3.58 (m, 1 H) 3.58–3.89 (m, 4 H) 4.17–4.46 (m, 1 H) 4.51 (m, J=14.95 Hz, 1 H) 4.59–4.75 (m, 1 H) 7.3 1–7.55 (m, 4 H) 7.73 (m, 1 H) 7.86 (m, 1 H) 8.11 (m, 1 H) | | |
| 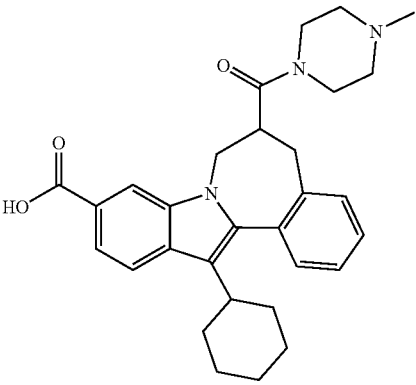 | ESI-MS m/z 486 (MH$^+$) | | |
| 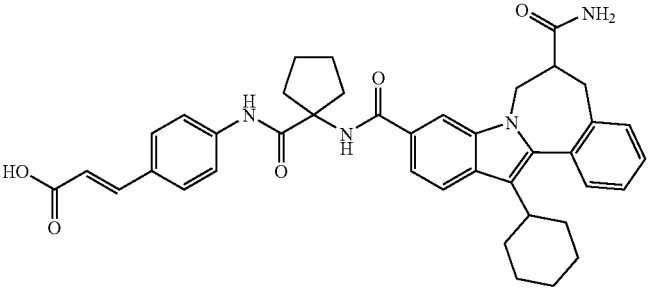 | ESI-MS m/z 659 (MH$^+$); 1H NMR (500 MHz, MeOD) δ 1.29 (m, 1 H) 1.48 (m, 2 H) 1.64 (m, 1 H) 1.77–2.27 (m, 12 H) 2.51 (m, 2 H) 2.73 (m, 1 H) 2.98 (m, 2 H) 3.17 (m, 1 H) 3.84 (m, 1 H) 4.68 (m, 1H) 6.41 (d, J=15.87 Hz, 1 H) 7.36–7.50 (m, 4 H) 7.56 (m, 3 H) 7.64 (m, 3 H) 7.89 (m, 1 H) 8.11 (s, 1 H) | | |

| Structure | Physiochemical Properties | IC$_{50}$ EC$_{50}$ |
|---|---|---|
| 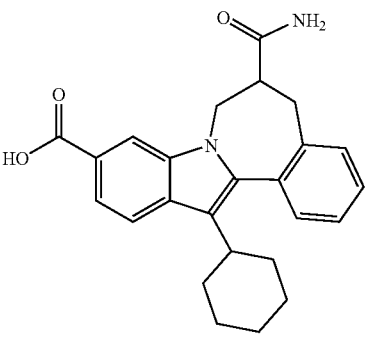 | ESI-MS m/z 403 (MH$^+$) | |
| 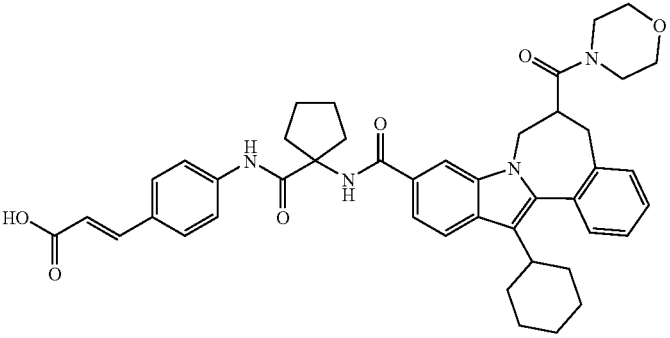 | ESI-MS m/z 729 (MH$^+$); 1H NMR (500 MHz, DMSO-D6) δ 1.13–1.83 (m, 9 H) 1.84–1.93 (m, 1 H) 1.94–2.44 (m, 8 H) 2.62–2.72 (m, 1 H) 2.86 (m, 1 H) 3.20–3.31 (m, 1 H) 3.34–3.42 (m, 1 H) 3.42–3.87 (m, 8 H) 3.93–4.03 (m, 1 H) 4.45–4.89 (m, 1 H) 6.45 (m, 1 H) 7.28–7.54 (m, 6 H) 7.60 (m, 2 H) 7.66 (m, 2 H) 7.83 (t, J=8.09 Hz, 1 H) 8.22 (m, 1 H) | |
| 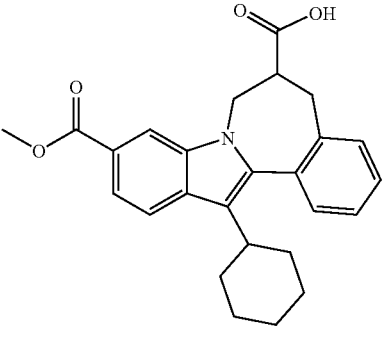 | ESI-MS m/z 418 (MH$^+$) | |
| 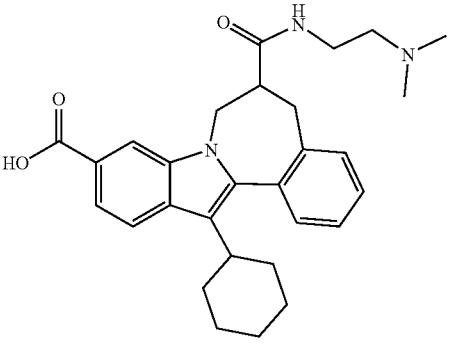 | ESI-MS m/z 474 (MH$^+$) | |

-continued
| Structure | Physiochemical Properties | IC$_{50}$ | EC$_{50}$ |
|---|---|---|---|
ESI-MS m/z 446 (MH$^+$)
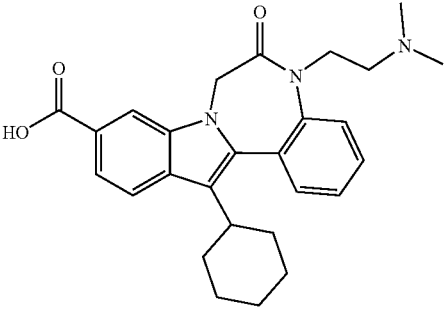
ESI-MS m/z 728 (MH$^+$)
1H NMR (500 MHz, MeOD) δ 1.32–1.55 (m, 5 H) 1.75–2.01 (m, 8H) 2.05–2.27 (m, 5 H) 2.51 (m, 2 H) 2.89 (s, 6 H) 2.95 (m, 1 H) 3.67 (m, 2H) 4.20 (m, 1 H) 5.72 (m, 1 H) 6.42 (d, J=16.18 Hz, 1 H) 7.54–7.71 (m, 11 H) 7.93 (d, J=8.55 Hz, 1 H) 8.21 (s, 1 H) 9.69 (s, 1 H)
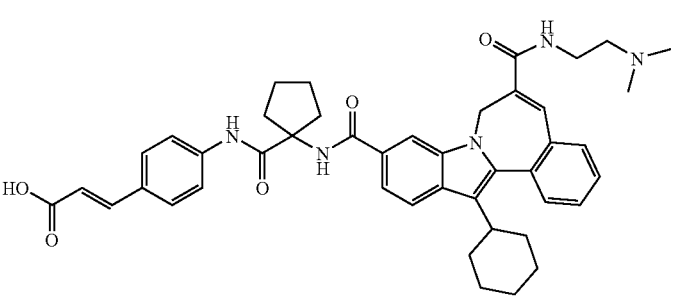
ESI-MS m/z 742 (MH$^+$)
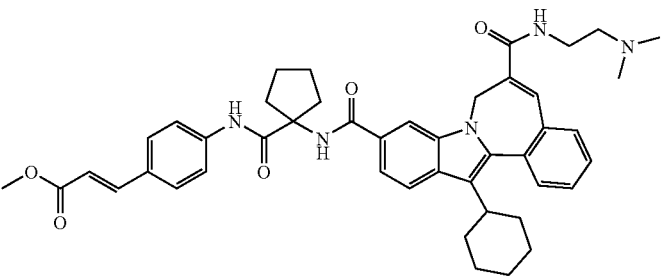
ESI-MS m/z 472 (MH$^+$); 1H NMR (500 MHz, MeOD) δ 1.14–1.31 (m, 1 H) 1.36–1.56 (m, 3 H) 1.73–1.87 (m, 2 H) 1.90–2.06 (m, 4H) 2.89 (m, 1 H) 2.95 (s, 6H) 3.36 (m, 2 H) 3.70 (m, 2 H) 4.17 (m, 1 H) 5.70 (m, 1 H) 7.52–7.69 (m, 4 H) 7.73 (m, 3 H) 7.89 (d, J=8.55 Hz, 1 H) 8.33 (s, 1 H)
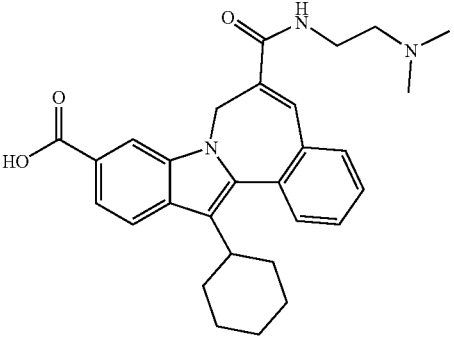

| Structure | Physiochemical Properties | IC$_{50}$ | EC$_{50}$ |
|---|---|---|---|
| 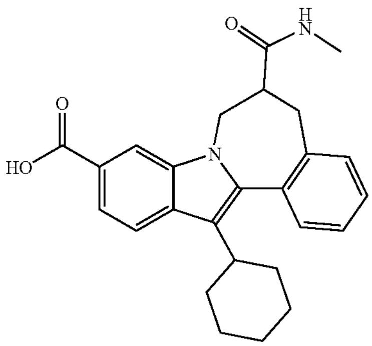 | ESI-MS m/z 417 (MH$^+$) | | |
| 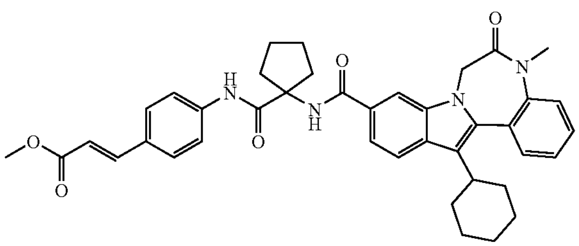 | ESI-MS m/z 659 (MH$^+$) | | |
| 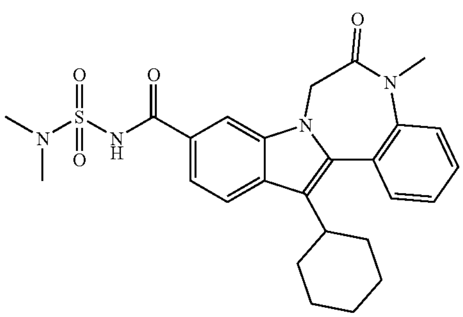 | ESI-MS m/z 495 (MH$^+$); 1H NMR (300 MHz, ACETONE-D6) δ ppm 1.17–1.68 (m, 5 H) 1.71–2.22 (m, 5 H) 2.98–3.06 (m, 6H) 3.31 (s, 3 H) 4.57 (d, J=14.64 Hz, 1 H 5.08 (d, J=14.64 Hz, 1 H)) 7.49 (m, H) 7.60–7.68 (m, 4 H) 7.78 (dd, J=8.60, 1.65 Hz, 1 H) 8.04 (d, J=8.78 Hz, 1 H) 8.41 (s, 1 H) | | |
| 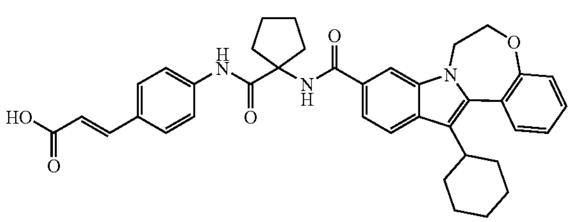 | ESI-MS m/z 618 (MH$^+$) | | |
| 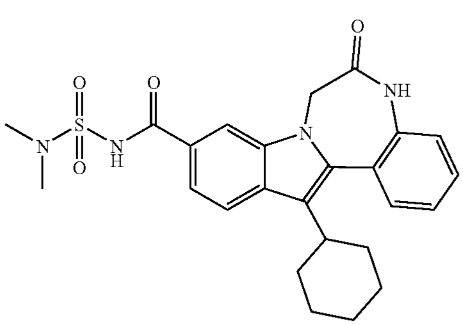 | ESI-MS m/z 481 (MH$^+$) | | |

-continued
| Structure | Physiochemical Properties | IC$_{50}$ | EC$_{50}$ |
|---|---|---|---|
| 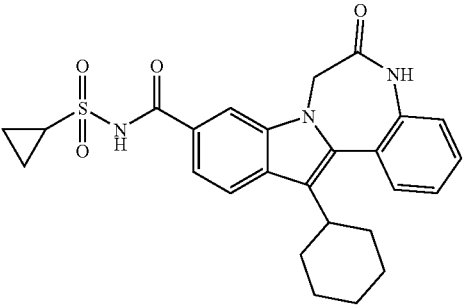 | ESI-MS m/z 478 (MH$^+$) | | |
| 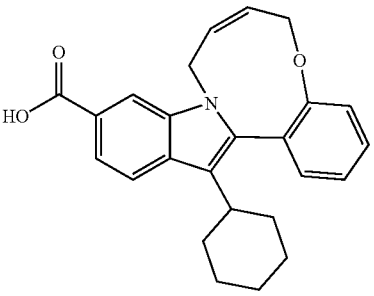 | ESI-MS m/z 388 (MH$^+$) | | |
| 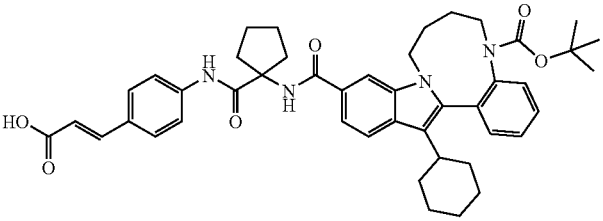 | ESI-MS m/z 745 (MH$^+$) | | |
| 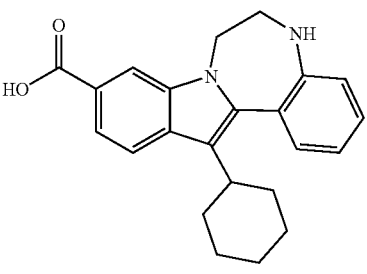 | ESI-MS m/z 361 (MH$^+$) | | |
| 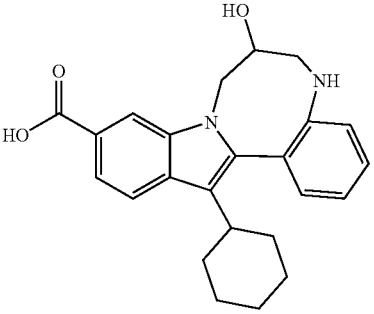 | ESI-MS m/z 391 (MH$^+$) | | |

-continued
| Structure | Physiochemical Properties | IC$_{50}$ | EC$_{50}$ |
|---|---|---|---|
| 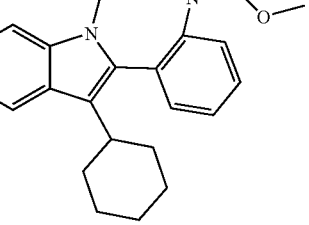 | ESI-MS m/z 491 (MH$^+$) | | |
| 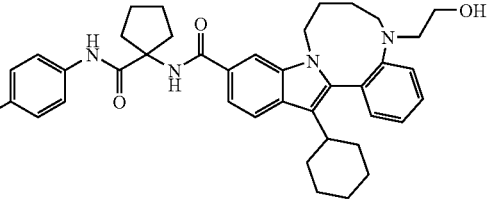 | ESI-MS m/z 689 (MH$^+$) | | |
| 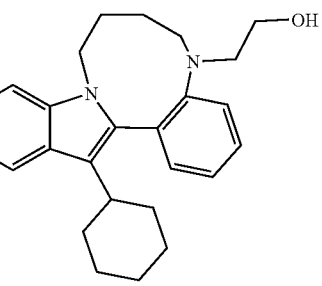 | ESI-MS m/z 433 (MH$^+$) | | |
| 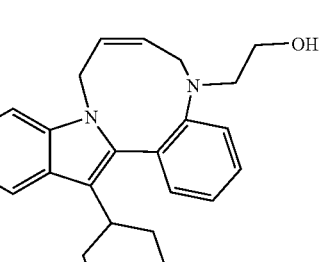 | ESI-MS m/z 431 (MH$^+$) | | |
| 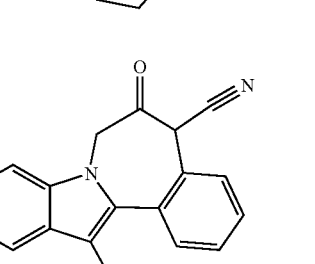 | ESI-MS m/z 399 (MH$^+$) | | |

-continued

| Structure | Physiochemical Properties | IC$_{50}$ | EC$_{50}$ |
|---|---|---|---|
| 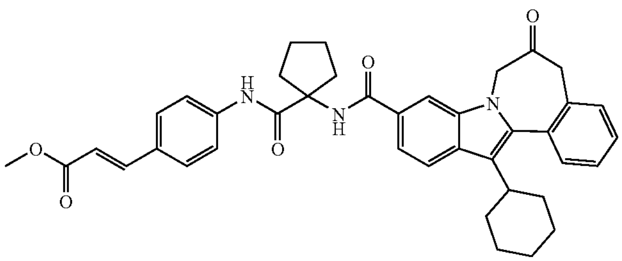 | ESI-MS m/z 644 (MH$^+$); 1H NMR (500 MHz, CHLOROFORM-D) δ 1.14–1.52 (m, 5 H) 1.60–1.69 (m, 1 H) 1.74–2.11 (m, 8 H) 2.20–2.31 (m, 2H) 2.58 (m, 2 H) 2.96 (m, 1 H) 3.58 (d, J=14.34 Hz, 1H) 3.80 (m, 4 H) 4.45 (d, J=18.01 Hz, 1 H) 4.97 (d, J=17.70 Hz, 1 H) 6.35 (d, J=15.87 Hz, 1 H) 6.45 (m, 1 H) 7.35 (d, J=7.32 Hz, 1 H) 7.38–7.51 (m, 5 H) 7.54 (m, 1 H) 7.63 (m, 3 H) 7.94 (m, 2 H) 10.36 (br s, 1 H) | | |
| 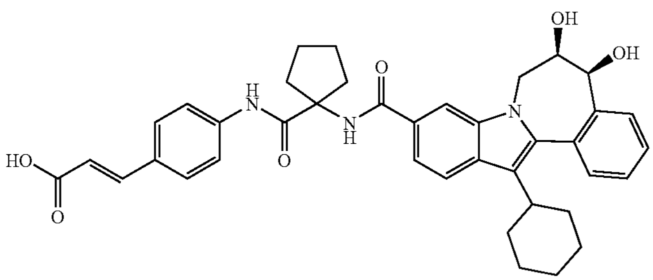 | ESI-MS m/z 648 (MH$^+$); 1H NMR (500 MHz, MeOD) δ 1.20–1.33 (m, 1 H) 1.35–1.55 (m, 2 H) 1.55–1.65 (m, 1 H) 1.74–1.99 (m, 7 H) 1.98–2.16 (m, 3 H) 2.17–2.26 (m, 2 H) 2.51 (m, 2 H) 2.95 (m, 1 H) 3.30 (d, J=10.38 Hz, 1 H) 4.41 (d, J4.58 Hz, 1 H) 4.54 (m, 1 H) 4.74 (dd, J=14.19, 7.17 Hz, 1 H) 6.39 (d, J=16.17 Hz, 1 H) 7.40–7.55 (m, 5 H) 7.62 (m, 4 H) 7.78 (d, J=7.63 Hz, 1 H) 7.89 (d, J=8.55 Hz, 1 H) 8.13 (s, 1 H) | | |
| 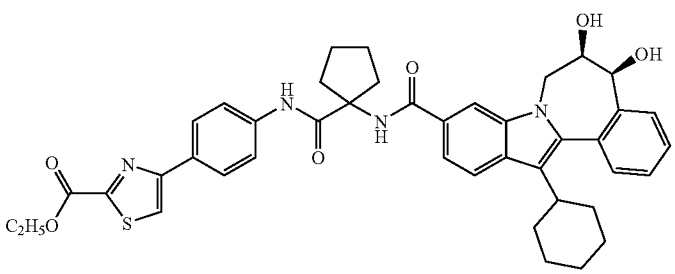 | 1H NMR (300 MHz, CHLOROFORM-D) δ ppm 1.15–2.74 (m, 25 H) 2.89 (s, 1 H) 3.59–3.79 (m, 1 H) 4.37–4.41 (m, J=6.22 Hz, 1 H) 4.47 (q, J=6.95 Hz, 2 H) 6.41 (s, 1 H) 7.26–7.40 (m, 5 H) 7.83–7.91 (m, 2 H) 7.94 (s, 1 H). | | |
| 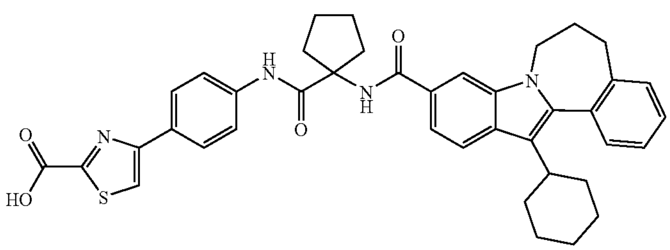 | MS m/z 673 (MH$^+$); 1H NMR (300 MHz, CHLOROFORM-D) δ ppm 1.14–2.73 (m, 22 H) 2.81–2.97 (m, 1 H) 3.60–3.77 (m, 1 H) 4.42 (dd, J=14.45, 6.40 Hz, 1 H) 4.42 (dd, J=14.45, 6.40 Hz, 2 H) 6.41 (s, 1 H) 7.66 (d, J=8.78 Hz, 2 H) 7.81–7.90 (m, 3 H) 7.93–7.98 (m, J=1.46 Hz, 1 H) 8.81–8.83 (m, J=1.83 Hz, 1 H). | | |
| 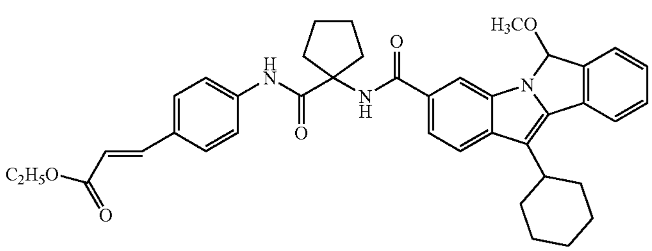 | MS m/z 645 (MH$^+$). | | |
| 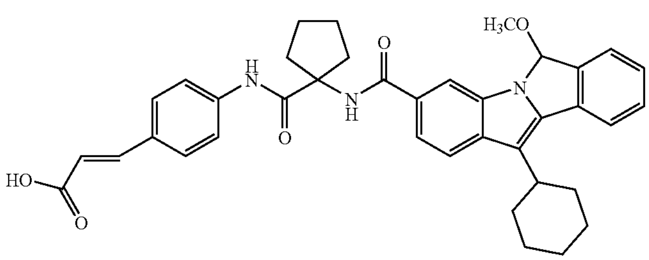 | MS m/z 616 (M − H). | | |

-continued

| Structure | Physiochemical Properties | IC$_{50}$ | EC$_{50}$ |
|---|---|---|---|
| 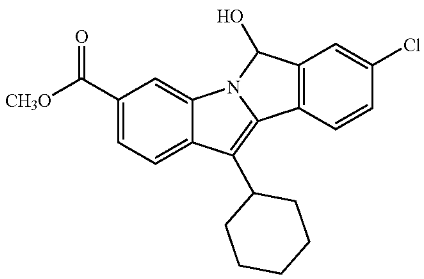 | MS m/z 394 (M − H); 1H NMR (300 MHz, Acetone) δ ppm 1.42–1.68 (m, 3H) 1.77–2.12 (m, 7H) 3.18–3.35 (m, 1H) 3.91 (s, 3 H) 6.72 (s, 1 H) 7.54 (dd, J=8.23, 2.01 Hz, 1 H) 7.64–7.76 (m, 2 H) 7.88 (dd, J=17.02, 8.23 Hz, 2 H) 8.22 (s, 1 H). | | |
| 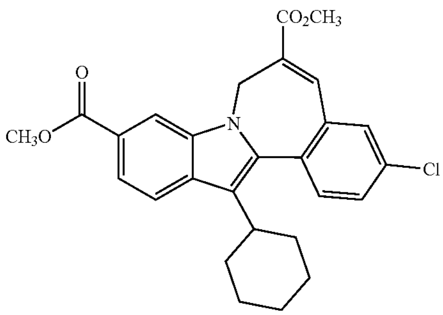 | MS m/z 464 (MH$^+$); 1H NMR (500 MHz, CHLOROFORM-D) δ ppm 1.13–2.20 (m, 39 H) 2.75–2.84 (m, 1 H) 3.85 (s, 3 H) 3.96 (s, 3H) 4.15–4.28 (m, 1 H) 5.62–5.79 (m, J=6.41 Hz, 1 H) 7.47–7.52 (m, 3 H) 7.76 (dd, 2 H) 7.87 (d, J=8.55 Hz, 1 H) 8.29 (s, 1 H). | | |
| 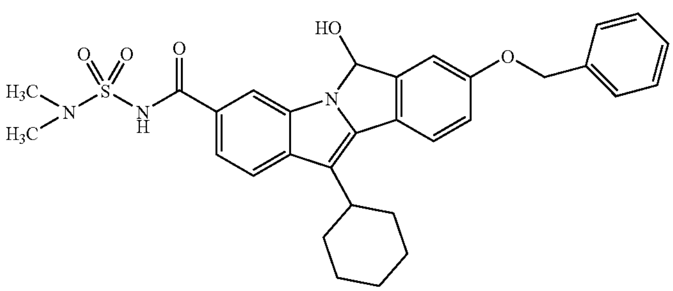 | MS m/z 558 (M − H); 1H NMR (500 MHz, CHLOROFORM-D) δ ppm 1.35–1.98 (m, 10 H) 3.06 (s, 6 H) 3.08–3.11 (m, J=7.93 Hz, 1 H) 4.95–4.96 (m, 2H) 6.48 (s, 1 H) 7.06 (dd, J=8.55, 2.44 Hz, 1 H) 7.32–7.58 (m, 8 H) 7.67 (d, J=8.55 Hz, 1 H) 7.73 (d, J=8.55 Hz, 1 H) 8.02 (s, 1 H) 8.69–8.85 (m, 1 H). | | |
| 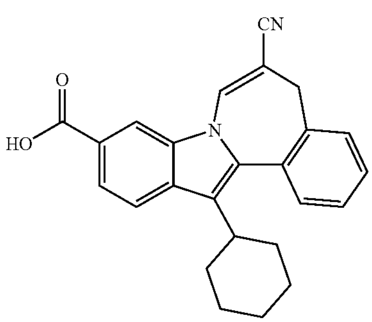 | MS m/z 384 (MH$^+$); 1H NMR (300 MHz, CHLOROFORM-D) δ ppm 0.98–2.56 (m, 10 H) 2.94–3.10 (m, 1H) 3.30 (s, 1H) 3.61–3.75 (m, 1H) 7.33–7.47 (m, 5H) 7.80 (s, 1 H) 7.90–8.06 (m, 3 H) 8.24 (s, 1 H). | | |
| | MS m/z 660 (MH$^+$); 1H NMR (500 MHz, CHLOROFORM-D) δ ppm 1.19–1.48(m, 10H) 1.64(d, 1 H) 1.76 (d, J=10.99 Hz, 2H) 1.81–1.93 (m, 5 H) 1.93–2.10 (m, 4 H) 2.20–2.37 (m, 3 H) 2.48 (d, J=7.63 Hz, 1 H) 2.55 (d, J=6.10 Hz, 3H) 2.80–2.93 (m, 1H) 3.58–3.72 (m, 1 H) 4.24 (q, J=7.02 Hz, 2H) 4.35–4.44 (m, 1 H) 6.34 (d, J=15.87 Hz, 1 H) 6.50 (s, 1 H) 6.80–6.91 (m, 2 H) 7.24 (d, J=8.24 Hz, 1 H) 7.30 (d, J=8.24 Hz, 1 H) 7.46 (d, J=8.55 Hz, 2 H) 7.58–7.66 (m, 3 H) 7.85 (d, 18.24 Hz, 1 H) 7.93 (s, 1 H). | | |

-continued

| Structure | Physiochemical Properties | IC$_{50}$ | EC$_{50}$ |
|---|---|---|---|
| | MS m/z 632 (MH$^+$);<br>1H NMR (500 MHz, MeOD) δ ppm 1.03–2.42 (m, 21 H) 2.49 (d, J=5.80 Hz, 1 H) 3.48–3.58 (m, 1H) 4.36–4.43 (m, 1 H) 6.29 (d, J=15.56 Hz, 1H) 7.09–7.15 (m, 1 H) 7.36–7.54 (m, 5 H) 7.73 (d, J=8.55 Hz, 1 H) 7.92 (s, 1 H) 8.24 (s, 1 H) 8.67–8.69 (m, 1 H). | | |
| 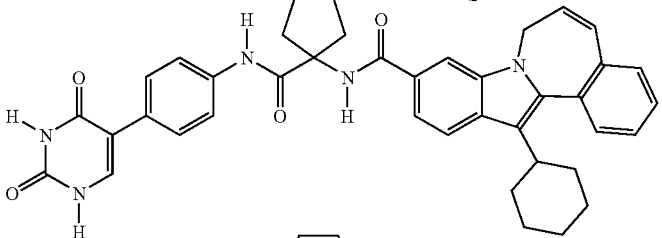 | MS m/z 654 (MH$^+$) | | |
| 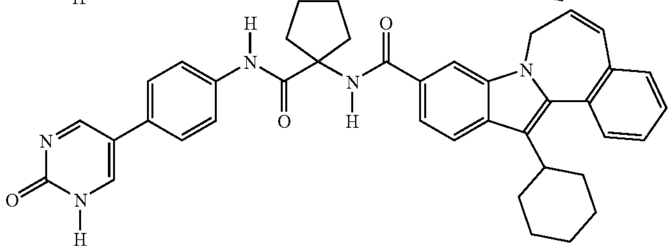 | MS m/z 638 (MH$^+$) | | |

13-Cyclohexyl-6,7-dihydro-7-oxo-5H-indolo[2,1-a][2,4]benzodiazepine-10-carboxylic acid and 13-cyclohexyl-6,7-dihydro-6-methyl-7-oxo-5H-indolo[2,1-a][2,4]benzodiazepine-10-carboxylic acid and related compounds may be prepared as shown in the scheme below.

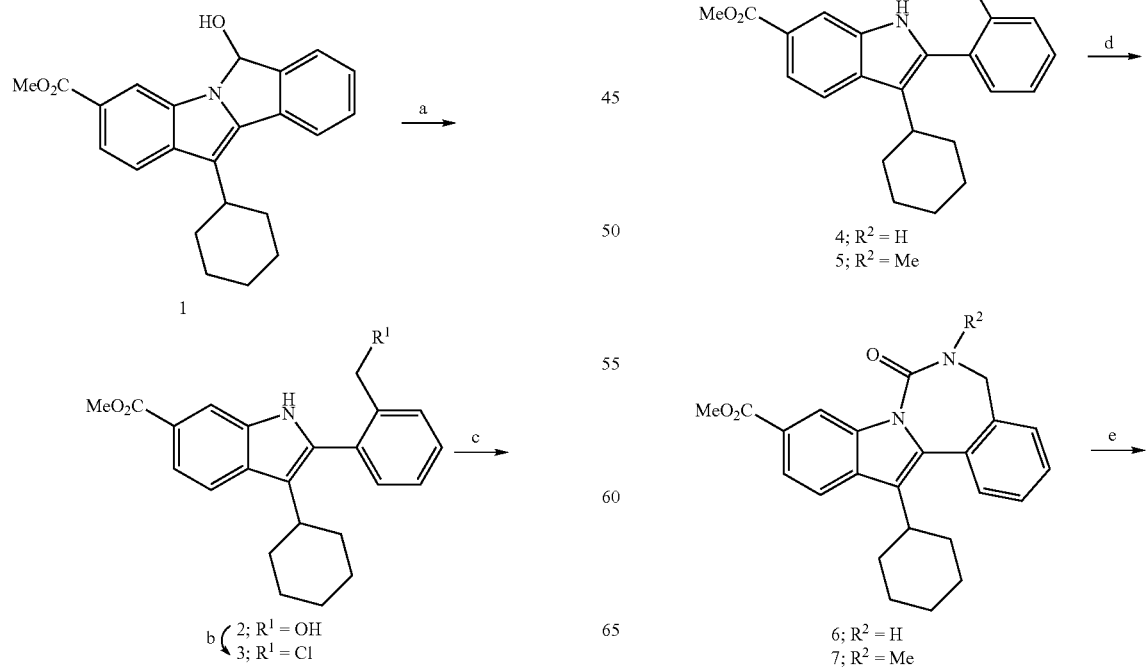

473

-continued

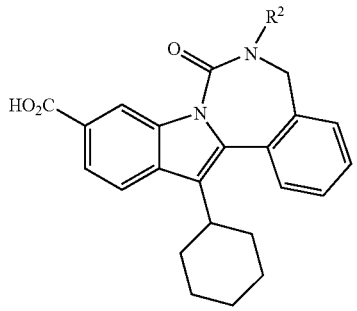

8; R² = H
9; R² = Me (a) NaBH₄, MeOH-THF, rt (b) SOCl2, CHCl₃ (c) R²NH₂, dioxane or THF, 60–90° C. (d) KOSiMe₃, THF, rt 13-Cyclohexyl-6,7-dihydro-7-oxo-5H-indolo[2,1-a][2,4]benzodiazepine-10-carboxylic acid. Sodium borohydride (37 mg, 1 mmol) was added to a stirred solution of 1 (181 mg, 0.5 mmol) in THF (5 mL) and MeOH (2 mL). The mixture was stirred at rt for 2 h and then quenched with 1N HCl, neutralized with 1N NaOH, extracted with EtOAc to afford pure alcohol 2 (180 mg, 99%): LC/MS m/e 364 (MH⁺). A mixture of alcohol 2 (150 mg, 0.4 mmol) and SOCl₂ (1 mL) in CHCl3 (5 mL) was stirred at rt for 2 h and heated to reflux for 15 min. Evaporation of excess SOCl₂ and CHCl3 gave the desired product 3 (152 mg, 96%): LC/MS m/e 382 (MH⁺). A stirred mixture of 3 (38 mg, 0.1 mmol) and anhydrous NH3 in dioxane (0.5M, 2 mL) in a sealed tube was heated at 90° C. for 16 h. Evaporation excess NH3 and dioxane afforde the desired amine 4 (35 mg, 99%): LC/MS m/e 363 (MH+). The amine 4 (35 mg) and 1,1'-carbonyldiimidazole (25 mg, 0.15 mmol) in an THF (2 mL) was heated to reflux for 1 h. The reaction was quenched with 0.5N HCl and extracted with EtOAc to afford the desired urea-bridge product 6 (36 mg, 96%): LC/MS m/e 389 (MH+). Methyl ester 6 (30 mg, 0.077 mmol) and KOSiMe3 (30 mg, 0.23 mmol) in an. THF (2 mL) was stirred for 16 h and then acidified with 0.5N HCl. The product extracted with EtOAc and purified by prep. HPLC to provide the desired acid 8 (23 mg, 79%): LC/MS m/e 375(MH+); 1H NMR (400 MHz, CHLOROFORM-D) δ ppm 1.25 (t, J=7.18 Hz, 1 H) 1.35–1.53 (m, 2 H) 1.57–1.72 (m, 1 H) 1.75–1.89 (m, 2 H) 1.91–2.01 (m, 1 H) 2.05–2.27 (m, 3 H) 2.95–3.08 (m, J=12.09, 12.09 Hz, 1 H) 4.02–4.16 (m, J=7.30, 7.30, 7.30 Hz, 1 H) 4.38–4.57 (m, 1 H) 7.36–7.57 (m, 4 H) 7.91–8.01 (m, 2 H) 8.73 (s, 1 H) 9.10 (s, 1 H).

13-cyclohexyl-6,7-dihydro-6-methyl-7-oxo-5H-indolo[2,1-a][2,4]benzodiazepine-10-carboxylic acid. Compound 9 was prepared by identical procedure except in place of NH₃, methylamine was used in amination step. LC/MS m/e 389 (MH+); 1H NMR (400 MHz, CHLOROFORM-D) δ ppm 1.16–1.30 (m, 1 H) 1.33–1.53 (m, 2 H) 1.62 (d, J=13.09 Hz, 1 H) 1.79 (d, J=10.07 Hz, 2 H) 1.92–2.00 (m, 1 H) 2.02–2.23 m, 3 H) 2.93–3.05 (m, 1 H) 3.21 (s, 3 H) 3.80 (d, J=14.60 Hz, 1 H) 4.65 (d, J=14.60 Hz, 1 H) 7.34–7.38 (m, 1 H) 7.39–7.44 (m, 1 H) 7.45–7.51 (m, 1 H) 7.51–7.55 (m, 1 H) 7.90–7.97 (m, 2 H) 8.82 (s, 1 H).

The present disclosure is not limited to the foregoing illustrative examples and encompasses other specific compounds without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula (I)

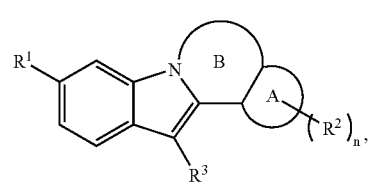

(I)

or a pharmaceutically acceptable salt thereof, wherein
n is 0, 1, 2, or 3;
A is a phenyl ring;
B is a seven-membered carbocyclic ring containing 0 or 1 double bonds wherein said ring is optionally substituted with one, two, three, or four substitutes independently selected from alkoxy, alkoxycarbonyl, alkyl, carboxy, cyano, cycloalkyl, halo, hydroxy, hydroxyalkyl, alkylaminoalkyl, dialkylaminoalkyl, NR⁴R⁵, (NR⁴R⁵)carbonyl, and oxo;
R¹ is selected from —C(O)NR⁴R⁵, —CO₂R⁴, 5-tetrazolyl, cyano,

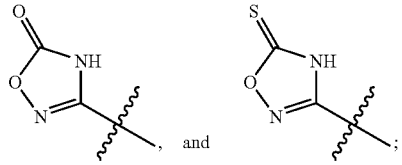

, and ;

each R² is independently selected from alkoxy, alkoxyalkyl, alkyl, alkylamino, amino, arylalkoxy, aryloxy, dialkylamino, halo, haloalkoxy, haloalkyl, hydroxy, and hydroxyalkyl; R³ is a five- to seven-membered cycloalkyl ring; R⁴is selected from hydrogen, alkyl, cycloalkyl, hydroxyalkyl, aminoalkyl, (alkylamino)alkyl, (dialkylamino)alkyl, aryl, arylalkyl, and (NR⁶R⁷)alkyl;
R⁵ is selected from hydrogen, alkyl, hydroxyalkyl, aminoalkyl, (alkylamino)alkyl, (dialkylamino)alkyl, aryl, arylalkyl, (NR⁶R⁷)alkyl, alkylcarbonyl, arylcarbonyl, (NR⁶R⁷)carbonyl, —S(O)₂R⁸, —S(O)₂NR⁶R⁷,

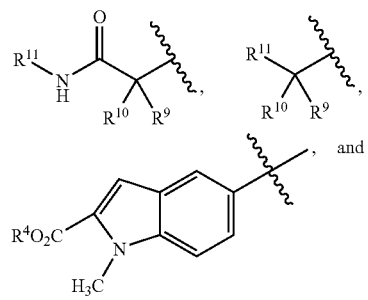

-continued

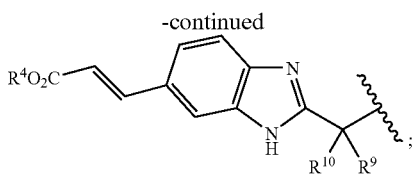

or NR⁴R⁵ taken together is pyrrolidinyl, piperidinyl, piperazinyl, homomorpholinyl, homopiperidinyl, morpholinyl, or thiomorpholinyl and is substituted with 0–2 substituents selected from the group consisting of alkyl, hydroxy, amino, alkylamino, dialkylamino, pyrrolidinyl, piperidinyl, and pyridinyl;

R⁶ and R⁷ are independently selected from hydrogen, alkyl and cycloalkyl;

R⁸ is selected from alkyl, cycloalkyl, aryl, and heteroaryl;

R⁹ and R¹⁰ are independently selected from hydrogen and alkyl; or

R⁹ and R¹⁰, together with the carbon atom to which they are attached, form a four- to seven-membered saturated ring optionally containing 1 or 2 heteroatoms selected from nitrogen, oxygen, and sulfur, wherein said ring is optionally substituted with one or two substituents independently selected from alkoxycarbonyl, alkyl, and oxo; and R¹¹ is a five- or six-membered saturated, partially saturated, or aromatic ring containing 0, 1, 2, or 3 heteroatoms selected from nitrogen, oxygen, and sulfur, wherein said ring is optionally substituted with one or two substituents independently selected from alkoxycarbonylalkenyl, alkoxycarbonylalkyl, alkyl, aryl, carboxy, carboxyalkenyl, carboxyalkyl, and heteroaryl, wherein said aryl and heteroaryl are further optionally substituted with one or two substituents independently selected from alkoxycarbonyl, alkoxycarbonylalkenyl, alkoxycarbonylalkyl, carboxy carboxyalkenyl, carboxyalkyl, and hydroxy;

or a pharmaceutically acceptable salt or solvate thereof.

2. The compound of claim 1 wherein B is a seven-membered carbocyclic ring containing 0 or 1 double bonds, wherein said ring is optionally substituted with one or two substituents independently selected from alkoxy, alkoxycarbonyl, carboxy, hydroxy, (NR⁴R⁵)carbonyl, and oxo.

3. The compound of claim 2 where R⁴ is selected from hydrogen, alkyl, hydroxyalkyl, aminoalkyl, (alkylamino)alkyl, (dialkylamino)alkyl, and (NR⁶R⁷)alkyl, R⁵ is selected from hydrogen, alkyl, hydroxyalkyl, aminoalkyl, (alkylamino)alkyl, (dialkylamino)alkyl, (NR⁶R⁷)alkyl, alkylcarbonyl, —S(O)₂R⁸, and —S(O)₂NR⁶R⁷, or NR⁴R⁵ taken together is pyrrolidinyl, piperidinyl, piperazinyl, homopiperidinyl, morpholinyl, or thiomorpholinyl and is substituted with 0–2 substituents selected from the group consisting of alkyl, hydroxy, amino, alkylamino, dialkylamino, pyrrolidinyl, piperidinyl, and pyridinyl.

4. The compound of claim 1 wherein R¹ is selected from —C(O)NR⁴R⁵ and —CO₂R⁴.

5. The compound of claim 1 wherein R¹ is —C(O)NR⁴R⁵, R⁴ is hydrogen, and R⁵ is —S(O)₂R⁸ or —S(O)₂NR⁶R⁷.

6. The compound of claim 1 wherein R¹ is —C(O)NR⁴R⁵, R⁴ is hydrogen, R⁵ is

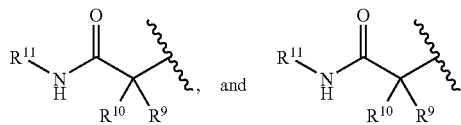

is selected from the group consisting of

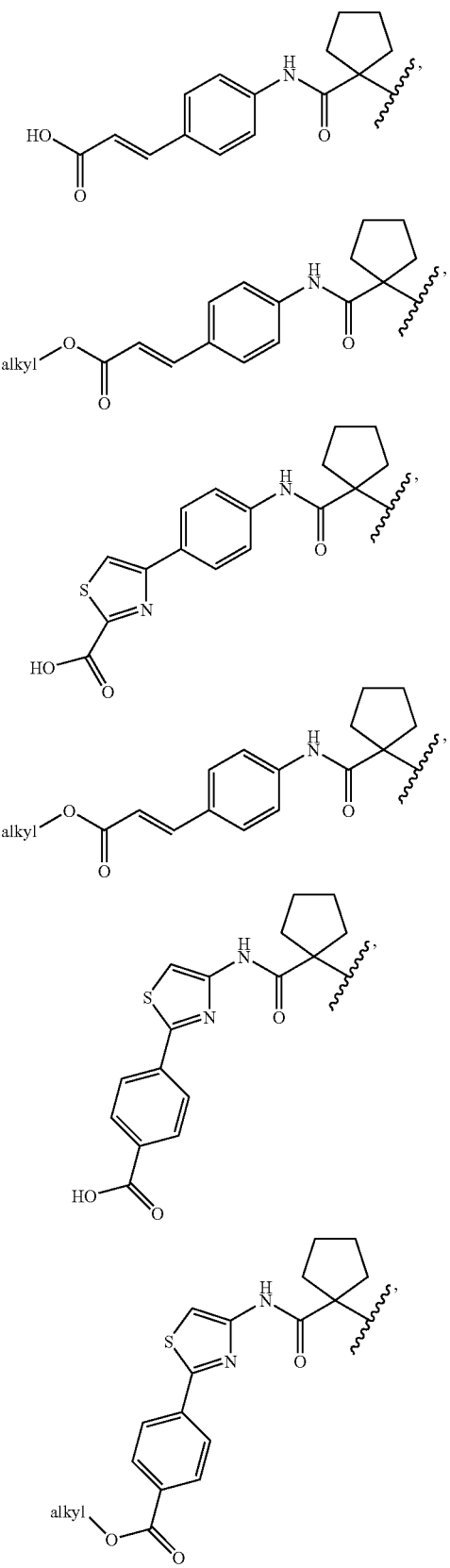

-continued

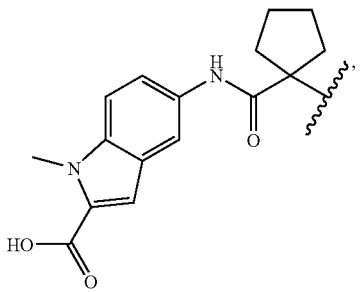

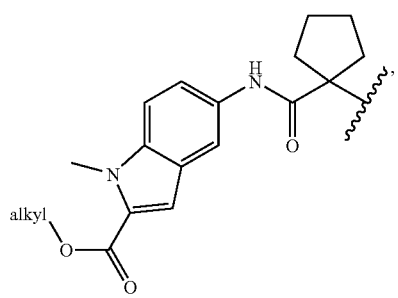

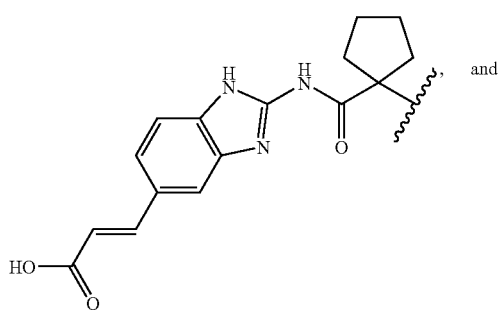

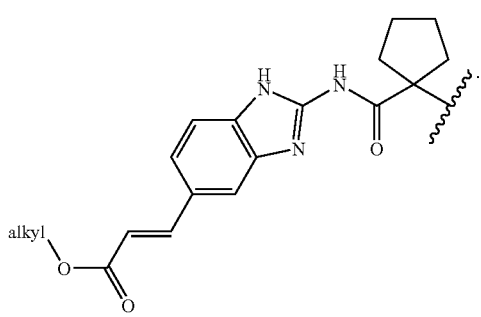

7. The compound of claim 1 wherein each $R^2$ is independently selected from halo, alkoxy, arylalkoxy, and hydroxy.

8. The compound of claim 1 wherein n is 0 or n is 1 and $R^2$ is halo or $C_{1-3}$alkoxy.

9. The compound of claim 1 according to formula (II)

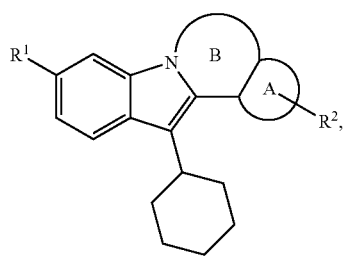

(II)

or a pharmaceutically acceptable salt thereof, wherein
n is 0 or 1;
A is phenyl;
B is a seven-membered carboxcylic ring containing 0 or 1 double bonds; whereing said ring is optionally substituted with one or two substituents independently selected from alkoxy, alkoxycarbonyl, carboxy, hydroxy, ($NR^4R^5$)carbonyl, and oxo;
$R^1$ is selected from —C(O)$NR^4R^5$, and —$CO_2R^4$;
$R^2$ is selected from alkoxy, arylalkoxy, and hydroxy;
$R^4$ is selected from hydrogen, alkyl, hydroxyalkyl, aminoalkyl, (alkylamino)alkyl, (dialkylamino)alkyl, alkyl;
$R^5$ is selected from hydrogen, alkyl, hydroxyalkyl, aminoalkyl, (alkylamino)alkyl, (dialkylamino)alkyl, alkyl, —S(O)$_2R^8$, —S(O)$_2NR^6R^7$,

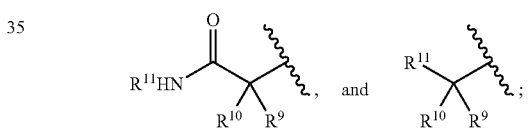

or $NR^4R^5$ taken together is pyrrolidinyl, piperidinyl, piperazinyl, homopiperidinyl, morpholinyl, or thiomorpholinyl and is substituted with 0–2 substituents selected from the group consisting of alkyl, hydroxy, amino, alkylamino, dialkylamino, pyrrolidinyl, piperidinyl, and pyridinyl;
$R^6$ and $R^7$ are independently selected from hydrogen and alkyl;
$R^8$ is selected from aryl, cycloalkyl, and heteroaryl;
$R^9$ and $R^{10}$ are independently selected from hydrogen and alkyl; or
$R^9$ and $R^{10}$, together with the carbon atom to which they are attached, form a four- to seven-membered saturated ring optionally containing 1 or 2 heteroatoms selected from nitrogen, oxygen, and sulfur; and
$R^{11}$ is a five- or six-membered aromatic ring containing 0, 1, 2, or 3 heteroatoms selected from nitrogen, oxygen, and sulfur, wherein said ring is optionally substituted with one substituent independently selected from alkoxycarbonylalkenyl, alkoxycarbonylalkyl, aryl, carboxyalkenyl, and carboxyalkyl, wherein said aryl is further optionally substituted with one substituent independently selected from carboxy and carboxyalkenyl.

10. A compound of claim 1 selected from the group consisting of

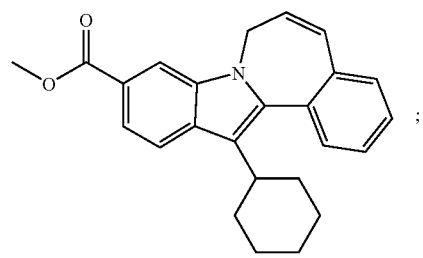
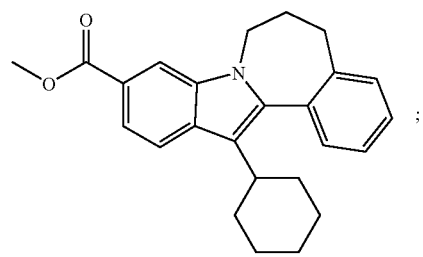
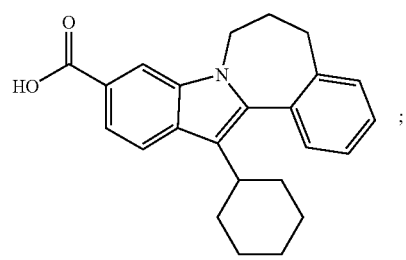
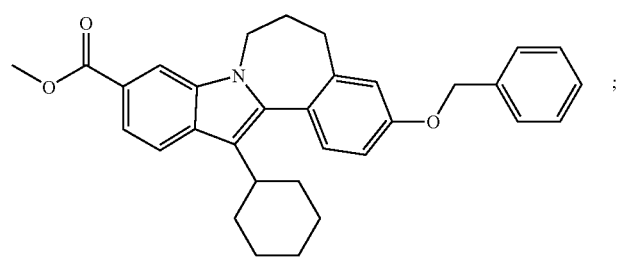
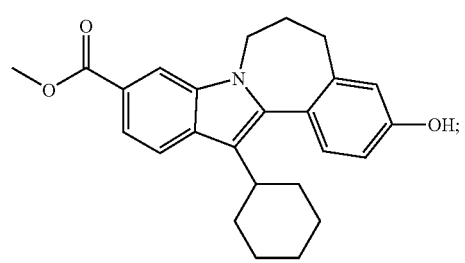
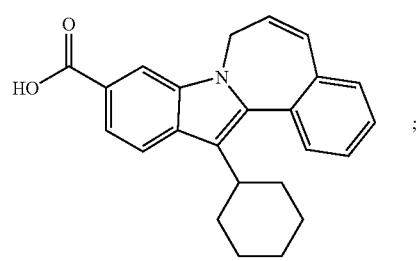

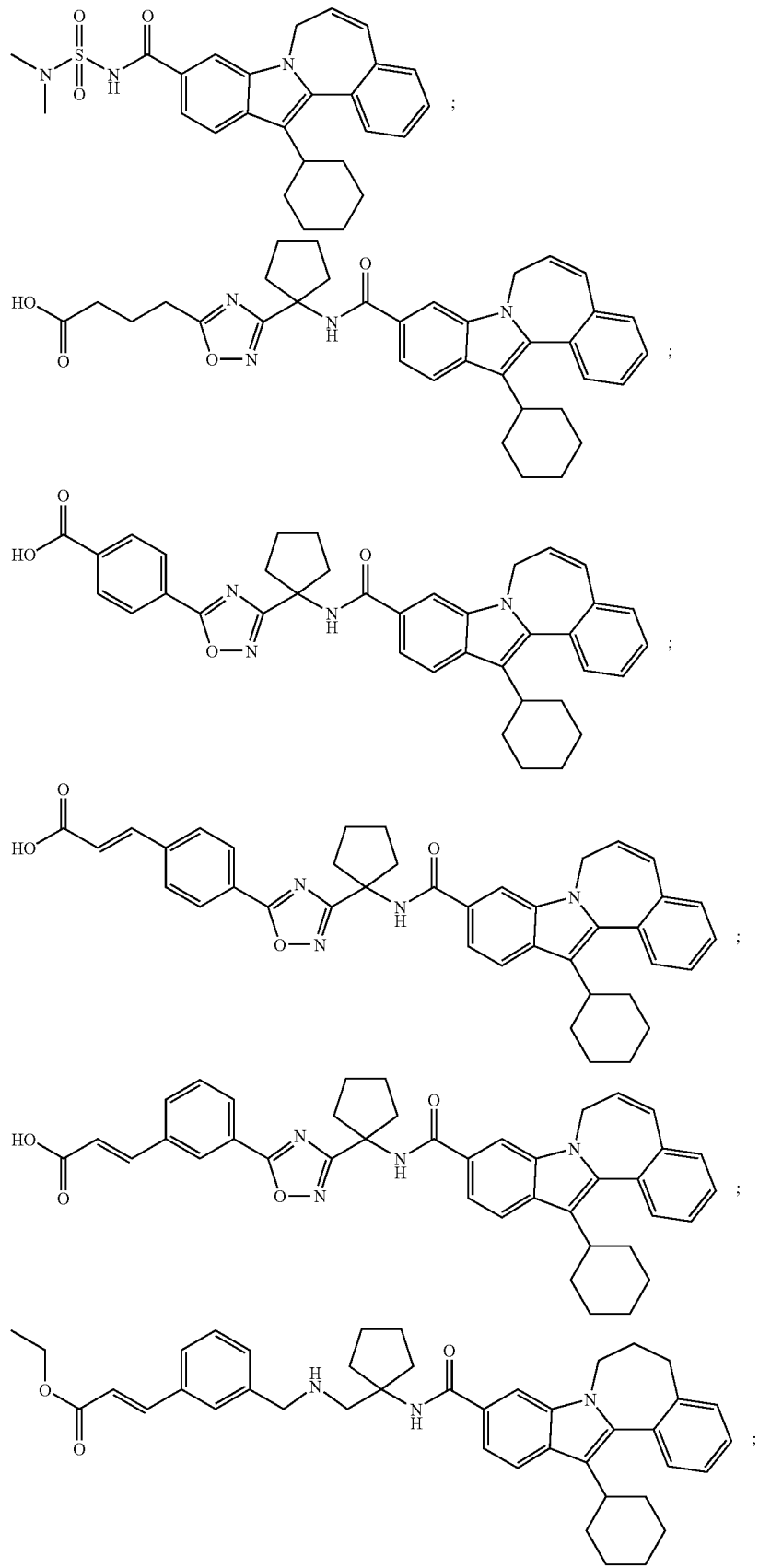

-continued
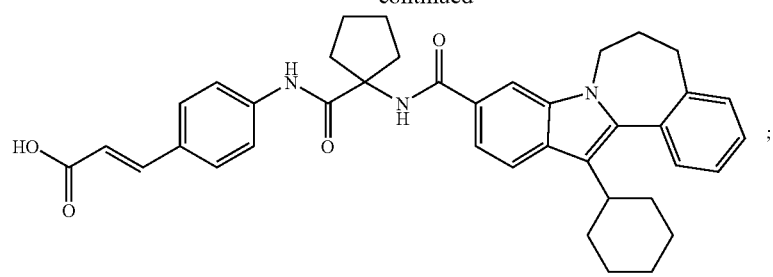
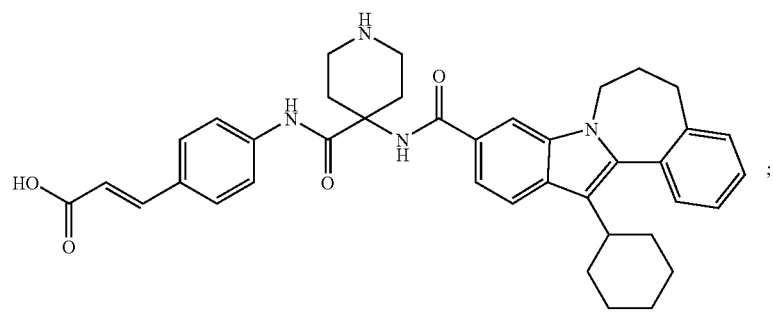
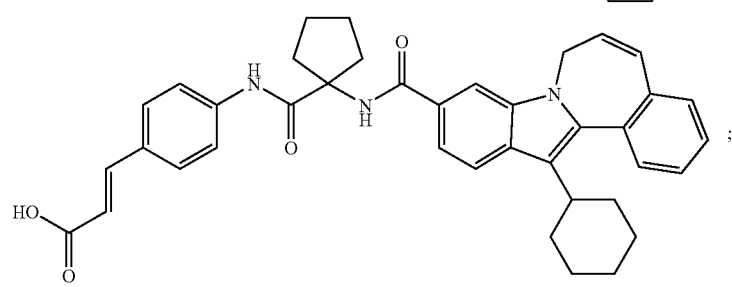
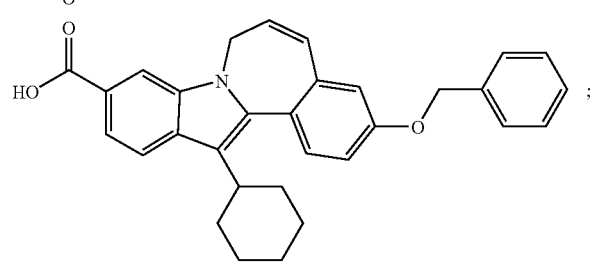
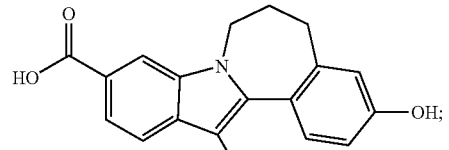
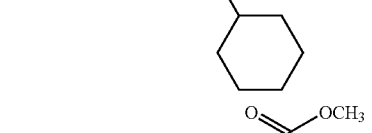
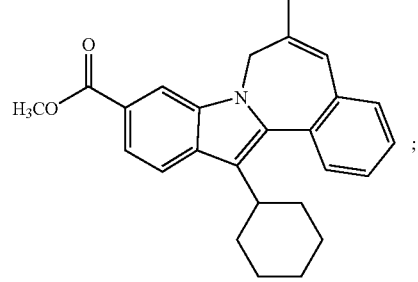

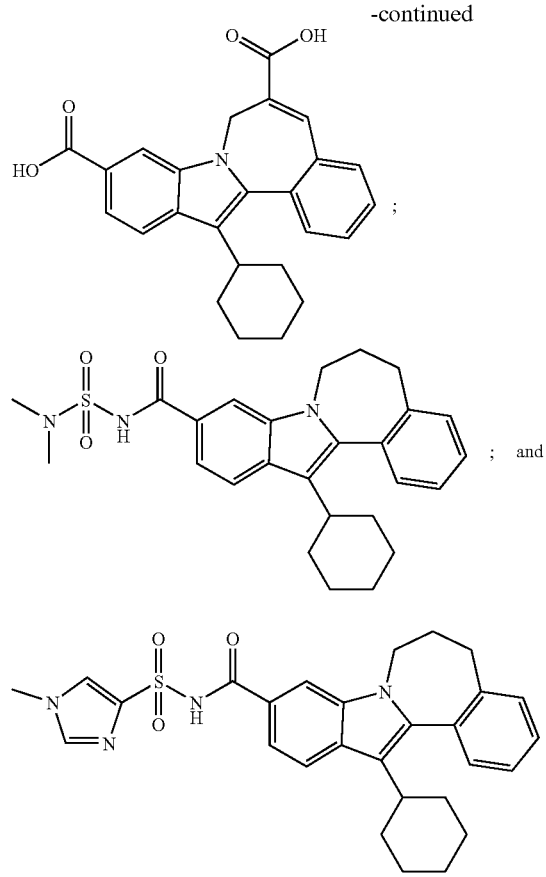
11. The compound of claim 1 selected from the group consisting of
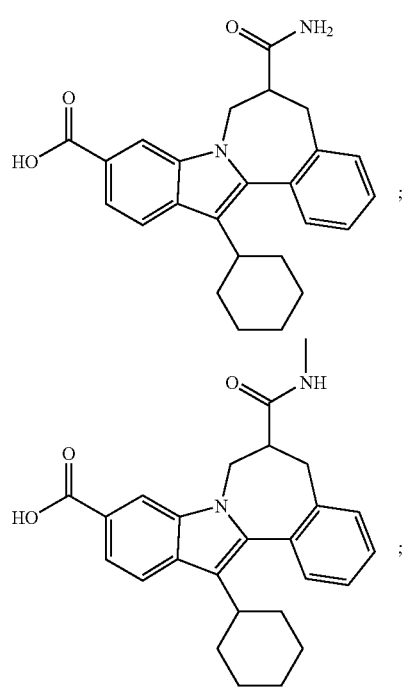
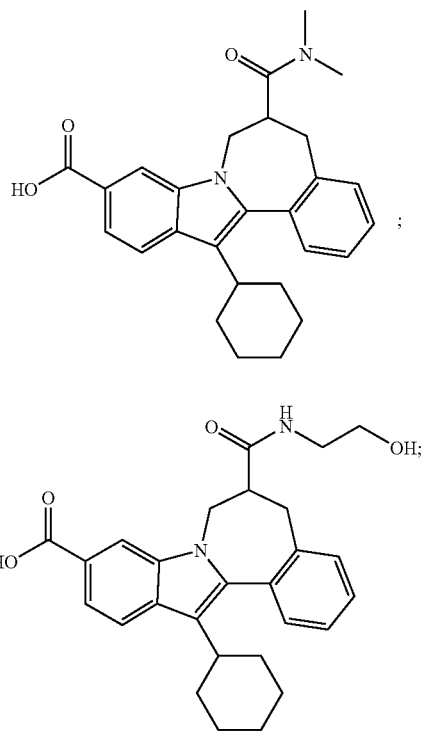

487
-continued
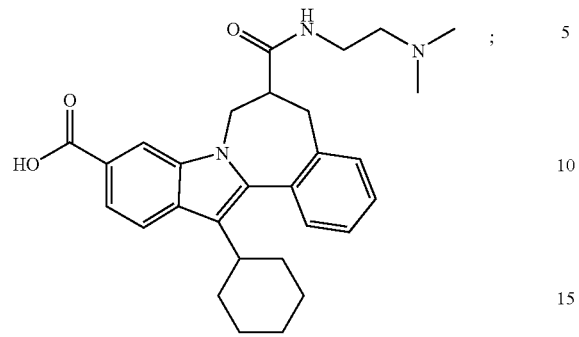
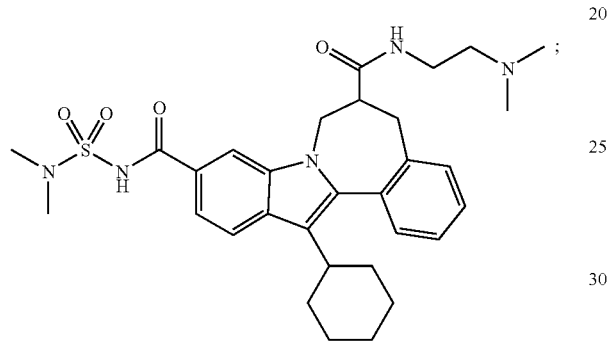
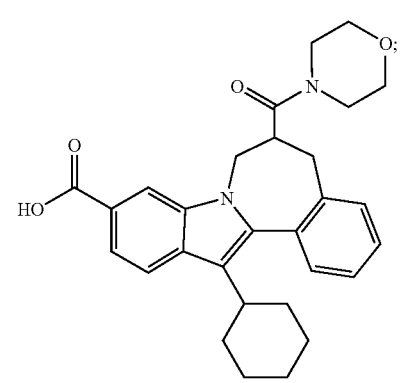
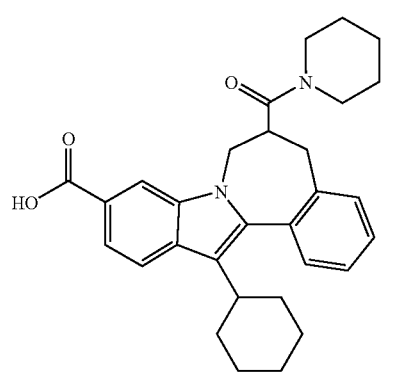
488
-continued
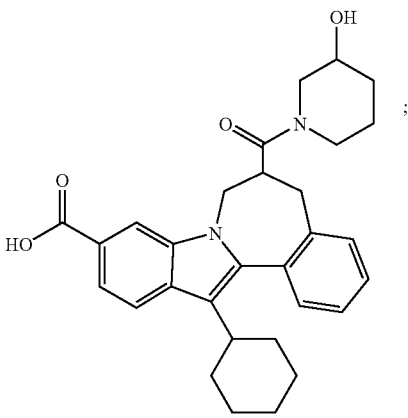
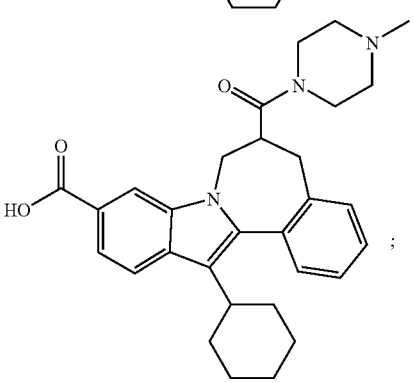
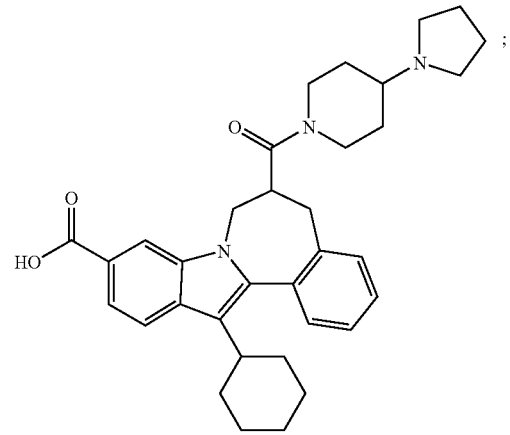
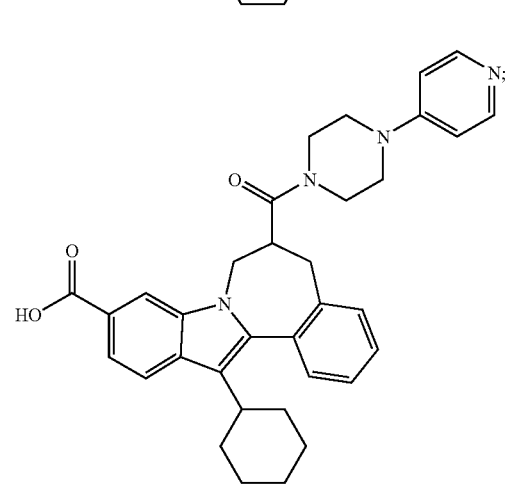

489
-continued
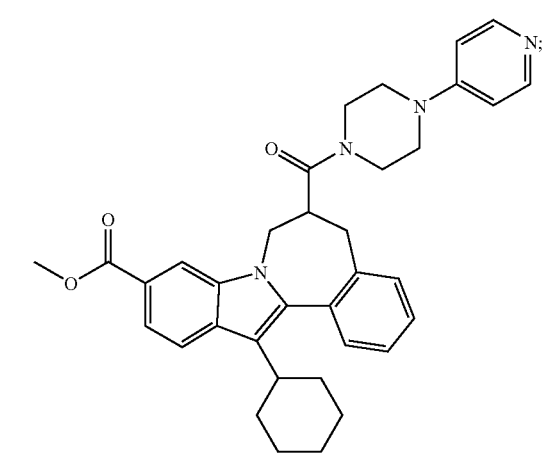
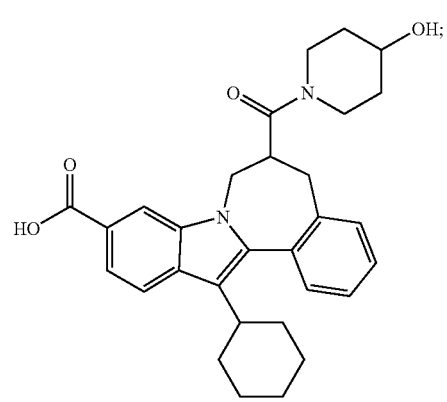
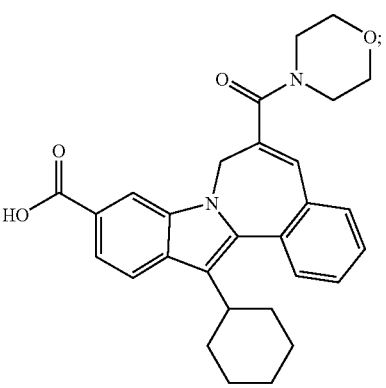
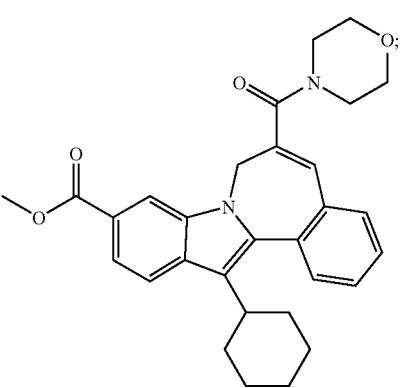
490
-continued
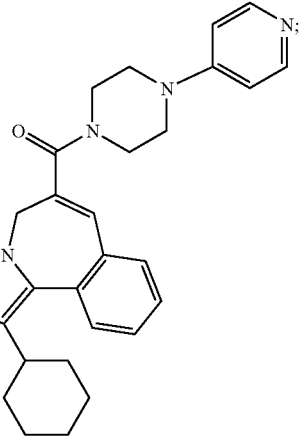
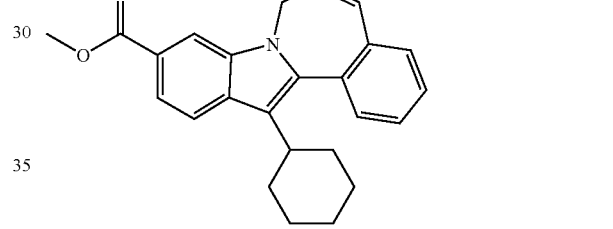
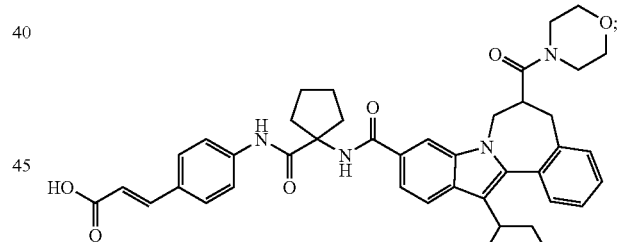
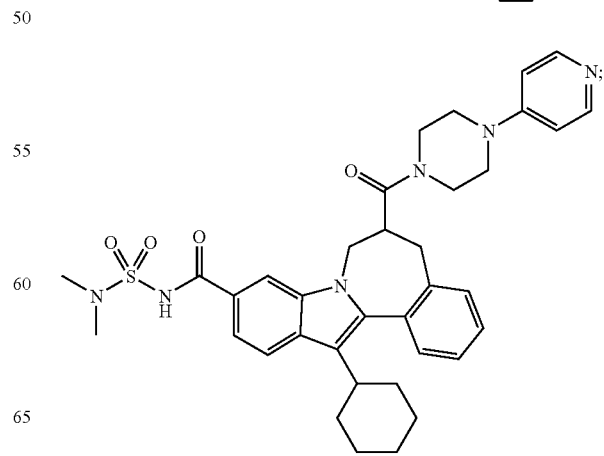

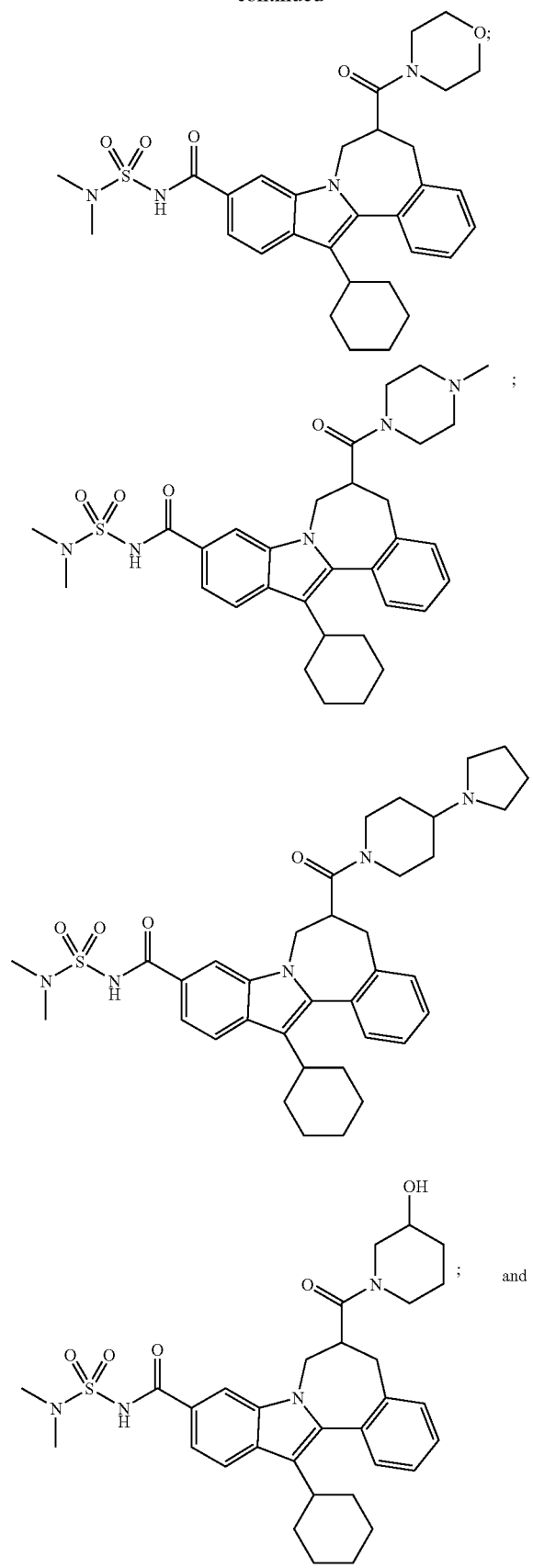

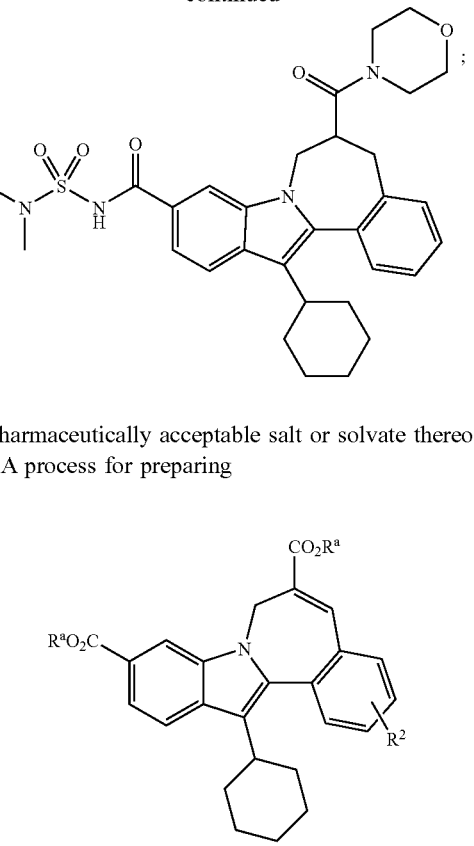

or a pharmaceutically acceptable salt or solvate thereof.

12. A process for preparing

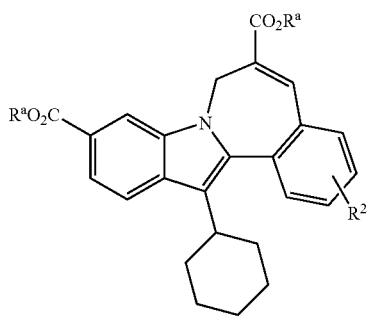

where $R^a$ is alkyl and $R^2$ is absent or is alkoxy or halo comprising reacting

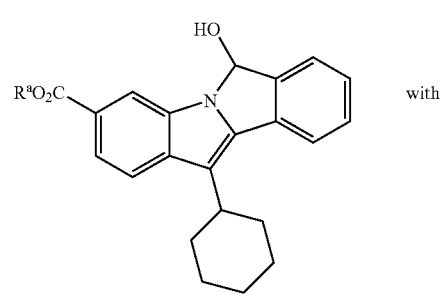

with

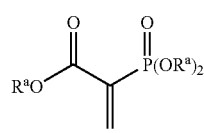

under basic conditions in a polar non-protic solvent.

13. A composition comprising a compound of claim 1, or a pharmaceutically acceptable salt thereof, and a pharmaceutically acceptable carrier.

14. The composition of claim 13 further comprising a compound having anti-HCV activity.

15. The composition of claim 14 wherein the compound having anti-HCV activity is an interferon.

16. The composition of claim 15 wherein the interferon is selected from interferon alpha 2B, pegylated interferon alpha, consensus interferon, interferon alpha 2A, and lymphoblastoid interferon tau.

17. The composition of claim 14 wherein the compound having anti-HCV activity is a cyclosporin.

18. The composition of claim 17 wherein the cyclosporin is cyclosporin A.

19. The composition of claim 14 wherein the compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

20. The composition of claim 13 further comprising an interferon and ribavirin.

21. The composition of claim 14 wherein the compound having anti-HCV activity is a small molecule compound.

22. The composition of claim 14 wherein the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

23. A method of treating an HCV infection in a patient, comprising administering to the patient a therapeutically effective amount of a compound of claim 1, or a pharmaceutically acceptable solvate or salt thereof.

24. The method of claim 23 further comprising administering another compound having anti-HCV activity prior to, after, or simultaneously with the compound of claim 1.

25. The method of claim 24 wherein the other compound having anti-HCV activity is an interferon.

26. The method of claim 25 wherein the interferon is selected from interferon alpha 2B, pegylated interferon alpha, consensus interferon, interferon alpha 2A, and lymphoblastoid interferon tau.

27. The method of claim 24 wherein the other compound having anti-HCV activity is a cyclosporin.

28. The method of claim 27 wherein the cyclosporin is cyclosporin A.

29. The method of claim 24 wherein the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

30. The method of claim 24 wherein the other compound having anti-HCV activity is a small molecule.

31. The method of claim 30 wherein the other compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

32. The method of claim 24 wherein the other compound having anti-HCV activity is effective to inhibit the function of target in the HCV life cycle other than the HCV NS5B protein.

* * * * *